US009840536B2

(12) United States Patent
Currie et al.

(10) Patent No.: US 9,840,536 B2
(45) Date of Patent: Dec. 12, 2017

(54) METHODS AND COMPOSITIONS FOR THE TREATMENT OF GASTROINTESTINAL DISORDERS

(71) Applicant: Ironwood Pharmaceuticals, Inc., Cambridge, MA (US)

(72) Inventors: Mark G. Currie, Sterling, MA (US); Shalina Mahajan-Miklos, Standford, CA (US); Li Jing Sun, New York, NY (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/936,258

(22) Filed: Nov. 9, 2015

(65) Prior Publication Data
US 2016/0168201 A1 Jun. 16, 2016

Related U.S. Application Data

(63) Continuation of application No. 14/024,552, filed on Sep. 11, 2013, now abandoned, which is a continuation of application No. 13/291,526, filed on Nov. 8, 2011, now abandoned, which is a continuation of application No. 12/568,107, filed on Sep. 28, 2009, now Pat. No. 8,101,579, which is a continuation of application No. 10/868,744, filed on Jun. 14, 2004, now abandoned.

(60) Provisional application No. 60/478,492, filed on Jun. 13, 2003, provisional application No. 60/532,361, filed on Dec. 23, 2003, provisional application No. 60/571,386, filed on May 14, 2004.

(51) Int. Cl.
| | | |
|---|---|---|
| *A61K 38/10* | (2006.01) | |
| *A61K 31/74* | (2006.01) | |
| *C07K 7/08* | (2006.01) | |
| *A61K 38/00* | (2006.01) | |

(52) U.S. Cl.
CPC ............... *C07K 7/08* (2013.01); *A61K 38/00* (2013.01)

(58) Field of Classification Search
None
See application file for complete search history.

(56) References Cited

U.S. PATENT DOCUMENTS

| | | |
|---|---|---|
| 5,140,102 A | 8/1992 | Currie |
| 5,250,534 A | 10/1993 | Bell et al. |
| 5,272,147 A | 12/1993 | Bell et al. |
| 5,346,901 A | 9/1994 | Bell et al. |
| 5,395,490 A | 3/1995 | Hoff |
| 5,426,107 A | 6/1995 | Bell et al. |
| 5,482,941 A | 1/1996 | Terrett et al. |
| 5,489,670 A | 2/1996 | Currie et al. |
| 5,591,742 A | 1/1997 | Bell et al. |
| 5,719,283 A | 2/1998 | Bell et al. |
| 5,734,053 A | 3/1998 | Terrett |
| 5,859,006 A | 1/1999 | Daugan |
| 5,879,656 A | 3/1999 | Waldman |
| 5,962,220 A | 10/1999 | Waldman |
| 5,969,097 A | 10/1999 | Wiegand et al. |
| 5,981,527 A | 11/1999 | Daugan et al. |
| 6,001,847 A | 12/1999 | Daugan et al. |
| 6,025,494 A | 2/2000 | Daugan |
| 6,060,037 A | 5/2000 | Waldman |
| 6,127,542 A | 10/2000 | Daugan et al. |
| 6,153,630 A | 11/2000 | Cavalla et al. |
| 6,218,400 B1 | 4/2001 | Daugan et al. |
| 6,300,335 B1 | 10/2001 | Campbell et al. |
| 6,306,870 B1 | 10/2001 | Bombrun |
| 6,316,438 B1 | 11/2001 | Yu et al. |
| 6,326,379 B1 | 12/2001 | Macor et al. |
| 6,331,543 B1 | 12/2001 | Garvey et al. |
| 6,369,059 B1 | 4/2002 | Daugan |
| 6,391,869 B1 | 5/2002 | Parks et al. |
| 6,462,044 B2 | 10/2002 | Garvey et al. |

(Continued)

FOREIGN PATENT DOCUMENTS

| | | |
|---|---|---|
| DE | 19543628 | 5/1997 |
| WO | WO9914239 | 3/1999 |

(Continued)

OTHER PUBLICATIONS

Amarante et al., "The κ-opioid agonist (±)-bremazocine elicits peripheral antinociception by activation of the L-arginine/nitric oxide/cyclic GMP pathway." European Journal of Pharmacology, 454:19-23, 2002.
Arita et al., "Purification and characterization of a heat-stable enterotoxin of Vibrio mimicus." FEMS Microbiology Letters, 79(1): 105-110, 1991.
Bakre, et al., "Expression and regulation of the cGMP-binding, cGMP-specific phosphodiesterase (PDE5) in human colonic epithelial cells: role in the induction of cellular refractoriness to the heat-stable enterotoxin peptide." J. Cell. Biochem., 77:159-167, 2000.
Beavo, J., "Cyclic Nucleotide Phosphordiesterases: Functional Implications of Multiple Isoforms" Physiol. Rev. 75(4): 725-748, 1995.
Beltowski, J., "Guanylin and related peptides." Journal of Physiology and Pharmacology 52(3): 351-375, 2001.
Bortolotti et al., "Sildenafil inhibits gastroduodenal motility" Ailment Pharmacol. Ther. 12:157-161, 2001.

(Continued)

*Primary Examiner* — Jeanette Lieb
(74) *Attorney, Agent, or Firm* — Honigman Miller Schwartz and Cohn LLP; Kelly T. Murphy; Jonathan P. O'Brien

(57) ABSTRACT

Compositions and related methods for treating IBS and other gastrointestinal disorders and conditions (e.g., gastrointestinal motility disorders, functional gastrointestinal disorders, gastroesophageal reflux disease (GERD), duodenogastric reflux, Crohn's disease, ulcerative colitis, inflammatory bowel disease, functional heartburn, dyspepsia (including functional dyspepsia or nonulcer dyspepsia), gastroparesis, chronic intestinal pseudo-obstruction (or colonic pseudoobstruction), and disorders and conditions associated with constipation, e.g., constipation associated with use of opiate pain killers, post-surgical constipation, and constipation associated with neuropathic disorders as well as other conditions and disorders are described. The compositions feature peptides that activate the guanylate cyclase C (GC-C) receptor.

4 Claims, 221 Drawing Sheets

(56) References Cited

U.S. PATENT DOCUMENTS

| | | | |
|---|---|---|---|
| 6,469,012 | B1 | 10/2002 | Ellis et al. |
| 6,534,511 | B1 | 3/2003 | Campbell |
| 6,576,644 | B2 | 6/2003 | Bi et al. |
| 6,586,403 | B1 | 7/2003 | Mathison et al. |
| 6,642,244 | B2 | 11/2003 | Macor et al. |
| 6,656,945 | B2 | 12/2003 | Campbell et al. |
| 6,784,179 | B2 | 8/2004 | Daugan |
| 6,835,737 | B2 | 12/2004 | Bi et al. |
| 6,872,721 | B2 | 3/2005 | Orme et al. |
| 6,930,113 | B2 | 8/2005 | Garvey et al. |
| 6,943,253 | B2 | 9/2005 | Vidal Juan et al. |
| 7,034,016 | B2 | 4/2006 | Gracia Ferrer et al. |
| 7,041,786 | B2 | 5/2006 | Shailubhai et al. |
| 7,173,042 | B2 | 2/2007 | Bi et al. |
| 7,378,430 | B2 | 5/2008 | Bi et al. |
| 7,384,958 | B2 | 6/2008 | Bi et al. |
| 7,494,979 | B2 | 2/2009 | Currie et al. |
| 8,101,579 | B2 | 1/2012 | Currie et al. |
| 2001/0044441 | A1 | 11/2001 | Campbell et al. |
| 2002/0019405 | A1 | 2/2002 | Garvey et al. |
| 2002/0119976 | A1 | 8/2002 | Daugan |
| 2002/0133008 | A1 | 9/2002 | Macor et al. |
| 2002/0177587 | A1 | 11/2002 | Bi et al. |
| 2003/0023087 | A1 | 1/2003 | Garvey et al. |
| 2003/0027824 | A1 | 2/2003 | Ellis et al. |
| 2003/0055070 | A1 | 3/2003 | Harrison et al. |
| 2003/0060627 | A1 | 3/2003 | Gracia Ferrer et al. |
| 2003/0073628 | A1 | 4/2003 | Shailubhai et al. |
| 2003/0176421 | A1 | 9/2003 | Watson et al. |
| 2003/0225128 | A1 | 12/2003 | Bi et al. |
| 2003/0232013 | A1 | 12/2003 | Siechman et al. |
| 2003/0232838 | A1 | 12/2003 | Vidal Juan et al. |
| 2004/0087599 | A1 | 5/2004 | Campbell et al. |
| 2004/0121961 | A1 | 6/2004 | Masferrer |
| 2004/0152868 | A1 | 8/2004 | Larsen et al. |
| 2004/0258687 | A1 | 12/2004 | Waldman et al. |
| 2004/0266989 | A1 | 12/2004 | Currie |
| 2005/0032684 | A1 | 2/2005 | Cetin et al. |
| 2005/0113358 | A1 | 5/2005 | Bi et al. |
| 2005/0192279 | A1 | 9/2005 | Barbay et al. |
| 2005/0209232 | A1 | 9/2005 | Barbay et al. |
| 2006/0094658 | A1 | 5/2006 | Currie et al. |
| 2007/0010450 | A1 | 1/2007 | Currie et al. |
| 2007/0117843 | A1 | 5/2007 | Bi et al. |
| 2007/0155775 | A1 | 7/2007 | Bi et al. |
| 2007/0155788 | A1 | 7/2007 | Bi et al. |
| 2008/0009498 | A1 | 1/2008 | Garvey et al. |
| 2009/0041675 | A1 | 2/2009 | Trifilieff |
| 2012/0108525 | A1 | 5/2012 | Currie et al. |

FOREIGN PATENT DOCUMENTS

| | | |
|---|---|---|
| WO | WO0125266 | 4/2001 |
| WO | WO0187888 | 11/2001 |
| WO | WO0238563 | 5/2002 |
| WO | WO02078683 | 10/2002 |
| WO | WO02098912 | 12/2002 |
| WO | WO02062369 | 8/2003 |
| WO | WO03072125 | 9/2003 |
| WO | WO2004071436 | 2/2004 |
| WO | WO02079235 | 6/2004 |
| WO | WO2004069165 | 8/2004 |
| WO | WO2006001931 | 1/2006 |

OTHER PUBLICATIONS

Camilleri, "Management of the Irritable Bowel Syndrome" Gastroenterology, 120:652-668, 2001.

Carrithers et al., "Guanylin and uroguanylin induce natriuresis in mice lacking guanylyl cyclase-C receptor." Kidney Intel. 65:40-53, 2004.

Carrithers et al., "Renal effects of uroguanylin and guanylin in vivo." Brazilian J. of Med. and Biol. Res. 32: 1337-1344, (1999).

Chan et al., "Amino Acid Sequence of Heat-stable Enterotoxin Produced by *Escherichia coil* Pathogenic for Man." The Journal of Biological Chemistry, 256(15): 7744-7746, 1981.

Degerman, et al., "Structure, localization, and regulation of cGMP-inhibited phosphodiesterase (PDE3)." J. Biol. Chem., 272(11): 6823-6826, 1997.

De Rosalmeida et al., "Sildenafil, a phosphodiesterase-5 inhibitor, delays gastric emptying and gastrointestinal transit of liquid in awake rats" Dig. Diseases and Sci. 48(10): 2064-2068, 2003.

Drossman, D.A., "The functional gastrointestinal disorders and the Rome II process" Gut 45: Supplement II: pp. 111-113, 1999.

Drossman, D.A., "Psychosocial aspects of the functional gastrointestinal disorders." Gut 45: Supplement II: 1125-1130, 1999.

Drossman et al., "U.S. Householder Survey of Functional Gastro-intestinal Disorders." Digestive Diseases and Sciences. 38(9): 1569-1580, 1993.

Elitsur et al., "The proximal convoluted tubule is a target for the uroguanylin-regulated natriuretic response." J. Pediatr. Gastroenterol. Nutr. 43:S74-81, 2006.

Fonteles et al., "Natriuretic and kaliuretic activities of guanylin and uroguanylin in the isolated perfused rat kidney." Am. J. Physiol., 275:F191-197, 1998.

Forte et al., "Lymphoguanylin: Cloning and Characterization of a Unique Member of the Guanylin Peptide Family." Endocrinology, 40(4): 1800-1806, 1999.

Forte et al., "Guanylin peptides: renal actions mediated by cyclic GMP." Am. J. Physiol. Renal Physiol. 278:180-191, 2000.

Forte et al., "Salt and water homeostasis: uroguanylin is a circulating peptide hormone with natriuretic activity." Amer. J. of Kidney Diseases 28(2):296-304, 1996.

Francis et al., "Cyclic Nucleotide Phosphodiesterases: Relating Structure and Function" Prog. in Nucl. Acid Res. & Mol. Biol. 65:1, 2001.

Fritz et al., "Stimulation of the nitric oxide-guanosine 3',5'-cyclic monophosphate pathway by sildenafil: effect on rectal muscle tone, distensibility, and perception in health and in irritable bowel syndrome" Am. J. of Gastroint. 98 (10):2253-2260, 2003.

Giannella, "*Escherichia coli* heat-stable enterotoxins, guanylins, and their receptors: What are they and what do they do?" The Journal of Laboratory and Clinical Medicine, 125(2): 173-181, 1995.

Gibson, "Phosphodiesterase 5 inhibitors and nitrergic transmission-from zaprinast to sildenafil." Eur. J. Pharmacol., 411: 1-110, 2001.

Greenberg et al., "Comparison of effects of uroguanylin, guanylin, and *Escherichia coli* heat-stable enterotoxin STa in mouse intestine and kidney: evidence that uroguanylin is an intestinal natriuretic hormone." J. of Investig. Med. 45 (5):276-283, 1997.

Gualillo et al., "Ghrelin, a widespread hormone: insights into molecular and cellular regulation of its expression and mechanism of action." FEBS Letters, 552:105-109, 2003.

Guarino et al., "Citrobacter freundii produces an 18-amino-acid heat-stable enterotoxin identical to the 18-amino-acid *Escherichia coli* heat-stable enterotoxin (ST la)." Infection and Immunity, 57(2): 649-652, 1989.

Huang et al., "Nucleotide sequence of a gene encoding the novel Yersinia enterocolitica heat-stable enterotoxin that includes a pro-region-like sequence in its mature toxin molecule." Microbial Pathogenesis, 22(2):89-97, 1997.

Izzo et al., "Nitric oxide-donating compounds and cyclic GMP depress the spontaneous contractile activity of the isolated rabbit jejunum." Pharmacol., 53: 109-113, 1996.

Jain et al., "Sildenafil-induced peripheral analgesia and activation of the nitric oxide-cyclic GMP pathway." Brain Research, 909:170-178, 2001.

Kikuchi et al., "Role of uroguanylin, a Peptide with natriuretic activity, in rats with experimental nephrotic syndrome." J. Amer. Soc. Nephrol. 16:392-397, 2005.

Kim et al., "Changes in ghrelin and ghrelin receptor expression according to feeding status." Neuroreport, 14(10): 1317-1320, 2003.

Kokot et al., "Guanylins—are they of nephrological relevance?" Nephron 84:201-205, 2000.

(56) References Cited

OTHER PUBLICATIONS

Kroening et al., "Guanosine 3',5'-cyclic monophosphate: a tapeworm-secreted signal molecule communicating with the rat host's small intestine." J.Parasitol. 89(6): 1136-1141, 2003.

Kuhn et al., "The circulating bioactive form of human guanylin is a high molecular weight peptide (10.3 kDa)." FEBS Letters, 318 (2): 205-209, 1993.

London et al., "Structure and activity of OK-GC: a kidney receptor guanylate cyclase activated by guanylin peptides." Am. J. Physiol. Renal Physiol. 276: 882-891, 1999.

Lorenz et al., "Uroguanylin knockout mice have increased blood pressure and impaired natriuretic response to enteral NaCl load." J. of Clinical Invest. 112(8): 1244-1254, 2003.

Marks, "Irritable Bowel Syndrome (IBS)" Accessed at <<http://vvw.medicinenet.com/irritable_bowl_syndrome/article.htm>>, Mar. 13, 2007, 13 pages.

Moreland, et al., "Sildenafil, a novel inhibitor of phosphodiesterase type 5 in human corpus cavernosum smooth muscle cells." Life Sciences, 62(20): PL 309-318, 1998.

Moseley et al., "Isolation and nucleotide sequence determination of a gene encoding a heat-stable enterotoxin of E. coli." Infection and Immunity, 39(3): 1167-1174, 1983.

Nzegwu et al., "Luminal capsaicin inhibits fluid secretion induced by exterotoxin E. coli Sta, but not by carbachol, in vivo in rat small and large intestines." Experimental Physiology, 81(2): 313-315, 1996.

Pap et al., "Beneficial effect of Drotaverine in Irritable Bowel Syndrome." Gastroenterology 114(4): G3359, 1998.

Patient Summary of Information about Viagra (sildenafil citrate) tablets; Pfizer Labs—Division of Pfizer Inc., NY NY 10017, Jan. 2010.

Pusztai, et al., "Phase I and II study of exisulind in combination with capecitabine in patients with metastatic breast cancer." J. Clin. Oncol., 21(18): 3454-3461, 2003.

Qian et al., "Expression of GG-C, a receptor-guanylate cyclase, and its endogenous ligands uroguanylin and guanylin along the rostrocaudal axis of the intestine." Endocrinology 141 (9): 3210-3224, 2000.

Ringel et al., "Irritable Bowel Syndrome." Annual Review of Medicine, 52: 319-338, 2001.

Rolfe et al., "Enterotoxin Escherichia coli STa activates a nitric oxide-dependent myenteric plexus secretory reflex in the rat ileum." The Journal of Physiology, 475(3): 531-537, 1994.

Rolfe et al., "Vagotomy inhibits the jejunal fluid secretion activated by luminal ilea Escherichia coli STa in the rat in vivo." Gut, 44:615-619, 1999.

Rudinger, "Characteristics of the amino acids as components of a peptide hormone sequence." In: Peptide Hormones, JA Parsons, Ed. pp. 1-7, 1976.

Santos-Neto et al., "Guanylin and its lysine-containing analogue in the isolated perfused rat kidney." Pharmacol. & Toxicol., 92: 114-120, 2003.

Sauvage et al., "Precursor structure, expression, and tissue distribution of human guanylin" Proc. Nat. Acad. of Sci. 89(19): 9089-9093, 1992.

Schulz et al., "Side chain contributions to the interconversion of the topological isomers of guanylin-like peptides" J. Pept. Sci. 11(6): 319-330, 2005.

Shailubhai, K., "Therapeutic Applications of Guanylate Cyclase-C Receptor Agonists", Current Opinion in Drug Discovery and Development, 5(2):261-268, Mar. 2002.

Sindic et al., "Cellular effects of guanylin and uroguanylin." J. Amer. Soc. Nephrol. 17: 607-616, 2006.

Sindic et al., "Guanylin and uroguanylin regulate electrolyte transport in isolated human cortical collecting ducts." Kidney Int. 67:1420-1427, 2005.

Sindic et al., "Mechanisms of actions of guanylin peptides in the kidney." Eur. J. Physiol. 450: 283-291, 2005.

Skelton et al., "Determination of the solution structure of the peptide hormone guanylin: observation of a novel form of topological stereoisomerism." Biochemistry 33(46): 13581-13592, 1994.

Smith et al., "Diagnosis and Treatment of Chronic Gastroparesis and Chronic Intestinal Pseudo-obstruction." Gastroenterol. Clin. N. Amer. 32:619-658, 2003.

So et al., "Nucleotide sequence of the bacterial transposon Tn1681 encoding a heat-stable (ST) toxin and its identification in enterotoxigenic Escherichia coli strains." Proceedings of the National Academy of Sciences of the U.S.A. 77(7)[Part 2: Biological Sciences]: 4011-4015, 1980.

Soares et al., "Dibutyryl-cyclic GMP induces peripheral antinociception via activation of ATP-sensitive K+ channels in the RAT PGE2-induced hyperalgesic paw." British Journal of Pharmacology, 134:127-131, 2001.

Stroh, M. "New hormone may lift Montezuma's vendetta." Science News 142, No. 1: 5, 1992.

Suttorp, et al., "Role of phosphodiesterases in the regulation of endothelial permeability in vitro." J. Clin. Invest., 91(4): 1421-1428, 1993.

Swenson et al., "The guanylin/STa receptor is expressed in crypts and apical epithelium throughout the mouse intestine." Bioch. & Biophys. Res. Comm. 225(3): 1009-1014, 1996.

Takao et al., "Amino acid sequence of heat-stable enterotoxin produced by Vibrio cholerae non-01." FEBS, 193(2): 250-254, 1985.

Takao et al., "Isolation, primary structure and synthesis of heat-stable enterotoxin produced by Yersinia enterocolitica." European Journal of Biochemistry, 152(1): 199-206, 1985.

Talley et al., "Irritable Bowel Syndrome in a Community: Symptom Subgroups, Risk." American Journal of Epidemiology, 142(1): 76-83, 1995.

Vaandrager et al., "Structure and function of the heat-stable enterotoxin receptor/guanylyl cyclase C." Molecular and Cellular Biochemistry, 230(1-2): 73-83, 2002.

Wang et al., "Effects of uroguanylin, an intestinal natriuretic peptide, on tubuloglomerular feedback." Hypertens. Res. 26(7): 577-582, 2003.

Wiegand et al., "Human guanylin: cDNA isolation, structure, and activity." FEBS Letters, 311:150-154, 1992.

Yuge et al., "A novel guanylin family (guanylin, uroguanylin, and renoguanylin) in eels: possible osmoregulatory hormones in intestine and kidney." Journal of Biological Chemistry. 278(25): 22726-22733 2003.

GenBank Accession No. QHECIB; GI:69638; Aimoto et al., Jun. 18, 1999.

GenBank Accession No. P01559; GI:123711; So et al., Oct. 25, 2004.

GenBank Accession No. AAA24653; GI:147878; Sekizaki et al., Apr. 26, 1993.

GenBank Accession No. P01560; GI:123707; Chan et al., Jun. 15, 2004.

GenBank Accession No. AAA27561; GI:295439; Ogawa et al., Jun. 12, 1993.

GenBank Accession No. P04429; GI:123712; Ogawa et al., Jun. 15, 2004.

GenBank Accession No. S34671; GI:421286; Rossolini et al., Apr. 12, 1995.

GenBank Accession No. CAA52209; GI:395161; Guglielmetti et al., Jul. 27, 1995.

GenBank Accession No. A54534; GI:628844; Arita et al., May 3, 1996.

GenBank Accession No. AAL02159; GI:15592919; Teixeira et al., Sep. 13, 2001.

GenBank Accession No. AAA18472; GI;487395; Mikulskis et al., May 26, 1994.

GenBank Accession No. S25659; GI:282047; Takao et al., Oct. 15, 1999.

GenBank Accession No. P74977; GI:3913874; Ramamurthy et al., Jun. 15, 2004.

GenBank Accession No. BAA23656; GI:2662339; Huang et al., Feb. 13, 1999.

(56) References Cited

OTHER PUBLICATIONS

GenBank Accession No. P31518; GI:399947; Ibrahim et al., Mar. 15, 2004.

GenBank Accession No. P07965; GI:3915589; Stieglitz et al., Jun. 15, 2004.

Binder et al. "Are things looking up for the treatment of gastroparesis? Sildenafil in animal models of diabetic gastropathy." Gastroenterology, 120(2): 576-577, 2001.

Lauber et al., "Solution structure of human proguanylin. The role of a hormone prosequence" J. Biol. Chem., 278 (26): 24118-24124, 2003.

Lazaro-Ibanez et al., "Participation of the nitric oxide-cyclic GMP-ATP-sensitive K+ channel pathway in the antinociceptive action of ketorolac." European Journal of Pharmacology, 426: 39-44, 2001.

Pro Gly Thr Cys Gly Glu Ile Cys Ala Tyr Ala Ala Cys Thr Gly Cys

Human Guanylin (SEQ ID NO:19)

| | | | | | | | | | | | | | | | | |
|---|---|---|---|---|---|---|---|---|---|---|---|---|---|---|---|---|
| --- | Gly | Thr | Cys | Gly | Glu | Ile | Cys | Ala | Tyr | Ala | Ala | Cys | Thr | Gly | Cys | (SEQ ID NO: 96) |
| --- | --- | Thr | Cys | Gly | Glu | Ile | Cys | Ala | Tyr | Ala | Ala | Cys | Thr | Gly | Cys | (SEQ ID NO: 97) |
| --- | --- | --- | Cys | Gly | Glu | Ile | Cys | Ala | Tyr | Ala | Ala | Cys | Thr | Gly | Cys | (SEQ ID NO: 98) |
| --- | --- | --- | Cys | --- | Glu | Ile | Cys | Ala | Tyr | Ala | Ala | Cys | Thr | Gly | Cys | (SEQ ID NO: 99) |
| --- | --- | --- | Cys | Gly | --- | Ile | Cys | Ala | Tyr | Ala | Ala | Cys | Thr | Gly | Cys | (SEQ ID NO: 100) |
| --- | --- | --- | Cys | Gly | Glu | --- | Cys | Ala | Tyr | Ala | Ala | Cys | Thr | Gly | Cys | (SEQ ID NO: 101) |
| --- | --- | --- | Cys | Gly | Glu | Ile | Cys | --- | Tyr | Ala | Ala | Cys | Thr | Gly | Cys | (SEQ ID NO: 102) |
| --- | --- | --- | Cys | Gly | Glu | Ile | Cys | Ala | --- | Ala | Ala | Cys | Thr | Gly | Cys | (SEQ ID NO: 103) |
| --- | --- | --- | Cys | Gly | Glu | Ile | Cys | Ala | Tyr | --- | Ala | Cys | Thr | Gly | Cys | (SEQ ID NO: 104) |
| --- | --- | --- | Cys | Gly | Glu | Ile | Cys | Ala | Tyr | Ala | --- | Cys | Thr | Gly | Cys | (SEQ ID NO: 105) |
| --- | --- | --- | Cys | Gly | Glu | Ile | Cys | Ala | Tyr | Ala | Ala | Cys | --- | Gly | Cys | (SEQ ID NO: 106) |
| --- | --- | --- | Cys | Gly | Glu | Ile | Cys | Ala | Tyr | Ala | Ala | Cys | Thr | --- | Cys | (SEQ ID NO: 107) |
| --- | --- | Thr | Cys | --- | Glu | Ile | Cys | Ala | Tyr | Ala | Ala | Cys | Thr | Gly | Cys | (SEQ ID NO: 108) |
| --- | --- | Thr | Cys | --- | --- | Ile | Cys | Ala | Tyr | Ala | Ala | Cys | Thr | Gly | Cys | (SEQ ID NO: 109) |
| --- | --- | Thr | Cys | --- | Glu | --- | Cys | Ala | Tyr | Ala | Ala | Cys | Thr | Gly | Cys | (SEQ ID NO: 110) |
| --- | --- | Thr | Cys | --- | Glu | Ile | Cys | --- | Tyr | Ala | Ala | Cys | Thr | Gly | Cys | (SEQ ID NO: 111) |
| --- | --- | Thr | Cys | --- | Glu | Ile | Cys | Ala | --- | Ala | Ala | Cys | Thr | Gly | Cys | (SEQ ID NO: 112) |
| --- | --- | Thr | Cys | --- | Glu | Ile | Cys | Ala | Tyr | --- | Ala | Cys | Thr | Gly | Cys | (SEQ ID NO: 113) |
| --- | --- | Thr | Cys | --- | Glu | Ile | Cys | Ala | Tyr | Ala | --- | Cys | Thr | Gly | Cys | (SEQ ID NO: 114) |
| --- | --- | Thr | Cys | --- | Glu | Ile | Cys | Ala | Tyr | Ala | Ala | Cys | --- | Gly | Cys | (SEQ ID NO: 115) |
| --- | --- | Thr | Cys | --- | Glu | Ile | Cys | Ala | Tyr | Ala | Ala | Cys | Thr | --- | Cys | (SEQ ID NO: 116) |
| --- | --- | Thr | Cys | Gly | --- | Ile | Cys | Ala | Tyr | Ala | Ala | Cys | Thr | Gly | Cys | (SEQ ID NO: 117) |
| --- | --- | Thr | Cys | Gly | --- | --- | Cys | Ala | Tyr | Ala | Ala | Cys | Thr | Gly | Cys | (SEQ ID NO: 118) |
| --- | --- | Thr | Cys | Gly | --- | Ile | Cys | --- | Tyr | Ala | Ala | Cys | Thr | Gly | Cys | (SEQ ID NO: 119) |
| --- | --- | Thr | Cys | Gly | --- | Ile | Cys | Ala | --- | Ala | Ala | Cys | Thr | Gly | Cys | (SEQ ID NO: 120) |
| --- | --- | Thr | Cys | Gly | --- | Ile | Cys | Ala | Tyr | --- | Ala | Cys | Thr | Gly | Cys | (SEQ ID NO: 121) |
| --- | --- | Thr | Cys | Gly | --- | Ile | Cys | Ala | Tyr | Ala | --- | Cys | Thr | Gly | Cys | (SEQ ID NO: 122) |
| --- | --- | Thr | Cys | Gly | --- | Ile | Cys | Ala | Tyr | Ala | Ala | Cys | --- | Gly | Cys | (SEQ ID NO: 123) |
| --- | --- | Thr | Cys | Gly | --- | Ile | Cys | Ala | Tyr | Ala | Ala | Cys | Thr | --- | Cys | (SEQ ID NO: 124) |
| --- | --- | Thr | Cys | Gly | Glu | --- | Cys | Ala | Tyr | Ala | Ala | Cys | Thr | Gly | Cys | (SEQ ID NO: 125) |
| --- | --- | Thr | Cys | Gly | Glu | --- | Cys | --- | Tyr | Ala | Ala | Cys | Thr | Gly | Cys | (SEQ ID NO: 126) |
| --- | --- | Thr | Cys | Gly | Glu | --- | Cys | Ala | --- | Ala | Ala | Cys | Thr | Gly | Cys | (SEQ ID NO: 127) |
| --- | --- | Thr | Cys | Gly | Glu | --- | Cys | Ala | Tyr | --- | Ala | Cys | Thr | Gly | Cys | (SEQ ID NO: 128) |
| --- | --- | Thr | Cys | Gly | Glu | --- | Cys | Ala | Tyr | Ala | --- | Cys | Thr | Gly | Cys | (SEQ ID NO: 129) |
| --- | --- | Thr | Cys | Gly | Glu | --- | Cys | Ala | Tyr | Ala | Ala | Cys | --- | Gly | Cys | (SEQ ID NO: 130) |
| --- | --- | Thr | Cys | Gly | Glu | --- | Cys | Ala | Tyr | Ala | Ala | Cys | Thr | --- | Cys | (SEQ ID NO: 131) |
| --- | --- | Thr | Cys | Gly | Glu | Ile | Cys | --- | Tyr | Ala | Ala | Cys | Thr | Gly | Cys | (SEQ ID NO: 132) |
| --- | --- | Thr | Cys | Gly | Glu | Ile | Cys | --- | --- | Ala | Ala | Cys | Thr | Gly | Cys | (SEQ ID NO: 133) |
| --- | --- | Thr | Cys | Gly | Glu | Ile | Cys | --- | Tyr | --- | Ala | Cys | Thr | Gly | Cys | (SEQ ID NO: 134) |
| --- | --- | Thr | Cys | Gly | Glu | Ile | Cys | --- | Tyr | Ala | --- | Cys | Thr | Gly | Cys | (SEQ ID NO: 135) |
| --- | --- | Thr | Cys | Gly | Glu | Ile | Cys | --- | Tyr | Ala | Ala | Cys | --- | Gly | Cys | (SEQ ID NO: 136) |
| --- | --- | Thr | Cys | Gly | Glu | Ile | Cys | --- | Tyr | Ala | Ala | Cys | Thr | --- | Cys | (SEQ ID NO: 137) |
| --- | --- | Thr | Cys | Gly | Glu | Ile | Cys | Ala | --- | Ala | Ala | Cys | Thr | Gly | Cys | (SEQ ID NO: 138) |
| --- | --- | Thr | Cys | Gly | Glu | Ile | Cys | Ala | --- | --- | Ala | Cys | Thr | Gly | Cys | (SEQ ID NO: 139) |

FIG. 1A

| | | | | | | | | | | | | |
|---|---|---|---|---|---|---|---|---|---|---|---|---|
| --- | --- | Thr | Cys | Gly | Glu | Ile | Cys | Ala | --- | Ala | --- | Cys | Thr | Gly | Cys | (SEQ ID NO: 140) |
| --- | --- | Thr | Cys | Gly | Glu | Ile | Cys | Ala | --- | Ala | Ala | Cys | --- | Gly | Cys | (SEQ ID NO: 141) |
| --- | --- | Thr | Cys | Gly | Glu | Ile | Cys | Ala | --- | Ala | Ala | Cys | Thr | --- | Cys | (SEQ ID NO: 142) |
| --- | --- | Thr | Cys | Gly | Glu | Ile | Cys | Ala | Tyr | --- | Ala | Cys | Thr | Gly | Cys | (SEQ ID NO: 143) |
| --- | --- | Thr | Cys | Gly | Glu | Ile | Cys | Ala | Tyr | --- | --- | Cys | Thr | Gly | Cys | (SEQ ID NO: 144) |
| --- | --- | Thr | Cys | Gly | Glu | Ile | Cys | Ala | Tyr | --- | Ala | Cys | --- | Gly | Cys | (SEQ ID NO: 145) |
| --- | --- | Thr | Cys | Gly | Glu | Ile | Cys | Ala | Tyr | --- | Ala | Cys | Thr | --- | Cys | (SEQ ID NO: 146) |
| --- | --- | Thr | Cys | Gly | Glu | Ile | Cys | Ala | Tyr | Ala | --- | Cys | Thr | Gly | Cys | (SEQ ID NO: 147) |
| --- | --- | Thr | Cys | Gly | Glu | Ile | Cys | Ala | Tyr | Ala | --- | Cys | --- | Gly | Cys | (SEQ ID NO: 148) |
| --- | --- | Thr | Cys | Gly | Glu | Ile | Cys | Ala | Tyr | Ala | --- | Cys | Thr | --- | Cys | (SEQ ID NO: 149) |
| --- | --- | Thr | Cys | Gly | Glu | Ile | Cys | Ala | Tyr | Ala | Ala | Cys | --- | Gly | Cys | (SEQ ID NO: 150) |
| --- | --- | Thr | Cys | Gly | Glu | Ile | Cys | Ala | Tyr | Ala | Ala | Cys | --- | --- | Cys | (SEQ ID NO: 151) |
| --- | --- | Thr | Cys | Gly | Glu | Ile | Cys | Ala | Tyr | Ala | Ala | Cys | Thr | --- | Cys | (SEQ ID NO: 152) |
| --- | Gly | --- | Cys | Gly | Glu | Ile | Cys | Ala | Tyr | Ala | Ala | Cys | Thr | Gly | Cys | (SEQ ID NO: 153) |
| --- | Gly | --- | Cys | --- | Glu | Ile | Cys | Ala | Tyr | Ala | Ala | Cys | Thr | Gly | Cys | (SEQ ID NO: 154) |
| --- | Gly | --- | Cys | --- | --- | Ile | Cys | Ala | Tyr | Ala | Ala | Cys | Thr | Gly | Cys | (SEQ ID NO: 155) |
| --- | Gly | --- | Cys | --- | Glu | --- | Cys | Ala | Tyr | Ala | Ala | Cys | Thr | Gly | Cys | (SEQ ID NO: 156) |
| --- | Gly | --- | Cys | --- | Glu | Ile | Cys | --- | Tyr | Ala | Ala | Cys | Thr | Gly | Cys | (SEQ ID NO: 157) |
| --- | Gly | --- | Cys | --- | Glu | Ile | Cys | Ala | --- | Ala | Ala | Cys | Thr | Gly | Cys | (SEQ ID NO: 158) |
| --- | Gly | --- | Cys | --- | Glu | Ile | Cys | Ala | Tyr | --- | Ala | Cys | Thr | Gly | Cys | (SEQ ID NO: 159) |
| --- | Gly | --- | Cys | --- | Glu | Ile | Cys | Ala | Tyr | Ala | --- | Cys | Thr | Gly | Cys | (SEQ ID NO: 160) |
| --- | Gly | --- | Cys | --- | Glu | Ile | Cys | Ala | Tyr | Ala | Ala | Cys | --- | Gly | Cys | (SEQ ID NO: 161) |
| --- | Gly | --- | Cys | --- | Glu | Ile | Cys | Ala | Tyr | Ala | Ala | Cys | Thr | --- | Cys | (SEQ ID NO: 162) |
| --- | Gly | --- | Cys | Gly | --- | Ile | Cys | Ala | Tyr | Ala | Ala | Cys | Thr | Gly | Cys | (SEQ ID NO: 163) |
| --- | Gly | --- | Cys | Gly | --- | --- | Cys | Ala | Tyr | Ala | Ala | Cys | Thr | Gly | Cys | (SEQ ID NO: 164) |
| --- | Gly | --- | Cys | Gly | --- | Ile | Cys | --- | Tyr | Ala | Ala | Cys | Thr | Gly | Cys | (SEQ ID NO: 165) |
| --- | Gly | --- | Cys | Gly | --- | Ile | Cys | Ala | --- | Ala | Ala | Cys | Thr | Gly | Cys | (SEQ ID NO: 166) |
| --- | Gly | --- | Cys | Gly | --- | Ile | Cys | Ala | Tyr | --- | Ala | Cys | Thr | Gly | Cys | (SEQ ID NO: 167) |
| --- | Gly | --- | Cys | Gly | --- | Ile | Cys | Ala | Tyr | Ala | --- | Cys | Thr | Gly | Cys | (SEQ ID NO: 168) |
| --- | Gly | --- | Cys | Gly | --- | Ile | Cys | Ala | Tyr | Ala | Ala | Cys | --- | Gly | Cys | (SEQ ID NO: 169) |
| --- | Gly | --- | Cys | Gly | --- | Ile | Cys | Ala | Tyr | Ala | Ala | Cys | Thr | --- | Cys | (SEQ ID NO: 170) |
| --- | Gly | --- | Cys | Gly | Glu | --- | Cys | Ala | Tyr | Ala | Ala | Cys | Thr | Gly | Cys | (SEQ ID NO: 171) |
| --- | Gly | --- | Cys | Gly | Glu | --- | Cys | --- | Tyr | Ala | Ala | Cys | Thr | Gly | Cys | (SEQ ID NO: 172) |
| --- | Gly | --- | Cys | Gly | Glu | --- | Cys | Ala | --- | Ala | Ala | Cys | Thr | Gly | Cys | (SEQ ID NO: 173) |
| --- | Gly | --- | Cys | Gly | Glu | --- | Cys | Ala | Tyr | --- | Ala | Cys | Thr | Gly | Cys | (SEQ ID NO: 174) |
| --- | Gly | --- | Cys | Gly | Glu | --- | Cys | Ala | Tyr | Ala | --- | Cys | Thr | Gly | Cys | (SEQ ID NO: 175) |
| --- | Gly | --- | Cys | Gly | Glu | --- | Cys | Ala | Tyr | Ala | Ala | Cys | --- | Gly | Cys | (SEQ ID NO: 176) |
| --- | Gly | --- | Cys | Gly | Glu | --- | Cys | Ala | Tyr | Ala | Ala | Cys | Thr | --- | Cys | (SEQ ID NO: 177) |
| --- | Gly | --- | Cys | Gly | Glu | Ile | Cys | --- | Tyr | Ala | Ala | Cys | Thr | Gly | Cys | (SEQ ID NO: 178) |
| --- | Gly | --- | Cys | Gly | Glu | Ile | Cys | --- | --- | Ala | Ala | Cys | Thr | Gly | Cys | (SEQ ID NO: 179) |
| --- | Gly | --- | Cys | Gly | Glu | Ile | Cys | --- | Tyr | --- | Ala | Cys | Thr | Gly | Cys | (SEQ ID NO: 180) |
| --- | Gly | --- | Cys | Gly | Glu | Ile | Cys | --- | Tyr | Ala | --- | Cys | Thr | Gly | Cys | (SEQ ID NO: 181) |
| --- | Gly | --- | Cys | Gly | Glu | Ile | Cys | --- | Tyr | Ala | Ala | Cys | --- | Gly | Cys | (SEQ ID NO: 182) |
| --- | Gly | --- | Cys | Gly | Glu | Ile | Cys | --- | Tyr | Ala | Ala | Cys | Thr | --- | Cys | (SEQ ID NO: 183) |
| --- | Gly | --- | Cys | Gly | Glu | Ile | Cys | Ala | --- | Ala | Ala | Cys | Thr | Gly | Cys | (SEQ ID NO: 184) |
| --- | Gly | --- | Cys | Gly | Glu | Ile | Cys | Ala | --- | --- | Ala | Cys | Thr | Gly | Cys | (SEQ ID NO: 185) |
| --- | Gly | --- | Cys | Gly | Glu | Ile | Cys | Ala | --- | Ala | --- | Cys | Thr | Gly | Cys | (SEQ ID NO: 186) |

FIG. 1B

```
--- Gly --- Cys Gly Glu Ile Cys Ala --- Ala Ala Cys --- Gly Cys  (SEQ ID NO: 187)
--- Gly --- Cys Gly Glu Ile Cys Ala --- Ala Ala Cys Thr --- Cys  (SEQ ID NO: 188)
--- Gly --- Cys Gly Glu Ile Cys Ala Tyr --- Ala Cys Thr Gly Cys  (SEQ ID NO: 189)
--- Gly --- Cys Gly Glu Ile Cys Ala Tyr --- --- Cys Thr Gly Cys  (SEQ ID NO: 190)
--- Gly --- Cys Gly Glu Ile Cys Ala Tyr --- Ala Cys --- Gly Cys  (SEQ ID NO: 191)
--- Gly --- Cys Gly Glu Ile Cys Ala Tyr --- Ala Cys Thr --- Cys  (SEQ ID NO: 192)
--- Gly --- Cys Gly Glu Ile Cys Ala Tyr Ala --- Cys Thr Gly Cys  (SEQ ID NO: 193)
--- Gly --- Cys Gly Glu Ile Cys Ala Tyr Ala --- Cys --- Gly Cys  (SEQ ID NO: 194)
--- Gly --- Cys Gly Glu Ile Cys Ala Tyr Ala --- Cys Thr --- Cys  (SEQ ID NO: 195)
--- Gly --- Cys Gly Glu Ile Cys Ala Tyr Ala Ala Cys --- Gly Cys  (SEQ ID NO: 196)
--- Gly --- Cys Gly Glu Ile Cys Ala Tyr Ala Ala Cys --- --- Cys  (SEQ ID NO: 197)
--- Gly --- Cys Gly Glu Ile Cys Ala Tyr Ala Ala Cys Thr --- Cys  (SEQ ID NO: 198)
--- Gly Thr Cys --- Glu Ile Cys Ala Tyr Ala Ala Cys Thr Gly Cys  (SEQ ID NO: 199)
--- Gly Thr Cys --- --- Ile Cys Ala Tyr Ala Ala Cys Thr Gly Cys  (SEQ ID NO: 200)
--- Gly Thr Cys --- --- --- Cys Ala Tyr Ala Ala Cys Thr Gly Cys  (SEQ ID NO: 201)
--- Gly Thr Cys --- --- Ile Cys --- Tyr Ala Ala Cys Thr Gly Cys  (SEQ ID NO: 202)
--- Gly Thr Cys --- --- Ile Cys Ala --- Ala Ala Cys Thr Gly Cys  (SEQ ID NO: 203)
--- Gly Thr Cys --- --- Ile Cys Ala Tyr --- Ala Cys Thr Gly Cys  (SEQ ID NO: 204)
--- Gly Thr Cys --- --- Ile Cys Ala Tyr Ala --- Cys Thr Gly Cys  (SEQ ID NO: 205)
--- Gly Thr Cys --- --- Ile Cys Ala Tyr Ala Ala Cys --- Gly Cys  (SEQ ID NO: 206)
--- Gly Thr Cys --- --- Ile Cys Ala Tyr Ala Ala Cys Thr --- Cys  (SEQ ID NO: 207)
--- Gly Thr Cys --- Glu --- Cys Ala Tyr Ala Ala Cys Thr Gly Cys  (SEQ ID NO: 208)
--- Gly Thr Cys --- Glu --- Cys --- Tyr Ala Ala Cys Thr Gly Cys  (SEQ ID NO: 209)
--- Gly Thr Cys --- Glu --- Cys Ala --- Ala Ala Cys Thr Gly Cys  (SEQ ID NO: 210)
--- Gly Thr Cys --- Glu --- Cys Ala Tyr --- Ala Cys Thr Gly Cys  (SEQ ID NO: 211)
--- Gly Thr Cys --- Glu --- Cys Ala Tyr Ala --- Cys Thr Gly Cys  (SEQ ID NO: 212)
--- Gly Thr Cys --- Glu --- Cys Ala Tyr Ala Ala Cys --- Gly Cys  (SEQ ID NO: 213)
--- Gly Thr Cys --- Glu --- Cys Ala Tyr Ala Ala Cys Thr --- Cys  (SEQ ID NO: 214)
--- Gly Thr Cys --- Glu Ile Cys --- Tyr Ala Ala Cys Thr Gly Cys  (SEQ ID NO: 215)
--- Gly Thr Cys --- Glu Ile Cys --- --- Ala Ala Cys Thr Gly Cys  (SEQ ID NO: 216)
--- Gly Thr Cys --- Glu Ile Cys --- Tyr --- Ala Cys Thr Gly Cys  (SEQ ID NO: 217)
--- Gly Thr Cys --- Glu Ile Cys --- Tyr Ala --- Cys Thr Gly Cys  (SEQ ID NO: 218)
--- Gly Thr Cys --- Glu Ile Cys --- Tyr Ala Ala Cys --- Gly Cys  (SEQ ID NO: 219)
--- Gly Thr Cys --- Glu Ile Cys --- Tyr Ala Ala Cys Thr --- Cys  (SEQ ID NO: 220)
--- Gly Thr Cys --- Glu Ile Cys Ala --- Ala Ala Cys Thr Gly Cys  (SEQ ID NO: 221)
--- Gly Thr Cys --- Glu Ile Cys Ala --- --- Ala Cys Thr Gly Cys  (SEQ ID NO: 222)
--- Gly Thr Cys --- Glu Ile Cys Ala --- Ala --- Cys Thr Gly Cys  (SEQ ID NO: 223)
--- Gly Thr Cys --- Glu Ile Cys Ala --- Ala Ala Cys --- Gly Cys  (SEQ ID NO: 224)
--- Gly Thr Cys --- Glu Ile Cys Ala --- Ala Ala Cys Thr --- Cys  (SEQ ID NO: 225)
--- Gly Thr Cys --- Glu Ile Cys Ala Tyr --- Ala Cys Thr Gly Cys  (SEQ ID NO: 226)
--- Gly Thr Cys --- Glu Ile Cys Ala Tyr --- --- Cys Thr Gly Cys  (SEQ ID NO: 227)
--- Gly Thr Cys --- Glu Ile Cys Ala Tyr --- Ala Cys --- Gly Cys  (SEQ ID NO: 228)
--- Gly Thr Cys --- Glu Ile Cys Ala Tyr --- Ala Cys Thr --- Cys  (SEQ ID NO: 229)
--- Gly Thr Cys --- Glu Ile Cys Ala Tyr Ala --- Cys Thr Gly Cys  (SEQ ID NO: 230)
--- Gly Thr Cys --- Glu Ile Cys Ala Tyr Ala --- Cys --- Gly Cys  (SEQ ID NO: 231)
--- Gly Thr Cys --- Glu Ile Cys Ala Tyr Ala --- Cys Thr --- Cys  (SEQ ID NO: 232)
--- Gly Thr Cys --- Glu Ile Cys Ala Tyr Ala Ala Cys --- Gly Cys  (SEQ ID NO: 233)
```

FIG. 1C

| | | | | | | | | | | | | |
|---|---|---|---|---|---|---|---|---|---|---|---|---|
| --- | Gly | Thr | Cys | --- | Glu | Ile | Cys | Ala | Tyr | Ala | Ala | Cys | --- | --- | Cys | (SEQ ID NO: 234) |



```
--- Gly Thr Cys --- Glu Ile Cys Ala Tyr Ala Ala Cys --- --- Cys   (SEQ ID NO: 234)
--- Gly Thr Cys --- Glu Ile Cys Ala Tyr Ala Ala Cys Thr --- Cys   (SEQ ID NO: 235)
--- Gly Thr Cys Gly --- Ile Cys Ala Tyr Ala Ala Cys Thr Gly Cys   (SEQ ID NO: 236)
--- Gly Thr Cys Gly --- --- Cys Ala Tyr Ala Ala Cys Thr Gly Cys   (SEQ ID NO: 237)
--- Gly Thr Cys Gly --- --- Cys --- Tyr Ala Ala Cys Thr Gly Cys   (SEQ ID NO: 238)
--- Gly Thr Cys Gly --- --- Cys Ala --- Ala Ala Cys Thr Gly Cys   (SEQ ID NO: 239)
--- Gly Thr Cys Gly --- --- Cys Ala Tyr --- Ala Cys Thr Gly Cys   (SEQ ID NO: 240)
--- Gly Thr Cys Gly --- --- Cys Ala Tyr Ala --- Cys Thr Gly Cys   (SEQ ID NO: 241)
--- Gly Thr Cys Gly --- --- Cys Ala Tyr Ala Ala Cys --- Gly Cys   (SEQ ID NO: 242)
--- Gly Thr Cys Gly --- --- Cys Ala Tyr Ala Ala Cys Thr --- Cys   (SEQ ID NO: 243)
--- Gly Thr Cys Gly --- Ile Cys --- Tyr Ala Ala Cys Thr Gly Cys   (SEQ ID NO: 244)
--- Gly Thr Cys Gly --- Ile Cys --- --- Ala Ala Cys Thr Gly Cys   (SEQ ID NO: 245)
--- Gly Thr Cys Gly --- Ile Cys --- Tyr --- Ala Cys Thr Gly Cys   (SEQ ID NO: 246)
--- Gly Thr Cys Gly --- Ile Cys --- Tyr Ala --- Cys Thr Gly Cys   (SEQ ID NO: 247)
--- Gly Thr Cys Gly --- Ile Cys --- Tyr Ala Ala Cys --- Gly Cys   (SEQ ID NO: 248)
--- Gly Thr Cys Gly --- Ile Cys --- Tyr Ala Ala Cys Thr --- Cys   (SEQ ID NO: 249)
--- Gly Thr Cys Gly --- Ile Cys Ala --- Ala Ala Cys Thr Gly Cys   (SEQ ID NO: 250)
--- Gly Thr Cys Gly --- Ile Cys Ala --- --- Ala Cys Thr Gly Cys   (SEQ ID NO: 251)
--- Gly Thr Cys Gly --- Ile Cys Ala --- Ala --- Cys Thr Gly Cys   (SEQ ID NO: 252)
--- Gly Thr Cys Gly --- Ile Cys Ala --- Ala Ala Cys --- Gly Cys   (SEQ ID NO: 253)
--- Gly Thr Cys Gly --- Ile Cys Ala --- Ala Ala Cys Thr --- Cys   (SEQ ID NO: 254)
--- Gly Thr Cys Gly --- Ile Cys Ala Tyr --- Ala Cys Thr Gly Cys   (SEQ ID NO: 255)
--- Gly Thr Cys Gly --- Ile Cys Ala Tyr --- --- Cys Thr Gly Cys   (SEQ ID NO: 256)
--- Gly Thr Cys Gly --- Ile Cys Ala Tyr --- Ala Cys --- Gly Cys   (SEQ ID NO: 257)
--- Gly Thr Cys Gly --- Ile Cys Ala Tyr --- Ala Cys Thr --- Cys   (SEQ ID NO: 258)
--- Gly Thr Cys Gly --- Ile Cys Ala Tyr Ala --- Cys Thr Gly Cys   (SEQ ID NO: 259)
--- Gly Thr Cys Gly --- Ile Cys Ala Tyr Ala --- Cys --- Gly Cys   (SEQ ID NO: 260)
--- Gly Thr Cys Gly --- Ile Cys Ala Tyr Ala --- Cys Thr --- Cys   (SEQ ID NO: 261)
--- Gly Thr Cys Gly --- Ile Cys Ala Tyr Ala Ala Cys --- Gly Cys   (SEQ ID NO: 262)
--- Gly Thr Cys Gly --- Ile Cys Ala Tyr Ala Ala Cys --- --- Cys   (SEQ ID NO: 263)
--- Gly Thr Cys Gly --- Ile Cys Ala Tyr Ala Ala Cys Thr --- Cys   (SEQ ID NO: 264)
--- Gly Thr Cys Gly Glu --- Cys Ala Tyr Ala Ala Cys Thr Gly Cys   (SEQ ID NO: 265)
--- Gly Thr Cys Gly Glu --- Cys --- Tyr Ala Ala Cys Thr Gly Cys   (SEQ ID NO: 266)
--- Gly Thr Cys Gly Glu --- Cys --- --- Ala Ala Cys Thr Gly Cys   (SEQ ID NO: 267)
--- Gly Thr Cys Gly Glu --- Cys --- Tyr --- Ala Cys Thr Gly Cys   (SEQ ID NO: 268)
--- Gly Thr Cys Gly Glu --- Cys --- Tyr Ala --- Cys Thr Gly Cys   (SEQ ID NO: 269)
--- Gly Thr Cys Gly Glu --- Cys --- Tyr Ala Ala Cys --- Gly Cys   (SEQ ID NO: 270)
--- Gly Thr Cys Gly Glu --- Cys --- Tyr Ala Ala Cys Thr --- Cys   (SEQ ID NO: 271)
--- Gly Thr Cys Gly Glu --- Cys Ala --- Ala Ala Cys Thr Gly Cys   (SEQ ID NO: 272)
--- Gly Thr Cys Gly Glu --- Cys Ala --- --- Ala Cys Thr Gly Cys   (SEQ ID NO: 273)
--- Gly Thr Cys Gly Glu --- Cys Ala --- Ala --- Cys Thr Gly Cys   (SEQ ID NO: 274)
--- Gly Thr Cys Gly Glu --- Cys Ala --- Ala Ala Cys --- Gly Cys   (SEQ ID NO: 275)
--- Gly Thr Cys Gly Glu --- Cys Ala --- Ala Ala Cys Thr --- Cys   (SEQ ID NO: 276)
--- Gly Thr Cys Gly Glu --- Cys Ala Tyr --- Ala Cys Thr Gly Cys   (SEQ ID NO: 277)
--- Gly Thr Cys Gly Glu --- Cys Ala Tyr --- --- Cys Thr Gly Cys   (SEQ ID NO: 278)
--- Gly Thr Cys Gly Glu --- Cys Ala Tyr --- Ala Cys --- Gly Cys   (SEQ ID NO: 279)
--- Gly Thr Cys Gly Glu --- Cys Ala Tyr --- Ala Cys Thr --- Cys   (SEQ ID NO: 280)
```

FIG. 1D

```
--- Gly Thr Cys Gly Glu --- Cys Ala Tyr Ala --- Cys Thr Gly Cys    (SEQ ID NO: 281)
--- Gly Thr Cys Gly Glu --- Cys Ala Tyr Ala --- Cys --- Gly Cys    (SEQ ID NO: 282)
--- Gly Thr Cys Gly Glu --- Cys Ala Tyr Ala --- Cys Thr --- Cys    (SEQ ID NO: 283)
--- Gly Thr Cys Gly Glu --- Cys Ala Tyr Ala Ala Cys --- Gly Cys    (SEQ ID NO: 284)
--- Gly Thr Cys Gly Glu --- Cys Ala Tyr Ala Ala Cys --- --- Cys    (SEQ ID NO: 285)
--- Gly Thr Cys Gly Glu --- Cys Ala Tyr Ala Ala Cys Thr --- Cys    (SEQ ID NO: 286)
--- Gly Thr Cys Gly Glu Ile Cys --- Tyr Ala Ala Cys Thr Gly Cys    (SEQ ID NO: 287)
--- Gly Thr Cys Gly Glu Ile Cys --- --- Ala Ala Cys Thr Gly Cys    (SEQ ID NO: 288)
--- Gly Thr Cys Gly Glu Ile Cys --- --- --- Ala Cys Thr Gly Cys    (SEQ ID NO: 289)
--- Gly Thr Cys Gly Glu Ile Cys --- --- Ala --- Cys Thr Gly Cys    (SEQ ID NO: 290)
--- Gly Thr Cys Gly Glu Ile Cys --- --- Ala Ala Cys --- Gly Cys    (SEQ ID NO: 291)
--- Gly Thr Cys Gly Glu Ile Cys --- --- Ala Ala Cys Thr --- Cys    (SEQ ID NO: 292)
--- Gly Thr Cys Gly Glu Ile Cys --- Tyr --- Ala Cys Thr Gly Cys    (SEQ ID NO: 293)
--- Gly Thr Cys Gly Glu Ile Cys --- Tyr --- --- Cys Thr Gly Cys    (SEQ ID NO: 294)
--- Gly Thr Cys Gly Glu Ile Cys --- Tyr --- Ala Cys --- Gly Cys    (SEQ ID NO: 295)
--- Gly Thr Cys Gly Glu Ile Cys --- Tyr --- Ala Cys Thr --- Cys    (SEQ ID NO: 296)
--- Gly Thr Cys Gly Glu Ile Cys --- Tyr Ala --- Cys Thr Gly Cys    (SEQ ID NO: 297)
--- Gly Thr Cys Gly Glu Ile Cys --- Tyr Ala --- Cys --- Gly Cys    (SEQ ID NO: 298)
--- Gly Thr Cys Gly Glu Ile Cys --- Tyr Ala --- Cys Thr --- Cys    (SEQ ID NO: 299)
--- Gly Thr Cys Gly Glu Ile Cys --- Tyr Ala Ala Cys --- Gly Cys    (SEQ ID NO: 300)
--- Gly Thr Cys Gly Glu Ile Cys --- Tyr Ala Ala Cys --- --- Cys    (SEQ ID NO: 301)
--- Gly Thr Cys Gly Glu Ile Cys --- Tyr Ala Ala Cys Thr --- Cys    (SEQ ID NO: 302)
--- Gly Thr Cys Gly Glu Ile Cys Ala --- Ala Ala Cys Thr Gly Cys    (SEQ ID NO: 303)
--- Gly Thr Cys Gly Glu Ile Cys Ala --- --- Ala Cys Thr Gly Cys    (SEQ ID NO: 304)
--- Gly Thr Cys Gly Glu Ile Cys Ala --- --- --- Cys Thr Gly Cys    (SEQ ID NO: 305)
--- Gly Thr Cys Gly Glu Ile Cys Ala --- --- Ala Cys --- Gly Cys    (SEQ ID NO: 306)
--- Gly Thr Cys Gly Glu Ile Cys Ala --- --- Ala Cys Thr --- Cys    (SEQ ID NO: 307)
--- Gly Thr Cys Gly Glu Ile Cys Ala --- Ala --- Cys Thr Gly Cys    (SEQ ID NO: 308)
--- Gly Thr Cys Gly Glu Ile Cys Ala --- Ala --- Cys --- Gly Cys    (SEQ ID NO: 309)
--- Gly Thr Cys Gly Glu Ile Cys Ala --- Ala --- Cys Thr --- Cys    (SEQ ID NO: 310)
--- Gly Thr Cys Gly Glu Ile Cys Ala --- Ala Ala Cys --- Gly Cys    (SEQ ID NO: 311)
--- Gly Thr Cys Gly Glu Ile Cys Ala --- Ala Ala Cys --- --- Cys    (SEQ ID NO: 312)
--- Gly Thr Cys Gly Glu Ile Cys Ala --- Ala Ala Cys Thr --- Cys    (SEQ ID NO: 313)
--- Gly Thr Cys Gly Glu Ile Cys Ala Tyr --- Ala Cys Thr Gly Cys    (SEQ ID NO: 314)
--- Gly Thr Cys Gly Glu Ile Cys Ala Tyr --- --- Cys Thr Gly Cys    (SEQ ID NO: 315)
--- Gly Thr Cys Gly Glu Ile Cys Ala Tyr --- --- Cys --- Gly Cys    (SEQ ID NO: 316)
--- Gly Thr Cys Gly Glu Ile Cys Ala Tyr --- --- Cys Thr --- Cys    (SEQ ID NO: 317)
--- Gly Thr Cys Gly Glu Ile Cys Ala Tyr --- Ala Cys --- Gly Cys    (SEQ ID NO: 318)
--- Gly Thr Cys Gly Glu Ile Cys Ala Tyr --- Ala Cys --- --- Cys    (SEQ ID NO: 319)
--- Gly Thr Cys Gly Glu Ile Cys Ala Tyr --- Ala Cys Thr --- Cys    (SEQ ID NO: 320)
--- Gly Thr Cys Gly Glu Ile Cys Ala Tyr Ala --- Cys Thr Gly Cys    (SEQ ID NO: 321)
--- Gly Thr Cys Gly Glu Ile Cys Ala Tyr Ala --- Cys --- Gly Cys    (SEQ ID NO: 322)
--- Gly Thr Cys Gly Glu Ile Cys Ala Tyr Ala --- Cys --- --- Cys    (SEQ ID NO: 323)
--- Gly Thr Cys Gly Glu Ile Cys Ala Tyr Ala --- Cys Thr --- Cys    (SEQ ID NO: 324)
--- Gly Thr Cys Gly Glu Ile Cys Ala Tyr Ala Ala Cys --- Gly Cys    (SEQ ID NO: 325)
--- Gly Thr Cys Gly Glu Ile Cys Ala Tyr Ala Ala Cys --- --- Cys    (SEQ ID NO: 326)
--- Gly Thr Cys Gly Glu Ile Cys Ala Tyr Ala Ala Cys Thr --- Cys    (SEQ ID NO: 327)
```

FIG. 1E

```
Pro --- Thr Cys Gly Glu Ile Cys Ala Tyr Ala Ala Cys Thr Gly Cys    (SEQ ID NO: 328)
Pro --- --- Cys Gly Glu Ile Cys Ala Tyr Ala Ala Cys Thr Gly Cys    (SEQ ID NO: 329)
Pro --- --- Cys --- Glu Ile Cys Ala Tyr Ala Ala Cys Thr Gly Cys    (SEQ ID NO: 330)
Pro --- --- Cys --- --- Ile Cys Ala Tyr Ala Ala Cys Thr Gly Cys    (SEQ ID NO: 331)
Pro --- --- Cys --- Glu --- Cys Ala Tyr Ala Ala Cys Thr Gly Cys    (SEQ ID NO: 332)
Pro --- --- Cys --- Glu Ile Cys --- Tyr Ala Ala Cys Thr Gly Cys    (SEQ ID NO: 333)
Pro --- --- Cys --- Glu Ile Cys Ala --- Ala Ala Cys Thr Gly Cys    (SEQ ID NO: 334)
Pro --- --- Cys --- Glu Ile Cys Ala Tyr --- Ala Cys Thr Gly Cys    (SEQ ID NO: 335)
Pro --- --- Cys --- Glu Ile Cys Ala Tyr Ala --- Cys Thr Gly Cys    (SEQ ID NO: 336)
Pro --- --- Cys --- Glu Ile Cys Ala Tyr Ala Ala Cys --- Gly Cys    (SEQ ID NO: 337)
Pro --- --- Cys --- Glu Ile Cys Ala Tyr Ala Ala Cys Thr --- Cys    (SEQ ID NO: 338)
Pro --- --- Cys Gly --- Ile Cys Ala Tyr Ala Ala Cys Thr Gly Cys    (SEQ ID NO: 339)
Pro --- --- Cys Gly --- --- Cys Ala Tyr Ala Ala Cys Thr Gly Cys    (SEQ ID NO: 340)
Pro --- --- Cys Gly --- Ile Cys --- Tyr Ala Ala Cys Thr Gly Cys    (SEQ ID NO: 341)
Pro --- --- Cys Gly --- Ile Cys Ala --- Ala Ala Cys Thr Gly Cys    (SEQ ID NO: 342)
Pro --- --- Cys Gly --- Ile Cys Ala Tyr --- Ala Cys Thr Gly Cys    (SEQ ID NO: 343)
Pro --- --- Cys Gly --- Ile Cys Ala Tyr Ala --- Cys Thr Gly Cys    (SEQ ID NO: 344)
Pro --- --- Cys Gly --- Ile Cys Ala Tyr Ala Ala Cys --- Gly Cys    (SEQ ID NO: 345)
Pro --- --- Cys Gly --- Ile Cys Ala Tyr Ala Ala Cys Thr --- Cys    (SEQ ID NO: 346)
Pro --- --- Cys Gly Glu --- Cys Ala Tyr Ala Ala Cys Thr Gly Cys    (SEQ ID NO: 347)
Pro --- --- Cys Gly Glu --- Cys --- Tyr Ala Ala Cys Thr Gly Cys    (SEQ ID NO: 348)
Pro --- --- Cys Gly Glu --- Cys Ala --- Ala Ala Cys Thr Gly Cys    (SEQ ID NO: 349)
Pro --- --- Cys Gly Glu --- Cys Ala Tyr --- Ala Cys Thr Gly Cys    (SEQ ID NO: 350)
Pro --- --- Cys Gly Glu --- Cys Ala Tyr Ala --- Cys Thr Gly Cys    (SEQ ID NO: 351)
Pro --- --- Cys Gly Glu --- Cys Ala Tyr Ala Ala Cys --- Gly Cys    (SEQ ID NO: 352)
Pro --- --- Cys Gly Glu --- Cys Ala Tyr Ala Ala Cys Thr --- Cys    (SEQ ID NO: 353)
Pro --- --- Cys Gly Glu Ile Cys --- Tyr Ala Ala Cys Thr Gly Cys    (SEQ ID NO: 354)
Pro --- --- Cys Gly Glu Ile Cys --- --- Ala Ala Cys Thr Gly Cys    (SEQ ID NO: 355)
Pro --- --- Cys Gly Glu Ile Cys --- Tyr --- Ala Cys Thr Gly Cys    (SEQ ID NO: 356)
Pro --- --- Cys Gly Glu Ile Cys --- Tyr Ala --- Cys Thr Gly Cys    (SEQ ID NO: 357)
Pro --- --- Cys Gly Glu Ile Cys --- Tyr Ala Ala Cys --- Gly Cys    (SEQ ID NO: 358)
Pro --- --- Cys Gly Glu Ile Cys --- Tyr Ala Ala Cys Thr --- Cys    (SEQ ID NO: 359)
Pro --- --- Cys Gly Glu Ile Cys Ala --- Ala Ala Cys Thr Gly Cys    (SEQ ID NO: 360)
Pro --- --- Cys Gly Glu Ile Cys Ala --- --- Ala Cys Thr Gly Cys    (SEQ ID NO: 361)
Pro --- --- Cys Gly Glu Ile Cys Ala --- Ala --- Cys Thr Gly Cys    (SEQ ID NO: 362)
Pro --- --- Cys Gly Glu Ile Cys Ala --- Ala Ala Cys --- Gly Cys    (SEQ ID NO: 363)
Pro --- --- Cys Gly Glu Ile Cys Ala --- Ala Ala Cys Thr --- Cys    (SEQ ID NO: 364)
Pro --- --- Cys Gly Glu Ile Cys Ala Tyr --- Ala Cys Thr Gly Cys    (SEQ ID NO: 365)
Pro --- --- Cys Gly Glu Ile Cys Ala Tyr --- --- Cys Thr Gly Cys    (SEQ ID NO: 366)
Pro --- --- Cys Gly Glu Ile Cys Ala Tyr --- Ala Cys --- Gly Cys    (SEQ ID NO: 367)
Pro --- --- Cys Gly Glu Ile Cys Ala Tyr --- Ala Cys Thr --- Cys    (SEQ ID NO: 368)
Pro --- --- Cys Gly Glu Ile Cys Ala Tyr Ala --- Cys Thr Gly Cys    (SEQ ID NO: 369)
Pro --- --- Cys Gly Glu Ile Cys Ala Tyr Ala --- Cys --- Gly Cys    (SEQ ID NO: 370)
Pro --- --- Cys Gly Glu Ile Cys Ala Tyr Ala --- Cys Thr --- Cys    (SEQ ID NO: 371)
Pro --- --- Cys Gly Glu Ile Cys Ala Tyr Ala Ala Cys --- Gly Cys    (SEQ ID NO: 372)
Pro --- --- Cys Gly Glu Ile Cys Ala Tyr Ala Ala Cys --- --- Cys    (SEQ ID NO: 373)
Pro --- --- Cys Gly Glu Ile Cys Ala Tyr Ala Ala Cys Thr --- Cys    (SEQ ID NO: 374)
```

FIG. 1F

```
Pro --- Thr Cys --- Glu Ile Cys Ala Tyr Ala Ala Cys Thr Gly Cys    (SEQ ID NO: 375)
Pro --- Thr Cys --- --- Ile Cys Ala Tyr Ala Ala Cys Thr Gly Cys    (SEQ ID NO: 376)
Pro --- Thr Cys --- --- --- Cys Ala Tyr Ala Ala Cys Thr Gly Cys    (SEQ ID NO: 377)
Pro --- Thr Cys --- --- Ile Cys --- Tyr Ala Ala Cys Thr Gly Cys    (SEQ ID NO: 378)
Pro --- Thr Cys --- --- Ile Cys Ala --- Ala Ala Cys Thr Gly Cys    (SEQ ID NO: 379)
Pro --- Thr Cys --- --- Ile Cys Ala Tyr --- Ala Cys Thr Gly Cys    (SEQ ID NO: 380)
Pro --- Thr Cys --- --- Ile Cys Ala Tyr Ala --- Cys Thr Gly Cys    (SEQ ID NO: 381)
Pro --- Thr Cys --- --- Ile Cys Ala Tyr Ala Ala Cys --- Gly Cys    (SEQ ID NO: 382)
Pro --- Thr Cys --- --- Ile Cys Ala Tyr Ala Ala Cys Thr --- Cys    (SEQ ID NO: 383)
Pro --- Thr Cys --- Glu --- Cys Ala Tyr Ala Ala Cys Thr Gly Cys    (SEQ ID NO: 384)
Pro --- Thr Cys --- Glu --- Cys --- Tyr Ala Ala Cys Thr Gly Cys    (SEQ ID NO: 385)
Pro --- Thr Cys --- Glu --- Cys Ala --- Ala Ala Cys Thr Gly Cys    (SEQ ID NO: 386)
Pro --- Thr Cys --- Glu --- Cys Ala Tyr --- Ala Cys Thr Gly Cys    (SEQ ID NO: 387)
Pro --- Thr Cys --- Glu --- Cys Ala Tyr Ala --- Cys Thr Gly Cys    (SEQ ID NO: 388)
Pro --- Thr Cys --- Glu --- Cys Ala Tyr Ala Ala Cys --- Gly Cys    (SEQ ID NO: 389)
Pro --- Thr Cys --- Glu --- Cys Ala Tyr Ala Ala Cys Thr --- Cys    (SEQ ID NO: 390)
Pro --- Thr Cys --- Glu Ile Cys --- Tyr Ala Ala Cys Thr Gly Cys    (SEQ ID NO: 391)
Pro --- Thr Cys --- Glu Ile Cys --- --- Ala Ala Cys Thr Gly Cys    (SEQ ID NO: 392)
Pro --- Thr Cys --- Glu Ile Cys --- Tyr --- Ala Cys Thr Gly Cys    (SEQ ID NO: 393)
Pro --- Thr Cys --- Glu Ile Cys --- Tyr Ala --- Cys Thr Gly Cys    (SEQ ID NO: 394)
Pro --- Thr Cys --- Glu Ile Cys --- Tyr Ala Ala Cys --- Gly Cys    (SEQ ID NO: 395)
Pro --- Thr Cys --- Glu Ile Cys --- Tyr Ala Ala Cys Thr --- Cys    (SEQ ID NO: 396)
Pro --- Thr Cys --- Glu Ile Cys Ala --- Ala Ala Cys Thr Gly Cys    (SEQ ID NO: 397)
Pro --- Thr Cys --- Glu Ile Cys Ala --- --- Ala Cys Thr Gly Cys    (SEQ ID NO: 398)
Pro --- Thr Cys --- Glu Ile Cys Ala --- Ala --- Cys Thr Gly Cys    (SEQ ID NO: 399)
Pro --- Thr Cys --- Glu Ile Cys Ala --- Ala Ala Cys --- Gly Cys    (SEQ ID NO: 400)
Pro --- Thr Cys --- Glu Ile Cys Ala --- Ala Ala Cys Thr --- Cys    (SEQ ID NO: 401)
Pro --- Thr Cys --- Glu Ile Cys Ala Tyr --- Ala Cys Thr Gly Cys    (SEQ ID NO: 402)
Pro --- Thr Cys --- Glu Ile Cys Ala Tyr --- --- Cys Thr Gly Cys    (SEQ ID NO: 403)
Pro --- Thr Cys --- Glu Ile Cys Ala Tyr --- Ala Cys --- Gly Cys    (SEQ ID NO: 404)
Pro --- Thr Cys --- Glu Ile Cys Ala Tyr --- Ala Cys Thr --- Cys    (SEQ ID NO: 405)
Pro --- Thr Cys --- Glu Ile Cys Ala Tyr Ala --- Cys Thr Gly Cys    (SEQ ID NO: 406)
Pro --- Thr Cys --- Glu Ile Cys Ala Tyr Ala --- Cys --- Gly Cys    (SEQ ID NO: 407)
Pro --- Thr Cys --- Glu Ile Cys Ala Tyr Ala --- Cys Thr --- Cys    (SEQ ID NO: 408)
Pro --- Thr Cys --- Glu Ile Cys Ala Tyr Ala Ala Cys --- Gly Cys    (SEQ ID NO: 409)
Pro --- Thr Cys --- Glu Ile Cys Ala Tyr Ala Ala Cys --- --- Cys    (SEQ ID NO: 410)
Pro --- Thr Cys --- Glu Ile Cys Ala Tyr Ala Ala Cys Thr --- Cys    (SEQ ID NO: 411)
Pro --- Thr Cys Gly --- Ile Cys Ala Tyr Ala Ala Cys Thr Gly Cys    (SEQ ID NO: 412)
Pro --- Thr Cys Gly --- --- Cys Ala Tyr Ala Ala Cys Thr Gly Cys    (SEQ ID NO: 413)
Pro --- Thr Cys Gly --- --- Cys --- Tyr Ala Ala Cys Thr Gly Cys    (SEQ ID NO: 414)
Pro --- Thr Cys Gly --- --- Cys Ala --- Ala Ala Cys Thr Gly Cys    (SEQ ID NO: 415)
Pro --- Thr Cys Gly --- --- Cys Ala Tyr --- Ala Cys Thr Gly Cys    (SEQ ID NO: 416)
Pro --- Thr Cys Gly --- --- Cys Ala Tyr Ala --- Cys Thr Gly Cys    (SEQ ID NO: 417)
Pro --- Thr Cys Gly --- --- Cys Ala Tyr Ala Ala Cys --- Gly Cys    (SEQ ID NO: 418)
Pro --- Thr Cys Gly --- --- Cys Ala Tyr Ala Ala Cys Thr --- Cys    (SEQ ID NO: 419)
Pro --- Thr Cys Gly --- Ile Cys --- Tyr Ala Ala Cys Thr Gly Cys    (SEQ ID NO: 420)
Pro --- Thr Cys Gly --- Ile Cys --- --- Ala Ala Cys Thr Gly Cys    (SEQ ID NO: 421)
```

FIG. 1G

```
Pro --- Thr Cys Gly --- Ile Cys --- Tyr --- Ala Cys Thr Gly Cys    (SEQ ID NO: 422)
Pro --- Thr Cys Gly --- Ile Cys --- Tyr Ala --- Cys Thr Gly Cys    (SEQ ID NO: 423)
Pro --- Thr Cys Gly --- Ile Cys --- Tyr Ala Ala Cys --- Gly Cys    (SEQ ID NO: 424)
Pro --- Thr Cys Gly --- Ile Cys --- Tyr Ala Ala Cys Thr --- Cys    (SEQ ID NO: 425)
Pro --- Thr Cys Gly --- Ile Cys Ala --- Ala Cys Thr Gly Cys        (SEQ ID NO: 426)
Pro --- Thr Cys Gly --- Ile Cys Ala --- --- Ala Cys Thr Gly Cys    (SEQ ID NO: 427)
Pro --- Thr Cys Gly --- Ile Cys Ala --- Ala --- Cys Thr Gly Cys    (SEQ ID NO: 428)
Pro --- Thr Cys Gly --- Ile Cys Ala --- Ala Ala Cys --- Gly Cys    (SEQ ID NO: 429)
Pro --- Thr Cys Gly --- Ile Cys Ala --- Ala Ala Cys Thr --- Cys    (SEQ ID NO: 430)
Pro --- Thr Cys Gly --- Ile Cys Ala Tyr --- Ala Cys Thr Gly Cys    (SEQ ID NO: 431)
Pro --- Thr Cys Gly --- Ile Cys Ala Tyr --- --- Cys Thr Gly Cys    (SEQ ID NO: 432)
Pro --- Thr Cys Gly --- Ile Cys Ala Tyr --- Ala Cys --- Gly Cys    (SEQ ID NO: 433)
Pro --- Thr Cys Gly --- Ile Cys Ala Tyr --- Ala Cys Thr --- Cys    (SEQ ID NO: 434)
Pro --- Thr Cys Gly --- Ile Cys Ala Tyr Ala --- Cys Thr Gly Cys    (SEQ ID NO: 435)
Pro --- Thr Cys Gly --- Ile Cys Ala Tyr Ala --- Cys --- Gly Cys    (SEQ ID NO: 436)
Pro --- Thr Cys Gly --- Ile Cys Ala Tyr Ala --- Cys Thr --- Cys    (SEQ ID NO: 437)
Pro --- Thr Cys Gly --- Ile Cys Ala Tyr Ala Ala Cys --- Gly Cys    (SEQ ID NO: 438)
Pro --- Thr Cys Gly --- Ile Cys Ala Tyr Ala Ala Cys --- --- Cys   (SEQ ID NO: 439)
Pro --- Thr Cys Gly --- Ile Cys Ala Tyr Ala Ala Cys Thr --- Cys    (SEQ ID NO: 440)
Pro --- Thr Cys Gly Glu --- Cys Ala Tyr Ala Ala Cys Thr Gly Cys    (SEQ ID NO: 441)
Pro --- Thr Cys Gly Glu --- Cys --- Tyr Ala Ala Cys Thr Gly Cys    (SEQ ID NO: 442)
Pro --- Thr Cys Gly Glu --- Cys --- --- Ala Ala Cys Thr Gly Cys    (SEQ ID NO: 443)
Pro --- Thr Cys Gly Glu --- Cys --- Tyr --- Ala Cys Thr Gly Cys    (SEQ ID NO: 444)
Pro --- Thr Cys Gly Glu --- Cys --- Tyr Ala --- Cys Thr Gly Cys    (SEQ ID NO: 445)
Pro --- Thr Cys Gly Glu --- Cys --- Tyr Ala Ala Cys --- Gly Cys    (SEQ ID NO: 446)
Pro --- Thr Cys Gly Glu --- Cys --- Tyr Ala Ala Cys Thr --- Cys    (SEQ ID NO: 447)
Pro --- Thr Cys Gly Glu --- Cys Ala --- Ala Ala Cys Thr Gly Cys    (SEQ ID NO: 448)
Pro --- Thr Cys Gly Glu --- Cys Ala --- --- Ala Cys Thr Gly Cys    (SEQ ID NO: 449)
Pro --- Thr Cys Gly Glu --- Cys Ala --- Ala --- Cys Thr Gly Cys    (SEQ ID NO: 450)
Pro --- Thr Cys Gly Glu --- Cys Ala --- Ala Ala Cys --- Gly Cys    (SEQ ID NO: 451)
Pro --- Thr Cys Gly Glu --- Cys Ala --- Ala Ala Cys Thr --- Cys    (SEQ ID NO: 452)
Pro --- Thr Cys Gly Glu --- Cys Ala Tyr --- Ala Cys Thr Gly Cys    (SEQ ID NO: 453)
Pro --- Thr Cys Gly Glu --- Cys Ala Tyr --- --- Cys Thr Gly Cys    (SEQ ID NO: 454)
Pro --- Thr Cys Gly Glu --- Cys Ala Tyr --- Ala Cys --- Gly Cys    (SEQ ID NO: 455)
Pro --- Thr Cys Gly Glu --- Cys Ala Tyr --- Ala Cys Thr --- Cys    (SEQ ID NO: 456)
Pro --- Thr Cys Gly Glu --- Cys Ala Tyr Ala --- Cys Thr Gly Cys    (SEQ ID NO: 457)
Pro --- Thr Cys Gly Glu --- Cys Ala Tyr Ala --- Cys --- Gly Cys    (SEQ ID NO: 458)
Pro --- Thr Cys Gly Glu --- Cys Ala Tyr Ala --- Cys Thr --- Cys    (SEQ ID NO: 459)
Pro --- Thr Cys Gly Glu --- Cys Ala Tyr Ala Ala Cys --- Gly Cys    (SEQ ID NO: 460)
Pro --- Thr Cys Gly Glu --- Cys Ala Tyr Ala Ala Cys --- --- Cys   (SEQ ID NO: 461)
Pro --- Thr Cys Gly Glu --- Cys Ala Tyr Ala Ala Cys Thr --- Cys    (SEQ ID NO: 462)
Pro --- Thr Cys Gly Glu Ile Cys --- Tyr Ala Ala Cys Thr Gly Cys    (SEQ ID NO: 463)
Pro --- Thr Cys Gly Glu Ile Cys --- --- Ala Ala Cys Thr Gly Cys    (SEQ ID NO: 464)
Pro --- Thr Cys Gly Glu Ile Cys --- --- --- Ala Cys Thr Gly Cys    (SEQ ID NO: 465)
Pro --- Thr Cys Gly Glu Ile Cys --- --- Ala --- Cys Thr Gly Cys    (SEQ ID NO: 466)
Pro --- Thr Cys Gly Glu Ile Cys --- --- Ala Ala Cys --- Gly Cys    (SEQ ID NO: 467)
Pro --- Thr Cys Gly Glu Ile Cys --- --- Ala Ala Cys Thr --- Cys    (SEQ ID NO: 468)
```

FIG. 1H

```
Pro --- Thr Cys Gly Glu Ile Cys --- Tyr --- Ala Cys Thr Gly Cys    (SEQ ID NO: 469)
Pro --- Thr Cys Gly Glu Ile

```
Pro Gly --- Cys --- Glu --- Cys Ala --- Ala Ala Cys Thr Gly Cys    (SEQ ID NO: 516)
Pro Gly --- Cys --- Glu --- Cys Ala Tyr --- Ala Cys Thr Gly Cys    (SEQ ID NO: 517)
Pro Gly --- Cys --- Glu --- Cys Ala Tyr Ala --- Cys Thr Gly Cys    (SEQ ID NO: 518)
Pro Gly --- Cys --- Glu --- Cys Ala Tyr Ala Ala Cys --- Gly Cys    (SEQ ID NO: 519)
Pro Gly --- Cys --- Glu --- Cys Ala Tyr Ala Ala Cys Thr --- Cys    (SEQ ID NO: 520)
Pro Gly --- Cys --- Glu Ile Cys --- Tyr Ala Ala Cys Thr Gly Cys    (SEQ ID NO: 521)
Pro Gly --- Cys --- Glu Ile Cys --- --- Ala Ala Cys Thr Gly Cys    (SEQ ID NO: 522)
Pro Gly --- Cys --- Glu Ile Cys --- Tyr --- Ala Cys Thr Gly Cys    (SEQ ID NO: 523)
Pro Gly --- Cys --- Glu Ile Cys --- Tyr Ala --- Cys Thr Gly Cys    (SEQ ID NO: 524)
Pro Gly --- Cys --- Glu Ile Cys --- Tyr Ala Ala Cys --- Gly Cys    (SEQ ID NO: 525)
Pro Gly --- Cys --- Glu Ile Cys --- Tyr Ala Ala Cys Thr --- Cys    (SEQ ID NO: 526)
Pro Gly --- Cys --- Glu Ile Cys Ala --- Ala Ala Cys Thr Gly Cys    (SEQ ID NO: 527)
Pro Gly --- Cys --- Glu Ile Cys Ala --- --- Ala Cys Thr Gly Cys    (SEQ ID NO: 528)
Pro Gly --- Cys --- Glu Ile Cys Ala --- Ala --- Cys Thr Gly Cys    (SEQ ID NO: 529)
Pro Gly --- Cys --- Glu Ile Cys Ala --- Ala Ala Cys --- Gly Cys    (SEQ ID NO: 530)
Pro Gly --- Cys --- Glu Ile Cys Ala --- Ala Ala Cys Thr --- Cys    (SEQ ID NO: 531)
Pro Gly --- Cys --- Glu Ile Cys Ala Tyr --- Ala Cys Thr Gly Cys    (SEQ ID NO: 532)
Pro Gly --- Cys --- Glu Ile Cys Ala Tyr --- --- Cys Thr Gly Cys    (SEQ ID NO: 533)
Pro Gly --- Cys --- Glu Ile Cys Ala Tyr --- Ala Cys --- Gly Cys    (SEQ ID NO: 534)
Pro Gly --- Cys --- Glu Ile Cys Ala Tyr --- Ala Cys Thr --- Cys    (SEQ ID NO: 535)
Pro Gly --- Cys --- Glu Ile Cys Ala Tyr Ala --- Cys Thr Gly Cys    (SEQ ID NO: 536)
Pro Gly --- Cys --- Glu Ile Cys Ala Tyr Ala --- Cys --- Gly Cys    (SEQ ID NO: 537)
Pro Gly --- Cys --- Glu Ile Cys Ala Tyr Ala --- Cys Thr --- Cys    (SEQ ID NO: 538)
Pro Gly --- Cys --- Glu Ile Cys Ala Tyr Ala Ala Cys --- Gly Cys    (SEQ ID NO: 539)
Pro Gly --- Cys --- Glu Ile Cys Ala Tyr Ala Ala Cys --- --- Cys    (SEQ ID NO: 540)
Pro Gly --- Cys --- Glu Ile Cys Ala Tyr Ala Ala Cys Thr --- Cys    (SEQ ID NO: 541)
Pro Gly --- Cys Gly --- Ile Cys Ala Tyr Ala Ala Cys Thr Gly Cys    (SEQ ID NO: 542)
Pro Gly --- Cys Gly --- --- Cys Ala Tyr Ala Ala Cys Thr Gly Cys    (SEQ ID NO: 543)
Pro Gly --- Cys Gly --- --- Cys --- Tyr Ala Ala Cys Thr Gly Cys    (SEQ ID NO: 544)
Pro Gly --- Cys Gly --- --- Cys Ala --- Ala Ala Cys Thr Gly Cys    (SEQ ID NO: 545)
Pro Gly --- Cys Gly --- --- Cys Ala Tyr --- Ala Cys Thr Gly Cys    (SEQ ID NO: 546)
Pro Gly --- Cys Gly --- --- Cys Ala Tyr Ala --- Cys Thr Gly Cys    (SEQ ID NO: 547)
Pro Gly --- Cys Gly --- --- Cys Ala Tyr Ala Ala Cys --- Gly Cys    (SEQ ID NO: 548)
Pro Gly --- Cys Gly --- --- Cys Ala Tyr Ala Ala Cys Thr --- Cys    (SEQ ID NO: 549)
Pro Gly --- Cys Gly --- Ile Cys --- Tyr Ala Ala Cys Thr Gly Cys    (SEQ ID NO: 550)
Pro Gly --- Cys Gly --- Ile Cys --- --- Ala Ala Cys Thr Gly Cys    (SEQ ID NO: 551)
Pro Gly --- Cys Gly --- Ile Cys --- Tyr --- Ala Cys Thr Gly Cys    (SEQ ID NO: 552)
Pro Gly --- Cys Gly --- Ile Cys --- Tyr Ala --- Cys Thr Gly Cys    (SEQ ID NO: 553)
Pro Gly --- Cys Gly --- Ile Cys --- Tyr Ala Ala Cys --- Gly Cys    (SEQ ID NO: 554)
Pro Gly --- Cys Gly --- Ile Cys --- Tyr Ala Ala Cys Thr --- Cys    (SEQ ID NO: 555)
Pro Gly --- Cys Gly --- Ile Cys Ala --- Ala Ala Cys Thr Gly Cys    (SEQ ID NO: 556)
Pro Gly --- Cys Gly --- Ile Cys Ala --- --- Ala Cys Thr Gly Cys    (SEQ ID NO: 557)
Pro Gly --- Cys Gly --- Ile Cys Ala --- Ala --- Cys Thr Gly Cys    (SEQ ID NO: 558)
Pro Gly --- Cys Gly --- Ile Cys Ala --- Ala Ala Cys --- Gly Cys    (SEQ ID NO: 559)
Pro Gly --- Cys Gly --- Ile Cys Ala --- Ala Ala Cys Thr --- Cys    (SEQ ID NO: 560)
Pro Gly --- Cys Gly --- Ile Cys Ala Tyr --- Ala Cys Thr Gly Cys    (SEQ ID NO: 561)
Pro Gly --- Cys Gly --- Ile Cys Ala Tyr --- --- Cys Thr Gly Cys    (SEQ ID NO: 562)
```

FIG. 1J

| | | | | | | | | | | |
|---|---|---|---|---|---|---|---|---|---|---|
| Pro Gly | --- | Cys Gly | --- | Ile Cys Ala Tyr | --- | Ala Cys | --- | Gly Cys | (SEQ ID NO: 563) |
| Pro Gly | --- | Cys Gly | --- | Ile Cys Ala Tyr | --- | Ala Cys Thr | --- | Cys | (SEQ ID NO: 564) |
| Pro Gly | --- | Cys Gly | --- | Ile Cys Ala Tyr Ala | --- | Cys Thr Gly Cys | (SEQ ID NO: 565) |
| Pro Gly | --- | Cys Gly | --- | Ile Cys Ala Tyr Ala | --- | Cys | --- | Gly Cys | (SEQ ID NO: 566) |
| Pro Gly | --- | Cys Gly | --- | Ile Cys Ala Tyr Ala | --- | Cys Thr | --- | Cys | (SEQ ID NO: 567) |
| Pro Gly | --- | Cys Gly | --- | Ile Cys Ala Tyr Ala Ala Cys | --- | Gly Cys | (SEQ ID NO: 568) |
| Pro Gly | --- | Cys Gly | --- | Ile Cys Ala Tyr Ala Ala Cys | --- | --- | Cys | (SEQ ID NO: 569) |
| Pro Gly | --- | Cys Gly | --- | Ile Cys Ala Tyr Ala Ala Cys Thr | --- | Cys | (SEQ ID NO: 570) |
| Pro Gly | --- | Cys Gly Glu | --- | Cys Ala Tyr Ala Ala Cys Thr Gly Cys | (SEQ ID NO: 571) |
| Pro Gly | --- | Cys Gly Glu | --- | Cys | --- | Tyr Ala Ala Cys Thr Gly Cys | (SEQ ID NO: 572) |
| Pro Gly | --- | Cys Gly Glu | --- | Cys | --- | --- | Ala Ala Cys Thr Gly Cys | (SEQ ID NO: 573) |
| Pro Gly | --- | Cys Gly Glu | --- | Cys | --- | Tyr | --- | Ala Cys Thr Gly Cys | (SEQ ID NO: 574) |
| Pro Gly | --- | Cys Gly Glu | --- | Cys | --- | Tyr Ala | --- | Cys Thr Gly Cys | (SEQ ID NO: 575) |
| Pro Gly | --- | Cys Gly Glu | --- | Cys | --- | Tyr Ala Ala Cys | --- | Gly Cys | (SEQ ID NO: 576) |
| Pro Gly | --- | Cys Gly Glu | --- | Cys | --- | Tyr Ala Ala Cys Thr | --- | Cys | (SEQ ID NO: 577) |
| Pro Gly | --- | Cys Gly Glu | --- | Cys Ala | --- | Ala Ala Cys Thr Gly Cys | (SEQ ID NO: 578) |
| Pro Gly | --- | Cys Gly Glu | --- | Cys Ala | --- | --- | Ala Cys Thr Gly Cys | (SEQ ID NO: 579) |
| Pro Gly | --- | Cys Gly Glu | --- | Cys Ala | --- | Ala | --- | Cys Thr Gly Cys | (SEQ ID NO: 580) |
| Pro Gly | --- | Cys Gly Glu | --- | Cys Ala | --- | Ala Ala Cys | --- | Gly Cys | (SEQ ID NO: 581) |
| Pro Gly | --- | Cys Gly Glu | --- | Cys Ala | --- | Ala Ala Cys Thr | --- | Cys | (SEQ ID NO: 582) |
| Pro Gly | --- | Cys Gly Glu | --- | Cys Ala Tyr | --- | Ala Cys Thr Gly Cys | (SEQ ID NO: 583) |
| Pro Gly | --- | Cys Gly Glu | --- | Cys Ala Tyr | --- | --- | Cys Thr Gly Cys | (SEQ ID NO: 584) |
| Pro Gly | --- | Cys Gly Glu | --- | Cys Ala Tyr | --- | Ala Cys | --- | Gly Cys | (SEQ ID NO: 585) |
| Pro Gly | --- | Cys Gly Glu | --- | Cys Ala Tyr | --- | Ala Cys Thr | --- | Cys | (SEQ ID NO: 586) |
| Pro Gly | --- | Cys Gly Glu | --- | Cys Ala Tyr Ala | --- | Cys Thr Gly Cys | (SEQ ID NO: 587) |
| Pro Gly | --- | Cys Gly Glu | --- | Cys Ala Tyr Ala | --- | Cys | --- | Gly Cys | (SEQ ID NO: 588) |
| Pro Gly | --- | Cys Gly Glu | --- | Cys Ala Tyr Ala | --- | Cys Thr | --- | Cys | (SEQ ID NO: 589) |
| Pro Gly | --- | Cys Gly Glu | --- | Cys Ala Tyr Ala Ala Cys | --- | Gly Cys | (SEQ ID NO: 590) |
| Pro Gly | --- | Cys Gly Glu | --- | Cys Ala Tyr Ala Ala Cys | --- | --- | Cys | (SEQ ID NO: 591) |
| Pro Gly | --- | Cys Gly Glu | --- | Cys Ala Tyr Ala Ala Cys Thr | --- | Cys | (SEQ ID NO: 592) |
| Pro Gly | --- | Cys Gly Glu Ile Cys | --- | Tyr Ala Ala Cys Thr Gly Cys | (SEQ ID NO: 593) |
| Pro Gly | --- | Cys Gly Glu Ile Cys | --- | --- | Ala Ala Cys Thr Gly Cys | (SEQ ID NO: 594) |
| Pro Gly | --- | Cys Gly Glu Ile Cys | --- | --- | --- | Ala Cys Thr Gly Cys | (SEQ ID NO: 595) |
| Pro Gly | --- | Cys Gly Glu Ile Cys | --- | --- | Ala | --- | Cys Thr Gly Cys | (SEQ ID NO: 596) |
| Pro Gly | --- | Cys Gly Glu Ile Cys | --- | --- | Ala Ala Cys | --- | Gly Cys | (SEQ ID NO: 597) |
| Pro Gly | --- | Cys Gly Glu Ile Cys | --- | --- | Ala Ala Cys Thr | --- | Cys | (SEQ ID NO: 598) |
| Pro Gly | --- | Cys Gly Glu Ile Cys | --- | Tyr | --- | Ala Cys Thr Gly Cys | (SEQ ID NO: 599) |
| Pro Gly | --- | Cys Gly Glu Ile Cys | --- | Tyr | --- | --- | Cys Thr Gly Cys | (SEQ ID NO: 600) |
| Pro Gly | --- | Cys Gly Glu Ile Cys | --- | Tyr | --- | Ala Cys | --- | Gly Cys | (SEQ ID NO: 601) |
| Pro Gly | --- | Cys Gly Glu Ile Cys | --- | Tyr | --- | Ala Cys Thr | --- | Cys | (SEQ ID NO: 602) |
| Pro Gly | --- | Cys Gly Glu Ile Cys | --- | Tyr Ala | --- | Cys Thr Gly Cys | (SEQ ID NO: 603) |
| Pro Gly | --- | Cys Gly Glu Ile Cys | --- | Tyr Ala | --- | Cys | --- | Gly Cys | (SEQ ID NO: 604) |
| Pro Gly | --- | Cys Gly Glu Ile Cys | --- | Tyr Ala | --- | Cys Thr | --- | Cys | (SEQ ID NO: 605) |
| Pro Gly | --- | Cys Gly Glu Ile Cys | --- | Tyr Ala Ala Cys | --- | Gly Cys | (SEQ ID NO: 606) |
| Pro Gly | --- | Cys Gly Glu Ile Cys | --- | Tyr Ala Ala Cys | --- | --- | Cys | (SEQ ID NO: 607) |
| Pro Gly | --- | Cys Gly Glu Ile Cys | --- | Tyr Ala Ala Cys Thr | --- | Cys | (SEQ ID NO: 608) |
| Pro Gly | --- | Cys Gly Glu Ile Cys Ala | --- | Ala Ala Cys Thr Gly Cys | (SEQ ID NO: 609) |

FIG. 1K

```
Pro Gly --- Cys Gly Glu Ile Cys Ala --- --- Ala Cys Thr Gly Cys   (SEQ ID NO: 610)
Pro Gly --- Cys Gly Glu Ile Cys Ala --- --- --- Cys Thr Gly Cys   (SEQ ID NO: 611)
Pro Gly --- Cys Gly Glu Ile Cys Ala --- --- Ala Cys --- Gly Cys   (SEQ ID NO: 612)
Pro Gly --- Cys Gly Glu Ile Cys Ala --- --- Ala Cys Thr --- Cys   (SEQ ID NO: 613)
Pro Gly --- Cys Gly Glu Ile Cys Ala --- Ala --- Cys Thr Gly Cys   (SEQ ID NO: 614)
Pro Gly --- Cys Gly Glu Ile Cys Ala --- Ala --- Cys --- Gly Cys   (SEQ ID NO: 615)
Pro Gly --- Cys Gly Glu Ile Cys Ala --- Ala --- Cys Thr --- Cys   (SEQ ID NO: 616)
Pro Gly --- Cys Gly Glu Ile Cys Ala --- Ala Ala Cys --- Gly Cys   (SEQ ID NO: 617)
Pro Gly --- Cys Gly Glu Ile Cys Ala --- Ala Ala Cys --- --- Cys   (SEQ ID NO: 618)
Pro Gly --- Cys Gly Glu Ile Cys Ala --- Ala Ala Cys Thr --- Cys   (SEQ ID NO: 619)
Pro Gly --- Cys Gly Glu Ile Cys Ala Tyr --- Ala Cys Thr Gly Cys   (SEQ ID NO: 620)
Pro Gly --- Cys Gly Glu Ile Cys Ala Tyr --- --- Cys Thr Gly Cys   (SEQ ID NO: 621)
Pro Gly --- Cys Gly Glu Ile Cys Ala Tyr --- --- Cys --- Gly Cys   (SEQ ID NO: 622)
Pro Gly --- Cys Gly Glu Ile Cys Ala Tyr --- --- Cys Thr --- Cys   (SEQ ID NO: 623)
Pro Gly --- Cys Gly Glu Ile Cys Ala Tyr --- Ala Cys --- Gly Cys   (SEQ ID NO: 624)
Pro Gly --- Cys Gly Glu Ile Cys Ala Tyr --- Ala Cys --- --- Cys   (SEQ ID NO: 625)
Pro Gly --- Cys Gly Glu Ile Cys Ala Tyr --- Ala Cys Thr --- Cys   (SEQ ID NO: 626)
Pro Gly --- Cys Gly Glu Ile Cys Ala Tyr Ala --- Cys Thr Gly Cys   (SEQ ID NO: 627)
Pro Gly --- Cys Gly Glu Ile Cys Ala Tyr Ala --- Cys --- Gly Cys   (SEQ ID NO: 628)
Pro Gly --- Cys Gly Glu Ile Cys Ala Tyr Ala --- Cys --- --- Cys   (SEQ ID NO: 629)
Pro Gly --- Cys Gly Glu Ile Cys Ala Tyr Ala --- Cys Thr --- Cys   (SEQ ID NO: 630)
Pro Gly --- Cys Gly Glu Ile Cys Ala Tyr Ala Ala Cys --- Gly Cys   (SEQ ID NO: 631)
Pro Gly --- Cys Gly Glu Ile Cys Ala Tyr Ala Ala Cys --- --- Cys   (SEQ ID NO: 632)
Pro Gly --- Cys Gly Glu Ile Cys Ala Tyr Ala Ala Cys Thr --- Cys   (SEQ ID NO: 633)
Pro Gly Thr Cys --- Glu Ile Cys Ala Tyr Ala Ala Cys Thr Gly Cys   (SEQ ID NO: 634)
Pro Gly Thr Cys --- --- Ile Cys Ala Tyr Ala Ala Cys Thr Gly Cys   (SEQ ID NO: 635)
Pro Gly Thr Cys --- --- --- Cys Ala Tyr Ala Ala Cys Thr Gly Cys   (SEQ ID NO: 636)
Pro Gly Thr Cys --- --- --- Cys --- Tyr Ala Ala Cys Thr Gly Cys   (SEQ ID NO: 637)
Pro Gly Thr Cys --- --- --- Cys Ala --- Ala Ala Cys Thr Gly Cys   (SEQ ID NO: 638)
Pro Gly Thr Cys --- --- --- Cys Ala Tyr --- Ala Cys Thr Gly Cys   (SEQ ID NO: 639)
Pro Gly Thr Cys --- --- --- Cys Ala Tyr Ala --- Cys Thr Gly Cys   (SEQ ID NO: 640)
Pro Gly Thr Cys --- --- --- Cys Ala Tyr Ala Ala Cys --- Gly Cys   (SEQ ID NO: 641)
Pro Gly Thr Cys --- --- --- Cys Ala Tyr Ala Ala Cys Thr --- Cys   (SEQ ID NO: 642)
Pro Gly Thr Cys --- --- Ile Cys --- Tyr Ala Ala Cys Thr Gly Cys   (SEQ ID NO: 643)
Pro Gly Thr Cys --- --- Ile Cys --- --- Ala Ala Cys Thr Gly Cys   (SEQ ID NO: 644)
Pro Gly Thr Cys --- --- Ile Cys --- Tyr --- Ala Cys Thr Gly Cys   (SEQ ID NO: 645)
Pro Gly Thr Cys --- --- Ile Cys --- Tyr Ala --- Cys Thr Gly Cys   (SEQ ID NO: 646)
Pro Gly Thr Cys --- --- Ile Cys --- Tyr Ala Ala Cys --- Gly Cys   (SEQ ID NO: 647)
Pro Gly Thr Cys --- --- Ile Cys --- Tyr Ala Ala Cys Thr --- Cys   (SEQ ID NO: 648)
Pro Gly Thr Cys --- --- Ile Cys Ala --- Ala Ala Cys Thr Gly Cys   (SEQ ID NO: 649)
Pro Gly Thr Cys --- --- Ile Cys Ala --- --- Ala Cys Thr Gly Cys   (SEQ ID NO: 650)
Pro Gly Thr Cys --- --- Ile Cys Ala --- Ala --- Cys Thr Gly Cys   (SEQ ID NO: 651)
Pro Gly Thr Cys --- --- Ile Cys Ala --- Ala Ala Cys --- Gly Cys   (SEQ ID NO: 652)
Pro Gly Thr Cys --- --- Ile Cys Ala --- Ala Ala Cys Thr --- Cys   (SEQ ID NO: 653)
Pro Gly Thr Cys --- --- Ile Cys Ala Tyr --- Ala Cys Thr Gly Cys   (SEQ ID NO: 654)
Pro Gly Thr Cys --- --- Ile Cys Ala Tyr --- --- Cys Thr Gly Cys   (SEQ ID NO: 655)
Pro Gly Thr Cys --- --- Ile Cys Ala Tyr --- Ala Cys --- Gly Cys   (SEQ ID NO: 656)
```

FIG. 1L

```
Pro Gly Thr Cys --- --- Ile Cys Ala Tyr --- Ala Cys Thr --- Cys     (SEQ ID NO: 657)
Pro Gly Thr Cys --- --- Ile Cys Ala Tyr Ala --- Cys Thr Gly Cys     (SEQ ID NO: 658)
Pro Gly Thr Cys --- --- Ile Cys Ala Tyr Ala --- Cys --- Gly Cys     (SEQ ID NO: 659)
Pro Gly Thr Cys --- --- Ile Cys Ala Tyr Ala --- Cys Thr --- Cys     (SEQ ID NO: 660)
Pro Gly Thr Cys --- --- Ile Cys Ala Tyr Ala Ala Cys --- Gly Cys     (SEQ ID NO: 661)
Pro Gly Thr Cys --- --- Ile Cys Ala Tyr Ala Ala Cys --- --- Cys     (SEQ ID NO: 662)
Pro Gly Thr Cys --- --- Ile Cys Ala Tyr Ala Ala Cys Thr --- Cys     (SEQ ID NO: 663)
Pro Gly Thr Cys --- Glu --- Cys Ala Tyr Ala Ala Cys Thr Gly Cys     (SEQ ID NO: 664)
Pro Gly Thr Cys --- Glu --- Cys --- Tyr Ala Ala Cys Thr Gly Cys     (SEQ ID NO: 665)
Pro Gly Thr Cys --- Glu --- Cys --- --- Ala Ala Cys Thr Gly Cys     (SEQ ID NO: 666)
Pro Gly Thr Cys --- Glu --- Cys --- Tyr --- Ala Cys Thr Gly Cys     (SEQ ID NO: 667)
Pro Gly Thr Cys --- Glu --- Cys --- Tyr Ala --- Cys Thr Gly Cys     (SEQ ID NO: 668)
Pro Gly Thr Cys --- Glu --- Cys --- Tyr Ala Ala Cys --- Gly Cys     (SEQ ID NO: 669)
Pro Gly Thr Cys --- Glu --- Cys --- Tyr Ala Ala Cys Thr --- Cys     (SEQ ID NO: 670)
Pro Gly Thr Cys --- Glu --- Cys Ala --- Ala Ala Cys Thr Gly Cys     (SEQ ID NO: 671)
Pro Gly Thr Cys --- Glu --- Cys Ala --- --- Ala Cys Thr Gly Cys     (SEQ ID NO: 672)
Pro Gly Thr Cys --- Glu --- Cys Ala --- Ala --- Cys Thr Gly Cys     (SEQ ID NO: 673)
Pro Gly Thr Cys --- Glu --- Cys Ala --- Ala Ala Cys --- Gly Cys     (SEQ ID NO: 674)
Pro Gly Thr Cys --- Glu --- Cys Ala --- Ala Ala Cys Thr --- Cys     (SEQ ID NO: 675)
Pro Gly Thr Cys --- Glu --- Cys Ala Tyr --- Ala Cys Thr Gly Cys     (SEQ ID NO: 676)
Pro Gly Thr Cys --- Glu --- Cys Ala Tyr --- --- Cys Thr Gly Cys     (SEQ ID NO: 677)
Pro Gly Thr Cys --- Glu --- Cys Ala Tyr --- Ala Cys --- Gly Cys     (SEQ ID NO: 678)
Pro Gly Thr Cys --- Glu --- Cys Ala Tyr --- Ala Cys Thr --- Cys     (SEQ ID NO: 679)
Pro Gly Thr Cys --- Glu --- Cys Ala Tyr Ala --- Cys Thr Gly Cys     (SEQ ID NO: 680)
Pro Gly Thr Cys --- Glu --- Cys Ala Tyr Ala --- Cys --- Gly Cys     (SEQ ID NO: 681)
Pro Gly Thr Cys --- Glu --- Cys Ala Tyr Ala --- Cys Thr --- Cys     (SEQ ID NO: 682)
Pro Gly Thr Cys --- Glu --- Cys Ala Tyr Ala Ala Cys --- Gly Cys     (SEQ ID NO: 683)
Pro Gly Thr Cys --- Glu --- Cys Ala Tyr Ala Ala Cys --- --- Cys     (SEQ ID NO: 684)
Pro Gly Thr Cys --- Glu --- Cys Ala Tyr Ala Ala Cys Thr --- Cys     (SEQ ID NO: 685)
Pro Gly Thr Cys --- Glu Ile Cys --- Tyr Ala Ala Cys Thr Gly Cys     (SEQ ID NO: 686)
Pro Gly Thr Cys --- Glu Ile Cys --- --- Ala Ala Cys Thr Gly Cys     (SEQ ID NO: 687)
Pro Gly Thr Cys --- Glu Ile Cys --- --- --- Ala Cys Thr Gly Cys     (SEQ ID NO: 688)
Pro Gly Thr Cys --- Glu Ile Cys --- --- Ala --- Cys Thr Gly Cys     (SEQ ID NO: 689)
Pro Gly Thr Cys --- Glu Ile Cys --- --- Ala Ala Cys --- Gly Cys     (SEQ ID NO: 690)
Pro Gly Thr Cys --- Glu Ile Cys --- --- Ala Ala Cys Thr --- Cys     (SEQ ID NO: 691)
Pro Gly Thr Cys --- Glu Ile Cys --- Tyr --- Ala Cys Thr Gly Cys     (SEQ ID NO: 692)
Pro Gly Thr Cys --- Glu Ile Cys --- Tyr --- --- Cys Thr Gly Cys     (SEQ ID NO: 693)
Pro Gly Thr Cys --- Glu Ile Cys --- Tyr --- Ala Cys --- Gly Cys     (SEQ ID NO: 694)
Pro Gly Thr Cys --- Glu Ile Cys --- Tyr --- Ala Cys Thr --- Cys     (SEQ ID NO: 695)
Pro Gly Thr Cys --- Glu Ile Cys --- Tyr Ala --- Cys Thr Gly Cys     (SEQ ID NO: 696)
Pro Gly Thr Cys --- Glu Ile Cys --- Tyr Ala --- Cys --- Gly Cys     (SEQ ID NO: 697)
Pro Gly Thr Cys --- Glu Ile Cys --- Tyr Ala --- Cys Thr --- Cys     (SEQ ID NO: 698)
Pro Gly Thr Cys --- Glu Ile Cys --- Tyr Ala Ala Cys --- Gly Cys     (SEQ ID NO: 699)
Pro Gly Thr Cys --- Glu Ile Cys --- Tyr Ala Ala Cys --- --- Cys     (SEQ ID NO: 700)
Pro Gly Thr Cys --- Glu Ile Cys --- Tyr Ala Ala Cys Thr --- Cys     (SEQ ID NO: 701)
Pro Gly Thr Cys --- Glu Ile Cys Ala --- Ala Ala Cys Thr Gly Cys     (SEQ ID NO: 702)
Pro Gly Thr Cys --- Glu Ile Cys Ala --- --- Ala Cys Thr Gly Cys     (SEQ ID NO: 703)
```

FIG. 1M

```
Pro Gly Thr Cys --- Glu Ile Cys Ala --- --- --- Cys Thr Gly Cys    (SEQ ID NO: 704)
Pro Gly Thr Cys --- Glu Ile Cys Ala --- --- Ala Cys --- Gly Cys    (SEQ ID NO: 705)
Pro Gly Thr Cys --- Glu Ile Cys Ala --- --- Ala Cys Thr --- Cys    (SEQ ID NO: 706)
Pro Gly Thr Cys --- Glu Ile Cys Ala --- Ala --- Cys Thr Gly Cys    (SEQ ID NO: 707)
Pro Gly Thr Cys --- Glu Ile Cys Ala --- Ala --- Cys --- Gly Cys    (SEQ ID NO: 708)
Pro Gly Thr Cys --- Glu Ile Cys Ala --- Ala --- Cys Thr --- Cys    (SEQ ID NO: 709)
Pro Gly Thr Cys --- Glu Ile Cys Ala --- Ala Ala Cys --- Gly Cys    (SEQ ID NO: 710)
Pro Gly Thr Cys --- Glu Ile Cys Ala --- Ala Ala Cys --- --- Cys    (SEQ ID NO: 711)
Pro Gly Thr Cys --- Glu Ile Cys Ala --- Ala Ala Cys Thr --- Cys    (SEQ ID NO: 712)
Pro Gly Thr Cys --- Glu Ile Cys Ala Tyr --- Ala Cys Thr Gly Cys    (SEQ ID NO: 713)
Pro Gly Thr Cys --- Glu Ile Cys Ala Tyr --- --- Cys Thr Gly Cys    (SEQ ID NO: 714)
Pro Gly Thr Cys --- Glu Ile Cys Ala Tyr --- --- Cys --- Gly Cys    (SEQ ID NO: 715)
Pro Gly Thr Cys --- Glu Ile Cys Ala Tyr --- --- Cys Thr --- Cys    (SEQ ID NO: 716)
Pro Gly Thr Cys --- Glu Ile Cys Ala Tyr --- Ala Cys --- Gly Cys    (SEQ ID NO: 717)
Pro Gly Thr Cys --- Glu Ile Cys Ala Tyr --- Ala Cys --- --- Cys    (SEQ ID NO: 718)
Pro Gly Thr Cys --- Glu Ile Cys Ala Tyr --- Ala Cys Thr --- Cys    (SEQ ID NO: 719)
Pro Gly Thr Cys --- Glu Ile Cys Ala Tyr Ala --- Cys Thr Gly Cys    (SEQ ID NO: 720)
Pro Gly Thr Cys --- Glu Ile Cys Ala Tyr Ala --- Cys --- Gly Cys    (SEQ ID NO: 721)
Pro Gly Thr Cys --- Glu Ile Cys Ala Tyr Ala --- Cys --- --- Cys    (SEQ ID NO: 722)
Pro Gly Thr Cys --- Glu Ile Cys Ala Tyr Ala --- Cys Thr --- Cys    (SEQ ID NO: 723)
Pro Gly Thr Cys --- Glu Ile Cys Ala Tyr Ala Ala Cys --- Gly Cys    (SEQ ID NO: 724)
Pro Gly Thr Cys --- Glu Ile Cys Ala Tyr Ala Ala Cys --- --- Cys    (SEQ ID NO: 725)
Pro Gly Thr Cys --- Glu Ile Cys Ala Tyr Ala Ala Cys Thr --- Cys    (SEQ ID NO: 726)
Pro Gly Thr Cys Gly --- Ile Cys Ala Tyr Ala Ala Cys Thr Gly Cys    (SEQ ID NO: 727)
Pro Gly Thr Cys Gly --- --- Cys Ala Tyr Ala Ala Cys Thr Gly Cys    (SEQ ID NO: 728)
Pro Gly Thr Cys Gly --- --- Cys --- Tyr Ala Ala Cys Thr Gly Cys    (SEQ ID NO: 729)
Pro Gly Thr Cys Gly --- --- Cys --- --- Ala Ala Cys Thr Gly Cys    (SEQ ID NO: 730)
Pro Gly Thr Cys Gly --- --- Cys --- Tyr --- Ala Cys Thr Gly Cys    (SEQ ID NO: 731)
Pro Gly Thr Cys Gly --- --- Cys --- Tyr Ala --- Cys Thr Gly Cys    (SEQ ID NO: 732)
Pro Gly Thr Cys Gly --- --- Cys --- Tyr Ala Ala Cys --- Gly Cys    (SEQ ID NO: 733)
Pro Gly Thr Cys Gly --- --- Cys --- Tyr Ala Ala Cys Thr --- Cys    (SEQ ID NO: 734)
Pro Gly Thr Cys Gly --- --- Cys Ala --- Ala Ala Cys Thr Gly Cys    (SEQ ID NO: 735)
Pro Gly Thr Cys Gly --- --- Cys Ala --- --- Ala Cys Thr Gly Cys    (SEQ ID NO: 736)
Pro Gly Thr Cys Gly --- --- Cys Ala --- Ala --- Cys Thr Gly Cys    (SEQ ID NO: 737)
Pro Gly Thr Cys Gly --- --- Cys Ala --- Ala Ala Cys --- Gly Cys    (SEQ ID NO: 738)
Pro Gly Thr Cys Gly --- --- Cys Ala --- Ala Ala Cys Thr --- Cys    (SEQ ID NO: 739)
Pro Gly Thr Cys Gly --- --- Cys Ala Tyr --- Ala Cys Thr Gly Cys    (SEQ ID NO: 740)
Pro Gly Thr Cys Gly --- --- Cys Ala Tyr --- --- Cys Thr Gly Cys    (SEQ ID NO: 741)
Pro Gly Thr Cys Gly --- --- Cys Ala Tyr --- Ala Cys --- Gly Cys    (SEQ ID NO: 742)
Pro Gly Thr Cys Gly --- --- Cys Ala Tyr --- Ala Cys Thr --- Cys    (SEQ ID NO: 743)
Pro Gly Thr Cys Gly --- --- Cys Ala Tyr Ala --- Cys Thr Gly Cys    (SEQ ID NO: 744)
Pro Gly Thr Cys Gly --- --- Cys Ala Tyr Ala --- Cys --- Gly Cys    (SEQ ID NO: 745)
Pro Gly Thr Cys Gly --- --- Cys Ala Tyr Ala --- Cys Thr --- Cys    (SEQ ID NO: 746)
Pro Gly Thr Cys Gly --- --- Cys Ala Tyr Ala Ala Cys --- Gly Cys    (SEQ ID NO: 747)
Pro Gly Thr Cys Gly --- --- Cys Ala Tyr Ala Ala Cys --- --- Cys    (SEQ ID NO: 748)
Pro Gly Thr Cys Gly --- --- Cys Ala Tyr Ala Ala Cys Thr --- Cys    (SEQ ID NO: 749)
Pro Gly Thr Cys Gly --- Ile Cys --- Tyr Ala Ala Cys Thr Gly Cys    (SEQ ID NO: 750)
```

FIG. 1N

```
Pro Gly Thr Cys Gly --- Ile Cys --- --- Ala Ala Cys Thr Gly Cys   (SEQ ID NO: 751)
Pro Gly Thr Cys Gly --- Ile Cys --- --- --- Ala Cys Thr Gly Cys   (SEQ ID NO: 752)
Pro Gly Thr Cys Gly --- Ile Cys --- --- Ala --- Cys Thr Gly Cys   (SEQ ID NO: 753)
Pro Gly Thr Cys Gly --- Ile Cys --- --- Ala Ala Cys --- Gly Cys   (SEQ ID NO: 754)
Pro Gly Thr Cys Gly --- Ile Cys --- --- Ala Ala Cys Thr --- Cys   (SEQ ID NO: 755)
Pro Gly Thr Cys Gly --- Ile Cys --- Tyr --- Ala Cys Thr Gly Cys   (SEQ ID NO: 756)
Pro Gly Thr Cys Gly --- Ile Cys --- Tyr --- --- Cys Thr Gly Cys   (SEQ ID NO: 757)
Pro Gly Thr Cys Gly --- Ile Cys --- Tyr --- Ala Cys --- Gly Cys   (SEQ ID NO: 758)
Pro Gly Thr Cys Gly --- Ile Cys --- Tyr --- Ala Cys Thr --- Cys   (SEQ ID NO: 759)
Pro Gly Thr Cys Gly --- Ile Cys --- Tyr Ala --- Cys Thr Gly Cys   (SEQ ID NO: 760)
Pro Gly Thr Cys Gly --- Ile Cys --- Tyr Ala --- Cys --- Gly Cys   (SEQ ID NO: 761)
Pro Gly Thr Cys Gly --- Ile Cys --- Tyr Ala --- Cys Thr --- Cys   (SEQ ID NO: 762)
Pro Gly Thr Cys Gly --- Ile Cys --- Tyr Ala Ala Cys --- Gly Cys   (SEQ ID NO: 763)
Pro Gly Thr Cys Gly --- Ile Cys --- Tyr Ala Ala Cys --- --- Cys   (SEQ ID NO: 764)
Pro Gly Thr Cys Gly --- Ile Cys --- Tyr Ala Ala Cys Thr --- Cys   (SEQ ID NO: 765)
Pro Gly Thr Cys Gly --- Ile Cys Ala --- Ala Ala Cys Thr Gly Cys   (SEQ ID NO: 766)
Pro Gly Thr Cys Gly --- Ile Cys Ala --- --- Ala Cys Thr Gly Cys   (SEQ ID NO: 767)
Pro Gly Thr Cys Gly --- Ile Cys Ala --- --- --- Cys Thr Gly Cys   (SEQ ID NO: 768)
Pro Gly Thr Cys Gly --- Ile Cys Ala --- --- Ala Cys --- Gly Cys   (SEQ ID NO: 769)
Pro Gly Thr Cys Gly --- Ile Cys Ala --- --- Ala Cys Thr --- Cys   (SEQ ID NO: 770)
Pro Gly Thr Cys Gly --- Ile Cys Ala --- Ala --- Cys Thr Gly Cys   (SEQ ID NO: 771)
Pro Gly Thr Cys Gly --- Ile Cys Ala --- Ala --- Cys --- Gly Cys   (SEQ ID NO: 772)
Pro Gly Thr Cys Gly --- Ile Cys Ala --- Ala --- Cys Thr --- Cys   (SEQ ID NO: 773)
Pro Gly Thr Cys Gly --- Ile Cys Ala --- Ala Ala Cys --- Gly Cys   (SEQ ID NO: 774)
Pro Gly Thr Cys Gly --- Ile Cys Ala --- Ala Ala Cys --- --- Cys   (SEQ ID NO: 775)
Pro Gly Thr Cys Gly --- Ile Cys Ala --- Ala Ala Cys Thr --- Cys   (SEQ ID NO: 776)
Pro Gly Thr Cys Gly --- Ile Cys Ala Tyr --- Ala Cys Thr Gly Cys   (SEQ ID NO: 777)
Pro Gly Thr Cys Gly --- Ile Cys Ala Tyr --- --- Cys Thr Gly Cys   (SEQ ID NO: 778)
Pro Gly Thr Cys Gly --- Ile Cys Ala Tyr --- --- Cys --- Gly Cys   (SEQ ID NO: 779)
Pro Gly Thr Cys Gly --- Ile Cys Ala Tyr --- --- Cys Thr --- Cys   (SEQ ID NO: 780)
Pro Gly Thr Cys Gly --- Ile Cys Ala Tyr --- Ala Cys --- Gly Cys   (SEQ ID NO: 781)
Pro Gly Thr Cys Gly --- Ile Cys Ala Tyr --- Ala Cys --- --- Cys   (SEQ ID NO: 782)
Pro Gly Thr Cys Gly --- Ile Cys Ala Tyr --- Ala Cys Thr --- Cys   (SEQ ID NO: 783)
Pro Gly Thr Cys Gly --- Ile Cys Ala Tyr Ala --- Cys Thr Gly Cys   (SEQ ID NO: 784)
Pro Gly Thr Cys Gly --- Ile Cys Ala Tyr Ala --- Cys --- Gly Cys   (SEQ ID NO: 785)
Pro Gly Thr Cys Gly --- Ile Cys Ala Tyr Ala --- Cys --- --- Cys   (SEQ ID NO: 786)
Pro Gly Thr Cys Gly --- Ile Cys Ala Tyr Ala --- Cys Thr --- Cys   (SEQ ID NO: 787)
Pro Gly Thr Cys Gly --- Ile Cys Ala Tyr Ala Ala Cys --- Gly Cys   (SEQ ID NO: 788)
Pro Gly Thr Cys Gly --- Ile Cys Ala Tyr Ala Ala Cys --- --- Cys   (SEQ ID NO: 789)
Pro Gly Thr Cys Gly --- Ile Cys Ala Tyr Ala Ala Cys Thr --- Cys   (SEQ ID NO: 790)
Pro Gly Thr Cys Gly Glu --- Cys Ala Tyr Ala Ala Cys Thr Gly Cys   (SEQ ID NO: 791)
Pro Gly Thr Cys Gly Glu --- Cys --- Tyr Ala Ala Cys Thr Gly Cys   (SEQ ID NO: 792)
Pro Gly Thr Cys Gly Glu --- Cys --- --- Ala Ala Cys Thr Gly Cys   (SEQ ID NO: 793)
Pro Gly Thr Cys Gly Glu --- Cys --- --- --- Ala Cys Thr Gly Cys   (SEQ ID NO: 794)
Pro Gly Thr Cys Gly Glu --- Cys --- --- Ala --- Cys Thr Gly Cys   (SEQ ID NO: 795)
Pro Gly Thr Cys Gly Glu --- Cys --- --- Ala Ala Cys --- Gly Cys   (SEQ ID NO: 796)
Pro Gly Thr Cys Gly Glu --- Cys --- --- Ala Ala Cys Thr --- Cys   (SEQ ID NO: 797)
```

FIG. 10

Pro Gly Thr Cys Gly Glu --- Cys --- Tyr --- Ala Cys Thr Gly Cys (SEQ ID NO: 798)
Pro Gly Thr Cys Gly Glu --- Cys --- Tyr --- --- Cys Thr Gly Cys (SEQ ID NO: 799)
Pro Gly Thr Cys Gly Glu --- Cys --- Tyr --- Ala Cys --- Gly Cys (SEQ ID NO: 800)
Pro Gly Thr Cys Gly Glu --- Cys --- Tyr --- Ala Cys Thr --- Cys (SEQ ID NO: 801)
Pro Gly Thr Cys Gly Glu --- Cys --- Tyr Ala --- Cys Thr Gly Cys (SEQ ID NO: 802)
Pro Gly Thr Cys Gly Glu --- Cys --- Tyr Ala --- Cys --- Gly Cys (SEQ ID NO: 803)
Pro Gly Thr Cys Gly Glu --- Cys --- Tyr Ala --- Cys Thr --- Cys (SEQ ID NO: 804)
Pro Gly Thr Cys Gly Glu --- Cys --- Tyr Ala Ala Cys --- Gly Cys (SEQ ID NO: 805)
Pro Gly Thr Cys Gly Glu --- Cys --- Tyr Ala Ala Cys --- --- Cys (SEQ ID NO: 806)
Pro Gly Thr Cys Gly Glu --- Cys --- Tyr Ala Ala Cys Thr --- Cys (SEQ ID NO: 807)
Pro Gly Thr Cys Gly Glu --- Cys Ala --- Ala Ala Cys Thr Gly Cys (SEQ ID NO: 808)
Pro Gly Thr Cys Gly Glu --- Cys Ala --- --- Ala Cys Thr Gly Cys (SEQ ID NO: 809)
Pro Gly Thr Cys Gly Glu --- Cys Ala --- --- --- Cys Thr Gly Cys (SEQ ID NO: 810)
Pro Gly Thr Cys Gly Glu --- Cys Ala --- --- Ala Cys --- Gly Cys (SEQ ID NO: 811)
Pro Gly Thr Cys Gly Glu --- Cys Ala --- --- Ala Cys Thr --- Cys (SEQ ID NO: 812)
Pro Gly Thr Cys Gly Glu --- Cys Ala --- Ala --- Cys Thr Gly Cys (SEQ ID NO: 813)
Pro Gly Thr Cys Gly Glu --- Cys Ala --- Ala --- Cys --- Gly Cys (SEQ ID NO: 814)
Pro Gly Thr Cys Gly Glu --- Cys Ala --- Ala --- Cys Thr --- Cys (SEQ ID NO: 815)
Pro Gly Thr Cys Gly Glu --- Cys Ala --- Ala Ala Cys --- Gly Cys (SEQ ID NO: 816)
Pro Gly Thr Cys Gly Glu --- Cys Ala --- Ala Ala Cys --- --- Cys (SEQ ID NO: 817)
Pro Gly Thr Cys Gly Glu --- Cys Ala --- Ala Ala Cys Thr --- Cys (SEQ ID NO: 818)
Pro Gly Thr Cys Gly Glu --- Cys Ala Tyr --- Ala Cys Thr Gly Cys (SEQ ID NO: 819)
Pro Gly Thr Cys Gly Glu --- Cys Ala Tyr --- --- Cys Thr Gly Cys (SEQ ID NO: 820)
Pro Gly Thr Cys Gly Glu --- Cys Ala Tyr --- --- Cys --- Gly Cys (SEQ ID NO: 821)
Pro Gly Thr Cys Gly Glu --- Cys Ala Tyr --- --- Cys Thr --- Cys (SEQ ID NO: 822)
Pro Gly Thr Cys Gly Glu --- Cys Ala Tyr --- Ala Cys --- Gly Cys (SEQ ID NO: 823)
Pro Gly Thr Cys Gly Glu --- Cys Ala Tyr --- Ala Cys --- --- Cys (SEQ ID NO: 824)
Pro Gly Thr Cys Gly Glu --- Cys Ala Tyr --- Ala Cys Thr --- Cys (SEQ ID NO: 825)
Pro Gly Thr Cys Gly Glu --- Cys Ala Tyr Ala --- Cys Thr Gly Cys (SEQ ID NO: 826)
Pro Gly Thr Cys Gly Glu --- Cys Ala Tyr Ala --- Cys --- Gly Cys (SEQ ID NO: 827)
Pro Gly Thr Cys Gly Glu --- Cys Ala Tyr Ala --- Cys --- --- Cys (SEQ ID NO: 828)
Pro Gly Thr Cys Gly Glu --- Cys Ala Tyr Ala --- Cys Thr --- Cys (SEQ ID NO: 829)
Pro Gly Thr Cys Gly Glu --- Cys Ala Tyr Ala Ala Cys --- Gly Cys (SEQ ID NO: 830)
Pro Gly Thr Cys Gly Glu --- Cys Ala Tyr Ala Ala Cys --- --- Cys (SEQ ID NO: 831)
Pro Gly Thr Cys Gly Glu --- Cys Ala Tyr Ala Ala Cys Thr --- Cys (SEQ ID NO: 832)
Pro Gly Thr Cys Gly Glu Ile Cys --- Tyr Ala Ala Cys Thr Gly Cys (SEQ ID NO: 833)
Pro Gly Thr Cys Gly Glu Ile Cys --- --- Ala Ala Cys Thr Gly Cys (SEQ ID NO: 834)
Pro Gly Thr Cys Gly Glu Ile Cys --- --- --- Ala Cys Thr Gly Cys (SEQ ID NO: 835)
Pro Gly Thr Cys Gly Glu Ile Cys --- --- --- --- Cys Thr Gly Cys (SEQ ID NO: 836)
Pro Gly Thr Cys Gly Glu Ile Cys --- --- --- Ala Cys --- Gly Cys (SEQ ID NO: 837)
Pro Gly Thr Cys Gly Glu Ile Cys --- --- --- Ala Cys Thr --- Cys (SEQ ID NO: 838)
Pro Gly Thr Cys Gly Glu Ile Cys --- --- Ala --- Cys Thr Gly Cys (SEQ ID NO: 839)
Pro Gly Thr Cys Gly Glu Ile Cys --- --- Ala --- Cys --- Gly Cys (SEQ ID NO: 840)
Pro Gly Thr Cys Gly Glu Ile Cys --- --- Ala --- Cys Thr --- Cys (SEQ ID NO: 841)
Pro Gly Thr Cys Gly Glu Ile Cys --- --- Ala Ala Cys --- Gly Cys (SEQ ID NO: 842)
Pro Gly Thr Cys Gly Glu Ile Cys --- --- Ala Ala Cys --- --- Cys (SEQ ID NO: 843)
Pro Gly Thr Cys Gly Glu Ile Cys --- --- Ala Ala Cys Thr --- Cys (SEQ ID NO: 844)

FIG. 1P

```
Pro Gly Thr Cys Gly Glu Ile Cys --- Tyr --- Ala Cys Thr Gly Cys    (SEQ ID NO: 845)
Pro Gly Thr Cys Gly Glu Ile Cys --- Tyr --- --- Cys Thr Gly Cys    (SEQ ID NO: 846)
Pro Gly Thr Cys Gly Glu Ile Cys --- Tyr --- --- Cys --- Gly Cys    (SEQ ID NO: 847)
Pro Gly Thr Cys Gly Glu Ile Cys --- Tyr --- --- Cys Thr --- Cys    (SEQ ID NO: 848)
Pro Gly Thr Cys Gly Glu Ile Cys --- Tyr --- Ala Cys --- Gly Cys    (SEQ ID NO: 849)
Pro Gly Thr Cys Gly Glu Ile Cys --- Tyr --- Ala Cys --- --- Cys    (SEQ ID NO: 850)
Pro Gly Thr Cys Gly Glu Ile Cys --- Tyr --- Ala Cys Thr --- Cys    (SEQ ID NO: 851)
Pro Gly Thr Cys Gly Glu Ile Cys --- Tyr Ala --- Cys Thr Gly Cys    (SEQ ID NO: 852)
Pro Gly Thr Cys Gly Glu Ile Cys --- Tyr Ala --- Cys --- Gly Cys    (SEQ ID NO: 853)
Pro Gly Thr Cys Gly Glu Ile Cys --- Tyr Ala --- Cys --- --- Cys    (SEQ ID NO: 854)
Pro Gly Thr Cys Gly Glu Ile Cys --- Tyr Ala --- Cys Thr --- Cys    (SEQ ID NO: 855)
Pro Gly Thr Cys Gly Glu Ile Cys --- Tyr Ala Ala Cys --- Gly Cys    (SEQ ID NO: 856)
Pro Gly Thr Cys Gly Glu Ile Cys --- Tyr Ala Ala Cys --- --- Cys    (SEQ ID NO: 857)
Pro Gly Thr Cys Gly Glu Ile Cys --- Tyr Ala Ala Cys Thr --- Cys    (SEQ ID NO: 858)
Pro Gly Thr Cys Gly Glu Ile Cys Ala --- Ala Ala Cys Thr Gly Cys    (SEQ ID NO: 859)
Pro Gly Thr Cys Gly Glu Ile Cys Ala --- --- Ala Cys Thr Gly Cys    (SEQ ID NO: 860)
Pro Gly Thr Cys Gly Glu Ile Cys Ala --- --- --- Cys Thr Gly Cys    (SEQ ID NO: 861)
Pro Gly Thr Cys Gly Glu Ile Cys Ala --- --- --- Cys --- Gly Cys    (SEQ ID NO: 862)
Pro Gly Thr Cys Gly Glu Ile Cys Ala --- --- --- Cys Thr --- Cys    (SEQ ID NO: 863)
Pro Gly Thr Cys Gly Glu Ile Cys Ala --- --- Ala Cys --- Gly Cys    (SEQ ID NO: 864)
Pro Gly Thr Cys Gly Glu Ile Cys Ala --- --- Ala Cys --- --- Cys    (SEQ ID NO: 865)
Pro Gly Thr Cys Gly Glu Ile Cys Ala --- --- Ala Cys Thr --- Cys    (SEQ ID NO: 866)
Pro Gly Thr Cys Gly Glu Ile Cys Ala --- Ala --- Cys Thr Gly Cys    (SEQ ID NO: 867)
Pro Gly Thr Cys Gly Glu Ile Cys Ala --- Ala --- Cys --- Gly Cys    (SEQ ID NO: 868)
Pro Gly Thr Cys Gly Glu Ile Cys Ala --- Ala --- Cys --- --- Cys    (SEQ ID NO: 869)
Pro Gly Thr Cys Gly Glu Ile Cys Ala --- Ala --- Cys Thr --- Cys    (SEQ ID NO: 870)
Pro Gly Thr Cys Gly Glu Ile Cys Ala --- Ala Ala Cys --- Gly Cys    (SEQ ID NO: 871)
Pro Gly Thr Cys Gly Glu Ile Cys Ala --- Ala Ala Cys --- --- Cys    (SEQ ID NO: 872)
Pro Gly Thr Cys Gly Glu Ile Cys Ala --- Ala Ala Cys Thr --- Cys    (SEQ ID NO: 873)
Pro Gly Thr Cys Gly Glu Ile Cys Ala Tyr --- Ala Cys Thr Gly Cys    (SEQ ID NO: 874)
Pro Gly Thr Cys Gly Glu Ile Cys Ala Tyr --- --- Cys Thr Gly Cys    (SEQ ID NO: 875)
Pro Gly Thr Cys Gly Glu Ile Cys Ala Tyr --- --- Cys --- Gly Cys    (SEQ ID NO: 876)
Pro Gly Thr Cys Gly Glu Ile Cys Ala Tyr --- --- Cys --- --- Cys    (SEQ ID NO: 877)
Pro Gly Thr Cys Gly Glu Ile Cys Ala Tyr --- --- Cys Thr --- Cys    (SEQ ID NO: 878)
Pro Gly Thr Cys Gly Glu Ile Cys Ala Tyr --- Ala Cys --- Gly Cys    (SEQ ID NO: 879)
Pro Gly Thr Cys Gly Glu Ile Cys Ala Tyr --- Ala Cys --- --- Cys    (SEQ ID NO: 880)
Pro Gly Thr Cys Gly Glu Ile Cys Ala Tyr --- Ala Cys Thr --- Cys    (SEQ ID NO: 881)
Pro Gly Thr Cys Gly Glu Ile Cys Ala Tyr Ala --- Cys Thr Gly Cys    (SEQ ID NO: 882)
Pro Gly Thr Cys Gly Glu Ile Cys Ala Tyr Ala --- Cys --- Gly Cys    (SEQ ID NO: 883)
Pro Gly Thr Cys Gly Glu Ile Cys Ala Tyr Ala --- Cys --- --- Cys    (SEQ ID NO: 884)
Pro Gly Thr Cys Gly Glu Ile Cys Ala Tyr Ala --- Cys Thr --- Cys    (SEQ ID NO: 885)
Pro Gly Thr Cys Gly Glu Ile Cys Ala Tyr Ala Ala Cys --- Gly Cys    (SEQ ID NO: 886)
Pro Gly Thr Cys Gly Glu Ile Cys Ala Tyr Ala Ala Cys --- --- Cys    (SEQ ID NO: 887)
Pro Gly Thr Cys Gly Glu Ile Cys Ala Tyr Ala Ala Cys Thr --- Cys    (SEQ ID NO: 888)
```

FIG. 1Q

| | |
|---|---|
| Pro Gly Xaa' Thr Cys Gly Glu Ile Cys Ala Tyr Ala Ala Cys Thr Gly Cys | (SEQ ID NO: 889) |
| Pro Gly Xaa' Thr Cys Gly Glu Ile Cys Ala Tyr Ala Ala Cys Thr Gly Cys | (SEQ ID NO: 890) |
| Pro Gly Xaa' Xaa' Thr Cys Gly Glu Ile Cys Ala Tyr Ala Ala Cys Thr Gly Cys | (SEQ ID NO: 891) |
| Pro Gly Xaa' Xaa' Xaa' Thr Cys Gly Glu Ile Cys Ala Tyr Ala Ala Cys Thr Gly Cys | (SEQ ID NO: 892) |
| Pro Gly Xaa' Xaa' Xaa' Thr Cys Gly Glu Ile Cys Ala Tyr Ala Ala Cys Thr Gly Cys | (SEQ ID NO: 893) |
| Pro Gly Xaa' Xaa' Xaa' Thr Cys Xaa' Glu Ile Cys Ala Tyr Ala Ala Cys Thr Gly Cys | (SEQ ID NO: 894) |
| Pro Gly Xaa' Xaa' Xaa' Thr Cys Gly Xaa' Ile Cys Ala Tyr Ala Ala Cys Thr Gly Cys | (SEQ ID NO: 895) |
| Pro Gly Xaa' Xaa' Xaa' Thr Cys Gly Glu Xaa' Ile Cys Ala Tyr Ala Ala Cys Thr Gly Cys | (SEQ ID NO: 896) |
| Pro Gly Xaa' Xaa' Xaa' Thr Cys Gly Glu Ile Cys Xaa' Ala Tyr Ala Ala Cys Thr Gly Cys | (SEQ ID NO: 897) |
| Pro Gly Xaa' Xaa' Xaa' Thr Cys Gly Glu Ile Cys Ala Xaa' Tyr Ala Ala Cys Thr Gly Cys | (SEQ ID NO: 898) |
| Pro Gly Xaa' Xaa' Xaa' Thr Cys Gly Glu Ile Cys Ala Tyr Xaa' Ala Ala Cys Thr Gly Cys | (SEQ ID NO: 899) |
| Pro Gly Xaa' Xaa' Xaa' Thr Cys Gly Glu Ile Cys Ala Tyr Ala Xaa' Ala Cys Thr Gly Cys | (SEQ ID NO: 900) |
| Pro Gly Xaa' Xaa' Xaa' Thr Cys Gly Glu Ile Cys Ala Tyr Ala Ala Xaa' Cys Thr Gly Cys | (SEQ ID NO: 901) |
| Pro Gly Xaa' Xaa' Xaa' Thr Cys Gly Glu Ile Cys Ala Tyr Ala Xaa' Ala Cys Thr Gly Cys | (SEQ ID NO: 902) |
| Pro Gly Xaa' Xaa' Xaa' Thr Cys Gly Glu Ile Cys Ala Tyr Ala Ala Cys Xaa' Thr Gly Cys | (SEQ ID NO: 903) |
| Pro Gly Xaa' Xaa' Xaa' Thr Cys Gly Glu Ile Cys Ala Tyr Ala Ala Cys Thr Xaa' Gly Cys | (SEQ ID NO: 904) |
| Pro Gly Xaa' Xaa' Xaa' Thr Cys Gly Glu Ile Cys Ala Tyr Ala Ala Cys Thr Gly Xaa' Cys | (SEQ ID NO: 905) |
| Pro Gly Xaa' Xaa' Xaa' Thr Cys Gly Glu Ile Cys Ala Tyr Ala Ala Cys Thr Gly Cys Xaa' | (SEQ ID NO: 906) |
| Pro Gly Xaa' Thr Xaa' Cys Gly Glu Ile Cys Ala Tyr Ala Ala Cys Thr Gly Cys | (SEQ ID NO: 907) |
| Pro Gly Xaa' Thr Xaa' Cys Xaa' Gly Glu Ile Cys Ala Tyr Ala Ala Cys Thr Gly Cys | (SEQ ID NO: 908) |
| Pro Gly Xaa' Thr Xaa' Cys Gly Xaa' Glu Ile Cys Ala Tyr Ala Ala Cys Thr Gly Cys | (SEQ ID NO: 909) |
| Pro Gly Xaa' Thr Xaa' Cys Gly Xaa' Glu Ile Cys Ala Tyr Ala Ala Cys Thr Gly Cys | (SEQ ID NO: 910) |
| Pro Gly Xaa' Thr Xaa' Cys Gly Glu Xaa' Ile Cys Ala Tyr Ala Ala Cys Thr Gly Cys | (SEQ ID NO: 911) |
| Pro Gly Xaa' Thr Xaa' Cys Gly Glu Ile Xaa' Cys Ala Tyr Ala Ala Cys Thr Gly Cys | (SEQ ID NO: 912) |
| Pro Gly Xaa' Thr Xaa' Cys Gly Glu Ile Cys Xaa' Ala Tyr Ala Ala Cys Thr Gly Cys | (SEQ ID NO: 913) |
| Pro Gly Xaa' Thr Xaa' Cys Gly Glu Ile Cys Ala Xaa' Tyr Ala Ala Cys Thr Gly Cys | (SEQ ID NO: 914) |
| Pro Gly Xaa' Thr Xaa' Cys Gly Glu Ile Cys Ala Tyr Xaa' Ala Ala Cys Thr Gly Cys | (SEQ ID NO: 915) |
| Pro Gly Xaa' Thr Xaa' Cys Gly Glu Ile Cys Ala Tyr Ala Xaa' Ala Cys Thr Gly Cys | (SEQ ID NO: 916) |
| Pro Gly Xaa' Thr Xaa' Cys Gly Glu Ile Cys Ala Tyr Ala Ala Xaa' Cys Thr Gly Cys | (SEQ ID NO: 917) |
| Pro Gly Xaa' Thr Xaa' Cys Gly Glu Ile Cys Ala Tyr Ala Ala Cys Xaa' Thr Gly Cys | (SEQ ID NO: 918) |
| Pro Gly Xaa' Thr Xaa' Cys Gly Glu Ile Cys Ala Tyr Ala Ala Cys Thr Xaa' Gly Cys | (SEQ ID NO: 919) |
| Pro Gly Xaa' Thr Xaa' Cys Gly Glu Ile Cys Ala Tyr Ala Ala Cys Thr Gly Xaa' Cys | (SEQ ID NO: 920) |
| Pro Gly Xaa' Thr Xaa' Cys Gly Glu Ile Cys Ala Tyr Ala Ala Cys Thr Gly Cys Xaa' | (SEQ ID NO: 921) |
| Pro Gly Xaa' Thr Xaa' Cys Xaa' Gly Glu Ile Cys Ala Tyr Ala Ala Cys Thr Gly Cys | (SEQ ID NO: 922) |

FIG. 2A

| | | | | | | | | | | |
|---|---|---|---|---|---|---|---|---|---|---|
| Pro | Gly | Xaa' | Xaa' | Xaa' | Gly | Glu | Ile | Cys | Ala | Tyr | Ala | Ala | Cys | Thr | Gly | Cys | (SEQ ID NO: 923) |

FIG. 2B

Pro Gly Xaa' Thr Cys Gly Glu Xaa' Ile Cys Ala Tyr Ala Ala Cys Xaa' Thr Gly Cys (SEQ ID NO: 957)
Pro Gly Xaa' Thr Cys Gly Glu Xaa' Ile Cys Ala Tyr Ala Ala Cys Thr Xaa' Gly Cys (SEQ ID NO: 958)
Pro Gly Xaa' Thr Cys Gly Glu Xaa' Ile Cys Ala Tyr Ala Ala Cys Thr Gly Xaa' Cys (SEQ ID NO: 959)
Pro Gly Xaa' Thr Cys Gly Glu Xaa' Ile Cys Ala Tyr Ala Ala Cys Thr Gly Cys Xaa' (SEQ ID NO: 960)
Pro Gly Xaa' Thr Cys Gly Glu Ile Xaa' Cys Ala Tyr Ala Ala Cys Thr Gly Cys (SEQ ID NO: 961)
Pro Gly Xaa' Thr Cys Gly Glu Ile Cys Xaa' Ala Tyr Ala Ala Cys Thr Gly Cys (SEQ ID NO: 962)
Pro Gly Xaa' Thr Cys Gly Glu Ile Cys Ala Xaa' Tyr Ala Ala Cys Thr Gly Cys (SEQ ID NO: 963)
Pro Gly Xaa' Thr Cys Gly Glu Ile Cys Ala Tyr Xaa' Ala Ala Cys Thr Gly Cys (SEQ ID NO: 964)
Pro Gly Xaa' Thr Cys Gly Glu Ile Cys Ala Tyr Ala Xaa' Ala Cys Thr Gly Cys (SEQ ID NO: 965)
Pro Gly Xaa' Thr Cys Gly Glu Ile Cys Ala Tyr Ala Ala Xaa' Cys Thr Gly Cys (SEQ ID NO: 966)
Pro Gly Xaa' Thr Cys Gly Glu Ile Cys Ala Tyr Ala Ala Cys Xaa' Thr Gly Cys (SEQ ID NO: 967)
Pro Gly Xaa' Thr Cys Gly Glu Ile Cys Ala Tyr Ala Ala Cys Thr Xaa' Gly Cys (SEQ ID NO: 968)
Pro Gly Xaa' Thr Cys Gly Glu Ile Cys Ala Tyr Ala Ala Cys Thr Gly Xaa' Cys (SEQ ID NO: 969)
Pro Gly Xaa' Thr Cys Gly Glu Ile Cys Ala Tyr Ala Ala Cys Thr Gly Cys Xaa' (SEQ ID NO: 970)
Pro Gly Xaa' Thr Cys Gly Glu Ile Cys Xaa' Ala Tyr Ala Ala Cys Thr Gly Cys (SEQ ID NO: 971)
Pro Gly Xaa' Thr Cys Gly Glu Ile Cys Ala Xaa' Tyr Ala Ala Cys Thr Gly Cys (SEQ ID NO: 972)
Pro Gly Xaa' Thr Cys Gly Glu Ile Cys Ala Tyr Xaa' Ala Ala Cys Thr Gly Cys (SEQ ID NO: 973)
Pro Gly Xaa' Thr Cys Gly Glu Ile Cys Ala Tyr Ala Xaa' Ala Cys Thr Gly Cys (SEQ ID NO: 974)
Pro Gly Xaa' Thr Cys Gly Glu Ile Cys Ala Tyr Ala Ala Xaa' Cys Thr Gly Cys (SEQ ID NO: 975)
Pro Gly Xaa' Thr Cys Gly Glu Ile Cys Ala Tyr Ala Ala Cys Xaa' Thr Gly Cys (SEQ ID NO: 976)
Pro Gly Xaa' Thr Cys Gly Glu Ile Cys Ala Tyr Ala Ala Cys Thr Xaa' Gly Cys (SEQ ID NO: 977)
Pro Gly Xaa' Thr Cys Gly Glu Ile Cys Ala Tyr Ala Ala Cys Thr Gly Xaa' Cys (SEQ ID NO: 978)
Pro Gly Xaa' Thr Cys Gly Glu Ile Cys Ala Tyr Ala Ala Cys Thr Gly Cys Xaa' (SEQ ID NO: 979)
Pro Gly Xaa' Thr Cys Gly Glu Ile Cys Ala Xaa' Tyr Ala Ala Cys Thr Gly Cys (SEQ ID NO: 980)
Pro Gly Xaa' Thr Cys Gly Glu Ile Cys Ala Tyr Xaa' Ala Ala Cys Thr Gly Cys (SEQ ID NO: 981)
Pro Gly Xaa' Thr Cys Gly Glu Ile Cys Ala Tyr Ala Xaa' Ala Cys Thr Gly Cys (SEQ ID NO: 982)
Pro Gly Xaa' Thr Cys Gly Glu Ile Cys Ala Tyr Ala Ala Xaa' Cys Thr Gly Cys (SEQ ID NO: 983)
Pro Gly Xaa' Thr Cys Gly Glu Ile Cys Ala Tyr Ala Ala Cys Xaa' Thr Gly Cys (SEQ ID NO: 984)
Pro Gly Xaa' Thr Cys Gly Glu Ile Cys Ala Tyr Ala Ala Cys Thr Xaa' Gly Cys (SEQ ID NO: 985)
Pro Gly Xaa' Thr Cys Gly Glu Ile Cys Ala Tyr Ala Ala Cys Thr Gly Xaa' Cys (SEQ ID NO: 986)
Pro Gly Xaa' Thr Cys Gly Glu Ile Cys Ala Tyr Ala Ala Cys Thr Gly Cys Xaa' (SEQ ID NO: 987)
Pro Gly Xaa' Thr Cys Gly Glu Ile Cys Ala Tyr Ala Ala Cys Thr Gly Cys (SEQ ID NO: 988)
Pro Gly Xaa' Thr Cys Gly Glu Ile Cys Ala Tyr Ala Ala Cys Thr Gly Xaa' Cys (SEQ ID NO: 989)
Pro Gly Xaa' Thr Cys Gly Glu Ile Cys Ala Xaa' Tyr Ala Ala Cys Thr Gly Cys Xaa' (SEQ ID NO: 990)

FIG. 2C

| | | | | | | | | | | | | |
|---|---|---|---|---|---|---|---|---|---|---|---|---|
| Pro | Gly | Xaa' | Thr | Cys | Gly | Glu | Ile | Cys | Ala | Tyr | Xaa' | Ala | Ala | Cys | Thr | Gly | Cys | (SEQ ID NO: 991) |
| Pro | Gly | Xaa' | Thr | Cys | Gly | Glu | Ile | Cys | Ala | Tyr | Xaa' | Ala | Xaa' | Ala | Cys | Thr | Gly | Cys | (SEQ ID NO: 992) |
| Pro | Gly | Xaa' | Thr | Cys | Gly | Glu | Ile | Cys | Ala | Tyr | Xaa' | Ala | Ala | Xaa' | Cys | Thr | Gly | Cys | (SEQ ID NO: 993) |
| Pro | Gly | Xaa' | Thr | Cys | Gly | Glu | Ile | Cys | Ala | Tyr | Xaa' | Ala | Ala | Cys | Xaa' | Thr | Gly | Cys | (SEQ ID NO: 994) |
| Pro | Gly | Xaa' | Thr | Cys | Gly | Glu | Ile | Cys | Ala | Tyr | Xaa' | Ala | Ala | Cys | Thr | Xaa' | Gly | Cys | (SEQ ID NO: 995) |
| Pro | Gly | Xaa' | Thr | Cys | Gly | Glu | Ile | Cys | Ala | Tyr | Xaa' | Ala | Ala | Cys | Thr | Gly | Xaa' | Cys | (SEQ ID NO: 996) |
| Pro | Gly | Xaa' | Thr | Cys | Gly | Glu | Ile | Cys | Ala | Tyr | Xaa' | Ala | Ala | Cys | Thr | Gly | Cys | Xaa' | (SEQ ID NO: 997) |
| Pro | Gly | Xaa' | Thr | Cys | Gly | Glu | Ile | Cys | Ala | Tyr | Ala | Ala | Cys | Thr | Gly | Cys | Xaa' | (SEQ ID NO: 998) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 999) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 1000) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 1001) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 1002) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 1003) |
| Pro | Gly | Xaa' | Thr | Cys | Gly | Glu | Ile | Cys | Ala | Tyr | Ala | Xaa' | Ala | Cys | Thr | Gly | Cys | Xaa' | (SEQ ID NO: 1004) |
| Pro | Gly | Xaa' | Thr | Cys | Gly | Glu | Ile | Cys | Ala | Tyr | Ala | Xaa' | Ala | Cys | Thr | Gly | Cys | Xaa' | (SEQ ID NO: 1005) |
| Pro | Gly | Xaa' | Thr | Cys | Gly | Glu | Ile | Cys | Ala | Tyr | Ala | Ala | Xaa' | Cys | Thr | Gly | Cys | (SEQ ID NO: 1006) |
| Pro | Gly | Xaa' | Thr | Cys | Gly | Glu | Ile | Cys | Ala | Tyr | Ala | Ala | Xaa' | Cys | Thr | Gly | Cys | (SEQ ID NO: 1007) |
| Pro | Gly | Xaa' | Thr | Cys | Gly | Glu | Ile | Cys | Ala | Tyr | Ala | Ala | Xaa' | Cys | Thr | Gly | Cys | (SEQ ID NO: 1008) |
| Pro | Gly | Xaa' | Thr | Cys | Gly | Glu | Ile | Cys | Ala | Tyr | Ala | Ala | Xaa' | Cys | Thr | Gly | Cys | (SEQ ID NO: 1009) |
| Pro | Gly | Xaa' | Thr | Cys | Gly | Glu | Ile | Cys | Ala | Tyr | Ala | Ala | Xaa' | Cys | Thr | Gly | Cys | Xaa' | (SEQ ID NO: 1010) |
| Pro | Gly | Xaa' | Thr | Cys | Gly | Glu | Ile | Cys | Ala | Tyr | Ala | Ala | Xaa' | Cys | Thr | Gly | Cys | Xaa' | (SEQ ID NO: 1011) |
| Pro | Gly | Xaa' | Thr | Cys | Gly | Glu | Ile | Cys | Ala | Tyr | Ala | Ala | Cys | Xaa' | Thr | Gly | Cys | (SEQ ID NO: 1012) |
| Pro | Gly | Xaa' | Thr | Cys | Gly | Glu | Ile | Cys | Ala | Tyr | Ala | Ala | Cys | Xaa' | Thr | Gly | Cys | (SEQ ID NO: 1013) |
| Pro | Gly | Xaa' | Thr | Cys | Gly | Glu | Ile | Cys | Ala | Tyr | Ala | Ala | Cys | Xaa' | Thr | Gly | Cys | (SEQ ID NO: 1014) |
| Pro | Gly | Xaa' | Thr | Cys | Gly | Glu | Ile | Cys | Ala | Tyr | Ala | Ala | Cys | Xaa' | Thr | Gly | Cys | Xaa' | (SEQ ID NO: 1015) |
| Pro | Gly | Xaa' | Thr | Cys | Gly | Glu | Ile | Cys | Ala | Tyr | Ala | Ala | Cys | Xaa' | Thr | Gly | Cys | Xaa' | (SEQ ID NO: 1016) |
| Pro | Gly | Xaa' | Thr | Cys | Gly | Glu | Ile | Cys | Ala | Tyr | Ala | Ala | Cys | Thr | Xaa' | Gly | Cys | (SEQ ID NO: 1017) |
| Pro | Gly | Xaa' | Thr | Cys | Gly | Glu | Ile | Cys | Ala | Tyr | Ala | Ala | Cys | Thr | Xaa' | Gly | Cys | (SEQ ID NO: 1018) |
| Pro | Gly | Xaa' | Thr | Cys | Gly | Glu | Ile | Cys | Ala | Tyr | Ala | Ala | Cys | Thr | Xaa' | Gly | Cys | Xaa' | (SEQ ID NO: 1019) |
| Pro | Gly | Xaa' | Thr | Cys | Gly | Glu | Ile | Cys | Ala | Tyr | Ala | Ala | Cys | Thr | Gly | Xaa' | Cys | (SEQ ID NO: 1020) |
| Pro | Gly | Xaa' | Thr | Cys | Gly | Glu | Ile | Cys | Ala | Tyr | Ala | Ala | Cys | Thr | Gly | Xaa' | Cys | Xaa' | (SEQ ID NO: 1021) |
| Pro | Gly | Xaa' | Thr | Cys | Gly | Glu | Ile | Cys | Ala | Tyr | Ala | Ala | Cys | Thr | Gly | Cys | Xaa' | (SEQ ID NO: 1022) |
| Pro | Gly | Xaa' | Thr | Cys | Gly | Glu | Ile | Cys | Ala | Tyr | Ala | Ala | Cys | Thr | Gly | Cys | Xaa' | (SEQ ID NO: 1023) |
| Pro | Gly | Xaa' | Thr | Cys | Gly | Glu | Ile | Cys | Ala | Tyr | Ala | Ala | Cys | Thr | Gly | Cys | Xaa' | (SEQ ID NO: 1024) |

FIG. 2D

| | | |
|---|---|---|
| Pro Gly Xaa' Thr Xaa' Thr Cys Gly Glu Ile Cys Ala Tyr Ala Ala Cys Thr Gly Cys Xaa' Xaa' | (SEQ ID NO: 1025) |
| Pro Gly Xaa' Thr Xaa' Cys Gly Glu Ile Cys Ala Tyr Ala Ala Cys Thr Gly Cys | (SEQ ID NO: 1026) |
| Pro Gly Xaa' Thr Xaa' Xaa' Cys Gly Glu Ile Cys Ala Tyr Ala Ala Cys Thr Gly Cys | (SEQ ID NO: 1027) |
| Pro Gly Xaa' Thr Xaa' Xaa' Cys Xaa' Gly Glu Ile Cys Ala Tyr Ala Ala Cys Thr Gly Cys | (SEQ ID NO: 1028) |
| Pro Gly Xaa' Thr Xaa' Xaa' Cys Xaa' Gly Xaa' Ile Cys Ala Tyr Ala Ala Cys Thr Gly Cys | (SEQ ID NO: 1029) |
| Pro Gly Xaa' Thr Xaa' Xaa' Cys Xaa' Gly Glu Xaa' Cys Ala Tyr Ala Ala Cys Thr Gly Cys | (SEQ ID NO: 1030) |
| Pro Gly Xaa' Thr Xaa' Xaa' Cys Xaa' Gly Glu Ile Xaa' Ala Tyr Ala Ala Cys Thr Gly Cys | (SEQ ID NO: 1031) |
| Pro Gly Xaa' Thr Xaa' Xaa' Cys Xaa' Gly Glu Ile Cys Xaa' Tyr Ala Ala Cys Thr Gly Cys | (SEQ ID NO: 1032) |
| Pro Gly Xaa' Thr Xaa' Xaa' Cys Xaa' Gly Glu Ile Cys Ala Xaa' Ala Ala Cys Thr Gly Cys | (SEQ ID NO: 1033) |
| Pro Gly Xaa' Thr Xaa' Xaa' Cys Xaa' Gly Glu Ile Cys Ala Tyr Xaa' Ala Cys Thr Gly Cys | (SEQ ID NO: 1034) |
| Pro Gly Xaa' Thr Xaa' Xaa' Cys Xaa' Gly Glu Ile Cys Ala Tyr Ala Xaa' Cys Thr Gly Cys | (SEQ ID NO: 1035) |
| Pro Gly Xaa' Thr Xaa' Xaa' Cys Xaa' Gly Glu Ile Cys Ala Tyr Ala Ala Xaa' Thr Gly Cys | (SEQ ID NO: 1036) |
| Pro Gly Xaa' Thr Xaa' Xaa' Cys Xaa' Gly Glu Ile Cys Ala Tyr Ala Ala Cys Xaa' Gly Cys | (SEQ ID NO: 1037) |
| Pro Gly Xaa' Thr Xaa' Xaa' Cys Xaa' Gly Glu Ile Cys Ala Tyr Ala Ala Cys Thr Xaa' Cys | (SEQ ID NO: 1038) |
| Pro Gly Xaa' Thr Xaa' Xaa' Cys Xaa' Gly Glu Ile Cys Ala Tyr Ala Ala Cys Thr Gly Xaa' | (SEQ ID NO: 1039) |
| Pro Gly Xaa' Thr Xaa' Xaa' Cys Xaa' Gly Xaa' Ile Cys Ala Tyr Ala Ala Cys Thr Gly Cys | (SEQ ID NO: 1040) |
| Pro Gly Xaa' Thr Xaa' Xaa' Cys Xaa' Gly Xaa' Ile Cys Ala Tyr Ala Ala Cys Thr Gly Cys Xaa' | (SEQ ID NO: 1041) |
| Pro Gly Xaa' Thr Xaa' Xaa' Cys Xaa' Gly Xaa' Ile Cys Ala Tyr Ala Ala Cys Thr Gly Cys | (SEQ ID NO: 1042) |
| Pro Gly Xaa' Thr Xaa' Xaa' Cys Xaa' Gly Glu Ile Cys Ala Tyr Ala Ala Cys Thr Gly Cys | (SEQ ID NO: 1043) |
| Pro Gly Xaa' Thr Xaa' Xaa' Cys Xaa' Gly Ile Ile Cys Ala Tyr Ala Ala Xaa' Cys Thr Gly Cys | (SEQ ID NO: 1044) |
| Pro Gly Xaa' Thr Xaa' Xaa' Cys Xaa' Gly Xaa' Ile Cys Ala Tyr Ala Ala Xaa' Cys Thr Gly Cys | (SEQ ID NO: 1045) |
| Pro Gly Xaa' Thr Xaa' Xaa' Cys Xaa' Gly Ile Ile Cys Ala Tyr Ala Ala Cys Thr Gly Cys | (SEQ ID NO: 1046) |
| Pro Gly Xaa' Thr Xaa' Xaa' Cys Xaa' Gly Ile Ile Cys Ala Tyr Xaa' Ala Cys Thr Gly Cys | (SEQ ID NO: 1047) |
| Pro Gly Xaa' Thr Xaa' Xaa' Cys Xaa' Gly Ile Ile Cys Ala Tyr Ala Ala Cys Thr Gly Cys | (SEQ ID NO: 1048) |
| Pro Gly Xaa' Thr Xaa' Xaa' Cys Xaa' Gly Ile Ile Cys Ala Tyr Ala Xaa' Cys Thr Gly Cys | (SEQ ID NO: 1049) |
| Pro Gly Xaa' Thr Xaa' Xaa' Cys Xaa' Gly Ile Ile Cys Ala Tyr Ala Ala Xaa' Thr Gly Cys | (SEQ ID NO: 1050) |
| Pro Gly Xaa' Thr Xaa' Xaa' Cys Xaa' Gly Ile Ile Cys Ala Tyr Ala Ala Cys Thr Gly Cys | (SEQ ID NO: 1051) |
| Pro Gly Xaa' Thr Xaa' Xaa' Cys Xaa' Gly Ile Ile Cys Ala Tyr Ala Ala Cys Thr Gly Cys | (SEQ ID NO: 1052) |
| Pro Gly Xaa' Thr Xaa' Xaa' Cys Xaa' Gly Ile Ile Cys Ala Tyr Ala Ala Cys Thr Gly Cys | (SEQ ID NO: 1053) |
| Pro Gly Xaa' Thr Xaa' Xaa' Cys Xaa' Gly Ile Ile Cys Ala Tyr Ala Ala Cys Thr Gly Cys Xaa' | (SEQ ID NO: 1054) |
| Pro Gly Xaa' Thr Xaa' Gly Cys Xaa' Gly Ile Ile Cys Ala Tyr Ala Ala Cys Thr Gly Cys | (SEQ ID NO: 1055) |
| Pro Gly Gly Thr Xaa' Xaa' Cys Gly Xaa' Ile Cys Ala Tyr Ala Ala Cys Thr Gly Cys Xaa' | (SEQ ID NO: 1056) |
| Pro Gly Gly Thr Xaa' Xaa' Cys Gly Ile Ile Cys Ala Tyr Ala Ala Cys Thr Gly Cys | (SEQ ID NO: 1057) |
| Pro Gly Xaa' Thr Xaa' Xaa' Cys Gly Xaa' Ile Cys Ala Tyr Ala Ala Cys Thr Gly Cys | (SEQ ID NO: 1058) |

FIG. 2E

Pro Gly Xaa' Thr Xaa' Cys Gly Xaa' Glu Ile Xaa' Cys Ala Tyr Ala Ala Cys Thr Gly Cys (SEQ ID NO: 1059)
Pro Gly Xaa' Thr Xaa' Cys Gly Xaa' Glu Ile Xaa' Cys Xaa' Ala Tyr Ala Ala Cys Thr Gly Cys (SEQ ID NO: 1060)
Pro Gly Xaa' Thr Xaa' Cys Gly Xaa' Glu Ile Xaa' Cys Ala Xaa' Tyr Ala Ala Cys Thr Gly Cys (SEQ ID NO: 1061)
Pro Gly Xaa' Thr Xaa' Cys Gly Xaa' Glu Ile Xaa' Cys Ala Tyr Xaa' Ala Ala Cys Thr Gly Cys (SEQ ID NO: 1062)
Pro Gly Xaa' Thr Xaa' Cys Gly Xaa' Glu Ile Xaa' Cys Ala Tyr Ala Xaa' Ala Cys Thr Gly Cys (SEQ ID NO: 1063)
Pro Gly Xaa' Thr Xaa' Cys Gly Xaa' Glu Ile Xaa' Cys Ala Tyr Ala Ala Xaa' Cys Thr Gly Cys (SEQ ID NO: 1064)
Pro Gly Xaa' Thr Xaa' Cys Gly Xaa' Glu Ile Xaa' Cys Ala Tyr Ala Ala Cys Xaa' Thr Gly Cys (SEQ ID NO: 1065)
Pro Gly Xaa' Thr Xaa' Cys Gly Xaa' Glu Ile Xaa' Cys Ala Tyr Ala Ala Cys Thr Xaa' Gly Cys (SEQ ID NO: 1066)
Pro Gly Xaa' Thr Xaa' Cys Gly Xaa' Glu Ile Xaa' Cys Ala Tyr Ala Ala Cys Thr Gly Xaa' Cys (SEQ ID NO: 1067)
Pro Gly Xaa' Thr Xaa' Cys Gly Xaa' Glu Ile Xaa' Cys Ala Tyr Ala Ala Cys Thr Gly Cys Xaa' (SEQ ID NO: 1068)
Pro Gly Xaa' Thr Xaa' Cys Gly Xaa' Glu Ile Xaa' Xaa' Ile Cys Ala Tyr Ala Ala Cys Thr Gly Cys (SEQ ID NO: 1069)
Pro Gly Xaa' Thr Xaa' Cys Gly Xaa' Glu Ile Xaa' Xaa' Ile Cys Xaa' Ala Tyr Ala Ala Cys Thr Gly Cys (SEQ ID NO: 1070)
Pro Gly Xaa' Thr Xaa' Cys Gly Xaa' Glu Ile Xaa' Xaa' Ile Cys Ala Xaa' Tyr Ala Ala Cys Thr Gly Cys (SEQ ID NO: 1071)
Pro Gly Xaa' Thr Xaa' Cys Gly Xaa' Glu Ile Xaa' Xaa' Ile Cys Ala Tyr Xaa' Ala Ala Cys Thr Gly Cys (SEQ ID NO: 1072)
Pro Gly Xaa' Thr Xaa' Cys Gly Xaa' Glu Ile Xaa' Xaa' Ile Cys Ala Tyr Ala Xaa' Ala Cys Thr Gly Cys (SEQ ID NO: 1073)
Pro Gly Xaa' Thr Xaa' Cys Gly Xaa' Glu Ile Xaa' Xaa' Ile Cys Ala Tyr Ala Ala Xaa' Cys Thr Gly Cys (SEQ ID NO: 1074)
Pro Gly Xaa' Thr Xaa' Cys Gly Xaa' Glu Ile Xaa' Xaa' Ile Cys Ala Tyr Ala Ala Cys Xaa' Thr Gly Cys (SEQ ID NO: 1075)
Pro Gly Xaa' Thr Xaa' Cys Gly Xaa' Glu Ile Xaa' Xaa' Ile Cys Ala Tyr Ala Ala Cys Thr Xaa' Gly Cys (SEQ ID NO: 1076)
Pro Gly Xaa' Thr Xaa' Cys Gly Xaa' Glu Ile Xaa' Xaa' Ile Cys Ala Tyr Ala Ala Cys Thr Gly Xaa' Cys (SEQ ID NO: 1077)
Pro Gly Xaa' Thr Xaa' Cys Gly Xaa' Glu Ile Xaa' Xaa' Ile Cys Ala Tyr Ala Ala Cys Thr Gly Cys Xaa' (SEQ ID NO: 1078)
Pro Gly Xaa' Thr Xaa' Cys Gly Xaa' Glu Ile Xaa' Cys Ala Tyr Ala Ala Cys Thr Gly Cys (SEQ ID NO: 1079)
Pro Gly Xaa' Thr Xaa' Cys Gly Xaa' Glu Ile Xaa' Cys Xaa' Ala Tyr Ala Ala Cys Thr Gly Cys (SEQ ID NO: 1080)
Pro Gly Xaa' Thr Xaa' Cys Gly Xaa' Glu Ile Xaa' Cys Ala Xaa' Tyr Ala Ala Cys Thr Gly Cys (SEQ ID NO: 1081)
Pro Gly Xaa' Thr Xaa' Cys Gly Xaa' Glu Ile Xaa' Cys Ala Tyr Xaa' Ala Ala Cys Thr Gly Cys (SEQ ID NO: 1082)
Pro Gly Xaa' Thr Xaa' Cys Gly Xaa' Glu Ile Xaa' Cys Ala Tyr Ala Xaa' Ala Cys Thr Gly Cys (SEQ ID NO: 1083)
Pro Gly Xaa' Thr Xaa' Cys Gly Xaa' Glu Ile Xaa' Cys Ala Tyr Ala Ala Xaa' Cys Thr Gly Cys (SEQ ID NO: 1084)
Pro Gly Xaa' Thr Xaa' Cys Gly Xaa' Glu Ile Xaa' Cys Ala Tyr Ala Ala Cys Xaa' Thr Gly Cys (SEQ ID NO: 1085)
Pro Gly Xaa' Thr Xaa' Cys Gly Xaa' Glu Ile Xaa' Cys Ala Tyr Ala Ala Cys Thr Xaa' Gly Cys (SEQ ID NO: 1086)
Pro Gly Xaa' Thr Xaa' Cys Gly Xaa' Glu Ile Xaa' Cys Ala Tyr Ala Ala Cys Thr Gly Xaa' Cys (SEQ ID NO: 1087)
Pro Gly Xaa' Thr Xaa' Cys Gly Xaa' Glu Ile Xaa' Cys Ala Tyr Ala Ala Cys Thr Gly Cys Xaa' (SEQ ID NO: 1088)
Pro Gly Xaa' Thr Xaa' Cys Gly Xaa' Glu Ile Ile Cys Ala Tyr Ala Ala Cys Thr Gly Cys (SEQ ID NO: 1089)
Pro Gly Xaa' Thr Xaa' Cys Gly Xaa' Glu Ile Ile Cys Xaa' Ala Tyr Ala Ala Cys Thr Gly Cys (SEQ ID NO: 1090)
Pro Gly Xaa' Thr Xaa' Cys Gly Xaa' Glu Ile Ile Cys Ala Xaa' Tyr Ala Ala Cys Thr Gly Cys Xaa' (SEQ ID NO: 1091)
Pro Gly Xaa' Thr Xaa' Cys Gly Xaa' Glu Ile Ile Cys Ala Tyr Ala Ala Cys Thr Gly Cys (SEQ ID NO: 1092)

FIG. 2F

| | | | | | | | | | | | |
|---|---|---|---|---|---|---|---|---|---|---|---|
| Pro Gly Xaa' Thr Xaa' Cys Gly Glu Ile Cys Xaa' Ala Tyr Ala Ala Cys Thr Gly Cys | (SEQ ID NO: 1093) |
| Pro Gly Xaa' Thr Xaa' Cys Gly Glu Ile Cys Xaa' Ala Xaa' Tyr Ala Ala Cys Thr Gly Cys | (SEQ ID NO: 1094) |
| Pro Gly Xaa' Thr Xaa' Cys Gly Glu Ile Cys Xaa' Ala Tyr Xaa' Ala Ala Cys Thr Gly Cys | (SEQ ID NO: 1095) |
| Pro Gly Xaa' Thr Xaa' Cys Gly Glu Ile Cys Xaa' Ala Tyr Ala Xaa' Ala Cys Thr Gly Cys | (SEQ ID NO: 1096) |
| Pro Gly Xaa' Thr Xaa' Cys Gly Glu Ile Cys Xaa' Ala Tyr Ala Ala Xaa' Cys Thr Gly Cys | (SEQ ID NO: 1097) |
| Pro Gly Xaa' Thr Xaa' Cys Gly Glu Ile Cys Xaa' Ala Tyr Ala Ala Cys Xaa' Thr Gly Cys | (SEQ ID NO: 1098) |
| Pro Gly Xaa' Thr Xaa' Cys Gly Glu Ile Cys Xaa' Ala Tyr Ala Ala Cys Thr Xaa' Gly Cys | (SEQ ID NO: 1099) |
| Pro Gly Xaa' Thr Xaa' Cys Gly Glu Ile Cys Xaa' Ala Tyr Ala Ala Cys Thr Gly Xaa' Cys | (SEQ ID NO: 1100) |
| Pro Gly Xaa' Thr Xaa' Cys Gly Glu Ile Cys Xaa' Ala Tyr Ala Ala Cys Thr Gly Cys Xaa' | (SEQ ID NO: 1101) |
| Pro Gly Xaa' Thr Xaa' Cys Gly Glu Ile Cys Ala Xaa' Ala Ala Cys Thr Gly Cys | (SEQ ID NO: 1102) |
| Pro Gly Xaa' Thr Xaa' Cys Gly Glu Ile Cys Xaa' Ala Xaa' Tyr Ala Ala Cys Thr Gly Cys | (SEQ ID NO: 1103) |
| Pro Gly Xaa' Thr Xaa' Cys Gly Glu Ile Cys Xaa' Tyr Xaa' Ala Ala Cys Thr Gly Cys | (SEQ ID NO: 1104) |
| Pro Gly Xaa' Thr Xaa' Cys Gly Glu Ile Cys Xaa' Tyr Ala Xaa' Ala Cys Thr Gly Cys | (SEQ ID NO: 1105) |
| Pro Gly Xaa' Thr Xaa' Cys Gly Glu Ile Cys Xaa' Tyr Ala Ala Xaa' Cys Thr Gly Cys | (SEQ ID NO: 1106) |
| Pro Gly Xaa' Thr Xaa' Cys Gly Glu Ile Cys Xaa' Tyr Ala Ala Cys Xaa' Thr Gly Cys | (SEQ ID NO: 1107) |
| Pro Gly Xaa' Thr Xaa' Cys Gly Glu Ile Cys Xaa' Tyr Ala Ala Cys Thr Xaa' Gly Cys | (SEQ ID NO: 1108) |
| Pro Gly Xaa' Thr Xaa' Cys Gly Glu Ile Cys Xaa' Tyr Ala Ala Cys Thr Gly Xaa' Cys | (SEQ ID NO: 1109) |
| Pro Gly Xaa' Thr Xaa' Cys Gly Glu Ile Cys Xaa' Tyr Ala Ala Cys Thr Gly Cys Xaa' | (SEQ ID NO: 1110) |
| Pro Gly Xaa' Thr Xaa' Cys Gly Glu Ile Cys Ala Tyr Xaa' Ala Ala Cys Thr Gly Cys | (SEQ ID NO: 1111) |
| Pro Gly Xaa' Thr Xaa' Cys Gly Glu Ile Cys Xaa' Ala Xaa' Ala Ala Cys Thr Gly Cys | (SEQ ID NO: 1112) |
| Pro Gly Xaa' Thr Xaa' Cys Gly Glu Ile Cys Xaa' Ala Xaa' Xaa' Ala Ala Cys Thr Gly Cys | (SEQ ID NO: 1113) |
| Pro Gly Xaa' Thr Xaa' Cys Gly Glu Ile Cys Xaa' Ala Xaa' Ala Xaa' Ala Cys Thr Gly Cys | (SEQ ID NO: 1114) |
| Pro Gly Xaa' Thr Xaa' Cys Gly Glu Ile Cys Xaa' Ala Xaa' Ala Ala Xaa' Cys Thr Gly Cys | (SEQ ID NO: 1115) |
| Pro Gly Xaa' Thr Xaa' Cys Gly Glu Ile Cys Xaa' Ala Xaa' Ala Ala Cys Xaa' Thr Gly Cys | (SEQ ID NO: 1116) |
| Pro Gly Xaa' Thr Xaa' Cys Gly Glu Ile Cys Xaa' Ala Xaa' Ala Ala Cys Thr Xaa' Gly Cys | (SEQ ID NO: 1117) |
| Pro Gly Xaa' Thr Xaa' Cys Gly Glu Ile Cys Xaa' Ala Xaa' Ala Ala Cys Thr Gly Xaa' Cys | (SEQ ID NO: 1118) |
| Pro Gly Xaa' Thr Xaa' Cys Gly Glu Ile Cys Xaa' Ala Xaa' Ala Ala Cys Thr Gly Cys Xaa' | (SEQ ID NO: 1119) |
| Pro Gly Xaa' Thr Xaa' Cys Gly Glu Ile Cys Ala Tyr Ala Xaa' Ala Cys Thr Gly Cys | (SEQ ID NO: 1120) |
| Pro Gly Xaa' Thr Xaa' Cys Gly Glu Ile Cys Ala Xaa' Ala Xaa' Ala Cys Thr Gly Cys | (SEQ ID NO: 1121) |
| Pro Gly Xaa' Thr Xaa' Cys Gly Glu Ile Cys Ala Xaa' Xaa' Ala Cys Thr Gly Cys | (SEQ ID NO: 1122) |
| Pro Gly Xaa' Thr Xaa' Cys Gly Glu Ile Cys Ala Xaa' Ala Xaa' Cys Thr Gly Cys | (SEQ ID NO: 1123) |
| Pro Gly Xaa' Thr Xaa' Cys Gly Glu Ile Cys Ala Xaa' Ala Cys Xaa' Thr Gly Cys | (SEQ ID NO: 1124) |
| Pro Gly Xaa' Thr Xaa' Cys Gly Glu Ile Cys Ala Tyr Ala Xaa' Cys Thr Gly Cys Xaa' | (SEQ ID NO: 1125) |
| Pro Gly Xaa' Thr Xaa' Cys Gly Glu Ile Cys Ala Ala Xaa' Cys Thr Gly Cys | (SEQ ID NO: 1126) |

FIG. 2G

| | | | | | | | | | | | | | |
|---|---|---|---|---|---|---|---|---|---|---|---|---|---|
| Pro | Gly | Xaa' | Thr | Xaa' | Cys | Gly | Glu | Ile | Cys | Ala | Tyr | Ala | Ala | Xaa' | Cys | Thr | Gly | Cys | (SEQ ID NO: 1127) |
| Pro | Gly | Xaa' | Thr | Xaa' | Cys | Gly | Glu | Ile | Cys | Ala | Tyr | Ala | Ala | Xaa' | Cys | Xaa' | Thr | Gly | Cys | (SEQ ID NO: 1128) |
| Pro | Gly | Xaa' | Thr | Xaa' | Cys | Gly | Glu | Ile | Cys | Ala | Tyr | Ala | Ala | Xaa' | Cys | Thr | Xaa' | Gly | Cys | (SEQ ID NO: 1129) |
| Pro | Gly | Xaa' | Thr | Xaa' | Cys | Gly | Glu | Ile | Cys | Ala | Tyr | Ala | Ala | Xaa' | Cys | Thr | Gly | Xaa' | Cys | (SEQ ID NO: 1130) |
| Pro | Gly | Xaa' | Thr | Xaa' | Cys | Gly | Glu | Ile | Cys | Ala | Tyr | Ala | Ala | Xaa' | Cys | Thr | Gly | Cys | Xaa' | (SEQ ID NO: 1131) |
| Pro | Gly | Xaa' | Thr | Xaa' | Cys | Gly | Glu | Ile | Cys | Ala | Tyr | Ala | Ala | Cys | Xaa' | Thr | Gly | Cys | (SEQ ID NO: 1132) |
| Pro | Gly | Xaa' | Thr | Xaa' | Cys | Gly | Glu | Ile | Cys | Ala | Tyr | Ala | Ala | Cys | Xaa' | Xaa' | Thr | Gly | Cys | (SEQ ID NO: 1133) |
| Pro | Gly | Xaa' | Thr | Xaa' | Cys | Gly | Glu | Ile | Cys | Ala | Tyr | Ala | Ala | Cys | Xaa' | Thr | Xaa' | Gly | Cys | (SEQ ID NO: 1134) |
| Pro | Gly | Xaa' | Thr | Xaa' | Cys | Gly | Glu | Ile | Cys | Ala | Tyr | Ala | Ala | Cys | Xaa' | Thr | Gly | Xaa' | Cys | (SEQ ID NO: 1135) |
| Pro | Gly | Xaa' | Thr | Xaa' | Cys | Gly | Glu | Ile | Cys | Ala | Tyr | Ala | Ala | Cys | Xaa' | Thr | Gly | Cys | Xaa' | (SEQ ID NO: 1136) |
| Pro | Gly | Xaa' | Thr | Xaa' | Cys | Gly | Glu | Ile | Cys | Ala | Tyr | Ala | Ala | Cys | Thr | Xaa' | Gly | Cys | (SEQ ID NO: 1137) |
| Pro | Gly | Xaa' | Thr | Xaa' | Cys | Gly | Glu | Ile | Cys | Ala | Tyr | Ala | Ala | Cys | Thr | Xaa' | Xaa' | Gly | Cys | (SEQ ID NO: 1138) |
| Pro | Gly | Xaa' | Thr | Xaa' | Cys | Gly | Glu | Ile | Cys | Ala | Tyr | Ala | Ala | Cys | Thr | Xaa' | Gly | Xaa' | Cys | (SEQ ID NO: 1139) |
| Pro | Gly | Xaa' | Thr | Xaa' | Cys | Gly | Glu | Ile | Cys | Ala | Tyr | Ala | Ala | Cys | Thr | Xaa' | Gly | Cys | Xaa' | (SEQ ID NO: 1140) |
| Pro | Gly | Xaa' | Thr | Xaa' | Cys | Gly | Glu | Ile | Cys | Ala | Tyr | Ala | Ala | Cys | Thr | Gly | Xaa' | Cys | (SEQ ID NO: 1141) |
| Pro | Gly | Xaa' | Thr | Xaa' | Cys | Gly | Glu | Ile | Cys | Ala | Tyr | Ala | Ala | Cys | Thr | Gly | Xaa' | Xaa' | Cys | (SEQ ID NO: 1142) |
| Pro | Gly | Xaa' | Thr | Xaa' | Cys | Gly | Glu | Ile | Cys | Ala | Tyr | Ala | Ala | Cys | Thr | Gly | Xaa' | Cys | Xaa' | (SEQ ID NO: 1143) |
| Pro | Gly | Xaa' | Thr | Xaa' | Cys | Gly | Glu | Ile | Cys | Ala | Tyr | Ala | Ala | Cys | Thr | Gly | Cys | Xaa' | (SEQ ID NO: 1144) |
| Pro | Gly | Xaa' | Thr | Xaa' | Cys | Gly | Glu | Ile | Cys | Ala | Tyr | Ala | Ala | Cys | Thr | Gly | Cys | Xaa' | Xaa' | (SEQ ID NO: 1145) |
| Pro | Gly | Xaa' | Thr | Cys | Xaa' | Gly | Glu | Ile | Cys | Ala | Tyr | Ala | Ala | Cys | Thr | Gly | Cys | (SEQ ID NO: 1146) |
| Pro | Gly | Cys | Xaa' | Xaa' | Thr | Xaa' | Gly | Glu | Ile | Cys | Ala | Tyr | Ala | Ala | Cys | Thr | Gly | Cys | (SEQ ID NO: 1147) |
| Pro | Gly | Cys | Xaa' | Thr | Xaa' | Xaa' | Gly | Glu | Ile | Cys | Ala | Tyr | Ala | Ala | Cys | Thr | Gly | Cys | (SEQ ID NO: 1148) |
| Pro | Gly | Cys | Xaa' | Thr | Xaa' | Gly | Xaa' | Glu | Ile | Cys | Ala | Tyr | Ala | Ala | Cys | Thr | Gly | Cys | (SEQ ID NO: 1149) |
| Pro | Gly | Cys | Xaa' | Thr | Xaa' | Gly | Glu | Xaa' | Ile | Cys | Ala | Tyr | Ala | Ala | Cys | Thr | Gly | Cys | (SEQ ID NO: 1150) |
| Pro | Gly | Cys | Xaa' | Thr | Xaa' | Gly | Glu | Ile | Xaa' | Cys | Ala | Tyr | Ala | Ala | Cys | Thr | Gly | Cys | (SEQ ID NO: 1151) |
| Pro | Gly | Cys | Xaa' | Thr | Xaa' | Gly | Glu | Ile | Cys | Xaa' | Ala | Tyr | Ala | Ala | Cys | Thr | Gly | Cys | (SEQ ID NO: 1152) |
| Pro | Gly | Cys | Xaa' | Thr | Xaa' | Gly | Glu | Ile | Cys | Ala | Xaa' | Tyr | Ala | Ala | Cys | Thr | Gly | Cys | (SEQ ID NO: 1153) |
| Pro | Gly | Cys | Xaa' | Thr | Xaa' | Gly | Glu | Ile | Cys | Ala | Tyr | Xaa' | Ala | Ala | Cys | Thr | Gly | Cys | (SEQ ID NO: 1154) |
| Pro | Gly | Cys | Xaa' | Thr | Xaa' | Gly | Glu | Ile | Cys | Ala | Tyr | Ala | Xaa' | Ala | Cys | Thr | Gly | Cys | (SEQ ID NO: 1155) |
| Pro | Gly | Cys | Xaa' | Thr | Xaa' | Gly | Glu | Ile | Cys | Ala | Tyr | Ala | Ala | Xaa' | Cys | Thr | Gly | Cys | (SEQ ID NO: 1156) |
| Pro | Gly | Cys | Xaa' | Thr | Xaa' | Gly | Glu | Ile | Cys | Ala | Tyr | Ala | Ala | Cys | Xaa' | Thr | Gly | Cys | (SEQ ID NO: 1157) |
| Pro | Gly | Cys | Xaa' | Thr | Xaa' | Gly | Glu | Ile | Cys | Ala | Tyr | Ala | Ala | Cys | Thr | Xaa' | Gly | Cys | (SEQ ID NO: 1158) |
| Pro | Gly | Cys | Xaa' | Thr | Xaa' | Gly | Glu | Ile | Cys | Ala | Tyr | Ala | Ala | Cys | Thr | Gly | Xaa' | Cys | (SEQ ID NO: 1159) |
| Pro | Gly | Cys | Xaa' | Thr | Xaa' | Gly | Glu | Ile | Cys | Ala | Tyr | Ala | Ala | Cys | Thr | Gly | Cys | Xaa' | (SEQ ID NO: 1160) |

FIG. 2H

```
Pro Gly Xaa' Thr Cys Xaa' Gly Xaa' Glu Ile Cys Ala Tyr Ala Ala Cys Thr Gly Cys      (SEQ ID NO: 1161)
Pro Gly Xaa' Thr Cys Xaa' Gly Xaa' Xaa' Glu Ile Cys Ala Tyr Ala Ala Cys Thr Gly Cys  (SEQ ID NO: 1162)
Pro Gly Xaa' Thr Cys Xaa' Gly Xaa' Glu Xaa' Ile Cys Ala Tyr Ala Ala Cys Thr Gly Cys  (SEQ ID NO: 1163)
Pro Gly Xaa' Thr Cys Xaa' Gly Xaa' Glu Ile Xaa' Cys Ala Tyr Ala Ala Cys Thr Gly Cys  (SEQ ID NO: 1164)
Pro Gly Xaa' Thr Cys Xaa' Gly Xaa' Glu Ile Cys Xaa' Ala Tyr Ala Ala Cys Thr Gly Cys  (SEQ ID NO: 1165)
Pro Gly Xaa' Thr Cys Xaa' Gly Xaa' Glu Ile Cys Ala Xaa' Tyr Ala Ala Cys Thr Gly Cys  (SEQ ID NO: 1166)
Pro Gly Xaa' Thr Cys Xaa' Gly Xaa' Glu Ile Cys Ala Tyr Xaa' Ala Ala Cys Thr Gly Cys  (SEQ ID NO: 1167)
Pro Gly Xaa' Thr Cys Xaa' Gly Xaa' Glu Ile Cys Ala Tyr Ala Xaa' Ala Cys Thr Gly Cys  (SEQ ID NO: 1168)
Pro Gly Xaa' Thr Cys Xaa' Gly Xaa' Glu Ile Cys Ala Tyr Ala Ala Xaa' Cys Thr Gly Cys  (SEQ ID NO: 1169)
Pro Gly Xaa' Thr Cys Xaa' Gly Xaa' Glu Ile Cys Ala Tyr Ala Ala Cys Xaa' Thr Gly Cys  (SEQ ID NO: 1170)
Pro Gly Xaa' Thr Cys Xaa' Gly Xaa' Glu Ile Cys Ala Tyr Ala Ala Cys Thr Xaa' Gly Cys  (SEQ ID NO: 1171)
Pro Gly Xaa' Thr Cys Xaa' Gly Xaa' Glu Ile Cys Ala Tyr Ala Ala Cys Thr Gly Xaa' Cys  (SEQ ID NO: 1172)
Pro Gly Xaa' Thr Cys Xaa' Gly Xaa' Glu Ile Cys Ala Tyr Ala Ala Cys Thr Gly Cys Xaa'  (SEQ ID NO: 1173)
Pro Gly Xaa' Thr Cys Xaa' Gly Glu Xaa' Ile Cys Ala Tyr Ala Ala Cys Thr Gly Cys      (SEQ ID NO: 1174)
Pro Gly Xaa' Thr Cys Xaa' Gly Xaa' Xaa' Ile Cys Ala Tyr Ala Ala Cys Thr Gly Cys     (SEQ ID NO: 1175)
Pro Gly Xaa' Thr Cys Xaa' Gly Xaa' Xaa' Xaa' Cys Ala Tyr Ala Ala Cys Thr Gly Cys    (SEQ ID NO: 1176)
Pro Gly Xaa' Thr Cys Xaa' Gly Xaa' Ile Xaa' Cys Ala Tyr Ala Ala Cys Thr Gly Cys     (SEQ ID NO: 1177)
Pro Gly Xaa' Thr Cys Xaa' Gly Xaa' Ile Cys Xaa' Ala Tyr Ala Ala Cys Thr Gly Cys     (SEQ ID NO: 1178)
Pro Gly Xaa' Thr Cys Xaa' Gly Xaa' Ile Cys Ala Xaa' Tyr Ala Ala Cys Thr Gly Cys     (SEQ ID NO: 1179)
Pro Gly Xaa' Thr Cys Xaa' Gly Xaa' Ile Cys Ala Tyr Xaa' Ala Ala Cys Thr Gly Cys     (SEQ ID NO: 1180)
Pro Gly Xaa' Thr Cys Xaa' Gly Xaa' Ile Cys Ala Tyr Ala Xaa' Ala Cys Thr Gly Cys     (SEQ ID NO: 1181)
Pro Gly Xaa' Thr Cys Xaa' Gly Xaa' Ile Cys Ala Tyr Ala Ala Xaa' Cys Thr Gly Cys     (SEQ ID NO: 1182)
Pro Gly Xaa' Thr Cys Xaa' Gly Xaa' Ile Cys Ala Tyr Ala Ala Cys Xaa' Thr Gly Cys     (SEQ ID NO: 1183)
Pro Gly Xaa' Thr Cys Xaa' Gly Xaa' Ile Cys Ala Tyr Ala Ala Cys Thr Xaa' Gly Cys     (SEQ ID NO: 1184)
Pro Gly Xaa' Thr Cys Xaa' Gly Xaa' Ile Cys Ala Tyr Ala Ala Cys Thr Gly Cys Xaa'     (SEQ ID NO: 1185)
Pro Gly Xaa' Thr Cys Xaa' Gly Glu Ile Xaa' Cys Ala Tyr Ala Ala Cys Thr Gly Cys      (SEQ ID NO: 1186)
Pro Gly Xaa' Thr Cys Xaa' Gly Xaa' Ile Xaa' Cys Ala Tyr Ala Ala Cys Thr Gly Cys     (SEQ ID NO: 1187)
Pro Gly Xaa' Thr Cys Xaa' Gly Xaa' Xaa' Xaa' Cys Ala Tyr Ala Ala Cys Thr Gly Cys    (SEQ ID NO: 1188)
Pro Gly Xaa' Thr Cys Xaa' Gly Xaa' Ile Xaa' Xaa' Ala Tyr Ala Ala Cys Thr Gly Cys    (SEQ ID NO: 1189)
Pro Gly Xaa' Thr Cys Xaa' Gly Xaa' Ile Xaa' Cys Xaa' Tyr Ala Ala Cys Thr Gly Cys    (SEQ ID NO: 1190)
Pro Gly Xaa' Thr Cys Xaa' Gly Xaa' Ile Xaa' Cys Ala Xaa' Ala Ala Cys Thr Gly Cys    (SEQ ID NO: 1191)
Pro Gly Xaa' Thr Cys Xaa' Gly Xaa' Ile Xaa' Cys Ala Tyr Xaa' Ala Cys Thr Gly Cys    (SEQ ID NO: 1192)
Pro Gly Xaa' Thr Cys Xaa' Gly Xaa' Ile Xaa' Cys Ala Tyr Ala Xaa' Cys Thr Gly Cys    (SEQ ID NO: 1193)
Pro Gly Xaa' Thr Cys Xaa' Gly Xaa' Ile Xaa' Cys Ala Tyr Ala Ala Xaa' Thr Gly Cys    (SEQ ID NO: 1194)
```

FIG. 2I

| | | | | | | | | | | | | |
|---|---|---|---|---|---|---|---|---|---|---|---|---|
| Pro | Gly | Xaa' | Thr | Cys | Xaa' | Gly | Glu | Ile | Cys | Ala | Tyr | Ala Ala Cys Thr Gly Xaa' Cys | (SEQ ID NO: 1195) |
| Pro | Gly | Xaa' | Thr | Cys | Xaa' | Gly | Glu | Ile | Cys | Ala | Tyr | Ala Ala Cys Thr Gly Cys Xaa' | (SEQ ID NO: 1196) |
| Pro | Gly | Xaa' | Thr | Cys | Xaa' | Gly | Glu | Ile | Cys | Xaa' | Tyr | Ala Ala Cys Thr Gly Cys | (SEQ ID NO: 1197) |
| Pro | Gly | Xaa' | Thr | Cys | Xaa' | Gly | Glu | Ile | Cys | Xaa' | Xaa' | Ala Ala Cys Thr Gly Gly Cys | (SEQ ID NO: 1198) |
| Pro | Gly | Xaa' | Thr | Cys | Xaa' | Gly | Glu | Ile | Cys | Xaa' | Tyr | Ala Ala Cys Thr Gly Gly Cys | (SEQ ID NO: 1199) |
| Pro | Gly | Xaa' | Thr | Cys | Xaa' | Gly | Glu | Ile | Cys | Xaa' | Tyr | Xaa' Ala Cys Thr Gly Gly Cys | (SEQ ID NO: 1200) |
| Pro | Gly | Xaa' | Thr | Cys | Xaa' | Gly | Glu | Ile | Cys | Xaa' | Tyr | Ala Xaa' Cys Thr Gly Gly Cys | (SEQ ID NO: 1201) |
| Pro | Gly | Xaa' | Thr | Cys | Xaa' | Gly | Glu | Ile | Cys | Xaa' | Tyr | Ala Ala Cys Xaa' Gly Gly Cys | (SEQ ID NO: 1202) |
| Pro | Gly | Xaa' | Thr | Cys | Xaa' | Gly | Glu | Ile | Cys | Xaa' | Tyr | Ala Ala Cys Thr Xaa' Gly Cys | (SEQ ID NO: 1203) |
| Pro | Gly | Xaa' | Thr | Cys | Xaa' | Gly | Glu | Ile | Cys | Xaa' | Tyr | Ala Ala Cys Thr Gly Xaa' Cys | (SEQ ID NO: 1204) |
| Pro | Gly | Xaa' | Thr | Cys | Xaa' | Gly | Glu | Ile | Cys | Xaa' | Tyr | Ala Ala Cys Thr Gly Cys Xaa' | (SEQ ID NO: 1205) |
| Pro | Gly | Xaa' | Thr | Cys | Xaa' | Gly | Glu | Ile | Cys | Ala | Xaa' | Ala Ala Cys Thr Gly Gly Cys | (SEQ ID NO: 1206) |
| Pro | Gly | Xaa' | Thr | Cys | Xaa' | Gly | Glu | Ile | Cys | Ala | Xaa' | Xaa' Ala Cys Thr Gly Gly Cys | (SEQ ID NO: 1207) |
| Pro | Gly | Xaa' | Thr | Cys | Xaa' | Gly | Glu | Ile | Cys | Ala | Xaa' | Ala Xaa' Cys Thr Gly Gly Cys | (SEQ ID NO: 1208) |
| Pro | Gly | Xaa' | Thr | Cys | Xaa' | Gly | Glu | Ile | Cys | Ala | Tyr | Xaa' Ala Cys Thr Gly Gly Cys | (SEQ ID NO: 1209) |
| Pro | Gly | Xaa' | Thr | Cys | Xaa' | Gly | Glu | Ile | Cys | Ala | Tyr | Ala Xaa' Cys Thr Gly Gly Cys | (SEQ ID NO: 1210) |
| Pro | Gly | Xaa' | Thr | Cys | Xaa' | Gly | Glu | Ile | Cys | Ala | Tyr | Xaa' Xaa' Cys Thr Gly Gly Cys | (SEQ ID NO: 1211) |
| Pro | Gly | Xaa' | Thr | Cys | Xaa' | Gly | Glu | Ile | Cys | Ala | Tyr | Ala Ala Cys Xaa' Gly Gly Cys | (SEQ ID NO: 1212) |
| Pro | Gly | Xaa' | Thr | Cys | Xaa' | Gly | Glu | Ile | Cys | Ala | Tyr | Ala Ala Cys Thr Xaa' Gly Cys | (SEQ ID NO: 1213) |
| Pro | Gly | Xaa' | Thr | Cys | Xaa' | Gly | Glu | Ile | Cys | Ala | Tyr | Ala Ala Cys Thr Gly Xaa' Cys | (SEQ ID NO: 1214) |
| Pro | Gly | Xaa' | Thr | Cys | Xaa' | Gly | Glu | Ile | Cys | Ala | Tyr | Ala Ala Cys Thr Gly Cys Xaa' | (SEQ ID NO: 1215) |
| Pro | Gly | Xaa' | Thr | Cys | Xaa' | Gly | Glu | Ile | Cys | Ala | Tyr | Ala Ala Ala Cys Thr Gly Cys | (SEQ ID NO: 1216) |
| Pro | Gly | Xaa' | Thr | Cys | Xaa' | Gly | Glu | Ile | Cys | Ala | Tyr | Xaa' Ala Ala Cys Thr Gly Gly Cys | (SEQ ID NO: 1217) |
| Pro | Gly | Xaa' | Thr | Cys | Xaa' | Gly | Glu | Ile | Cys | Ala | Tyr | Ala Xaa' Ala Cys Thr Gly Gly Cys | (SEQ ID NO: 1218) |
| Pro | Gly | Xaa' | Thr | Cys | Xaa' | Gly | Glu | Ile | Cys | Ala | Tyr | Ala Ala Xaa' Cys Thr Gly Gly Cys | (SEQ ID NO: 1219) |
| Pro | Gly | Xaa' | Thr | Cys | Xaa' | Gly | Glu | Ile | Cys | Ala | Tyr | Ala Ala Cys Xaa' Thr Gly Gly Cys | (SEQ ID NO: 1220) |
| Pro | Gly | Xaa' | Thr | Cys | Xaa' | Gly | Glu | Ile | Cys | Ala | Tyr | Ala Ala Cys Xaa' Gly Cys Xaa' | (SEQ ID NO: 1221) |
| Pro | Gly | Xaa' | Thr | Cys | Xaa' | Gly | Glu | Ile | Cys | Ala | Tyr | Ala Xaa' Ala Cys Thr Gly Cys | (SEQ ID NO: 1222) |
| Pro | Gly | Xaa' | Thr | Cys | Xaa' | Gly | Glu | Ile | Cys | Ala | Tyr | Ala Ala Xaa' Ala Cys Thr Gly Cys | (SEQ ID NO: 1223) |
| Pro | Gly | Xaa' | Thr | Cys | Xaa' | Gly | Glu | Ile | Cys | Ala | Tyr | Ala Xaa' Ala Cys Thr Gly Cys | (SEQ ID NO: 1224) |
| Pro | Gly | Xaa' | Thr | Cys | Xaa' | Gly | Glu | Ile | Cys | Ala | Tyr | Ala Xaa' Xaa' Ala Cys Thr Gly Cys | (SEQ ID NO: 1225) |
| Pro | Gly | Xaa' | Thr | Cys | Xaa' | Gly | Glu | Ile | Cys | Ala | Tyr | Ala Xaa' Ala Cys Xaa' Thr Gly Cys | (SEQ ID NO: 1226) |
| Pro | Gly | Xaa' | Thr | Cys | Xaa' | Gly | Glu | Ile | Cys | Ala | Tyr | Ala Xaa' Ala Cys Thr Xaa' Gly Cys | (SEQ ID NO: 1227) |
| Pro | Gly | Xaa' | Thr | Cys | Xaa' | Gly | Glu | Ile | Cys | Ala | Tyr | Ala Cys Xaa' Ala Cys Thr Gly Cys | (SEQ ID NO: 1228) |

FIG. 2J

| | | | | | | | | | | | | |
|---|---|---|---|---|---|---|---|---|---|---|---|---|
| Pro | Gly | Xaa' | Thr | Cys | Xaa' | Gly | Glu | Ile | Cys | Ala | Tyr | Ala | Xaa' | Ala | Cys | Thr | Gly | Xaa' | Cys | (SEQ ID NO: 1229) |

FIG. 2K

```
Pro Gly Xaa' Thr Cys Gly Xaa' Xaa' Glu Ile Cys Ala Tyr Ala Ala Cys Thr Gly Xaa' Cys      (SEQ ID NO: 1263)
Pro Gly Xaa' Thr Cys Gly Xaa' Xaa' Glu Ile Cys Ala Tyr Ala Ala Cys Thr Gly Cys Xaa'      (SEQ ID NO: 1264)
Pro Gly Xaa' Thr Cys Gly Xaa' Glu Ile Cys Ala Tyr Ala Ala Cys Thr Gly Cys                (SEQ ID NO: 1265)
Pro Gly Xaa' Thr Cys Gly Xaa' Xaa' Ile Cys Ala Tyr Ala Ala Cys Thr Gly Cys               (SEQ ID NO: 1266)
Pro Gly Xaa' Thr Cys Gly Xaa' Xaa' Glu Ile Cys Ala' Ile Cys Xaa' Ala Ala Cys Thr Gly Cys (SEQ ID NO: 1267)
Pro Gly Xaa' Thr Cys Gly Xaa' Xaa' Glu Ile Cys Xaa' Ala Tyr Ala Ala Cys Thr Gly Cys      (SEQ ID NO: 1268)
Pro Gly Xaa' Thr Cys Gly Xaa' Xaa' Glu Ile Cys Ala Xaa' Tyr Ala Ala Cys Thr Gly Cys      (SEQ ID NO: 1269)
Pro Gly Xaa' Thr Cys Gly Xaa' Xaa' Glu Ile Cys Ala Tyr Xaa' Ala Ala Cys Thr Gly Cys      (SEQ ID NO: 1270)
Pro Gly Xaa' Thr Cys Gly Xaa' Xaa' Glu Ile Cys Ala Tyr Ala Xaa' Ala Cys Thr Gly Cys      (SEQ ID NO: 1271)
Pro Gly Xaa' Thr Cys Gly Xaa' Xaa' Glu Ile Cys Ala Tyr Ala Ala Xaa' Cys Thr Gly Cys      (SEQ ID NO: 1272)
Pro Gly Xaa' Thr Cys Gly Xaa' Xaa' Glu Ile Cys Ala Tyr Ala Ala Cys Xaa' Thr Gly Cys      (SEQ ID NO: 1273)
Pro Gly Xaa' Thr Cys Gly Xaa' Xaa' Glu Ile Cys Ala Tyr Ala Ala Cys Thr Xaa' Gly Cys      (SEQ ID NO: 1274)
Pro Gly Xaa' Thr Cys Gly Xaa' Xaa' Glu Ile Cys Ala Tyr Ala Ala Cys Thr Gly Xaa' Cys      (SEQ ID NO: 1275)
Pro Gly Xaa' Thr Cys Gly Xaa' Xaa' Glu Ile Cys Ala Tyr Ala Ala Cys Thr Gly Cys Xaa'      (SEQ ID NO: 1276)
Pro Gly Xaa' Thr Cys Gly Xaa' Ile Cys Ala Tyr Ala Ala Cys Thr Gly Cys                    (SEQ ID NO: 1277)
Pro Gly Xaa' Thr Cys Gly Ile Cys Ala Tyr Ala Ala Cys Thr Gly Cys                         (SEQ ID NO: 1278)
Pro Gly Xaa' Thr Cys Gly Xaa' Xaa' Glu Ile Cys Xaa' Ala Tyr Ala Ala Cys Thr Gly Cys      (SEQ ID NO: 1279)
Pro Gly Xaa' Thr Cys Gly Xaa' Xaa' Glu Ile Cys Xaa' Ala Tyr Ala Ala Cys Thr Gly Cys      (SEQ ID NO: 1280)
Pro Gly Xaa' Thr Cys Gly Xaa' Xaa' Glu Ile Cys Ala Xaa' Tyr Ala Ala Cys Thr Gly Cys      (SEQ ID NO: 1281)
Pro Gly Xaa' Thr Cys Gly Xaa' Xaa' Glu Ile Cys Ala Tyr Xaa' Ala Ala Cys Thr Gly Cys      (SEQ ID NO: 1282)
Pro Gly Xaa' Thr Cys Gly Xaa' Xaa' Glu Ile Cys Ala Tyr Ala Xaa' Ala Cys Thr Gly Cys      (SEQ ID NO: 1283)
Pro Gly Xaa' Thr Cys Gly Xaa' Xaa' Glu Ile Cys Ala Tyr Ala Ala Xaa' Cys Thr Gly Cys      (SEQ ID NO: 1284)
Pro Gly Xaa' Thr Cys Gly Xaa' Xaa' Glu Ile Cys Ala Tyr Ala Ala Cys Xaa' Thr Gly Cys      (SEQ ID NO: 1285)
Pro Gly Xaa' Thr Cys Gly Xaa' Xaa' Glu Ile Cys Ala Tyr Ala Ala Cys Thr Xaa' Gly Cys      (SEQ ID NO: 1286)
Pro Gly Xaa' Thr Cys Gly Xaa' Xaa' Glu Ile Cys Ala Tyr Ala Ala Cys Thr Gly Xaa' Cys      (SEQ ID NO: 1287)
Pro Gly Xaa' Thr Cys Gly Xaa' Xaa' Glu Ile Cys Ala Tyr Ala Ala Cys Thr Gly Cys Xaa'      (SEQ ID NO: 1288)
Pro Gly Xaa' Thr Cys Gly Xaa' Ile Cys Ala Tyr Ala Ala Cys Thr Gly Cys                    (SEQ ID NO: 1289)
Pro Gly Xaa' Thr Cys Gly Ile Cys Ala Tyr Ala Ala Cys Thr Gly Cys                         (SEQ ID NO: 1290)
Pro Gly Xaa' Thr Cys Gly Xaa' Ile Cys Xaa' Ala Tyr Ala Ala Cys Thr Gly Cys               (SEQ ID NO: 1291)
Pro Gly Xaa' Thr Cys Gly Xaa' Ile Cys Ala Xaa' Tyr Ala Ala Cys Thr Gly Cys               (SEQ ID NO: 1292)
Pro Gly Xaa' Thr Cys Gly Xaa' Ile Cys Ala Tyr Xaa' Ala Ala Cys Thr Gly Cys               (SEQ ID NO: 1293)
Pro Gly Xaa' Thr Cys Gly Xaa' Ile Cys Ala Tyr Ala Xaa' Ala Cys Thr Gly Cys               (SEQ ID NO: 1294)
Pro Gly Xaa' Thr Cys Gly Xaa' Ile Cys Ala Tyr Ala Ala Xaa' Cys Thr Gly Cys               (SEQ ID NO: 1295)
Pro Gly Xaa' Thr Cys Gly Xaa' Ile Cys Ala Tyr Ala Ala Cys Thr Xaa' Gly Xaa' Cys          (SEQ ID NO: 1296)
```

FIG. 2L

| | | | | | | | | | | |
|---|---|---|---|---|---|---|---|---|---|---|
| Pro Gly Xaa' Thr Cys Gly Xaa' Glu Ile Cys Xaa' Ala Tyr Ala Ala Cys Thr Gly Cys Xaa' | (SEQ ID NO: 1297) |
| Pro Gly Xaa' Thr Cys Gly Xaa' Glu Ile Cys Ala Xaa' Tyr Ala Ala Cys Thr Gly Cys | (SEQ ID NO: 1298) |
| Pro Gly Xaa' Thr Cys Gly Xaa' Glu Ile Cys Ala Xaa' Tyr Ala Ala Cys Thr Gly Cys | (SEQ ID NO: 1299) |
| Pro Gly Xaa' Thr Cys Gly Xaa' Glu Ile Cys Ala Xaa' Tyr Xaa' Ala Ala Cys Thr Gly Cys | (SEQ ID NO: 1300) |
| Pro Gly Xaa' Thr Cys Gly Xaa' Glu Ile Cys Ala Xaa' Tyr Ala Xaa' Ala Cys Thr Gly Cys | (SEQ ID NO: 1301) |
| Pro Gly Xaa' Thr Cys Gly Xaa' Glu Ile Cys Ala Xaa' Tyr Ala Ala Xaa' Cys Thr Gly Cys | (SEQ ID NO: 1302) |
| Pro Gly Xaa' Thr Cys Gly Xaa' Glu Ile Cys Ala Xaa' Tyr Ala Ala Cys Xaa' Thr Gly Cys | (SEQ ID NO: 1303) |
| Pro Gly Xaa' Thr Cys Gly Xaa' Glu Ile Cys Ala Xaa' Tyr Ala Ala Cys Thr Xaa' Gly Cys | (SEQ ID NO: 1304) |
| Pro Gly Xaa' Thr Cys Gly Xaa' Glu Ile Cys Ala Xaa' Tyr Ala Ala Cys Thr Gly Xaa' Cys | (SEQ ID NO: 1305) |
| Pro Gly Xaa' Thr Cys Gly Xaa' Glu Ile Cys Ala Xaa' Tyr Ala Ala Cys Thr Gly Cys Xaa' | (SEQ ID NO: 1306) |
| Pro Gly Xaa' Thr Cys Gly Xaa' Glu Ile Cys Ala Ala Tyr Xaa' Ala Ala Cys Thr Gly Cys | (SEQ ID NO: 1307) |
| Pro Gly Xaa' Thr Cys Gly Xaa' Glu Ile Cys Ala Ala Tyr Xaa' Ala Ala Cys Thr Gly Cys | (SEQ ID NO: 1308) |
| Pro Gly Xaa' Thr Cys Gly Xaa' Glu Ile Cys Ala Ala Tyr Xaa' Xaa' Ala Ala Cys Thr Gly Cys | (SEQ ID NO: 1309) |
| Pro Gly Xaa' Thr Cys Gly Xaa' Glu Ile Cys Ala Ala Tyr Xaa' Ala Xaa' Ala Cys Thr Gly Cys | (SEQ ID NO: 1310) |
| Pro Gly Xaa' Thr Cys Gly Xaa' Glu Ile Cys Ala Ala Tyr Xaa' Ala Ala Xaa' Cys Thr Gly Cys | (SEQ ID NO: 1311) |
| Pro Gly Xaa' Thr Cys Gly Xaa' Glu Ile Cys Ala Ala Tyr Xaa' Ala Ala Cys Xaa' Thr Gly Cys | (SEQ ID NO: 1312) |
| Pro Gly Xaa' Thr Cys Gly Xaa' Glu Ile Cys Ala Ala Tyr Xaa' Ala Ala Cys Thr Xaa' Gly Cys | (SEQ ID NO: 1313) |
| Pro Gly Xaa' Thr Cys Gly Xaa' Glu Ile Cys Ala Ala Tyr Xaa' Ala Ala Cys Thr Gly Xaa' Cys | (SEQ ID NO: 1314) |
| Pro Gly Xaa' Thr Cys Gly Xaa' Glu Ile Cys Ala Ala Tyr Xaa' Ala Ala Cys Thr Gly Cys Xaa' | (SEQ ID NO: 1315) |
| Pro Gly Xaa' Thr Cys Gly Xaa' Glu Ile Cys Ala Ala Tyr Ala Xaa' Ala Cys Thr Gly Cys | (SEQ ID NO: 1316) |
| Pro Gly Xaa' Thr Cys Gly Xaa' Glu Ile Cys Ala Ala Tyr Ala Xaa' Ala Cys Thr Gly Cys | (SEQ ID NO: 1317) |
| Pro Gly Xaa' Thr Cys Gly Xaa' Glu Ile Cys Ala Ala Tyr Ala Xaa' Xaa' Ala Cys Thr Gly Cys | (SEQ ID NO: 1318) |
| Pro Gly Xaa' Thr Cys Gly Xaa' Glu Ile Cys Ala Ala Tyr Ala Xaa' Ala Xaa' Cys Thr Gly Cys | (SEQ ID NO: 1319) |
| Pro Gly Xaa' Thr Cys Gly Xaa' Glu Ile Cys Ala Ala Tyr Ala Xaa' Ala Cys Xaa' Thr Gly Cys | (SEQ ID NO: 1320) |
| Pro Gly Xaa' Thr Cys Gly Xaa' Glu Ile Cys Ala Ala Tyr Ala Xaa' Ala Cys Thr Xaa' Gly Cys | (SEQ ID NO: 1321) |
| Pro Gly Xaa' Thr Cys Gly Xaa' Glu Ile Cys Ala Ala Tyr Ala Xaa' Ala Cys Thr Gly Xaa' Cys | (SEQ ID NO: 1322) |
| Pro Gly Xaa' Thr Cys Gly Xaa' Glu Ile Cys Ala Ala Tyr Ala Xaa' Ala Cys Thr Gly Cys Xaa' | (SEQ ID NO: 1323) |
| Pro Gly Xaa' Thr Cys Gly Xaa' Glu Ile Cys Ala Ala Tyr Ala Ala Xaa' Cys Thr Gly Cys | (SEQ ID NO: 1324) |
| Pro Gly Xaa' Thr Cys Gly Xaa' Glu Ile Cys Ala Ala Tyr Ala Ala Xaa' Cys Thr Gly Cys | (SEQ ID NO: 1325) |
| Pro Gly Xaa' Thr Cys Gly Xaa' Glu Ile Cys Ala Ala Tyr Ala Ala Xaa' Cys Thr Gly Cys Xaa' | (SEQ ID NO: 1326) |
| Pro Gly Xaa' Thr Cys Gly Xaa' Glu Ile Cys Ala Ala Tyr Ala Ala Cys Xaa' Thr Gly Cys | (SEQ ID NO: 1327) |
| Pro Gly Xaa' Thr Cys Gly Xaa' Glu Ile Cys Ala Ala Tyr Ala Ala Cys Xaa' Thr Gly Cys | (SEQ ID NO: 1328) |
| Pro Gly Xaa' Thr Cys Gly Xaa' Glu Ile Cys Ala Ala Tyr Ala Ala Cys Xaa' Thr Gly Cys | (SEQ ID NO: 1329) |
| Pro Gly Xaa' Thr Cys Gly Xaa' Glu Ile Cys Ala Ala Tyr Ala Ala Cys Xaa' Thr Gly Cys | (SEQ ID NO: 1330) |

FIG. 2M

| | | | | | | | | | | | | |
|---|---|---|---|---|---|---|---|---|---|---|---|---|
| Pro Gly Xaa' Thr Cys Gly Xaa' Glu Ile Cys Ala Tyr Ala Ala Cys Xaa' Thr Gly Xaa' Cys | (SEQ ID NO: 1331) |
| Pro Gly Xaa' Thr Cys Gly Xaa' Glu Ile Cys Ala Tyr Ala Ala Cys Xaa' Thr Gly Cys Xaa' | (SEQ ID NO: 1332) |
| Pro Gly Xaa' Thr Cys Gly Xaa' Glu Ile Cys Ala Tyr Ala Ala Cys Xaa' Thr Xaa' Gly Cys | (SEQ ID NO: 1333) |
| Pro Gly Xaa' Thr Cys Gly Xaa' Glu Ile Cys Ala Tyr Ala Ala Cys Xaa' Xaa' Gly Cys | (SEQ ID NO: 1334) |
| Pro Gly Xaa' Thr Cys Gly Xaa' Glu Ile Cys Ala Tyr Ala Ala Cys Thr Xaa' Gly Xaa' Cys | (SEQ ID NO: 1335) |
| Pro Gly Xaa' Thr Cys Gly Xaa' Glu Ile Cys Ala Tyr Ala Ala Cys Thr Xaa' Gly Cys Xaa' | (SEQ ID NO: 1336) |
| Pro Gly Xaa' Thr Cys Gly Xaa' Glu Ile Cys Ala Tyr Ala Ala Cys Thr Xaa' Xaa' Gly Cys | (SEQ ID NO: 1337) |
| Pro Gly Xaa' Thr Cys Gly Xaa' Glu Ile Cys Ala Tyr Ala Ala Cys Thr Gly Xaa' Xaa' Cys | (SEQ ID NO: 1338) |
| Pro Gly Xaa' Thr Cys Gly Xaa' Glu Ile Cys Ala Tyr Ala Ala Cys Thr Gly Xaa' Cys Xaa' | (SEQ ID NO: 1339) |
| Pro Gly Xaa' Thr Cys Gly Xaa' Glu Ile Cys Ala Tyr Ala Ala Cys Thr Gly Cys Xaa' | (SEQ ID NO: 1340) |
| Pro Gly Xaa' Thr Cys Gly Xaa' Glu Ile Cys Ala Tyr Ala Ala Cys Thr Gly Xaa' Cys Xaa' | (SEQ ID NO: 1341) |
| Pro Gly Xaa' Thr Cys Gly Glu Xaa' Ile Cys Ala Tyr Ala Ala Cys Thr Gly Cys | (SEQ ID NO: 1342) |
| Pro Gly Xaa' Thr Cys Gly Glu Xaa' Ile Cys Ala Tyr Ala Ala Cys Thr Gly Cys | (SEQ ID NO: 1343) |
| Pro Gly Xaa' Thr Cys Gly Xaa' Xaa' Ile Cys Ala Tyr Ala Ala Cys Thr Gly Cys | (SEQ ID NO: 1344) |
| Pro Gly Xaa' Thr Cys Gly Xaa' Xaa' Xaa' Cys Ala Tyr Ala Ala Cys Thr Gly Cys | (SEQ ID NO: 1345) |
| Pro Gly Xaa' Thr Cys Gly Xaa' Xaa' Ile Xaa' Ala Tyr Ala Ala Cys Thr Gly Cys | (SEQ ID NO: 1346) |
| Pro Gly Xaa' Thr Cys Gly Xaa' Xaa' Ile Cys Xaa' Tyr Ala Ala Cys Thr Gly Cys | (SEQ ID NO: 1347) |
| Pro Gly Xaa' Thr Cys Gly Xaa' Xaa' Ile Cys Ala Xaa' Ala Ala Cys Thr Gly Cys | (SEQ ID NO: 1348) |
| Pro Gly Xaa' Thr Cys Gly Xaa' Xaa' Ile Cys Ala Tyr Xaa' Ala Cys Thr Gly Cys | (SEQ ID NO: 1349) |
| Pro Gly Xaa' Thr Cys Gly Xaa' Xaa' Ile Cys Ala Tyr Ala Xaa' Cys Thr Gly Cys | (SEQ ID NO: 1350) |
| Pro Gly Xaa' Thr Cys Gly Xaa' Xaa' Ile Cys Ala Tyr Ala Ala Xaa' Thr Gly Cys | (SEQ ID NO: 1351) |
| Pro Gly Xaa' Thr Cys Gly Xaa' Xaa' Ile Cys Ala Tyr Ala Ala Cys Xaa' Thr Gly Xaa' Cys | (SEQ ID NO: 1352) |
| Pro Gly Xaa' Thr Cys Gly Xaa' Xaa' Ile Cys Ala Tyr Ala Ala Cys Thr Gly Cys Xaa' | (SEQ ID NO: 1353) |
| Pro Gly Xaa' Thr Cys Gly Xaa' Xaa' Ile Cys Ala Tyr Ala Ala Cys Thr Gly Xaa' Cys Xaa' | (SEQ ID NO: 1354) |
| Pro Gly Xaa' Thr Cys Gly Glu Ile Xaa' Cys Ala Tyr Ala Ala Cys Thr Gly Cys | (SEQ ID NO: 1355) |

| | | | | | | | | | | | |
|---|---|---|---|---|---|---|---|---|---|---|---|
| Pro | Gly | Xaa' | Thr | Cys | Gly | Glu | Xaa' | Ile | Xaa' | Cys | Ala | Tyr | Ala | Ala | Cys | Thr | Gly | Cys | Xaa' | (SEQ ID NO: 1365) |
| Pro | Gly | Xaa' | Thr | Cys | Gly | Glu | Xaa' | Ile | Cys | Ala | Tyr | Ala | Ala | Cys | Thr | Gly | Cys | | (SEQ ID NO: 1366) |
| Pro | Gly | Xaa' | Thr | Cys | Gly | Glu | Xaa' | Ile | Cys | Xaa' | Ala | Tyr | Ala | Ala | Cys | Thr | Gly | Cys | | (SEQ ID NO: 1367) |
| Pro | Gly | Xaa' | Thr | Cys | Gly | Glu | Xaa' | Ile | Cys | Xaa' | Ala | Tyr | Ala | Xaa' | Cys | Thr | Gly | Cys | | (SEQ ID NO: 1368) |
| Pro | Gly | Xaa' | Thr | Cys | Gly | Glu | Xaa' | Ile | Cys | Xaa' | Ala | Tyr | Xaa' | Ala | Cys | Thr | Gly | Cys | | (SEQ ID NO: 1369) |
| Pro | Gly | Xaa' | Thr | Cys | Gly | Glu | Xaa' | Ile | Cys | Xaa' | Ala | Tyr | Ala | Ala | Cys | Thr | Gly | Cys | | (SEQ ID NO: 1370) |
| Pro | Gly | Xaa' | Thr | Cys | Gly | Glu | Xaa' | Ile | Cys | Xaa' | Ala | Tyr | Ala | Xaa' | Cys | Thr | Gly | Cys | | (SEQ ID NO: 1371) |
| Pro | Gly | Xaa' | Thr | Cys | Gly | Glu | Xaa' | Ile | Cys | Xaa' | Ala | Tyr | Ala | Ala | Cys | Xaa' | Gly | Cys | | (SEQ ID NO: 1372) |
| Pro | Gly | Xaa' | Thr | Cys | Gly | Glu | Xaa' | Ile | Cys | Xaa' | Ala | Tyr | Ala | Ala | Cys | Thr | Gly | Xaa' | | (SEQ ID NO: 1373) |
| Pro | Gly | Xaa' | Thr | Cys | Gly | Glu | Xaa' | Ile | Cys | Xaa' | Ala | Tyr | Ala | Ala | Cys | Thr | Gly | Cys | Xaa' | (SEQ ID NO: 1374) |
| Pro | Gly | Xaa' | Thr | Cys | Gly | Glu | Xaa' | Ile | Cys | Ala | Xaa' | Tyr | Ala | Ala | Cys | Thr | Gly | Cys | | (SEQ ID NO: 1375) |
| Pro | Gly | Xaa' | Thr | Cys | Gly | Glu | Xaa' | Ile | Cys | Ala | Xaa' | Tyr | Ala | Ala | Cys | Thr | Gly | Cys | | (SEQ ID NO: 1376) |
| Pro | Gly | Xaa' | Thr | Cys | Gly | Glu | Xaa' | Ile | Cys | Ala | Xaa' | Xaa' | Ala | Ala | Cys | Thr | Gly | Cys | | (SEQ ID NO: 1377) |
| Pro | Gly | Xaa' | Thr | Cys | Gly | Glu | Xaa' | Ile | Cys | Ala | Xaa' | Tyr | Xaa' | Ala | Cys | Thr | Gly | Cys | | (SEQ ID NO: 1378) |
| Pro | Gly | Xaa' | Thr | Cys | Gly | Glu | Xaa' | Ile | Cys | Ala | Xaa' | Tyr | Ala | Xaa' | Cys | Thr | Gly | Cys | | (SEQ ID NO: 1379) |
| Pro | Gly | Xaa' | Thr | Cys | Gly | Glu | Xaa' | Ile | Cys | Ala | Xaa' | Tyr | Ala | Ala | Cys | Thr | Gly | Cys | | (SEQ ID NO: 1380) |
| Pro | Gly | Xaa' | Thr | Cys | Gly | Glu | Xaa' | Ile | Cys | Ala | Xaa' | Tyr | Ala | Ala | Xaa' | Thr | Gly | Cys | | (SEQ ID NO: 1381) |
| Pro | Gly | Xaa' | Thr | Cys | Gly | Glu | Xaa' | Ile | Cys | Ala | Xaa' | Tyr | Ala | Ala | Cys | Xaa' | Gly | Cys | | (SEQ ID NO: 1382) |
| Pro | Gly | Xaa' | Thr | Cys | Gly | Glu | Xaa' | Ile | Cys | Ala | Xaa' | Tyr | Ala | Ala | Cys | Thr | Xaa' | Cys | | (SEQ ID NO: 1383) |
| Pro | Gly | Xaa' | Thr | Cys | Gly | Glu | Xaa' | Ile | Cys | Ala | Xaa' | Tyr | Ala | Ala | Cys | Thr | Gly | Xaa' | | (SEQ ID NO: 1384) |
| Pro | Gly | Xaa' | Thr | Cys | Gly | Glu | Xaa' | Ile | Cys | Ala | Xaa' | Tyr | Ala | Ala | Cys | Thr | Gly | Cys | Xaa' | (SEQ ID NO: 1385) |
| Pro | Gly | Xaa' | Thr | Cys | Gly | Glu | Xaa' | Ile | Cys | Ala | Tyr | Xaa' | Ala | Ala | Cys | Thr | Gly | Cys | | (SEQ ID NO: 1386) |
| Pro | Gly | Xaa' | Thr | Cys | Gly | Glu | Xaa' | Ile | Cys | Ala | Tyr | Xaa' | Ala | Ala | Cys | Thr | Gly | Cys | | (SEQ ID NO: 1387) |
| Pro | Gly | Xaa' | Thr | Cys | Gly | Glu | Xaa' | Ile | Cys | Ala | Tyr | Ala | Xaa' | Ala | Cys | Thr | Gly | Cys | | (SEQ ID NO: 1388) |
| Pro | Gly | Xaa' | Thr | Cys | Gly | Glu | Xaa' | Ile | Cys | Ala | Tyr | Ala | Xaa' | Ala | Cys | Thr | Gly | Cys | | (SEQ ID NO: 1389) |
| Pro | Gly | Xaa' | Thr | Cys | Gly | Glu | Xaa' | Ile | Cys | Ala | Tyr | Ala | Xaa' | Ala | Cys | Thr | Gly | Cys | | (SEQ ID NO: 1390) |
| Pro | Gly | Xaa' | Thr | Cys | Gly | Glu | Xaa' | Ile | Cys | Ala | Tyr | Ala | Xaa' | Ala | Cys | Thr | Gly | Cys | | (SEQ ID NO: 1391) |
| Pro | Gly | Xaa' | Thr | Cys | Gly | Glu | Xaa' | Ile | Cys | Ala | Tyr | Xaa' | Ala | Ala | Cys | Thr | Gly | Cys | Xaa' | (SEQ ID NO: 1392) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1393) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1394) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1395) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1396) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1397) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1398) |

FIG. 20

| | | | | | | | | | | | |
|---|---|---|---|---|---|---|---|---|---|---|---|
| Pro | Gly | Xaa' | Thr | Cys | Gly | Glu | Xaa' | Ile | Cys | Ala | Tyr | Ala | Xaa' | Ala | Cys | Thr | Gly | Cys | Xaa' | (SEQ ID NO: 1399) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1400) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1401) |
| Pro | Gly | Xaa' | Thr | Cys | Gly | Glu | Xaa' | Ile | Cys | Ala | Tyr | Ala | Ala | Xaa' | Cys | Xaa' | Thr | Gly | Cys | (SEQ ID NO: 1402) |
| Pro | Gly | Xaa' | Thr | Cys | Gly | Glu | Xaa' | Ile | Cys | Ala | Tyr | Ala | Ala | Xaa' | Cys | Thr | Gly | Cys | | (SEQ ID NO: 1403) |
| Pro | Gly | Xaa' | Thr | Cys | Gly | Glu | Xaa' | Ile | Cys | Ala | Tyr | Ala | Ala | Xaa' | Cys | Thr | Xaa' | Gly | Cys | (SEQ ID NO: 1404) |
| Pro | Gly | Xaa' | Thr | Cys | Gly | Glu | Xaa' | Ile | Cys | Ala | Tyr | Ala | Ala | Xaa' | Cys | Thr | Gly | Cys | Xaa' | (SEQ ID NO: 1405) |
| Pro | Gly | Xaa' | Thr | Cys | Gly | Glu | Xaa' | Ile | Cys | Ala | Tyr | Ala | Ala | Cys | Xaa' | Thr | Gly | Cys | | (SEQ ID NO: 1406) |
| Pro | Gly | Xaa' | Thr | Cys | Gly | Glu | Xaa' | Ile | Cys | Ala | Tyr | Ala | Ala | Cys | Xaa' | Thr | Gly | Cys | | (SEQ ID NO: 1407) |
| Pro | Gly | Xaa' | Thr | Cys | Gly | Glu | Xaa' | Ile | Cys | Ala | Tyr | Ala | Ala | Cys | Xaa' | Xaa' | Thr | Gly | Cys | (SEQ ID NO: 1408) |
| Pro | Gly | Xaa' | Thr | Cys | Gly | Glu | Xaa' | Ile | Cys | Ala | Tyr | Ala | Ala | Cys | Xaa' | Thr | Gly | Cys | | (SEQ ID NO: 1409) |
| Pro | Gly | Xaa' | Thr | Cys | Gly | Glu | Xaa' | Ile | Cys | Ala | Tyr | Ala | Ala | Cys | Xaa' | Thr | Xaa' | Gly | Cys | (SEQ ID NO: 1410) |
| Pro | Gly | Xaa' | Thr | Cys | Gly | Glu | Xaa' | Ile | Cys | Ala | Tyr | Ala | Ala | Cys | Xaa' | Thr | Gly | Cys | | (SEQ ID NO: 1411) |
| Pro | Gly | Xaa' | Thr | Cys | Gly | Glu | Xaa' | Ile | Cys | Ala | Tyr | Ala | Ala | Cys | Thr | Xaa' | Xaa' | Gly | Cys | (SEQ ID NO: 1412) |
| Pro | Gly | Xaa' | Thr | Cys | Gly | Glu | Xaa' | Ile | Cys | Ala | Tyr | Ala | Ala | Cys | Thr | Xaa' | Gly | Cys | | (SEQ ID NO: 1413) |
| Pro | Gly | Xaa' | Thr | Cys | Gly | Glu | Xaa' | Ile | Cys | Ala | Tyr | Ala | Ala | Cys | Thr | Xaa' | Gly | Cys | Xaa' | (SEQ ID NO: 1414) |
| Pro | Gly | Xaa' | Thr | Cys | Gly | Glu | Xaa' | Ile | Cys | Ala | Tyr | Ala | Ala | Cys | Thr | Gly | Xaa' | Cys | | (SEQ ID NO: 1415) |
| Pro | Gly | Xaa' | Thr | Cys | Gly | Glu | Xaa' | Ile | Cys | Ala | Tyr | Ala | Ala | Cys | Thr | Gly | Xaa' | Cys | Xaa' | (SEQ ID NO: 1416) |
| Pro | Gly | Xaa' | Thr | Cys | Gly | Glu | Xaa' | Ile | Cys | Ala | Tyr | Ala | Ala | Cys | Thr | Gly | Cys | Xaa' | | (SEQ ID NO: 1417) |
| Pro | Gly | Xaa' | Thr | Cys | Gly | Glu | Xaa' | Ile | Cys | Ala | Tyr | Ala | Ala | Cys | Thr | Gly | Cys | Xaa' | Xaa' | (SEQ ID NO: 1418) |
| Pro | Gly | Xaa' | Thr | Cys | Gly | Glu | Ile | Xaa' | Cys | Ala | Tyr | Ala | Ala | Cys | Thr | Gly | Cys | Xaa' | | (SEQ ID NO: 1419) |
| Pro | Gly | Xaa' | Thr | Cys | Gly | Glu | Ile | Ile | Xaa' | Cys | Ala | Tyr | Ala | Ala | Cys | Thr | Gly | Cys | | (SEQ ID NO: 1420) |
| Pro | Gly | Xaa' | Thr | Cys | Gly | Ile | Ile | Xaa' | Xaa' | Ala | Tyr | Ala | Ala | Cys | Thr | Gly | Cys | | | (SEQ ID NO: 1421) |
| Pro | Gly | Xaa' | Thr | Cys | Gly | Ile | Ile | Xaa' | Xaa' | Cys | Ala | Tyr | Ala | Ala | Cys | Thr | Gly | Cys | | (SEQ ID NO: 1422) |
| Pro | Gly | Xaa' | Thr | Cys | Gly | Ile | Ile | Xaa' | Xaa' | Cys | Ala | Tyr | Ala | Ala | Cys | Thr | Gly | Cys | | (SEQ ID NO: 1423) |
| Pro | Gly | Xaa' | Thr | Cys | Gly | Ile | Ile | Xaa' | Xaa' | Cys | Ala | Tyr | Xaa' | Ala | Ala | Cys | Thr | Gly | Cys | (SEQ ID NO: 1424) |
| Pro | Gly | Xaa' | Thr | Cys | Gly | Ile | Ile | Xaa' | Xaa' | Cys | Ala | Tyr | Xaa' | Ala | Ala | Cys | Thr | Gly | Cys | (SEQ ID NO: 1425) |
| Pro | Gly | Xaa' | Thr | Cys | Gly | Ile | Ile | Xaa' | Xaa' | Cys | Ala | Tyr | Xaa' | Ala | Ala | Cys | Thr | Gly | Cys | (SEQ ID NO: 1426) |
| Pro | Gly | Xaa' | Thr | Cys | Gly | Ile | Ile | Xaa' | Xaa' | Cys | Ala | Tyr | Ala | Xaa' | Ala | Cys | Thr | Gly | Cys | (SEQ ID NO: 1427) |
| Pro | Gly | Xaa' | Thr | Cys | Gly | Ile | Ile | Xaa' | Xaa' | Cys | Ala | Tyr | Ala | Xaa' | Ala | Cys | Thr | Gly | Cys | (SEQ ID NO: 1428) |
| Pro | Gly | Xaa' | Thr | Cys | Gly | Ile | Ile | Xaa' | Xaa' | Cys | Ala | Tyr | Ala | Xaa' | Ala | Cys | Thr | Gly | Cys | (SEQ ID NO: 1429) |
| Pro | Gly | Xaa' | Thr | Cys | Gly | Ile | Ile | Xaa' | Xaa' | Cys | Ala | Tyr | Ala | Ala | Xaa' | Cys | Thr | Gly | Cys | (SEQ ID NO: 1430) |
| Pro | Gly | Xaa' | Thr | Cys | Gly | Ile | Ile | Xaa' | Cys | Xaa' | Ala | Tyr | Ala | Ala | Cys | Thr | Gly | Cys | Xaa' | (SEQ ID NO: 1431) |
| Pro | Gly | Xaa' | Thr | Cys | Gly | Ile | Ile | Xaa' | Cys | Xaa' | Ala | Tyr | Ala | Ala | Cys | Thr | Gly | Cys | | (SEQ ID NO: 1432) |

FIG. 2P

| | | | | | | | | | | |
|---|---|---|---|---|---|---|---|---|---|---|
| Pro Gly Xaa' Thr Cys Gly Glu Ile Xaa' Cys Xaa' Ala Tyr Ala Ala Cys Thr Gly Cys | (SEQ ID NO: 1433) |
| Pro Gly Xaa' Thr Cys Gly Glu Ile Xaa' Cys Xaa' Ala Tyr Ala Ala Cys Thr Gly Cys | (SEQ ID NO: 1434) |
| Pro Gly Xaa' Thr Cys Gly Glu Ile Xaa' Cys Xaa' Ala Tyr Xaa' Ala Cys Thr Gly Cys | (SEQ ID NO: 1435) |
| Pro Gly Xaa' Thr Cys Gly Glu Ile Xaa' Cys Xaa' Ala Tyr Ala Xaa' Cys Thr Gly Cys | (SEQ ID NO: 1436) |
| Pro Gly Xaa' Thr Cys Gly Glu Ile Xaa' Cys Xaa' Ala Tyr Ala Ala Cys Thr Gly Cys | (SEQ ID NO: 1437) |
| Pro Gly Xaa' Thr Cys Gly Glu Ile Xaa' Cys Xaa' Ala Tyr Ala Ala Cys Xaa' Gly Cys | (SEQ ID NO: 1438) |
| Pro Gly Xaa' Thr Cys Gly Glu Ile Xaa' Cys Xaa' Ala Tyr Ala Ala Cys Thr Xaa' Cys | (SEQ ID NO: 1439) |
| Pro Gly Xaa' Thr Cys Gly Glu Ile Xaa' Cys Xaa' Ala Tyr Ala Ala Cys Thr Gly Xaa' | (SEQ ID NO: 1440) |
| Pro Gly Xaa' Thr Cys Gly Glu Ile Xaa' Cys Xaa' Ala Tyr Ala Ala Cys Thr Gly Cys Xaa' | (SEQ ID NO: 1441) |
| Pro Gly Xaa' Thr Cys Gly Glu Ile Xaa' Cys Ala Ala Tyr Ala Ala Cys Thr Gly Cys | (SEQ ID NO: 1442) |
| Pro Gly Xaa' Thr Cys Gly Glu Ile Xaa' Cys Ala Xaa' Tyr Ala Ala Cys Thr Gly Cys | (SEQ ID NO: 1443) |
| Pro Gly Xaa' Thr Cys Gly Glu Ile Xaa' Cys Ala Ala Xaa' Ala Ala Cys Thr Gly Cys | (SEQ ID NO: 1444) |
| Pro Gly Xaa' Thr Cys Gly Glu Ile Xaa' Cys Ala Ala Tyr Xaa' Ala Cys Thr Gly Cys | (SEQ ID NO: 1445) |
| Pro Gly Xaa' Thr Cys Gly Glu Ile Xaa' Cys Ala Ala Tyr Ala Xaa' Cys Thr Gly Cys | (SEQ ID NO: 1446) |
| Pro Gly Xaa' Thr Cys Gly Glu Ile Xaa' Cys Ala Ala Tyr Ala Ala Cys Xaa' Gly Cys | (SEQ ID NO: 1447) |
| Pro Gly Xaa' Thr Cys Gly Glu Ile Xaa' Cys Ala Ala Tyr Ala Ala Cys Thr Xaa' Cys | (SEQ ID NO: 1448) |
| Pro Gly Xaa' Thr Cys Gly Glu Ile Xaa' Cys Ala Ala Tyr Ala Ala Cys Thr Gly Xaa' | (SEQ ID NO: 1449) |
| Pro Gly Xaa' Thr Cys Gly Glu Ile Xaa' Cys Ala Ala Tyr Ala Ala Cys Thr Gly Cys Xaa' | (SEQ ID NO: 1450) |
| Pro Gly Xaa' Thr Cys Gly Glu Ile Xaa' Cys Ala Tyr Xaa' Ala Ala Cys Thr Gly Cys | (SEQ ID NO: 1451) |
| Pro Gly Xaa' Thr Cys Gly Glu Ile Xaa' Cys Ala Tyr Xaa' Ala Ala Cys Thr Gly Cys | (SEQ ID NO: 1452) |
| Pro Gly Xaa' Thr Cys Gly Glu Ile Xaa' Cys Ala Tyr Xaa' Ala Ala Cys Thr Gly Cys | (SEQ ID NO: 1453) |
| Pro Gly Xaa' Thr Cys Gly Glu Ile Xaa' Cys Ala Tyr Xaa' Ala Ala Cys Thr Gly Cys | (SEQ ID NO: 1454) |
| Pro Gly Xaa' Thr Cys Gly Glu Ile Xaa' Cys Ala Tyr Xaa' Ala Ala Cys Thr Gly Cys | (SEQ ID NO: 1455) |
| Pro Gly Xaa' Thr Cys Gly Glu Ile Xaa' Cys Ala Tyr Xaa' Ala Ala Cys Thr Gly Cys | (SEQ ID NO: 1456) |
| Pro Gly Xaa' Thr Cys Gly Glu Ile Xaa' Cys Ala Tyr Xaa' Ala Ala Cys Thr Gly Cys Xaa' | (SEQ ID NO: 1457) |
| Pro Gly Xaa' Thr Cys Gly Glu Ile Xaa' Cys Ala Tyr Ala Xaa' Ala Cys Thr Gly Cys | (SEQ ID NO: 1458) |
| Pro Gly Xaa' Thr Cys Gly Glu Ile Xaa' Cys Ala Tyr Ala Xaa' Ala Cys Thr Gly Cys | (SEQ ID NO: 1459) |
| Pro Gly Xaa' Thr Cys Gly Glu Ile Xaa' Cys Ala Tyr Ala Ala Xaa' Cys Thr Gly Cys | (SEQ ID NO: 1460) |
| Pro Gly Xaa' Thr Cys Gly Glu Ile Xaa' Cys Ala Tyr Ala Ala Xaa' Cys Thr Gly Cys | (SEQ ID NO: 1461) |
| Pro Gly Xaa' Thr Cys Gly Glu Ile Xaa' Cys Ala Tyr Ala Ala Xaa' Cys Thr Gly Cys | (SEQ ID NO: 1462) |
| Pro Gly Xaa' Thr Cys Gly Glu Ile Xaa' Cys Ala Tyr Ala Ala Xaa' Cys Thr Gly Cys | (SEQ ID NO: 1463) |
| Pro Gly Xaa' Thr Cys Gly Glu Ile Xaa' Cys Ala Tyr Ala Ala Xaa' Cys Thr Gly Cys | (SEQ ID NO: 1464) |
| Pro Gly Xaa' Thr Cys Gly Glu Ile Xaa' Cys Ala Tyr Ala Ala Xaa' Cys Thr Gly Cys Xaa' | (SEQ ID NO: 1465) |
| Pro Gly Xaa' Thr Cys Gly Glu Ile Xaa' Cys Ala Tyr Ala Ala Xaa' Cys Thr Gly Cys | (SEQ ID NO: 1466) |

FIG. 2Q

FIG. 2R

| | | | | | | | | | | | | | |
|---|---|---|---|---|---|---|---|---|---|---|---|---|---|
| Pro | Gly | Xaa' | Thr | Cys | Gly | Glu | Ile | Xaa' | Ala | Tyr | Ala | Ala | Xaa' | Xaa' | Cys | Thr | Gly | Cys | (SEQ ID NO: 1467) |
| Pro | Gly | Xaa' | Thr | Cys | Gly | Glu | Ile | Xaa' | Cys | Ala | Tyr | Ala | Ala | Xaa' | Cys | Xaa' | Thr | Gly | Cys | (SEQ ID NO: 1468) |
| Pro | Gly | Xaa' | Thr | Cys | Gly | Glu | Ile | Xaa' | Cys | Ala | Tyr | Ala | Ala | Xaa' | Cys | Thr | Xaa' | Gly | Cys | (SEQ ID NO: 1469) |
| Pro | Gly | Xaa' | Thr | Cys | Gly | Glu | Ile | Xaa' | Cys | Ala | Tyr | Ala | Ala | Xaa' | Cys | Thr | Gly | Xaa' | Cys | (SEQ ID NO: 1470) |
| Pro | Gly | Xaa' | Thr | Cys | Gly | Glu | Ile | Xaa' | Cys | Ala | Tyr | Ala | Ala | Xaa' | Cys | Thr | Gly | Cys | Xaa' | (SEQ ID NO: 1471) |
| Pro | Gly | Xaa' | Thr | Cys | Gly | Glu | Ile | Xaa' | Cys | Ala | Tyr | Ala | Ala | Xaa' | Xaa' | Cys | Thr | Gly | Cys | (SEQ ID NO: 1472) |
| Pro | Gly | Xaa' | Thr | Cys | Gly | Glu | Ile | Xaa' | Cys | Ala | Tyr | Ala | Ala | Cys | Xaa' | Xaa' | Thr | Gly | Cys | (SEQ ID NO: 1473) |
| Pro | Gly | Xaa' | Thr | Cys | Gly | Glu | Ile | Xaa' | Cys | Ala | Tyr | Ala | Ala | Cys | Xaa' | Thr | Xaa' | Gly | Cys | (SEQ ID NO: 1474) |
| Pro | Gly | Xaa' | Thr | Cys | Gly | Glu | Ile | Xaa' | Cys | Ala | Tyr | Ala | Ala | Cys | Xaa' | Thr | Gly | Xaa' | Cys | (SEQ ID NO: 1475) |
| Pro | Gly | Xaa' | Thr | Cys | Gly | Glu | Ile | Xaa' | Cys | Ala | Tyr | Ala | Ala | Cys | Xaa' | Thr | Gly | Cys | Xaa' | (SEQ ID NO: 1476) |
| Pro | Gly | Xaa' | Thr | Cys | Gly | Glu | Ile | Xaa' | Cys | Ala | Tyr | Ala | Ala | Cys | Thr | Xaa' | Xaa' | Gly | Cys | (SEQ ID NO: 1477) |
| Pro | Gly | Xaa' | Thr | Cys | Gly | Glu | Ile | Xaa' | Cys | Ala | Tyr | Ala | Ala | Cys | Thr | Xaa' | Gly | Xaa' | Cys | (SEQ ID NO: 1478) |
| Pro | Gly | Xaa' | Thr | Cys | Gly | Glu | Ile | Xaa' | Cys | Ala | Tyr | Ala | Ala | Cys | Thr | Xaa' | Gly | Cys | Xaa' | (SEQ ID NO: 1479) |
| Pro | Gly | Xaa' | Thr | Cys | Gly | Glu | Ile | Xaa' | Cys | Ala | Tyr | Ala | Ala | Cys | Thr | Gly | Xaa' | Xaa' | Cys | (SEQ ID NO: 1480) |
| Pro | Gly | Xaa' | Thr | Cys | Gly | Glu | Ile | Xaa' | Cys | Ala | Tyr | Ala | Ala | Cys | Thr | Gly | Xaa' | Cys | Xaa' | (SEQ ID NO: 1481) |
| Pro | Gly | Xaa' | Thr | Cys | Gly | Glu | Ile | Xaa' | Cys | Ala | Tyr | Ala | Ala | Cys | Thr | Gly | Cys | Xaa' | Xaa' | (SEQ ID NO: 1482) |
| Pro | Gly | Xaa' | Thr | Cys | Gly | Glu | Ile | Cys | Xaa' | Ala | Tyr | Ala | Ala | Xaa' | Xaa' | Thr | Gly | Cys | (SEQ ID NO: 1483) |
| Pro | Gly | Xaa' | Thr | Cys | Gly | Glu | Ile | Cys | Xaa' | Ala | Tyr | Ala | Ala | Xaa' | Thr | Xaa' | Gly | Cys | (SEQ ID NO: 1484) |
| Pro | Gly | Xaa' | Thr | Cys | Gly | Glu | Ile | Cys | Xaa' | Ala | Tyr | Ala | Ala | Xaa' | Thr | Gly | Xaa' | Cys | (SEQ ID NO: 1485) |
| Pro | Gly | Xaa' | Thr | Cys | Gly | Glu | Ile | Cys | Xaa' | Ala | Tyr | Ala | Ala | Xaa' | Thr | Gly | Cys | Xaa' | (SEQ ID NO: 1486) |
| Pro | Gly | Xaa' | Thr | Cys | Gly | Glu | Ile | Cys | Xaa' | Ala | Tyr | Ala | Ala | Cys | Thr | Gly | Cys | (SEQ ID NO: 1487) |
| Pro | Gly | Xaa' | Thr | Cys | Gly | Glu | Ile | Cys | Xaa' | Xaa' | Ala | Tyr | Ala | Ala | Cys | Thr | Gly | Cys | (SEQ ID NO: 1488) |
| Pro | Gly | Xaa' | Thr | Cys | Gly | Glu | Ile | Cys | Xaa' | Ala | Xaa' | Tyr | Ala | Ala | Cys | Thr | Gly | Cys | (SEQ ID NO: 1489) |
| Pro | Gly | Xaa' | Thr | Cys | Gly | Glu | Ile | Cys | Xaa' | Ala | Tyr | Xaa' | Ala | Ala | Cys | Thr | Gly | Cys | (SEQ ID NO: 1490) |
| Pro | Gly | Xaa' | Thr | Cys | Gly | Glu | Ile | Cys | Xaa' | Ala | Tyr | Ala | Xaa' | Ala | Cys | Thr | Gly | Cys | (SEQ ID NO: 1491) |
| Pro | Gly | Xaa' | Thr | Cys | Gly | Glu | Ile | Cys | Xaa' | Ala | Tyr | Ala | Ala | Xaa' | Cys | Thr | Gly | Cys | (SEQ ID NO: 1492) |
| Pro | Gly | Xaa' | Thr | Cys | Gly | Glu | Ile | Cys | Xaa' | Ala | Tyr | Ala | Ala | Cys | Xaa' | Thr | Gly | Cys | (SEQ ID NO: 1493) |
| Pro | Gly | Xaa' | Thr | Cys | Gly | Glu | Ile | Cys | Xaa' | Ala | Tyr | Ala | Ala | Cys | Thr | Xaa' | Gly | Cys | (SEQ ID NO: 1494) |
| Pro | Gly | Xaa' | Thr | Cys | Gly | Glu | Ile | Cys | Xaa' | Ala | Tyr | Ala | Ala | Cys | Thr | Gly | Xaa' | Cys | (SEQ ID NO: 1495) |
| Pro | Gly | Xaa' | Thr | Cys | Gly | Glu | Ile | Cys | Xaa' | Ala | Tyr | Ala | Ala | Cys | Thr | Gly | Cys | Xaa' | (SEQ ID NO: 1496) |
| Pro | Gly | Xaa' | Thr | Cys | Gly | Glu | Ile | Cys | Ala | Xaa' | Xaa' | Tyr | Ala | Ala | Cys | Thr | Gly | Cys | (SEQ ID NO: 1497) |
| Pro | Gly | Xaa' | Thr | Cys | Gly | Glu | Ile | Cys | Ala | Xaa' | Tyr | Xaa' | Ala | Ala | Cys | Thr | Gly | Cys | (SEQ ID NO: 1498) |
| Pro | Gly | Xaa' | Thr | Cys | Gly | Glu | Ile | Cys | Ala | Xaa' | Tyr | Ala | Xaa' | Ala | Cys | Thr | Gly | Cys | (SEQ ID NO: 1499) |
| Pro | Gly | Xaa' | Thr | Cys | Gly | Glu | Ile | Cys | Ala | Xaa' | Tyr | Ala | Ala | Xaa' | Cys | Thr | Gly | Cys | (SEQ ID NO: 1500) |

FIG. 2S

| | | | | | | | | | | | | | | | | | | | | |
|---|---|---|---|---|---|---|---|---|---|---|---|---|---|---|---|---|---|---|---|---|
| Pro | Gly | Xaa' | Thr | Cys | Gly | Glu | Ile | Cys | Xaa' | Ala | Tyr | Xaa' | Ala | Ala | Xaa' | Cys | Thr | Gly | Cys | (SEQ ID NO: 1501) |
| Pro | Gly | Xaa' | Thr | Cys | Gly | Glu | Ile | Cys | Xaa' | Ala | Tyr | Xaa' | Ala | Ala | Xaa' | Cys | Thr | Gly | Cys | (SEQ ID NO: 1502) |
| Pro | Gly | Xaa' | Thr | Cys | Gly | Glu | Ile | Cys | Xaa' | Ala | Tyr | Xaa' | Ala | Ala | Xaa' | Cys | Thr | Gly | Cys | (SEQ ID NO: 1503) |
| Pro | Gly | Xaa' | Thr | Cys | Gly | Glu | Ile | Cys | Xaa' | Ala | Tyr | Xaa' | Ala | Ala | Xaa' | Cys | Thr | Gly | Cys | (SEQ ID NO: 1504) |
| Pro | Gly | Xaa' | Thr | Cys | Gly | Glu | Ile | Cys | Xaa' | Ala | Tyr | Xaa' | Ala | Ala | Xaa' | Cys | Thr | Gly | Xaa' | (SEQ ID NO: 1505) |
| Pro | Gly | Xaa' | Thr | Cys | Gly | Glu | Ile | Cys | Xaa' | Ala | Tyr | Xaa' | Ala | Ala | Cys | Thr | Gly | Cys | | (SEQ ID NO: 1506) |
| Pro | Gly | Xaa' | Thr | Cys | Gly | Glu | Ile | Cys | Xaa' | Ala | Tyr | Xaa' | Ala | Ala | Ala | Cys | Thr | Gly | Cys | (SEQ ID NO: 1507) |
| Pro | Gly | Xaa' | Thr | Cys | Gly | Glu | Ile | Cys | Xaa' | Ala | Tyr | Xaa' | Ala | Ala | Ala | Cys | Thr | Gly | Cys | (SEQ ID NO: 1508) |
| Pro | Gly | Xaa' | Thr | Cys | Gly | Glu | Ile | Cys | Xaa' | Ala | Tyr | Xaa' | Ala | Ala | Ala | Cys | Thr | Gly | Cys | (SEQ ID NO: 1509) |
| Pro | Gly | Xaa' | Thr | Cys | Gly | Glu | Ile | Cys | Xaa' | Ala | Tyr | Xaa' | Ala | Ala | Ala | Cys | Thr | Gly | Cys | (SEQ ID NO: 1510) |
| Pro | Gly | Xaa' | Thr | Cys | Gly | Glu | Ile | Cys | Xaa' | Ala | Tyr | Xaa' | Ala | Ala | Ala | Cys | Thr | Gly | Cys | (SEQ ID NO: 1511) |
| Pro | Gly | Xaa' | Thr | Cys | Gly | Glu | Ile | Cys | Xaa' | Ala | Tyr | Xaa' | Ala | Ala | Ala | Cys | Thr | Gly | Cys | (SEQ ID NO: 1512) |
| Pro | Gly | Xaa' | Thr | Cys | Gly | Glu | Ile | Cys | Xaa' | Ala | Tyr | Xaa' | Ala | Ala | Ala | Cys | Thr | Gly | Cys | (SEQ ID NO: 1513) |
| Pro | Gly | Xaa' | Thr | Cys | Gly | Glu | Ile | Cys | Xaa' | Ala | Tyr | Ala | Xaa' | Ala | Ala | Cys | Thr | Gly | Cys | (SEQ ID NO: 1514) |
| Pro | Gly | Xaa' | Thr | Cys | Gly | Glu | Ile | Cys | Xaa' | Ala | Tyr | Ala | Xaa' | Ala | Ala | Cys | Thr | Gly | Cys | (SEQ ID NO: 1515) |
| Pro | Gly | Xaa' | Thr | Cys | Gly | Glu | Ile | Cys | Xaa' | Ala | Tyr | Ala | Xaa' | Ala | Ala | Cys | Thr | Gly | Cys | (SEQ ID NO: 1516) |
| Pro | Gly | Xaa' | Thr | Cys | Gly | Glu | Ile | Cys | Xaa' | Ala | Tyr | Ala | Xaa' | Ala | Ala | Cys | Thr | Gly | Cys | (SEQ ID NO: 1517) |
| Pro | Gly | Xaa' | Thr | Cys | Gly | Glu | Ile | Cys | Xaa' | Ala | Tyr | Ala | Xaa' | Ala | Ala | Cys | Thr | Gly | Cys | (SEQ ID NO: 1518) |
| Pro | Gly | Xaa' | Thr | Cys | Gly | Glu | Ile | Cys | Xaa' | Ala | Tyr | Ala | Xaa' | Ala | Ala | Cys | Thr | Gly | Cys | (SEQ ID NO: 1519) |
| Pro | Gly | Xaa' | Thr | Cys | Gly | Glu | Ile | Cys | Xaa' | Ala | Tyr | Ala | Xaa' | Ala | Ala | Cys | Thr | Gly | Cys | (SEQ ID NO: 1520) |
| Pro | Gly | Xaa' | Thr | Cys | Gly | Glu | Ile | Cys | Xaa' | Ala | Tyr | Ala | Ala | Xaa' | Ala | Cys | Thr | Gly | Xaa' | (SEQ ID NO: 1521) |
| Pro | Gly | Xaa' | Thr | Cys | Gly | Glu | Ile | Cys | Xaa' | Ala | Tyr | Ala | Ala | Xaa' | Ala | Cys | Thr | Gly | Cys | (SEQ ID NO: 1522) |
| Pro | Gly | Xaa' | Thr | Cys | Gly | Glu | Ile | Cys | Xaa' | Ala | Tyr | Ala | Ala | Xaa' | Ala | Cys | Thr | Gly | Cys | (SEQ ID NO: 1523) |
| Pro | Gly | Xaa' | Thr | Cys | Gly | Glu | Ile | Cys | Xaa' | Ala | Tyr | Ala | Ala | Xaa' | Ala | Cys | Thr | Gly | Cys | (SEQ ID NO: 1524) |
| Pro | Gly | Xaa' | Thr | Cys | Gly | Glu | Ile | Cys | Xaa' | Ala | Tyr | Ala | Ala | Xaa' | Ala | Cys | Thr | Gly | Cys | (SEQ ID NO: 1525) |
| Pro | Gly | Xaa' | Thr | Cys | Gly | Glu | Ile | Cys | Xaa' | Ala | Tyr | Ala | Ala | Xaa' | Ala | Cys | Thr | Gly | Cys | (SEQ ID NO: 1526) |
| Pro | Gly | Xaa' | Thr | Cys | Gly | Glu | Ile | Cys | Xaa' | Ala | Tyr | Ala | Ala | Cys | Thr | Gly | Cys | | | (SEQ ID NO: 1527) |
| Pro | Gly | Xaa' | Thr | Cys | Gly | Glu | Ile | Cys | Xaa' | Ala | Tyr | Ala | Ala | Ala | Cys | Thr | Gly | Cys | | (SEQ ID NO: 1528) |
| Pro | Gly | Xaa' | Thr | Cys | Gly | Glu | Ile | Cys | Xaa' | Ala | Tyr | Ala | Ala | Ala | Xaa' | Cys | Thr | Gly | Cys | (SEQ ID NO: 1529) |
| Pro | Gly | Xaa' | Thr | Cys | Gly | Glu | Ile | Cys | Xaa' | Ala | Tyr | Ala | Ala | Ala | Xaa' | Cys | Thr | Gly | Cys | (SEQ ID NO: 1530) |
| Pro | Gly | Xaa' | Thr | Cys | Gly | Glu | Ile | Cys | Xaa' | Ala | Tyr | Ala | Ala | Ala | Thr | Cys | Gly | Cys | | (SEQ ID NO: 1531) |
| Pro | Gly | Xaa' | Thr | Cys | Gly | Glu | Ile | Cys | Xaa' | Ala | Tyr | Ala | Ala | Ala | Xaa' | Cys | Xaa' | Gly | Cys | (SEQ ID NO: 1532) |
| Pro | Gly | Xaa' | Thr | Cys | Gly | Glu | Ile | Cys | Xaa' | Ala | Tyr | Ala | Ala | Ala | Thr | Cys | Xaa' | Gly | Cys | (SEQ ID NO: 1533) |
| Pro | Gly | Xaa' | Thr | Cys | Gly | Glu | Ile | Cys | Xaa' | Ala | Tyr | Ala | Ala | Ala | Thr | Cys | Xaa' | Gly | Cys | (SEQ ID NO: 1534) |

Pro Gly Xaa' Thr Cys Gly Glu Ile Cys Xaa' Ala Tyr Ala Ala Cys Thr Xaa' Gly Cys Xaa' (SEQ ID NO: 1535)
Pro Gly Xaa' Thr Cys Gly Glu Ile Cys Xaa' Ala Tyr Ala Ala Cys Thr Gly Xaa' (SEQ ID NO: 1536)
Pro Gly Xaa' Thr Cys Gly Glu Ile Cys Xaa' Ala Tyr Ala Ala Cys Thr Gly Cys (SEQ ID NO: 1537)
Pro Gly Xaa' Thr Cys Gly Glu Ile Cys Xaa' Ala Tyr Ala Ala Cys Thr Gly Xaa' Cys Xaa' (SEQ ID NO: 1538)
Pro Gly Xaa' Thr Cys Gly Glu Ile Cys Xaa' Ala Tyr Ala Ala Cys Thr Gly Cys Xaa' (SEQ ID NO: 1539)
Pro Gly Xaa' Thr Cys Gly Glu Ile Cys Xaa' Ala Tyr Ala Ala Cys Thr Gly Xaa' Cys Xaa' (SEQ ID NO: 1540)
Pro Gly Xaa' Thr Cys Gly Glu Ile Cys Ala Xaa' Tyr Ala Ala Cys Thr Gly Cys (SEQ ID NO: 1541)
Pro Gly Xaa' Thr Cys Gly Glu Ile Cys Xaa' Ala Xaa' Tyr Ala Ala Cys Thr Gly Cys (SEQ ID NO: 1543)
Pro Gly Xaa' Thr Cys Gly Glu Ile Cys Xaa' Ala Xaa' Tyr Ala Ala Cys Thr Ala Cys Thr Gly Cys (SEQ ID NO: 1544)
Pro Gly Xaa' Thr Cys Gly Glu Ile Cys Xaa' Ala Xaa' Tyr Xaa' Ala Ala Cys Thr Gly Cys (SEQ ID NO: 1545)
Pro Gly Xaa' Thr Cys Gly Glu Ile Cys Xaa' Ala Xaa' Tyr Ala Ala Xaa' Cys Thr Gly Cys (SEQ ID NO: 1546)
Pro Gly Xaa' Thr Cys Gly Glu Ile Cys Xaa' Ala Xaa' Tyr Ala Ala Cys Xaa' Thr Gly Cys (SEQ ID NO: 1547)
Pro Gly Xaa' Thr Cys Gly Glu Ile Cys Xaa' Ala Xaa' Tyr Ala Ala Cys Thr Xaa' Gly Cys (SEQ ID NO: 1548)
Pro Gly Xaa' Thr Cys Gly Glu Ile Cys Xaa' Ala Xaa' Tyr Ala Ala Cys Thr Gly Xaa' Cys (SEQ ID NO: 1549)
Pro Gly Xaa' Thr Cys Gly Glu Ile Cys Xaa' Ala Xaa' Tyr Ala Ala Cys Thr Gly Cys Xaa' (SEQ ID NO: 1550)
Pro Gly Xaa' Thr Cys Gly Glu Ile Cys Xaa' Xaa' Tyr Xaa' Ala Ala Cys Thr Gly Cys (SEQ ID NO: 1551)
Pro Gly Xaa' Thr Cys Gly Glu Ile Cys Xaa' Xaa' Tyr Xaa' Ala Xaa' Ala Cys Thr Gly Cys (SEQ ID NO: 1552)
Pro Gly Xaa' Thr Cys Gly Glu Ile Cys Xaa' Xaa' Tyr Xaa' Ala Ala Xaa' Cys Thr Gly Cys (SEQ ID NO: 1553)
Pro Gly Xaa' Thr Cys Gly Glu Ile Cys Xaa' Xaa' Tyr Xaa' Ala Ala Cys Xaa' Thr Gly Cys (SEQ ID NO: 1554)
Pro Gly Xaa' Thr Cys Gly Glu Ile Cys Xaa' Xaa' Tyr Xaa' Ala Ala Cys Thr Xaa' Gly Cys (SEQ ID NO: 1555)
Pro Gly Xaa' Thr Cys Gly Glu Ile Cys Xaa' Xaa' Tyr Xaa' Ala Ala Cys Thr Gly Xaa' Cys (SEQ ID NO: 1556)
Pro Gly Xaa' Thr Cys Gly Glu Ile Cys Xaa' Xaa' Tyr Xaa' Ala Ala Cys Thr Gly Cys Xaa' (SEQ ID NO: 1557)
Pro Gly Xaa' Thr Cys Gly Glu Ile Cys Xaa' Ala Xaa' Tyr Xaa' Ala Xaa' Cys Thr Gly Cys (SEQ ID NO: 1558)
Pro Gly Xaa' Thr Cys Gly Glu Ile Cys Xaa' Ala Xaa' Tyr Xaa' Ala Xaa' Cys Thr Gly Cys (SEQ ID NO: 1559)
Pro Gly Xaa' Thr Cys Gly Glu Ile Cys Xaa' Ala Xaa' Tyr Xaa' Ala Ala Cys Xaa' Thr Gly Cys (SEQ ID NO: 1560)
Pro Gly Xaa' Thr Cys Gly Glu Ile Cys Xaa' Ala Xaa' Tyr Xaa' Ala Ala Cys Thr Xaa' Gly Cys (SEQ ID NO: 1561)
Pro Gly Xaa' Thr Cys Gly Glu Ile Cys Xaa' Ala Xaa' Tyr Xaa' Ala Ala Cys Thr Gly Xaa' Cys (SEQ ID NO: 1562)
Pro Gly Xaa' Thr Cys Gly Glu Ile Cys Xaa' Ala Xaa' Tyr Xaa' Ala Ala Cys Thr Gly Cys Xaa' (SEQ ID NO: 1563)
Pro Gly Xaa' Thr Cys Gly Glu Ile Cys Xaa' Ala Ala Tyr Xaa' Ala Xaa' Cys Thr Gly Cys (SEQ ID NO: 1564)
Pro Gly Xaa' Thr Cys Gly Glu Ile Cys Xaa' Ala Ala Tyr Xaa' Ala Xaa' Cys Thr Gly Cys Xaa' (SEQ ID NO: 1565)
Pro Gly Xaa' Thr Cys Gly Glu Ile Cys Ala Ala Tyr Xaa' Xaa' Cys Thr Gly Cys (SEQ ID NO: 1566)
Pro Gly Xaa' Thr Cys Gly Glu Ile Cys Ala Ala Tyr Xaa' Xaa' Cys Thr Gly Cys (SEQ ID NO: 1567)
Pro Gly Xaa' Thr Cys Gly Glu Ile Cys Ala Ala Tyr Xaa' Xaa' Cys Thr Gly Cys (SEQ ID NO: 1568)

FIG. 2T

FIG. 2U

| | | | | | | | | | | | | |
|---|---|---|---|---|---|---|---|---|---|---|---|---|
| Pro | Gly | Xaa' | Thr | Cys | Gly | Glu | Ile | Cys | Ala | Tyr | Ala | Ala | Xaa' | Cys | Thr | Gly | Cys | (SEQ ID NO: 1603) |
| Pro | Gly | Xaa' | Thr | Cys | Gly | Glu | Ile | Cys | Ala | Tyr | Ala | Ala | Xaa' | Cys | Xaa' | Gly | Cys | (SEQ ID NO: 1604) |
| Pro | Gly | Xaa' | Thr | Cys | Gly | Glu | Ile | Cys | Ala | Tyr | Ala | Ala | Xaa' | Cys | Thr | Xaa' | Cys | (SEQ ID NO: 1605) |
| Pro | Gly | Xaa' | Thr | Cys | Gly | Glu | Ile | Cys | Ala | Tyr | Ala | Ala | Xaa' | Cys | Thr | Gly | Xaa' | (SEQ ID NO: 1606) |
| Pro | Gly | Xaa' | Thr | Cys | Gly | Glu | Ile | Cys | Ala | Tyr | Ala | Xaa' | Cys | Thr | Gly | Cys | (SEQ ID NO: 1607) |
| Pro | Gly | Xaa' | Thr | Cys | Gly | Glu | Ile | Cys | Ala | Tyr | Ala | Xaa' | Cys | Xaa' | Gly | Cys | (SEQ ID NO: 1608) |
| Pro | Gly | Xaa' | Thr | Cys | Gly | Glu | Ile | Cys | Ala | Tyr | Ala | Xaa' | Cys | Thr | Gly | Cys | (SEQ ID NO: 1609) |
| Pro | Gly | Xaa' | Thr | Cys | Gly | Glu | Ile | Cys | Ala | Tyr | Ala | Xaa' | Cys | Thr | Xaa' | Cys | (SEQ ID NO: 1610) |
| Pro | Gly | Xaa' | Thr | Cys | Gly | Glu | Ile | Cys | Ala | Tyr | Ala | Xaa' | Cys | Thr | Gly | Xaa' | Cys | (SEQ ID NO: 1611) |
| Pro | Gly | Xaa' | Thr | Cys | Gly | Glu | Ile | Cys | Ala | Tyr | Ala | Xaa' | Cys | Thr | Gly | Cys | Xaa' | (SEQ ID NO: 1612) |
| Pro | Gly | Xaa' | Thr | Cys | Gly | Glu | Ile | Cys | Ala | Tyr | Ala | Xaa' | Xaa' | Thr | Gly | Cys | (SEQ ID NO: 1613) |
| Pro | Gly | Xaa' | Thr | Cys | Gly | Glu | Ile | Cys | Ala | Tyr | Ala | Xaa' | Xaa' | Xaa' | Gly | Cys | (SEQ ID NO: 1614) |
| Pro | Gly | Xaa' | Thr | Cys | Gly | Glu | Ile | Cys | Ala | Tyr | Ala | Xaa' | Xaa' | Thr | Xaa' | Cys | (SEQ ID NO: 1615) |
| Pro | Gly | Xaa' | Thr | Cys | Gly | Glu | Ile | Cys | Ala | Tyr | Ala | Xaa' | Xaa' | Thr | Gly | Xaa' | (SEQ ID NO: 1616) |
| Pro | Gly | Xaa' | Thr | Cys | Gly | Glu | Ile | Cys | Ala | Tyr | Ala | Xaa' | Xaa' | Cys | Thr | Gly | Cys | (SEQ ID NO: 1617) |
| Pro | Gly | Xaa' | Thr | Cys | Gly | Glu | Ile | Cys | Ala | Tyr | Ala | Xaa' | Xaa' | Cys | Xaa' | Gly | Cys | (SEQ ID NO: 1618) |
| Pro | Gly | Xaa' | Thr | Cys | Gly | Glu | Ile | Cys | Ala | Tyr | Ala | Xaa' | Xaa' | Cys | Thr | Xaa' | Cys | (SEQ ID NO: 1619) |
| Pro | Gly | Xaa' | Thr | Cys | Gly | Glu | Ile | Cys | Ala | Tyr | Ala | Xaa' | Xaa' | Cys | Thr | Gly | Xaa' | (SEQ ID NO: 1620) |
| Pro | Gly | Xaa' | Thr | Cys | Gly | Glu | Ile | Cys | Ala | Tyr | Ala | Xaa' | Xaa' | Cys | Thr | Gly | Cys | Xaa' | (SEQ ID NO: 1621) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 1622) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 1623) |
| Pro | Gly | Xaa' | Thr | Cys | Gly | Glu | Ile | Cys | Ala | Tyr | Ala | Xaa' | Ala | Cys | Ala | Cys | Thr | Gly | Cys | (SEQ ID NO: 1624) |
| Pro | Gly | Xaa' | Thr | Cys | Gly | Glu | Ile | Cys | Ala | Tyr | Ala | Xaa' | Ala | Xaa' | Cys | Thr | Gly | Cys | (SEQ ID NO: 1625) |
| Pro | Gly | Xaa' | Thr | Cys | Gly | Glu | Ile | Cys | Ala | Tyr | Ala | Xaa' | Ala | Xaa' | Cys | Thr | Gly | Cys | (SEQ ID NO: 1626) |
| Pro | Gly | Xaa' | Thr | Cys | Gly | Glu | Ile | Cys | Ala | Tyr | Ala | Xaa' | Ala | Cys | Thr | Xaa' | Gly | Cys | (SEQ ID NO: 1627) |
| Pro | Gly | Xaa' | Thr | Cys | Gly | Glu | Ile | Cys | Ala | Tyr | Ala | Xaa' | Ala | Cys | Thr | Gly | Xaa' | Cys | (SEQ ID NO: 1628) |
| Pro | Gly | Xaa' | Thr | Cys | Gly | Glu | Ile | Cys | Ala | Tyr | Ala | Xaa' | Ala | Cys | Thr | Gly | Cys | Xaa' | (SEQ ID NO: 1629) |
| Pro | Gly | Xaa' | Thr | Cys | Gly | Glu | Ile | Cys | Ala | Tyr | Ala | Xaa' | Ala | Xaa' | Cys | Thr | Gly | Cys | (SEQ ID NO: 1630) |
| Pro | Gly | Xaa' | Thr | Cys | Gly | Glu | Ile | Cys | Ala | Tyr | Ala | Xaa' | Ala | Xaa' | Cys | Xaa' | Gly | Cys | (SEQ ID NO: 1631) |
| Pro | Gly | Xaa' | Thr | Cys | Gly | Glu | Ile | Cys | Ala | Tyr | Ala | Xaa' | Ala | Xaa' | Cys | Thr | Xaa' | Cys | (SEQ ID NO: 1632) |
| Pro | Gly | Xaa' | Thr | Cys | Gly | Glu | Ile | Cys | Ala | Tyr | Ala | Xaa' | Ala | Xaa' | Cys | Thr | Gly | Cys | (SEQ ID NO: 1633) |
| Pro | Gly | Xaa' | Thr | Cys | Gly | Glu | Ile | Cys | Ala | Tyr | Ala | Xaa' | Ala | Xaa' | Cys | Thr | Gly | Xaa' | Cys | (SEQ ID NO: 1634) |
| Pro | Gly | Xaa' | Thr | Cys | Gly | Glu | Ile | Cys | Ala | Tyr | Ala | Xaa' | Ala | Xaa' | Cys | Thr | Gly | Cys | Xaa' | (SEQ ID NO: 1635) |
| Pro | Gly | Xaa' | Thr | Cys | Gly | Glu | Ile | Cys | Ala | Tyr | Ala | Xaa' | Ala | Cys | Thr | Gly | Cys | (SEQ ID NO: 1636) |

FIG. 2V

| | | | | | | | | | | | | |
|---|---|---|---|---|---|---|---|---|---|---|---|---|
| Pro | Gly | Xaa' | Thr | Cys | Gly | Glu | Ile | Cys | Ala | Tyr | Ala | Xaa' | Ala | Cys | Xaa' | Xaa' | Thr | Gly | Cys | (SEQ ID NO: 1637) |
| Pro | Gly | Xaa' | Thr | Cys | Gly | Glu | Ile | Cys | Ala | Tyr | Ala | Xaa' | Ala | Cys | Xaa' | Thr | Gly | Cys | | (SEQ ID NO: 1638) |
| Pro | Gly | Xaa' | Thr | Cys | Gly | Glu | Ile | Cys | Ala | Tyr | Ala | Xaa' | Ala | Cys | Xaa' | Thr | Gly | Xaa' | Cys | (SEQ ID NO: 1639) |
| Pro | Gly | Xaa' | Thr | Cys | Gly | Glu | Ile | Cys | Ala | Tyr | Ala | Xaa' | Ala | Cys | Xaa' | Thr | Gly | Cys | Xaa' | (SEQ ID NO: 1640) |
| Pro | Gly | Xaa' | Thr | Cys | Gly | Glu | Ile | Cys | Ala | Tyr | Ala | Xaa' | Ala | Cys | Xaa' | Thr | Xaa' | Gly | Cys | (SEQ ID NO: 1641) |
| Pro | Gly | Xaa' | Thr | Cys | Gly | Glu | Ile | Cys | Ala | Tyr | Ala | Xaa' | Ala | Cys | Thr | Xaa' | Gly | Cys | | (SEQ ID NO: 1642) |
| Pro | Gly | Xaa' | Thr | Cys | Gly | Glu | Ile | Cys | Ala | Tyr | Ala | Xaa' | Ala | Cys | Thr | Xaa' | Gly | Xaa' | Cys | (SEQ ID NO: 1643) |
| Pro | Gly | Xaa' | Thr | Cys | Gly | Glu | Ile | Cys | Ala | Tyr | Ala | Xaa' | Ala | Cys | Thr | Xaa' | Gly | Cys | Xaa' | (SEQ ID NO: 1644) |
| Pro | Gly | Xaa' | Thr | Cys | Gly | Glu | Ile | Cys | Ala | Tyr | Ala | Xaa' | Ala | Cys | Thr | Gly | Xaa' | Cys | | (SEQ ID NO: 1645) |
| Pro | Gly | Xaa' | Thr | Cys | Gly | Glu | Ile | Cys | Ala | Tyr | Ala | Xaa' | Ala | Cys | Thr | Gly | Xaa' | Xaa' | Cys | (SEQ ID NO: 1646) |
| Pro | Gly | Xaa' | Thr | Cys | Gly | Glu | Ile | Cys | Ala | Tyr | Ala | Xaa' | Ala | Cys | Thr | Gly | Xaa' | Cys | Xaa' | (SEQ ID NO: 1647) |
| Pro | Gly | Xaa' | Thr | Cys | Gly | Glu | Ile | Cys | Ala | Tyr | Ala | Xaa' | Ala | Cys | Thr | Gly | Cys | Xaa' | | (SEQ ID NO: 1648) |
| Pro | Gly | Xaa' | Thr | Cys | Gly | Glu | Ile | Cys | Ala | Tyr | Ala | Xaa' | Ala | Cys | Thr | Gly | Cys | Xaa' | Xaa' | (SEQ ID NO: 1649) |
| Pro | Gly | Xaa' | Thr | Cys | Gly | Glu | Ile | Cys | Ala | Tyr | Ala | Ala | Xaa' | Cys | Thr | Gly | Cys | | | (SEQ ID NO: 1650) |
| Pro | Gly | Xaa' | Thr | Cys | Gly | Glu | Ile | Cys | Ala | Tyr | Ala | Ala | Xaa' | Xaa' | Cys | Thr | Gly | Cys | | (SEQ ID NO: 1651) |
| Pro | Gly | Xaa' | Thr | Cys | Gly | Glu | Ile | Cys | Ala | Tyr | Ala | Ala | Xaa' | Xaa' | Cys | Xaa' | Thr | Gly | Cys | (SEQ ID NO: 1652) |
| Pro | Gly | Xaa' | Thr | Cys | Gly | Glu | Ile | Cys | Ala | Tyr | Ala | Ala | Xaa' | Cys | Xaa' | Thr | Gly | Cys | | (SEQ ID NO: 1653) |
| Pro | Gly | Xaa' | Thr | Cys | Gly | Glu | Ile | Cys | Ala | Tyr | Ala | Ala | Xaa' | Cys | Xaa' | Thr | Gly | Xaa' | Cys | (SEQ ID NO: 1654) |
| Pro | Gly | Xaa' | Thr | Cys | Gly | Glu | Ile | Cys | Ala | Tyr | Ala | Ala | Xaa' | Cys | Xaa' | Thr | Gly | Cys | Xaa' | (SEQ ID NO: 1655) |
| Pro | Gly | Xaa' | Thr | Cys | Gly | Glu | Ile | Cys | Ala | Tyr | Ala | Ala | Xaa' | Cys | Xaa' | Thr | Xaa' | Gly | Cys | (SEQ ID NO: 1656) |
| Pro | Gly | Xaa' | Thr | Cys | Gly | Glu | Ile | Cys | Ala | Tyr | Ala | Ala | Xaa' | Cys | Thr | Xaa' | Gly | Cys | | (SEQ ID NO: 1657) |
| Pro | Gly | Xaa' | Thr | Cys | Gly | Glu | Ile | Cys | Ala | Tyr | Ala | Ala | Xaa' | Cys | Thr | Xaa' | Gly | Xaa' | Cys | (SEQ ID NO: 1658) |
| Pro | Gly | Xaa' | Thr | Cys | Gly | Glu | Ile | Cys | Ala | Tyr | Ala | Ala | Xaa' | Cys | Thr | Xaa' | Gly | Cys | Xaa' | (SEQ ID NO: 1659) |
| Pro | Gly | Xaa' | Thr | Cys | Gly | Glu | Ile | Cys | Ala | Tyr | Ala | Ala | Xaa' | Cys | Thr | Gly | Xaa' | Cys | | (SEQ ID NO: 1660) |
| Pro | Gly | Xaa' | Thr | Cys | Gly | Glu | Ile | Cys | Ala | Tyr | Ala | Ala | Xaa' | Cys | Thr | Gly | Xaa' | Xaa' | Cys | (SEQ ID NO: 1661) |
| Pro | Gly | Xaa' | Thr | Cys | Gly | Glu | Ile | Cys | Ala | Tyr | Ala | Ala | Xaa' | Cys | Thr | Gly | Xaa' | Cys | Xaa' | (SEQ ID NO: 1662) |
| Pro | Gly | Xaa' | Thr | Cys | Gly | Glu | Ile | Cys | Ala | Tyr | Ala | Ala | Xaa' | Cys | Thr | Gly | Cys | Xaa' | | (SEQ ID NO: 1663) |
| Pro | Gly | Xaa' | Thr | Cys | Gly | Glu | Ile | Cys | Ala | Tyr | Ala | Ala | Xaa' | Cys | Thr | Gly | Cys | Xaa' | Xaa' | (SEQ ID NO: 1664) |
| Pro | Gly | Xaa' | Thr | Cys | Gly | Glu | Ile | Cys | Ala | Tyr | Ala | Ala | Xaa' | Cys | Thr | Gly | Cys | | | (SEQ ID NO: 1665) |
| Pro | Gly | Xaa' | Thr | Cys | Gly | Glu | Ile | Cys | Ala | Tyr | Ala | Ala | Xaa' | Cys | Xaa' | Thr | Gly | Cys | | (SEQ ID NO: 1666) |
| Pro | Gly | Xaa' | Thr | Cys | Gly | Glu | Ile | Cys | Ala | Tyr | Ala | Ala | Xaa' | Cys | Xaa' | Thr | Gly | Xaa' | Cys | (SEQ ID NO: 1667) |
| Pro | Gly | Xaa' | Thr | Cys | Gly | Glu | Ile | Cys | Ala | Tyr | Ala | Ala | Xaa' | Cys | Xaa' | Thr | Gly | Cys | Xaa' | (SEQ ID NO: 1668) |
| Pro | Gly | Xaa' | Thr | Cys | Gly | Glu | Ile | Cys | Ala | Tyr | Ala | Ala | Xaa' | Cys | Thr | Gly | Cys | Xaa' | | (SEQ ID NO: 1669) |
| Pro | Gly | Xaa' | Thr | Cys | Gly | Glu | Ile | Cys | Ala | Tyr | Ala | Ala | Xaa' | Cys | Thr | Gly | Cys | Xaa' | Xaa' | (SEQ ID NO: 1670) |

FIG. 2W

| | | | | | | | | | | |
|---|---|---|---|---|---|---|---|---|---|---|
| Pro Gly Xaa' | Thr Cys | Gly Glu | Ile Cys | Ala | Tyr Ala | Ala Cys | Xaa' | Thr Gly Cys | | (SEQ ID NO: 1671) |
| Pro Gly Xaa' | Thr Cys | Gly Glu | Ile Cys | Ala | Tyr Ala | Ala Cys | Xaa' | Xaa' Thr Gly Cys | | (SEQ ID NO: 1672) |
| Pro Gly Xaa' | Thr Cys | Gly Glu | Ile Cys | Ala | Tyr Ala | Ala Cys | Xaa' | Xaa' Xaa' Thr Gly Cys | | (SEQ ID NO: 1673) |
| Pro Gly Xaa' | Thr Cys | Gly Glu | Ile Cys | Ala | Tyr Ala | Ala Cys | Xaa' | Xaa' Xaa' Thr Xaa' Gly Cys | | (SEQ ID NO: 1674) |
| Pro Gly Xaa' | Thr Cys | Gly Glu | Ile Cys | Ala | Tyr Ala | Ala Cys | Xaa' | Xaa' Xaa' Thr Xaa' Gly Xaa' Cys | | (SEQ ID NO: 1675) |
| Pro Gly Xaa' | Thr Cys | Gly Glu | Ile Cys | Ala | Tyr Ala | Ala Cys | Xaa' | Xaa' Xaa' Thr Xaa' Gly Xaa' Xaa' Cys | | (SEQ ID NO: 1676) |
| Pro Gly Xaa' | Thr Cys | Gly Glu | Ile Cys | Ala | Tyr Ala | Ala Cys | Xaa' | Xaa' Xaa' Thr Xaa' Gly Xaa' Cys | | (SEQ ID NO: 1677) |
| Pro Gly Xaa' | Thr Cys | Gly Glu | Ile Cys | Ala | Tyr Ala | Ala Cys | Xaa' | Xaa' Thr Xaa' Xaa' Gly Cys | | (SEQ ID NO: 1678) |
| Pro Gly Xaa' | Thr Cys | Gly Glu | Ile Cys | Ala | Tyr Ala | Ala Cys | Xaa' | Xaa' Thr Xaa' Xaa' Gly Xaa' Cys | | (SEQ ID NO: 1679) |
| Pro Gly Xaa' | Thr Cys | Gly Glu | Ile Cys | Ala | Tyr Ala | Ala Cys | Xaa' | Xaa' Thr Xaa' Xaa' Gly Xaa' Xaa' Cys | | (SEQ ID NO: 1680) |
| Pro Gly Xaa' | Thr Cys | Gly Glu | Ile Cys | Ala | Tyr Ala | Ala Cys | Xaa' | Xaa' Thr Xaa' Gly Xaa' Xaa' Cys | | (SEQ ID NO: 1681) |
| Pro Gly Xaa' | Thr Cys | Gly Glu | Ile Cys | Ala | Tyr Ala | Ala Cys | Xaa' | Xaa' Thr Gly Xaa' Xaa' Cys | | (SEQ ID NO: 1682) |
| Pro Gly Xaa' | Thr Cys | Gly Glu | Ile Cys | Ala | Tyr Ala | Ala Cys | Xaa' | Xaa' Thr Gly Xaa' Cys Xaa' | | (SEQ ID NO: 1683) |
| Pro Gly Xaa' | Thr Cys | Gly Glu | Ile Cys | Ala | Tyr Ala | Ala Cys | Xaa' | Xaa' Thr Gly Cys Xaa' | | (SEQ ID NO: 1684) |
| Pro Gly Xaa' | Thr Cys | Gly Glu | Ile Cys | Ala | Tyr Ala | Ala Cys | Xaa' | Xaa' Thr Gly Cys Xaa' Xaa' | | (SEQ ID NO: 1685) |
| Pro Gly Xaa' | Thr Cys | Gly Glu | Ile Cys | Ala | Tyr Ala | Ala Cys | Thr | Xaa' Gly Cys | | (SEQ ID NO: 1686) |
| Pro Gly Xaa' | Thr Cys | Gly Glu | Ile Cys | Ala | Tyr Ala | Ala Cys | Thr | Xaa' Xaa' Gly Cys | | (SEQ ID NO: 1687) |
| Pro Gly Xaa' | Thr Cys | Gly Glu | Ile Cys | Ala | Tyr Ala | Ala Cys | Thr | Xaa' Xaa' Xaa' Gly Cys | | (SEQ ID NO: 1688) |
| Pro Gly Xaa' | Thr Cys | Gly Glu | Ile Cys | Ala | Tyr Ala | Ala Cys | Thr | Xaa' Xaa' Xaa' Gly Xaa' Cys | | (SEQ ID NO: 1689) |
| Pro Gly Xaa' | Thr Cys | Gly Glu | Ile Cys | Ala | Tyr Ala | Ala Cys | Thr | Xaa' Xaa' Xaa' Gly Xaa' Xaa' Cys | | (SEQ ID NO: 1690) |
| Pro Gly Xaa' | Thr Cys | Gly Glu | Ile Cys | Ala | Tyr Ala | Ala Cys | Thr | Xaa' Xaa' Gly Xaa' Cys | | (SEQ ID NO: 1691) |
| Pro Gly Xaa' | Thr Cys | Gly Glu | Ile Cys | Ala | Tyr Ala | Ala Cys | Thr | Xaa' Xaa' Gly Xaa' Xaa' Cys | | (SEQ ID NO: 1692) |
| Pro Gly Xaa' | Thr Cys | Gly Glu | Ile Cys | Ala | Tyr Ala | Ala Cys | Thr | Xaa' Xaa' Gly Cys Xaa' | | (SEQ ID NO: 1693) |
| Pro Gly Xaa' | Thr Cys | Gly Glu | Ile Cys | Ala | Tyr Ala | Ala Cys | Thr | Xaa' Xaa' Gly Cys Xaa' Xaa' | | (SEQ ID NO: 1694) |
| Pro Gly Xaa' | Thr Cys | Gly Glu | Ile Cys | Ala | Tyr Ala | Ala Cys | Thr | Xaa' Gly Xaa' Cys Xaa' | | (SEQ ID NO: 1695) |
| Pro Gly Xaa' | Thr Cys | Gly Glu | Ile Cys | Ala | Tyr Ala | Ala Cys | Thr | Xaa' Gly Xaa' Cys | | (SEQ ID NO: 1696) |
| Pro Gly Xaa' | Thr Cys | Gly Glu | Ile Cys | Ala | Tyr Ala | Ala Cys | Thr | Gly Xaa' Xaa' Cys | | (SEQ ID NO: 1697) |
| Pro Gly Xaa' | Thr Cys | Gly Glu | Ile Cys | Ala | Tyr Ala | Ala Cys | Thr | Gly Xaa' Xaa' Xaa' Cys | | (SEQ ID NO: 1698) |
| Pro Gly Xaa' | Thr Cys | Gly Glu | Ile Cys | Ala | Tyr Ala | Ala Cys | Thr | Gly Xaa' Xaa' Cys Xaa' | | (SEQ ID NO: 1699) |
| Pro Gly Xaa' | Thr Cys | Gly Glu | Ile Cys | Ala | Tyr Ala | Ala Cys | Thr | Gly Xaa' Cys Xaa' | | (SEQ ID NO: 1700) |
| Pro Gly Xaa' | Thr Cys | Gly Glu | Ile Cys | Ala | Tyr Ala | Ala Cys | Thr | Gly Xaa' Cys Xaa' Xaa' | | (SEQ ID NO: 1701) |
| Pro Gly Xaa' | Thr Cys | Gly Glu | Ile Cys | Ala | Tyr Ala | Ala Cys | Thr | Gly Cys Xaa' | | (SEQ ID NO: 1702) |
| Pro Gly Xaa' | Thr Cys | Gly Glu | Ile Cys | Ala | Tyr Ala | Ala Cys | Thr | Gly Cys Xaa' Xaa' | | (SEQ ID NO: 1703) |
| Pro Gly Xaa' | Thr Cys | Gly Glu | Ile Cys | Ala | Tyr Ala | Ala Cys | Thr | Gly Cys Xaa' Xaa' Xaa' | | (SEQ ID NO: 1704) |

FIG. 2X

| | | | | | | | | | | | | | | | | |
|---|---|---|---|---|---|---|---|---|---|---|---|---|---|---|---|---|
| Pro | Gly | Thr | Xaa' | Cys | Gly | Glu | Ile | Cys | Ala | Tyr | Ala | Ala | Cys | Thr | Gly | Cys | (SEQ ID NO: 1705) |
| Pro | Gly | Thr | Xaa' | Xaa' | Gly | Glu | Ile | Cys | Ala | Tyr | Ala | Ala | Cys | Thr | Gly | Cys | (SEQ ID NO: 1706) |
| Pro | Gly | Thr | Xaa' | Xaa' | Cys | Gly | Ile | Cys | Ala | Tyr | Ala | Ala | Cys | Thr | Gly | Cys | (SEQ ID NO: 1707) |
| Pro | Gly | Thr | Xaa' | Xaa' | Cys | Xaa' | Ile | Cys | Ala | Tyr | Ala | Ala | Cys | Thr | Gly | Cys | (SEQ ID NO: 1708) |
| Pro | Gly | Thr | Xaa' | Xaa' | Cys | Xaa' | Glu | Cys | Ala | Tyr | Ala | Ala | Cys | Thr | Gly | Cys | (SEQ ID NO: 1709) |
| Pro | Gly | Thr | Xaa' | Xaa' | Cys | Xaa' | Gly | Cys | Ala | Tyr | Ala | Ala | Cys | Thr | Gly | Cys | (SEQ ID NO: 1710) |
| Pro | Gly | Thr | Xaa' | Xaa' | Cys | Xaa' | Gly | Xaa' | Ala | Tyr | Ala | Ala | Cys | Thr | Gly | Cys | (SEQ ID NO: 1711) |
| Pro | Gly | Thr | Xaa' | Xaa' | Cys | Xaa' | Gly | Ile | Xaa' | Tyr | Ala | Ala | Cys | Thr | Gly | Cys | (SEQ ID NO: 1712) |
| Pro | Gly | Thr | Xaa' | Xaa' | Cys | Xaa' | Gly | Ile | Cys | Xaa' | Ala | Ala | Cys | Thr | Gly | Cys | (SEQ ID NO: 1713) |
| Pro | Gly | Thr | Xaa' | Xaa' | Cys | Xaa' | Gly | Ile | Cys | Ala | Xaa' | Ala | Cys | Thr | Gly | Cys | (SEQ ID NO: 1714) |
| Pro | Gly | Thr | Xaa' | Xaa' | Cys | Xaa' | Gly | Ile | Cys | Ala | Tyr | Xaa' | Cys | Thr | Gly | Cys | (SEQ ID NO: 1715) |
| Pro | Gly | Thr | Xaa' | Xaa' | Cys | Xaa' | Gly | Ile | Cys | Ala | Tyr | Ala | Xaa' | Thr | Gly | Cys | (SEQ ID NO: 1716) |
| Pro | Gly | Thr | Xaa' | Xaa' | Cys | Xaa' | Gly | Ile | Cys | Ala | Tyr | Ala | Cys | Xaa' | Gly | Cys | (SEQ ID NO: 1717) |
| Pro | Gly | Thr | Xaa' | Xaa' | Cys | Xaa' | Gly | Ile | Cys | Ala | Tyr | Ala | Cys | Thr | Xaa' | Cys | (SEQ ID NO: 1718) |
| Pro | Gly | Thr | Xaa' | Xaa' | Cys | Xaa' | Gly | Ile | Cys | Ala | Tyr | Ala | Cys | Thr | Gly | Xaa' | (SEQ ID NO: 1719) |
| Pro | Gly | Thr | Xaa' | Xaa' | Cys | Xaa' | Gly | Ile | Cys | Ala | Tyr | Ala | Cys | Thr | Gly | Cys | (SEQ ID NO: 1720) |
| Pro | Gly | Thr | Xaa' | Xaa' | Cys | Xaa' | Gly | Xaa' | Xaa' | Tyr | Ala | Ala | Cys | Thr | Gly | Cys | (SEQ ID NO: 1721) |
| Pro | Gly | Thr | Xaa' | Xaa' | Cys | Xaa' | Gly | Xaa' | Ala | Xaa' | Ala | Ala | Cys | Thr | Gly | Cys | (SEQ ID NO: 1722) |
| Pro | Gly | Thr | Xaa' | Xaa' | Cys | Xaa' | Gly | Ile | Xaa' | Xaa' | Ala | Ala | Cys | Thr | Gly | Cys | (SEQ ID NO: 1723) |
| Pro | Gly | Thr | Xaa' | Xaa' | Cys | Xaa' | Glu | Ile | Cys | Ala | Tyr | Ala | Xaa' | Thr | Gly | Cys | (SEQ ID NO: 1724) |
| Pro | Gly | Thr | Xaa' | Xaa' | Cys | Xaa' | Glu | Ile | Xaa' | Ala | Tyr | Ala | Cys | Thr | Gly | Cys | (SEQ ID NO: 1725) |
| Pro | Gly | Thr | Xaa' | Xaa' | Cys | Xaa' | Glu | Xaa' | Ile | Ala | Tyr | Xaa' | Ala | Cys | Thr | Gly | Cys | (SEQ ID NO: 1726) |
| Pro | Gly | Thr | Xaa' | Xaa' | Cys | Xaa' | Glu | Ile | Cys | Ala | Tyr | Ala' | Ala | Cys | Thr | Gly | Cys | (SEQ ID NO: 1727) |
| Pro | Gly | Thr | Xaa' | Xaa' | Cys | Xaa' | Glu | Ile | Cys | Ala | Tyr | Ala | Ala | Cys | Thr | Gly | Cys | (SEQ ID NO: 1728) |
| Pro | Gly | Thr | Xaa' | Xaa' | Cys | Xaa' | Glu | Ile | Cys | Ala | Tyr | Ala | Ala | Cys | Thr | Gly | Cys | (SEQ ID NO: 1729) |
| Pro | Gly | Thr | Xaa' | Xaa' | Cys | Xaa' | Glu | Ile | Cys | Ala | Tyr | Xaa' | Ala | Cys | Thr | Gly | Cys | (SEQ ID NO: 1730) |
| Pro | Gly | Thr | Xaa' | Xaa' | Cys | Xaa' | Glu | Ile | Cys | Ala | Xaa' | Ala | Ala | Cys | Thr | Gly | Cys | (SEQ ID NO: 1731) |
| Pro | Gly | Thr | Xaa' | Xaa' | Cys | Xaa' | Glu | Ile | Cys | Xaa' | Tyr | Ala | Ala | Cys | Thr | Gly | Cys | (SEQ ID NO: 1732) |
| Pro | Gly | Thr | Xaa' | Xaa' | Cys | Xaa' | Glu | Ile | Xaa' | Ala | Tyr | Ala | Ala | Cys | Thr | Gly | Xaa' | (SEQ ID NO: 1733) |
| Pro | Gly | Thr | Xaa' | Xaa' | Cys | Xaa' | Glu | Xaa' | Cys | Ala | Tyr | Ala | Ala | Cys | Thr | Gly | Cys | (SEQ ID NO: 1734) |
| Pro | Gly | Thr | Xaa' | Cys | Gly | Xaa' | Ile | Cys | Ala | Tyr | Ala | Ala | Cys | Thr | Gly | Cys | (SEQ ID NO: 1735) |
| Pro | Gly | Thr | Xaa' | Gly | Xaa' | Glu | Ile | Cys | Ala | Tyr | Ala | Ala | Cys | Thr | Gly | Cys | (SEQ ID NO: 1736) |
| Pro | Gly | Thr | Xaa' | Xaa' | Gly | Xaa' | Ile | Cys | Ala | Tyr | Ala | Ala | Cys | Thr | Gly | Cys | (SEQ ID NO: 1737) |
| Pro | Gly | Thr | Xaa' | Xaa' | Cys | Xaa' | Xaa' | Ile | Cys | Ala | Tyr | Ala | Ala | Cys | Thr | Gly | Cys | (SEQ ID NO: 1738) |

FIG. 2Y

| Pro Gly Thr Xaa' Cys Gly Xaa' Glu Ile Xaa' Cys Ala Tyr Ala Ala Cys Thr Gly Cys | (SEQ ID NO: 1739) |
|---|---|
| Pro Gly Thr Xaa' Cys Gly Xaa' Glu Ile Xaa' Cys Xaa' Ala Tyr Ala Ala Cys Thr Gly Cys | (SEQ ID NO: 1740) |
| Pro Gly Thr Xaa' Cys Gly Xaa' Glu Ile Xaa' Cys Ala Xaa' Tyr Ala Ala Cys Thr Gly Cys | (SEQ ID NO: 1741) |
| Pro Gly Thr Xaa' Cys Gly Xaa' Glu Ile Xaa' Cys Ala Ala Tyr Xaa' Ala Ala Cys Thr Gly Cys | (SEQ ID NO: 1742) |
| Pro Gly Thr Xaa' Cys Gly Xaa' Glu Ile Xaa' Cys Ala Ala Tyr Ala Xaa' Ala Cys Thr Gly Cys | (SEQ ID NO: 1743) |
| Pro Gly Thr Xaa' Cys Gly Xaa' Glu Ile Xaa' Cys Ala Ala Tyr Ala Ala Xaa' Cys Thr Gly Cys | (SEQ ID NO: 1744) |
| Pro Gly Thr Xaa' Cys Gly Xaa' Glu Ile Xaa' Cys Ala Ala Tyr Ala Ala Cys Xaa' Thr Gly Cys | (SEQ ID NO: 1745) |
| Pro Gly Thr Xaa' Cys Gly Xaa' Glu Ile Xaa' Cys Ala Ala Tyr Ala Ala Cys Thr Xaa' Gly Cys | (SEQ ID NO: 1746) |
| Pro Gly Thr Xaa' Cys Gly Xaa' Glu Ile Xaa' Cys Ala Ala Tyr Ala Ala Cys Thr Gly Xaa' Cys | (SEQ ID NO: 1747) |
| Pro Gly Thr Xaa' Cys Gly Xaa' Glu Ile Xaa' Cys Ala Ala Tyr Ala Ala Cys Thr Gly Cys Xaa' | (SEQ ID NO: 1748) |
| Pro Gly Thr Xaa' Cys Gly Glu Xaa' Ile Cys Ala Ala Tyr Ala Ala Cys Thr Gly Cys | (SEQ ID NO: 1749) |
| Pro Gly Thr Xaa' Cys Gly Glu Ile Xaa' Cys Ala Ala Tyr Ala Ala Cys Thr Gly Cys | (SEQ ID NO: 1750) |
| Pro Gly Thr Xaa' Cys Gly Glu Ile Xaa' Cys Ala Ala Tyr Ala Ala Cys Thr Gly Cys | (SEQ ID NO: 1751) |
| Pro Gly Thr Xaa' Cys Gly Glu Ile Xaa' Cys Xaa' Ala Tyr Ala Ala Cys Thr Gly Cys | (SEQ ID NO: 1752) |
| Pro Gly Thr Xaa' Cys Gly Glu Ile Xaa' Cys Ala Xaa' Tyr Ala Ala Cys Thr Gly Cys | (SEQ ID NO: 1753) |
| Pro Gly Thr Xaa' Cys Gly Glu Ile Xaa' Cys Ala Ala Tyr Xaa' Ala Ala Cys Thr Gly Cys | (SEQ ID NO: 1754) |
| Pro Gly Thr Xaa' Cys Gly Glu Ile Xaa' Cys Ala Ala Tyr Ala Xaa' Ala Cys Thr Gly Cys | (SEQ ID NO: 1755) |
| Pro Gly Thr Xaa' Cys Gly Glu Ile Xaa' Cys Ala Ala Tyr Ala Ala Xaa' Cys Thr Gly Cys | (SEQ ID NO: 1756) |
| Pro Gly Thr Xaa' Cys Gly Glu Ile Xaa' Cys Ala Ala Tyr Ala Ala Cys Xaa' Thr Gly Cys | (SEQ ID NO: 1757) |
| Pro Gly Thr Xaa' Cys Gly Glu Ile Xaa' Cys Ala Ala Tyr Ala Ala Cys Thr Xaa' Gly Cys | (SEQ ID NO: 1758) |
| Pro Gly Thr Xaa' Cys Gly Glu Ile Xaa' Cys Ala Ala Tyr Ala Ala Cys Thr Gly Xaa' Cys | (SEQ ID NO: 1759) |
| Pro Gly Thr Xaa' Cys Gly Glu Ile Xaa' Cys Ala Ala Tyr Ala Ala Cys Thr Gly Cys Xaa' | (SEQ ID NO: 1760) |
| Pro Gly Thr Xaa' Cys Gly Glu Ile Xaa' Cys Ala Ala Tyr Ala Ala Cys Thr Gly Cys | (SEQ ID NO: 1761) |
| Pro Gly Thr Xaa' Cys Gly Glu Ile Xaa' Cys Xaa' Ala Tyr Ala Ala Cys Thr Gly Cys | (SEQ ID NO: 1762) |
| Pro Gly Thr Xaa' Cys Gly Glu Ile Xaa' Cys Ala Xaa' Tyr Ala Ala Cys Thr Gly Cys | (SEQ ID NO: 1763) |
| Pro Gly Thr Xaa' Cys Gly Glu Ile Xaa' Cys Ala Ala Tyr Xaa' Ala Ala Cys Thr Gly Cys | (SEQ ID NO: 1764) |
| Pro Gly Thr Xaa' Cys Gly Glu Ile Xaa' Cys Ala Ala Tyr Ala Xaa' Ala Cys Thr Gly Cys | (SEQ ID NO: 1765) |
| Pro Gly Thr Xaa' Cys Gly Glu Ile Xaa' Cys Ala Ala Tyr Ala Ala Xaa' Cys Thr Gly Cys | (SEQ ID NO: 1766) |
| Pro Gly Thr Xaa' Cys Gly Glu Ile Xaa' Cys Ala Ala Tyr Ala Ala Cys Xaa' Thr Gly Cys | (SEQ ID NO: 1767) |
| Pro Gly Thr Xaa' Cys Gly Glu Ile Xaa' Cys Ala Ala Tyr Ala Ala Cys Thr Xaa' Gly Cys | (SEQ ID NO: 1768) |
| Pro Gly Thr Xaa' Cys Gly Glu Ile Xaa' Cys Ala Ala Tyr Ala Ala Cys Thr Gly Xaa' Cys | (SEQ ID NO: 1769) |
| Pro Gly Thr Xaa' Cys Gly Glu Ile Xaa' Cys Ala Ala Tyr Ala Ala Cys Thr Gly Cys Xaa' | (SEQ ID NO: 1770) |
| Pro Gly Thr Xaa' Cys Xaa' Ala Ala Tyr Ala Ala Cys Thr Gly Cys | (SEQ ID NO: 1771) |
| Pro G

| | | | | | | | | | | | | |
|---|---|---|---|---|---|---|---|---|---|---|---|---|
| Pro | Gly | Thr | Xaa' | Xaa' | Cys | Gly | Glu | Ile | Cys | Ala | Xaa' | Xaa' | Ala | Tyr | Ala | Ala | Cys | Thr | Gly | Cys | (SEQ ID NO: 1773) |
| Pro | Gly | Thr | Xaa' | Xaa' | Cys | Gly | Glu | Ile | Cys | Ala | Xaa' | Ala | Tyr | Ala | Ala | Cys | Thr | Gly | Cys | (SEQ ID NO: 1774) |
| Pro | Gly | Thr | Xaa' | Xaa' | Cys | Gly | Glu | Ile | Cys | Ala | Xaa' | Tyr | Xaa' | Ala | Ala | Cys | Thr | Gly | Cys | (SEQ ID NO: 1775) |
| Pro | Gly | Thr | Xaa' | Xaa' | Cys | Gly | Glu | Ile | Cys | Ala | Xaa' | Tyr | Ala | Xaa' | Ala | Cys | Thr | Gly | Cys | (SEQ ID NO: 1776) |
| Pro | Gly | Thr | Xaa' | Xaa' | Cys | Gly | Glu | Ile | Cys | Ala | Xaa' | Tyr | Ala | Ala | Xaa' | Cys | Thr | Gly | Cys | (SEQ ID NO: 1777) |
| Pro | Gly | Thr | Xaa' | Xaa' | Cys | Gly | Glu | Ile | Cys | Ala | Xaa' | Tyr | Ala | Ala | Cys | Xaa' | Thr | Gly | Cys | (SEQ ID NO: 1778) |
| Pro | Gly | Thr | Xaa' | Xaa' | Cys | Gly | Glu | Ile | Cys | Ala | Xaa' | Tyr | Ala | Ala | Cys | Thr | Xaa' | Gly | Cys | (SEQ ID NO: 1779) |
| Pro | Gly | Thr | Xaa' | Xaa' | Cys | Gly | Glu | Ile | Cys | Ala | Xaa' | Tyr | Ala | Ala | Cys | Thr | Gly | Xaa' | Cys | (SEQ ID NO: 1780) |
| Pro | Gly | Thr | Xaa' | Xaa' | Cys | Gly | Glu | Ile | Cys | Ala | Xaa' | Tyr | Ala | Ala | Cys | Thr | Gly | Cys | Xaa' | (SEQ ID NO: 1781) |
| Pro | Gly | Thr | Xaa' | Xaa' | Cys | Gly | Glu | Ile | Cys | Ala | Xaa. | Tyr | Ala | Ala | Cys | Thr | Gly | Cys | (SEQ ID NO: 1782) |
| Pro | Gly | Thr | Xaa' | Xaa' | Cys | Gly | Glu | Ile | Cys | Ala | Xaa' | Tyr | Xaa' | Ala | Ala | Cys | Thr | Gly | Cys | (SEQ ID NO: 1783) |
| Pro | Gly | Thr | Xaa' | Xaa' | Cys | Gly | Glu | Ile | Cys | Ala | Xaa' | Tyr | Xaa' | Ala | Xaa' | Cys | Thr | Gly | Cys | (SEQ ID NO: 1784) |
| Pro | Gly | Thr | Xaa' | Xaa' | Cys | Gly | Glu | Ile | Cys | Ala | Xaa' | Tyr | Xaa' | Ala | Cys | Xaa' | Thr | Gly | Cys | (SEQ ID NO: 1785) |
| Pro | Gly | Thr | Xaa' | Xaa' | Cys | Gly | Glu | Ile | Cys | Ala | Xaa' | Tyr | Xaa' | Ala | Cys | Thr | Xaa' | Gly | Cys | (SEQ ID NO: 1786) |
| Pro | Gly | Thr | Xaa' | Xaa' | Cys | Gly | Glu | Ile | Cys | Ala | Xaa' | Tyr | Xaa' | Ala | Cys | Thr | Gly | Xaa' | Cys | (SEQ ID NO: 1787) |
| Pro | Gly | Thr | Xaa' | Xaa' | Cys | Gly | Glu | Ile | Cys | Ala | Xaa' | Tyr | Xaa' | Ala | Cys | Thr | Gly | Cys | Xaa' | (SEQ ID NO: 1788) |
| Pro | Gly | Thr | Xaa' | Xaa' | Cys | Gly | Glu | Ile | Cys | Ala | Xaa' | Tyr | Xaa' | Ala | Cys | Thr | Gly | Cys | (SEQ ID NO: 1789) |
| Pro | Gly | Thr | Xaa' | Xaa' | Cys | Gly | Glu | Ile | Cys | Ala | Tyr | Xaa' | Ala | Ala | Cys | Thr | Gly | Cys | (SEQ ID NO: 1790) |
| Pro | Gly | Thr | Xaa' | Xaa' | Cys | Gly | Glu | Ile | Cys | Ala | Tyr | Xaa' | Ala | Xaa' | Cys | Thr | Gly | Cys | (SEQ ID NO: 1791) |
| Pro | Gly | Thr | Xaa' | Xaa' | Cys | Gly | Glu | Ile | Cys | Ala | Tyr | Xaa' | Ala | Cys | Xaa' | Thr | Gly | Cys | (SEQ ID NO: 1792) |
| Pro | Gly | Thr | Xaa' | Xaa' | Cys | Gly | Glu | Ile | Cys | Ala | Tyr | Xaa' | Ala | Cys | Thr | Xaa' | Gly | Cys | (SEQ ID NO: 1793) |
| Pro | Gly | Thr | Xaa' | Xaa' | Cys | Gly | Glu | Ile | Cys | Ala | Tyr | Xaa' | Ala | Cys | Thr | Gly | Xaa' | Cys | (SEQ ID NO: 1794) |
| Pro | Gly | Thr | Xaa' | Xaa' | Cys | Gly | Glu | Ile | Cys | Ala | Tyr | Xaa' | Ala | Cys | Thr | Gly | Cys | Xaa' | (SEQ ID NO: 1795) |
| Pro | Gly | Thr | Xaa' | Xaa' | Cys | Gly | Glu | Ile | Cys | Ala | Tyr | Ala | Xaa' | Ala | Cys | Thr | Gly | Cys | (SEQ ID NO: 1796) |
| Pro | Gly | Thr | Xaa' | Xaa' | Cys | Gly | Glu | Ile | Cys | Ala | Tyr | Ala | Xaa' | Cys | Xaa' | Thr | Gly | Cys | (SEQ ID NO: 1797) |
| Pro | Gly | Thr | Xaa' | Xaa' | Cys | Gly | Glu | Ile | Cys | Ala | Tyr | Ala | Xaa' | Cys | Thr | Xaa' | Gly | Cys | (SEQ ID NO: 1798) |
| Pro | Gly | Thr | Xaa' | Xaa' | Cys | Gly | Glu | Ile | Cys | Ala | Tyr | Ala | Xaa' | Cys | Thr | Gly | Xaa' | Cys | (SEQ ID NO: 1799) |
| Pro | Gly | Thr | Xaa' | Xaa' | Cys | Gly | Glu | Ile | Cys | Ala | Tyr | Ala | Xaa' | Cys | Thr | Gly | Cys | (SEQ ID NO: 1800) |
| Pro | Gly | Thr | Xaa' | Xaa' | Cys | Gly | Glu | Ile | Cys | Ala | Tyr | Ala | Xaa' | Ala | Cys | Thr | Gly | Cys | (SEQ ID NO: 1801) |
| Pro | Gly | Thr | Xaa' | Xaa' | Cys | Gly | Glu | Ile | Cys | Ala | Tyr | Ala | Ala | Cys | Xaa' | Thr | Gly | Cys | (SEQ ID NO: 1802) |
| Pro | Gly | Thr | Xaa' | Xaa' | Cys | Gly | Glu | Ile | Cys | Ala | Tyr | Ala | Ala | Cys | Thr | Xaa' | Gly | Cys | (SEQ ID NO: 1803) |
| Pro | Gly | Thr | Xaa' | Xaa' | Cys | Gly | Glu | Ile | Cys | Ala | Tyr | Ala | Ala | Cys | Thr | Gly | Xaa' | Cys | (SEQ ID NO: 1804) |
| Pro | Gly | Thr | Xaa' | Xaa' | Cys | Gly | Glu | Ile | Cys | Ala | Tyr | Ala | Ala | Cys | Thr | Gly | Cys | Xaa' | (SEQ ID NO: 1805) |
| Pro | Gly | Thr | Xaa' | Xaa' | Cys | Gly | Glu | Ile | Cys | Ala | Tyr | Ala | Ala | Xaa' | Cys | Thr | Gly | Cys | (SEQ ID NO: 1806) |

FIG. 2AA

FIG. 2AB

| Sequence | SEQ ID NO |
|---|---|
| Pro Gly Thr Xaa' Xaa' Cys Gly Glu Ile Cys Ala Tyr Ala Ala Xaa' Xaa' Cys Thr Gly Cys | (SEQ ID NO: 1807) |
| Pro Gly Thr Xaa' Xaa' Cys Gly Glu Ile Cys Ala Tyr Ala Ala Xaa' Xaa' Cys Xaa' Gly Cys | (SEQ ID NO: 1808) |
| Pro Gly Thr Xaa' Xaa' Cys Gly Glu Ile Cys Ala Tyr Ala Ala Xaa' Xaa' Cys Thr Gly Cys | (SEQ ID NO: 1809) |
| Pro Gly Thr Xaa' Xaa' Cys Gly Glu Ile Cys Ala Tyr Ala Ala Xaa' Xaa' Cys Thr Gly Cys | (SEQ ID NO: 1810) |
| Pro Gly Thr Xaa' Xaa' Cys Gly Glu Ile Cys Ala Tyr Ala Ala Xaa' Xaa' Cys Thr Gly Xaa' | (SEQ ID NO: 1811) |
| Pro Gly Thr Xaa' Xaa' Cys Gly Glu Ile Cys Ala Tyr Ala Ala Xaa' Xaa' Cys Thr Gly Cys | (SEQ ID NO: 1812) |
| Pro Gly Thr Xaa' Xaa' Cys Gly Glu Ile Cys Ala Tyr Ala Ala Ala Xaa' Cys Thr Gly Cys | (SEQ ID NO: 1813) |
| Pro Gly Thr Xaa' Xaa' Cys Gly Glu Ile Cys Ala Tyr Ala Ala Xaa' Xaa' Cys Thr Gly Cys | (SEQ ID NO: 1814) |
| Pro Gly Thr Xaa' Xaa' Cys Gly Glu Ile Cys Ala Tyr Ala Ala Xaa' Xaa' Cys Thr Gly Cys | (SEQ ID NO: 1815) |
| Pro Gly Thr Xaa' Xaa' Cys Gly Glu Ile Cys Ala Tyr Ala Ala Xaa' Xaa' Cys Thr Gly Xaa' | (SEQ ID NO: 1816) |
| Pro Gly Thr Xaa' Xaa' Cys Gly Glu Ile Cys Ala Tyr Ala Ala Xaa' Xaa' Cys Gly Cys | (SEQ ID NO: 1817) |
| Pro Gly Thr Xaa' Xaa' Cys Gly Glu Ile Cys Ala Tyr Ala Ala Xaa' Xaa' Cys Gly Xaa' Cys | (SEQ ID NO: 1818) |
| Pro Gly Thr Xaa' Xaa' Cys Gly Glu Ile Cys Ala Tyr Ala Ala Xaa' Xaa' Cys Gly Cys | (SEQ ID NO: 1819) |
| Pro Gly Thr Xaa' Xaa' Cys Gly Glu Ile Cys Ala Tyr Ala Ala Xaa' Xaa' Cys Gly Xaa' | (SEQ ID NO: 1820) |
| Pro Gly Thr Xaa' Xaa' Cys Gly Glu Ile Cys Ala Tyr Ala Ala Xaa' Thr Gly Cys | (SEQ ID NO: 1821) |
| Pro Gly Thr Xaa' Xaa' Cys Gly Glu Ile Cys Ala Tyr Ala Ala Xaa' Xaa' Cys Thr Xaa' Cys | (SEQ ID NO: 1822) |
| Pro Gly Thr Xaa' Xaa' Cys Gly Glu Ile Cys Ala Tyr Ala Ala Xaa' Xaa' Cys Thr Cys Xaa' | (SEQ ID NO: 1823) |
| Pro Gly Thr Xaa' Xaa' Cys Gly Glu Ile Cys Ala Tyr Ala Ala Xaa' Xaa' Cys Gly Cys Xaa' | (SEQ ID NO: 1824) |
| Pro Gly Thr Xaa' Xaa' Cys Gly Glu Ile Cys Ala Tyr Ala Ala Xaa' Xaa' Cys Gly Cys Xaa' | (SEQ ID NO: 1825) |
| Pro Gly Thr Xaa' Xaa' Cys Gly Glu Ile Cys Ala Tyr Ala Ala Xaa' Xaa' Cys Gly Cys | (SEQ ID NO: 1826) |
| Pro Gly Thr Cys Xaa' Gly Glu Ile Cys Ala Tyr Ala Ala Cys Thr Gly Cys | (SEQ ID NO: 1827) |
| Pro Gly Thr Xaa' Cys Xaa' Gly Xaa' Ile Cys Ala Tyr Ala Ala Tyr Ala Ala Cys Thr Gly Cys | (SEQ ID NO: 1828) |
| Pro Gly Thr Xaa' Cys Gly Xaa' Ile Cys Xaa' Ile Cys Ala Tyr Ala Ala Cys Thr Gly Cys | (SEQ ID NO: 1829) |
| Pro Gly Thr Xaa' Cys Xaa' Gly Glu Xaa' Ile Cys Ala Tyr Ala Ala Cys Thr Gly Cys | (SEQ ID NO: 1830) |
| Pro Gly Thr Xaa' Cys Xaa' Gly Glu Ile Xaa' Ala Tyr Ala Ala Cys Thr Gly Cys | (SEQ ID NO: 1831) |
| Pro Gly Thr Xaa' Cys Xaa' Gly Glu Ile Cys Xaa' Ala Tyr Xaa' Ala Ala Cys Thr Gly Cys | (SEQ ID NO: 1832) |
| Pro Gly Thr Xaa' Cys Xaa' Gly Glu Ile Cys Ala Xaa' Tyr Ala Ala Cys Thr Gly Cys | (SEQ ID NO: 1833) |
| Pro Gly Thr Xaa' Cys Xaa' Gly Glu Ile Cys Ala Tyr Xaa' Ala Ala Cys Thr Gly Cys | (SEQ ID NO: 1834) |
| Pro Gly Thr Xaa' Cys Xaa' Gly Glu Ile Cys Ala Tyr Ala Xaa' Ala Cys Thr Gly Cys | (SEQ ID NO: 1835) |
| Pro Gly Thr Xaa' Cys Xaa' Gly Glu Ile Cys Ala Tyr Ala Ala Xaa' Cys Thr Gly Cys | (SEQ ID NO: 1836) |
| Pro Gly Thr Xaa' Cys Xaa' Gly Glu Ile Cys Ala Tyr Ala Ala Cys Xaa' Thr Gly Cys | (SEQ ID NO: 1837) |
| Pro Gly Thr Xaa' Cys Xaa' Gly Glu Ile Cys Ala Tyr Ala Ala Cys Thr Xaa' Gly Cys | (SEQ ID NO: 1838) |
| Pro Gly Thr Xaa' Cys Xaa' Gly Glu Ile Cys Ala Tyr Ala Ala Cys Thr Gly Xaa' Cys | (SEQ ID NO: 1839) |
| Pro Gly Thr Xaa' Cys Xaa' Gly Glu Ile Cys Ala Tyr Ala Ala Cys Thr Gly Cys Xaa' | (SEQ ID NO: 1840) |

| | | | | | | | | | | | | |
|---|---|---|---|---|---|---|---|---|---|---|---|---|
| Pro | Gly | Thr | Xaa' | Cys | Xaa' | Gly | Xaa' | Glu | Ile | Cys | Ala | Tyr | Ala | Ala | Cys | Thr | Gly | Cys | (SEQ ID NO: 1841) |
| Pro | Gly | Thr | Xaa' | Cys | Xaa' | Gly | Xaa' | Glu | Ile | Cys | Ala | Tyr | Ala | Ala | Cys | Thr | Gly | Cys | (SEQ ID NO: 1842) |
| Pro | Gly | Thr | Xaa' | Cys | Xaa' | Gly | Xaa' | Glu | Ile | Cys | Ala | Tyr | Ala | Ala | Cys | Thr | Gly | Cys | (SEQ ID NO: 1843) |
| Pro | Gly | Thr | Xaa' | Cys | Xaa' | Gly | Xaa' | Glu | Ile | Cys | Xaa' | Tyr | Ala | Ala | Cys | Thr | Gly | Cys | (SEQ ID NO: 1844) |
| Pro | Gly | Thr | Xaa' | Cys | Xaa' | Gly | Xaa' | Glu | Ile | Cys | Xaa' | Tyr | Ala | Ala | Cys | Thr | Gly | Cys | (SEQ ID NO: 1845) |
| Pro | Gly | Thr | Xaa' | Cys | Xaa' | Gly | Xaa' | Glu | Ile | Cys | Ala | Xaa' | Ala | Ala | Cys | Thr | Gly | Cys | (SEQ ID NO: 1846) |
| Pro | Gly | Thr | Xaa' | Cys | Xaa' | Gly | Xaa' | Glu | Ile | Cys | Ala | Tyr | Xaa' | Ala | Cys | Thr | Gly | Cys | (SEQ ID NO: 1847) |
| Pro | Gly | Thr | Xaa' | Cys | Xaa' | Gly | Xaa' | Glu | Ile | Cys | Ala | Tyr | Ala | Xaa' | Cys | Thr | Gly | Cys | (SEQ ID NO: 1848) |
| Pro | Gly | Thr | Xaa' | Cys | Xaa' | Gly | Xaa' | Glu | Ile | Cys | Ala | Tyr | Ala | Ala | Cys | Xaa' | Gly | Cys | (SEQ ID NO: 1849) |
| Pro | Gly | Thr | Xaa' | Cys | Xaa' | Gly | Xaa' | Glu | Ile | Cys | Ala | Tyr | Ala | Ala | Cys | Thr | Xaa' | Cys | (SEQ ID NO: 1850) |
| Pro | Gly | Thr | Xaa' | Cys | Xaa' | Gly | Xaa' | Glu | Ile | Cys | Ala | Tyr | Ala | Ala | Cys | Thr | Gly | Xaa' | (SEQ ID NO: 1851) |
| Pro | Gly | Thr | Xaa' | Cys | Xaa' | Gly | Xaa' | Glu | Ile | Cys | Ala | Tyr | Ala | Ala | Cys | Thr | Gly | Cys | (SEQ ID NO: 1852) |
| Pro | Gly | Thr | Xaa' | Cys | Xaa' | Gly | Xaa' | Glu | Ile | Cys | Ala | Tyr | Ala | Ala | Cys | Thr | Gly | Cys | (SEQ ID NO: 1853) |
| Pro | Gly | Thr | Xaa' | Cys | Xaa' | Gly | Glu | Xaa' | Ile | Cys | Ala | Tyr | Ala | Ala | Cys | Thr | Gly | Cys | (SEQ ID NO: 1854) |
| Pro | Gly | Thr | Xaa' | Cys | Xaa' | Gly | Glu | Xaa' | Ile | Cys | Ala | Tyr | Ala | Ala | Cys | Thr | Gly | Cys | (SEQ ID NO: 1855) |
| Pro | Gly | Thr | Xaa' | Cys | Xaa' | Gly | Glu | Xaa' | Ile | Cys | Ala | Tyr | Ala | Ala | Cys | Thr | Gly | Cys | (SEQ ID NO: 1856) |
| Pro | Gly | Thr | Xaa' | Cys | Xaa' | Gly | Glu | Xaa' | Ile | Cys | Xaa' | Tyr | Ala | Ala | Cys | Thr | Gly | Cys | (SEQ ID NO: 1857) |
| Pro | Gly | Thr | Xaa' | Cys | Xaa' | Gly | Glu | Xaa' | Ile | Cys | Ala | Xaa' | Ala | Ala | Cys | Thr | Gly | Cys | (SEQ ID NO: 1858) |
| Pro | Gly | Thr | Xaa' | Cys | Xaa' | Gly | Glu | Xaa' | Ile | Cys | Ala | Tyr | Xaa' | Ala | Cys | Thr | Gly | Cys | (SEQ ID NO: 1859) |
| Pro | Gly | Thr | Xaa' | Cys | Xaa' | Gly | Glu | Xaa' | Ile | Cys | Ala | Tyr | Ala | Xaa' | Cys | Thr | Gly | Cys | (SEQ ID NO: 1860) |
| Pro | Gly | Thr | Xaa' | Cys | Xaa' | Gly | Glu | Xaa' | Ile | Cys | Ala | Tyr | Ala | Ala | Cys | Xaa' | Gly | Cys | (SEQ ID NO: 1861) |
| Pro | Gly | Thr | Xaa' | Cys | Xaa' | Gly | Glu | Xaa' | Ile | Cys | Ala | Tyr | Ala | Ala | Cys | Thr | Xaa' | Cys | (SEQ ID NO: 1862) |
| Pro | Gly | Thr | Xaa' | Cys | Xaa' | Gly | Glu | Xaa' | Ile | Cys | Ala | Tyr | Ala | Ala | Cys | Thr | Gly | Xaa' | (SEQ ID NO: 1863) |
| Pro | Gly | Thr | Xaa' | Cys | Xaa' | Gly | Glu | Ile | Xaa' | Cys | Ala | Tyr | Ala | Ala | Cys | Thr | Gly | Cys | (SEQ ID NO: 1864) |
| Pro | Gly | Thr | Xaa' | Cys | Xaa' | Gly | Glu | Ile | Xaa' | Cys | Ala | Tyr | Ala | Ala | Cys | Thr | Gly | Cys | (SEQ ID NO: 1865) |
| Pro | Gly | Thr | Xaa' | Cys | Xaa' | Gly | Glu | Ile | Xaa' | Cys | Ala | Tyr | Ala | Ala | Cys | Thr | Gly | Cys | (SEQ ID NO: 1866) |
| Pro | Gly | Thr | Xaa' | Cys | Xaa' | Gly | Glu | Ile | Xaa' | Cys | Xaa' | Tyr | Ala | Ala | Cys | Thr | Gly | Cys | (SEQ ID NO: 1867) |
| Pro | Gly | Thr | Xaa' | Cys | Xaa' | Gly | Glu | Ile | Xaa' | Cys | Ala | Xaa' | Ala | Ala | Cys | Thr | Gly | Cys | (SEQ ID NO: 1868) |
| Pro | Gly | Thr | Xaa' | Cys | Xaa' | Gly | Glu | Ile | Xaa' | Cys | Ala | Tyr | Xaa' | Ala | Cys | Thr | Gly | Cys | (SEQ ID NO: 1869) |
| Pro | Gly | Thr | Xaa' | Cys | Xaa' | Gly | Glu | Ile | Xaa' | Cys | Ala | Tyr | Ala | Xaa' | Cys | Thr | Gly | Cys | (SEQ ID NO: 1870) |
| Pro | Gly | Thr | Xaa' | Cys | Xaa' | Gly | Glu | Ile | Xaa' | Cys | Ala | Tyr | Ala | Ala | Cys | Xaa' | Gly | Cys | (SEQ ID NO: 1871) |
| Pro | Gly | Thr | Xaa' | Cys | Xaa' | Gly | Glu | Ile | Xaa' | Cys | Ala | Tyr | Ala | Ala | Cys | Thr | Xaa' | Cys | (SEQ ID NO: 1872) |
| Pro | Gly | Thr | Xaa' | Cys | Xaa' | Gly | Glu | Ile | Xaa' | Cys | Ala | Tyr | Ala | Ala | Cys | Thr | Gly | Xaa' | (SEQ ID NO: 1873) |
| Pro | Gly | Thr | Xaa' | Cys | Xaa' | Gly | Glu | Ile | Xaa' | Cys | Ala | Tyr | Ala | Ala | Cys | Thr | Gly | Cys | (SEQ ID NO: 1874) |

FIG. 2AC

| | | | | | | | | | | |
|---|---|---|---|---|---|---|---|---|---|---|
| Pro Gly Thr Xaa' Cys Xaa' Gly Glu Ile Xaa' Cys Ala Tyr Ala Ala Cys Thr Gly Xaa' Cys | (SEQ ID NO: 1875) |
| Pro Gly Thr Xaa' Cys Xaa' Gly Glu Ile Xaa' Cys Ala Tyr Ala Ala Cys Thr Gly Xaa' Cys | (SEQ ID NO: 1876) |
| Pro Gly Thr Xaa' Cys Xaa' Gly Glu Ile Xaa' Cys Xaa' Tyr Ala Ala Cys Thr Gly Cys | (SEQ ID NO: 1877) |
| Pro Gly Thr Xaa' Cys Xaa' Gly Glu Ile Xaa' Cys Xaa' Ala Xaa' Ala Ala Cys Thr Gly Cys | (SEQ ID NO: 1878) |
| Pro Gly Thr Xaa' Cys Xaa' Gly Glu Ile Xaa' Cys Xaa' Ala Tyr Ala Ala Cys Thr Gly Cys | (SEQ ID NO: 1879) |
| Pro Gly Thr Xaa' Cys Xaa' Gly Glu Ile Xaa' Cys Xaa' Ala Tyr Xaa' Ala Ala Cys Thr Gly Cys | (SEQ ID NO: 1880) |
| Pro Gly Thr Xaa' Cys Xaa' Gly Glu Ile Xaa' Cys Xaa' Ala Tyr Ala Xaa' Ala Cys Thr Gly Cys | (SEQ ID NO: 1881) |
| Pro Gly Thr Xaa' Cys Xaa' Gly Glu Ile Xaa' Cys Xaa' Ala Tyr Ala Xaa' Ala Cys Thr Gly Cys | (SEQ ID NO: 1882) |
| Pro Gly Thr Xaa' Cys Xaa' Gly Glu Ile Xaa' Cys Xaa' Ala Tyr Ala Ala Xaa' Cys Thr Gly Cys | (SEQ ID NO: 1883) |
| Pro Gly Thr Xaa' Cys Xaa' Gly Glu Ile Xaa' Cys Xaa' Ala Tyr Ala Ala Xaa' Cys Thr Gly Cys | (SEQ ID NO: 1884) |
| Pro Gly Thr Xaa' Cys Xaa' Gly Glu Ile Xaa' Cys Xaa' Ala Tyr Ala Ala Cys Xaa' Thr Gly Cys | (SEQ ID NO: 1885) |
| Pro Gly Thr Xaa' Cys Xaa' Gly Glu Ile Xaa' Cys Xaa' Ala Tyr Ala Ala Cys Xaa' Gly Xaa' Cys | (SEQ ID NO: 1886) |
| Pro Gly Thr Xaa' Cys Xaa' Gly Glu Ile Xaa' Cys Ala Xaa' Tyr Ala Ala Cys Thr Gly Cys | (SEQ ID NO: 1887) |
| Pro Gly Thr Xaa' Cys Xaa' Gly Glu Ile Xaa' Cys Ala Xaa' Xaa' Ala Ala Cys Thr Gly Cys | (SEQ ID NO: 1888) |
| Pro Gly Thr Xaa' Cys Xaa' Gly Glu Ile Xaa' Cys Ala Xaa' Tyr Ala Ala Cys Thr Gly Cys | (SEQ ID NO: 1889) |
| Pro Gly Thr Xaa' Cys Xaa' Gly Glu Ile Xaa' Cys Ala Xaa' Tyr Xaa' Ala Ala Cys Thr Gly Cys | (SEQ ID NO: 1890) |
| Pro Gly Thr Xaa' Cys Xaa' Gly Glu Ile Xaa' Cys Ala Xaa' Tyr Ala Xaa' Ala Cys Thr Gly Cys | (SEQ ID NO: 1891) |
| Pro Gly Thr Xaa' Cys Xaa' Gly Glu Ile Xaa' Cys Ala Xaa' Tyr Ala Xaa' Cys Thr Gly Cys | (SEQ ID NO: 1892) |
| Pro Gly Thr Xaa' Cys Xaa' Gly Glu Ile Xaa' Cys Ala Xaa' Tyr Ala Ala Xaa' Cys Thr Gly Cys | (SEQ ID NO: 1893) |
| Pro Gly Thr Xaa' Cys Xaa' Gly Glu Ile Xaa' Cys Ala Xaa' Tyr Ala Ala Cys Xaa' Gly Xaa' Cys | (SEQ ID NO: 1894) |
| Pro Gly Thr Xaa' Cys Xaa' Gly Glu Ile Xaa' Cys Ala Xaa' Tyr Ala Ala Cys Thr Xaa' Cys | (SEQ ID NO: 1895) |
| Pro Gly Thr Xaa' Cys Xaa' Gly Glu Ile Xaa' Cys Ala Xaa' Tyr Ala Ala Cys Thr Gly Xaa' Cys | (SEQ ID NO: 1896) |
| Pro Gly Thr Xaa' Cys Xaa' Gly Glu Ile Xaa' Cys Ala Ala Xaa' Ala Ala Cys Thr Gly Cys | (SEQ ID NO: 1897) |
| Pro Gly Thr Xaa' Cys Xaa' Gly Glu Ile Xaa' Cys Ala Tyr Xaa' Ala Ala Cys Thr Gly Cys | (SEQ ID NO: 1898) |
| Pro Gly Thr Xaa' Cys Xaa' Gly Glu Ile Xaa' Cys Ala Tyr Xaa' Xaa' Ala Ala Cys Thr Gly Cys | (SEQ ID NO: 1899) |
| Pro Gly Thr Xaa' Cys Xaa' Gly Glu Ile Xaa' Cys Ala Tyr Xaa' Ala Ala Cys Thr Gly Cys | (SEQ ID NO: 1900) |
| Pro Gly Thr Xaa' Cys Xaa' Gly Glu Ile Xaa' Cys Ala Tyr Xaa' Ala Xaa' Ala Cys Thr Gly Cys | (SEQ ID NO: 1901) |
| Pro Gly Thr Xaa' Cys Xaa' Gly Glu Ile Xaa' Cys Ala Tyr Xaa' Ala Xaa' Cys Thr Gly Cys | (SEQ ID NO: 1902) |
| Pro Gly Thr Xaa' Cys Xaa' Gly Glu Ile Xaa' Cys Ala Tyr Xaa' Ala Ala Xaa' Cys Thr Gly Cys | (SEQ ID NO: 1903) |
| Pro Gly Thr Xaa' Cys Xaa' Gly Glu Ile Xaa' Cys Ala Tyr Xaa' Ala Ala Cys Xaa' Gly Xaa' Cys | (SEQ ID NO: 1904) |
| Pro Gly Thr Xaa' Cys Xaa' Gly Glu Ile Xaa' Cys Ala Tyr Ala Xaa' Ala Cys Thr Gly Cys | (SEQ ID NO: 1905) |
| Pro Gly Thr Xaa' Cys Xaa' Gly Glu Ile Xaa' Cys Ala Tyr Ala Xaa' Xaa' Ala Cys Thr Gly Cys | (SEQ ID NO: 1906) |
| Pro Gly Thr Xaa' Cys Xaa' Gly Glu Ile Xaa' Cys Ala Tyr Ala Xaa' Ala Cys Thr Gly Cys | (SEQ ID NO: 1907) |
| Pro Gly Thr Xaa' Cys Xaa' Gly Glu Ile Xaa' Cys Ala Tyr Ala Xaa' Ala Cys Xaa' Thr Gly Cys | (SEQ ID NO: 1908) |

FIG. 2AD

FIG. 2AE

```
Pro Gly Thr Xaa' Cys Gly Xaa' Xaa' Glu Ile Cys Ala Tyr Ala Ala Cys Thr Gly Xaa' Cys    (SEQ ID NO: 1943)
Pro Gly Thr Xaa' Cys Gly Xaa' Xaa' Glu Ile Cys Ala Tyr Ala Ala Cys Thr Gly Xaa' Cys    (SEQ ID NO: 1944)
Pro Gly Thr Xaa' Cys Gly Xaa' Glu Ile Xaa' Ile Cys Ala Tyr Ala Ala Cys Thr Gly Cys Xaa' (SEQ ID NO: 1945)
Pro Gly Thr Xaa' Cys Gly Xaa' Xaa' Ile Cys Ala Tyr Ala Ala Cys Thr Gly Cys             (SEQ ID NO: 1946)
Pro Gly Thr Xaa' Cys Gly Xaa' Xaa' Ile Cys Ala Tyr Ala Ala Cys Thr Gly Cys             (SEQ ID NO: 1947)
Pro Gly Thr Xaa' Cys Gly Xaa' Xaa' Ile Cys Xaa' Ala Tyr Ala Ala Cys Thr Gly Cys        (SEQ ID NO: 1948)
Pro Gly Thr Xaa' Cys Gly Xaa' Xaa' Ile Cys Xaa' Ala Xaa' Tyr Ala Ala Cys Thr Gly Cys   (SEQ ID NO: 1949)
Pro Gly Thr Xaa' Cys Gly Xaa' Xaa' Ile Cys Ala Tyr Xaa' Ala Ala Cys Thr Gly Cys        (SEQ ID NO: 1950)
Pro Gly Thr Xaa' Cys Gly Xaa' Xaa' Ile Cys Ala Tyr Ala Xaa' Ala Cys Thr Gly Cys        (SEQ ID NO: 1951)
Pro Gly Thr Xaa' Cys Gly Xaa' Xaa' Ile Cys Ala Tyr Ala Ala Cys Xaa' Thr Gly Cys        (SEQ ID NO: 1952)
Pro Gly Thr Xaa' Cys Gly Xaa' Xaa' Ile Cys Ala Tyr Ala Ala Cys Thr Xaa' Gly Cys        (SEQ ID NO: 1953)
Pro Gly Thr Xaa' Cys Gly Xaa' Xaa' Ile Cys Ala Tyr Ala Ala Cys Thr Gly Xaa' Cys        (SEQ ID NO: 1954)
Pro Gly Thr Xaa' Cys Gly Xaa' Xaa' Ile Cys Ala Tyr Ala Ala Cys Thr Gly Xaa' Cys        (SEQ ID NO: 1955)
Pro Gly Thr Xaa' Cys Gly Xaa' Xaa' Ile Cys Ala Tyr Ala Ala Cys Thr Gly Cys Xaa'        (SEQ ID NO: 1956)
Pro Gly Thr Xaa' Cys Gly Xaa' Ile Xaa' Cys Ala Tyr Ala Ala Cys Thr Gly Cys             (SEQ ID NO: 1957)
Pro Gly Thr Xaa' Cys Gly Xaa' Ile Xaa' Cys Xaa' Ala Tyr Ala Ala Cys Thr Gly Cys        (SEQ ID NO: 1958)
Pro Gly Thr Xaa' Cys Gly Xaa' Ile Xaa' Cys Xaa' Ala Xaa' Tyr Ala Ala Cys Thr Gly Cys   (SEQ ID NO: 1959)
Pro Gly Thr Xaa' Cys Gly Xaa' Ile Xaa' Cys Ala Tyr Xaa' Ala Ala Cys Thr Gly Cys        (SEQ ID NO: 1960)
Pro Gly Thr Xaa' Cys Gly Xaa' Ile Xaa' Cys Ala Tyr Ala Xaa' Ala Cys Thr Gly Cys        (SEQ ID NO: 1961)
Pro Gly Thr Xaa' Cys Gly Xaa' Ile Xaa' Cys Ala Tyr Ala Ala Cys Xaa' Thr Gly Cys        (SEQ ID NO: 1962)
Pro Gly Thr Xaa' Cys Gly Xaa' Ile Xaa' Cys Ala Tyr Ala Ala Cys Thr Xaa' Gly Cys        (SEQ ID NO: 1963)
Pro Gly Thr Xaa' Cys Gly Xaa' Ile Xaa' Cys Ala Tyr Ala Ala Cys Thr Gly Xaa' Cys        (SEQ ID NO: 1964)
Pro Gly Thr Xaa' Cys Gly Xaa' Ile Xaa' Cys Ala Tyr Ala Ala Cys Thr Gly Xaa' Cys        (SEQ ID NO: 1965)
Pro Gly Thr Xaa' Cys Gly Xaa' Ile Xaa' Cys Ala Tyr Ala Ala Cys Thr Gly Cys Xaa'        (SEQ ID NO: 1966)
Pro Gly Thr Xaa' Cys Gly Xaa' Ile Cys Xaa' Ala Tyr Ala Ala Cys Thr Gly Cys             (SEQ ID NO: 1967)
Pro Gly Thr Xaa' Cys Gly Xaa' Ile Cys Xaa' Ala Xaa' Tyr Ala Ala Cys Thr Gly Cys        (SEQ ID NO: 1968)
Pro Gly Thr Xaa' Cys Gly Xaa' Ile Cys Ala Tyr Xaa' Ala Ala Cys Thr Gly Cys             (SEQ ID NO: 1969)
Pro Gly Thr Xaa' Cys Gly Xaa' Ile Cys Ala Tyr Ala Xaa' Ala Cys Thr Gly Cys             (SEQ ID NO: 1970)
Pro Gly Thr Xaa' Cys Gly Xaa' Ile Cys Ala Tyr Ala Ala Cys Xaa' Thr Gly Cys             (SEQ ID NO: 1971)
Pro Gly Thr Xaa' Cys Gly Xaa' Ile Cys Ala Tyr Ala Ala Cys Thr Xaa' Gly Cys             (SEQ ID NO: 1972)
Pro Gly Thr Xaa' Cys Gly Xaa' Ile Cys Ala Tyr Ala Ala Cys Thr Gly Xaa' Cys             (SEQ ID NO: 1973)
Pro Gly Thr Xaa' Cys Gly Xaa' Ile Cys Ala Tyr Ala Ala Cys Thr Gly Xaa' Cys             (SEQ ID NO: 1974)
Pro Gly Thr Xaa' Cys Gly Xaa' Ile Cys Ala Tyr Ala Ala Cys Thr Gly Cys Xaa'             (SEQ ID NO: 1975)
Pro Gly Thr Xaa' Cys Gly Xaa' Ile Cys Ala Tyr Ala Ala Cys Thr Gly Xaa' Cys             (SEQ ID NO: 1976)
```

FIG. 2AF

| | | | | | | | | | | |
|---|---|---|---|---|---|---|---|---|---|---|
| Pro Gly Thr Xaa' Cys Gly Xaa' Glu Ile Cys Xaa' Ala Tyr Ala Ala Cys Thr Gly Cys Xaa' | (SEQ ID NO: 1977) |
| Pro Gly Thr Xaa' Cys Gly Xaa' Glu Ile Cys Ala Xaa' Tyr Ala Ala Cys Thr Gly Cys | (SEQ ID NO: 1978) |
| Pro Gly Thr Xaa' Cys Gly Xaa' Glu Ile Cys Ala Xaa' Xaa' Tyr Ala Ala Cys Thr Gly Cys | (SEQ ID NO: 1979) |
| Pro Gly Thr Xaa' Cys Gly Xaa' Glu Ile Cys Ala Xaa' Tyr Ala Ala Cys Thr Gly Cys | (SEQ ID NO: 1980) |
| Pro Gly Thr Xaa' Cys Gly Xaa' Glu Ile Cys Ala Xaa' Tyr Ala Xaa' Ala Cys Thr Gly Cys | (SEQ ID NO: 1981) |
| Pro Gly Thr Xaa' Cys Gly Xaa' Glu Ile Cys Ala Xaa' Tyr Ala Ala Cys Thr Gly Cys | (SEQ ID NO: 1982) |
| Pro Gly Thr Xaa' Cys Gly Xaa' Glu Ile Cys Ala Xaa' Tyr Ala Xaa' Cys Thr Gly Cys | (SEQ ID NO: 1983) |
| Pro Gly Thr Xaa' Cys Gly Xaa' Glu Ile Cys Ala Xaa' Tyr Xaa' Cys Thr Gly Cys | (SEQ ID NO: 1984) |
| Pro Gly Thr Xaa' Cys Gly Xaa' Glu Ile Cys Ala Xaa' Tyr Ala Ala Cys Thr Gly Xaa' Cys | (SEQ ID NO: 1985) |
| Pro Gly Thr Xaa' Cys Gly Xaa' Glu Ile Cys Ala Xaa' Tyr Ala Ala Cys Thr Gly Cys Xaa' | (SEQ ID NO: 1986) |
| Pro Gly Thr Xaa' Cys Gly Xaa' Glu Ile Cys Ala Tyr Xaa' Ala Ala Cys Thr Gly Cys | (SEQ ID NO: 1987) |
| Pro Gly Thr Xaa' Cys Gly Xaa' Glu Ile Cys Ala Tyr Xaa' Ala Ala Cys Thr Gly Cys | (SEQ ID NO: 1988) |
| Pro Gly Thr Xaa' Cys Gly Xaa' Glu Ile Cys Ala Tyr Xaa' Ala Xaa' Ala Cys Thr Gly Cys | (SEQ ID NO: 1989) |
| Pro Gly Thr Xaa' Cys Gly Xaa' Glu Ile Cys Ala Tyr Xaa' Ala Ala Cys Thr Gly Cys | (SEQ ID NO: 1990) |
| Pro Gly Thr Xaa' Cys Gly Xaa' Glu Ile Cys Ala Tyr Xaa' Xaa' Ala Cys Thr Gly Cys | (SEQ ID NO: 1991) |
| Pro Gly Thr Xaa' Cys Gly Xaa' Glu Ile Cys Ala Tyr Xaa' Ala Xaa' Cys Thr Gly Cys | (SEQ ID NO: 1992) |
| Pro Gly Thr Xaa' Cys Gly Xaa' Glu Ile Cys Ala Tyr Xaa' Ala Xaa' Cys Thr Gly Cys | (SEQ ID NO: 1993) |
| Pro Gly Thr Xaa' Cys Gly Xaa' Glu Ile Cys Ala Tyr Xaa' Ala Xaa' Cys Thr Gly Cys Xaa' | (SEQ ID NO: 1994) |
| Pro Gly Thr Xaa' Cys Gly Xaa' Glu Ile Cys Ala Tyr Ala Xaa' Ala Cys Thr Gly Cys | (SEQ ID NO: 1995) |
| Pro Gly Thr Xaa' Cys Gly Xaa' Glu Ile Cys Ala Tyr Ala Xaa' Ala Cys Thr Gly Cys | (SEQ ID NO: 1996) |
| Pro Gly Thr Xaa' Cys Gly Xaa' Glu Ile Cys Ala Tyr Ala Xaa' Ala Xaa' Cys Thr Gly Cys | (SEQ ID NO: 1997) |
| Pro Gly Thr Xaa' Cys Gly Xaa' Glu Ile Cys Ala Tyr Ala Xaa' Ala Cys Thr Gly Cys | (SEQ ID NO: 1998) |
| Pro Gly Thr Xaa' Cys Gly Xaa' Glu Ile Cys Ala Tyr Ala Xaa' Ala Cys Thr Gly Xaa' Cys | (SEQ ID NO: 1999) |
| Pro Gly Thr Xaa' Cys Gly Xaa' Glu Ile Cys Ala Tyr Ala Xaa' Ala Cys Thr Gly Cys Xaa' | (SEQ ID NO: 2000) |
| Pro Gly Thr Xaa' Cys Gly Xaa' Glu Ile Cys Ala Tyr Ala Ala Xaa' Cys Thr Gly Cys | (SEQ ID NO: 2001) |
| Pro Gly Thr Xaa' Cys Gly Xaa' Glu Ile Cys Ala Tyr Ala Ala Xaa' Cys Thr Gly Cys | (SEQ ID NO: 2002) |
| Pro Gly Thr Xaa' Cys Gly Xaa' Glu Ile Cys Ala Tyr Ala Ala Xaa' Cys Thr Gly Cys | (SEQ ID NO: 2003) |
| Pro Gly Thr Xaa' Cys Gly Xaa' Glu Ile Cys Ala Tyr Ala Ala Xaa' Cys Thr Gly Cys | (SEQ ID NO: 2004) |
| Pro Gly Thr Xaa' Cys Gly Xaa' Glu Ile Cys Ala Tyr Ala Ala Xaa' Cys Thr Gly Cys | (SEQ ID NO: 2005) |
| Pro Gly Thr Xaa' Cys Gly Xaa' Glu Ile Cys Ala Tyr Ala Ala Xaa' Cys Thr Gly Cys Xaa' | (SEQ ID NO: 2006) |
| Pro Gly Thr Xaa' Cys Gly Xaa' Glu Ile Cys Ala Tyr Ala Ala Cys Xaa' Thr Gly Cys | (SEQ ID NO: 2007) |
| Pro Gly Thr Xaa' Cys Gly Xaa' Glu Ile Cys Ala Tyr Ala Ala Cys Xaa' Thr Gly Cys | (SEQ ID NO: 2008) |
| Pro Gly Thr Xaa' Cys Gly Xaa' Glu Ile Cys Ala Tyr Ala Ala Cys Xaa' Thr Gly Cys | (SEQ ID NO: 2009) |
| Pro Gly Thr Xaa' Cys Gly Xaa' Glu Ile Cys Ala Tyr Ala Ala Cys Xaa' Thr Gly Cys | (SEQ ID NO: 2010) |

FIG. 2AG

| | | | | | | | | | | | | | | |
|---|---|---|---|---|---|---|---|---|---|---|---|---|---|---|
| Pro | Gly | Thr | Xaa' | Cys | Gly | Xaa' | Glu | Ile | Cys | Ala | Tyr | Ala | Ala | Cys | Xaa' | Thr | Gly | Xaa' | Cys | (SEQ ID NO: 2011) |
| Pro | Gly | Thr | Xaa' | Cys | Gly | Xaa' | Glu | Ile | Cys | Ala | Tyr | Ala | Ala | Cys | Xaa' | Thr | Gly | Cys | Xaa' | (SEQ ID NO: 2012) |
| Pro | Gly | Thr | Xaa' | Cys | Gly | Xaa' | Glu | Ile | Cys | Ala | Tyr | Ala | Ala | Cys | Thr | Xaa' | Gly | Cys | (SEQ ID NO: 2013) |
| Pro | Gly | Thr | Xaa' | Cys | Gly | Xaa' | Glu | Ile | Cys | Ala | Tyr | Ala | Ala | Cys | Thr | Xaa' | Xaa' | Gly | Cys | (SEQ ID NO: 2014) |
| Pro | Gly | Thr | Xaa' | Cys | Gly | Xaa' | Glu | Ile | Cys | Ala | Tyr | Ala | Ala | Cys | Thr | Xaa' | Gly | Xaa' | Cys | (SEQ ID NO: 2015) |
| Pro | Gly | Thr | Xaa' | Cys | Gly | Xaa' | Glu | Ile | Cys | Ala | Tyr | Ala | Ala | Cys | Thr | Xaa' | Gly | Cys | Xaa' | (SEQ ID NO: 2016) |
| Pro | Gly | Thr | Xaa' | Cys | Gly | Xaa' | Glu | Ile | Cys | Ala | Tyr | Ala | Ala | Cys | Thr | Gly | Xaa' | Cys | (SEQ ID NO: 2017) |
| Pro | Gly | Thr | Xaa' | Cys | Gly | Xaa' | Glu | Ile | Cys | Ala | Tyr | Ala | Ala | Cys | Thr | Gly | Xaa' | Xaa' | Cys | (SEQ ID NO: 2018) |
| Pro | Gly | Thr | Xaa' | Cys | Gly | Xaa' | Glu | Ile | Cys | Ala | Tyr | Ala | Ala | Cys | Thr | Gly | Xaa' | Cys | Xaa' | (SEQ ID NO: 2019) |
| Pro | Gly | Thr | Xaa' | Cys | Gly | Xaa' | Glu | Ile | Cys | Ala | Tyr | Ala | Ala | Cys | Thr | Gly | Cys | Xaa' | (SEQ ID NO: 2020) |
| Pro | Gly | Thr | Xaa' | Cys | Gly | Xaa' | Glu | Ile | Cys | Ala | Tyr | Ala | Ala | Cys | Thr | Gly | Cys | Xaa' | Xaa' | (SEQ ID NO: 2021) |
| Pro | Gly | Thr | Xaa' | Cys | Gly | Glu | Ile | Cys | Ala | Tyr | Ala | Ala | Cys | Thr | Gly | Cys | (SEQ ID NO: 2022) |
| Pro | Gly | Thr | Xaa' | Cys | Gly | Glu | Ile | Cys | Ala | Tyr | Ala | Ala | Cys | Thr | Gly | Cys | (SEQ ID NO: 2023) |
| Pro | Gly | Thr | Xaa' | Cys | Gly | Glu | Xaa' | Ile | Cys | Ala | Tyr | Ala | Ala | Cys | Thr | Gly | Cys | (SEQ ID NO: 2024) |
| Pro | Gly | Thr | Xaa' | Cys | Gly | Glu | Xaa' | Xaa' | Ile | Cys | Ala | Tyr | Ala | Ala | Cys | Thr | Gly | Cys | (SEQ ID NO: 2025) |
| Pro | Gly | Thr | Xaa' | Cys | Gly | Glu | Xaa' | Ile | Xaa' | Cys | Ala | Tyr | Ala | Ala | Cys | Thr | Gly | Cys | (SEQ ID NO: 2026) |
| Pro | Gly | Thr | Xaa' | Cys | Gly | Glu | Xaa' | Ile | Cys | Xaa' | Ala | Tyr | Ala | Ala | Cys | Thr | Gly | Cys | (SEQ ID NO: 2027) |
| Pro | Gly | Thr | Xaa' | Cys | Gly | Glu | Xaa' | Ile | Cys | Ala | Xaa' | Tyr | Ala | Ala | Cys | Thr | Gly | Cys | (SEQ ID NO: 2028) |
| Pro | Gly | Thr | Xaa' | Cys | Gly | Glu | Xaa' | Ile | Cys | Ala | Tyr | Xaa' | Ala | Ala | Cys | Thr | Gly | Cys | (SEQ ID NO: 2029) |
| Pro | Gly | Thr | Xaa' | Cys | Gly | Glu | Xaa' | Ile | Cys | Ala | Tyr | Ala | Xaa' | Ala | Cys | Thr | Gly | Cys | (SEQ ID NO: 2030) |
| Pro | Gly | Thr | Xaa' | Cys | Gly | Glu | Xaa' | Ile | Cys | Ala | Tyr | Ala | Ala | Xaa' | Cys | Thr | Gly | Cys | (SEQ ID NO: 2031) |
| Pro | Gly | Thr | Xaa' | Cys | Gly | Glu | Xaa' | Ile | Cys | Ala | Tyr | Ala | Ala | Cys | Xaa' | Thr | Gly | Cys | (SEQ ID NO: 2032) |
| Pro | Gly | Thr | Xaa' | Cys | Gly | Glu | Xaa' | Ile | Cys | Ala | Tyr | Ala | Ala | Cys | Thr | Xaa' | Gly | Cys | (SEQ ID NO: 2033) |
| Pro | Gly | Thr | Xaa' | Cys | Gly | Glu | Xaa' | Ile | Cys | Ala | Tyr | Ala | Ala | Cys | Thr | Gly | Xaa' | Cys | (SEQ ID NO: 2034) |
| Pro | Gly | Thr | Xaa' | Cys | Gly | Glu | Xaa' | Ile | Cys | Ala | Tyr | Ala | Ala | Cys | Thr | Gly | Cys | Xaa' | (SEQ ID NO: 2035) |
| Pro | Gly | Thr | Xaa' | Cys | Gly | Glu | Ile | Xaa' | Cys | Ala | Tyr | Ala | Ala | Cys | Thr | Gly | Cys | (SEQ ID NO: 2036) |
| Pro | Gly | Thr | Xaa' | Cys | Gly | Glu | Ile | Cys | Xaa' | Ala | Tyr | Ala | Ala | Cys | Thr | Gly | Cys | (SEQ ID NO: 2037) |
| Pro | Gly | Thr | Xaa' | Cys | Gly | Glu | Ile | Cys | Ala | Xaa' | Tyr | Ala | Ala | Cys | Thr | Gly | Cys | (SEQ ID NO: 2038) |
| Pro | Gly | Thr | Xaa' | Cys | Gly | Glu | Ile | Cys | Ala | Tyr | Xaa' | Ala | Ala | Cys | Thr | Gly | Cys | (SEQ ID NO: 2039) |
| Pro | Gly | Thr | Xaa' | Cys | Gly | Glu | Ile | Cys | Ala | Tyr | Ala | Xaa' | Ala | Cys | Thr | Gly | Cys | (SEQ ID NO: 2040) |
| Pro | Gly | Thr | Xaa' | Cys | Gly | Glu | Ile | Cys | Ala | Tyr | Ala | Ala | Xaa' | Cys | Thr | Gly | Cys | (SEQ ID NO: 2041) |
| Pro | Gly | Thr | Xaa' | Cys | Gly | Glu | Ile | Cys | Ala | Tyr | Ala | Ala | Cys | Xaa' | Thr | Gly | Cys | (SEQ ID NO: 2042) |
| Pro | Gly | Thr | Xaa' | Cys | Gly | Glu | Ile | Cys | Ala | Tyr | Ala | Ala | Cys | Thr | Xaa' | Gly | Cys | (SEQ ID NO: 2043) |
| Pro | Gly | Thr | Xaa' | Cys | Gly | Glu | Ile | Cys | Ala | Tyr | Ala | Ala | Cys | Thr | Gly | Xaa' | Cys | (SEQ ID NO: 2044) |

FIG. 2AH

| | | | | | | | | | | | | | |
|---|---|---|---|---|---|---|---|---|---|---|---|---|---|
| Pro | Gly | Thr | Xaa' | Cys | Gly | Glu | Xaa' | Ile | Xaa' | Cys | Ala | Tyr | Ala | Ala | Cys | Thr | Gly | Cys | Xaa' | (SEQ ID NO: 2045) |
| Pro | Gly | Thr | Xaa' | Cys | Gly | Glu | Xaa' | Ile | Cys | Xaa' | Ala | Tyr | Ala | Ala | Cys | Thr | Gly | Cys | Xaa' | (SEQ ID NO: 2046) |
| Pro | Gly | Thr | Xaa' | Cys | Gly | Glu | Xaa' | Ile | Cys | Xaa' | Ala | Tyr | Ala | Ala | Cys | Thr | Gly | Cys | Xaa' | (SEQ ID NO: 2047) |
| Pro | Gly | Thr | Xaa' | Cys | Gly | Glu | Xaa' | Ile | Cys | Xaa' | Xaa' | Tyr | Ala | Ala | Cys | Thr | Gly | Cys | Xaa' | (SEQ ID NO: 2048) |
| Pro | Gly | Thr | Xaa' | Cys | Gly | Glu | Xaa' | Ile | Cys | Xaa' | Ala | Tyr | Xaa' | Ala | Cys | Thr | Gly | Cys | Xaa' | (SEQ ID NO: 2049) |
| Pro | Gly | Thr | Xaa' | Cys | Gly | Glu | Xaa' | Ile | Cys | Xaa' | Ala | Tyr | Ala | Xaa' | Cys | Thr | Gly | Cys | Xaa' | (SEQ ID NO: 2050) |
| Pro | Gly | Thr | Xaa' | Cys | Gly | Glu | Xaa' | Ile | Cys | Xaa' | Ala | Tyr | Ala | Ala | Cys | Xaa' | Gly | Cys | Xaa' | (SEQ ID NO: 2051) |
| Pro | Gly | Thr | Xaa' | Cys | Gly | Glu | Xaa' | Ile | Cys | Xaa' | Ala | Tyr | Ala | Ala | Cys | Thr | Xaa' | Cys | Xaa' | (SEQ ID NO: 2052) |
| Pro | Gly | Thr | Xaa' | Cys | Gly | Glu | Xaa' | Ile | Cys | Xaa' | Ala | Tyr | Ala | Ala | Cys | Thr | Gly | Cys | Xaa' | (SEQ ID NO: 2053) |
| Pro | Gly | Thr | Xaa' | Cys | Gly | Glu | Xaa' | Ile | Cys | Xaa' | Ala | Tyr | Ala | Ala | Cys | Thr | Gly | Xaa' | Cys | (SEQ ID NO: 2054) |
| Pro | Gly | Thr | Xaa' | Cys | Gly | Glu | Xaa' | Ile | Cys | Xaa' | Ala | Tyr | Ala | Ala | Cys | Thr | Gly | Cys | Xaa' | (SEQ ID NO: 2055) |
| Pro | Gly | Thr | Xaa' | Cys | Gly | Glu | Xaa' | Ile | Cys | Ala | Xaa' | Xaa' | Ala | Ala | Cys | Thr | Gly | Cys | Cys | (SEQ ID NO: 2056) |
| Pro | Gly | Thr | Xaa' | Cys | Gly | Glu | Xaa' | Ile | Cys | Ala | Xaa' | Tyr | Xaa' | Ala | Cys | Thr | Gly | Cys | Cys | (SEQ ID NO: 2057) |
| Pro | Gly | Thr | Xaa' | Cys | Gly | Glu | Xaa' | Ile | Cys | Ala | Xaa' | Tyr | Ala | Xaa' | Cys | Thr | Gly | Cys | Cys | (SEQ ID NO: 2058) |
| Pro | Gly | Thr | Xaa' | Cys | Gly | Glu | Xaa' | Ile | Cys | Ala | Xaa' | Tyr | Ala | Ala | Cys | Thr | Gly | Cys | Cys | (SEQ ID NO: 2059) |
| Pro | Gly | Thr | Xaa' | Cys | Gly | Glu | Xaa' | Ile | Cys | Ala | Xaa' | Tyr | Ala | Ala | Cys | Thr | Gly | Cys | Cys | (SEQ ID NO: 2060) |
| Pro | Gly | Thr | Xaa' | Cys | Gly | Glu | Xaa' | Ile | Cys | Ala | Xaa' | Tyr | Ala | Ala | Cys | Thr | Gly | Cys | Xaa' | (SEQ ID NO: 2061) |
| Pro | Gly | Thr | Xaa' | Cys | Gly | Glu | Xaa' | Ile | Cys | Ala | Xaa' | Tyr | Ala | Ala | Cys | Thr | Gly | Cys | Cys | (SEQ ID NO: 2062) |
| Pro | Gly | Thr | Xaa' | Cys | Gly | Glu | Xaa' | Ile | Cys | Ala | Xaa' | Tyr | Ala | Ala | Cys | Thr | Gly | Xaa' | Cys | (SEQ ID NO: 2063) |
| Pro | Gly | Thr | Xaa' | Cys | Gly | Glu | Xaa' | Ile | Cys | Ala | Xaa' | Tyr | Ala | Ala | Cys | Thr | Gly | Cys | Xaa' | (SEQ ID NO: 2064) |
| Pro | Gly | Thr | Xaa' | Cys | Gly | Glu | Xaa' | Ile | Cys | Ala | Ala | Xaa' | Xaa' | Ala | Cys | Thr | Gly | Cys | Cys | (SEQ ID NO: 2065) |
| Pro | Gly | Thr | Xaa' | Cys | Gly | Glu | Xaa' | Ile | Cys | Ala | Ala | Xaa' | Ala | Xaa' | Cys | Thr | Gly | Cys | Cys | (SEQ ID NO: 2066) |
| Pro | Gly | Thr | Xaa' | Cys | Gly | Glu | Xaa' | Ile | Cys | Ala | Ala | Xaa' | Ala | Ala | Cys | Thr | Gly | Cys | Cys | (SEQ ID NO: 2067) |
| Pro | Gly | Thr | Xaa' | Cys | Gly | Glu | Xaa' | Ile | Cys | Ala | Ala | Xaa' | Ala | Ala | Cys | Thr | Gly | Cys | Xaa' | (SEQ ID NO: 2068) |
| Pro | Gly | Thr | Xaa' | Cys | Gly | Glu | Xaa' | Ile | Cys | Ala | Ala | Xaa' | Ala | Ala | Cys | Thr | Gly | Cys | Cys | (SEQ ID NO: 2069) |
| Pro | Gly | Thr | Xaa' | Cys | Gly | Glu | Xaa' | Ile | Cys | Ala | Ala | Xaa' | Ala | Ala | Cys | Thr | Gly | Cys | Cys | (SEQ ID NO: 2070) |
| Pro | Gly | Thr | Xaa' | Cys | Gly | Glu | Xaa' | Ile | Cys | Ala | Ala | Xaa' | Ala | Ala | Cys | Thr | Gly | Cys | Xaa' | (SEQ ID NO: 2071) |
| Pro | Gly | Thr | Xaa' | Cys | Gly | Glu | Xaa' | Ile | Cys | Ala | Ala | Xaa' | Ala | Ala | Cys | Thr | Gly | Cys | Cys | (SEQ ID NO: 2072) |
| Pro | Gly | Thr | Xaa' | Cys | Gly | Glu | Xaa' | Ile | Cys | Ala | Ala | Tyr | Xaa' | Xaa' | Cys | Thr | Gly | Cys | Cys | (SEQ ID NO: 2073) |
| Pro | Gly | Thr | Xaa' | Cys | Gly | Glu | Xaa' | Ile | Cys | Ala | Ala | Tyr | Xaa' | Ala | Cys | Xaa' | Gly | Cys | Cys | (SEQ ID NO: 2074) |
| Pro | Gly | Thr | Xaa' | Cys | Gly | Glu | Xaa' | Ile | Cys | Ala | Ala | Tyr | Xaa' | Ala | Cys | Thr | Gly | Cys | Cys | (SEQ ID NO: 2075) |
| Pro | Gly | Thr | Xaa' | Cys | Gly | Glu | Xaa' | Ile | Cys | Ala | Ala | Tyr | Xaa' | Ala | Cys | Thr | Gly | Cys | Cys | (SEQ ID NO: 2076) |
| Pro | Gly | Thr | Xaa' | Cys | Gly | Glu | Xaa' | Ile | Cys | Ala | Ala | Tyr | Xaa' | Ala | Cys | Thr | Gly | Cys | Cys | (SEQ ID NO: 2077) |
| Pro | Gly | Thr | Xaa' | Cys | Gly | Glu | Xaa' | Ile | Cys | Ala | Ala | Tyr | Ala | Xaa' | Cys | Thr | Gly | Xaa' | Cys | (SEQ ID NO: 2078) |

FIG. 2AI

| | | | | | | | | | | | | |
|---|---|---|---|---|---|---|---|---|---|---|---|---|
| Pro Gly Thr Xaa' Cys Gly Glu Xaa' Ile Cys Ala Tyr Ala Xaa' Ala Cys Thr Gly Cys Xaa' | (SEQ ID NO: 2079) |
| Pro Gly Thr Xaa' Cys Gly Glu Xaa' Ile Cys Ala Tyr Ala Ala Xaa' Cys Thr Gly Cys | (SEQ ID NO: 2080) |
| Pro Gly Thr Xaa' Cys Gly Glu Xaa' Ile Cys Ala Tyr Ala Ala Xaa' Cys Xaa' Thr Gly Cys | (SEQ ID NO: 2081) |
| Pro Gly Thr Xaa' Cys Gly Glu Xaa' Ile Cys Ala Tyr Ala Ala Xaa' Cys Xaa' Thr Gly Cys | (SEQ ID NO: 2082) |
| Pro Gly Thr Xaa' Cys Gly Glu Xaa' Ile Cys Ala Tyr Ala Ala Xaa' Cys Thr Gly Xaa' Cys | (SEQ ID NO: 2083) |
| Pro Gly Thr Xaa' Cys Gly Glu Xaa' Ile Cys Ala Tyr Ala Ala Xaa' Cys Thr Gly Xaa' Cys | (SEQ ID NO: 2084) |
| Pro Gly Thr Xaa' Cys Gly Glu Xaa' Ile Cys Ala Tyr Ala Ala Xaa' Cys Thr Gly Cys Xaa' | (SEQ ID NO: 2085) |
| Pro Gly Thr Xaa' Cys Gly Glu Xaa' Ile Cys Ala Tyr Ala Ala Ala Cys Xaa' Thr Gly Cys | (SEQ ID NO: 2086) |
| Pro Gly Thr Xaa' Cys Gly Glu Xaa' Ile Cys Ala Tyr Ala Ala Ala Cys Xaa' Thr Gly Cys | (SEQ ID NO: 2087) |
| Pro Gly Thr Xaa' Cys Gly Glu Xaa' Ile Cys Ala Tyr Ala Ala Ala Cys Xaa' Thr Gly Cys | (SEQ ID NO: 2088) |
| Pro Gly Thr Xaa' Cys Gly Glu Xaa' Ile Cys Ala Tyr Ala Ala Ala Cys Xaa' Thr Gly Cys | (SEQ ID NO: 2089) |
| Pro Gly Thr Xaa' Cys Gly Glu Xaa' Ile Cys Ala Tyr Ala Ala Ala Cys Thr Gly Xaa' Cys | (SEQ ID NO: 2090) |
| Pro Gly Thr Xaa' Cys Gly Glu Xaa' Ile Cys Ala Tyr Ala Ala Ala Cys Thr Gly Xaa' Cys | (SEQ ID NO: 2091) |
| Pro Gly Thr Xaa' Cys Gly Glu Xaa' Ile Cys Ala Tyr Ala Ala Ala Cys Thr Gly Cys Xaa' | (SEQ ID NO: 2092) |
| Pro Gly Thr Xaa' Cys Gly Glu Xaa' Ile Cys Ala Tyr Ala Ala Xaa' Cys Xaa' Gly Cys Xaa' | (SEQ ID NO: 2093) |
| Pro Gly Thr Xaa' Cys Gly Glu Xaa' Ile Cys Ala Tyr Ala Ala Xaa' Cys Thr Gly Cys Xaa' | (SEQ ID NO: 2094) |
| Pro Gly Thr Xaa' Cys Gly Glu Xaa' Ile Cys Ala Tyr Ala Ala Xaa' Cys Xaa' Gly Cys | (SEQ ID NO: 2095) |
| Pro Gly Thr Xaa' Cys Gly Glu Xaa' Ile Cys Ala Tyr Ala Ala Xaa' Cys Thr Gly Xaa' Cys | (SEQ ID NO: 2096) |
| Pro Gly Thr Xaa' Cys Gly Glu Xaa' Ile Cys Ala Tyr Ala Ala Xaa' Cys Thr Gly Xaa' Cys Xaa' | (SEQ ID NO: 2097) |
| Pro Gly Thr Xaa' Cys Gly Glu Xaa' Ile Cys Ala Tyr Ala Ala Xaa' Cys Thr Gly Cys Xaa' | (SEQ ID NO: 2098) |
| Pro Gly Thr Xaa' Cys Gly Glu Xaa' Ile Xaa' Ala Tyr Ala Ala Ala Cys Thr Gly Cys | (SEQ ID NO: 2099) |
| Pro Gly Thr Xaa' Cys Gly Glu Ile Ile Xaa' Ala Tyr Ala Ala Ala Cys Thr Gly Cys | (SEQ ID NO: 2100) |
| Pro Gly Thr Xaa' Cys Gly Glu Ile Ile Xaa' Ala Tyr Ala Ala Ala Cys Thr Gly Cys | (SEQ ID NO: 2101) |
| Pro Gly Thr Xaa' Cys Gly Glu Ile Ile Xaa' Ala Tyr Ala Ala Ala Cys Thr Gly Cys | (SEQ ID NO: 2102) |
| Pro Gly Thr Xaa' Cys Gly Glu Ile Ile Xaa' Ala Tyr Ala Xaa' Ala Cys Thr Gly Cys | (SEQ ID NO: 2103) |
| Pro Gly Thr Xaa' Cys Gly Glu Ile Ile Xaa' Ala Tyr Ala Ala Cys Thr Ala Cys Thr Gly Cys | (SEQ ID NO: 2104) |
| Pro Gly Thr Xaa' Cys Gly Glu Ile Ile Xaa' Cys Ala Tyr Xaa' Ala Ala Cys Thr Gly Cys | (SEQ ID NO: 2105) |
| Pro Gly Thr Xaa' Cys Gly Glu Ile Ile Xaa' Cys Ala Tyr Xaa' Ala Ala Cys Thr Gly Cys | (SEQ ID NO: 2106) |
| Pro Gly Thr Xaa' Cys Gly Glu Ile Ile Xaa' Cys Ala Tyr Ala Ala Cys Thr Thr Gly Cys | (SEQ ID NO: 2107) |
| Pro Gly Thr Xaa' Cys Gly Glu Ile Ile Xaa' Cys Ala Tyr Ala Ala Cys Xaa' Thr Gly Cys | (SEQ ID NO: 2108) |
| Pro Gly Thr Xaa' Cys Gly Glu Ile Ile Xaa' Cys Ala Tyr Ala Ala Cys Xaa' Thr Gly Cys | (SEQ ID NO: 2109) |
| Pro Gly Thr Xaa' Cys Gly Glu Ile Ile Xaa' Cys Ala Tyr Ala Ala Cys Thr Gly Xaa' Cys | (SEQ ID NO: 2110) |
| Pro Gly Thr Xaa' Cys Gly Glu Ile Ile Xaa' Cys Ala Tyr Ala Ala Cys Thr Gly Xaa' Cys | (SEQ ID NO: 2111) |
| Pro Gly Thr Xaa' Cys Gly Glu Ile Ile Xaa' Cys Xaa' Ala Tyr Ala Ala Cys Thr Gly Cys | (SEQ ID NO: 2112) |

FIG. 2AJ

| | | | | | | | | | | |
|---|---|---|---|---|---|---|---|---|---|---|
| Pro | Gly | Thr | Xaa' | Cys | Gly | Glu | Ile | Xaa' | Cys | Xaa' | Ala | Tyr | Ala | Ala | Cys | Thr | Gly | Cys | (SEQ ID NO: 2113) |
| Pro | Gly | Thr | Xaa' | Cys | Gly | Glu | Ile | Xaa' | Cys | Xaa' | Ala | Xaa' | Ala | Ala | Cys | Thr | Gly | Cys | (SEQ ID NO: 2114) |
| Pro | Gly | Thr | Xaa' | Cys | Gly | Glu | Ile | Xaa' | Cys | Xaa' | Ala | Tyr | Xaa' | Ala | Cys | Thr | Gly | Cys | (SEQ ID NO: 2115) |
| Pro | Gly | Thr | Xaa' | Cys | Gly | Glu | Ile | Xaa' | Cys | Xaa' | Ala | Tyr | Ala | Xaa' | Cys | Thr | Gly | Cys | (SEQ ID NO: 2116) |
| Pro | Gly | Thr | Xaa' | Cys | Gly | Glu | Ile | Xaa' | Cys | Xaa' | Ala | Tyr | Ala | Ala | Cys | Xaa' | Gly | Cys | (SEQ ID NO: 2117) |
| Pro | Gly | Thr | Xaa' | Cys | Gly | Glu | Ile | Xaa' | Cys | Xaa' | Ala | Tyr | Ala | Ala | Cys | Thr | Gly | Cys | (SEQ ID NO: 2118) |
| Pro | Gly | Thr | Xaa' | Cys | Gly | Glu | Ile | Xaa' | Cys | Xaa' | Ala | Tyr | Ala | Ala | Cys | Thr | Xaa' | Cys | (SEQ ID NO: 2119) |
| Pro | Gly | Thr | Xaa' | Cys | Gly | Glu | Ile | Xaa' | Cys | Xaa' | Ala | Tyr | Ala | Ala | Cys | Thr | Gly | Xaa' | (SEQ ID NO: 2120) |
| Pro | Gly | Thr | Xaa' | Cys | Gly | Glu | Ile | Xaa' | Cys | Ala | Ala | Tyr | Ala | Ala | Cys | Thr | Gly | Cys | (SEQ ID NO: 2121) |
| Pro | Gly | Thr | Xaa' | Cys | Gly | Glu | Ile | Xaa' | Cys | Ala | Xaa' | Tyr | Ala | Ala | Cys | Thr | Gly | Cys | (SEQ ID NO: 2122) |
| Pro | Gly | Thr | Xaa' | Cys | Gly | Glu | Ile | Xaa' | Cys | Ala | Ala | Xaa' | Ala | Ala | Cys | Thr | Gly | Cys | (SEQ ID NO: 2123) |
| Pro | Gly | Thr | Xaa' | Cys | Gly | Glu | Ile | Xaa' | Cys | Ala | Ala | Tyr | Xaa' | Ala | Cys | Thr | Gly | Cys | (SEQ ID NO: 2124) |
| Pro | Gly | Thr | Xaa' | Cys | Gly | Glu | Ile | Xaa' | Cys | Ala | Ala | Tyr | Ala | Xaa' | Cys | Thr | Gly | Cys | (SEQ ID NO: 2125) |
| Pro | Gly | Thr | Xaa' | Cys | Gly | Glu | Ile | Xaa' | Cys | Ala | Ala | Tyr | Ala | Ala | Cys | Xaa' | Gly | Cys | (SEQ ID NO: 2126) |
| Pro | Gly | Thr | Xaa' | Cys | Gly | Glu | Ile | Xaa' | Cys | Ala | Ala | Tyr | Ala | Ala | Cys | Thr | Xaa' | Cys | (SEQ ID NO: 2127) |
| Pro | Gly | Thr | Xaa' | Cys | Gly | Glu | Ile | Xaa' | Cys | Ala | Ala | Tyr | Ala | Ala | Cys | Thr | Gly | Xaa' | (SEQ ID NO: 2128) |
| Pro | Gly | Thr | Xaa' | Cys | Gly | Glu | Ile | Xaa' | Cys | Ala | Xaa' | Tyr | Ala | Ala | Cys | Thr | Gly | Cys | (SEQ ID NO: 2129) |
| Pro | Gly | Thr | Xaa' | Cys | Gly | Glu | Ile | Xaa' | Cys | Ala | Ala | Xaa' | Ala | Ala | Cys | Thr | Gly | Cys | (SEQ ID NO: 2130) |
| Pro | Gly | Thr | Xaa' | Cys | Gly | Glu | Ile | Xaa' | Cys | Ala | Ala | Tyr | Xaa' | Ala | Cys | Thr | Gly | Cys | (SEQ ID NO: 2131) |
| Pro | Gly | Thr | Xaa' | Cys | Gly | Glu | Ile | Xaa' | Cys | Ala | Ala | Tyr | Ala | Xaa' | Cys | Thr | Gly | Cys | (SEQ ID NO: 2132) |
| Pro | Gly | Thr | Xaa' | Cys | Gly | Glu | Ile | Xaa' | Cys | Ala | Ala | Tyr | Ala | Ala | Cys | Xaa' | Gly | Cys | (SEQ ID NO: 2133) |
| Pro | Gly | Thr | Xaa' | Cys | Gly | Glu | Ile | Xaa' | Cys | Ala | Ala | Tyr | Ala | Ala | Cys | Thr | Xaa' | Cys | (SEQ ID NO: 2134) |
| Pro | Gly | Thr | Xaa' | Cys | Gly | Glu | Ile | Xaa' | Cys | Ala | Ala | Tyr | Ala | Ala | Cys | Thr | Gly | Xaa' | (SEQ ID NO: 2135) |
| Pro | Gly | Thr | Xaa' | Cys | Gly | Glu | Ile | Xaa' | Cys | Ala | Ala | Xaa' | Ala | Ala | Cys | Thr | Gly | Cys | (SEQ ID NO: 2136) |
| Pro | Gly | Thr | Xaa' | Cys | Gly | Glu | Ile | Xaa' | Cys | Ala | Ala | Tyr | Xaa' | Ala | Cys | Thr | Gly | Xaa' | (SEQ ID NO: 2137) |
| Pro | Gly | Thr | Xaa' | Cys | Gly | Glu | Ile | Xaa' | Cys | Ala | Ala | Tyr | Ala | Xaa' | Cys | Thr | Gly | Cys | (SEQ ID NO: 2138) |
| Pro | Gly | Thr | Xaa' | Cys | Gly | Glu | Ile | Xaa' | Cys | Ala | Ala | Tyr | Ala | Ala | Cys | Xaa' | Gly | Cys | (SEQ ID NO: 2139) |
| Pro | Gly | Thr | Xaa' | Cys | Gly | Glu | Ile | Xaa' | Cys | Ala | Xaa' | Tyr | Ala | Ala | Cys | Thr | Gly | Cys | (SEQ ID NO: 2140) |
| Pro | Gly | Thr | Xaa' | Cys | Gly | Glu | Ile | Xaa' | Cys | Xaa' | Ala | Tyr | Ala | Ala | Cys | Thr | Gly | Cys | (SEQ ID NO: 2141) |
| Pro | Gly | Thr | Xaa' | Cys | Gly | Glu | Ile | Xaa' | Cys | Ala | Ala | Tyr | Xaa' | Ala | Cys | Thr | Gly | Cys | (SEQ ID NO: 2142) |
| Pro | Gly | Thr | Xaa' | Cys | Gly | Glu | Ile | Xaa' | Cys | Ala | Ala | Tyr | Ala | Xaa' | Cys | Thr | Gly | Cys | (SEQ ID NO: 2143) |
| Pro | Gly | Thr | Xaa' | Cys | Gly | Glu | Ile | Xaa' | Cys | Ala | Ala | Tyr | Ala | Ala | Cys | Thr | Gly | Xaa' | (SEQ ID NO: 2144) |
| Pro | Gly | Thr | Xaa' | Cys | Gly | Glu | Ile | Xaa' | Cys | Ala | Ala | Tyr | Ala | Ala | Cys | Thr | Gly | Cys | (SEQ ID NO: 2145) |
| Pro | Gly | Thr | Xaa' | Cys | Gly | Glu | Ile | Xaa' | Cys | Ala | Ala | Tyr | Ala | Ala | Xaa' | Cys | Thr | Gly | Cys | (SEQ ID NO: 2146) |

FIG. 2AK

| | | | | | | | | | | | | |
|---|---|---|---|---|---|---|---|---|---|---|---|---|
| Pro | Gly | Thr | Xaa' | Cys | Gly | Glu | Ile | Xaa' | Cys | Ala | Tyr | Ala | Ala | Xaa' | Cys | Xaa' | Thr | Gly | Cys | (SEQ ID NO: 2147) |
| Pro | Gly | Thr | Xaa' | Cys | Gly | Glu | Ile | Xaa' | Cys | Ala | Tyr | Ala | Ala | Xaa' | Cys | Thr | Xaa' | Gly | Cys | (SEQ ID NO: 2148) |
| Pro | Gly | Thr | Xaa' | Cys | Gly | Glu | Ile | Xaa' | Cys | Ala | Tyr | Ala | Ala | Xaa' | Cys | Thr | Gly | Xaa' | Cys | (SEQ ID NO: 2149) |
| Pro | Gly | Thr | Xaa' | Cys | Gly | Glu | Ile | Xaa' | Cys | Ala | Tyr | Ala | Ala | Xaa' | Cys | Thr | Gly | Cys | Xaa' | (SEQ ID NO: 2150) |
| Pro | Gly | Thr | Xaa' | Cys | Gly | Glu | Ile | Xaa' | Cys | Ala | Tyr | Ala | Ala | Cys | Xaa' | Xaa' | Thr | Gly | Cys | (SEQ ID NO: 2151) |
| Pro | Gly | Thr | Xaa' | Cys | Gly | Glu | Ile | Xaa' | Cys | Ala | Tyr | Ala | Ala | Cys | Xaa' | Thr | Xaa' | Gly | Cys | (SEQ ID NO: 2152) |
| Pro | Gly | Thr | Xaa' | Cys | Gly | Glu | Ile | Xaa' | Cys | Ala | Tyr | Ala | Ala | Cys | Xaa' | Thr | Gly | Xaa' | Cys | (SEQ ID NO: 2153) |
| Pro | Gly | Thr | Xaa' | Cys | Gly | Glu | Ile | Xaa' | Cys | Ala | Tyr | Ala | Ala | Cys | Xaa' | Thr | Gly | Cys | Xaa' | (SEQ ID NO: 2154) |
| Pro | Gly | Thr | Xaa' | Cys | Gly | Glu | Ile | Xaa' | Cys | Ala | Tyr | Ala | Ala | Cys | Thr | Xaa' | Xaa' | Gly | Cys | (SEQ ID NO: 2155) |
| Pro | Gly | Thr | Xaa' | Cys | Gly | Glu | Ile | Xaa' | Cys | Ala | Tyr | Ala | Ala | Cys | Thr | Xaa' | Gly | Xaa' | Cys | (SEQ ID NO: 2156) |
| Pro | Gly | Thr | Xaa' | Cys | Gly | Glu | Ile | Xaa' | Cys | Ala | Tyr | Ala | Ala | Cys | Thr | Xaa' | Gly | Cys | Xaa' | (SEQ ID NO: 2157) |
| Pro | Gly | Thr | Xaa' | Cys | Gly | Glu | Ile | Xaa' | Cys | Ala | Tyr | Ala | Ala | Cys | Thr | Gly | Xaa' | Xaa' | Cys | (SEQ ID NO: 2158) |
| Pro | Gly | Thr | Xaa' | Cys | Gly | Glu | Ile | Xaa' | Cys | Ala | Tyr | Ala | Ala | Cys | Thr | Gly | Xaa' | Cys | Xaa' | (SEQ ID NO: 2159) |
| Pro | Gly | Thr | Xaa' | Cys | Gly | Glu | Ile | Xaa' | Cys | Ala | Tyr | Ala | Ala | Cys | Thr | Gly | Cys | Xaa' | Xaa' | (SEQ ID NO: 2160) |
| Pro | Gly | Thr | Xaa' | Cys | Gly | Glu | Ile | Cys | Xaa' | Xaa' | Tyr | Ala | Ala | Cys | Thr | Gly | Xaa' | Cys | | (SEQ ID NO: 2161) |
| Pro | Gly | Thr | Xaa' | Cys | Gly | Glu | Ile | Cys | Xaa' | Ala | Xaa' | Ala | Ala | Cys | Thr | Gly | Xaa' | Cys | | (SEQ ID NO: 2162) |
| Pro | Gly | Thr | Xaa' | Cys | Gly | Glu | Ile | Cys | Xaa' | Ala | Tyr | Xaa' | Ala | Cys | Thr | Gly | Xaa' | Cys | | (SEQ ID NO: 2163) |
| Pro | Gly | Thr | Xaa' | Cys | Gly | Glu | Ile | Cys | Xaa' | Ala | Tyr | Ala | Xaa' | Cys | Thr | Gly | Cys | Xaa' | | (SEQ ID NO: 2164) |
| Pro | Gly | Thr | Xaa' | Cys | Gly | Glu | Ile | Cys | Xaa' | Ala | Tyr | Ala | Ala | Cys | Thr | Gly | Cys | | | (SEQ ID NO: 2165) |
| Pro | Gly | Thr | Xaa' | Cys | Gly | Glu | Ile | Cys | Xaa' | Ala | Tyr | Ala | Ala | Cys | Thr | Gly | Cys | | | (SEQ ID NO: 2166) |
| Pro | Gly | Thr | Xaa' | Cys | Gly | Glu | Ile | Cys | Xaa' | Ala | Tyr | Ala | Ala | Cys | Thr | Gly | Cys | | | (SEQ ID NO: 2167) |
| Pro | Gly | Thr | Xaa' | Cys | Gly | Glu | Ile | Cys | Xaa' | Xaa' | Tyr | Ala | Ala | Cys | Thr | Gly | Cys | | | (SEQ ID NO: 2168) |
| Pro | Gly | Thr | Xaa' | Cys | Gly | Glu | Ile | Cys | Xaa' | Xaa' | Ala | Tyr | Ala | Ala | Cys | Thr | Gly | Cys | | (SEQ ID NO: 2169) |
| Pro | Gly | Thr | Xaa' | Cys | Gly | Glu | Ile | Cys | Xaa' | Ala | Tyr | Xaa' | Ala | Ala | Cys | Thr | Gly | Cys | | (SEQ ID NO: 2170) |
| Pro | Gly | Thr | Xaa' | Cys | Gly | Glu | Ile | Cys | Xaa' | Ala | Tyr | Ala | Xaa' | Ala | Cys | Thr | Gly | Cys | | (SEQ ID NO: 2171) |
| Pro | Gly | Thr | Xaa' | Cys | Gly | Glu | Ile | Cys | Xaa' | Ala | Tyr | Ala | Ala | Xaa' | Cys | Thr | Gly | Cys | | (SEQ ID NO: 2172) |
| Pro | Gly | Thr | Xaa' | Cys | Gly | Glu | Ile | Cys | Xaa' | Ala | Tyr | Ala | Ala | Cys | Xaa' | Thr | Gly | Cys | | (SEQ ID NO: 2173) |
| Pro | Gly | Thr | Xaa' | Cys | Gly | Glu | Ile | Cys | Xaa' | Ala | Tyr | Ala | Ala | Cys | Thr | Xaa' | Gly | Cys | | (SEQ ID NO: 2174) |
| Pro | Gly | Thr | Xaa' | Cys | Gly | Glu | Ile | Cys | Xaa' | Ala | Tyr | Ala | Ala | Cys | Thr | Gly | Xaa' | Cys | | (SEQ ID NO: 2175) |
| Pro | Gly | Thr | Xaa' | Cys | Gly | Glu | Ile | Cys | Xaa' | Ala | Tyr | Ala | Ala | Cys | Thr | Gly | Cys | Xaa' | | (SEQ ID NO: 2176) |
| Pro | Gly | Thr | Xaa' | Cys | Gly | Glu | Ile | Cys | Ala | Xaa' | Xaa' | Ala | Ala | Cys | Thr | Gly | Cys | | | (SEQ ID NO: 2177) |
| Pro | Gly | Thr | Xaa' | Cys | Gly | Glu | Ile | Cys | Ala | Xaa' | Tyr | Ala | Ala | Xaa' | Cys | Thr | Gly | Cys | | (SEQ ID NO: 2178) |
| Pro | Gly | Thr | Xaa' | Cys | Gly | Glu | Ile | Cys | Ala | Xaa' | Tyr | Ala | Ala | Cys | Xaa' | Thr | Gly | Cys | | (SEQ ID NO: 2179) |
| Pro | Gly | Thr | Xaa' | Cys | Gly | Glu | Ile | Cys | Ala | Xaa' | Tyr | Ala | Ala | Cys | Thr | Xaa' | Gly | Cys | | (SEQ ID NO: 2180) |

FIG. 2AL

| | | | | | | | | | | | | |
|---|---|---|---|---|---|---|---|---|---|---|---|---|
| Pro | Gly | Thr | Xaa' | Cys | Gly | Glu | Ile | Cys | Xaa' | Ala | Xaa' | Ala | Xaa' | Cys | Thr | Gly | Cys | (SEQ ID NO: 2181) |
| Pro | Gly | Thr | Xaa' | Cys | Gly | Glu | Ile | Cys | Xaa' | Ala | Xaa' | Tyr | Ala | Ala | Cys | Xaa' | Gly | Cys | (SEQ ID NO: 2182) |
| Pro | Gly | Thr | Xaa' | Cys | Gly | Glu | Ile | Cys | Xaa' | Ala | Xaa' | Tyr | Ala | Ala | Cys | Thr | Gly | Cys | (SEQ ID NO: 2183) |
| Pro | Gly | Thr | Xaa' | Cys | Gly | Glu | Ile | Cys | Xaa' | Ala | Xaa' | Tyr | Ala | Ala | Cys | Thr | Xaa' | Cys | (SEQ ID NO: 2184) |
| Pro | Gly | Thr | Xaa' | Cys | Gly | Glu | Ile | Cys | Xaa' | Ala | Xaa' | Tyr | Ala | Ala | Cys | Thr | Gly | Xaa' | (SEQ ID NO: 2185) |
| Pro | Gly | Thr | Xaa' | Cys | Gly | Glu | Ile | Cys | Xaa' | Ala | Tyr | Xaa' | Ala | Cys | Thr | Gly | Cys | (SEQ ID NO: 2186) |
| Pro | Gly | Thr | Xaa' | Cys | Gly | Glu | Ile | Cys | Xaa' | Ala | Tyr | Xaa' | Ala | Ala | Cys | Thr | Gly | Cys | (SEQ ID NO: 2187) |
| Pro | Gly | Thr | Xaa' | Cys | Gly | Glu | Ile | Cys | Xaa' | Ala | Tyr | Xaa' | Ala | Cys | Thr | Gly | Cys | (SEQ ID NO: 2188) |
| Pro | Gly | Thr | Xaa' | Cys | Gly | Glu | Ile | Cys | Xaa' | Ala | Tyr | Ala | Ala | Cys | Xaa' | Gly | Cys | (SEQ ID NO: 2189) |
| Pro | Gly | Thr | Xaa' | Cys | Gly | Glu | Ile | Cys | Xaa' | Ala | Tyr | Ala | Ala | Cys | Thr | Gly | Cys | (SEQ ID NO: 2190) |
| Pro | Gly | Thr | Xaa' | Cys | Gly | Glu | Ile | Cys | Xaa' | Ala | Tyr | Ala | Ala | Cys | Thr | Gly | Xaa' | (SEQ ID NO: 2191) |
| Pro | Gly | Thr | Xaa' | Cys | Gly | Glu | Ile | Cys | Xaa' | Ala | Tyr | Xaa' | Ala | Ala | Cys | Thr | Gly | Cys | (SEQ ID NO: 2192) |
| Pro | Gly | Thr | Xaa' | Cys | Gly | Glu | Ile | Cys | Xaa' | Ala | Tyr | Ala | Ala | Cys | Thr | Gly | Xaa' | Cys | (SEQ ID NO: 2193) |
| Pro | Gly | Thr | Xaa' | Cys | Gly | Glu | Ile | Cys | Xaa' | Ala | Tyr | Ala | Xaa' | Ala | Cys | Thr | Gly | Cys | (SEQ ID NO: 2194) |
| Pro | Gly | Thr | Xaa' | Cys | Gly | Glu | Ile | Cys | Xaa' | Ala | Tyr | Ala | Xaa' | Cys | Thr | Gly | Cys | (SEQ ID NO: 2195) |
| Pro | Gly | Thr | Xaa' | Cys | Gly | Glu | Ile | Cys | Xaa' | Ala | Tyr | Ala | Ala | Cys | Thr | Gly | Cys | (SEQ ID NO: 2196) |
| Pro | Gly | Thr | Xaa' | Cys | Gly | Glu | Ile | Cys | Xaa' | Ala | Tyr | Ala | Xaa' | Cys | Thr | Gly | Cys | (SEQ ID NO: 2197) |
| Pro | Gly | Thr | Xaa' | Cys | Gly | Glu | Ile | Cys | Xaa' | Ala | Tyr | Ala | Ala | Cys | Thr | Xaa' | Gly | Cys | (SEQ ID NO: 2198) |
| Pro | Gly | Thr | Xaa' | Cys | Gly | Glu | Ile | Cys | Xaa' | Ala | Tyr | Ala | Ala | Xaa' | Cys | Thr | Gly | Cys | (SEQ ID NO: 2199) |
| Pro | Gly | Thr | Xaa' | Cys | Gly | Glu | Ile | Cys | Xaa' | Ala | Tyr | Ala | Ala | Xaa' | Cys | Thr | Gly | Cys | (SEQ ID NO: 2200) |
| Pro | Gly | Thr | Xaa' | Cys | Gly | Glu | Ile | Cys | Xaa' | Ala | Tyr | Ala | Ala | Xaa' | Cys | Thr | Gly | Cys | (SEQ ID NO: 2201) |
| Pro | Gly | Thr | Xaa' | Cys | Gly | Glu | Ile | Cys | Xaa' | Ala | Tyr | Ala | Ala | Xaa' | Cys | Thr | Gly | Cys | (SEQ ID NO: 2202) |
| Pro | Gly | Thr | Xaa' | Cys | Gly | Glu | Ile | Cys | Xaa' | Ala | Tyr | Ala | Ala | Xaa' | Cys | Thr | Gly | Cys | (SEQ ID NO: 2203) |
| Pro | Gly | Thr | Xaa' | Cys | Gly | Glu | Ile | Cys | Xaa' | Ala | Tyr | Ala | Ala | Ala | Cys | Thr | Gly | Cys | (SEQ ID NO: 2204) |
| Pro | Gly | Thr | Xaa' | Cys | Gly | Glu | Ile | Cys | Xaa' | Ala | Tyr | Ala | Ala | Ala | Cys | Thr | Gly | Xaa' | (SEQ ID NO: 2205) |
| Pro | Gly | Thr | Xaa' | Cys | Gly | Glu | Ile | Cys | Xaa' | Ala | Tyr | Ala | Ala | Ala | Cys | Xaa' | Gly | Cys | (SEQ ID NO: 2206) |
| Pro | Gly | Thr | Xaa' | Cys | Gly | Glu | Ile | Cys | Xaa' | Ala | Tyr | Ala | Ala | Ala | Cys | Thr | Gly | Cys | (SEQ ID NO: 2207) |
| Pro | Gly | Thr | Xaa' | Cys | Gly | Glu | Ile | Cys | Xaa' | Ala | Tyr | Ala | Ala | Ala | Cys | Xaa' | Gly | Cys | (SEQ ID NO: 2208) |
| Pro | Gly | Thr | Xaa' | Cys | Gly | Glu | Ile | Cys | Xaa' | Ala | Tyr | Ala | Ala | Ala | Cys | Thr | Gly | Cys | (SEQ ID NO: 2209) |
| Pro | Gly | Thr | Xaa' | Cys | Gly | Glu | Ile | Cys | Xaa' | Ala | Tyr | Ala | Ala | Ala | Cys | Thr | Xaa' | Cys | (SEQ ID NO: 2210) |
| Pro | Gly | Thr | Xaa' | Cys | Gly | Glu | Ile | Cys | Xaa' | Ala | Tyr | Ala | Ala | Ala | Cys | Thr | Gly | Xaa' | (SEQ ID NO: 2211) |
| Pro | Gly | Thr | Xaa' | Cys | Gly | Glu | Ile | Cys | Xaa' | Ala | Tyr | Ala | Ala | Ala | Cys | Xaa' | Gly | Cys | (SEQ ID NO: 2212) |
| Pro | Gly | Thr | Xaa' | Cys | Gly | Glu | Ile | Cys | Xaa' | Ala | Tyr | Ala | Ala | Ala | Cys | Thr | Gly | Xaa' | Cys | (SEQ ID NO: 2213) |
| Pro | Gly | Thr | Xaa' | Cys | Gly | Glu | Ile | Cys | Xaa' | Ala | Tyr | Ala | Ala | Ala | Cys | Thr | Gly | Xaa' | Cys | (SEQ ID NO: 2214) |

FIG. 2AM

FIG. 2AN

| | | | | | | | | | | | | |
|---|---|---|---|---|---|---|---|---|---|---|---|---|
| Pro | Gly | Thr | Xaa' | Cys | Gly | Glu | Ile | Cys | Ala | Xaa' | Tyr | Ala | Ala | Xaa' | Cys | Thr | Xaa' | Gly | Cys | (SEQ ID NO: 2249) |
| Pro | Gly | Thr | Xaa' | Cys | Gly | Glu | Ile | Cys | Ala | Xaa' | Tyr | Ala | Ala | Xaa' | Cys | Thr | Gly | Xaa' | Cys | (SEQ ID NO: 2250) |
| Pro | Gly | Thr | Xaa' | Cys | Gly | Glu | Ile | Cys | Ala | Xaa' | Tyr | Ala | Ala | Xaa' | Cys | Thr | Gly | Cys | Xaa' | (SEQ ID NO: 2251) |
| Pro | Gly | Thr | Xaa' | Cys | Gly | Glu | Ile | Cys | Ala | Xaa' | Tyr | Ala | Ala | Ala | Cys | Xaa' | Thr | Gly | Cys | (SEQ ID NO: 2252) |
| Pro | Gly | Thr | Xaa' | Cys | Gly | Glu | Ile | Cys | Ala | Xaa' | Tyr | Ala | Ala | Ala | Cys | Xaa' | Thr | Gly | Cys | (SEQ ID NO: 2253) |
| Pro | Gly | Thr | Xaa' | Cys | Gly | Glu | Ile | Cys | Ala | Xaa' | Tyr | Ala | Ala | Ala | Cys | Thr | Xaa' | Gly | Cys | (SEQ ID NO: 2254) |
| Pro | Gly | Thr | Xaa' | Cys | Gly | Glu | Ile | Cys | Ala | Xaa' | Tyr | Ala | Ala | Ala | Cys | Thr | Gly | Xaa' | Cys | (SEQ ID NO: 2255) |
| Pro | Gly | Thr | Xaa' | Cys | Gly | Glu | Ile | Cys | Ala | Xaa' | Tyr | Ala | Ala | Ala | Cys | Thr | Gly | Cys | Xaa' | (SEQ ID NO: 2256) |
| Pro | Gly | Thr | Xaa' | Cys | Gly | Glu | Ile | Cys | Ala | Ala | Tyr | Xaa' | Ala | Ala | Cys | Thr | Gly | Cys | | (SEQ ID NO: 2257) |
| Pro | Gly | Thr | Xaa' | Cys | Gly | Glu | Ile | Cys | Ala | Ala | Tyr | Xaa' | Ala | Xaa' | Cys | Thr | Gly | Cys | | (SEQ ID NO: 2258) |
| Pro | Gly | Thr | Xaa' | Cys | Gly | Glu | Ile | Cys | Ala | Ala | Tyr | Xaa' | Ala | Xaa' | Cys | Thr | Gly | Xaa' | Cys | (SEQ ID NO: 2259) |
| Pro | Gly | Thr | Xaa' | Cys | Gly | Glu | Ile | Cys | Ala | Ala | Tyr | Xaa' | Ala | Xaa' | Cys | Thr | Gly | Cys | Xaa' | (SEQ ID NO: 2260) |
| Pro | Gly | Thr | Xaa' | Cys | Gly | Glu | Ile | Cys | Ala | Ala | Tyr | Xaa' | Ala | Ala | Cys | Thr | Gly | Xaa' | Cys | (SEQ ID NO: 2261) |
| Pro | Gly | Thr | Xaa' | Cys | Gly | Glu | Ile | Cys | Ala | Ala | Tyr | Xaa' | Ala | Ala | Cys | Thr | Gly | Xaa' | Cys | (SEQ ID NO: 2262) |
| Pro | Gly | Thr | Xaa' | Cys | Gly | Glu | Ile | Cys | Ala | Ala | Tyr | Xaa' | Ala | Ala | Cys | Thr | Gly | Cys | Xaa' | (SEQ ID NO: 2263) |
| Pro | Gly | Thr | Xaa' | Cys | Gly | Glu | Ile | Cys | Ala | Ala | Tyr | Xaa' | Ala | Ala | Cys | Thr | Gly | Cys | Xaa' | (SEQ ID NO: 2264) |
| Pro | Gly | Thr | Xaa' | Cys | Gly | Glu | Ile | Cys | Ala | Ala | Tyr | Ala | Xaa' | Ala | Cys | Thr | Gly | Cys | | (SEQ ID NO: 2265) |
| Pro | Gly | Thr | Xaa' | Cys | Gly | Glu | Ile | Cys | Ala | Ala | Tyr | Ala | Xaa' | Xaa' | Cys | Thr | Gly | Cys | | (SEQ ID NO: 2266) |
| Pro | Gly | Thr | Xaa' | Cys | Gly | Glu | Ile | Cys | Ala | Ala | Tyr | Ala | Xaa' | Ala | Cys | Thr | Gly | Cys | | (SEQ ID NO: 2267) |
| Pro | Gly | Thr | Xaa' | Cys | Gly | Glu | Ile | Cys | Ala | Ala | Tyr | Ala | Xaa' | Ala | Cys | Thr | Gly | Xaa' | Cys | (SEQ ID NO: 2268) |
| Pro | Gly | Thr | Xaa' | Cys | Gly | Glu | Ile | Cys | Ala | Ala | Tyr | Ala | Xaa' | Ala | Cys | Thr | Gly | Cys | Xaa' | (SEQ ID NO: 2269) |
| Pro | Gly | Thr | Xaa' | Cys | Gly | Glu | Ile | Cys | Ala | Ala | Tyr | Ala | Xaa' | Xaa' | Cys | Thr | Gly | Cys | | (SEQ ID NO: 2270) |
| Pro | Gly | Thr | Xaa' | Cys | Gly | Glu | Ile | Cys | Ala | Ala | Tyr | Ala | Xaa' | Ala | Cys | Xaa' | Thr | Gly | Cys | (SEQ ID NO: 2271) |
| Pro | Gly | Thr | Xaa' | Cys | Gly | Glu | Ile | Cys | Ala | Ala | Tyr | Ala | Xaa' | Ala | Cys | Thr | Xaa' | Gly | Cys | (SEQ ID NO: 2272) |
| Pro | Gly | Thr | Xaa' | Cys | Gly | Glu | Ile | Cys | Ala | Ala | Tyr | Ala | Xaa' | Ala | Cys | Thr | Gly | Xaa' | Cys | (SEQ ID NO: 2273) |
| Pro | Gly | Thr | Xaa' | Cys | Gly | Glu | Ile | Cys | Ala | Ala | Tyr | Ala | Xaa' | Ala | Cys | Thr | Gly | Cys | Xaa' | (SEQ ID NO: 2274) |
| Pro | Gly | Thr | Xaa' | Cys | Gly | Glu | Ile | Cys | Ala | Ala | Tyr | Ala | Ala | Xaa' | Cys | Xaa' | Thr | Gly | Cys | (SEQ ID NO: 2275) |
| Pro | Gly | Thr | Xaa' | Cys | Gly | Glu | Ile | Cys | Ala | Ala | Tyr | Ala | Ala | Xaa' | Cys | Xaa' | Thr | Gly | Cys | (SEQ ID NO: 2276) |
| Pro | Gly | Thr | Xaa' | Cys | Gly | Glu | Ile | Cys | Ala | Ala | Tyr | Ala | Ala | Xaa' | Cys | Thr | Xaa' | Gly | Cys | (SEQ ID NO: 2277) |
| Pro | Gly | Thr | Xaa' | Cys | Gly | Glu | Ile | Cys | Ala | Ala | Tyr | Ala | Ala | Xaa' | Cys | Thr | Gly | Xaa' | Cys | (SEQ ID NO: 2278) |
| Pro | Gly | Thr | Xaa' | Cys | Gly | Glu | Ile | Cys | Ala | Ala | Tyr | Ala | Ala | Xaa' | Cys | Thr | Gly | Cys | Xaa' | (SEQ ID NO: 2279) |
| Pro | Gly | Thr | Xaa' | Cys | Gly | Glu | Ile | Cys | Ala | Ala | Tyr | Ala | Ala | Ala | Cys | Xaa' | Thr | Gly | Cys | (SEQ ID NO: 2280) |
| Pro | Gly | Thr | Xaa' | Cys | Gly | Glu | Ile | Cys | Ala | Ala | Tyr | Ala | Ala | Ala | Cys | Xaa' | Thr | Gly | Cys | (SEQ ID NO: 2281) |
| Pro | Gly | Thr | Xaa' | Cys | Gly | Glu | Ile | Cys | Ala | Ala | Tyr | Ala | Ala | Ala | Cys | Thr | Xaa' | Gly | Cys | (SEQ ID NO: 2282) |

FIG. 2AO

FIG. 2AP

| | | | | | | | | | | | | |
|---|---|---|---|---|---|---|---|---|---|---|---|---|
| Pro | Gly | Thr | Xaa' | Cys | Gly | Glu | Ile | Cys | Ala | Tyr | Ala | Xaa' | Xaa' | Thr | Gly | Cys | (SEQ ID NO: 2317) |
| Pro | Gly | Thr | Xaa' | Cys | Gly | Glu | Ile | Cys | Ala | Tyr | Ala | Xaa' | Xaa' | Thr | Xaa' | Gly | Cys | (SEQ ID NO: 2318) |
| Pro | Gly | Thr | Xaa' | Cys | Gly | Glu | Ile | Cys | Ala | Tyr | Ala | Xaa' | Xaa' | Thr | Gly | Xaa' | Cys | (SEQ ID NO: 2319) |
| Pro | Gly | Thr | Xaa' | Cys | Gly | Glu | Ile | Cys | Ala | Tyr | Ala | Xaa' | Xaa' | Thr | Gly | Cys | Xaa' | (SEQ ID NO: 2320) |
| Pro | Gly | Thr | Xaa' | Cys | Gly | Glu | Ile | Cys | Ala | Tyr | Ala | Xaa' | Xaa' | Thr | Xaa' | Gly | Cys | (SEQ ID NO: 2321) |
| Pro | Gly | Thr | Xaa' | Cys | Gly | Glu | Ile | Cys | Ala | Tyr | Ala | Xaa' | Xaa' | Cys | Thr | Xaa' | Gly | Cys | (SEQ ID NO: 2322) |
| Pro | Gly | Thr | Xaa' | Cys | Gly | Glu | Ile | Cys | Ala | Tyr | Ala | Xaa' | Xaa' | Cys | Thr | Gly | Xaa' | Cys | (SEQ ID NO: 2323) |
| Pro | Gly | Thr | Xaa' | Cys | Gly | Glu | Ile | Cys | Ala | Tyr | Ala | Xaa' | Xaa' | Cys | Thr | Gly | Cys | Xaa' | (SEQ ID NO: 2324) |
| Pro | Gly | Thr | Xaa' | Cys | Gly | Glu | Ile | Cys | Ala | Tyr | Ala | Xaa' | Xaa' | Thr | Gly | Xaa' | Cys | (SEQ ID NO: 2325) |
| Pro | Gly | Thr | Xaa' | Cys | Gly | Glu | Ile | Cys | Ala | Tyr | Ala | Xaa' | Xaa' | Thr | Gly | Xaa' | Cys | Xaa' | (SEQ ID NO: 2326) |
| Pro | Gly | Thr | Xaa' | Cys | Gly | Glu | Ile | Cys | Ala | Tyr | Ala | Xaa' | Xaa' | Thr | Gly | Xaa' | Cys | Xaa' | (SEQ ID NO: 2327) |
| Pro | Gly | Thr | Xaa' | Cys | Gly | Glu | Ile | Cys | Ala | Tyr | Ala | Xaa' | Xaa' | Thr | Gly | Cys | Xaa' | (SEQ ID NO: 2328) |
| Pro | Gly | Thr | Xaa' | Cys | Gly | Glu | Ile | Cys | Ala | Tyr | Ala | Xaa' | Xaa' | Cys | Thr | Gly | Cys | (SEQ ID NO: 2329) |
| Pro | Gly | Thr | Xaa' | Cys | Gly | Glu | Ile | Cys | Ala | Tyr | Ala | Xaa' | Xaa' | Cys | Thr | Gly | Cys | (SEQ ID NO: 2330) |
| Pro | Gly | Thr | Xaa' | Cys | Gly | Glu | Ile | Cys | Ala | Tyr | Ala | Ala | Xaa' | Xaa' | Cys | Thr | Gly | Cys | (SEQ ID NO: 2331) |
| Pro | Gly | Thr | Xaa' | Cys | Gly | Glu | Ile | Cys | Ala | Tyr | Ala | Ala | Xaa' | Xaa' | Cys | Thr | Xaa' | Gly | Cys | (SEQ ID NO: 2332) |
| Pro | Gly | Thr | Xaa' | Cys | Gly | Glu | Ile | Cys | Ala | Tyr | Ala | Ala | Xaa' | Xaa' | Cys | Thr | Gly | Xaa' | Cys | (SEQ ID NO: 2333) |
| Pro | Gly | Thr | Xaa' | Cys | Gly | Glu | Ile | Cys | Ala | Tyr | Ala | Ala | Xaa' | Xaa' | Cys | Thr | Gly | Cys | Xaa' | (SEQ ID NO: 2334) |
| Pro | Gly | Thr | Xaa' | Cys | Gly | Glu | Ile | Cys | Ala | Tyr | Ala | Ala | Xaa' | Xaa' | Cys | Thr | Xaa' | Gly | Cys | (SEQ ID NO: 2335) |
| Pro | Gly | Thr | Xaa' | Cys | Gly | Glu | Ile | Cys | Ala | Tyr | Ala | Ala | Xaa' | Xaa' | Cys | Thr | Xaa' | Gly | Cys | Xaa' | (SEQ ID NO: 2336) |
| Pro | Gly | Thr | Xaa' | Cys | Gly | Glu | Ile | Cys | Ala | Tyr | Ala | Ala | Xaa' | Xaa' | Cys | Thr | Gly | Cys | Xaa' | (SEQ ID NO: 2337) |
| Pro | Gly | Thr | Xaa' | Cys | Gly | Glu | Ile | Cys | Ala | Tyr | Ala | Ala | Xaa' | Xaa' | Cys | Xaa' | Thr | Gly | Cys | (SEQ ID NO: 2338) |
| Pro | Gly | Thr | Xaa' | Cys | Gly | Glu | Ile | Cys | Ala | Tyr | Ala | Ala | Xaa' | Xaa' | Cys | Xaa' | Thr | Xaa' | Gly | Cys | (SEQ ID NO: 2339) |
| Pro | Gly | Thr | Xaa' | Cys | Gly | Glu | Ile | Cys | Ala | Tyr | Ala | Ala | Xaa' | Xaa' | Cys | Xaa' | Thr | Gly | Xaa' | Cys | (SEQ ID NO: 2340) |
| Pro | Gly | Thr | Xaa' | Cys | Gly | Glu | Ile | Cys | Ala | Tyr | Ala | Ala | Xaa' | Xaa' | Cys | Xaa' | Thr | Gly | Cys | Xaa' | (SEQ ID NO: 2341) |
| Pro | Gly | Thr | Xaa' | Cys | Gly | Glu | Ile | Cys | Ala | Tyr | Ala | Ala | Xaa' | Xaa' | Cys | Thr | Gly | Cys | (SEQ ID NO: 2342) |
| Pro | Gly | Thr | Xaa' | Cys | Gly | Glu | Ile | Cys | Ala | Tyr | Ala | Ala | Xaa' | Xaa' | Cys | Thr | Xaa' | Gly | Cys | (SEQ ID NO: 2343) |
| Pro | Gly | Thr | Xaa' | Cys | Gly | Glu | Ile | Cys | Ala | Tyr | Ala | Ala | Xaa' | Xaa' | Cys | Thr | Gly | Xaa' | Cys | (SEQ ID NO: 2344) |
| Pro | Gly | Thr | Xaa' | Cys | Gly | Glu | Ile | Cys | Ala | Tyr | Ala | Ala | Xaa' | Xaa' | Cys | Thr | Gly | Cys | Xaa' | (SEQ ID NO: 2345) |
| Pro | Gly | Thr | Xaa' | Cys | Gly | Glu | Ile | Cys | Ala | Tyr | Ala | Ala | Xaa' | Xaa' | Thr | Gly | Cys | (SEQ ID NO: 2346) |
| Pro | Gly | Thr | Xaa' | Cys | Gly | Glu | Ile | Cys | Ala | Tyr | Ala | Ala | Xaa' | Xaa' | Thr | Xaa' | Gly | Cys | (SEQ ID NO: 2347) |
| Pro | Gly | Thr | Xaa' | Cys | Gly | Glu | Ile | Cys | Ala | Tyr | Ala | Ala | Xaa' | Xaa' | Thr | Gly | Xaa' | Cys | (SEQ ID NO: 2348) |
| Pro | Gly | Thr | Xaa' | Cys | Gly | Glu | Ile | Cys | Ala | Tyr | Ala | Ala | Xaa' | Xaa' | Thr | Gly | Cys | Xaa' | (SEQ ID NO: 2349) |
| Pro | Gly | Thr | Xaa' | Cys | Gly | Glu | Ile | Cys | Ala | Tyr | Ala | Ala | Xaa' | Xaa' | Thr | Gly | Cys | Xaa' | (SEQ ID NO: 2350) |

FIG. 2AQ

| Sequence | SEQ ID NO |
|---|---|
| Pro Gly Thr Xaa' Cys Gly Glu Ile Cys Ala Tyr Ala Cys Xaa' Thr Gly Cys | (SEQ ID NO: 2351) |
| Pro Gly Thr Xaa' Cys Gly Glu Ile Cys Ala Tyr Ala Cys Xaa' Xaa' Thr Gly Cys | (SEQ ID NO: 2352) |
| Pro Gly Thr Xaa' Cys Gly Glu Ile Cys Ala Tyr Ala Cys Xaa' Xaa' Xaa' Thr Gly Cys | (SEQ ID NO: 2353) |
| Pro Gly Thr Xaa' Cys Gly Glu Ile Cys Ala Tyr Ala Cys Xaa' Xaa' Xaa' Xaa' Thr Gly Cys | (SEQ ID NO: 2354) |
| Pro Gly Thr Xaa' Cys Gly Glu Ile Cys Ala Tyr Ala Cys Xaa' Xaa' Xaa' Xaa' Thr Gly Xaa' Cys | (SEQ ID NO: 2355) |
| Pro Gly Thr Xaa' Cys Gly Glu Ile Cys Ala Tyr Ala Cys Xaa' Xaa' Xaa' Thr Gly Cys Xaa' | (SEQ ID NO: 2356) |
| Pro Gly Thr Xaa' Cys Gly Glu Ile Cys Ala Tyr Ala Cys Xaa' Xaa' Thr Xaa' Gly Cys | (SEQ ID NO: 2357) |
| Pro Gly Thr Xaa' Cys Gly Glu Ile Cys Ala Tyr Ala Cys Xaa' Xaa' Thr Xaa' Xaa' Gly Cys | (SEQ ID NO: 2358) |
| Pro Gly Thr Xaa' Cys Gly Glu Ile Cys Ala Tyr Ala Cys Xaa' Xaa' Thr Xaa' Xaa' Gly Xaa' Cys | (SEQ ID NO: 2359) |
| Pro Gly Thr Xaa' Cys Gly Glu Ile Cys Ala Tyr Ala Cys Xaa' Xaa' Thr Xaa' Gly Cys Xaa' | (SEQ ID NO: 2360) |
| Pro Gly Thr Xaa' Cys Gly Glu Ile Cys Ala Tyr Ala Cys Xaa' Thr Gly Xaa' Cys | (SEQ ID NO: 2361) |
| Pro Gly Thr Xaa' Cys Gly Glu Ile Cys Ala Tyr Ala Cys Xaa' Thr Gly Xaa' Xaa' Cys | (SEQ ID NO: 2362) |
| Pro Gly Thr Xaa' Cys Gly Glu Ile Cys Ala Tyr Ala Cys Xaa' Thr Gly Xaa' Xaa' Xaa' Cys | (SEQ ID NO: 2363) |
| Pro Gly Thr Xaa' Cys Gly Glu Ile Cys Ala Tyr Ala Cys Xaa' Thr Gly Cys Xaa' | (SEQ ID NO: 2364) |
| Pro Gly Thr Xaa' Cys Gly Glu Ile Cys Ala Tyr Ala Cys Xaa' Thr Gly Cys Xaa' Xaa' | (SEQ ID NO: 2365) |
| Pro Gly Thr Xaa' Cys Gly Glu Ile Cys Ala Tyr Ala Cys Thr Gly Cys | (SEQ ID NO: 2366) |
| Pro Gly Thr Xaa' Cys Gly Glu Ile Cys Ala Tyr Ala Cys Thr Xaa' Gly Cys | (SEQ ID NO: 2367) |
| Pro Gly Thr Xaa' Cys Gly Glu Ile Cys Ala Tyr Ala Cys Thr Xaa' Xaa' Gly Cys | (SEQ ID NO: 2368) |
| Pro Gly Thr Xaa' Cys Gly Glu Ile Cys Ala Tyr Ala Cys Thr Xaa' Xaa' Xaa' Gly Cys | (SEQ ID NO: 2369) |
| Pro Gly Thr Xaa' Cys Gly Glu Ile Cys Ala Tyr Ala Cys Thr Xaa' Xaa' Xaa' Gly Xaa' Cys | (SEQ ID NO: 2370) |
| Pro Gly Thr Xaa' Cys Gly Glu Ile Cys Ala Tyr Ala Cys Thr Xaa' Xaa' Gly Cys Xaa' | (SEQ ID NO: 2371) |
| Pro Gly Thr Xaa' Cys Gly Glu Ile Cys Ala Tyr Ala Cys Thr Xaa' Gly Xaa' Cys | (SEQ ID NO: 2372) |
| Pro Gly Thr Xaa' Cys Gly Glu Ile Cys Ala Tyr Ala Cys Thr Xaa' Gly Xaa' Xaa' Cys | (SEQ ID NO: 2373) |
| Pro Gly Thr Xaa' Cys Gly Glu Ile Cys Ala Tyr Ala Cys Thr Xaa' Gly Cys Xaa' | (SEQ ID NO: 2374) |
| Pro Gly Thr Xaa' Cys Gly Glu Ile Cys Ala Tyr Ala Cys Thr Gly Xaa' Cys | (SEQ ID NO: 2375) |
| Pro Gly Thr Xaa' Cys Gly Glu Ile Cys Ala Tyr Ala Cys Thr Gly Xaa' Xaa' Cys | (SEQ ID NO: 2376) |
| Pro Gly Thr Xaa' Cys Gly Glu Ile Cys Ala Tyr Ala Cys Thr Gly Xaa' Xaa' Cys | (SEQ ID NO: 2377) |
| Pro Gly Thr Xaa' Cys Gly Glu Ile Cys Ala Tyr Ala Cys Thr Gly Xaa' Xaa' Xaa' Cys | (SEQ ID NO: 2378) |
| Pro Gly Thr Xaa' Cys Gly Glu Ile Cys Ala Tyr Ala Cys Thr Gly Xaa' Xaa' Xaa' Xaa' Cys | (SEQ ID NO: 2379) |
| Pro Gly Thr Xaa' Cys Gly Glu Ile Cys Ala Tyr Ala Cys Thr Gly Xaa' Xaa' Cys Xaa' | (SEQ ID NO: 2380) |
| Pro Gly Thr Xaa' Cys Gly Glu Ile Cys Ala Tyr Ala Cys Thr Gly Xaa' Cys Xaa' | (SEQ ID NO: 2381) |
| Pro Gly Thr Xaa' Cys Gly Glu Ile Cys Ala Tyr Ala Cys Thr Gly Cys Xaa' | (SEQ ID NO: 2382) |
| Pro Gly Thr Xaa' Cys Gly Glu Ile Cys Ala Tyr Ala Cys Thr Gly Cys Xaa' Xaa' | (SEQ ID NO: 2383) |
| Pro Gly Thr Xaa' Cys Gly Glu Ile Cys Ala Tyr Ala Cys Thr Gly Cys Xaa' Xaa' Xaa' | (SEQ ID NO: 2384) |

FIG. 2AR

| | | | |
|---|---|---|---|
Pro Gly Thr Cys Gly Glu Ile Cys Ala Tyr Ala Ala Cys Thr Gly Cys | (SEQ ID NO: 2385)
Pro Gly Thr Cys Xaa' Gly Glu Ile Cys Ala Tyr Ala Tyr Ala Ala Cys Thr Gly Cys | (SEQ ID NO: 2386)
Pro Gly Thr Cys Xaa' Xaa' Glu Ile Cys Ala Tyr Ala Ala Cys Thr Gly Cys | (SEQ ID NO: 2387)
Pro Gly Thr Cys Xaa' Xaa' Gly Glu Ile Cys Ala Tyr Ala Ala Cys Thr Gly Cys | (SEQ ID NO: 2388)
Pro Gly Thr Cys Xaa' Xaa' Xaa' Glu Ile Cys Ala Tyr Ala Ala Cys Thr Gly Cys | (SEQ ID NO: 2389)
Pro Gly Thr Cys Xaa' Xaa' Gly Xaa' Ile Cys Ala Tyr Ala Ala Cys Thr Gly Cys | (SEQ ID NO: 2390)
Pro Gly Thr Cys Xaa' Xaa' Gly Glu Xaa' Ile Cys Ala Tyr Ala Ala Cys Thr Gly Cys | (SEQ ID NO: 2391)
Pro Gly Thr Cys Xaa' Xaa' Gly Glu Ile Cys Xaa' Ala Tyr Ala Ala Cys Thr Gly Cys | (SEQ ID NO: 2392)
Pro Gly Thr Cys Xaa' Xaa' Gly Glu Ile Cys Ala Xaa' Tyr Ala Ala Cys Thr Gly Cys | (SEQ ID NO: 2393)
Pro Gly Thr Cys Xaa' Xaa' Gly Glu Ile Cys Ala Tyr Xaa' Ala Ala Cys Thr Gly Cys | (SEQ ID NO: 2394)
Pro Gly Thr Cys Xaa' Xaa' Gly Glu Ile Cys Ala Tyr Ala Xaa' Ala Cys Thr Gly Cys | (SEQ ID NO: 2395)
Pro Gly Thr Cys Xaa' Xaa' Gly Glu Ile Cys Ala Tyr Ala Ala Xaa' Cys Thr Gly Cys | (SEQ ID NO: 2396)
Pro Gly Thr Cys Xaa' Xaa' Gly Glu Ile Cys Ala Tyr Ala Ala Cys Xaa' Thr Gly Cys | (SEQ ID NO: 2397)
Pro Gly Thr Cys Xaa' Xaa' Gly Glu Ile Cys Ala Tyr Ala Ala Cys Thr Xaa' Gly Cys | (SEQ ID NO: 2398)
Pro Gly Thr Cys Xaa' Xaa' Gly Glu Ile Cys Ala Tyr Ala Ala Cys Thr Gly Xaa' Cys | (SEQ ID NO: 2399)
Pro Gly Thr Cys Xaa' Xaa' Gly Glu Ile Cys Ala Tyr Ala Ala Cys Thr Gly Cys Xaa' | (SEQ ID NO: 2400)
Pro Gly Thr Cys Xaa' Xaa' Gly Xaa' Ile Cys Ala Tyr Ala Ala Cys Thr Gly Cys | (SEQ ID NO: 2401)
Pro Gly Thr Cys Xaa' Xaa' Gly Xaa' Xaa' Ile Cys Ala Tyr Ala Ala Cys Thr Gly Cys | (SEQ ID NO: 2402)
Pro Gly Thr Cys Xaa' Xaa' Gly Xaa' Ile Cys Xaa' Ala Tyr Ala Ala Cys Thr Gly Cys | (SEQ ID NO: 2403)
Pro Gly Thr Cys Xaa' Xaa' Gly Xaa' Ile Cys Ala Xaa' Tyr Ala Ala Cys Thr Gly Cys | (SEQ ID NO: 2404)
Pro Gly Thr Cys Xaa' Xaa' Gly Xaa' Ile Cys Ala Tyr Xaa' Ala Ala Cys Thr Gly Cys | (SEQ ID NO: 2405)
Pro Gly Thr Cys Xaa' Xaa' Gly Xaa' Ile Cys Ala Tyr Ala Xaa' Ala Cys Thr Gly Cys | (SEQ ID NO: 2406)
Pro Gly Thr Cys Xaa' Xaa' Gly Xaa' Ile Cys Ala Tyr Ala Ala Xaa' Cys Thr Gly Cys | (SEQ ID NO: 2407)
Pro Gly Thr Cys Xaa' Xaa' Gly Xaa' Ile Cys Ala Tyr Ala Ala Cys Xaa' Thr Gly Cys | (SEQ ID NO: 2408)
Pro Gly Thr Cys Xaa' Xaa' Gly Xaa' Ile Cys Ala Tyr Ala Ala Cys Thr Xaa' Gly Cys | (SEQ ID NO: 2409)
Pro Gly Thr Cys Xaa' Xaa' Gly Xaa' Ile Cys Ala Tyr Ala Ala Cys Thr Gly Xaa' Cys | (SEQ ID NO: 2410)
Pro Gly Thr Cys Xaa' Xaa' Gly Xaa' Ile Cys Ala Tyr Ala Ala Cys Thr Gly Cys Xaa' | (SEQ ID NO: 2411)
Pro Gly Thr Cys Xaa' Xaa' Gly Xaa' Xaa' Ile Cys Ala Tyr Ala Ala Cys Thr Gly Cys | (SEQ ID NO: 2412)
Pro Gly Thr Cys Xaa' Xaa' Gly Xaa' Xaa' Ile Cys Xaa' Ala Tyr Ala Ala Cys Thr Gly Cys | (SEQ ID NO: 2413)
Pro Gly Thr Cys Xaa' Xaa' Gly Xaa' Xaa' Ile Cys Ala Xaa' Tyr Ala Ala Cys Thr Gly Cys | (SEQ ID NO: 2414)
Pro Gly Thr Cys Xaa' Xaa' Gly Xaa' Xaa' Ile Cys Ala Tyr Xaa' Ala Ala Cys Thr Gly Cys | (SEQ ID NO: 2415)
Pro Gly Thr Cys Xaa' Xaa' Gly Xaa' Xaa' Ile Cys Ala Tyr Ala Xaa' Ala Cys Thr Gly Cys | (SEQ ID NO: 2416)
Pro Gly Thr Cys Xaa' Xaa' Gly Xaa' Xaa' Ile Cys Ala Tyr Ala Ala Xaa' Cys Thr Gly Cys | (SEQ ID NO: 2417)
Pro Gly Thr Cys Xaa' Xaa' Gly Xaa' Xaa' Ile Cys Ala Tyr Ala Ala Cys Xaa' Thr Gly Cys | (SEQ ID NO: 2418)

FIG. 2AS

Pro Gly Thr Cys Xaa' Xaa' Gly Glu Xaa' Ile Cys Ala Tyr Xaa' Ala Ala Cys Thr Gly Cys (SEQ ID NO: 2419)
Pro Gly Thr Cys Xaa' Xaa' Gly Glu Xaa' Ile Cys Ala Tyr Ala Ala Xaa' Ala Cys Thr Gly Cys (SEQ ID NO: 2420)
Pro Gly Thr Cys Xaa' Xaa' Gly Glu Xaa' Ile Cys Ala Tyr Ala Ala Ala Cys Xaa' Gly Cys (SEQ ID NO: 2421)
Pro Gly Thr Cys Xaa' Xaa' Gly Glu Xaa' Ile Cys Ala Tyr Ala Ala Ala Cys Thr Xaa' Cys (SEQ ID NO: 2422)
Pro Gly Thr Cys Xaa' Xaa' Gly Glu Xaa' Ile Cys Ala Tyr Ala Ala Ala Cys Thr Gly Xaa' (SEQ ID NO: 2423)
Pro Gly Thr Cys Xaa' Xaa' Gly Glu Xaa' Ile Cys Ala Tyr Ala Ala Ala Cys Thr Gly Cys Xaa' (SEQ ID NO: 2424)
Pro Gly Thr Cys Xaa' Xaa' Gly Glu Xaa' Ile Cys Ala' Tyr Ala Ala Ala Cys Thr Gly Cys (SEQ ID NO: 2425)
Pro Gly Thr Cys Xaa' Xaa' Gly Glu Ile Xaa' Cys Ala Tyr Ala Ala Ala Cys Thr Gly Cys (SEQ ID NO: 2426)
Pro Gly Thr Cys Xaa' Xaa' Gly Glu Ile Cys Xaa' Ala Tyr Ala Ala Ala Cys Thr Gly Cys (SEQ ID NO: 2427)
Pro Gly Thr Cys Xaa' Xaa' Gly Glu Ile Cys Xaa' Tyr Ala Ala Ala Cys Thr Gly Cys (SEQ ID NO: 2428)
Pro Gly Thr Cys Xaa' Xaa' Gly Glu Ile Cys Ala Xaa' Ala Ala Ala Cys Thr Gly Cys (SEQ ID NO: 2429)
Pro Gly Thr Cys Xaa' Xaa' Gly Glu Ile Cys Ala Tyr Xaa' Ala Ala Cys Thr Gly Cys (SEQ ID NO: 2430)
Pro Gly Thr Cys Xaa' Xaa' Gly Glu Ile Cys Ala Tyr Ala Xaa' Ala Cys Thr Gly Cys (SEQ ID NO: 2431)
Pro Gly Thr Cys Xaa' Xaa' Gly Glu Ile Cys Ala Tyr Ala Ala Xaa' Cys Thr Gly Cys (SEQ ID NO: 2432)
Pro Gly Thr Cys Xaa' Xaa' Gly Glu Ile Cys Ala Tyr Ala Ala Ala Xaa' Thr Gly Cys (SEQ ID NO: 2433)
Pro Gly Thr Cys Xaa' Xaa' Gly Glu Ile Cys Ala Tyr Ala Ala Ala Cys Xaa' Gly Cys (SEQ ID NO: 2434)
Pro Gly Thr Cys Xaa' Xaa' Gly Glu Ile Cys Ala Tyr Ala Ala Ala Cys Thr Xaa' Cys (SEQ ID NO: 2435)
Pro Gly Thr Cys Xaa' Xaa' Gly Glu Ile Cys Ala Tyr Ala Ala Ala Cys Thr Gly Xaa' (SEQ ID NO: 2436)
Pro Gly Thr Cys Xaa' Xaa' Gly Glu Ile Cys Ala Tyr Ala Ala Ala Cys Thr Gly Cys Xaa' (SEQ ID NO: 2437)
Pro Gly Thr Cys Xaa' Xaa' Gly Glu Ile Cys Xaa' Ala Tyr Ala Ala Ala Cys Thr Gly Cys (SEQ ID NO: 2438)
Pro Gly Thr Cys Xaa' Xaa' Gly Glu Ile Cys Ala Xaa' Tyr Ala Ala Ala Cys Thr Gly Cys (SEQ ID NO: 2439)
Pro Gly Thr Cys Xaa' Xaa' Gly Glu Ile Cys Ala Tyr Xaa' Ala Ala Ala Cys Thr Gly Cys (SEQ ID NO: 2440)
Pro Gly Thr Cys Xaa' Xaa' Gly Glu Ile Cys Ala Tyr Ala Xaa' Ala Ala Cys Thr Gly Cys (SEQ ID NO: 2441)
Pro Gly Thr Cys Xaa' Xaa' Gly Glu Ile Cys Ala Tyr Ala Ala Xaa' Ala Cys Thr Gly Cys (SEQ ID NO: 2442)
Pro Gly Thr Cys Xaa' Xaa' Gly Glu Ile Cys Ala Tyr Ala Ala Ala Xaa' Cys Thr Gly Cys (SEQ ID NO: 2443)
Pro Gly Thr Cys Xaa' Xaa' Gly Glu Ile Cys Ala Tyr Ala Ala Ala Cys Xaa' Thr Gly Cys (SEQ ID NO: 2444)
Pro Gly Thr Cys Xaa' Xaa' Gly Glu Ile Cys Ala Tyr Ala Ala Ala Cys Thr Xaa' Gly Cys (SEQ ID NO: 2445)
Pro Gly Thr Cys Xaa' Xaa' Gly Glu Ile Cys Ala Tyr Ala Ala Ala Cys Thr Gly Xaa' Cys (SEQ ID NO: 2446)
Pro Gly Thr Cys Xaa' Xaa' Gly Glu Ile Cys Ala Tyr Ala Ala Ala Cys Thr Gly Cys Xaa' (SEQ ID NO: 2447)
Pro Gly Thr Cys Xaa' Xaa' Gly Glu Ile Cys Ala Xaa' Tyr Ala Ala Ala Cys Thr Gly Cys (SEQ ID NO: 2448)
Pro Gly Thr Cys Xaa' Xaa' Gly Glu Ile Cys Ala Xaa' Tyr Ala Ala Ala Cys Thr Gly Cys (SEQ ID NO: 2449)
Pro Gly Thr Cys Xaa' Xaa' Gly Glu Ile Cys Ala Xaa' Tyr Ala Ala Ala Cys Thr Gly Cys (SEQ ID NO: 2450)
Pro Gly Thr Cys Xaa' Xaa' Gly Glu Ile Cys Ala Xaa' Tyr Ala Ala Ala Cys Thr Gly Cys (SEQ ID NO: 2451)
Pro Gly Thr Cys Xaa' Xaa' Gly Glu Ile Cys Ala Xaa' Tyr Ala Ala Ala Cys Thr Gly Cys (SEQ ID NO: 2452)

FIG. 2AT

| | | | | | | | | | | | | |
|---|---|---|---|---|---|---|---|---|---|---|---|---|
| Pro | Gly | Thr | Cys | Xaa' | Xaa' | Gly | Glu | Ile | Cys | Ala | Xaa' | Tyr | Ala | Ala | Cys | Thr | Xaa' | Gly | Cys | (SEQ ID NO: 2453) |
| Pro | Gly | Thr | Cys | Xaa' | Xaa' | Gly | Glu | Ile | Cys | Ala | Xaa' | Tyr | Ala | Ala | Cys | Thr | Gly | Xaa' | Cys | (SEQ ID NO: 2454) |
| Pro | Gly | Thr | Cys | Xaa' | Xaa' | Gly | Glu | Ile | Cys | Ala | Xaa' | Tyr | Ala | Ala | Cys | Thr | Gly | Cys | Xaa' | (SEQ ID NO: 2455) |
| Pro | Gly | Thr | Cys | Xaa' | Xaa' | Gly | Glu | Ile | Cys | Ala | Xaa' | Tyr | Ala | Ala | Cys | Xaa' | Thr | Gly | Cys | (SEQ ID NO: 2456) |
| Pro | Gly | Thr | Cys | Xaa' | Xaa' | Gly | Glu | Ile | Cys | Ala | Xaa' | Tyr | Xaa' | Ala | Cys | Thr | Gly | Cys | | (SEQ ID NO: 2457) |
| Pro | Gly | Thr | Cys | Xaa' | Xaa' | Gly | Glu | Ile | Cys | Ala | Xaa' | Tyr | Ala | Xaa' | Cys | Thr | Gly | Cys | | (SEQ ID NO: 2458) |
| Pro | Gly | Thr | Cys | Xaa' | Xaa' | Gly | Glu | Ile | Cys | Ala | Xaa' | Tyr | Ala | Ala | Xaa' | Cys | Thr | Gly | Cys | (SEQ ID NO: 2459) |
| Pro | Gly | Thr | Cys | Xaa' | Xaa' | Gly | Glu | Ile | Cys | Ala | Xaa' | Tyr | Ala | Ala | Cys | Xaa' | Thr | Gly | Cys | (SEQ ID NO: 2460) |
| Pro | Gly | Thr | Cys | Xaa' | Xaa' | Gly | Glu | Ile | Cys | Ala | Xaa' | Tyr | Ala | Ala | Cys | Thr | Xaa' | Gly | Cys | (SEQ ID NO: 2461) |
| Pro | Gly | Thr | Cys | Xaa' | Xaa' | Gly | Glu | Ile | Cys | Ala | Xaa' | Tyr | Ala | Ala | Cys | Thr | Gly | Xaa' | Cys | (SEQ ID NO: 2462) |
| Pro | Gly | Thr | Cys | Xaa' | Xaa' | Gly | Glu | Ile | Cys | Ala | Xaa' | Tyr | Ala | Ala | Cys | Thr | Gly | Cys | Xaa' | (SEQ ID NO: 2463) |
| Pro | Gly | Thr | Cys | Xaa' | Xaa' | Gly | Glu | Ile | Cys | Ala | Xaa' | Tyr | Ala | Ala | Cys | Thr | Gly | Cys | | (SEQ ID NO: 2464) |
| Pro | Gly | Thr | Cys | Xaa' | Xaa' | Gly | Glu | Ile | Cys | Ala | Xaa' | Tyr | Ala | Ala | Cys | Thr | Gly | Cys | | (SEQ ID NO: 2465) |
| Pro | Gly | Thr | Cys | Xaa' | Xaa' | Gly | Glu | Ile | Cys | Ala | Xaa' | Tyr | Ala | Ala | Cys | Thr | Gly | Cys | | (SEQ ID NO: 2466) |
| Pro | Gly | Thr | Cys | Xaa' | Xaa' | Gly | Glu | Ile | Cys | Ala | Xaa' | Tyr | Ala | Xaa' | Cys | Thr | Gly | Cys | | (SEQ ID NO: 2467) |
| Pro | Gly | Thr | Cys | Xaa' | Xaa' | Gly | Glu | Ile | Cys | Ala | Xaa' | Tyr | Ala | Ala | Xaa' | Cys | Thr | Gly | Cys | (SEQ ID NO: 2468) |
| Pro | Gly | Thr | Cys | Xaa' | Xaa' | Gly | Glu | Ile | Cys | Ala | Xaa' | Tyr | Ala | Ala | Cys | Xaa' | Thr | Gly | Cys | (SEQ ID NO: 2469) |
| Pro | Gly | Thr | Cys | Xaa' | Xaa' | Gly | Glu | Ile | Cys | Ala | Xaa' | Tyr | Ala | Ala | Cys | Thr | Xaa' | Gly | Cys | (SEQ ID NO: 2470) |
| Pro | Gly | Thr | Cys | Xaa' | Xaa' | Gly | Glu | Ile | Cys | Ala | Xaa' | Tyr | Ala | Ala | Cys | Thr | Gly | Xaa' | Cys | (SEQ ID NO: 2471) |
| Pro | Gly | Thr | Cys | Xaa' | Xaa' | Gly | Glu | Ile | Cys | Ala | Xaa' | Tyr | Ala | Ala | Cys | Thr | Gly | Cys | | (SEQ ID NO: 2472) |
| Pro | Gly | Thr | Cys | Xaa' | Xaa' | Gly | Glu | Ile | Cys | Ala | Xaa' | Tyr | Ala | Ala | Cys | Xaa' | Thr | Gly | Cys | (SEQ ID NO: 2473) |
| Pro | Gly | Thr | Cys | Xaa' | Xaa' | Gly | Glu | Ile | Cys | Ala | Xaa' | Tyr | Ala | Xaa' | Cys | Thr | Gly | Cys | | (SEQ ID NO: 2474) |
| Pro | Gly | Thr | Cys | Xaa' | Xaa' | Gly | Glu | Ile | Cys | Ala | Xaa' | Tyr | Ala | Ala | Xaa' | Cys | Thr | Gly | Cys | (SEQ ID NO: 2475) |
| Pro | Gly | Thr | Cys | Xaa' | Xaa' | Gly | Glu | Ile | Cys | Ala | Xaa' | Tyr | Ala | Ala | Cys | Thr | Gly | Cys | Xaa' | (SEQ ID NO: 2476) |
| Pro | Gly | Thr | Cys | Xaa' | Xaa' | Gly | Glu | Ile | Cys | Ala | Ala | Tyr | Ala | Ala | Cys | Thr | Gly | Cys | | (SEQ ID NO: 2477) |
| Pro | Gly | Thr | Cys | Xaa' | Xaa' | Gly | Glu | Ile | Cys | Ala | Ala | Tyr | Ala | Ala | Cys | Xaa' | Thr | Gly | Cys | (SEQ ID NO: 2478) |
| Pro | Gly | Thr | Cys | Xaa' | Xaa' | Gly | Glu | Ile | Cys | Ala | Ala | Tyr | Ala | Ala | Cys | Thr | Xaa' | Gly | Cys | (SEQ ID NO: 2479) |
| Pro | Gly | Thr | Cys | Xaa' | Xaa' | Gly | Glu | Ile | Cys | Ala | Ala | Tyr | Ala | Ala | Cys | Thr | Gly | Xaa' | Cys | (SEQ ID NO: 2480) |
| Pro | Gly | Thr | Cys | Xaa' | Xaa' | Gly | Glu | Ile | Cys | Ala | Ala | Tyr | Ala | Ala | Cys | Thr | Gly | Cys | Xaa' | (SEQ ID NO: 2481) |
| Pro | Gly | Thr | Cys | Xaa' | Xaa' | Gly | Glu | Ile | Cys | Ala | Ala | Tyr | Xaa' | Ala | Cys | Thr | Gly | Cys | | (SEQ ID NO: 2482) |
| Pro | Gly | Thr | Cys | Xaa' | Xaa' | Gly | Glu | Ile | Cys | Ala | Ala | Tyr | Ala | Xaa' | Cys | Thr | Gly | Cys | | (SEQ ID NO: 2483) |
| Pro | Gly | Thr | Cys | Xaa' | Xaa' | Gly | Glu | Ile | Cys | Ala | Ala | Tyr | Ala | Ala | Xaa' | Cys | Thr | Gly | Cys | (SEQ ID NO: 2484) |
| Pro | Gly | Thr | Cys | Xaa' | Xaa' | Gly | Glu | Ile | Cys | Ala | Ala | Tyr | Ala | Ala | Cys | Thr | Xaa' | Gly | Cys | (SEQ ID NO: 2485) |
| Pro | Gly | Thr | Cys | Xaa' | Xaa' | Gly | Glu | Ile | Cys | Ala | Ala | Tyr | Ala | Ala | Cys | Thr | Gly | Xaa' | Cys | (SEQ ID NO: 2486) |

FIG. 2AU

| Sequence | SEQ ID NO |
|---|---|
| Pro Gly Thr Cys Xaa' Gly Glu Ile Cys Ala Tyr Ala Ala Cys Thr Gly Xaa' Xaa' Cys | (SEQ ID NO: 2487) |
| Pro Gly Thr Cys Xaa' Gly Glu Ile Cys Ala Tyr Ala Ala Cys Thr Gly Xaa' Cys Xaa' | (SEQ ID NO: 2488) |
| Pro Gly Thr Cys Xaa' Gly Glu Ile Cys Ala Tyr Ala Ala Cys Thr Gly Cys Xaa' | (SEQ ID NO: 2489) |
| Pro Gly Thr Cys Xaa' Gly Glu Ile Cys Ala Tyr Ala Ala Cys Thr Gly Cys Xaa' | (SEQ ID NO: 2490) |
| Pro Gly Thr Cys Xaa' Gly Xaa' Ile Cys Ala Tyr Ala Ala Cys Thr Gly Cys Xaa' | (SEQ ID NO: 2491) |
| Pro Gly Thr Cys Xaa' Gly Glu Ile Cys Ala Tyr Ala Ala Cys Thr Gly Cys | (SEQ ID NO: 2492) |
| Pro Gly Thr Cys Xaa' Gly Xaa' Xaa' Glu Ile Cys Ala Tyr Ala Ala Cys Thr Gly Cys | (SEQ ID NO: 2493) |
| Pro Gly Thr Cys Xaa' Gly Xaa' Xaa' Glu Ile Cys Ala Tyr Ala Ala Cys Thr Gly Cys | (SEQ ID NO: 2494) |
| Pro Gly Thr Cys Xaa' Gly Xaa' Xaa' Glu Ile Cys Ala Tyr Ala Ala Cys Thr Gly Cys | (SEQ ID NO: 2495) |
| Pro Gly Thr Cys Xaa' Gly Xaa' Xaa' Xaa' Ile Cys Ala Tyr Ala Ala Cys Thr Gly Cys | (SEQ ID NO: 2496) |
| Pro Gly Thr Cys Xaa' Gly Xaa' Xaa' Glu Xaa' Cys Ala Tyr Ala Ala Cys Thr Gly Cys | (SEQ ID NO: 2497) |
| Pro Gly Thr Cys Xaa' Gly Xaa' Xaa' Glu Ile Cys Ala Tyr Ala Ala Cys Thr Gly Cys | (SEQ ID NO: 2498) |
| Pro Gly Thr Cys Xaa' Gly Xaa' Xaa' Glu Ile Cys Xaa' Tyr Ala Ala Cys Thr Gly Cys | (SEQ ID NO: 2499) |
| Pro Gly Thr Cys Xaa' Gly Xaa' Xaa' Glu Ile Cys Ala Xaa' Ala Ala Cys Thr Gly Cys | (SEQ ID NO: 2500) |
| Pro Gly Thr Cys Xaa' Gly Xaa' Xaa' Glu Ile Cys Ala Tyr Xaa' Ala Cys Thr Gly Cys | (SEQ ID NO: 2501) |
| Pro Gly Thr Cys Xaa' Gly Xaa' Xaa' Glu Ile Cys Ala Tyr Ala Xaa' Cys Thr Gly Cys | (SEQ ID NO: 2502) |
| Pro Gly Thr Cys Xaa' Gly Xaa' Xaa' Glu Ile Cys Ala Tyr Ala Ala Cys Xaa' Gly Cys | (SEQ ID NO: 2503) |
| Pro Gly Thr Cys Xaa' Gly Xaa' Xaa' Glu Ile Cys Ala Tyr Ala Ala Cys Thr Xaa' Cys | (SEQ ID NO: 2504) |
| Pro Gly Thr Cys Xaa' Gly Xaa' Xaa' Glu Xaa' Cys Ala Tyr Ala Ala Cys Thr Gly Cys | (SEQ ID NO: 2505) |
| Pro Gly Thr Cys Xaa' Gly Xaa' Xaa' Xaa' Ile Cys Ala Tyr Ala Ala Cys Thr Gly Cys | (SEQ ID NO: 2506) |
| Pro Gly Thr Cys Xaa' Gly Xaa' Xaa' Ile Xaa' Cys Ala Tyr Ala Ala Cys Thr Gly Cys | (SEQ ID NO: 2507) |
| Pro Gly Thr Cys Xaa' Gly Xaa' Xaa' Ile Xaa' Cys Ala Tyr Ala Ala Cys Thr Gly Cys | (SEQ ID NO: 2508) |
| Pro Gly Thr Cys Xaa' Gly Xaa' Xaa' Ile Xaa' Cys Ala Tyr Ala Ala Cys Thr Gly Cys | (SEQ ID NO: 2509) |
| Pro Gly Thr Cys Xaa' Gly Xaa' Xaa' Ile Xaa' Cys Ala Tyr Ala Ala Cys Thr Gly Cys | (SEQ ID NO: 2510) |
| Pro Gly Thr Cys Xaa' Gly Xaa' Xaa' Ile Xaa' Cys Ala Tyr Xaa' Ala Cys Thr Gly Cys | (SEQ ID NO: 2511) |
| Pro Gly Thr Cys Xaa' Gly Xaa' Xaa' Ile Xaa' Cys Ala Tyr Ala Xaa' Cys Thr Gly Cys | (SEQ ID NO: 2512) |
| Pro Gly Thr Cys Xaa' Gly Xaa' Xaa' Ile Xaa' Cys Ala Tyr Ala Ala Cys' Thr Gly Cys | (SEQ ID NO: 2513) |
| Pro Gly Thr Cys Xaa' Gly Xaa' Xaa' Ile Xaa' Cys Ala Tyr Ala Ala Cys Xaa' Gly Cys | (SEQ ID NO: 2514) |
| Pro Gly Thr Cys Xaa' Gly Xaa' Ile Xaa' Cys Ala Tyr Ala Ala Cys Thr Gly Xaa' Cys | (SEQ ID NO: 2515) |
| Pro Gly Thr Cys Xaa' Gly Xaa' Ile Xaa' Cys Ala Tyr Ala Ala Cys Thr Gly Cys Xaa' | (SEQ ID NO: 2516) |
| Pro Gly Thr Cys Xaa' Gly Xaa' Ile Xaa' Cys Xaa' Ala Tyr Ala Ala Cys Thr Gly Cys | (SEQ ID NO: 2517) |
| Pro Gly Thr Cys Xaa' Gly Xaa' Ile Ile Xaa' Cys Xaa' Tyr Ala Ala Cys Thr Gly Cys | (SEQ ID NO: 2518) |
| Pro Gly Thr Cys Xaa' Gly Xaa' Ile Ile Xaa' Cys Ala Xaa' Ala Ala Cys Thr Gly Cys | (SEQ ID NO: 2519) |
| Pro Gly Thr Cys Xaa' Gly Xaa' Ile Ile Xaa' Cys Ala Xaa' Ala Ala Cys Thr Gly Cys | (SEQ ID NO: 2520) |

FIG. 2AV

| Sequence | SEQ ID NO |
|---|---|
| Pro Gly Thr Cys Xaa' Gly Xaa' Glu Ile Xaa' Cys Ala Tyr Xaa' Ala Ala Cys Thr Gly Cys | (SEQ ID NO: 2521) |
| Pro Gly Thr Cys Xaa' Gly Xaa' Glu Ile Xaa' Cys Ala Tyr Xaa' Ala Xaa' Cys Thr Gly Cys | (SEQ ID NO: 2522) |
| Pro Gly Thr Cys Xaa' Gly Xaa' Glu Ile Xaa' Cys Ala Tyr Ala Xaa' Cys Thr Gly Cys | (SEQ ID NO: 2523) |
| Pro Gly Thr Cys Xaa' Gly Xaa' Glu Ile Xaa' Cys Ala Tyr Ala Ala Xaa' Thr Gly Cys | (SEQ ID NO: 2524) |
| Pro Gly Thr Cys Xaa' Gly Xaa' Glu Ile Xaa' Cys Ala Tyr Ala Ala Cys Xaa' Gly Cys | (SEQ ID NO: 2525) |
| Pro Gly Thr Cys Xaa' Gly Xaa' Glu Ile Xaa' Cys Ala Tyr Ala Ala Cys Thr Xaa' Cys | (SEQ ID NO: 2526) |
| Pro Gly Thr Cys Xaa' Gly Xaa' Glu Ile Xaa' Cys Ala Tyr Ala Ala Cys Thr Gly Xaa' | (SEQ ID NO: 2527) |
| Pro Gly Thr Cys Xaa' Gly Xaa' Glu Ile Cys Xaa' Ala Tyr Ala Ala Cys Thr Gly Cys | (SEQ ID NO: 2528) |
| Pro Gly Thr Cys Xaa' Gly Xaa' Glu Ile Cys Xaa' Ala Tyr Ala Ala Cys Thr Gly Cys | (SEQ ID NO: 2529) |
| Pro Gly Thr Cys Xaa' Gly Xaa' Glu Ile Cys Xaa' Xaa' Tyr Ala Ala Cys Thr Gly Cys | (SEQ ID NO: 2530) |
| Pro Gly Thr Cys Xaa' Gly Xaa' Glu Ile Cys Xaa' Ala Xaa' Ala Ala Cys Thr Gly Cys | (SEQ ID NO: 2531) |
| Pro Gly Thr Cys Xaa' Gly Xaa' Glu Ile Cys Xaa' Ala Tyr Xaa' Ala Cys Thr Gly Cys | (SEQ ID NO: 2532) |
| Pro Gly Thr Cys Xaa' Gly Xaa' Glu Ile Cys Xaa' Ala Tyr Ala Xaa' Cys Thr Gly Cys | (SEQ ID NO: 2533) |
| Pro Gly Thr Cys Xaa' Gly Xaa' Glu Ile Cys Xaa' Ala Tyr Ala Ala Xaa' Thr Gly Cys | (SEQ ID NO: 2534) |
| Pro Gly Thr Cys Xaa' Gly Xaa' Glu Ile Cys Xaa' Ala Tyr Ala Ala Cys Xaa' Gly Cys | (SEQ ID NO: 2535) |
| Pro Gly Thr Cys Xaa' Gly Xaa' Glu Ile Cys Xaa' Ala Tyr Ala Ala Cys Thr Xaa' Cys | (SEQ ID NO: 2536) |
| Pro Gly Thr Cys Xaa' Gly Xaa' Glu Ile Cys Xaa' Ala Tyr Ala Ala Cys Thr Gly Xaa' | (SEQ ID NO: 2537) |
| Pro Gly Thr Cys Xaa' Gly Xaa' Glu Ile Cys Ala Xaa' Tyr Ala Ala Cys Thr Gly Cys | (SEQ ID NO: 2538) |
| Pro Gly Thr Cys Xaa' Gly Xaa' Glu Ile Cys Ala Xaa' Xaa' Ala Ala Cys Thr Gly Cys | (SEQ ID NO: 2539) |
| Pro Gly Thr Cys Xaa' Gly Xaa' Glu Ile Cys Ala Xaa' Tyr Xaa' Ala Cys Thr Gly Cys | (SEQ ID NO: 2540) |
| Pro Gly Thr Cys Xaa' Gly Xaa' Glu Ile Cys Ala Xaa' Tyr Ala Xaa' Cys Thr Gly Cys | (SEQ ID NO: 2541) |
| Pro Gly Thr Cys Xaa' Gly Xaa' Glu Ile Cys Ala Xaa' Tyr Ala Ala Xaa' Thr Gly Cys | (SEQ ID NO: 2542) |
| Pro Gly Thr Cys Xaa' Gly Xaa' Glu Ile Cys Ala Xaa' Tyr Ala Ala Cys Xaa' Gly Cys | (SEQ ID NO: 2543) |
| Pro Gly Thr Cys Xaa' Gly Xaa' Glu Ile Cys Ala Xaa' Tyr Ala Ala Cys Thr Xaa' Cys | (SEQ ID NO: 2544) |
| Pro Gly Thr Cys Xaa' Gly Xaa' Glu Ile Cys Ala Xaa' Tyr Ala Ala Cys Thr Gly Xaa' | (SEQ ID NO: 2545) |
| Pro Gly Thr Cys Xaa' Gly Xaa' Glu Ile Cys Ala Tyr Xaa' Ala Ala Cys Thr Gly Cys | (SEQ ID NO: 2546) |
| Pro Gly Thr Cys Xaa' Gly Xaa' Glu Ile Cys Ala Tyr Xaa' Xaa' Ala Cys Thr Gly Cys | (SEQ ID NO: 2547) |
| Pro Gly Thr Cys Xaa' Gly Xaa' Glu Ile Cys Ala Tyr Xaa' Ala Xaa' Cys Thr Gly Cys | (SEQ ID NO: 2548) |
| Pro Gly Thr Cys Xaa' Gly Xaa' Glu Ile Cys Ala Tyr Xaa' Ala Ala Xaa' Thr Gly Cys | (SEQ ID NO: 2549) |
| Pro Gly Thr Cys Xaa' Gly Xaa' Glu Ile Cys Ala Tyr Xaa' Ala Ala Cys Xaa' Gly Cys | (SEQ ID NO: 2550) |
| Pro Gly Thr Cys Xaa' Gly Xaa' Glu Ile Cys Ala Tyr Xaa' Ala Ala Cys Thr Xaa' Cys | (SEQ ID NO: 2551) |
| Pro Gly Thr Cys Xaa' Gly Xaa' Glu Ile Cys Ala Tyr Xaa' Ala Ala Cys Thr Gly Xaa' | (SEQ ID NO: 2552) |
| Pro Gly Thr Cys Xaa' Gly Xaa' Glu Ile Cys Ala Tyr Ala Xaa' Ala Cys Thr Gly Cys | (SEQ ID NO: 2553) |
| Pro Gly Thr Cys Xaa' Gly Xaa' Glu Ile Cys Ala Tyr Ala Xaa' Xaa' Cys Thr Gly Xaa' | (SEQ ID NO: 2554) |

FIG. 2AW

```
Pro Gly Thr Cys Xaa' Gly Xaa' Glu Ile Cys Ala Tyr Ala Xaa' Ala Cys Thr Gly Cys       (SEQ ID NO: 2555)
Pro Gly Thr Cys Xaa' Gly Xaa' Glu Ile Cys Ala Tyr Ala Xaa' Ala Cys Thr Gly Cys       (SEQ ID NO: 2556)
Pro Gly Thr Cys Xaa' Gly Xaa' Glu Ile Cys Ala Tyr Ala Xaa' Ala Xaa' Ala Cys Thr Gly Cys  (SEQ ID NO: 2557)
Pro Gly Thr Cys Xaa' Gly Xaa' Glu Ile Cys Ala Tyr Ala Xaa' Ala Xaa' Cys Thr Gly Cys   (SEQ ID NO: 2558)
Pro Gly Thr Cys Xaa' Gly Xaa' Glu Ile Cys Ala Tyr Ala Xaa' Cys Xaa' Thr Gly Cys       (SEQ ID NO: 2559)
Pro Gly Thr Cys Xaa' Gly Xaa' Glu Ile Cys Ala Tyr Ala Xaa' Cys Thr Xaa' Gly Cys       (SEQ ID NO: 2560)
Pro Gly Thr Cys Xaa' Gly Xaa' Glu Ile Cys Ala Tyr Ala Xaa' Cys Thr Gly Xaa' Cys       (SEQ ID NO: 2561)
Pro Gly Thr Cys Xaa' Gly Xaa' Glu Ile Cys Ala Tyr Ala Xaa' Cys Thr Gly Cys Xaa'       (SEQ ID NO: 2562)
Pro Gly Thr Cys Xaa' Gly Xaa' Glu Ile Cys Ala Tyr Ala Ala Xaa' Xaa' Cys Thr Gly Cys   (SEQ ID NO: 2563)
Pro Gly Thr Cys Xaa' Gly Xaa' Glu Ile Cys Ala Tyr Ala Ala Xaa' Cys Xaa' Thr Gly Cys   (SEQ ID NO: 2564)
Pro Gly Thr Cys Xaa' Gly Xaa' Glu Ile Cys Ala Tyr Ala Ala Xaa' Cys Thr Xaa' Gly Cys   (SEQ ID NO: 2565)
Pro Gly Thr Cys Xaa' Gly Xaa' Glu Ile Cys Ala Tyr Ala Ala Xaa' Cys Thr Gly Xaa' Cys   (SEQ ID NO: 2566)
Pro Gly Thr Cys Xaa' Gly Xaa' Glu Ile Cys Ala Tyr Ala Ala Xaa' Cys Thr Gly Cys Xaa'   (SEQ ID NO: 2567)
Pro Gly Thr Cys Xaa' Gly Xaa' Glu Ile Cys Ala Tyr Ala Ala Cys Xaa' Xaa' Thr Gly Cys   (SEQ ID NO: 2568)
Pro Gly Thr Cys Xaa' Gly Xaa' Glu Ile Cys Ala Tyr Ala Ala Cys Xaa' Thr Xaa' Gly Cys   (SEQ ID NO: 2569)
Pro Gly Thr Cys Xaa' Gly Xaa' Glu Ile Cys Ala Tyr Ala Ala Cys Xaa' Thr Gly Xaa' Cys   (SEQ ID NO: 2570)
Pro Gly Thr Cys Xaa' Gly Xaa' Glu Ile Cys Ala Tyr Ala Ala Cys Xaa' Thr Gly Cys Xaa'   (SEQ ID NO: 2571)
Pro Gly Thr Cys Xaa' Gly Xaa' Glu Ile Cys Ala Tyr Ala Ala Cys Thr Xaa' Xaa' Gly Cys   (SEQ ID NO: 2572)
Pro Gly Thr Cys Xaa' Gly Xaa' Glu Ile Cys Ala Tyr Ala Ala Cys Thr Xaa' Gly Cys       (SEQ ID NO: 2573)
Pro Gly Thr Cys Xaa' Gly Xaa' Glu Ile Cys Ala Tyr Ala Ala Cys Thr Xaa' Gly Cys Xaa'   (SEQ ID NO: 2574)
Pro Gly Thr Cys Xaa' Gly Xaa' Glu Ile Cys Ala Tyr Ala Ala Cys Thr Gly Xaa' Xaa' Cys   (SEQ ID NO: 2575)
Pro Gly Thr Cys Xaa' Gly Xaa' Glu Ile Cys Ala Tyr Ala Ala Cys Thr Gly Xaa' Cys Xaa'   (SEQ ID NO: 2576)
Pro Gly Thr Cys Xaa' Gly Xaa' Glu Ile Cys Ala Tyr Ala Ala Cys Thr Gly Cys Xaa'       (SEQ ID NO: 2577)
Pro Gly Thr Cys Xaa' Gly Xaa' Glu Ile Cys Ala Tyr Ala Ala Cys Thr Gly Cys Xaa' Xaa'   (SEQ ID NO: 2578)
Pro Gly Thr Cys Xaa' Gly Xaa' Glu Ile Cys Ala Tyr Xaa' Ala Ala Cys Thr Gly Cys Xaa'   (SEQ ID NO: 2579)
Pro Gly Thr Cys Xaa' Gly Xaa' Glu Ile Cys Ala Tyr Xaa' Ala Ala Cys Thr Gly Cys       (SEQ ID NO: 2580)
Pro Gly Thr Cys Xaa' Gly Xaa' Glu Ile Cys Ala Tyr Xaa' Ala Ala Cys Thr Gly Cys Xaa'   (SEQ ID NO: 2581)
Pro Gly Thr Cys Xaa' Gly Xaa' Glu Ile Cys Ala Tyr Xaa' Ala Ala Cys Thr Gly Cys       (SEQ ID NO: 2582)
Pro Gly Thr Cys Xaa' Gly Glu Xaa' Ile Cys Ala Tyr Ala Ala Cys Thr Gly Cys           (SEQ ID NO: 2583)
Pro Gly Thr Cys Xaa' Gly Glu Xaa' Ile Cys Xaa' Ala Tyr Ala Ala Cys Thr Gly Cys       (SEQ ID NO: 2584)
Pro Gly Thr Cys Xaa' Gly Glu Xaa' Ile Xaa' Cys Ala Tyr Ala Ala Cys Thr Gly Cys       (SEQ ID NO: 2585)
Pro Gly Thr Cys Xaa' Gly Glu Xaa' Ile Cys Xaa' Ala Tyr Ala Ala Cys Thr Gly Cys       (SEQ ID NO: 2586)
Pro Gly Thr Cys Xaa' Gly Glu Xaa' Ile Cys Ala Tyr Xaa' Ala Ala Cys Thr Gly Cys       (SEQ ID NO: 2587)
Pro Gly Thr Cys Xaa' Gly Glu Xaa' Ile Cys Ala Tyr Xaa' Ala Ala Cys Thr Gly Cys       (SEQ ID NO: 2588)
```

FIG. 2AX

FIG. 2AY

| | | | | | | | | | | |
|---|---|---|---|---|---|---|---|---|---|---|
| Pro Gly Thr Cys Xaa' | Gly Glu Xaa' | Ile Cys | Ala | Tyr | Ala | Ala | Cys | Thr | Gly Xaa' Cys | (SEQ ID NO: 2623) |
| Pro Gly Thr Cys Xaa' | Gly Glu Xaa' | Ile Cys | Ala | Xaa' | Ala | Ala | Cys | Thr | Gly Cys Xaa' | (SEQ ID NO: 2624) |
| Pro Gly Thr Cys Xaa' | Gly Glu Xaa' | Ile Cys | Ala | Tyr | Xaa' | Ala | Cys | Thr | Gly Cys | (SEQ ID NO: 2625) |
| Pro Gly Thr Cys Xaa' | Gly Glu Xaa' | Ile Cys | Ala | Tyr | Ala | Xaa' | Cys | Thr | Gly Gly Cys | (SEQ ID NO: 2626) |
| Pro Gly Thr Cys Xaa' | Gly Glu Xaa' | Ile Cys | Ala | Tyr | Ala | Ala | Xaa' | Thr | Gly Gly Cys | (SEQ ID NO: 2627) |
| Pro Gly Thr Cys Xaa' | Gly Glu Xaa' | Ile Cys | Ala | Tyr | Ala | Ala | Cys | Xaa' | Gly Gly Cys | (SEQ ID NO: 2628) |
| Pro Gly Thr Cys Xaa' | Gly Glu Xaa' | Ile Cys | Ala | Tyr | Ala | Ala | Cys | Thr | Xaa' Gly Cys | (SEQ ID NO: 2629) |
| Pro Gly Thr Cys Xaa' | Gly Glu Xaa' | Ile Cys | Ala | Tyr | Ala | Ala | Cys | Thr | Gly Xaa' Cys | (SEQ ID NO: 2630) |
| Pro Gly Thr Cys Xaa' | Gly Glu Xaa' | Ile Cys | Ala | Tyr | Ala | Ala | Cys | Thr | Gly Cys Xaa' | (SEQ ID NO: 2631) |
| Pro Gly Thr Cys Xaa' | Gly Glu Xaa' | Ile Cys | Ala | Tyr | Ala | Ala | Cys | Thr | Gly Cys | (SEQ ID NO: 2632) |
| Pro Gly Thr Cys Xaa' | Gly Glu Xaa' | Ile Cys | Ala | Xaa' | Xaa' | Ala | Cys | Thr | Gly Gly Cys | (SEQ ID NO: 2633) |
| Pro Gly Thr Cys Xaa' | Gly Glu Xaa' | Ile Cys | Ala | Xaa' | Ala | Xaa' | Cys | Thr | Gly Gly Cys | (SEQ ID NO: 2634) |
| Pro Gly Thr Cys Xaa' | Gly Glu Xaa' | Ile Cys | Ala | Xaa' | Ala | Ala | Xaa' | Thr | Gly Gly Cys | (SEQ ID NO: 2635) |
| Pro Gly Thr Cys Xaa' | Gly Glu Xaa' | Ile Cys | Ala | Xaa' | Ala | Ala | Cys | Xaa' | Gly Gly Cys | (SEQ ID NO: 2636) |
| Pro Gly Thr Cys Xaa' | Gly Glu Xaa' | Ile Cys | Ala | Xaa' | Ala | Ala | Cys | Thr | Xaa' Gly Cys | (SEQ ID NO: 2637) |
| Pro Gly Thr Cys Xaa' | Gly Glu Xaa' | Ile Cys | Ala | Xaa' | Ala | Ala | Cys | Thr | Gly Xaa' Cys | (SEQ ID NO: 2638) |
| Pro Gly Thr Cys Xaa' | Gly Glu Xaa' | Ile Cys | Ala | Xaa' | Ala | Ala | Cys | Thr | Gly Cys Xaa' | (SEQ ID NO: 2639) |
| Pro Gly Thr Cys Xaa' | Gly Glu Xaa' | Ile Cys | Ala | Xaa' | Ala | Ala | Cys | Thr | Gly Cys | (SEQ ID NO: 2640) |
| Pro Gly Thr Cys Xaa' | Gly Glu Xaa' | Ile Cys | Ala | Tyr | Xaa' | Xaa' | Cys | Thr | Gly Gly Cys | (SEQ ID NO: 2641) |
| Pro Gly Thr Cys Xaa' | Gly Glu Xaa' | Ile Cys | Ala | Tyr | Xaa' | Ala | Xaa' | Thr | Gly Gly Cys | (SEQ ID NO: 2642) |
| Pro Gly Thr Cys Xaa' | Gly Glu Xaa' | Ile Cys | Ala | Tyr | Xaa' | Ala | Cys | Xaa' | Gly Gly Cys | (SEQ ID NO: 2643) |
| Pro Gly Thr Cys Xaa' | Gly Glu Xaa' | Ile Cys | Ala | Tyr | Xaa' | Ala | Cys | Thr | Xaa' Gly Cys | (SEQ ID NO: 2644) |
| Pro Gly Thr Cys Xaa' | Gly Glu Xaa' | Ile Cys | Ala | Tyr | Xaa' | Ala | Cys | Thr | Gly Xaa' Cys | (SEQ ID NO: 2645) |
| Pro Gly Thr Cys Xaa' | Gly Glu Xaa' | Ile Cys | Ala | Tyr | Xaa' | Ala | Cys | Thr | Gly Cys Xaa' | (SEQ ID NO: 2646) |
| Pro Gly Thr Cys Xaa' | Gly Glu Xaa' | Ile Cys | Ala | Tyr | Xaa' | Ala | Cys | Thr | Gly Cys | (SEQ ID NO: 2647) |
| Pro Gly Thr Cys Xaa' | Gly Glu Xaa' | Ile Cys | Ala | Tyr | Ala | Xaa' | Xaa' | Thr | Gly Gly Cys | (SEQ ID NO: 2648) |
| Pro Gly Thr Cys Xaa' | Gly Glu Xaa' | Ile Cys | Ala | Tyr | Ala | Xaa' | Cys | Xaa' | Gly Gly Cys | (SEQ ID NO: 2649) |
| Pro Gly Thr Cys Xaa' | Gly Glu Xaa' | Ile Cys | Ala | Tyr | Ala | Xaa' | Cys | Thr | Xaa' Gly Cys | (SEQ ID NO: 2650) |
| Pro Gly Thr Cys Xaa' | Gly Glu Xaa' | Ile Cys | Ala | Tyr | Ala | Xaa' | Cys | Thr | Gly Xaa' Cys | (SEQ ID NO: 2651) |
| Pro Gly Thr Cys Xaa' | Gly Glu Xaa' | Ile Cys | Ala | Tyr | Ala | Xaa' | Cys | Thr | Gly Cys Xaa' | (SEQ ID NO: 2652) |
| Pro Gly Thr Cys Xaa' | Gly Glu Xaa' | Ile Cys | Ala | Tyr | Ala | Xaa' | Cys | Thr | Gly Cys | (SEQ ID NO: 2653) |
| Pro Gly Thr Cys Xaa' | Gly Glu Xaa' | Ile Cys | Ala | Tyr | Ala | Ala | Xaa' | Xaa' | Gly Cys Xaa' | (SEQ ID NO: 2654) |
| Pro Gly Thr Cys Xaa' | Gly Glu Xaa' | Ile Cys | Ala | Tyr | Ala | Ala | Xaa' | Thr | Gly Xaa' Cys | (SEQ ID NO: 2655) |
| Pro Gly Thr Cys Xaa' | Gly Glu Xaa' | Ile Cys | Ala | Tyr | Ala | Ala | Xaa' | Thr | Gly Xaa' Cys | (SEQ ID NO: 2656) |

FIG. 2AZ

| | | | | | | | | | |
|---|---|---|---|---|---|---|---|---|---|
| Pro Gly Thr Cys Xaa' Gly Glu Xaa' Ile Cys Ala Tyr Ala Ala Cys Thr Gly Xaa' Cys Xaa' | (SEQ ID NO: 2657) |
| Pro Gly Thr Cys Xaa' Gly Glu Xaa' Ile Cys Ala Tyr Ala Ala Cys Thr Gly Cys Xaa' | (SEQ ID NO: 2658) |
| Pro Gly Thr Cys Xaa' Gly Glu Xaa' Ile Cys Ala Tyr Ala Ala Cys Thr Gly Cys Xaa' Xaa' | (SEQ ID NO: 2659) |
| Pro Gly Thr Cys Xaa' Gly Glu Xaa' Ile Cys Ala Tyr Ala Ala Cys Thr Gly Cys | (SEQ ID NO: 2660) |
| Pro Gly Thr Cys Xaa' Gly Glu Xaa' Ile Cys Ala Cys Ala Tyr Ala Ala Cys Thr Gly Cys | (SEQ ID NO: 2661) |
| Pro Gly Thr Cys Xaa' Gly Glu Xaa' Ile Cys Xaa' Cys Ala Tyr Ala Ala Cys Thr Gly Cys | (SEQ ID NO: 2662) |
| Pro Gly Thr Cys Xaa' Gly Glu Xaa' Ile Cys Xaa' Cys Ala Tyr Ala Ala Cys Thr Gly Cys | (SEQ ID NO: 2663) |
| Pro Gly Thr Cys Xaa' Gly Glu Xaa' Ile Cys Ala Cys Xaa' Tyr Ala Ala Cys Thr Gly Cys | (SEQ ID NO: 2664) |
| Pro Gly Thr Cys Xaa' Gly Glu Xaa' Ile Cys Ala Cys Ala Tyr Xaa' Ala Cys Thr Gly Cys | (SEQ ID NO: 2665) |
| Pro Gly Thr Cys Xaa' Gly Glu Xaa' Ile Cys Ala Cys Ala Tyr Ala Xaa' Cys Thr Gly Cys | (SEQ ID NO: 2666) |
| Pro Gly Thr Cys Xaa' Gly Glu Xaa' Ile Cys Ala Cys Ala Tyr Ala Ala Cys Xaa' Gly Cys | (SEQ ID NO: 2667) |
| Pro Gly Thr Cys Xaa' Gly Glu Xaa' Ile Cys Ala Cys Ala Tyr Ala Ala Cys Thr Gly Cys | (SEQ ID NO: 2668) |
| Pro Gly Thr Cys Xaa' Gly Glu Xaa' Ile Cys Xaa' Cys Xaa' Tyr Ala Ala Cys Thr Gly Cys | (SEQ ID NO: 2669) |
| Pro Gly Thr Cys Xaa' Gly Glu Xaa' Ile Cys Ala Cys Ala Tyr Xaa' Ala Cys Thr Gly Xaa' Cys | (SEQ ID NO: 2670) |
| Pro Gly Thr Cys Xaa' Gly Glu Xaa' Ile Cys Ala Cys Ala Tyr Ala Ala Cys Thr Gly Cys Xaa' | (SEQ ID NO: 2671) |
| Pro Gly Thr Cys Xaa' Gly Glu Xaa' Ile Cys Xaa' Ala Xaa' Ala Tyr Ala Ala Cys Thr Gly Cys | (SEQ ID NO: 2672) |
| Pro Gly Thr Cys Xaa' Gly Glu Xaa' Ile Cys Xaa' Xaa' Ala Tyr Ala Ala Cys Thr Gly Cys | (SEQ ID NO: 2673) |
| Pro Gly Thr Cys Xaa' Gly Glu Xaa' Ile Cys Xaa' Xaa' Tyr Xaa' Ala Ala Cys Thr Gly Cys | (SEQ ID NO: 2674) |
| Pro Gly Thr Cys Xaa' Gly Glu Xaa' Ile Cys Xaa' Xaa' Tyr Xaa' Ala Ala Cys Thr Gly Cys | (SEQ ID NO: 2675) |
| Pro Gly Thr Cys Xaa' Gly Glu Xaa' Ile Cys Xaa' Xaa' Ala Tyr Xaa' Ala Cys Thr Gly Cys | (SEQ ID NO: 2676) |
| Pro Gly Thr Cys Xaa' Gly Glu Xaa' Ile Cys Xaa' Xaa' Ala Tyr Ala Xaa' Cys Thr Gly Cys | (SEQ ID NO: 2677) |
| Pro Gly Thr Cys Xaa' Gly Glu Xaa' Ile Cys Xaa' Xaa' Ala Tyr Ala Ala Cys Xaa' Thr Gly Cys | (SEQ ID NO: 2678) |
| Pro Gly Thr Cys Xaa' Gly Glu Xaa' Ile Cys Xaa' Xaa' Ala Tyr Ala Ala Cys Thr Gly Cys | (SEQ ID NO: 2679) |
| Pro Gly Thr Cys Xaa' Gly Glu Xaa' Ile Cys Xaa' Xaa' Ala Tyr Ala Ala Cys Thr Gly Xaa' Cys | (SEQ ID NO: 2680) |
| Pro Gly Thr Cys Xaa' Gly Glu Xaa' Ile Cys Xaa' Ala Ala Tyr Ala Ala Cys Thr Gly Cys Xaa' | (SEQ ID NO: 2681) |
| Pro Gly Thr Cys Xaa' Gly Glu Xaa' Ile Cys Ala Xaa' Tyr Ala Ala Cys Thr Gly Cys | (SEQ ID NO: 2682) |
| Pro Gly Thr Cys Xaa' Gly Glu Xaa' Ile Cys Ala Xaa' Tyr Ala Ala Cys Thr Gly Cys | (SEQ ID NO: 2683) |
| Pro Gly Thr Cys Xaa' Gly Glu Xaa' Ile Cys Ala Xaa' Ala Tyr Xaa' Ala Cys Thr Gly Cys | (SEQ ID NO: 2684) |
| Pro Gly Thr Cys Xaa' Gly Glu Xaa' Ile Cys Ala Xaa' Ala Tyr Ala Xaa' Cys Thr Gly Cys | (SEQ ID NO: 2685) |
| Pro Gly Thr Cys Xaa' Gly Glu Xaa' Ile Cys Ala Xaa' Ala Tyr Ala Ala Cys Xaa' Gly Cys | (SEQ ID NO: 2686) |
| Pro Gly Thr Cys Xaa' Gly Glu Xaa' Ile Cys Ala Xaa' Ala Tyr Ala Ala Cys Thr Xaa' Cys | (SEQ ID NO: 2687) |
| Pro Gly Thr Cys Xaa' Gly Glu Xaa' Ile Cys Ala Xaa' Ala Tyr Ala Ala Cys Thr Gly Xaa' Cys | (SEQ ID NO: 2688) |
| Pro Gly Thr Cys Xaa' Gly Glu Xaa' Ile Cys Ala Xaa' Ala Tyr Ala Ala Cys Thr Gly Cys Xaa' | (SEQ ID NO: 2689) |
| Pro Gly Thr Cys Xaa' Gly Glu Xaa' Ile Cys Ala Xaa' Ala Tyr Ala Ala Cys Thr Gly Xaa' Cys Xaa' | (SEQ ID NO: 2690) |

FIG. 2BA

| | | | | | | | | | | |
|---|---|---|---|---|---|---|---|---|---|---|
| Pro Gly Thr Cys Xaa' Gly Glu Ile Xaa' Cys Ala Tyr Xaa' Ala Ala Cys Thr Gly Cys | (SEQ ID NO: 2691) |
| Pro Gly Thr Cys Xaa' Gly Glu Ile Xaa' Cys Ala Tyr Xaa' Ala Ala Cys Thr Gly Cys | (SEQ ID NO: 2692) |
| Pro Gly Thr Cys Xaa' Gly Glu Ile Xaa' Cys Ala Tyr Xaa' Ala Ala Cys Thr Gly Cys | (SEQ ID NO: 2693) |
| Pro Gly Thr Cys Xaa' Gly Glu Ile Xaa' Cys Ala Tyr Xaa' Ala Ala Cys Thr Gly Cys | (SEQ ID NO: 2694) |
| Pro Gly Thr Cys Xaa' Gly Glu Ile Xaa' Cys Ala Tyr Xaa' Ala Ala Cys Thr Gly Cys | (SEQ ID NO: 2695) |
| Pro Gly Thr Cys Xaa' Gly Glu Ile Xaa' Cys Ala Tyr Xaa' Ala Ala Cys Thr Gly Cys | (SEQ ID NO: 2696) |
| Pro Gly Thr Cys Xaa' Gly Glu Ile Xaa' Cys Ala Tyr Xaa' Ala Ala Cys Thr Gly Xaa' | (SEQ ID NO: 2697) |
| Pro Gly Thr Cys Xaa' Gly Glu Ile Xaa' Cys Ala Tyr Xaa' Ala Ala Cys Thr Gly Cys | (SEQ ID NO: 2698) |
| Pro Gly Thr Cys Xaa' Gly Glu Ile Xaa' Cys Ala Tyr Ala Xaa' Ala Cys Thr Gly Cys | (SEQ ID NO: 2699) |
| Pro Gly Thr Cys Xaa' Gly Glu Ile Xaa' Cys Ala Tyr Ala Xaa' Xaa' Ala Cys Thr Gly Cys | (SEQ ID NO: 2700) |
| Pro Gly Thr Cys Xaa' Gly Glu Ile Xaa' Cys Ala Tyr Ala Xaa' Xaa' Ala Cys Thr Gly Cys | (SEQ ID NO: 2701) |
| Pro Gly Thr Cys Xaa' Gly Glu Ile Xaa' Cys Ala Tyr Ala Xaa' Xaa' Ala Cys Thr Gly Cys | (SEQ ID NO: 2702) |
| Pro Gly Thr Cys Xaa' Gly Glu Ile Xaa' Cys Ala Tyr Ala Xaa' Xaa' Ala Cys Thr Gly Cys | (SEQ ID NO: 2703) |
| Pro Gly Thr Cys Xaa' Gly Glu Ile Xaa' Cys Ala Tyr Ala Xaa' Ala Cys Thr Gly Cys | (SEQ ID NO: 2704) |
| Pro Gly Thr Cys Xaa' Gly Glu Ile Xaa' Cys Ala Tyr Ala Xaa' Ala Cys Thr Gly Xaa' | (SEQ ID NO: 2705) |
| Pro Gly Thr Cys Xaa' Gly Glu Ile Xaa' Cys Ala Tyr Ala Xaa' Ala Cys Thr Gly Cys | (SEQ ID NO: 2706) |
| Pro Gly Thr Cys Xaa' Gly Glu Ile Xaa' Cys Ala Tyr Ala Ala Xaa' Cys Thr Gly Cys | (SEQ ID NO: 2707) |
| Pro Gly Thr Cys Xaa' Gly Glu Ile Xaa' Cys Ala Tyr Ala Ala Xaa' Cys Thr Gly Cys | (SEQ ID NO: 2708) |
| Pro Gly Thr Cys Xaa' Gly Glu Ile Xaa' Cys Ala Tyr Ala Ala Xaa' Cys Thr Gly Cys | (SEQ ID NO: 2709) |
| Pro Gly Thr Cys Xaa' Gly Glu Ile Xaa' Cys Ala Tyr Ala Ala Xaa' Cys Thr Gly Cys | (SEQ ID NO: 2710) |
| Pro Gly Thr Cys Xaa' Gly Glu Ile Xaa' Cys Ala Tyr Ala Ala Xaa' Cys Thr Gly Xaa' | (SEQ ID NO: 2711) |
| Pro Gly Thr Cys Xaa' Gly Glu Ile Xaa' Cys Ala Tyr Ala Ala Xaa' Cys Thr Gly Cys | (SEQ ID NO: 2712) |
| Pro Gly Thr Cys Xaa' Gly Glu Ile Xaa' Cys Ala Tyr Ala Ala Cys Xaa' Thr Gly Cys | (SEQ ID NO: 2713) |
| Pro Gly Thr Cys Xaa' Gly Glu Ile Xaa' Cys Ala Tyr Ala Ala Cys Xaa' Thr Gly Cys | (SEQ ID NO: 2714) |
| Pro Gly Thr Cys Xaa' Gly Glu Ile Xaa' Cys Ala Tyr Ala Ala Cys Xaa' Thr Gly Cys | (SEQ ID NO: 2715) |
| Pro Gly Thr Cys Xaa' Gly Glu Ile Xaa' Cys Ala Tyr Ala Ala Cys Xaa' Thr Gly Xaa' | (SEQ ID NO: 2716) |
| Pro Gly Thr Cys Xaa' Gly Glu Ile Xaa' Cys Ala Tyr Ala Ala Cys Thr Xaa' Gly Cys | (SEQ ID NO: 2717) |
| Pro Gly Thr Cys Xaa' Gly Glu Ile Xaa' Cys Ala Tyr Ala Ala Cys Thr Xaa' Gly Cys | (SEQ ID NO: 2718) |
| Pro Gly Thr Cys Xaa' Gly Glu Ile Xaa' Cys Ala Tyr Ala Ala Cys Thr Xaa' Gly Cys | (SEQ ID NO: 2719) |
| Pro Gly Thr Cys Xaa' Gly Glu Ile Xaa' Cys Ala Tyr Ala Ala Cys Thr Xaa' Gly Xaa' | (SEQ ID NO: 2720) |
| Pro Gly Thr Cys Xaa' Gly Glu Ile Xaa' Cys Ala Tyr Ala Ala Cys Thr Gly Xaa' Cys | (SEQ ID NO: 2721) |
| Pro Gly Thr Cys Xaa' Gly Glu Ile Xaa' Cys Ala Tyr Ala Ala Cys Thr Gly Xaa' Cys | (SEQ ID NO: 2722) |
| Pro Gly Thr Cys Xaa' Gly Glu Ile Xaa' Cys Ala Tyr Ala Ala Cys Thr Gly Xaa' Cys | (SEQ ID NO: 2723) |
| Pro Gly Thr Cys Xaa' Gly Glu Ile Xaa' Cys Ala Tyr Ala Ala Cys Thr Gly Xaa' | (SEQ ID NO: 2724) |

FIG. 2BB

| | | | | | | | | | | |
|---|---|---|---|---|---|---|---|---|---|---|
| Pro Gly Thr Cys Xaa' Gly Glu Ile Xaa' Cys Ala Tyr Ala Ala Cys Thr Gly Cys Xaa' Xaa' | (SEQID NO: 2725) |
| Pro Gly Thr Cys Xaa' Gly Glu Ile Cys Xaa' Ala Tyr Ala Ala Cys Thr Gly Cys | (SEQID NO: 2726) |
| Pro Gly Thr Cys Xaa' Gly Glu Ile Cys Xaa' Xaa' Tyr Ala Ala Cys Thr Gly Cys | (SEQID NO: 2727) |
| Pro Gly Thr Cys Xaa' Gly Glu Ile Cys Xaa' Ala Tyr Ala Ala Cys Thr Gly Cys | (SEQID NO: 2728) |
| Pro Gly Thr Cys Xaa' Gly Glu Ile Cys Xaa' Ala Xaa' Ala Ala Cys Thr Gly Cys | (SEQID NO: 2729) |
| Pro Gly Thr Cys Xaa' Gly Glu Ile Cys Xaa' Ala Tyr Xaa' Ala Ala Cys Thr Gly Cys | (SEQID NO: 2730) |
| Pro Gly Thr Cys Xaa' Gly Glu Ile Cys Xaa' Ala Tyr Ala Xaa' Ala Cys Thr Gly Cys | (SEQID NO: 2731) |
| Pro Gly Thr Cys Xaa' Gly Glu Ile Cys Xaa' Ala Tyr Ala Ala Xaa' Cys Thr Gly Cys | (SEQID NO: 2732) |
| Pro Gly Thr Cys Xaa' Gly Glu Ile Cys Xaa' Ala Tyr Ala Ala Cys Xaa' Thr Gly Cys | (SEQID NO: 2733) |
| Pro Gly Thr Cys Xaa' Gly Glu Ile Cys Xaa' Ala Tyr Ala Ala Cys Thr Xaa' Gly Cys | (SEQID NO: 2734) |
| Pro Gly Thr Cys Xaa' Gly Glu Ile Cys Xaa' Ala Tyr Ala Ala Cys Thr Gly Xaa' Cys | (SEQID NO: 2735) |
| Pro Gly Thr Cys Xaa' Gly Glu Ile Cys Xaa' Ala Tyr Ala Ala Cys Thr Gly Cys Xaa' | (SEQID NO: 2736) |
| Pro Gly Thr Cys Xaa' Gly Glu Ile Cys Ala Xaa' Tyr Ala Ala Cys Thr Gly Cys | (SEQID NO: 2737) |
| Pro Gly Thr Cys Xaa' Gly Glu Ile Cys Ala Xaa' Tyr Ala Ala Cys Thr Gly Cys | (SEQID NO: 2738) |
| Pro Gly Thr Cys Xaa' Gly Glu Ile Cys Ala Xaa' Xaa' Ala Ala Cys Thr Gly Cys | (SEQID NO: 2739) |
| Pro Gly Thr Cys Xaa' Gly Glu Ile Cys Ala Xaa' Tyr Xaa' Ala Cys Thr Gly Cys | (SEQID NO: 2740) |
| Pro Gly Thr Cys Xaa' Gly Glu Ile Cys Ala Xaa' Tyr Ala Xaa' Cys Thr Gly Cys | (SEQID NO: 2741) |
| Pro Gly Thr Cys Xaa' Gly Glu Ile Cys Ala Xaa' Tyr Ala Ala Xaa' Thr Gly Cys | (SEQID NO: 2742) |
| Pro Gly Thr Cys Xaa' Gly Glu Ile Cys Ala Xaa' Tyr Ala Ala Cys Xaa' Thr Gly Cys | (SEQID NO: 2743) |
| Pro Gly Thr Cys Xaa' Gly Glu Ile Cys Ala Xaa' Tyr Ala Ala Cys Thr Xaa' Gly Cys | (SEQID NO: 2744) |
| Pro Gly Thr Cys Xaa' Gly Glu Ile Cys Ala Xaa' Tyr Ala Ala Cys Thr Gly Xaa' Cys | (SEQID NO: 2745) |
| Pro Gly Thr Cys Xaa' Gly Glu Ile Cys Ala Xaa' Tyr Ala Ala Cys Thr Gly Cys Xaa' | (SEQID NO: 2746) |
| Pro Gly Thr Cys Xaa' Gly Glu Ile Cys Ala Tyr Xaa' Ala Ala Cys Thr Gly Cys | (SEQID NO: 2747) |
| Pro Gly Thr Cys Xaa' Gly Glu Ile Cys Ala Tyr Xaa' Xaa' Ala Cys Thr Gly Cys | (SEQID NO: 2748) |
| Pro Gly Thr Cys Xaa' Gly Glu Ile Cys Ala Tyr Xaa' Ala Xaa' Cys Thr Gly Cys | (SEQID NO: 2749) |
| Pro Gly Thr Cys Xaa' Gly Glu Ile Cys Ala Tyr Xaa' Ala Ala Xaa' Thr Gly Cys | (SEQID NO: 2750) |
| Pro Gly Thr Cys Xaa' Gly Glu Ile Cys Ala Tyr Xaa' Ala Ala Cys Xaa' Thr Gly Cys | (SEQID NO: 2751) |
| Pro Gly Thr Cys Xaa' Gly Glu Ile Cys Ala Tyr Xaa' Ala Ala Cys Thr Xaa' Gly Cys | (SEQID NO: 2752) |
| Pro Gly Thr Cys Xaa' Gly Glu Ile Cys Ala Tyr Xaa' Ala Ala Cys Thr Gly Xaa' Cys | (SEQID NO: 2753) |
| Pro Gly Thr Cys Xaa' Gly Glu Ile Cys Ala Tyr Xaa' Ala Ala Cys Thr Gly Cys Xaa' | (SEQID NO: 2754) |
| Pro Gly Thr Cys Xaa' Gly Glu Ile Cys Ala Tyr Ala Xaa' Ala Cys Thr Gly Cys | (SEQID NO: 2755) |
| Pro Gly Thr Cys Xaa' Gly Glu Ile Cys Ala Tyr Ala Xaa' Xaa' Cys Thr Gly Cys | (SEQID NO: 2756) |
| Pro Gly Thr Cys Xaa' Gly Glu Ile Cys Ala Tyr Ala Xaa' Ala Xaa' Thr Gly Cys | (SEQID NO: 2757) |
| Pro Gly Thr Cys Xaa' Gly Glu Ile Cys Ala Tyr Ala Xaa' Ala Cys Xaa' Thr Gly Cys | (SEQID NO: 2758) |

FIG. 2BC

| | | | | | | | | | | | | |
|---|---|---|---|---|---|---|---|---|---|---|---|---|
| Pro | Gly | Thr | Cys | Xaa' | Gly | Glu | Ile | Cys | Xaa' | Ala | Tyr | Ala | Xaa' | Ala | Cys | Thr | Gly | Xaa' | Cys | (SEQ ID NO: 2759) |
| Pro | Gly | Thr | Cys | Xaa' | Gly | Glu | Ile | Cys | Xaa' | Ala | Tyr | Ala | Xaa' | Ala | Cys | Thr | Gly | Cys | Xaa' | (SEQ ID NO: 2760) |
| Pro | Gly | Thr | Cys | Xaa' | Gly | Glu | Ile | Cys | Xaa' | Ala | Tyr | Ala | Xaa' | Ala | Cys | Xaa' | Cys | Thr | Gly | Cys | (SEQ ID NO: 2761) |
| Pro | Gly | Thr | Cys | Xaa' | Gly | Glu | Ile | Cys | Xaa' | Ala | Tyr | Ala | Xaa' | Ala | Cys | Xaa' | Cys | Thr | Gly | Cys | (SEQ ID NO: 2762) |
| Pro | Gly | Thr | Cys | Xaa' | Gly | Glu | Ile | Cys | Xaa' | Ala | Tyr | Ala | Xaa' | Ala | Cys | Xaa' | Thr | Gly | Cys | (SEQ ID NO: 2763) |
| Pro | Gly | Thr | Cys | Xaa' | Gly | Glu | Ile | Cys | Xaa' | Ala | Tyr | Ala | Xaa' | Ala | Cys | Xaa' | Thr | Xaa' | Gly | Cys | (SEQ ID NO: 2764) |
| Pro | Gly | Thr | Cys | Xaa' | Gly | Glu | Ile | Cys | Xaa' | Ala | Tyr | Ala | Xaa' | Ala | Cys | Xaa' | Thr | Gly | Xaa' | Cys | (SEQ ID NO: 2765) |
| Pro | Gly | Thr | Cys | Xaa' | Gly | Glu | Ile | Cys | Xaa' | Ala | Tyr | Ala | Xaa' | Ala | Cys | Xaa' | Thr | Gly | Cys | Xaa' | (SEQ ID NO: 2766) |
| Pro | Gly | Thr | Cys | Xaa' | Gly | Glu | Ile | Cys | Xaa' | Ala | Tyr | Ala | Xaa' | Ala | Cys | Ala | Cys | Thr | Gly | Cys | (SEQ ID NO: 2767) |
| Pro | Gly | Thr | Cys | Xaa' | Gly | Glu | Ile | Cys | Xaa' | Ala | Tyr | Ala | Xaa' | Ala | Cys | Xaa' | Thr | Gly | Cys | (SEQ ID NO: 2768) |
| Pro | Gly | Thr | Cys | Xaa' | Gly | Glu | Ile | Cys | Xaa' | Ala | Tyr | Ala | Xaa' | Ala | Cys | Xaa' | Thr | Xaa' | Gly | Cys | (SEQ ID NO: 2769) |
| Pro | Gly | Thr | Cys | Xaa' | Gly | Glu | Ile | Cys | Xaa' | Ala | Tyr | Ala | Xaa' | Ala | Cys | Xaa' | Thr | Gly | Xaa' | Cys | (SEQ ID NO: 2770) |
| Pro | Gly | Thr | Cys | Xaa' | Gly | Glu | Ile | Cys | Xaa' | Ala | Tyr | Ala | Xaa' | Ala | Cys | Xaa' | Thr | Gly | Cys | Xaa' | (SEQ ID NO: 2771) |
| Pro | Gly | Thr | Cys | Xaa' | Gly | Glu | Ile | Cys | Xaa' | Ala | Tyr | Ala | Xaa' | Ala | Cys | Xaa' | Gly | Cys | (SEQ ID NO: 2772) |
| Pro | Gly | Thr | Cys | Xaa' | Gly | Glu | Ile | Cys | Xaa' | Ala | Tyr | Ala | Xaa' | Ala | Cys | Xaa' | Xaa' | Gly | Cys | (SEQ ID NO: 2773) |
| Pro | Gly | Thr | Cys | Xaa' | Gly | Glu | Ile | Cys | Xaa' | Ala | Tyr | Ala | Xaa' | Ala | Cys | Xaa' | Gly | Xaa' | Cys | (SEQ ID NO: 2774) |
| Pro | Gly | Thr | Cys | Xaa' | Gly | Glu | Ile | Cys | Xaa' | Ala | Tyr | Ala | Xaa' | Ala | Cys | Xaa' | Gly | Cys | Xaa' | (SEQ ID NO: 2775) |
| Pro | Gly | Thr | Cys | Xaa' | Gly | Glu | Ile | Cys | Xaa' | Ala | Tyr | Ala | Xaa' | Ala | Cys | Thr | Xaa' | Gly | Cys | (SEQ ID NO: 2776) |
| Pro | Gly | Thr | Cys | Xaa' | Gly | Glu | Ile | Cys | Xaa' | Ala | Tyr | Ala | Xaa' | Ala | Cys | Thr | Gly | Xaa' | Cys | (SEQ ID NO: 2777) |
| Pro | Gly | Thr | Cys | Xaa' | Gly | Glu | Ile | Cys | Xaa' | Ala | Tyr | Ala | Xaa' | Ala | Cys | Thr | Gly | Cys | Xaa' | (SEQ ID NO: 2778) |
| Pro | Gly | Thr | Cys | Xaa' | Gly | Glu | Ile | Cys | Xaa' | Ala | Tyr | Ala | Xaa' | Ala | Cys | Thr | Gly | Cys | Xaa' | (SEQ ID NO: 2779) |
| Pro | Gly | Thr | Cys | Xaa' | Gly | Glu | Ile | Cys | Xaa' | Ala | Tyr | Ala | Xaa' | Ala | Cys | Thr | Gly | Cys | Xaa' | (SEQ ID NO: 2780) |
| Pro | Gly | Thr | Cys | Xaa' | Gly | Glu | Ile | Cys | Ala | Xaa' | Tyr | Ala | Xaa' | Ala | Cys | Thr | Gly | Cys | (SEQ ID NO: 2781) |
| Pro | Gly | Thr | Cys | Xaa' | Gly | Glu | Ile | Cys | Ala | Xaa' | Tyr | Ala | Ala | Cys | Thr | Gly | Cys | (SEQ ID NO: 2782) |
| Pro | Gly | Thr | Cys | Xaa' | Gly | Glu | Ile | Cys | Ala | Xaa' | Tyr | Xaa' | Ala | Ala | Cys | Thr | Gly | Cys | (SEQ ID NO: 2783) |
| Pro | Gly | Thr | Cys | Xaa' | Gly | Glu | Ile | Cys | Ala | Xaa' | Tyr | Xaa' | Ala | Ala | Cys | Thr | Gly | Cys | (SEQ ID NO: 2784) |
| Pro | Gly | Thr | Cys | Xaa' | Gly | Glu | Ile | Cys | Ala | Xaa' | Tyr | Ala | Xaa' | Ala | Cys | Thr | Gly | Cys | (SEQ ID NO: 2785) |
| Pro | Gly | Thr | Cys | Xaa' | Gly | Glu | Ile | Cys | Ala | Xaa' | Tyr | Ala | Ala | Cys | Xaa' | Thr | Gly | Cys | (SEQ ID NO: 2786) |
| Pro | Gly | Thr | Cys | Xaa' | Gly | Glu | Ile | Cys | Ala | Xaa' | Tyr | Ala | Ala | Cys | Thr | Xaa' | Gly | Cys | (SEQ ID NO: 2787) |
| Pro | Gly | Thr | Cys | Xaa' | Gly | Glu | Ile | Cys | Ala | Xaa' | Tyr | Ala | Ala | Cys | Thr | Gly | Xaa' | Cys | (SEQ ID NO: 2788) |
| Pro | Gly | Thr | Cys | Xaa' | Gly | Glu | Ile | Cys | Ala | Xaa' | Tyr | Ala | Ala | Cys | Thr | Gly | Cys | Xaa' | (SEQ ID NO: 2789) |
| Pro | Gly | Thr | Cys | Xaa' | Gly | Glu | Ile | Cys | Ala | Xaa' | Tyr | Xaa' | Ala | Cys | Thr | Gly | Cys | (SEQ ID NO: 2790) |
| Pro | Gly | Thr | Cys | Xaa' | Gly | Glu | Ile | Cys | Ala | Xaa' | Tyr | Xaa' | Ala | Ala | Cys | Thr | Gly | Cys | (SEQ ID NO: 2791) |
| Pro | Gly | Thr | Cys | Xaa' | Gly | Glu | Ile | Cys | Ala | Xaa' | Tyr | Xaa' | Ala | Ala | Cys | Thr | Gly | Cys | (SEQ ID NO: 2792) |

FIG. 2BD

| | | | | | | | | | | | | |
|---|---|---|---|---|---|---|---|---|---|---|---|---|
| Pro | Gly | Thr | Cys | Xaa' | Gly | Glu | Ile | Cys | Ala | Xaa' | Tyr | Xaa' | Ala | Cys | Thr | Gly | Cys | (SEQ ID NO: 2793) |
| Pro | Gly | Thr | Cys | Xaa' | Gly | Glu | Ile | Cys | Ala | Xaa' | Tyr | Xaa' | Ala | Ala | Cys | Thr | Gly | Cys | (SEQ ID NO: 2794) |
| Pro | Gly | Thr | Cys | Xaa' | Gly | Glu | Ile | Cys | Ala | Xaa' | Tyr | Xaa' | Ala | Ala | Cys | Xaa' | Thr | Gly | Cys | (SEQ ID NO: 2795) |
| Pro | Gly | Thr | Cys | Xaa' | Gly | Glu | Ile | Cys | Ala | Xaa' | Tyr | Xaa' | Ala | Ala | Cys | Xaa' | Thr | Gly | Cys | (SEQ ID NO: 2796) |
| Pro | Gly | Thr | Cys | Xaa' | Gly | Glu | Ile | Cys | Ala | Xaa' | Tyr | Xaa' | Ala | Ala | Cys | Xaa' | Thr | Gly | Cys | (SEQ ID NO: 2797) |
| Pro | Gly | Thr | Cys | Xaa' | Gly | Glu | Ile | Cys | Ala | Xaa' | Tyr | Xaa' | Ala | Ala | Cys | Xaa' | Thr | Gly | Cys | (SEQ ID NO: 2798) |
| Pro | Gly | Thr | Cys | Xaa' | Gly | Glu | Ile | Cys | Ala | Xaa' | Tyr | Ala | Xaa' | Ala | Cys | Thr | Gly | Cys | Xaa' | (SEQ ID NO: 2799) |
| Pro | Gly | Thr | Cys | Xaa' | Gly | Glu | Ile | Cys | Ala | Xaa' | Tyr | Ala | Xaa' | Ala | Cys | Thr | Gly | Cys | (SEQ ID NO: 2800) |
| Pro | Gly | Thr | Cys | Xaa' | Gly | Glu | Ile | Cys | Ala | Xaa' | Tyr | Ala | Xaa' | Ala | Cys | Thr | Gly | Cys | (SEQ ID NO: 2801) |
| Pro | Gly | Thr | Cys | Xaa' | Gly | Glu | Ile | Cys | Ala | Xaa' | Tyr | Ala | Xaa' | Ala | Cys | Xaa' | Thr | Gly | Cys | (SEQ ID NO: 2802) |
| Pro | Gly | Thr | Cys | Xaa' | Gly | Glu | Ile | Cys | Ala | Xaa' | Tyr | Ala | Xaa' | Ala | Cys | Xaa' | Thr | Gly | Cys | (SEQ ID NO: 2803) |
| Pro | Gly | Thr | Cys | Xaa' | Gly | Glu | Ile | Cys | Ala | Xaa' | Tyr | Ala | Xaa' | Ala | Cys | Xaa' | Thr | Gly | Cys | (SEQ ID NO: 2804) |
| Pro | Gly | Thr | Cys | Xaa' | Gly | Glu | Ile | Cys | Ala | Xaa' | Tyr | Ala | Xaa' | Ala | Cys | Xaa' | Thr | Gly | Cys | (SEQ ID NO: 2805) |
| Pro | Gly | Thr | Cys | Xaa' | Gly | Glu | Ile | Cys | Ala | Xaa' | Tyr | Ala | Xaa' | Ala | Cys | Xaa' | Thr | Gly | Cys | (SEQ ID NO: 2806) |
| Pro | Gly | Thr | Cys | Xaa' | Gly | Glu | Ile | Cys | Ala | Xaa' | Tyr | Ala | Ala | Xaa' | Cys | Thr | Gly | Cys | Xaa' | (SEQ ID NO: 2807) |
| Pro | Gly | Thr | Cys | Xaa' | Gly | Glu | Ile | Cys | Ala | Xaa' | Tyr | Ala | Ala | Xaa' | Cys | Thr | Gly | Cys | (SEQ ID NO: 2808) |
| Pro | Gly | Thr | Cys | Xaa' | Gly | Glu | Ile | Cys | Ala | Xaa' | Tyr | Ala | Ala | Xaa' | Cys | Thr | Gly | Cys | (SEQ ID NO: 2809) |
| Pro | Gly | Thr | Cys | Xaa' | Gly | Glu | Ile | Cys | Ala | Xaa' | Tyr | Ala | Ala | Xaa' | Cys | Xaa' | Thr | Gly | Cys | (SEQ ID NO: 2810) |
| Pro | Gly | Thr | Cys | Xaa' | Gly | Glu | Ile | Cys | Ala | Xaa' | Tyr | Ala | Ala | Xaa' | Cys | Xaa' | Thr | Gly | Cys | (SEQ ID NO: 2811) |
| Pro | Gly | Thr | Cys | Xaa' | Gly | Glu | Ile | Cys | Ala | Xaa' | Tyr | Ala | Ala | Xaa' | Cys | Xaa' | Thr | Gly | Cys | (SEQ ID NO: 2812) |
| Pro | Gly | Thr | Cys | Xaa' | Gly | Glu | Ile | Cys | Ala | Xaa' | Tyr | Ala | Ala | Xaa' | Cys | Xaa' | Thr | Gly | Cys | (SEQ ID NO: 2813) |
| Pro | Gly | Thr | Cys | Xaa' | Gly | Glu | Ile | Cys | Ala | Xaa' | Tyr | Ala | Ala | Xaa' | Cys | Xaa' | Thr | Gly | Cys | (SEQ ID NO: 2814) |
| Pro | Gly | Thr | Cys | Xaa' | Gly | Glu | Ile | Cys | Ala | Xaa' | Tyr | Ala | Ala | Ala | Cys | Thr | Gly | Cys | Xaa' | (SEQ ID NO: 2815) |
| Pro | Gly | Thr | Cys | Xaa' | Gly | Glu | Ile | Cys | Ala | Xaa' | Tyr | Ala | Ala | Ala | Cys | Thr | Gly | Cys | (SEQ ID NO: 2816) |
| Pro | Gly | Thr | Cys | Xaa' | Gly | Glu | Ile | Cys | Ala | Xaa' | Tyr | Ala | Ala | Ala | Cys | Thr | Gly | Cys | (SEQ ID NO: 2817) |
| Pro | Gly | Thr | Cys | Xaa' | Gly | Glu | Ile | Cys | Ala | Xaa' | Tyr | Ala | Ala | Ala | Cys | Xaa' | Thr | Gly | Cys | (SEQ ID NO: 2818) |
| Pro | Gly | Thr | Cys | Xaa' | Gly | Glu | Ile | Cys | Ala | Xaa' | Tyr | Ala | Ala | Ala | Cys | Xaa' | Thr | Gly | Cys | (SEQ ID NO: 2819) |
| Pro | Gly | Thr | Cys | Xaa' | Gly | Glu | Ile | Cys | Ala | Xaa' | Tyr | Ala | Ala | Ala | Cys | Xaa' | Thr | Gly | Cys | (SEQ ID NO: 2820) |
| Pro | Gly | Thr | Cys | Xaa' | Gly | Glu | Ile | Cys | Ala | Xaa' | Tyr | Ala | Ala | Ala | Cys | Xaa' | Thr | Gly | Cys | (SEQ ID NO: 2821) |
| Pro | Gly | Thr | Cys | Xaa' | Gly | Glu | Ile | Cys | Ala | Xaa' | Tyr | Ala | Ala | Ala | Cys | Xaa' | Thr | Gly | Cys | (SEQ ID NO: 2822) |
| Pro | Gly | Thr | Cys | Xaa' | Gly | Glu | Ile | Cys | Ala | Xaa' | Tyr | Xaa' | Ala | Ala | Cys | Thr | Gly | Cys | Xaa' | (SEQ ID NO: 2823) |
| Pro | Gly | Thr | Cys | Xaa' | Gly | Glu | Ile | Cys | Ala | Xaa' | Tyr | Xaa' | Ala | Ala | Cys | Xaa' | Thr | Gly | Cys | Xaa' | (SEQ ID NO: 2824) |
| Pro | Gly | Thr | Cys | Xaa' | Gly | Glu | Ile | Cys | Ala | Tyr | Xaa' | Ala | Ala | Cys | Thr | Gly | Cys | Xaa' | (SEQ ID NO: 2825) |
| Pro | Gly | Thr | Cys | Xaa' | Gly | Glu | Ile | Cys | Ala | Ala | Tyr | Xaa' | Ala | Ala | Cys | Thr | Gly | Cys | (SEQ ID NO: 2826) |

FIG. 2BE

| | | | | | | | | | | | | |
|---|---|---|---|---|---|---|---|---|---|---|---|---|
| Pro Gly Thr Cys Xaa' Gly Glu Ile Cys Ala Tyr Xaa' Ala Ala Cys Thr Gly Cys | (SEQ ID NO: 2827) |
| Pro Gly Thr Cys Xaa' Gly Glu Ile Cys Ala Tyr Xaa' Xaa' Ala Ala Cys Thr Gly Cys | (SEQ ID NO: 2828) |
| Pro Gly Thr Cys Xaa' Gly Glu Ile Cys Ala Tyr Xaa' Xaa' Ala Xaa' Ala Cys Thr Gly Cys | (SEQ ID NO: 2829) |
| Pro Gly Thr Cys Xaa' Gly Glu Ile Cys Ala Tyr Xaa' Xaa' Ala Ala Xaa' Cys Thr Gly Cys | (SEQ ID NO: 2830) |
| Pro Gly Thr Cys Xaa' Gly Glu Ile Cys Ala Tyr Xaa' Xaa' Ala Ala Cys Xaa' Thr Gly Cys | (SEQ ID NO: 2831) |
| Pro Gly Thr Cys Xaa' Gly Glu Ile Cys Ala Tyr Xaa' Xaa' Ala Ala Cys Thr Xaa' Gly Cys | (SEQ ID NO: 2832) |
| Pro Gly Thr Cys Xaa' Gly Glu Ile Cys Ala Tyr Xaa' Xaa' Ala Ala Cys Thr Gly Xaa' Cys | (SEQ ID NO: 2833) |
| Pro Gly Thr Cys Xaa' Gly Glu Ile Cys Ala Tyr Xaa' Xaa' Ala Ala Cys Thr Gly Cys Xaa' | (SEQ ID NO: 2834) |
| Pro Gly Thr Cys Xaa' Gly Glu Ile Cys Ala Tyr Xaa' Ala Xaa' Ala Cys Thr Gly Cys | (SEQ ID NO: 2835) |
| Pro Gly Thr Cys Xaa' Gly Glu Ile Cys Ala Tyr Xaa' Ala Xaa' Ala Cys Thr Gly Cys | (SEQ ID NO: 2836) |
| Pro Gly Thr Cys Xaa' Gly Glu Ile Cys Ala Tyr Xaa' Ala Xaa' Ala Xaa' Cys Thr Gly Cys | (SEQ ID NO: 2837) |
| Pro Gly Thr Cys Xaa' Gly Glu Ile Cys Ala Tyr Xaa' Ala Xaa' Ala Cys Xaa' Thr Gly Cys | (SEQ ID NO: 2838) |
| Pro Gly Thr Cys Xaa' Gly Glu Ile Cys Ala Tyr Xaa' Ala Xaa' Ala Cys Thr Xaa' Gly Cys | (SEQ ID NO: 2839) |
| Pro Gly Thr Cys Xaa' Gly Glu Ile Cys Ala Tyr Xaa' Ala Xaa' Ala Cys Thr Gly Xaa' Cys | (SEQ ID NO: 2840) |
| Pro Gly Thr Cys Xaa' Gly Glu Ile Cys Ala Tyr Xaa' Ala Xaa' Ala Cys Thr Gly Cys Xaa' | (SEQ ID NO: 2841) |
| Pro Gly Thr Cys Xaa' Gly Glu Ile Cys Ala Tyr Xaa' Ala Ala Xaa' Cys Thr Gly Cys | (SEQ ID NO: 2842) |
| Pro Gly Thr Cys Xaa' Gly Glu Ile Cys Ala Tyr Xaa' Ala Ala Xaa' Xaa' Cys Thr Gly Cys | (SEQ ID NO: 2843) |
| Pro Gly Thr Cys Xaa' Gly Glu Ile Cys Ala Tyr Xaa' Ala Ala Xaa' Cys Xaa' Thr Gly Cys | (SEQ ID NO: 2844) |
| Pro Gly Thr Cys Xaa' Gly Glu Ile Cys Ala Tyr Xaa' Ala Ala Xaa' Cys Thr Xaa' Gly Cys | (SEQ ID NO: 2845) |
| Pro Gly Thr Cys Xaa' Gly Glu Ile Cys Ala Tyr Xaa' Ala Ala Xaa' Cys Thr Gly Xaa' Cys | (SEQ ID NO: 2846) |
| Pro Gly Thr Cys Xaa' Gly Glu Ile Cys Ala Tyr Xaa' Ala Ala Xaa' Cys Thr Gly Cys Xaa' | (SEQ ID NO: 2847) |
| Pro Gly Thr Cys Xaa' Gly Glu Ile Cys Ala Tyr Xaa' Ala Ala Cys Xaa' Thr Gly Cys | (SEQ ID NO: 2848) |
| Pro Gly Thr Cys Xaa' Gly Glu Ile Cys Ala Tyr Xaa' Ala Ala Cys Xaa' Xaa' Thr Gly Cys | (SEQ ID NO: 2849) |
| Pro Gly Thr Cys Xaa' Gly Glu Ile Cys Ala Tyr Xaa' Ala Ala Cys Xaa' Thr Xaa' Gly Cys | (SEQ ID NO: 2850) |
| Pro Gly Thr Cys Xaa' Gly Glu Ile Cys Ala Tyr Xaa' Ala Ala Cys Xaa' Thr Gly Xaa' Cys | (SEQ ID NO: 2851) |
| Pro Gly Thr Cys Xaa' Gly Glu Ile Cys Ala Tyr Xaa' Ala Ala Cys Xaa' Thr Gly Cys Xaa' | (SEQ ID NO: 2852) |
| Pro Gly Thr Cys Xaa' Gly Glu Ile Cys Ala Tyr Xaa' Ala Ala Cys Thr Xaa' Gly Cys | (SEQ ID NO: 2853) |
| Pro Gly Thr Cys Xaa' Gly Glu Ile Cys Ala Tyr Xaa' Ala Ala Cys Thr Xaa' Xaa' Gly Cys | (SEQ ID NO: 2854) |
| Pro Gly Thr Cys Xaa' Gly Glu Ile Cys Ala Tyr Xaa' Ala Ala Cys Thr Xaa' Gly Xaa' Cys | (SEQ ID NO: 2855) |
| Pro Gly Thr Cys Xaa' Gly Glu Ile Cys Ala Tyr Xaa' Ala Ala Cys Thr Xaa' Gly Cys Xaa' | (SEQ ID NO: 2856) |
| Pro Gly Thr Cys Xaa' Gly Glu Ile Cys Ala Tyr Xaa' Ala Ala Cys Thr Gly Xaa' Cys | (SEQ ID NO: 2857) |
| Pro Gly Thr Cys Xaa' Gly Glu Ile Cys Ala Tyr Xaa' Ala Ala Cys Thr Gly Xaa' Xaa' Cys | (SEQ ID NO: 2858) |
| Pro Gly Thr Cys Xaa' Gly Glu Ile Cys Ala Tyr Xaa' Ala Ala Cys Thr Gly Xaa' Cys Xaa' | (SEQ ID NO: 2859) |
| Pro Gly Thr Cys Xaa' Gly Glu Ile Cys Ala Tyr Xaa' Ala Ala Cys Thr Gly Cys Xaa' | (SEQ ID NO: 2860) |

FIG. 2BF

FIG. 2BG

Pro Gly Thr Cys Xaa' Gly Glu Ile Cys Ala Tyr Xaa' Ala Ala Cys Thr Gly Cys Xaa' Xaa' (SEQ ID NO: 2851)
Pro Gly Thr Cys Xaa' Gly Glu Ile Cys Ala Tyr Ala Xaa' Ala Cys Thr Gly Cys (SEQ ID NO: 2852)
Pro Gly Thr Cys Xaa' Gly Glu Ile Cys Ala Tyr Ala Xaa' Xaa' Ala Cys Ala Cys Thr Gly Cys (SEQ ID NO: 2853)
Pro Gly Thr Cys Xaa' Gly Glu Ile Cys Ala Tyr Ala Xaa' Xaa' Xaa' Ala Cys Thr Gly Cys (SEQ ID NO: 2854)
Pro Gly Thr Cys Xaa' Gly Glu Ile Cys Ala Tyr Ala Xaa' Xaa' Xaa' Ala Cys Xaa' Cys Thr Gly Cys (SEQ ID NO: 2855)
Pro Gly Thr Cys Xaa' Gly Glu Ile Cys Ala Tyr Ala Xaa' Xaa' Xaa' Ala Cys Xaa' Thr Gly Cys (SEQ ID NO: 2856)
Pro Gly Thr Cys Xaa' Gly Glu Ile Cys Ala Tyr Ala Xaa' Xaa' Xaa' Ala Cys Thr Gly Xaa' Cys (SEQ ID NO: 2857)
Pro Gly Thr Cys Xaa' Gly Glu Ile Cys Ala Tyr Ala Xaa' Xaa' Xaa' Ala Cys Thr Gly Xaa' Cys (SEQ ID NO: 2858)
Pro Gly Thr Cys Xaa' Gly Glu Ile Cys Ala Tyr Ala Xaa' Xaa' Xaa' Ala Cys Thr Gly Cys Xaa' (SEQ ID NO: 2859)
Pro Gly Thr Cys Xaa' Gly Glu Ile Cys Ala Tyr Ala Xaa' Xaa' Ala Xaa' Cys Thr Gly Cys (SEQ ID NO: 2860)
Pro Gly Thr Cys Xaa' Gly Glu Ile Cys Ala Tyr Ala Xaa' Xaa' Ala Xaa' Cys Xaa' Cys Thr Gly Cys (SEQ ID NO: 2861)
Pro Gly Thr Cys Xaa' Gly Glu Ile Cys Ala Tyr Ala Xaa' Xaa' Ala Xaa' Cys Xaa' Thr Gly Cys (SEQ ID NO: 2862)
Pro Gly Thr Cys Xaa' Gly Glu Ile Cys Ala Tyr Ala Xaa' Xaa' Ala Xaa' Cys Thr Gly Xaa' Cys (SEQ ID NO: 2863)
Pro Gly Thr Cys Xaa' Gly Glu Ile Cys Ala Tyr Ala Xaa' Xaa' Ala Xaa' Cys Thr Gly Cys Xaa' (SEQ ID NO: 2864)
Pro Gly Thr Cys Xaa' Gly Glu Ile Cys Ala Tyr Ala Xaa' Ala Xaa' Xaa' Cys Thr Gly Cys (SEQ ID NO: 2865)
Pro Gly Thr Cys Xaa' Gly Glu Ile Cys Ala Tyr Ala Xaa' Ala Xaa' Xaa' Cys Xaa' Cys Thr Gly Cys (SEQ ID NO: 2866)
Pro Gly Thr Cys Xaa' Gly Glu Ile Cys Ala Tyr Ala Xaa' Ala Xaa' Xaa' Cys Xaa' Thr Gly Cys (SEQ ID NO: 2867)
Pro Gly Thr Cys Xaa' Gly Glu Ile Cys Ala Tyr Ala Xaa' Ala Xaa' Xaa' Cys Thr Gly Xaa' Cys (SEQ ID NO: 2868)
Pro Gly Thr Cys Xaa' Gly Glu Ile Cys Ala Tyr Ala Xaa' Ala Xaa' Xaa' Cys Thr Gly Cys Xaa' (SEQ ID NO: 2869)
Pro Gly Thr Cys Xaa' Gly Glu Ile Cys Ala Tyr Ala Ala Xaa' Xaa' Xaa' Cys Thr Gly Cys (SEQ ID NO: 2870)
Pro Gly Thr Cys Xaa' Gly Glu Ile Cys Ala Tyr Ala Ala Xaa' Xaa' Xaa' Cys Xaa' Cys Thr Gly Cys (SEQ ID NO: 2871)
Pro Gly Thr Cys Xaa' Gly Glu Ile Cys Ala Tyr Ala Ala Xaa' Xaa' Xaa' Cys Xaa' Thr Gly Cys (SEQ ID NO: 2872)
Pro Gly Thr Cys Xaa' Gly Glu Ile Cys Ala Tyr Ala Ala Xaa' Xaa' Xaa' Cys Thr Gly Xaa' Cys (SEQ ID NO: 2873)
Pro Gly Thr Cys Xaa' Gly Glu Ile Cys Ala Tyr Ala Ala Xaa' Xaa' Xaa' Cys Thr Gly Cys Xaa' (SEQ ID NO: 2874)
Pro Gly Thr Cys Xaa' Gly Glu Ile Cys Ala Tyr Ala Xaa' Xaa' Xaa' Xaa' Cys Thr Gly Cys (SEQ ID NO: 2875)
Pro Gly Thr Cys Xaa' Gly Glu Ile Cys Ala Tyr Ala Xaa' Xaa' Xaa' Xaa' Cys Xaa' Cys Thr Gly Cys (SEQ ID NO: 2876)
Pro Gly Thr Cys Xaa' Gly Glu Ile Cys Ala Tyr Ala Xaa' Xaa' Xaa' Xaa' Cys Xaa' Thr Gly Cys (SEQ ID NO: 2877)
Pro Gly Thr Cys Xaa' Gly Glu Ile Cys Ala Tyr Ala Xaa' Xaa' Xaa' Xaa' Cys Thr Gly Xaa' Cys (SEQ ID NO: 2878)
Pro Gly Thr Cys Xaa' Gly Glu Ile Cys Ala Tyr Ala Xaa' Xaa' Xaa' Xaa' Cys Thr Gly Cys Xaa' (SEQ ID NO: 2879)
Pro Gly Thr Cys Xaa' Gly Glu Ile Cys Ala Tyr Ala Ala Xaa' Xaa' Xaa' Thr Xaa' Gly Cys (SEQ ID NO: 2880)
Pro Gly Thr Cys Xaa' Gly Glu Ile Cys Ala Tyr Ala Ala Xaa' Xaa' Xaa' Thr Gly Xaa' Cys (SEQ ID NO: 2881)
Pro Gly Thr Cys Xaa' Gly Glu Ile Cys Ala Tyr Ala Ala Xaa' Xaa' Xaa' Thr Gly Cys Xaa' (SEQ ID NO: 2882)
Pro Gly Thr Cys Xaa' Gly Glu Ile Cys Ala Tyr Ala Ala Xaa' Xaa' Xaa' Thr Gly Xaa' Cys Xaa' (SEQ ID NO: 2883)
Pro Gly Thr Cys Xaa' Gly Glu Ile Cys Ala Tyr Ala Ala Xaa' Xaa' Xaa' Gly Xaa' Cys Xaa' (SEQ ID NO: 2884)
Pro Gly Thr Cys Xaa' Gly Glu Ile Cys Ala Tyr Ala Ala Xaa' Xaa' Xaa' Gly Cys Xaa' (SEQ ID NO: 2885)
Pro Gly Thr Cys Xaa' Gly Glu Ile Cys Ala Tyr Ala Ala Ala Xaa' Xaa' Gly Xaa' Cys (SEQ ID NO: 2886)
Pro Gly Thr Cys Xaa' Gly Glu Ile Cys Ala Tyr Ala Ala Ala Xaa' Xaa' Gly Cys Xaa' (SEQ ID NO: 2887)
Pro Gly Thr Cys Xaa' Gly Glu Ile Cys Ala Tyr Ala Ala Ala Xaa' Xaa' Gly Cys Xaa' (SEQ ID NO: 2888)
Pro Gly Thr Cys Xaa' Gly Glu Ile Cys Ala Tyr Ala Ala Ala Xaa' Xaa' Gly Cys Xaa' Xaa' (SEQ ID NO: 2889)
Pro Gly Thr Cys Xaa' Gly Glu Ile Cys Ala Tyr Ala Ala Ala Xaa' Xaa' Cys Xaa' Thr Gly Cys (SEQ ID NO: 2890)
Pro Gly Thr Cys Xaa' Gly Glu Ile Cys Ala Tyr Ala Ala Ala Xaa' Xaa' Cys Thr Gly Cys (SEQ ID NO: 2891)
Pro Gly Thr Cys Xaa' Gly Glu Ile Cys Ala Tyr Ala Ala Ala Xaa' Xaa' Cys Xaa' Cys Thr Gly Cys (SEQ ID NO: 2892)
Pro Gly Thr Cys Xaa' Gly Glu Ile Cys Ala Tyr Ala Ala Ala Xaa' Xaa' Xaa' Thr Gly Cys (SEQ ID NO: 2893)
Pro Gly Thr Cys Xaa' Gly Glu Ile Cys Ala Tyr Ala Ala Xaa' Xaa' Xaa' Cys Thr Xaa' Gly Cys (SEQ ID NO: 2894)

| | |
|---|---|
| Pro Gly Thr Cys Xaa' Gly Glu Ile Cys Ala Tyr Ala Ala Xaa' Cys Thr Gly Xaa' Cys | (SEQ ID NO: 2895) |
| Pro Gly Thr Cys Xaa' Gly Glu Ile Cys Ala Tyr Ala Ala Xaa' Cys Thr Gly Xaa' Cys | (SEQ ID NO: 2896) |
| Pro Gly Thr Cys Xaa' Gly Glu Ile Cys Ala Tyr Ala Ala Xaa' Cys Xaa' Thr Gly Cys | (SEQ ID NO: 2897) |
| Pro Gly Thr Cys Xaa' Gly Glu Ile Cys Ala Tyr Ala Ala Xaa' Cys Xaa' Thr Gly Cys | (SEQ ID NO: 2898) |
| Pro Gly Thr Cys Xaa' Gly Glu Ile Cys Ala Tyr Ala Ala Xaa' Cys Xaa' Thr Gly Cys | (SEQ ID NO: 2899) |
| Pro Gly Thr Cys Xaa' Gly Glu Ile Cys Ala Tyr Ala Ala Xaa' Cys Thr Xaa' Gly Cys | (SEQ ID NO: 2900) |
| Pro Gly Thr Cys Xaa' Gly Glu Ile Cys Ala Tyr Ala Ala Xaa' Cys Thr Xaa' Gly Cys | (SEQ ID NO: 2901) |
| Pro Gly Thr Cys Xaa' Gly Glu Ile Cys Ala Tyr Ala Ala Xaa' Cys Thr Xaa' Gly Cys | (SEQ ID NO: 2902) |
| Pro Gly Thr Cys Xaa' Gly Glu Ile Cys Ala Tyr Ala Ala Xaa' Cys Thr Xaa' Gly Cys | (SEQ ID NO: 2903) |
| Pro Gly Thr Cys Xaa' Gly Glu Ile Cys Ala Tyr Ala Ala Xaa' Cys Thr Xaa' Gly Cys | (SEQ ID NO: 2904) |
| Pro Gly Thr Cys Xaa' Gly Glu Ile Cys Ala Tyr Ala Ala Xaa' Cys Thr Gly Cys Xaa' | (SEQ ID NO: 2905) |
| Pro Gly Thr Cys Xaa' Gly Glu Ile Cys Ala Tyr Ala Ala Xaa' Cys Thr Gly Xaa' Cys | (SEQ ID NO: 2906) |
| Pro Gly Thr Cys Xaa' Gly Glu Ile Cys Ala Tyr Ala Ala Xaa' Cys Thr Xaa' Cys Xaa' | (SEQ ID NO: 2907) |
| Pro Gly Thr Cys Xaa' Gly Glu Ile Cys Ala Tyr Ala Ala Xaa' Cys Thr Gly Cys Xaa' | (SEQ ID NO: 2908) |
| Pro Gly Thr Cys Xaa' Gly Glu Ile Cys Ala Tyr Ala Ala Xaa' Cys Thr Gly Cys Xaa' | (SEQ ID NO: 2909) |
| Pro Gly Thr Cys Xaa' Gly Glu Ile Cys Ala Tyr Ala Ala Cys Xaa' Thr Gly Cys | (SEQ ID NO: 2910) |
| Pro Gly Thr Cys Xaa' Gly Glu Ile Cys Ala Tyr Ala Ala Cys Xaa' Thr Gly Cys | (SEQ ID NO: 2911) |
| Pro Gly Thr Cys Xaa' Gly Glu Ile Cys Ala Tyr Ala Ala Cys Xaa' Xaa' Thr Gly Cys | (SEQ ID NO: 2912) |
| Pro Gly Thr Cys Xaa' Gly Glu Ile Cys Ala Tyr Ala Ala Cys Xaa' Xaa' Thr Gly Cys | (SEQ ID NO: 2913) |
| Pro Gly Thr Cys Xaa' Gly Glu Ile Cys Ala Tyr Ala Ala Cys Xaa' Xaa' Thr Gly Cys | (SEQ ID NO: 2914) |
| Pro Gly Thr Cys Xaa' Gly Glu Ile Cys Ala Tyr Ala Ala Cys Xaa' Xaa' Thr Gly Cys | (SEQ ID NO: 2915) |
| Pro Gly Thr Cys Xaa' Gly Glu Ile Cys Ala Tyr Ala Ala Cys Xaa' Thr Gly Xaa' Cys | (SEQ ID NO: 2916) |
| Pro Gly Thr Cys Xaa' Gly Glu Ile Cys Ala Tyr Ala Ala Cys Xaa' Thr Gly Xaa' Cys | (SEQ ID NO: 2917) |
| Pro Gly Thr Cys Xaa' Gly Glu Ile Cys Ala Tyr Ala Ala Cys Xaa' Thr Xaa' Gly Cys | (SEQ ID NO: 2918) |
| Pro Gly Thr Cys Xaa' Gly Glu Ile Cys Ala Tyr Ala Ala Cys Xaa' Thr Xaa' Gly Cys | (SEQ ID NO: 2919) |
| Pro Gly Thr Cys Xaa' Gly Glu Ile Cys Ala Tyr Ala Ala Cys Xaa' Thr Xaa' Gly Cys | (SEQ ID NO: 2920) |
| Pro Gly Thr Cys Xaa' Gly Glu Ile Cys Ala Tyr Ala Ala Cys Xaa' Thr Gly Cys Xaa' | (SEQ ID NO: 2921) |
| Pro Gly Thr Cys Xaa' Gly Glu Ile Cys Ala Tyr Ala Ala Cys Xaa' Thr Gly Xaa' Cys | (SEQ ID NO: 2922) |
| Pro Gly Thr Cys Xaa' Gly Glu Ile Cys Ala Tyr Ala Ala Cys Xaa' Thr Gly Cys Xaa' | (SEQ ID NO: 2923) |
| Pro Gly Thr Cys Xaa' Gly Glu Ile Cys Ala Tyr Ala Ala Cys Xaa' Thr Gly Cys Xaa' | (SEQ ID NO: 2924) |
| Pro Gly Thr Cys Xaa' Gly Glu Ile Cys Ala Tyr Ala Ala Cys Xaa' Thr Gly Cys Xaa' | (SEQ ID NO: 2925) |
| Pro Gly Thr Cys Xaa' Gly Glu Ile Cys Ala Tyr Ala Ala Cys Xaa' Thr Xaa' Gly Cys | (SEQ ID NO: 2926) |
| Pro Gly Thr Cys Xaa' Gly Glu Ile Cys Ala Tyr Ala Ala Cys Thr Xaa' Xaa' Gly Cys | (SEQ ID NO: 2927) |
| Pro Gly Thr Cys Xaa' Gly Glu Ile Cys Ala Tyr Ala Ala Cys Thr Xaa' Xaa' Gly Cys | (SEQ ID NO: 2928) |

FIG. 2BH

| | SEQ ID NO |
|---|---|
| Pro Gly Thr Cys Xaa' Gly Glu Ile Cys Ala Tyr Ala Ala Cys Thr Xaa' Xaa' Gly Xaa' Cys | (SEQ ID NO: 2929) |
| Pro Gly Thr Cys Xaa' Gly Glu Ile Cys Ala Tyr Ala Ala Cys Thr Xaa' Xaa' Gly Cys Xaa' | (SEQ ID NO: 2930) |
| Pro Gly Thr Cys Xaa' Gly Glu Ile Cys Ala Tyr Ala Ala Cys Thr Xaa' Xaa' Gly Xaa' Cys | (SEQ ID NO: 2931) |
| Pro Gly Thr Cys Xaa' Gly Glu Ile Cys Ala Tyr Ala Ala Cys Thr Xaa' Xaa' Gly Xaa' Cys | (SEQ ID NO: 2932) |
| Pro Gly Thr Cys Xaa' Gly Glu Ile Cys Ala Tyr Ala Ala Cys Thr Xaa' Xaa' Xaa' Cys Xaa' | (SEQ ID NO: 2933) |
| Pro Gly Thr Cys Xaa' Gly Glu Ile Cys Ala Tyr Ala Ala Cys Thr Xaa' Xaa' Gly Cys Xaa' | (SEQ ID NO: 2934) |
| Pro Gly Thr Cys Xaa' Gly Glu Ile Cys Ala Tyr Ala Ala Cys Thr Xaa' Xaa' Gly Cys Xaa' | (SEQ ID NO: 2935) |
| Pro Gly Thr Cys Xaa' Gly Glu Ile Cys Ala Tyr Ala Ala Cys Thr Xaa' Gly Xaa' Cys | (SEQ ID NO: 2936) |
| Pro Gly Thr Cys Xaa' Gly Glu Ile Cys Ala Tyr Ala Ala Cys Thr Xaa' Xaa' Gly Xaa' Cys | (SEQ ID NO: 2937) |
| Pro Gly Thr Cys Xaa' Gly Glu Ile Cys Ala Tyr Ala Ala Cys Thr Xaa' Xaa' Xaa' Cys Xaa' | (SEQ ID NO: 2938) |
| Pro Gly Thr Cys Xaa' Gly Glu Ile Cys Ala Tyr Ala Ala Cys Thr Xaa' Xaa' Gly Xaa' Cys | (SEQ ID NO: 2939) |
| Pro Gly Thr Cys Xaa' Gly Glu Ile Cys Ala Tyr Ala Ala Cys Thr Xaa' Xaa' Gly Cys Xaa' | (SEQ ID NO: 2940) |
| Pro Gly Thr Cys Xaa' Gly Glu Ile Cys Ala Tyr Ala Ala Cys Thr Xaa' Xaa' Xaa' Cys Xaa' | (SEQ ID NO: 2941) |
| Pro Gly Thr Cys Xaa' Gly Glu Ile Cys Ala Tyr Ala Ala Cys Thr Xaa' Gly Cys Xaa' | (SEQ ID NO: 2942) |
| Pro Gly Thr Cys Xaa' Gly Glu Ile Cys Ala Tyr Ala Ala Cys Thr Xaa' Xaa' Xaa' Xaa' | (SEQ ID NO: 2943) |
| Pro Gly Thr Cys Xaa' Gly Glu Ile Cys Ala Tyr Ala Ala Cys Thr Xaa' Xaa' Xaa' Xaa' | (SEQ ID NO: 2944) |
| Pro Gly Thr Cys Xaa' Gly Glu Ile Cys Ala Tyr Ala Ala Cys Thr Gly Cys | (SEQ ID NO: 2945) |
| Pro Gly Thr Cys Gly Xaa' Xaa' Ile Cys Ala Tyr Ala Ala Cys Thr Gly Cys | (SEQ ID NO: 2946) |
| Pro Gly Thr Cys Xaa' Xaa' Xaa' Xaa' Cys Ala Tyr Ala Ala Cys Thr Gly Cys | (SEQ ID NO: 2947) |
| Pro Gly Thr Cys Xaa' Xaa' Glu Ile Cys Ala Tyr Ala Ala Cys Thr Gly Cys | (SEQ ID NO: 2948) |
| Pro Gly Thr Cys Xaa' Xaa' Xaa' Ile Cys Ala Tyr Ala Ala Cys Xaa' Thr Gly Cys | (SEQ ID NO: 2949) |
| Pro Gly Thr Cys Xaa' Xaa' Glu Ile Cys Xaa' Tyr Ala Ala Cys Thr Gly Cys | (SEQ ID NO: 2950) |
| Pro Gly Thr Cys Xaa' Xaa' Glu Ile Cys Ala Tyr Ala Ala Cys Thr Gly Cys | (SEQ ID NO: 2951) |
| Pro Gly Thr Cys Xaa' Xaa' Glu Ile Cys Ala xaa' Tyr Ala Ala Cys Thr. Gly Cys | (SEQ ID NO: 2952) |
| Pro Gly Thr Cys Xaa' Xaa' Glu Ile Cys Ala Tyr Ala Ala Cys Thr Gly Cys | (SEQ ID NO: 2953) |
| Pro Gly Thr Cys Xaa' Xaa' Glu Ile Cys Ala Tyr Ala Xaa' Ala Cys Thr Gly Cys | (SEQ ID NO: 2954) |
| Pro Gly Thr Cys Xaa' Xaa' Glu Ile Cys Ala Tyr Ala Ala Xaa' Cys Thr Gly Cys | (SEQ ID NO: 2955) |
| Pro Gly Thr Cys Xaa' Xaa' Glu Ile Cys Ala Tyr Ala Ala Cys Xaa' Thr Gly Cys | (SEQ ID NO: 2956) |
| Pro Gly Thr Cys Xaa' Xaa' Glu Ile Cys Ala Tyr Ala Ala Cys Thr Xaa' Gly Cys | (SEQ ID NO: 2957) |
| Pro Gly Thr Cys Xaa' Xaa' Glu Ile Cys Ala Tyr Ala Ala Cys Thr Gly Xaa' Cys | (SEQ ID NO: 2958) |
| Pro Gly Thr Cys Xaa' Xaa' Glu Ile Cys Ala Tyr Ala Ala Cys Thr Gly Cys Xaa' | (SEQ ID NO: 2959) |
| Pro Gly Thr Cys Xaa' Glu Xaa' Ile Cys Ala Tyr Ala Ala Cys Thr Gly Cys | (SEQ ID NO: 2960) |
| Pro Gly Thr Cys Xaa' Glu Ile Xaa' Cys Ala Tyr Ala Ala Cys Thr Gly Cys | (SEQ ID NO: 2961) |
| Pro Gly Thr Cys Xaa' Glu Ile Cys Xaa' Ala Tyr Ala Ala Cys Thr Gly Cys | (SEQ ID NO: 2962) |

FIG. 2BI

Pro Gly Thr Cys Gly Xaa' Xaa' Glu Xaa' Ile Cys Xaa' Ala Tyr Ala Ala Cys Thr Gly Cys (SEQID NO: 2963 )
Pro Gly Thr Cys Gly Xaa' Xaa' Glu Xaa' Ile Cys Ala Xaa' Tyr Ala Ala Cys Thr Gly Cys (SEQID NO: 2964 )
Pro Gly Thr Cys Gly Xaa' Xaa' Glu Xaa' Ile Cys Ala Tyr Xaa' Ala Ala Cys Thr Gly Cys (SEQID NO: 2965 )
Pro Gly Thr Cys Gly Xaa' Xaa' Glu Xaa' Ile Cys Ala Tyr Ala Xaa' Ala Cys Thr Gly Cys (SEQID NO: 2966 )
Pro Gly Thr Cys Gly Xaa' Xaa' Glu Xaa' Ile Cys Ala Tyr Ala Ala Xaa' Cys Thr Gly Cys (SEQID NO: 2967 )
Pro Gly Thr Cys Gly Xaa' Xaa' Glu Xaa' Ile Cys Ala Tyr Ala Ala Cys Xaa' Thr Gly Cys (SEQID NO: 2968 )
Pro Gly Thr Cys Gly Xaa' Xaa' Glu Xaa' Ile Cys Ala Tyr Ala Ala Cys Thr Xaa' Gly Cys (SEQID NO: 2969 )
Pro Gly Thr Cys Gly Xaa' Xaa' Glu Xaa' Ile Cys Ala Tyr Ala Ala Cys Thr Gly Xaa' Cys (SEQID NO: 2970 )
Pro Gly Thr Cys Gly Xaa' Xaa' Glu Xaa' Ile Cys Ala Tyr Ala Ala Cys Thr Gly Cys Xaa' (SEQID NO: 2971 )
Pro Gly Thr Cys Gly Xaa' Xaa' Glu Ile Xaa' Cys Ala Tyr Ala Ala Cys Thr Gly Cys (SEQID NO: 2972 )
Pro Gly Thr Cys Gly Xaa' Xaa' Glu Ile Xaa' Xaa' Cys Ala Tyr Ala Ala Cys Thr Gly Cys (SEQID NO: 2973 )
Pro Gly Thr Cys Gly Xaa' Xaa' Glu Ile Xaa' Cys Xaa' Ala Tyr Ala Ala Cys Thr Gly Cys (SEQID NO: 2974 )
Pro Gly Thr Cys Gly Xaa' Xaa' Glu Ile Xaa' Cys Ala Xaa' Tyr Ala Ala Cys Thr Gly Cys (SEQID NO: 2975 )
Pro Gly Thr Cys Gly Xaa' Xaa' Glu Ile Xaa' Cys Ala Tyr Xaa' Ala Ala Cys Thr Gly Cys (SEQID NO: 2976 )
Pro Gly Thr Cys Gly Xaa' Xaa' Glu Ile Xaa' Cys Ala Tyr Ala Xaa' Ala Cys Thr Gly Cys (SEQID NO: 2977 )
Pro Gly Thr Cys Gly Xaa' Xaa' Glu Ile Xaa' Cys Ala Tyr Ala Ala Xaa' Cys Thr Gly Cys (SEQID NO: 2978 )
Pro Gly Thr Cys Gly Xaa' Xaa' Glu Ile Xaa' Cys Ala Tyr Ala Ala Cys Xaa' Thr Gly Cys (SEQID NO: 2979 )
Pro Gly Thr Cys Gly Xaa' Xaa' Glu Ile Xaa' Cys Ala Tyr Ala Ala Cys Thr Xaa' Gly Cys (SEQID NO: 2980 )
Pro Gly Thr Cys Gly Xaa' Xaa' Glu Ile Xaa' Cys Ala Tyr Ala Ala Cys Thr Gly Xaa' Cys (SEQID NO: 2981 )
Pro Gly Thr Cys Gly Xaa' Xaa' Glu Ile Xaa' Cys Ala Tyr Ala Ala Cys Thr Gly Cys Xaa' (SEQID NO: 2982 )
Pro Gly Thr Cys Gly Xaa' Xaa' Glu Ile Cys Xaa' Ala Tyr Ala Ala Cys Thr Gly Cys (SEQID NO: 2983 )
Pro Gly Thr Cys Gly Xaa' Xaa' Glu Ile Cys Xaa' Xaa' Ala Tyr Ala Ala Cys Thr Gly Cys (SEQID NO: 2984 )
Pro Gly Thr Cys Gly Xaa' Xaa' Glu Ile Cys Xaa' Ala Xaa' Tyr Ala Ala Cys Thr Gly Cys (SEQID NO: 2985 )
Pro Gly Thr Cys Gly Xaa' Xaa' Glu Ile Cys Xaa' Ala Tyr Xaa' Ala Ala Cys Thr Gly Cys (SEQID NO: 2986 )
Pro Gly Thr Cys Gly Xaa' Xaa' Glu Ile Cys Xaa' Ala Tyr Ala Xaa' Ala Cys Thr Gly Cys (SEQID NO: 2987 )
Pro Gly Thr Cys Gly Xaa' Xaa' Glu Ile Cys Xaa' Ala Tyr Ala Ala Xaa' Cys Thr Gly Cys (SEQID NO: 2988 )
Pro Gly Thr Cys Gly Xaa' Xaa' Glu Ile Cys Xaa' Ala Tyr Ala Ala Cys Xaa' Thr Gly Cys (SEQID NO: 2989 )
Pro Gly Thr Cys Gly Xaa' Xaa' Glu Ile Cys Xaa' Ala Tyr Ala Ala Cys Thr Xaa' Gly Cys (SEQID NO: 2990 )
Pro Gly Thr Cys Gly Xaa' Xaa' Glu Ile Cys Xaa' Ala Tyr Ala Ala Cys Thr Gly Xaa' Cys (SEQID NO: 2991 )
Pro Gly Thr Cys Gly Xaa' Xaa' Glu Ile Cys Xaa' Ala Tyr Ala Ala Cys Thr Gly Cys Xaa' (SEQID NO: 2992 )
Pro Gly Thr Cys Gly Xaa' Xaa' Glu Ile Cys Ala Xaa' Tyr Ala Ala Cys Thr Gly Cys (SEQID NO: 2993 )
Pro Gly Thr Cys Gly Xaa' Xaa' Glu Ile Cys Ala Xaa' Xaa' Tyr Ala Ala Cys Thr Gly Cys (SEQID NO: 2994 )
Pro Gly Thr Cys Gly Xaa' Xaa' Glu Ile Cys Ala Xaa' Tyr Xaa' Ala Ala Cys Thr Gly Cys (SEQID NO: 2995 )
Pro Gly Thr Cys Gly Xaa' Xaa' Glu Ile Cys Ala Xaa' Tyr Ala Xaa' Ala Cys Thr Gly Cys (SEQID NO: 2996 )

FIG. 2BJ

| | | | | | | | | | | | |
|---|---|---|---|---|---|---|---|---|---|---|---|
| Pro Gly Thr Cys Gly Xaa' Xaa' Glu Ile Cys Ala Tyr Ala Ala Xaa' Tyr Ala Ala Xaa' Cys Thr Gly Cys | (SEQ ID NO: 2997) |
| Pro Gly Thr Cys Gly Xaa' Xaa' Glu Ile Cys Ala Tyr Ala Ala Xaa' Tyr Ala Ala Xaa' Cys Thr Gly Cys | (SEQ ID NO: 2998) |
| Pro Gly Thr Cys Gly Xaa' Xaa' Glu Ile Cys Ala Tyr Ala Ala Xaa' Tyr Ala Ala Xaa' Cys Thr Gly Cys | (SEQ ID NO: 2999) |
| Pro Gly Thr Cys Gly Xaa' Xaa' Glu Ile Cys Ala Tyr Ala Ala Xaa' Tyr Ala Ala Xaa' Cys Thr Gly Cys | (SEQ ID NO: 3000) |
| Pro Gly Thr Cys Gly Xaa' Xaa' Glu Ile Cys Ala Tyr Ala Ala Xaa' Tyr Ala Ala Xaa' Cys Thr Gly Cys | (SEQ ID NO: 3001) |
| Pro Gly Thr Cys Gly Xaa' Xaa' Glu Ile Cys Ala Tyr Ala Ala Xaa' Tyr Ala Ala Xaa' Cys Thr Gly Cys | (SEQ ID NO: 3002) |
| Pro Gly Thr Cys Gly Xaa' Xaa' Glu Ile Cys Ala Tyr Ala Ala Xaa' Tyr Xaa' Ala Cys Thr Gly Cys | (SEQ ID NO: 3003) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3004) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3005) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3006) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3007) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3008) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3009) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3010) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3011) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3012) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3013) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3014) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3015) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3016) |
| Pro Gly Thr Cys Gly Xaa' Xaa' Glu Ile Cys Ala Tyr Ala Ala Xaa' Ala Xaa' Ala Cys Thr Gly Cys | (SEQ ID NO: 3017) |
| Pro Gly Thr Cys Gly Xaa' Xaa' Glu Ile Cys Ala Tyr Ala Ala Xaa' Xaa' Ala Cys Thr Gly Cys | (SEQ ID NO: 3018) |
| Pro Gly Thr Cys Gly Xaa' Xaa' Glu Ile Cys Ala Tyr Ala Ala Xaa' Xaa' Ala Cys Thr Gly Cys | (SEQ ID NO: 3019) |
| Pro Gly Thr Cys Gly Xaa' Xaa' Glu Ile Cys Ala Tyr Ala Ala Xaa' Xaa' Ala Cys Thr Gly Cys | (SEQ ID NO: 3020) |
| Pro Gly Thr Cys Gly Xaa' Xaa' Glu Ile Cys Ala Tyr Ala Ala Xaa' Xaa' Ala Cys Thr Gly Cys | (SEQ ID NO: 3021) |
| Pro Gly Thr Cys Gly Xaa' Xaa' Glu Ile Cys Ala Tyr Ala Ala Xaa' Xaa' Ala Cys Thr Gly Cys | (SEQ ID NO: 3022) |
| Pro Gly Thr Cys Gly Xaa' Xaa' Glu Ile Cys Ala Tyr Ala Ala Xaa' Xaa' Ala Cys Thr Gly Cys | (SEQ ID NO: 3023) |
| Pro Gly Thr Cys Gly Xaa' Xaa' Glu Ile Cys Ala Tyr Ala Ala Xaa' Thr Xaa' Gly Cys | (SEQ ID NO: 3024) |
| Pro Gly Thr Cys Gly Xaa' Xaa' Glu Ile Cys Ala Tyr Ala Ala Xaa' Thr Xaa' Gly Cys | (SEQ ID NO: 3025) |
| Pro Gly Thr Cys Gly Xaa' Xaa' Glu Ile Cys Ala Tyr Ala Ala Xaa' Thr Xaa' Gly Cys | (SEQ ID NO: 3026) |
| Pro Gly Thr Cys Gly Xaa' Xaa' Glu Ile Cys Ala Tyr Ala Ala Xaa' Thr Xaa' Gly Cys | (SEQ ID NO: 3027) |
| Pro Gly Thr Cys Gly Xaa' Xaa' Glu Ile Cys Ala Tyr Ala Ala Xaa' Thr Xaa' Gly Cys | (SEQ ID NO: 3028) |
| Pro Gly Thr Cys Gly Xaa' Xaa' Glu Ile Cys Ala Tyr Ala Ala Thr Xaa' Gly Cys | (SEQ ID NO: 3029) |
| Pro Gly Thr Cys Gly Xaa' Xaa' Glu Ile Cys Ala Tyr Ala Ala Thr Xaa' Gly Cys | (SEQ ID NO: 3030) |

FIG. 2BK

| | | |
|---|---|---|
| Pro Gly Thr Cys Gly Xaa' Xaa' Glu Ile Cys Ala Tyr Ala Ala Cys Thr Xaa' Gly Cys Xaa' | (SEQ ID NO: 3031) |
| Pro Gly Thr Cys Gly Xaa' Xaa' Glu Ile Cys Ala Tyr Ala Ala Cys Thr Gly Xaa' Cys | (SEQ ID NO: 3032) |
| Pro Gly Thr Cys Gly Xaa' Xaa' Glu Ile Cys Ala Tyr Ala Ala Cys Thr Gly Xaa' Cys Xaa' | (SEQ ID NO: 3033) |
| Pro Gly Thr Cys Gly Xaa' Xaa' Glu Ile Cys Ala Tyr Ala Ala Cys Thr Gly Xaa' Cys Xaa' | (SEQ ID NO: 3034) |
| Pro Gly Thr Cys Gly Xaa' Xaa' Glu Ile Cys Ala Tyr Ala Ala Cys Thr Gly Xaa' Cys Xaa' | (SEQ ID NO: 3035) |
| Pro Gly Thr Cys Gly Xaa' Xaa' Glu Ile Cys Ala Tyr Ala Ala Cys Thr Gly Xaa' Cys Xaa' | (SEQ ID NO: 3036) |
| Pro Gly Thr Cys Gly Xaa' Xaa' Glu Ile Cys Ala Tyr Ala Ala Cys Thr Gly Xaa' Cys Xaa' | (SEQ ID NO: 3037) |
| Pro Gly Thr Cys Gly Xaa' Glu Xaa' Ile Cys Ala Tyr Ala Ala Cys Thr Gly Cys | (SEQ ID NO: 3038) |
| Pro Gly Thr Cys Gly Xaa' Xaa' Glu Ile Cys Ala Tyr Ala Ala Cys Thr Gly Cys | (SEQ ID NO: 3039) |
| Pro Gly Thr Cys Gly Xaa' Xaa' Glu Xaa' Ile Cys Ala Tyr Ala Ala Cys Thr Gly Cys | (SEQ ID NO: 3040) |
| Pro Gly Thr Cys Gly Xaa' Xaa' Glu Xaa' Ile Cys Xaa' Ala Tyr Ala Ala Cys Thr Gly Cys | (SEQ ID NO: 3041) |
| Pro Gly Thr Cys Gly Xaa' Xaa' Glu Xaa' Ile Cys Xaa' Ala Tyr Ala Ala Cys Thr Gly Cys | (SEQ ID NO: 3042) |
| Pro Gly Thr Cys Gly Xaa' Xaa' Glu Xaa' Ile Cys Xaa' Ala Tyr Xaa' Ala Ala Cys Thr Gly Cys | (SEQ ID NO: 3043) |
| Pro Gly Thr Cys Gly Xaa' Xaa' Glu Xaa' Ile Cys Xaa' Ala Tyr Xaa' Ala Ala Cys Thr Gly Cys | (SEQ ID NO: 3044) |
| Pro Gly Thr Cys Gly Xaa' Xaa' Glu Xaa' Ile Cys Xaa' Ala Tyr Ala Xaa' Ala Cys Thr Gly Cys | (SEQ ID NO: 3045) |
| Pro Gly Thr Cys Gly Xaa' Xaa' Glu Xaa' Ile Cys Xaa' Ala Tyr Ala Ala Xaa' Cys Thr Gly Cys | (SEQ ID NO: 3046) |
| Pro Gly Thr Cys Gly Xaa' Xaa' Glu Xaa' Ile Cys Xaa' Ala Tyr Ala Ala Cys Thr Xaa' Gly Cys | (SEQ ID NO: 3047) |
| Pro Gly Thr Cys Gly Xaa' Xaa' Glu Xaa' Ile Cys Xaa' Ala Tyr Ala Ala Cys Thr Gly Xaa' Cys | (SEQ ID NO: 3048) |
| Pro Gly Thr Cys Gly Xaa' Xaa' Glu Xaa' Ile Cys Xaa' Ala Tyr Ala Ala Cys Thr Gly Cys Xaa' | (SEQ ID NO: 3049) |
| Pro Gly Thr Cys Gly Xaa' Xaa' Glu Xaa' Ile Xaa' Cys Ala Tyr Ala Ala Cys Thr Gly Cys | (SEQ ID NO: 3050) |
| Pro Gly Thr Cys Gly Xaa' Xaa' Glu Xaa' Ile Xaa' Cys Xaa' Ala Tyr Ala Ala Cys Thr Gly Cys | (SEQ ID NO: 3051) |
| Pro Gly Thr Cys Gly Xaa' Xaa' Glu Xaa' Ile Xaa' Cys Xaa' Ala Tyr Xaa' Ala Ala Cys Thr Gly Cys | (SEQ ID NO: 3052) |
| Pro Gly Thr Cys Gly Xaa' Xaa' Glu Xaa' Ile Xaa' Cys Xaa' Ala Tyr Xaa' Ala Ala Cys Thr Gly Cys | (SEQ ID NO: 3053) |
| Pro Gly Thr Cys Gly Xaa' Xaa' Glu Xaa' Ile Xaa' Cys Xaa' Ala Tyr Ala Xaa' Ala Cys Thr Gly Cys | (SEQ ID NO: 3054) |
| Pro Gly Thr Cys Gly Xaa' Xaa' Glu Xaa' Ile Xaa' Cys Xaa' Ala Tyr Ala Ala Xaa' Cys Thr Gly Cys | (SEQ ID NO: 3055) |
| Pro Gly Thr Cys Gly Xaa' Xaa' Glu Xaa' Ile Xaa' Cys Xaa' Ala Tyr Ala Ala Cys Xaa' Thr Gly Cys | (SEQ ID NO: 3056) |
| Pro Gly Thr Cys Gly Xaa' Xaa' Glu Xaa' Ile Xaa' Cys Xaa' Ala Tyr Ala Ala Cys Thr Xaa' Gly Cys | (SEQ ID NO: 3057) |
| Pro Gly Thr Cys Gly Xaa' Xaa' Glu Xaa' Ile Xaa' Cys Xaa' Ala Tyr Ala Ala Cys Thr Gly Xaa' Cys | (SEQ ID NO: 3058) |
| Pro Gly Thr Cys Gly Xaa' Xaa' Glu Xaa' Ile Xaa' Cys Xaa' Ala Tyr Ala Ala Cys Thr Gly Cys Xaa' | (SEQ ID NO: 3059) |
| Pro Gly Thr Cys Gly Xaa' Xaa' Glu Xaa' Ile Cys Xaa' Ala Tyr Ala Ala Cys Thr Gly Cys | (SEQ ID NO: 3060) |
| Pro Gly Thr Cys Gly Xaa' Glu Xaa' Ile Cys Xaa' Ala Tyr Ala Ala Cys Thr Gly Cys | (SEQ ID NO: 3061) |
| Pro Gly Thr Cys Gly Xaa' Xaa' Glu Xaa' Ile Cys Xaa' Xaa' Ala Tyr Ala Ala Cys Thr Gly Cys | (SEQ ID NO: 3062) |
| Pro Gly Thr Cys Gly Xaa' Xaa' Glu Xaa' Ile Cys Xaa' Xaa' Ala Tyr Ala Ala Cys Thr Gly Cys | (SEQ ID NO: 3063) |
| Pro Gly Thr Cys Gly Xaa' Xaa' Glu Xaa' Ile Cys Xaa' Ala Tyr Xaa' Ala Ala Cys Thr Gly Cys | (SEQ ID NO: 3064) |

FIG. 2BL

| | | | | | | | | | | |
|---|---|---|---|---|---|---|---|---|---|---|
| Pro Gly Thr Cys Gly Xaa' Glu Xaa' Ile Cys Xaa' Ala Tyr Ala Xaa' Ala Cys Thr Gly Cys | (SEQ ID NO: 3065) |
| Pro Gly Thr Cys Gly Xaa' Glu Xaa' Ile Cys Xaa' Ala Tyr Ala Xaa' Ala Cys Thr Gly Cys | (SEQ ID NO: 3066) |
| Pro Gly Thr Cys Gly Xaa' Glu Xaa' Ile Cys Xaa' Ala Tyr Ala Xaa' Ala Cys Thr Gly Cys | (SEQ ID NO: 3067) |
| Pro Gly Thr Cys Gly Xaa' Glu Xaa' Ile Cys Xaa' Ala Tyr Ala Xaa' Ala Cys Thr Gly Cys | (SEQ ID NO: 3068) |
| Pro Gly Thr Cys Gly Xaa' Glu Xaa' Ile Cys Xaa' Ala Tyr Ala Xaa' Ala Cys Thr Gly Xaa' | (SEQ ID NO: 3069) |
| Pro Gly Thr Cys Gly Xaa' Glu Xaa' Ile Cys Xaa' Ala Tyr Ala Xaa' Ala Cys Thr Gly Cys | (SEQ ID NO: 3070) |
| Pro Gly Thr Cys Gly Xaa' Glu Xaa' Ile Cys Ala Tyr Ala Xaa' Ala Cys Thr Gly Cys | (SEQ ID NO: 3071) |
| Pro Gly Thr Cys Gly Xaa' Glu Xaa' Ile Cys Ala Xaa' Tyr Ala Ala Cys Thr Gly Cys | (SEQ ID NO: 3072) |
| Pro Gly Thr Cys Gly Xaa' Glu Xaa' Ile Cys Xaa' Tyr Ala Xaa' Ala Cys Thr Gly Cys | (SEQ ID NO: 3073) |
| Pro Gly Thr Cys Gly Xaa' Glu Xaa' Ile Cys Xaa' Tyr Ala Ala Xaa' Ala Cys Thr Gly Cys | (SEQ ID NO: 3074) |
| Pro Gly Thr Cys Gly Xaa' Glu Xaa' Ile Cys Xaa' Tyr Ala Ala Xaa' Ala Cys Thr Gly Cys | (SEQ ID NO: 3075) |
| Pro Gly Thr Cys Gly Xaa' Glu Xaa' Ile Cys Xaa' Tyr Ala Ala Xaa' Ala Cys Thr Gly Cys | (SEQ ID NO: 3076) |
| Pro Gly Thr Cys Gly Xaa' Glu Xaa' Ile Cys Xaa' Tyr Ala Xaa' Ala Cys Thr Gly Cys | (SEQ ID NO: 3077) |
| Pro Gly Thr Cys Gly Xaa' Glu Xaa' Ile Cys Xaa' Tyr Ala Ala Xaa' Ala Cys Thr Gly Xaa' | (SEQ ID NO: 3078) |
| Pro Gly Thr Cys Gly Xaa' Glu Xaa' Ile Cys Xaa' Tyr Ala Ala Cys Thr Gly Cys Xaa' | (SEQ ID NO: 3079) |
| Pro Gly Thr Cys Gly Xaa' Glu Xaa' Ile Cys Xaa' Tyr Ala Ala Cys Thr Gly Cys | (SEQ ID NO: 3080) |
| Pro Gly Thr Cys Gly Xaa' Glu Xaa' Ile Cys Xaa' Tyr Ala Xaa' Ala Ala Cys Thr Gly Cys | (SEQ ID NO: 3081) |
| Pro Gly Thr Cys Gly Xaa' Glu Xaa' Ile Cys Xaa' Tyr Ala Xaa' Ala Cys Thr Gly Cys | (SEQ ID NO: 3082) |
| Pro Gly Thr Cys Gly Xaa' Glu Xaa' Ile Cys Xaa' Tyr Ala Xaa' Ala Cys Thr Gly Cys | (SEQ ID NO: 3083) |
| Pro Gly Thr Cys Gly Xaa' Glu Xaa' Ile Cys Xaa' Tyr Ala Ala Xaa' Ala Cys Thr Gly Cys | (SEQ ID NO: 3084) |
| Pro Gly Thr Cys Gly Xaa' Glu Xaa' Ile Cys Xaa' Tyr Ala Ala Xaa' Ala Cys Thr Gly Cys | (SEQ ID NO: 3085) |
| Pro Gly Thr Cys Gly Xaa' Glu Xaa' Ile Cys Xaa' Tyr Ala Ala Cys Thr Gly Cys Xaa' | (SEQ ID NO: 3086) |
| Pro Gly Thr Cys Gly Xaa' Glu Xaa' Ile Cys Xaa' Tyr Ala Ala Xaa' Ala Cys Thr Gly Cys Xaa' | (SEQ ID NO: 3087) |
| Pro Gly Thr Cys Gly Xaa' Glu Xaa' Ile Cys Ala Tyr Ala Ala Cys Thr Gly Cys | (SEQ ID NO: 3088) |
| Pro Gly Thr Cys Gly Xaa' Glu Xaa' Ile Cys Xaa' Tyr Ala Xaa' Ala Ala Cys Thr Gly Cys | (SEQ ID NO: 3089) |
| Pro Gly Thr Cys Gly Xaa' Glu Xaa' Ile Cys Xaa' Tyr Ala Xaa' Ala Cys Thr Gly Cys | (SEQ ID NO: 3090) |
| Pro Gly Thr Cys Gly Xaa' Glu Xaa' Ile Cys Xaa' Tyr Ala Xaa' Ala Cys Thr Gly Cys | (SEQ ID NO: 3091) |
| Pro Gly Thr Cys Gly Xaa' Glu Xaa' Ile Cys Xaa' Tyr Ala Ala Xaa' Ala Cys Thr Gly Cys | (SEQ ID NO: 3092) |
| Pro Gly Thr Cys Gly Xaa' Glu Xaa' Ile Cys Xaa' Tyr Ala Ala Xaa' Ala Cys Thr Gly Cys | (SEQ ID NO: 3093) |
| Pro Gly Thr Cys Gly Xaa' Glu Xaa' Ile Cys Xaa' Tyr Ala Ala Xaa' Ala Cys Thr Gly Cys Xaa' | (SEQ ID NO: 3094) |
| Pro Gly Thr Cys Gly Xaa' Glu Xaa' Ile Cys Xaa' Tyr Ala Ala Xaa' Ala Cys Thr Gly Cys | (SEQ ID NO: 3095) |
| Pro Gly Thr Cys Gly Xaa' Glu Xaa' Ile Cys Xaa' Tyr Ala Ala Xaa' Cys Thr Gly Cys | (SEQ ID NO: 3096) |
| Pro Gly Thr Cys Gly Xaa' Glu Xaa' Ile Cys Xaa' Tyr Ala Ala Xaa' Cys Xaa' Thr Gly Cys | (SEQ ID NO: 3097) |
| Pro Gly Thr Cys Gly Xaa' Glu Xaa' Ile Cys Ala Tyr Ala Ala Xaa' Cys Thr Xaa' Gly Cys | (SEQ ID NO: 3098) |

FIG. 2BM

| Sequence | SEQ ID NO |
|---|---|
| Pro Gly Thr Cys Gly Xaa' Glu Xaa' Ile Cys Ala Tyr Ala Ala Xaa' Cys Thr Gly Xaa' Cys | (SEQ ID NO: 3099) |
| Pro Gly Thr Cys Gly Xaa' Glu Xaa' Ile Cys Ala Tyr Ala Ala Xaa' Cys Thr Gly Cys Xaa' | (SEQ ID NO: 3100) |
| Pro Gly Thr Cys Gly Xaa' Glu Xaa' Ile Cys Ala Tyr Ala Ala Cys Xaa' Thr Gly Cys | (SEQ ID NO: 3101) |
| Pro Gly Thr Cys Gly Xaa' Glu Xaa' Ile Cys Ala Tyr Ala Ala Cys Xaa' Thr Gly Xaa' Cys | (SEQ ID NO: 3102) |
| Pro Gly Thr Cys Gly Xaa' Glu Xaa' Ile Cys Ala Tyr Ala Ala Cys Xaa' Xaa' Thr Gly Cys | (SEQ ID NO: 3103) |
| Pro Gly Thr Cys Gly Xaa' Glu Xaa' Ile Cys Ala Tyr Ala Ala Cys Xaa' Thr Gly Xaa' Cys | (SEQ ID NO: 3104) |
| Pro Gly Thr Cys Gly Xaa' Glu Xaa' Ile Cys Ala Tyr Ala Ala Cys Xaa' Thr Gly Cys Xaa' | (SEQ ID NO: 3105) |
| Pro Gly Thr Cys Gly Xaa' Glu Xaa' Ile Cys Ala Tyr Ala Ala Cys Xaa' Thr Xaa' Gly Cys | (SEQ ID NO: 3106) |
| Pro Gly Thr Cys Gly Xaa' Glu Xaa' Ile Cys Ala Tyr Ala Ala Cys Thr Xaa' Gly Xaa' Cys | (SEQ ID NO: 3107) |
| Pro Gly Thr Cys Gly Xaa' Glu Xaa' Ile Cys Ala Tyr Ala Ala Cys Thr Xaa' Gly Cys Xaa' | (SEQ ID NO: 3108) |
| Pro Gly Thr Cys Gly Xaa' Glu Xaa' Ile Cys Ala Tyr Ala Ala Cys Thr Gly Xaa' Cys Xaa' | (SEQ ID NO: 3109) |
| Pro Gly Thr Cys Gly Xaa' Glu Xaa' Ile Cys Ala Tyr Ala Ala Cys Thr Gly Xaa' Cys | (SEQ ID NO: 3110) |
| Pro Gly Thr Cys Gly Xaa' Glu Xaa' Ile Cys Ala Tyr Ala Ala Cys Thr Gly Xaa' Xaa' Cys | (SEQ ID NO: 3111) |
| Pro Gly Thr Cys Gly Xaa' Glu Xaa' Ile Cys Ala Tyr Ala Ala Cys Thr Gly Xaa' Cys Xaa' | (SEQ ID NO: 3112) |
| Pro Gly Thr Cys Gly Xaa' Glu Xaa' Ile Cys Ala Tyr Ala Ala Cys Thr Gly Cys Xaa' Xaa' | (SEQ ID NO: 3113) |
| Pro Gly Thr Cys Gly Xaa' Glu Ile Xaa' Cys Ala Tyr Ala Ala Cys Thr Gly Cys Xaa' | (SEQ ID NO: 3114) |
| Pro Gly Thr Cys Gly Xaa' Glu Ile Xaa' Cys Ala Tyr Ala Ala Cys Thr Gly Cys | (SEQ ID NO: 3115) |
| Pro Gly Thr Cys Gly Xaa' Glu Ile Xaa' Cys Xaa' Ala Tyr Ala Ala Cys Thr Gly Cys | (SEQ ID NO: 3116) |
| Pro Gly Thr Cys Gly Xaa' Glu Ile Xaa' Cys Xaa' Ala Tyr Ala Ala Cys Thr Gly Cys | (SEQ ID NO: 3117) |
| Pro Gly Thr Cys Gly Xaa' Glu Ile Xaa' Cys Xaa' Ala Tyr Xaa' Ala Ala Cys Thr Gly Cys | (SEQ ID NO: 3118) |
| Pro Gly Thr Cys Gly Xaa' Glu Ile Xaa' Cys Xaa' Ala Tyr Ala Xaa' Ala Cys Thr Gly Cys | (SEQ ID NO: 3119) |
| Pro Gly Thr Cys Gly Xaa' Glu Ile Xaa' Cys Xaa' Ala Tyr Ala Ala Cys Thr Gly Cys | (SEQ ID NO: 3120) |
| Pro Gly Thr Cys Gly Xaa' Glu Ile Xaa' Cys Xaa' Ala Tyr Ala Ala Xaa' Cys Thr Gly Cys | (SEQ ID NO: 3121) |
| Pro Gly Thr Cys Gly Xaa' Glu Ile Xaa' Cys Xaa' Ala Tyr Ala Ala Cys Xaa' Thr Gly Cys | (SEQ ID NO: 3122) |
| Pro Gly Thr Cys Gly Xaa' Glu Ile Xaa' Cys Xaa' Ala Tyr Ala Ala Cys Thr Xaa' Gly Cys | (SEQ ID NO: 3123) |
| Pro Gly Thr Cys Gly Xaa' Glu Ile Xaa' Cys Xaa' Ala Tyr Ala Ala Cys Thr Gly Xaa' Cys | (SEQ ID NO: 3124) |
| Pro Gly Thr Cys Gly Xaa' Glu Ile Xaa' Cys Xaa' Ala Tyr Ala Ala Cys Thr Gly Cys Xaa' | (SEQ ID NO: 3125) |
| Pro Gly Thr Cys Gly Xaa' Glu Ile Ile Cys Xaa' Ala Tyr Ala Xaa' Ala Cys Thr Gly Cys Xaa' | (SEQ ID NO: 3126) |
| Pro Gly Thr Cys Gly Xaa' Glu Ile Ile Cys Xaa' Ala Tyr Ala Ala Cys Thr Gly Cys | (SEQ ID NO: 3127) |
| Pro Gly Thr Cys Gly Xaa' Glu Ile Ile Cys Xaa' Xaa' Ala Tyr Ala Ala Cys Thr Gly Cys | (SEQ ID NO: 3128) |
| Pro Gly Thr Cys Gly Xaa' Glu Ile Ile Cys Xaa' Ala Tyr Xaa' Ala Ala Cys Thr Gly Cys | (SEQ ID NO: 3129) |
| Pro Gly Thr Cys Gly Xaa' Glu Ile Ile Cys Xaa' Ala Tyr Ala Xaa' Ala Cys Thr Gly Cys | (SEQ ID NO: 3130) |
| Pro Gly Thr Cys Gly Xaa' Glu Ile Ile Cys Xaa' Ala Tyr Ala Ala Xaa' Cys Thr Gly Cys | (SEQ ID NO: 3131) |
| Pro Gly Thr Cys Gly Xaa' Glu Ile Ile Cys Xaa' Ala Tyr Ala Ala Xaa' Cys Thr Gly Cys | (SEQ ID NO: 3132) |

FIG. 2BN

| | | | | | | | | | | | |
|---|---|---|---|---|---|---|---|---|---|---|---|
| Pro | Gly | Thr | Cys | Gly | Xaa' | Glu | Ile | Xaa' | Cys | Ala | Xaa' | Ala | Tyr | Ala | Ala | Cys | Xaa' | Thr | Gly | Cys | (SEQ ID NO: 3133) |
| Pro | Gly | Thr | Cys | Gly | Xaa' | Glu | Ile | Xaa' | Cys | Ala | Xaa' | Ala | Tyr | Ala | Ala | Cys | Xaa' | Thr | Gly | Cys | (SEQ ID NO: 3134) |
| Pro | Gly | Thr | Cys | Gly | Xaa' | Glu | Ile | Xaa' | Cys | Ala | Xaa' | Ala | Tyr | Ala | Ala | Cys | Thr | Gly | Cys | Xaa' | (SEQ ID NO: 3135) |
| Pro | Gly | Thr | Cys | Gly | Xaa' | Glu | Ile | Xaa' | Cys | Ala | Xaa' | Ala | Tyr | Ala | Ala | Cys | Thr | Gly | Cys | Xaa' | (SEQ ID NO: 3136) |
| Pro | Gly | Thr | Cys | Gly | Xaa' | Glu | Ile | Xaa' | Cys | Ala | Xaa' | Ala | Tyr | Ala | Ala | Cys | Thr | Gly | Cys | | (SEQ ID NO: 3137) |
| Pro | Gly | Thr | Cys | Gly | Xaa' | Glu | Ile | Xaa' | Cys | Ala | Xaa' | Xaa' | Tyr | Ala | Ala | Cys | Xaa' | Thr | Gly | Cys | (SEQ ID NO: 3138) |
| Pro | Gly | Thr | Cys | Gly | Xaa' | Glu | Ile | Xaa' | Cys | Ala | Xaa' | Tyr | Xaa' | Ala | Ala | Cys | Xaa' | Thr | Gly | Cys | (SEQ ID NO: 3139) |
| Pro | Gly | Thr | Cys | Gly | Xaa' | Glu | Ile | Xaa' | Cys | Ala | Xaa' | Tyr | Ala | Xaa' | Ala | Cys | Xaa' | Thr | Gly | Cys | (SEQ ID NO: 3140) |
| Pro | Gly | Thr | Cys | Gly | Xaa' | Glu | Ile | Xaa' | Cys | Ala | Xaa' | Tyr | Ala | Ala | Xaa' | Cys | Xaa' | Thr | Gly | Cys | (SEQ ID NO: 3141) |
| Pro | Gly | Thr | Cys | Gly | Xaa' | Glu | Ile | Xaa' | Cys | Ala | Xaa' | Tyr | Ala | Ala | Cys | Xaa' | Thr | Gly | Cys | | (SEQ ID NO: 3142) |
| Pro | Gly | Thr | Cys | Gly | Xaa' | Glu | Ile | Xaa' | Cys | Ala | Xaa' | Tyr | Ala | Ala | Cys | Xaa' | Thr | Gly | Cys | | (SEQ ID NO: 3143) |
| Pro | Gly | Thr | Cys | Gly | Xaa' | Glu | Ile | Xaa' | Cys | Ala | Xaa' | Tyr | Ala | Ala | Cys | Thr | Xaa' | Gly | Cys | | (SEQ ID NO: 3144) |
| Pro | Gly | Thr | Cys | Gly | Xaa' | Glu | Ile | Xaa' | Cys | Ala | Xaa' | Tyr | Ala | Ala | Cys | Thr | Gly | Xaa' | Cys | | (SEQ ID NO: 3145) |
| Pro | Gly | Thr | Cys | Gly | Xaa' | Glu | Ile | Xaa' | Cys | Ala | Xaa' | Tyr | Ala | Ala | Cys | Thr | Gly | Cys | | | (SEQ ID NO: 3146) |
| Pro | Gly | Thr | Cys | Gly | Xaa' | Glu | Ile | Xaa' | Cys | Ala | Tyr | Xaa' | Ala | Ala | Cys | Xaa' | Thr | Gly | Cys | | (SEQ ID NO: 3147) |
| Pro | Gly | Thr | Cys | Gly | Xaa' | Glu | Ile | Xaa' | Cys | Ala | Tyr | Ala | Xaa' | Ala | Cys | Xaa' | Thr | Gly | Cys | | (SEQ ID NO: 3148) |
| Pro | Gly | Thr | Cys | Gly | Xaa' | Glu | Ile | Xaa' | Cys | Ala | Tyr | Ala | Ala | Xaa' | Cys | Xaa' | Thr | Gly | Cys | | (SEQ ID NO: 3149) |
| Pro | Gly | Thr | Cys | Gly | Xaa' | Glu | Ile | Xaa' | Cys | Ala | Tyr | Ala | Ala | Cys | Xaa' | Thr | Gly | Cys | | | (SEQ ID NO: 3150) |
| Pro | Gly | Thr | Cys | Gly | Xaa' | Glu | Ile | Xaa' | Cys | Ala | Tyr | Ala | Ala | Cys | Xaa' | Thr | Gly | Cys | | | (SEQ ID NO: 3151) |
| Pro | Gly | Thr | Cys | Gly | Xaa' | Glu | Ile | Xaa' | Cys | Ala | Tyr | Ala | Ala | Cys | Thr | Xaa' | Gly | Cys | | | (SEQ ID NO: 3152) |
| Pro | Gly | Thr | Cys | Gly | Xaa' | Glu | Ile | Xaa' | Cys | Ala | Tyr | Ala | Ala | Cys | Thr | Gly | Xaa' | Cys | | | (SEQ ID NO: 3153) |
| Pro | Gly | Thr | Cys | Gly | Xaa' | Glu | Ile | Xaa' | Cys | Ala | Tyr | Ala | Ala | Cys | Thr | Gly | Cys | Xaa' | | | (SEQ ID NO: 3154) |
| Pro | Gly | Thr | Cys | Gly | Xaa' | Glu | Ile | Xaa' | Cys | Xaa' | Ala | Tyr | Ala | Ala | Cys | Thr | Gly | Cys | | | (SEQ ID NO: 3155) |
| Pro | Gly | Thr | Cys | Gly | Xaa' | Glu | Ile | Xaa' | Cys | Xaa' | Ala | Tyr | Ala | Ala | Cys | Thr | Gly | Cys | | | (SEQ ID NO: 3156) |
| Pro | Gly | Thr | Cys | Gly | Xaa' | Glu | Ile | Xaa' | Cys | Ala | Xaa' | Ala | Tyr | Ala | Ala | Cys | Thr | Gly | Cys | | (SEQ ID NO: 3157) |
| Pro | Gly | Thr | Cys | Gly | Xaa' | Glu | Ile | Xaa' | Cys | Ala | Xaa' | Tyr | Ala | Ala | Cys | Thr | Gly | Cys | | | (SEQ ID NO: 3158) |
| Pro | Gly | Thr | Cys | Gly | Xaa' | Glu | Ile | Xaa' | Cys | Ala | Tyr | Xaa' | Ala | Ala | Cys | Thr | Gly | Cys | | | (SEQ ID NO: 3159) |
| Pro | Gly | Thr | Cys | Gly | Xaa' | Glu | Ile | Xaa' | Cys | Ala | Tyr | Ala | Xaa' | Ala | Cys | Thr | Gly | Cys | | | (SEQ ID NO: 3160) |
| Pro | Gly | Thr | Cys | Gly | Xaa' | Glu | Ile | Xaa' | Cys | Ala | Tyr | Ala | Ala | Xaa' | Cys | Thr | Gly | Cys | | | (SEQ ID NO: 3161) |
| Pro | Gly | Thr | Cys | Gly | Xaa' | Glu | Ile | Xaa' | Cys | Ala | Tyr | Ala | Ala | Cys | Xaa' | Thr | Gly | Cys | | | (SEQ ID NO: 3162) |
| Pro | Gly | Thr | Cys | Gly | Xaa' | Glu | Ile | Xaa' | Cys | Ala | Tyr | Ala | Ala | Cys | Thr | Xaa' | Gly | Cys | | | (SEQ ID NO: 3163) |
| Pro | Gly | Thr | Cys | Gly | Xaa' | Glu | Ile | Xaa' | Cys | Ala | Tyr | Ala | Ala | Cys | Thr | Gly | Xaa' | Cys | | | (SEQ ID NO: 3164) |
| Pro | Gly | Thr | Cys | Gly | Xaa' | Glu | Ile | Xaa' | Cys | Ala | Tyr | Ala | Ala | Cys | Thr | Gly | Cys | Xaa' | | | (SEQ ID NO: 3165) |
| Pro | Gly | Thr | Cys | Gly | Xaa' | Glu | Ile | Xaa' | Cys | Ala | Ala | Tyr | Ala | Ala | Cys | Thr | Gly | Cys | Xaa' | | (SEQ ID NO: 3166) |

FIG. 2BO

| | | |
|---|---|---|
| Pro Gly Thr Cys Gly Xaa' Glu Ile Xaa' Cys Xaa' Ala Tyr Ala Ala Cys Xaa' Thr Gly Cys | | (SEQID NO: 3167) |
| Pro Gly Thr Cys Gly Xaa' Glu Ile Xaa' Cys Xaa' Ala Tyr Ala Ala Cys Xaa' Thr Gly Cys | | (SEQID NO: 3168) |
| Pro Gly Thr Cys Gly Xaa' Glu Ile Xaa' Cys Xaa' Ala Tyr Ala Ala Cys Xaa' Thr Gly Cys | | (SEQID NO: 3169) |
| Pro Gly Thr Cys Gly Xaa' Glu Ile Xaa' Cys Xaa' Ala Tyr Ala Ala Cys Xaa' Thr Gly Cys Xaa' | | (SEQID NO: 3170) |
| Pro Gly Thr Cys Gly Xaa' Glu Ile Xaa' Cys Xaa' Ala Tyr Ala Ala Cys Xaa' Thr Gly Cys Xaa' | | (SEQID NO: 3171) |
| Pro Gly Thr Cys Gly Xaa' Glu Ile Xaa' Cys Xaa' Ala Tyr Ala Ala Cys Xaa' Thr Gly Cys | | (SEQID NO: 3172) |
| Pro Gly Thr Cys Gly Xaa' Glu Ile Xaa' Cys Xaa' Ala Tyr Ala Ala Cys Xaa' Gly Cys | | (SEQID NO: 3173) |
| Pro Gly Thr Cys Gly Xaa' Glu Ile Xaa' Cys Xaa' Ala Tyr Ala Ala Cys Xaa' Gly Cys | | (SEQID NO: 3174) |
| Pro Gly Thr Cys Gly Xaa' Glu Ile Xaa' Cys Xaa' Ala Tyr Ala Ala Cys Xaa' Gly Cys Xaa' | | (SEQID NO: 3175) |
| Pro Gly Thr Cys Gly Xaa' Glu Ile Xaa' Cys Xaa' Ala Tyr Ala Ala Cys Xaa' Gly Cys Xaa' | | (SEQID NO: 3176) |
| Pro Gly Thr Cys Gly Xaa' Glu Ile Xaa' Cys Xaa' Ala Tyr Ala Ala Cys Xaa' Cys | | (SEQID NO: 3177) |
| Pro Gly Thr Cys Gly Xaa' Glu Ile Xaa' Cys Xaa' Ala Tyr Ala Ala Cys Xaa' Cys Xaa' | | (SEQID NO: 3178) |
| Pro Gly Thr Cys Gly Xaa' Glu Ile Xaa' Cys Xaa' Ala Tyr Ala Ala Cys Xaa' Cys Xaa' | | (SEQID NO: 3179) |
| Pro Gly Thr Cys Gly Xaa' Glu Ile Xaa' Cys Xaa' Ala Tyr Ala Ala Cys Xaa' Cys | | (SEQID NO: 3180) |
| Pro Gly Thr Cys Gly Xaa' Glu Ile Cys Xaa' Ala Tyr Ala Ala Cys Thr Gly Cys | | (SEQID NO: 3181) |
| Pro Gly Thr Cys Gly Xaa' Glu Ile Cys Xaa' Ala Tyr Ala Ala Cys Thr Gly Cys | | (SEQID NO: 3182) |
| Pro Gly Thr Cys Gly Xaa' Glu Ile Cys Xaa' Ala Tyr Ala Ala Cys Thr Gly Cys | | (SEQID NO: 3183) |
| Pro Gly Thr Cys Gly Xaa' Glu Ile Cys Xaa' Ala Tyr Ala Ala Cys Thr Gly Cys Xaa' | | (SEQID NO: 3184) |
| Pro Gly Thr Cys Gly Xaa' Glu Ile Cys Xaa' Ala Tyr Ala Ala Cys Thr Gly Cys Xaa' | | (SEQID NO: 3185) |
| Pro Gly Thr Cys Gly Xaa' Glu Ile Cys Xaa' Ala Xaa' Ala Ala Cys Thr Gly Cys | | (SEQID NO: 3186) |
| Pro Gly Thr Cys Gly Xaa' Glu Ile Cys Xaa' Ala Xaa' Ala Ala Cys Thr Gly Cys | | (SEQID NO: 3187) |
| Pro Gly Thr Cys Gly Xaa' Glu Ile Cys Xaa' Ala Xaa' Ala Ala Cys Thr Gly Cys | | (SEQID NO: 3188) |
| Pro Gly Thr Cys Gly Xaa' Glu Ile Cys Xaa' Ala Xaa' Ala Ala Cys Thr Gly Cys Xaa' | | (SEQID NO: 3189) |
| Pro Gly Thr Cys Gly Xaa' Glu Ile Cys Xaa' Ala Xaa' Ala Ala Cys Thr Gly Cys Xaa' | | (SEQID NO: 3190) |
| Pro Gly Thr Cys Gly Xaa' Glu Ile Cys Xaa' Ala Xaa' Ala Ala Cys Thr Gly Cys | | (SEQID NO: 3191) |
| Pro Gly Thr Cys Gly Xaa' Glu Ile Cys Xaa' Ala Xaa' Ala Ala Cys Gly Cys | | (SEQID NO: 3192) |
| Pro Gly Thr Cys Gly Xaa' Glu Ile Cys Xaa' Ala Xaa' Ala Ala Cys Gly Cys | | (SEQID NO: 3193) |
| Pro Gly Thr Cys Gly Xaa' Glu Ile Cys Xaa' Ala Xaa' Ala Ala Cys Gly Cys | | (SEQID NO: 3194) |
| Pro Gly Thr Cys Gly Xaa' Glu Ile Cys Xaa' Ala Xaa' Ala Ala Cys Gly Cys Xaa' | | (SEQID NO: 3195) |
| Pro Gly Thr Cys Gly Xaa' Glu Ile Cys Xaa' Ala Xaa' Ala Ala Cys Gly Cys Xaa' | | (SEQID NO: 3196) |
| Pro Gly Thr Cys Gly Xaa' Glu Ile Cys Xaa' Ala Xaa' Ala Ala Cys Xaa' Thr Gly Cys | | (SEQID NO: 3197) |
| Pro Gly Thr Cys Gly Xaa' Glu Ile Cys Xaa' Ala Xaa' Ala Ala Cys Xaa' Thr Gly Cys | | (SEQID NO: 3198) |
| Pro Gly Thr Cys Gly Xaa' Glu Ile Cys Xaa' Ala Xaa' Ala Ala Cys Xaa' Gly Cys | | (SEQID NO: 3199) |
| Pro Gly Thr Cys Gly Xaa' Glu Ile Cys Xaa' Ala Xaa' Ala Ala Cys Thr Gly Cys Xaa' | | (SEQID NO: 3200) |

FIG. 2BP

| | | | | | | | | | | |
|---|---|---|---|---|---|---|---|---|---|---|
| Pro Gly Thr Cys Gly Xaa' Glu Ile Cys Xaa' Ala Tyr Xaa' Ala Ala Cys Thr Gly Cys | (SEQ ID NO: 3201) |
| Pro Gly Thr Cys Gly Xaa' Glu Ile Cys Xaa' Ala Tyr Xaa' Ala Xaa' Ala Cys Thr Gly Cys | (SEQ ID NO: 3202) |
| Pro Gly Thr Cys Gly Xaa' Glu Ile Cys Xaa' Ala Tyr Xaa' Ala Ala Xaa' Cys Thr Gly Cys | (SEQ ID NO: 3203) |
| Pro Gly Thr Cys Gly Xaa' Glu Ile Cys Xaa' Ala Tyr Xaa' Ala Ala Cys Xaa' Thr Gly Cys | (SEQ ID NO: 3204) |
| Pro Gly Thr Cys Gly Xaa' Glu Ile Cys Xaa' Ala Tyr Xaa' Ala Ala Cys Thr Xaa' Gly Cys | (SEQ ID NO: 3205) |
| Pro Gly Thr Cys Gly Xaa' Glu Ile Cys Xaa' Ala Tyr Xaa' Ala Ala Cys Thr Gly Xaa' Cys | (SEQ ID NO: 3206) |
| Pro Gly Thr Cys Gly Xaa' Glu Ile Cys Xaa' Ala Tyr Xaa' Ala Ala Cys Thr Gly Cys Xaa' | (SEQ ID NO: 3207) |
| Pro Gly Thr Cys Gly Xaa' Glu Ile Cys Xaa' Ala Tyr Xaa' Ala Ala Cys Thr Gly Cys | (SEQ ID NO: 3208) |
| Pro Gly Thr Cys Gly Xaa' Glu Ile Cys Xaa' Ala Tyr Ala Xaa' Ala Cys Thr Gly Cys | (SEQ ID NO: 3209) |
| Pro Gly Thr Cys Gly Xaa' Glu Ile Cys Xaa' Ala Tyr Ala Ala Xaa' Cys Thr Gly Cys | (SEQ ID NO: 3210) |
| Pro Gly Thr Cys Gly Xaa' Glu Ile Cys Xaa' Ala Tyr Ala Ala Cys Xaa' Thr Gly Cys | (SEQ ID NO: 3211) |
| Pro Gly Thr Cys Gly Xaa' Glu Ile Cys Xaa' Ala Tyr Ala Ala Cys Thr Xaa' Gly Cys | (SEQ ID NO: 3212) |
| Pro Gly Thr Cys Gly Xaa' Glu Ile Cys Xaa' Ala Tyr Ala Ala Cys Thr Gly Xaa' Cys | (SEQ ID NO: 3213) |
| Pro Gly Thr Cys Gly Xaa' Glu Ile Cys Xaa' Ala Tyr Ala Ala Cys Thr Gly Cys Xaa' | (SEQ ID NO: 3214) |
| Pro Gly Thr Cys Gly Xaa' Glu Ile Cys Xaa' Ala Tyr Ala Ala Cys Thr Gly Cys | (SEQ ID NO: 3215) |
| Pro Gly Thr Cys Gly Xaa' Glu Ile Cys Xaa' Ala Tyr Ala Xaa' Ala Cys Thr Gly Cys | (SEQ ID NO: 3216) |
| Pro Gly Thr Cys Gly Xaa' Glu Ile Cys Xaa' Ala Tyr Ala Ala Xaa' Cys Thr Gly Cys | (SEQ ID NO: 3217) |
| Pro Gly Thr Cys Gly Xaa' Glu Ile Cys Xaa' Ala Tyr Ala Ala Cys Xaa' Thr Gly Cys | (SEQ ID NO: 3218) |
| Pro Gly Thr Cys Gly Xaa' Glu Ile Cys Xaa' Ala Tyr Ala Ala Cys Thr Xaa' Gly Cys | (SEQ ID NO: 3219) |
| Pro Gly Thr Cys Gly Xaa' Glu Ile Cys Xaa' Ala Tyr Ala Ala Cys Thr Gly Xaa' Cys | (SEQ ID NO: 3220) |
| Pro Gly Thr Cys Gly Xaa' Glu Ile Cys Xaa' Ala Tyr Ala Ala Cys Thr Gly Cys Xaa' | (SEQ ID NO: 3221) |
| Pro Gly Thr Cys Gly Xaa' Glu Ile Cys Xaa' Ala Tyr Ala Ala Cys Thr Gly Cys | (SEQ ID NO: 3222) |
| Pro Gly Thr Cys Gly Xaa' Glu Ile Cys Xaa' Ala Tyr Ala Xaa' Ala Cys Thr Gly Cys | (SEQ ID NO: 3223) |
| Pro Gly Thr Cys Gly Xaa' Glu Ile Cys Xaa' Ala Tyr Ala Ala Xaa' Cys Thr Gly Cys | (SEQ ID NO: 3224) |
| Pro Gly Thr Cys Gly Xaa' Glu Ile Cys Xaa' Ala Tyr Ala Ala Cys Xaa' Thr Gly Cys | (SEQ ID NO: 3225) |
| Pro Gly Thr Cys Gly Xaa' Glu Ile Cys Xaa' Ala Tyr Ala Ala Cys Thr Xaa' Gly Cys | (SEQ ID NO: 3226) |
| Pro Gly Thr Cys Gly Xaa' Glu Ile Cys Xaa' Ala Tyr Ala Ala Cys Thr Gly Xaa' Cys | (SEQ ID NO: 3227) |
| Pro Gly Thr Cys Gly Xaa' Glu Ile Cys Xaa' Ala Tyr Ala Ala Cys Thr Gly Cys Xaa' | (SEQ ID NO: 3228) |
| Pro Gly Thr Cys Gly Xaa' Glu Ile Cys Xaa' Ala Tyr Ala Ala Cys Thr Gly Cys | (SEQ ID NO: 3229) |
| Pro Gly Thr Cys Gly Xaa' Glu Ile Cys Xaa' Ala Tyr Ala Xaa' Ala Cys Thr Gly Cys | (SEQ ID NO: 3230) |
| Pro Gly Thr Cys Gly Xaa' Glu Ile Cys Xaa' Ala Tyr Ala Ala Xaa' Cys Thr Gly Cys | (SEQ ID NO: 3231) |
| Pro Gly Thr Cys Gly Xaa' Glu Ile Cys Xaa' Ala Tyr Ala Ala Cys Xaa' Thr Gly Cys | (SEQ ID NO: 3232) |
| Pro Gly Thr Cys Gly Xaa' Glu Ile Cys Xaa' Ala Tyr Ala Ala Cys Thr Gly Xaa' Cys | (SEQ ID NO: 3233) |
| Pro Gly Thr Cys Gly Xaa' Glu Ile Cys Xaa' Ala Tyr Ala Ala Cys Thr Gly Cys Xaa' | (SEQ ID NO: 3234) |

FIG. 2BQ

| | | | | | | | | | | | | |
|---|---|---|---|---|---|---|---|---|---|---|---|---|
| Pro | Gly | Thr | Cys | Gly | Xaa' | Glu | Ile | Cys | Xaa' | Ala | Tyr | Ala | Ala | Cys | Thr | Gly | Cys | Xaa' | Xaa' | (SEQ ID NO: 3235) |
| Pro | Gly | Thr | Cys | Gly | Xaa' | Glu | Ile | Cys | Xaa' | Ala | Tyr | Ala | Ala | Cys | Thr | Gly | Cys | | | (SEQ ID NO: 3236) |
| Pro | Gly | Thr | Cys | Gly | Xaa' | Glu | Ile | Cys | Xaa' | Ala | Tyr | Ala | Ala | Cys | Thr | Gly | Cys | | | (SEQ ID NO: 3237) |
| Pro | Gly | Thr | Cys | Gly | Xaa' | Glu | Ile | Cys | Xaa' | Ala | Xaa' | Tyr | Ala | Ala | Cys | Thr | Gly | Cys | | (SEQ ID NO: 3238) |
| Pro | Gly | Thr | Cys | Gly | Xaa' | Glu | Ile | Cys | Xaa' | Ala | Xaa' | Tyr | Ala | Ala | Cys | Thr | Gly | Cys | | (SEQ ID NO: 3239) |
| Pro | Gly | Thr | Cys | Gly | Xaa' | Glu | Ile | Cys | Xaa' | Ala | Xaa' | Tyr | Ala | Ala | Cys | Thr | Gly | Cys | | (SEQ ID NO: 3240) |
| Pro | Gly | Thr | Cys | Gly | Xaa' | Glu | Ile | Cys | Xaa' | Ala | Xaa' | Tyr | Ala | Ala | Cys | Thr | Gly | Cys | | (SEQ ID NO: 3241) |
| Pro | Gly | Thr | Cys | Gly | Xaa' | Glu | Ile | Cys | Xaa' | Ala | Xaa' | Tyr | Ala | Ala | Cys | Thr | Gly | Cys | | (SEQ ID NO: 3242) |
| Pro | Gly | Thr | Cys | Gly | Xaa' | Glu | Ile | Cys | Xaa' | Ala | Xaa' | Tyr | Ala | Ala | Cys | Thr | Gly | Cys | | (SEQ ID NO: 3243) |
| Pro | Gly | Thr | Cys | Gly | Xaa' | Glu | Ile | Cys | Xaa' | Ala | Xaa' | Tyr | Ala | Ala | Cys | Thr | Gly | Xaa' | Cys | (SEQ ID NO: 3244) |
| Pro | Gly | Thr | Cys | Gly | Xaa' | Glu | Ile | Cys | Xaa' | Ala | Xaa' | Tyr | Ala | Ala | Cys | Thr | Gly | Cys | Xaa' | (SEQ ID NO: 3245) |
| Pro | Gly | Thr | Cys | Gly | Xaa' | Glu | Ile | Cys | Xaa' | Ala | Xaa' | Tyr | Xaa' | Ala | Ala | Cys | Thr | Gly | Cys | (SEQ ID NO: 3246) |
| Pro | Gly | Thr | Cys | Gly | Xaa' | Glu | Ile | Cys | Xaa' | Ala | Xaa' | Tyr | Xaa' | Ala | Ala | Cys | Thr | Gly | Cys | (SEQ ID NO: 3247) |
| Pro | Gly | Thr | Cys | Gly | Xaa' | Glu | Ile | Cys | Xaa' | Ala | Xaa' | Tyr | Xaa' | Ala | Ala | Cys | Thr | Gly | Cys | (SEQ ID NO: 3248) |
| Pro | Gly | Thr | Cys | Gly | Xaa' | Glu | Ile | Cys | Xaa' | Ala | Xaa' | Tyr | Xaa' | Ala | Xaa' | Cys | Thr | Gly | Cys | (SEQ ID NO: 3249) |
| Pro | Gly | Thr | Cys | Gly | Xaa' | Glu | Ile | Cys | Xaa' | Ala | Xaa' | Tyr | Xaa' | Ala | Xaa' | Cys | Thr | Gly | Cys | (SEQ ID NO: 3250) |
| Pro | Gly | Thr | Cys | Gly | Xaa' | Glu | Ile | Cys | Xaa' | Ala | Xaa' | Tyr | Xaa' | Ala | Xaa' | Cys | Thr | Gly | Cys | (SEQ ID NO: 3251) |
| Pro | Gly | Thr | Cys | Gly | Xaa' | Glu | Ile | Cys | Xaa' | Ala | Xaa' | Tyr | Xaa' | Ala | Xaa' | Cys | Thr | Gly | Xaa' | Cys | (SEQ ID NO: 3252) |
| Pro | Gly | Thr | Cys | Gly | Xaa' | Glu | Ile | Cys | Xaa' | Ala | Xaa' | Tyr | Xaa' | Ala | Xaa' | Cys | Thr | Gly | Cys | | (SEQ ID NO: 3253) |
| Pro | Gly | Thr | Cys | Gly | Xaa' | Glu | Ile | Cys | Xaa' | Ala | Xaa' | Tyr | Ala | Xaa' | Xaa' | Ala | Cys | Thr | Gly | Cys | (SEQ ID NO: 3254) |
| Pro | Gly | Thr | Cys | Gly | Xaa' | Glu | Ile | Cys | Xaa' | Ala | Xaa' | Tyr | Ala | Xaa' | Xaa' | Ala | Cys | Thr | Gly | Cys | (SEQ ID NO: 3255) |
| Pro | Gly | Thr | Cys | Gly | Xaa' | Glu | Ile | Cys | Xaa' | Ala | Xaa' | Tyr | Ala | Xaa' | Ala | Cys | Xaa' | Thr | Gly | Cys | (SEQ ID NO: 3256) |
| Pro | Gly | Thr | Cys | Gly | Xaa' | Glu | Ile | Cys | Xaa' | Ala | Xaa' | Tyr | Ala | Xaa' | Ala | Cys | Xaa' | Thr | Gly | Cys | (SEQ ID NO: 3257) |
| Pro | Gly | Thr | Cys | Gly | Xaa' | Glu | Ile | Cys | Xaa' | Ala | Xaa' | Tyr | Ala | Xaa' | Ala | Cys | Xaa' | Thr | Gly | Cys | (SEQ ID NO: 3258) |
| Pro | Gly | Thr | Cys | Gly | Xaa' | Glu | Ile | Cys | Xaa' | Ala | Xaa' | Tyr | Ala | Xaa' | Ala | Cys | Xaa' | Thr | Gly | Cys | (SEQ ID NO: 3259) |
| Pro | Gly | Thr | Cys | Gly | Xaa' | Glu | Ile | Cys | Xaa' | Ala | Xaa' | Tyr | Ala | Xaa' | Ala | Cys | Thr | Gly | Cys | Xaa' | (SEQ ID NO: 3260) |
| Pro | Gly | Thr | Cys | Gly | Xaa' | Glu | Ile | Cys | Xaa' | Ala | Xaa' | Tyr | Ala | Ala | Xaa' | Cys | Thr | Gly | Cys | | (SEQ ID NO: 3261) |
| Pro | Gly | Thr | Cys | Gly | Xaa' | Glu | Ile | Cys | Xaa' | Ala | Xaa' | Tyr | Ala | Ala | Xaa' | Cys | Thr | Gly | Cys | | (SEQ ID NO: 3262) |
| Pro | Gly | Thr | Cys | Gly | Xaa' | Glu | Ile | Cys | Xaa' | Ala | Xaa' | Tyr | Ala | Ala | Xaa' | Cys | Thr | Gly | Cys | | (SEQ ID NO: 3263) |
| Pro | Gly | Thr | Cys | Gly | Xaa' | Glu | Ile | Cys | Xaa' | Ala | Xaa' | Tyr | Ala | Ala | Xaa' | Cys | Thr | Gly | Cys | | (SEQ ID NO: 3264) |
| Pro | Gly | Thr | Cys | Gly | Xaa' | Glu | Ile | Cys | Xaa' | Ala | Xaa' | Tyr | Ala | Ala | Xaa' | Cys | Thr | Gly | Cys | | (SEQ ID NO: 3265) |
| Pro | Gly | Thr | Cys | Gly | Xaa' | Glu | Ile | Cys | Xaa' | Ala | Xaa' | Tyr | Ala | Ala | Xaa' | Cys | Thr | Gly | Xaa' | Cys | (SEQ ID NO: 3266) |
| Pro | Gly | Thr | Cys | Gly | Xaa' | Glu | Ile | Cys | Xaa' | Ala | Xaa' | Tyr | Ala | Ala | Xaa' | Cys | Thr | Gly | Cys | | (SEQ ID NO: 3267) |
| Pro | Gly | Thr | Cys | Gly | Xaa' | Glu | Ile | Cys | Xaa' | Ala | Xaa' | Tyr | Ala | Ala | Cys | Xaa' | Thr | Gly | Cys | | (SEQ ID NO: 3268) |

FIG. 2BR

| | | | | | | | | | | |
|---|---|---|---|---|---|---|---|---|---|---|
| Pro | Gly | Thr | Cys | Gly | Xaa' | Glu | Ile | Cys | Ala | Xaa' | Tyr | Ala | Ala | Cys | Xaa' | Thr | Xaa' | Gly | Cys | (SEQ ID NO: 3269) |
| Pro | Gly | Thr | Cys | Gly | Xaa' | Glu | Ile | Cys | Ala | Xaa' | Tyr | Ala | Ala | Cys | Xaa' | Thr | Gly | Xaa' | Cys | (SEQ ID NO: 3270) |
| Pro | Gly | Thr | Cys | Gly | Xaa' | Glu | Ile | Cys | Ala | Xaa' | Tyr | Ala | Ala | Cys | Xaa' | Thr | Gly | Cys | Xaa' | (SEQ ID NO: 3271) |
| Pro | Gly | Thr | Cys | Gly | Xaa' | Glu | Ile | Cys | Ala | Xaa' | Tyr | Ala | Ala | Cys | Thr | Xaa' | Gly | Cys |   | (SEQ ID NO: 3272) |
| Pro | Gly | Thr | Cys | Gly | Xaa' | Glu | Ile | Cys | Ala | Xaa' | Tyr | Ala | Ala | Cys | Thr | Gly | Xaa' | Cys |   | (SEQ ID NO: 3273) |
| Pro | Gly | Thr | Cys | Gly | Xaa' | Glu | Ile | Cys | Ala | Xaa' | Tyr | Ala | Ala | Cys | Thr | Gly | Cys | Xaa' |   | (SEQ ID NO: 3274) |
| Pro | Gly | Thr | Cys | Gly | Xaa' | Glu | Ile | Cys | Ala | Xaa' | Tyr | Ala | Ala | Cys | Xaa' | Thr | Gly | Cys |   | (SEQ ID NO: 3275) |
| Pro | Gly | Thr | Cys | Gly | Xaa' | Glu | Ile | Cys | Ala | Xaa' | Tyr | Ala | Ala | Cys | Thr | Gly | Xaa' | Cys |   | (SEQ ID NO: 3276) |
| Pro | Gly | Thr | Cys | Gly | Xaa' | Glu | Ile | Cys | Ala | Xaa' | Tyr | Ala | Ala | Cys | Thr | Gly | Cys | Xaa' |   | (SEQ ID NO: 3277) |
| Pro | Gly | Thr | Cys | Gly | Xaa' | Glu | Ile | Cys | Ala | Xaa' | Tyr | Ala | Ala | Cys | Xaa' | Thr | Gly | Cys | Xaa' | (SEQ ID NO: 3278) |
| Pro | Gly | Thr | Cys | Gly | Xaa' | Glu | Ile | Cys | Ala | Xaa' | Tyr | Ala | Ala | Cys | Thr | Gly | Cys | Xaa' |   | (SEQ ID NO: 3279) |
| Pro | Gly | Thr | Cys | Gly | Xaa' | Glu | Ile | Cys | Ala | Tyr | Xaa' | Ala | Ala | Cys | Thr | Gly | Cys |   |   | (SEQ ID NO: 3280) |
| Pro | Gly | Thr | Cys | Gly | Xaa' | Glu | Ile | Cys | Ala | Tyr | Xaa' | Ala | Ala | Cys | Thr | Gly | Cys |   |   | (SEQ ID NO: 3281) |
| Pro | Gly | Thr | Cys | Gly | Xaa' | Glu | Ile | Cys | Ala | Tyr | Xaa' | Ala | Ala | Cys | Thr | Gly | Cys |   |   | (SEQ ID NO: 3282) |
| Pro | Gly | Thr | Cys | Gly | Xaa' | Glu | Ile | Cys | Ala | Tyr | Xaa' | Ala | Ala | Cys | Ala | Thr | Gly | Cys |   | (SEQ ID NO: 3283) |
| Pro | Gly | Tyr | Cys | Gly | Xaa' | Glu | Ile | Cys | Ala | Tyr | Xaa' | Ala | Xaa' | Ala | Cys | Ala | Thr | Gly | Cys | (SEQ ID NO: 3284) |
| Pro | Gly | Thr | Cys | Gly | Xaa' | Glu | Ile | Cys | Ala | Tyr | Xaa' | Ala | Xaa' | Ala | Cys | Ala | Thr | Gly | Cys | (SEQ ID NO: 3285) |
| Pro | Gly | Thr | Cys | Gly | Xaa' | Glu | Ile | Cys | Ala | Tyr | Xaa' | Ala | Xaa' | Ala | Cys | Ala | Thr | Gly | Cys | (SEQ ID NO: 3286) |
| Pro | Gly | Thr | Cys | Gly | Xaa' | Glu | Ile | Cys | Ala | Tyr | Xaa' | Ala | Xaa' | Ala | Cys | Xaa' | Thr | Gly | Cys | (SEQ ID NO: 3287) |
| Pro | Gly | Thr | Cys | Gly | Xaa' | Glu | Ile | Cys | Ala | Tyr | Xaa' | Ala | Xaa' | Ala | Cys | Thr | Xaa' | Gly | Cys | (SEQ ID NO: 3288) |
| Pro | Gly | Thr | Cys | Gly | Xaa' | Glu | Ile | Cys | Ala | Tyr | Xaa' | Ala | Xaa' | Ala | Cys | Thr | Gly | Xaa' | Cys | (SEQ ID NO: 3289) |
| Pro | Gly | Thr | Cys | Gly | Xaa' | Glu | Ile | Cys | Ala | Tyr | Xaa' | Ala | Xaa' | Ala | Cys | Thr | Gly | Cys | Xaa' | (SEQ ID NO: 3290) |
| Pro | Gly | Thr | Cys | Gly | Xaa' | Glu | Ile | Cys | Ala | Tyr | Xaa' | Ala | Ala | Xaa' | Cys | Thr | Gly | Cys |   | (SEQ ID NO: 3291) |
| Pro | Gly | Thr | Cys | Gly | Xaa' | Glu | Ile | Cys | Ala | Tyr | Xaa' | Ala | Ala | Xaa' | Cys | Xaa' | Thr | Gly | Cys | (SEQ ID NO: 3292) |
| Pro | Gly | Thr | Cys | Gly | Xaa' | Glu | Ile | Cys | Ala | Tyr | Xaa' | Ala | Ala | Xaa' | Cys | Thr | Xaa' | Gly | Cys | (SEQ ID NO: 3293) |
| Pro | Gly | Thr | Cys | Gly | Xaa' | Glu | Ile | Cys | Ala | Tyr | Xaa' | Ala | Ala | Xaa' | Cys | Thr | Gly | Xaa' | Cys | (SEQ ID NO: 3294) |
| Pro | Gly | Thr | Cys | Gly | Xaa' | Glu | Ile | Cys | Ala | Tyr | Xaa' | Ala | Ala | Xaa' | Cys | Thr | Gly | Cys | Xaa' | (SEQ ID NO: 3295) |
| Pro | Gly | Thr | Cys | Gly | Xaa' | Glu | Ile | Cys | Ala | Tyr | Xaa' | Ala | Ala | Ala | Xaa' | Cys | Thr | Gly | Cys | (SEQ ID NO: 3296) |
| Pro | Gly | Thr | Cys | Gly | Xaa' | Glu | Ile | Cys | Ala | Tyr | Xaa' | Ala | Ala | Xaa' | Cys | Thr | Gly | Cys |   | (SEQ ID NO: 3297) |
| Pro | Gly | Thr | Cys | Gly | Xaa' | Glu | Ile | Cys | Ala | Tyr | Xaa' | Ala | Ala | Xaa' | Cys | Thr | Gly | Cys |   | (SEQ ID NO: 3298) |
| Pro | Gly | Thr | Cys | Gly | Xaa' | Glu | Ile | Cys | Ala | Tyr | Xaa' | Ala | Ala | Xaa' | Cys | Xaa' | Thr | Gly | Cys | (SEQ ID NO: 3299) |
| Pro | Gly | Thr | Cys | Gly | Xaa' | Glu | Ile | Cys | Ala | Tyr | Xaa' | Ala | Ala | Xaa' | Cys | Thr | Xaa' | Gly | Cys | (SEQ ID NO: 3300) |
| Pro | Gly | Thr | Cys | Gly | Xaa' | Glu | Ile | Cys | Ala | Tyr | Xaa' | Ala | Ala | Xaa' | Cys | Thr | Gly | Xaa' | Cys | (SEQ ID NO: 3301) |
| Pro | Gly | Thr | Cys | Gly | Xaa' | Glu | Ile | Cys | Ala | Tyr | Xaa' | Ala | Ala | Xaa' | Cys | Thr | Gly | Cys | Xaa' | (SEQ ID NO: 3302) |

FIG. 2BS

| | | | | | | | | | | | |
|---|---|---|---|---|---|---|---|---|---|---|---|
| Pro Gly Thr Cys Gly Xaa' | Glu Ile Cys Ala Tyr Xaa' | Ala Ala Cys Xaa' | Thr Gly Cys | | (SEQ ID NO: 3303) |
| Pro Gly Thr Cys Gly Xaa' | Glu Ile Cys Ala Tyr Xaa' | Ala Ala Cys Xaa' | Xaa' Thr Gly Cys | | (SEQ ID NO: 3304) |
| Pro Gly Thr Cys Gly Xaa' | Glu Ile Cys Ala Tyr Xaa' | Ala Ala Cys Xaa' | Thr Xaa' Gly Cys | | (SEQ ID NO: 3305) |
| Pro Gly Thr Cys Gly Xaa' | Glu Ile Cys Ala Tyr Xaa' | Ala Ala Cys Xaa' | Thr Gly Xaa' Cys | | (SEQ ID NO: 3306) |
| Pro Gly Thr Cys Gly Xaa' | Glu Ile Cys Ala Tyr Xaa' | Ala Ala Cys Xaa' | Thr Gly Cys Xaa' | | (SEQ ID NO: 3307) |
| Pro Gly Thr Cys Gly Xaa' | Glu Ile Cys Ala Tyr Xaa' | Ala Ala Cys Xaa' | Xaa' Thr Gly Cys | | (SEQ ID NO: 3308) |
| Pro Gly Thr Cys Gly Xaa' | Glu Ile Cys Ala Tyr Xaa' | Ala Ala Cys Xaa' | Xaa' Gly Cys | | (SEQ ID NO: 3309) |
| Pro Gly Thr Cys Gly Xaa' | Glu Ile Cys Ala Tyr Xaa' | Ala Ala Cys Xaa' | Xaa' Gly Xaa' Cys | | (SEQ ID NO: 3310) |
| Pro Gly Thr Cys Gly Xaa' | Glu Ile Cys Ala Tyr Xaa' | Ala Ala Cys Xaa' | Xaa' Gly Cys Xaa' | | (SEQ ID NO: 3311) |
| Pro Gly Thr Cys Gly Xaa' | Glu Ile Cys Ala Tyr Xaa' | Ala Ala Cys Xaa' | Thr Gly Cys | | (SEQ ID NO: 3312) |
| Pro Gly Thr Cys Gly Xaa' | Glu Ile Cys Ala Tyr Xaa' | Ala Ala Cys Xaa' | Xaa' Thr Gly Cys | | (SEQ ID NO: 3313) |
| Pro Gly Thr Cys Gly Xaa' | Glu Ile Cys Ala Tyr Xaa' | Ala Ala Cys Xaa' | Xaa' Cys Xaa' | | (SEQ ID NO: 3314) |
| Pro Gly Thr Cys Gly Xaa' | Glu Ile Cys Ala Tyr Xaa' | Ala Ala Cys Xaa' | Gly Cys Xaa' | | (SEQ ID NO: 3315) |
| Pro Gly Thr Cys Gly Xaa' | Glu Ile Cys Ala Tyr Xaa' | Ala Ala Cys Xaa' | Thr Gly Cys Xaa' | | (SEQ ID NO: 3316) |
| Pro Gly Thr Cys Gly Xaa' | Glu Ile Cys Ala Tyr Ala | Xaa' Ala Cys Xaa' | Thr Gly Cys | | (SEQ ID NO: 3317) |
| Pro Gly Thr Cys Gly Xaa' | Glu Ile Cys Ala Tyr Ala | Xaa' Ala Cys Xaa' | Ala Cys Thr Gly Cys | | (SEQ ID NO: 3318) |
| Pro Gly Thr Cys Gly Xaa' | Glu Ile Cys Ala Tyr Ala | Xaa' Ala Cys Ala | Cys Thr Gly Cys | | (SEQ ID NO: 3319) |
| Pro Gly Thr Cys Gly Xaa' | Glu Ile Cys Ala Tyr Ala | Xaa' Ala Cys Xaa' | Cys Thr Gly Cys | | (SEQ ID NO: 3320) |
| Pro Gly Thr Cys Gly Xaa' | Glu Ile Cys Ala Tyr Ala | Xaa' Ala Xaa' Cys Xaa' | Thr Gly Cys Xaa' | | (SEQ ID NO: 3321) |
| Pro Gly Thr Cys Gly Xaa' | Glu Ile Cys Ala Tyr Ala | Xaa' Ala Cys Xaa' | Thr Xaa' Gly Cys | | (SEQ ID NO: 3322) |
| Pro Gly Thr Cys Gly Xaa' | Glu Ile Cys Ala Tyr Ala | Xaa' Ala Cys Xaa' | Thr Gly Xaa' Cys | | (SEQ ID NO: 3323) |
| Pro Gly Thr Cys Gly Xaa' | Glu Ile Cys Ala Tyr Ala | Xaa' Ala Cys Xaa' | Thr Gly Cys Xaa' | | (SEQ ID NO: 3324) |
| Pro Gly Thr Cys Gly Xaa' | Glu Ile Cys Ala Tyr Ala | Xaa' Ala Cys Xaa' | Cys Thr Gly Cys | | (SEQ ID NO: 3325) |
| Pro Gly Thr Cys Gly Xaa' | Glu Ile Cys Ala Tyr Ala | Xaa' Ala Xaa' Cys Xaa' | Thr Gly Cys | | (SEQ ID NO: 3326) |
| Pro Gly Thr Cys Gly Xaa' | Glu Ile Cys Ala Tyr Ala | Xaa' Ala Cys Xaa' | Thr Xaa' Gly Cys | | (SEQ ID NO: 3327) |
| Pro Gly Thr Cys Gly Xaa' | Glu Ile Cys Ala Tyr Ala | Xaa' Ala Cys Xaa' | Thr Gly Xaa' Cys | | (SEQ ID NO: 3328) |
| Pro Gly Thr Cys Gly Xaa' | Glu Ile Cys Ala Tyr Ala | Xaa' Ala Cys Xaa' | Thr Gly Cys Xaa' | | (SEQ ID NO: 3329) |
| Pro Gly Thr Cys Gly Xaa' | Glu Ile Cys Ala Tyr Ala | Xaa' Ala Cys Ala | Cys Thr Gly Cys | | (SEQ ID NO: 3330) |
| Pro Gly Thr Cys Gly Xaa' | Glu Ile Cys Ala Tyr Ala | Xaa' Ala Cys Ala | Thr Gly Cys | | (SEQ ID NO: 3331) |
| Pro Gly Thr Cys Gly Xaa' | Glu Ile Cys Ala Tyr Ala | Xaa' Ala Cys Ala | Cys Thr Gly Cys | | (SEQ ID NO: 3332) |
| Pro Gly Thr Cys Gly Xaa' | Glu Ile Cys Ala Tyr Ala | Xaa' Ala Cys Ala | Xaa' Thr Gly Cys | | (SEQ ID NO: 3333) |
| Pro Gly Thr Cys Gly Xaa' | Glu Ile Cys Ala Tyr Ala | Xaa' Ala Cys Ala | Thr Xaa' Gly Cys | | (SEQ ID NO: 3334) |
| Pro Gly Thr Cys Gly Xaa' | Glu Ile Cys Ala Tyr Ala | Xaa' Ala Cys Ala | Thr Gly Xaa' Cys | | (SEQ ID NO: 3335) |
| Pro Gly Thr Cys Gly Xaa' | Glu Ile Cys Ala Tyr Ala | Xaa' Ala Cys Ala | Thr Gly Cys Xaa' | | (SEQ ID NO: 3336) |

FIG. 2BT

| | | | | | | | | | | | |
|---|---|---|---|---|---|---|---|---|---|---|---|
| Pro | Gly | Thr | Cys | Gly | Xaa' | Glu | Ile | Cys | Ala | Tyr | Ala Cys Thr Xaa' Xaa' Gly Cys | (SEQ ID NO: 3337) |
| Pro | Gly | Thr | Cys | Gly | Xaa' | Glu | Ile | Cys | Ala | Tyr | Ala Cys Thr Xaa' Ala Gly Xaa' Cys | (SEQ ID NO: 3338) |
| Pro | Gly | Thr | Cys | Gly | Xaa' | Glu | Ile | Cys | Ala | Tyr | Ala Cys Thr Xaa' Ala Gly Cys Xaa' | (SEQ ID NO: 3339) |
| Pro | Gly | Thr | Cys | Gly | Xaa' | Glu | Ile | Cys | Ala | Tyr | Ala Cys Thr Xaa' Ala Gly Xaa' Cys | (SEQ ID NO: 3340) |
| Pro | Gly | Thr | Cys | Gly | Xaa' | Glu | Ile | Cys | Ala | Tyr | Ala Cys Thr Xaa' Ala Cys Xaa' Xaa' | (SEQ ID NO: 3341) |

*(Note: Due to image resolution limitations, only partial transcription shown. The figure contains a repetitive sequence listing with SEQ ID NOs: 3337 through 3370, each showing variants of the peptide sequence "Pro Gly Thr Cys Gly Xaa' Glu Ile Cys Ala Tyr Ala Cys Thr..." with varying C-terminal residues.)*

FIG. 2BU

Pro Gly Thr Cys Gly Xaa' Glu Ile Cys Ala Tyr Ala Ala Cys Xaa' Xaa' Thr Gly Cys Xaa' (SEQ ID NO: 3371)
Pro Gly Thr Cys Gly Xaa' Glu Ile Cys Ala Tyr Ala Ala Cys Xaa' Xaa' Thr Gly Cys (SEQ ID NO: 3372)
Pro Gly Thr Cys Gly Xaa' Glu Ile Cys Ala Tyr Ala Ala Cys Xaa' Xaa' Thr Xaa' Gly Cys (SEQ ID NO: 3373)
Pro Gly Thr Cys Gly Xaa' Glu Ile Cys Ala Tyr Ala Ala Cys Xaa' Xaa' Thr Xaa' Gly Cys (SEQ ID NO: 3374)
Pro Gly Thr Cys Gly Xaa' Glu Ile Cys Ala Tyr Ala Ala Cys Xaa' Xaa' Thr Xaa' Gly Cys Xaa' (SEQ ID NO: 3375)
Pro Gly Thr Cys Gly Xaa' Glu Ile Cys Ala Tyr Ala Ala Cys Xaa' Xaa' Thr Xaa' Gly Cys Xaa' (SEQ ID NO: 3376)
Pro Gly Thr Cys Gly Xaa' Glu Ile Cys Ala Tyr Ala Ala Cys Xaa' Xaa' Thr Gly Xaa' Cys (SEQ ID NO: 3377)
Pro Gly Thr Cys Gly Xaa' Glu Ile Cys Ala Tyr Ala Ala Cys Xaa' Xaa' Thr Gly Xaa' Cys Xaa' (SEQ ID NO: 3378)
Pro Gly Thr Cys Gly Xaa' Glu Ile Cys Ala Tyr Ala Ala Cys Xaa' Xaa' Thr Gly Cys Xaa' (SEQ ID NO: 3379)
Pro Gly Thr Cys Gly Xaa' Glu Ile Cys Ala Tyr Ala Ala Cys Xaa' Xaa' Thr Gly Cys Xaa' (SEQ ID NO: 3380)
Pro Gly Thr Cys Gly Xaa' Glu Ile Cys Ala Tyr Ala Ala Cys Thr Xaa' Xaa' Gly Cys (SEQ ID NO: 3381)
Pro Gly Thr Cys Gly Xaa' Glu Ile Cys Ala Tyr Ala Ala Cys Thr Xaa' Xaa' Gly Cys (SEQ ID NO: 3382)
Pro Gly Thr Cys Gly Xaa' Glu Ile Cys Ala Tyr Ala Ala Cys Thr Xaa' Xaa' Xaa' Gly Cys (SEQ ID NO: 3383)
Pro Gly Thr Cys Gly Xaa' Glu Ile Cys Ala Tyr Ala Ala Cys Thr Xaa' Xaa' Xaa' Gly Cys (SEQ ID NO: 3384)
Pro Gly Thr Cys Gly Xaa' Glu Ile Cys Ala Tyr Ala Ala Cys Thr Xaa' Xaa' Gly Cys Xaa' (SEQ ID NO: 3385)
Pro Gly Thr Cys Gly Xaa' Glu Ile Cys Ala Tyr Ala Ala Cys Thr Xaa' Xaa' Gly Cys (SEQ ID NO: 3386)
Pro Gly Thr Cys Gly Xaa' Glu Ile Cys Ala Tyr Ala Ala Cys Thr Xaa' Gly Xaa' Xaa' Cys (SEQ ID NO: 3387)
Pro Gly Thr Cys Gly Xaa' Glu Ile Cys Ala Tyr Ala Ala Cys Thr Xaa' Gly Xaa' Cys Xaa' (SEQ ID NO: 3388)
Pro Gly Thr Cys Gly Xaa' Glu Ile Cys Ala Tyr Ala Ala Cys Thr Xaa' Gly Xaa' Cys Xaa' (SEQ ID NO: 3389)
Pro Gly Thr Cys Gly Xaa' Glu Ile Cys Ala Tyr Ala Ala Cys Thr Xaa' Gly Cys Xaa' (SEQ ID NO: 3390)
Pro Gly Thr Cys Gly Xaa' Glu Ile Cys Ala Tyr Ala Ala Cys Thr Xaa' Gly Cys (SEQ ID NO: 3391)
Pro Gly Thr Cys Gly Xaa' Glu Ile Cys Ala Tyr Ala Ala Cys Thr Gly Xaa' Xaa' Cys (SEQ ID NO: 3392)
Pro Gly Thr Cys Gly Xaa' Glu Ile Cys Ala Tyr Ala Ala Cys Thr Gly Xaa' Xaa' Xaa' Cys (SEQ ID NO: 3393)
Pro Gly Thr Cys Gly Xaa' Glu Ile Cys Ala Tyr Ala Ala Cys Thr Gly Xaa' Xaa' Gly Cys (SEQ ID NO: 3394)
Pro Gly Thr Cys Gly Xaa' Glu Ile Cys Ala Tyr Ala Ala Cys Thr Gly Xaa' Xaa' Cys Xaa' (SEQ ID NO: 3395)
Pro Gly Thr Cys Gly Xaa' Glu Ile Cys Ala Tyr Ala Ala Cys Thr Gly Xaa' Cys Xaa' Xaa' (SEQ ID NO: 3396)
Pro Gly Thr Cys Gly Xaa' Glu Ile Cys Ala Tyr Ala Ala Cys Thr Gly Cys Xaa' (SEQ ID NO: 3397)
Pro Gly Thr Cys Gly Xaa' Glu Ile Cys Ala Tyr Ala Ala Cys Gly Cys Xaa' (SEQ ID NO: 3398)
Pro Gly Thr Cys Gly Xaa' Glu Ile Cys Ala Tyr Ala Ala Cys Gly Cys Thr Gly Cys (SEQ ID NO: 3399)
Pro Gly Thr Cys Gly Xaa' Glu Ile Cys Ala Tyr Ala Ala Cys Ile Cys Ala Ala Cys Thr Gly Cys (SEQ ID NO: 3400)
Pro Gly Thr Cys Gly Xaa' Glu Ile Cys Ala Tyr Ala Ala Cys Ile Cys Ala Tyr Ala Ala Cys Thr Gly Cys (SEQ ID NO: 3401)
Pro Gly Thr Cys Gly Xaa' Glu Xaa' Xaa' Xaa' Xaa' Xaa' Xaa' Xaa' Cys Ala Tyr Ala Ala Cys Thr Gly Cys (SEQ ID NO: 3402)
Pro Gly Thr Cys Gly Xaa' Glu Xaa' Xaa' Xaa' Xaa' Xaa' Xaa' Xaa' Ile Cys Ala Tyr Ala Ala Cys Thr Gly Cys (SEQ ID NO: 3403)
Pro Gly Thr Cys Gly Glu Xaa' Xaa' Xaa' Xaa' Xaa' Xaa' Xaa' Ile Xaa' Cys Ala Tyr Ala Ala Cys Thr Gly Cys (SEQ ID NO: 3404)

FIG. 2BV

Pro Gly Thr Cys Gly Glu Xaa' Xaa' Xaa' Ile Cys Xaa' Ala Tyr Ala Ala Cys Thr Gly Cys (SEQID NO: 3405 )
Pro Gly Thr Cys Gly Glu Xaa' Xaa' Xaa' Ile Cys Ala Xaa' Tyr Ala Ala Cys Thr Gly Cys (SEQID NO: 3406 )
Pro Gly Thr Cys Gly Glu Xaa' Xaa' Xaa' Ile Cys Ala Tyr Xaa' Ala Ala Cys Thr Gly Cys (SEQID NO: 3407 )
Pro Gly Thr Cys Gly Glu Xaa' Xaa' Xaa' Ile Cys Ala Tyr Ala Xaa' Ala Cys Thr Gly Cys (SEQID NO: 3408 )
Pro Gly Thr Cys Gly Glu Xaa' Xaa' Xaa' Ile Cys Ala Tyr Ala Ala Xaa' Cys Thr Gly Cys (SEQID NO: 3409 )
Pro Gly Thr Cys Gly Glu Xaa' Xaa' Xaa' Ile Cys Ala Tyr Ala Ala Cys Xaa' Thr Gly Cys (SEQID NO: 3410 )
Pro Gly Thr Cys Gly Glu Xaa' Xaa' Xaa' Ile Cys Ala Tyr Ala Ala Cys Thr Xaa' Gly Cys (SEQID NO: 3411 )
Pro Gly Thr Cys Gly Glu Xaa' Xaa' Xaa' Ile Cys Ala Tyr Ala Ala Cys Thr Gly Xaa' Cys (SEQID NO: 3412 )
Pro Gly Thr Cys Gly Glu Xaa' Xaa' Xaa' Ile Cys Ala Tyr Ala Ala Cys Thr Gly Cys Xaa' (SEQID NO: 3413 )
Pro Gly Thr Cys Gly Glu Xaa' Xaa' Ile Xaa' Cys Ala Tyr Ala Ala Cys Thr Gly Cys (SEQID NO: 3414 )
Pro Gly Thr Cys Gly Glu Xaa' Xaa' Ile Xaa' Xaa' Cys Ala Tyr Ala Ala Cys Thr Gly Cys (SEQID NO: 3415 )
Pro Gly Thr Cys Gly Glu Xaa' Xaa' Ile Xaa' Cys Xaa' Ala Tyr Ala Ala Cys Thr Gly Cys (SEQID NO: 3416 )
Pro Gly Thr Cys Gly Glu Xaa' Xaa' Ile Xaa' Cys Ala Xaa' Tyr Ala Ala Cys Thr Gly Cys (SEQID NO: 3417 )
Pro Gly Thr Cys Gly Glu Xaa' Xaa' Ile Xaa' Cys Ala Tyr Xaa' Ala Ala Cys Thr Gly Cys (SEQID NO: 3418 )
Pro Gly Thr Cys Gly Glu Xaa' Xaa' Ile Xaa' Cys Ala Tyr Ala Xaa' Ala Cys Thr Gly Cys (SEQID NO: 3419 )
Pro Gly Thr Cys Gly Glu Xaa' Xaa' Ile Xaa' Cys Ala Tyr Ala Ala Xaa' Cys Thr Gly Cys (SEQID NO: 3420 )
Pro Gly Thr Cys Gly Glu Xaa' Xaa' Ile Xaa' Cys Ala Tyr Ala Ala Cys Xaa' Thr Gly Cys (SEQID NO: 3421 )
Pro Gly Thr Cys Gly Glu Xaa' Xaa' Ile Xaa' Cys Ala Tyr Ala Ala Cys Thr Xaa' Gly Cys (SEQID NO: 3422 )
Pro Gly Thr Cys Gly Glu Xaa' Xaa' Ile Xaa' Cys Ala Tyr Ala Ala Cys Thr Gly Xaa' Cys (SEQID NO: 3423 )
Pro Gly Thr Cys Gly Glu Xaa' Xaa' Ile Xaa' Cys Ala Tyr Ala Ala Cys Thr Gly Cys Xaa' (SEQID NO: 3424 )
Pro Gly Thr Cys Gly Glu Xaa' Xaa' Ile Cys Xaa' Ala Tyr Ala Ala Cys Thr Gly Cys (SEQID NO: 3425 )
Pro Gly Thr Cys Gly Glu Xaa' Xaa' Ile Cys Xaa' Xaa' Ala Tyr Ala Ala Cys Thr Gly Cys (SEQID NO: 3426 )
Pro Gly Thr Cys Gly Glu Xaa' Xaa' Ile Cys Xaa' Ala Xaa' Tyr Ala Ala Cys Thr Gly Cys (SEQID NO: 3427 )
Pro Gly Thr Cys Gly Glu Xaa' Xaa' Ile Cys Xaa' Ala Tyr Xaa' Ala Ala Cys Thr Gly Cys (SEQID NO: 3428 )
Pro Gly Thr Cys Gly Glu Xaa' Xaa' Ile Cys Xaa' Ala Tyr Ala Xaa' Ala Cys Thr Gly Cys (SEQID NO: 3429 )
Pro Gly Thr Cys Gly Glu Xaa' Xaa' Ile Cys Xaa' Ala Tyr Ala Ala Xaa' Cys Thr Gly Cys (SEQID NO: 3430 )
Pro Gly Thr Cys Gly Glu Xaa' Xaa' Ile Cys Xaa' Ala Tyr Ala Ala Cys Xaa' Thr Gly Cys (SEQID NO: 3431 )
Pro Gly Thr Cys Gly Glu Xaa' Xaa' Ile Cys Xaa' Ala Tyr Ala Ala Cys Thr Xaa' Gly Cys (SEQID NO: 3432 )
Pro Gly Thr Cys Gly Glu Xaa' Xaa' Ile Cys Xaa' Ala Tyr Ala Ala Cys Thr Gly Xaa' Cys (SEQID NO: 3433 )
Pro Gly Thr Cys Gly Glu Xaa' Xaa' Ile Cys Xaa' Ala Tyr Ala Ala Cys Thr Gly Cys Xaa' (SEQID NO: 3434 )
Pro Gly Thr Cys Gly Glu Xaa' Xaa' Ile Cys Ala Xaa' Tyr Ala Ala Cys Thr Gly Cys (SEQID NO: 3435 )
Pro Gly Thr Cys Gly Glu Xaa' Xaa' Ile Cys Ala Xaa' Xaa' Tyr Ala Ala Cys Thr Gly Cys (SEQID NO: 3436 )
Pro Gly Thr Cys Gly Glu Xaa' Xaa' Ile Cys Ala Xaa' Tyr Xaa' Ala Ala Cys Thr Gly Cys (SEQID NO: 3437 )
Pro Gly Thr Cys Gly Glu Xaa' Xaa' Ile Cys Ala Xaa' Tyr Ala Xaa' Ala Cys Thr Gly Cys (SEQID NO: 3438 )

FIG. 2BW

```
Pro Gly Thr Cys Gly Glu Xaa' Ile Cys Ala Tyr Ala Ala Xaa' Cys Thr Gly Cys      (SEQ ID NO: 3439)
Pro Gly Thr Cys Gly Glu Xaa' Ile Cys Ala Tyr Ala Ala Xaa' Cys Thr Gly Cys      (SEQ ID NO: 3440)
Pro Gly Thr Cys Gly Glu Xaa' Ile Cys Ala Tyr Ala Ala Xaa' Cys Thr Gly Cys      (SEQ ID NO: 3441)
Pro Gly Thr Cys Gly Glu Xaa' Ile Cys Ala Tyr Ala Ala Xaa' Cys Thr Gly Cys      (SEQ ID NO: 3442)
Pro Gly Thr Cys Gly Glu Xaa' Ile Cys Ala Tyr Ala Ala Xaa' Cys Thr Gly Xaa'     (SEQ ID NO: 3443)
Pro Gly Thr Cys Gly Glu Xaa' Ile Cys Ala Tyr Xaa' Ala Ala Cys Thr Gly Cys      (SEQ ID NO: 3444)
Pro Gly Thr Cys Gly Glu Xaa' Ile Cys Ala Tyr Xaa' Ala Ala Cys Thr Gly Cys      (SEQ ID NO: 3445)
Pro Gly Thr Cys Gly Glu Xaa' Ile Cys Ala Tyr Xaa' Ala Ala Cys Thr Gly Cys      (SEQ ID NO: 3446)
Pro Gly Thr Cys Gly Glu Xaa' Ile Cys Ala Tyr Xaa' Ala Ala Cys Thr Gly Cys      (SEQ ID NO: 3447)
Pro Gly Thr Cys Gly Glu Xaa' Ile Cys Ala Tyr Xaa' Ala Ala Cys Thr Gly Cys      (SEQ ID NO: 3448)
Pro Gly Thr Cys Gly Glu Xaa' Ile Cys Ala Tyr Xaa' Ala Ala Cys Thr Gly Cys      (SEQ ID NO: 3449)
Pro Gly Thr Cys Gly Glu Xaa' Ile Cys Ala Tyr Xaa' Ala Ala Cys Thr Gly Xaa'     (SEQ ID NO: 3450)
Pro Gly Thr-Cys Gly Glu Xaa' Ile Cys Ala Tyr Ala Xaa' Ala Cys Thr Gly Cys      (SEQ ID NO: 3451)
Pro Gly Thr Cys Gly Glu Xaa' Ile Cys Ala Tyr Ala Xaa' Ala Cys Thr Gly Cys      (SEQ ID NO: 3452)
Pro Gly Thr Cys Gly Glu Xaa' Ile Cys Ala Tyr Ala Xaa' Ala Cys Thr Gly Cys      (SEQ ID NO: 3453)
Pro Gly Thr Cys Gly Glu Xaa' Ile Cys Ala Tyr Ala Xaa' Ala Cys Thr Gly Cys      (SEQ ID NO: 3454)
Pro Gly Thr Cys Gly Glu Xaa' Ile Cys Ala Tyr Ala Xaa' Ala Cys Thr Gly Cys      (SEQ ID NO: 3455)
Pro Gly Thr Cys Gly Glu Xaa' Ile Cys Ala Tyr Ala Xaa' Ala Cys Thr Gly Cys      (SEQ ID NO: 3456)
Pro Gly Thr Cys Gly Glu Xaa' Ile Cys Ala Tyr Ala Xaa' Ala Cys Thr Gly Xaa'     (SEQ ID NO: 3457)
Pro Gly Thr Cys Gly Glu Xaa' Ile Cys Ala Tyr Ala Ala Xaa' Cys Thr Gly Cys      (SEQ ID NO: 3458)
Pro Gly Thr Cys Gly Glu Xaa' Ile Cys Ala Tyr Ala Ala Xaa' Cys Thr Gly Cys      (SEQ ID NO: 3459)
Pro Gly Thr Cys Gly Glu Xaa' Ile Cys Ala Tyr Ala Ala Xaa' Cys Thr Gly Cys      (SEQ ID NO: 3460)
Pro Gly Thr Cys Gly Glu Xaa' Ile Cys Ala Tyr Ala Ala Xaa' Cys Thr Gly Cys      (SEQ ID NO: 3461)
Pro Gly Thr Cys Gly Glu Xaa' Ile Cys Ala Tyr Ala Ala Xaa' Cys Thr Gly Cys      (SEQ ID NO: 3462)
Pro Gly Thr Cys Gly Glu Xaa' Ile Cys Ala Tyr Ala Ala Xaa' Cys Thr Gly Cys      (SEQ ID NO: 3463)
Pro Gly Thr Cys Gly Glu Xaa' Ile Cys Ala Tyr Ala Ala Xaa' Cys Thr Gly Xaa'     (SEQ ID NO: 3464)
Pro Gly Thr Cys Gly Glu Xaa' Ile Cys Ala Tyr Ala Ala Cys Xaa' Thr Gly Cys      (SEQ ID NO: 3465)
Pro Gly Thr Cys Gly Glu Xaa' Ile Cys Ala Tyr Ala Ala Cys Xaa' Thr Gly Cys      (SEQ ID NO: 3466)
Pro Gly Thr Cys Gly Glu Xaa' Ile Cys Ala Tyr Ala Ala Cys Xaa' Thr Gly Cys      (SEQ ID NO: 3467)
Pro Gly Thr Cys Gly Glu Xaa' Ile Cys Ala Tyr Ala Ala Cys Xaa' Thr Gly Cys      (SEQ ID NO: 3468)
Pro Gly Thr Cys Gly Glu Xaa' Ile Cys Ala Tyr Ala Ala Cys Xaa' Thr Gly Cys      (SEQ ID NO: 3469)
Pro Gly Thr Cys Gly Glu Xaa' Ile Cys Ala Tyr Ala Ala Cys Thr Xaa' Gly Cys      (SEQ ID NO: 3470)
Pro Gly Thr Cys Gly Glu Xaa' Ile Cys Ala Tyr Ala Ala Cys Thr Xaa' Gly Cys      (SEQ ID NO: 3471)
Pro Gly Thr Cys Gly Glu Xaa' Ile Cys Ala Tyr Ala Ala Cys Thr Xaa' Gly Cys      (SEQ ID NO: 3472)
```

FIG. 2BX

| | | | | | | | | | | | | |
|---|---|---|---|---|---|---|---|---|---|---|---|---|
| Pro | Gly | Thr | Cys | Gly | Glu | Xaa' | Ile | Cys | Ala | Tyr | Ala | Ala | Cys | Thr | Xaa' | Gly | Cys | Xaa' | (SEQ ID NO: 3473) |
| Pro | Gly | Thr | Cys | Gly | Glu | Xaa' | Ile | Cys | Ala | Tyr | Ala | Ala | Cys | Thr | Gly | Xaa' | Cys | | (SEQ ID NO: 3474) |
| Pro | Gly | Thr | Cys | Gly | Glu | Xaa' | Ile | Cys | Ala | Tyr | Ala | Ala | Cys | Thr | Gly | Xaa' | Cys | Xaa' | (SEQ ID NO: 3475) |
| Pro | Gly | Thr | Cys | Gly | Glu | Xaa' | Ile | Cys | Ala | Tyr | Ala | Ala | Cys | Thr | Gly | Cys | Xaa' | | (SEQ ID NO: 3476) |
| Pro | Gly | Thr | Cys | Gly | Glu | Xaa' | Ile | Cys | Ala | Tyr | Ala | Ala | Cys | Thr | Gly | Cys | Xaa' | | (SEQ ID NO: 3477) |
| Pro | Gly | Thr | Cys | Gly | Glu | Xaa' | Ile | Cys | Ala | Tyr | Ala | Ala | Cys | Thr | Gly | Cys | Xaa' | Xaa' | (SEQ ID NO: 3478) |
| Pro | Gly | Thr | Cys | Gly | Glu | Xaa' | Ile | Cys | Ala | Tyr | Ala | Ala | Cys | Thr | Gly | Cys | | | (SEQ ID NO: 3479) |
| Pro | Gly | Thr | Cys | Gly | Glu | Xaa' | Ile | Xaa' | Cys | Ala | Tyr | Ala | Ala | Cys | Thr | Gly | Cys | | (SEQ ID NO: 3480) |
| Pro | Gly | Thr | Cys | Gly | Glu | Xaa' | Ile | Xaa' | Cys | Ala | Tyr | Ala | Ala | Cys | Thr | Gly | Cys | | (SEQ ID NO: 3481) |
| Pro | Gly | Thr | Cys | Gly | Glu | Xaa' | Ile | Xaa' | Cys | Xaa' | Ala | Tyr | Ala | Ala | Cys | Thr | Gly | Cys | (SEQ ID NO: 3482) |
| Pro | Gly | Thr | Cys | Gly | Glu | Xaa' | Ile | Xaa' | Cys | Xaa' | Ala | Tyr | Ala | Ala | Cys | Thr | Gly | Cys | (SEQ ID NO: 3483) |
| Pro | Gly | Thr | Cys | Gly | Glu | Xaa' | Ile | Xaa' | Cys | Xaa' | Ala | Tyr | Ala | Ala | Cys | Thr | Gly | Cys | (SEQ ID NO: 3484) |
| Pro | Gly | Thr | Cys | Gly | Glu | Xaa' | Ile | Xaa' | Cys | Xaa' | Ala | Tyr | Ala | Xaa' | Ala | Cys | Thr | Gly | Cys | (SEQ ID NO: 3485) |
| Pro | Gly | Thr | Cys | Gly | Glu | Xaa' | Ile | Xaa' | Cys | Xaa' | Ala | Tyr | Ala | Xaa' | Ala | Cys | Thr | Gly | Cys | (SEQ ID NO: 3486) |
| Pro | Gly | Thr | Cys | Gly | Glu | Xaa' | Ile | Xaa' | Cys | Xaa' | Ala | Tyr | Ala | Ala | Cys | Xaa' | Thr | Gly | Cys | (SEQ ID NO: 3487) |
| Pro | Gly | Thr | Cys | Gly | Glu | Xaa' | Ile | Xaa' | Cys | Xaa' | Ala | Tyr | Ala | Ala | Cys | Thr | Gly | Xaa' | Cys | (SEQ ID NO: 3488) |
| Pro | Gly | Thr | Cys | Gly | Glu | Xaa' | Ile | Xaa' | Cys | Xaa' | Ala | Tyr | Ala | Ala | Cys | Thr | Gly | Xaa' | Cys | (SEQ ID NO: 3489) |
| Pro | Gly | Thr | Cys | Gly | Glu | Xaa' | Ile | Xaa' | Cys | Xaa' | Ala | Tyr | Ala | Ala | Cys | Thr | Gly | Cys | Xaa' | (SEQ ID NO: 3490) |
| Pro | Gly | Thr | Cys | Gly | Glu | Xaa' | Ile | Xaa' | Cys | Xaa' | Ala | Ala | Ala | Cys | Thr | Gly | Cys | | (SEQ ID NO: 3491) |
| Pro | Gly | Thr | Cys | Gly | Glu | Xaa' | Ile | Xaa' | Cys | Xaa' | Xaa' | Ala | Tyr | Ala | Ala | Cys | Thr | Gly | Cys | (SEQ ID NO: 3492) |
| Pro | Gly | Thr | Cys | Gly | Glu | Xaa' | Ile | Xaa' | Cys | Xaa' | Ala | Xaa' | Tyr | Ala | Ala | Cys | Thr | Gly | Cys | (SEQ ID NO: 3493) |
| Pro | Gly | Thr | Cys | Gly | Glu | Xaa' | Ile | Xaa' | Cys | Xaa' | Ala | Tyr | Xaa' | Ala | Ala | Cys | Thr | Gly | Cys | (SEQ ID NO: 3494) |
| Pro | Gly | Thr | Cys | Gly | Glu | Xaa' | Ile | Xaa' | Cys | Xaa' | Ala | Tyr | Ala | Xaa' | Ala | Cys | Thr | Gly | Cys | Xaa' | (SEQ ID NO: 3495) |
| Pro | Gly | Thr | Cys | Gly | Glu | Xaa' | Ile | Xaa' | Cys | Xaa' | Ala | Tyr | Ala | Ala | Xaa' | Cys | Thr | Gly | Cys | (SEQ ID NO: 3496) |
| Pro | Gly | Thr | Cys | Gly | Glu | Xaa' | Ile | Xaa' | Cys | Xaa' | Ala | Tyr | Ala | Ala | Cys | Xaa' | Thr | Gly | Cys | (SEQ ID NO: 3497) |
| Pro | Gly | Thr | Cys | Gly | Glu | Xaa' | Ile | Xaa' | Cys | Xaa' | Ala | Tyr | Ala | Ala | Cys | Thr | Xaa' | Gly | Cys | (SEQ ID NO: 3498) |
| Pro | Gly | Thr | Cys | Gly | Glu | Xaa' | Ile | Xaa' | Cys | Xaa' | Ala | Tyr | Ala | Ala | Cys | Thr | Gly | Xaa' | Cys | (SEQ ID NO: 3499) |
| Pro | Gly | Thr | Cys | Gly | Glu | Xaa' | Ile | Xaa' | Cys | Xaa' | Ala | Tyr | Ala | Ala | Cys | Thr | Gly | Cys | Xaa' | (SEQ ID NO: 3500) |
| Pro | Gly | Thr | Cys | Gly | Glu | Xaa' | Ile | Xaa' | Cys | Ala | Xaa' | Tyr | Ala | Ala | Cys | Thr | Gly | Cys | | (SEQ ID NO: 3501) |
| Pro | Gly | Thr | Cys | Gly | Glu | Xaa' | Ile | Xaa' | Cys | Ala | Tyr | Xaa' | Ala | Ala | Cys | Thr | Gly | Cys | | (SEQ ID NO: 3502) |
| Pro | Gly | Thr | Cys | Gly | Glu | Xaa' | Ile | Xaa' | Cys | Ala | Tyr | Ala | Xaa' | Ala | Cys | Thr | Gly | Cys | | (SEQ ID NO: 3503) |
| Pro | Gly | Thr | Cys | Gly | Glu | Xaa' | Ile | Xaa' | Cys | Ala | Tyr | Ala | Ala | Xaa' | Cys | Thr | Gly | Cys | | (SEQ ID NO: 3504) |
| Pro | Gly | Thr | Cys | Gly | Glu | Xaa' | Ile | Xaa' | Cys | Ala | Tyr | Ala | Ala | Cys | Xaa' | Thr | Gly | Cys | | (SEQ ID NO: 3505) |
| Pro | Gly | Thr | Cys | Gly | Glu | Xaa' | Ile | Xaa' | Cys | Ala | Tyr | Ala | Ala | Cys | Xaa' | Thr | Gly | Cys | | (SEQ ID NO: 3506) |

FIG. 2BY

| | | | | | | | | | | | | |
|---|---|---|---|---|---|---|---|---|---|---|---|---|
| Pro | Gly | Thr | Cys | Gly | Glu | Xaa' | Ile | Xaa' | Cys | Ala | Xaa' | Tyr | Ala | Ala | Xaa' | Tyr | Ala | Ala | Cys | Thr | Xaa' | Gly | Cys | (SEQ ID NO: 3507) |
| Pro | Gly | Thr | Cys | Gly | Glu | Xaa' | Ile | Xaa' | Cys | Ala | Xaa' | Tyr | Ala | Ala | Xaa' | Tyr | Ala | Ala | Cys | Thr | Xaa' | Gly | Cys | (SEQ ID NO: 3508) |

(Figure 2BZ — table of peptide sequences SEQ ID NO: 3507 through 3540, each of the form:
Pro Gly Thr Cys Gly Glu Xaa' Ile Xaa' Cys Ala Xaa' Tyr Ala Ala Xaa' Tyr Ala Ala Cys Thr Xaa' Gly Cys, with Xaa/Xaa' variations at positions across rows.)

FIG. 2BZ

| | | | | | | | | | | | | |
|---|---|---|---|---|---|---|---|---|---|---|---|---|
| Pro | Gly | Thr | Cys | Gly | Glu | Xaa' | Ile | Xaa' | Cys | Ala | Tyr | Ala | Ala | Cys | Thr | Gly | Xaa' | Xaa' | Cys | (SEQID NO: 3541) |
| Pro | Gly | Thr | Cys | Gly | Glu | Xaa' | Ile | Xaa' | Cys | Ala | Tyr | Ala | Ala | Cys | Thr | Gly | Xaa' | Cys | Xaa' | (SEQID NO: 3542) |
| Pro | Gly | Thr | Cys | Gly | Glu | Xaa' | Ile | Xaa' | Cys | Ala | Tyr | Ala | Ala | Cys | Thr | Gly | Cys | Xaa' | (SEQID NO: 3543) |
| Pro | Gly | Thr | Cys | Gly | Glu | Xaa' | Ile | Xaa' | Cys | Ala | Tyr | Ala | Ala | Cys | Thr | Gly | Xaa' | Cys | (SEQID NO: 3544) |
| Pro | Gly | Thr | Cys | Gly | Glu | Xaa' | Ile | Xaa' | Cys | Ala | Tyr | Ala | Ala | Cys | Thr | Gly | Cys | (SEQID NO: 3545) |
| Pro | Gly | Thr | Cys | Gly | Glu | Xaa' | Ile | Cys | Xaa' | Ala | Tyr | Ala | Ala | Cys | Thr | Gly | Cys | (SEQID NO: 3546) |
| Pro | Gly | Thr | Cys | Gly | Glu | Xaa' | Ile | Cys | Xaa' | Xaa' | Tyr | Ala | Ala | Cys | Thr | Gly | Xaa' | Gly | Cys | (SEQID NO: 3547) |
| Pro | Gly | Thr | Cys | Gly | Glu | Xaa' | Ile | Cys | Xaa' | Xaa' | Ala | Xaa' | Ala | Ala | Cys | Thr | Gly | Xaa' | Gly | Cys | (SEQID NO: 3548) |
| Pro | Gly | Thr | Cys | Gly | Glu | Xaa' | Ile | Cys | Xaa' | Xaa' | Ala | Tyr | Xaa' | Ala | Ala | Cys | Thr | Gly | Xaa' | Gly | Cys | (SEQID NO: 3549) |
| Pro | Gly | Thr | Cys | Gly | Glu | Xaa' | Ile | Cys | Xaa' | Xaa' | Ala | Tyr | Ala | Xaa' | Ala | Cys | Thr | Gly | Xaa' | Gly | Cys | (SEQID NO: 3550) |
| Pro | Gly | Thr | Cys | Gly | Glu | Xaa' | Ile | Cys | Xaa' | Xaa' | Ala | Tyr | Ala | Ala | Xaa' | Cys | Thr | Gly | Xaa' | Gly | Cys | (SEQID NO: 3551) |
| Pro | Gly | Thr | Cys | Gly | Glu | Xaa' | Ile | Cys | Xaa' | Xaa' | Ala | Tyr | Ala | Ala | Cys | Xaa' | Thr | Gly | Xaa' | Gly | Cys | (SEQID NO: 3552) |
| Pro | Gly | Thr | Cys | Gly | Glu | Xaa' | Ile | Cys | Xaa' | Xaa' | Ala | Tyr | Ala | Ala | Cys | Thr | Xaa' | Gly | Xaa' | Gly | Cys | (SEQID NO: 3553) |
| Pro | Gly | Thr | Cys | Gly | Glu | Xaa' | Ile | Cys | Xaa' | Xaa' | Ala | Tyr | Ala | Ala | Cys | Thr | Gly | Xaa' | Xaa' | Gly | Cys | (SEQID NO: 3554) |
| Pro | Gly | Thr | Cys | Gly | Glu | Xaa' | Ile | Cys | Xaa' | Xaa' | Ala | Tyr | Ala | Ala | Cys | Thr | Gly | Xaa' | Gly | Xaa' | Cys | (SEQID NO: 3555) |
| Pro | Gly | Thr | Cys | Gly | Glu | Xaa' | Ile | Cys | Xaa' | Xaa' | Ala | Xaa' | Xaa' | Ala | Ala | Cys | Thr | Gly | Gly | Cys | (SEQID NO: 3556) |
| Pro | Gly | Thr | Cys | Gly | Glu | Xaa' | Ile | Cys | Xaa' | Xaa' | Ala | Xaa' | Tyr | Ala | Ala | Cys | Thr | Gly | Gly | Cys | (SEQID NO: 3557) |
| Pro | Gly | Thr | Cys | Gly | Glu | Xaa' | Ile | Cys | Xaa' | Xaa' | Ala | Xaa' | Tyr | Ala | Ala | Cys | Thr | Gly | Gly | Cys | (SEQID NO: 3558) |
| Pro | Gly | Thr | Cys | Gly | Glu | Xaa' | Ile | Cys | Xaa' | Xaa' | Ala | Tyr | Xaa' | Ala | Ala | Cys | Thr | Gly | Gly | Cys | (SEQID NO: 3559) |
| Pro | Gly | Thr | Cys | Gly | Glu | Xaa' | Ile | Cys | Xaa' | Xaa' | Ala | Tyr | Xaa' | Ala | Ala | Cys | Thr | Gly | Gly | Cys | (SEQID NO: 3560) |
| Pro | Gly | Thr | Cys | Gly | Glu | Xaa' | Ile | Cys | Xaa' | Xaa' | Ala | Tyr | Ala | Xaa' | Ala | Cys | Thr | Gly | Gly | Cys | (SEQID NO: 3561) |
| Pro | Gly | Thr | Cys | Gly | Glu | Xaa' | Ile | Cys | Xaa' | Xaa' | Ala | Tyr | Ala | Xaa' | Ala | Cys | Thr | Gly | Gly | Cys | (SEQID NO: 3562) |
| Pro | Gly | Thr | Cys | Gly | Glu | Xaa' | Ile | Cys | Xaa' | Xaa' | Ala | Tyr | Ala | Ala | Xaa' | Cys | Thr | Gly | Gly | Cys | (SEQID NO: 3563) |
| Pro | Gly | Thr | Cys | Gly | Glu | Xaa' | Ile | Cys | Xaa' | Xaa' | Ala | Tyr | Ala | Ala | Cys | Xaa' | Thr | Gly | Xaa' | Cys | (SEQID NO: 3564) |
| Pro | Gly | Thr | Cys | Gly | Glu | Xaa' | Ile | Cys | Xaa' | Xaa' | Ala | Tyr | Ala | Ala | Cys | Thr | Xaa' | Gly | Cys | (SEQID NO: 3565) |
| Pro | Gly | Thr | Cys | Gly | Glu | Xaa' | Ile | Cys | Xaa' | Xaa' | Ala | Xaa' | Xaa' | Ala | Ala | Cys | Thr | Gly | Xaa' | Cys | (SEQID NO: 3566) |
| Pro | Gly | Thr | Cys | Gly | Glu | Xaa' | Ile | Cys | Xaa' | Xaa' | Ala | Xaa' | Tyr | Ala | Ala | Cys | Thr | Gly | Xaa' | Cys | (SEQID NO: 3567) |
| Pro | Gly | Thr | Cys | Gly | Glu | Xaa' | Ile | Cys | Xaa' | Xaa' | Ala | Tyr | Xaa' | Ala | Ala | Cys | Thr | Gly | Xaa' | Cys | (SEQID NO: 3568) |
| Pro | Gly | Thr | Cys | Gly | Glu | Xaa' | Ile | Cys | Xaa' | Xaa' | Ala | Tyr | Ala | Xaa' | Ala | Cys | Thr | Gly | Xaa' | Cys | (SEQID NO: 3569) |
| Pro | Gly | Thr | Cys | Gly | Glu | Xaa' | Ile | Cys | Xaa' | Xaa' | Ala | Tyr | Ala | Ala | Xaa' | Cys | Thr | Gly | Xaa' | Cys | (SEQID NO: 3570) |
| Pro | Gly | Thr | Cys | Gly | Glu | Xaa' | Ile | Cys | Xaa' | Xaa' | Ala | Tyr | Ala | Ala | Cys | Xaa' | Thr | Gly | Xaa' | Cys | (SEQID NO: 3571) |
| Pro | Gly | Thr | Cys | Gly | Glu | Xaa' | Ile | Cys | Xaa' | Ala | Tyr | Ala | Ala | Cys | Thr | Gly | Xaa' | Cys | (SEQID NO: 3572) |
| Pro | Gly | Thr | Cys | Gly | Glu | Xaa' | Ile | Cys | Xaa' | Ala | Xaa' | Ala | Xaa' | Ala | Cys | Thr | Gly | Cys | (SEQID NO: 3573) |
| Pro | Gly | Thr | Cys | Gly | Glu | Xaa' | Ile | Cys | Xaa' | Ala | Tyr | Ala | Xaa' | Xaa' | Ala | Cys | Thr | Gly | Cys | (SEQID NO: 3574) |

FIG. 2CA

| Sequence | SEQ ID NO |
|---|---|
| Pro Gly Thr Cys Gly Glu Xaa' Ile Cys Xaa' Ala Tyr Ala Xaa' Ala Cys Thr Gly Cys | (SEQ ID NO: 3575) |
| Pro Gly Thr Cys Gly Glu Xaa' Ile Cys Xaa' Ala Tyr Ala Xaa' Ala Cys Xaa' Thr Gly Cys | (SEQ ID NO: 3576) |
| Pro Gly Thr Cys Gly Glu Xaa' Ile Cys Xaa' Ala Tyr Ala Xaa' Ala Cys Thr Xaa' Gly Cys | (SEQ ID NO: 3577) |
| Pro Gly Thr Cys Gly Glu Xaa' Ile Cys Xaa' Ala Tyr Ala Xaa' Ala Cys Thr Gly Xaa' Cys | (SEQ ID NO: 3578) |
| Pro Gly Thr Cys Gly Glu Xaa' Ile Cys Xaa' Ala Tyr Ala Xaa' Ala Cys Thr Gly Cys Xaa' | (SEQ ID NO: 3579) |
| Pro Gly Thr Cys Gly Glu Xaa' Ile Cys Xaa' Ala Tyr Ala Xaa' Ala Xaa' Cys Thr Gly Cys | (SEQ ID NO: 3580) |
| Pro Gly Thr Cys Gly Glu Xaa' Ile Cys Xaa' Ala Tyr Ala Xaa' Ala Xaa' Cys Thr Gly Cys | (SEQ ID NO: 3581) |
| Pro Gly Thr Cys Gly Glu Xaa' Ile Cys Xaa' Ala Tyr Ala Xaa' Ala Xaa' Cys Xaa' Thr Gly Cys | (SEQ ID NO: 3582) |
| Pro Gly Thr Cys Gly Glu Xaa' Ile Cys Xaa' Ala Tyr Ala Xaa' Ala Xaa' Cys Thr Xaa' Gly Cys | (SEQ ID NO: 3583) |
| Pro Gly Thr Cys Gly Glu Xaa' Ile Cys Xaa' Ala Tyr Ala Xaa' Ala Xaa' Cys Thr Gly Xaa' Cys | (SEQ ID NO: 3584) |
| Pro Gly Thr Cys Gly Glu Xaa' Ile Cys Xaa' Ala Tyr Ala Xaa' Ala Xaa' Cys Thr Gly Cys Xaa' | (SEQ ID NO: 3585) |
| Pro Gly Thr Cys Gly Glu Xaa' Ile Cys Xaa' Ala Tyr Ala Xaa' Ala Cys Xaa' Thr Gly Cys | (SEQ ID NO: 3586) |
| Pro Gly Thr Cys Gly Glu Xaa' Ile Cys Xaa' Ala Tyr Ala Xaa' Ala Cys Xaa' Thr Gly Cys | (SEQ ID NO: 3587) |
| Pro Gly Thr Cys Gly Glu Xaa' Ile Cys Xaa' Ala Tyr Ala Xaa' Ala Cys Xaa' Thr Gly Cys | (SEQ ID NO: 3588) |
| Pro Gly Thr Cys Gly Glu Xaa' Ile Cys Xaa' Ala Tyr Ala Xaa' Ala Cys Xaa' Thr Gly Cys | (SEQ ID NO: 3589) |
| Pro Gly Thr Cys Gly Glu Xaa' Ile Cys Xaa' Ala Tyr Ala Xaa' Ala Cys Xaa' Thr Gly Cys Xaa' | (SEQ ID NO: 3590) |
| Pro Gly Thr Cys Gly Glu Xaa' Ile Cys Xaa' Ala Tyr Ala Xaa' Ala Cys Xaa' Thr Gly Cys | (SEQ ID NO: 3591) |
| Pro Gly Thr Cys Gly Glu Xaa' Ile Cys Xaa' Ala Tyr Ala Xaa' Ala Cys Xaa' Thr Gly Cys | (SEQ ID NO: 3592) |
| Pro Gly Thr Cys Gly Glu Xaa' Ile Cys Xaa' Ala Tyr Ala Xaa' Ala Cys Xaa' Thr Gly Cys | (SEQ ID NO: 3593) |
| Pro Gly Thr Cys Gly Glu Xaa' Ile Cys Xaa' Ala Tyr Ala Xaa' Ala Cys Xaa' Thr Gly Cys | (SEQ ID NO: 3594) |
| Pro Gly Thr Cys Gly Glu Xaa' Ile Cys Xaa' Ala Tyr Ala Xaa' Ala Cys Xaa' Thr Gly Cys Xaa' | (SEQ ID NO: 3595) |
| Pro Gly Thr Cys Gly Glu Xaa' Ile Cys Xaa' Ala Tyr Ala Xaa' Ala Cys Thr Gly Xaa' Cys | (SEQ ID NO: 3596) |
| Pro Gly Thr Cys Gly Glu Xaa' Ile Cys Xaa' Ala Tyr Ala Xaa' Ala Cys Thr Gly Xaa' Cys Xaa' | (SEQ ID NO: 3597) |
| Pro Gly Thr Cys Gly Glu Xaa' Ile Cys Ala Ala Tyr Ala Ala Ala Cys Thr Gly Cys | (SEQ ID NO: 3598) |
| Pro Gly Thr Cys Gly Glu Xaa' Ile Cys Ala Ala Tyr Ala Ala Ala Cys Thr Gly Cys Xaa' | (SEQ ID NO: 3599) |
| Pro Gly Thr Cys Gly Glu Xaa' Ile Cys Ala Ala Tyr Xaa' Ala Ala Cys Thr Gly Cys | (SEQ ID NO: 3600) |
| Pro Gly Thr Cys Gly Glu Xaa' Ile Cys Ala Ala Tyr Xaa' Ala Ala Cys Thr Gly Cys | (SEQ ID NO: 3601) |
| Pro Gly Thr Cys Gly Glu Xaa' Ile Cys Xaa' Ala Tyr Xaa' Ala Ala Cys Thr Gly Cys | (SEQ ID NO: 3602) |
| Pro Gly Thr Cys Gly Glu Xaa' Ile Cys Xaa' Ala Tyr Xaa' Ala Ala Cys Thr Gly Cys | (SEQ ID NO: 3603) |
| Pro Gly Thr Cys Gly Glu Xaa' Ile Cys Xaa' Ala Tyr Xaa' Ala Ala Cys Thr Gly Cys | (SEQ ID NO: 3604) |
| Pro Gly Thr Cys Gly Glu Xaa' Ile Cys Xaa' Ala Tyr Xaa' Ala Ala Cys Thr Gly Cys | (SEQ ID NO: 3605) |
| Pro Gly Thr Cys Gly Glu Xaa' Ile Cys Xaa' Ala Tyr Xaa' Ala Ala Cys Xaa' Gly Cys | (SEQ ID NO: 3606) |
| Pro Gly Thr Cys Gly Glu Xaa' Ile Cys Xaa' Ala Tyr Xaa' Ala Ala Cys Thr Xaa' Gly Cys | (SEQ ID NO: 3607) |
| Pro Gly Thr Cys Gly Glu Xaa' Ile Cys Ala Ala Tyr Ala Ala Cys Thr Gly Xaa' Cys | (SEQ ID NO: 3608) |

FIG. 2CB

| | | | | | | | | | | | |
|---|---|---|---|---|---|---|---|---|---|---|---|
| Pro | Gly | Thr | Cys | Gly | Glu | Xaa' | Ile | Cys | Ala | Xaa' | Xaa' | Tyr | Ala | Ala | Cys | Thr | Gly | Cys | Xaa' | (SEQ ID NO: 3609) |
| Pro | Gly | Thr | Cys | Gly | Glu | Xaa' | Ile | Cys | Ala | Xaa' | Tyr | Xaa' | Ala | Ala | Cys | Thr | Gly | Gly | Cys | (SEQ ID NO: 3610) |
| Pro | Gly | Thr | Cys | Gly | Glu | Xaa' | Ile | Cys | Ala | Xaa' | Tyr | Xaa' | Ala | Ala | Cys | Thr | Gly | Gly | Cys | (SEQ ID NO: 3611) |
| Pro | Gly | Thr | Cys | Gly | Glu | Xaa' | Ile | Cys | Ala | Xaa' | Tyr | Xaa' | Ala | Ala | Cys | Thr | Gly | Gly | Cys | (SEQ ID NO: 3612) |
| Pro | Gly | Thr | Cys | Gly | Glu | Xaa' | Ile | Cys | Ala | Xaa' | Tyr | Xaa' | Ala | Ala | Xaa' | Thr | Gly | Gly | Cys | (SEQ ID NO: 3613) |
| Pro | Gly | Thr | Cys | Gly | Glu | Xaa' | Ile | Cys | Ala | Xaa' | Tyr | Xaa' | Ala | Ala | Cys | Xaa' | Gly | Gly | Cys | (SEQ ID NO: 3614) |
| Pro | Gly | Thr | Cys | Gly | Glu | Xaa' | Ile | Cys | Ala | Xaa' | Tyr | Xaa' | Ala | Ala | Cys | Thr | Xaa' | Gly | Cys | (SEQ ID NO: 3615) |
| Pro | Gly | Thr | Cys | Gly | Glu | Xaa' | Ile | Cys | Ala | Xaa' | Tyr | Xaa' | Ala | Ala | Cys | Thr | Gly | Xaa' | Cys | (SEQ ID NO: 3616) |
| Pro | Gly | Thr | Cys | Gly | Glu | Xaa' | Ile | Cys | Ala | Xaa' | Tyr | Xaa' | Ala | Ala | Cys | Thr | Gly | Gly | Xaa' | (SEQ ID NO: 3617) |
| Pro | Gly | Thr | Cys | Gly | Glu | Xaa' | Ile | Cys | Ala | Xaa' | Tyr | Ala | Xaa' | Ala | Cys | Thr | Gly | Gly | Cys | (SEQ ID NO: 3618) |
| Pro | Gly | Thr | Cys | Gly | Glu | Xaa' | Ile | Cys | Ala | Xaa' | Tyr | Ala | Xaa' | Ala | Cys | Thr | Gly | Gly | Cys | (SEQ ID NO: 3619) |
| Pro | Gly | Thr | Cys | Gly | Glu | Xaa' | Ile | Cys | Ala | Xaa' | Tyr | Ala | Xaa' | Ala | Cys | Thr | Gly | Gly | Cys | (SEQ ID NO: 3620) |
| Pro | Gly | Thr | Cys | Gly | Glu | Xaa' | Ile | Cys | Ala | Xaa' | Tyr | Ala | Xaa' | Ala | Xaa' | Thr | Gly | Gly | Cys | (SEQ ID NO: 3621) |
| Pro | Gly | Thr | Cys | Gly | Glu | Xaa' | Ile | Cys | Ala | Xaa' | Tyr | Ala | Xaa' | Ala | Cys | Xaa' | Gly | Gly | Cys | (SEQ ID NO: 3622) |
| Pro | Gly | Thr | Cys | Gly | Glu | Xaa' | Ile | Cys | Ala | Xaa' | Tyr | Ala | Xaa' | Ala | Cys | Thr | Xaa' | Gly | Cys | (SEQ ID NO: 3623) |
| Pro | Gly | Thr | Cys | Gly | Glu | Xaa' | Ile | Cys | Ala | Xaa' | Tyr | Ala | Xaa' | Ala | Cys | Thr | Gly | Xaa' | Cys | (SEQ ID NO: 3624) |
| Pro | Gly | Thr | Cys | Gly | Glu | Xaa' | Ile | Cys | Ala | Xaa' | Tyr | Ala | Xaa' | Ala | Cys | Thr | Gly | Gly | Xaa' | (SEQ ID NO: 3625) |
| Pro | Gly | Thr | Cys | Gly | Glu | Xaa' | Ile | Cys | Ala | Xaa' | Tyr | Ala | Ala | Xaa' | Cys | Thr | Gly | Gly | Cys | (SEQ ID NO: 3626) |
| Pro | Gly | Thr | Cys | Gly | Glu | Xaa' | Ile | Cys | Ala | Xaa' | Tyr | Ala | Ala | Xaa' | Cys | Thr | Gly | Gly | Cys | (SEQ ID NO: 3627) |
| Pro | Gly | Thr | Cys | Gly | Glu | Xaa' | Ile | Cys | Ala | Xaa' | Tyr | Ala | Ala | Xaa' | Xaa' | Thr | Gly | Gly | Cys | (SEQ ID NO: 3628) |
| Pro | Gly | Thr | Cys | Gly | Glu | Xaa' | Ile | Cys | Ala | Xaa' | Tyr | Ala | Ala | Xaa' | Cys | Xaa' | Gly | Gly | Cys | (SEQ ID NO: 3629) |
| Pro | Gly | Thr | Cys | Gly | Glu | Xaa' | Ile | Cys | Ala | Xaa' | Tyr | Ala | Ala | Xaa' | Cys | Thr | Xaa' | Gly | Cys | (SEQ ID NO: 3630) |
| Pro | Gly | Thr | Cys | Gly | Glu | Xaa' | Ile | Cys | Ala | Xaa' | Tyr | Ala | Ala | Xaa' | Cys | Thr | Gly | Xaa' | Cys | (SEQ ID NO: 3631) |
| Pro | Gly | Thr | Cys | Gly | Glu | Xaa' | Ile | Cys | Ala | Xaa' | Tyr | Ala | Ala | Xaa' | Cys | Thr | Gly | Gly | Xaa' | (SEQ ID NO: 3632) |
| Pro | Gly | Thr | Cys | Gly | Glu | Xaa' | Ile | Cys | Ala | Xaa' | Tyr | Ala | Ala | Cys | Xaa' | Thr | Gly | Gly | Cys | (SEQ ID NO: 3633) |
| Pro | Gly | Thr | Cys | Gly | Glu | Xaa' | Ile | Cys | Ala | Xaa' | Tyr | Ala | Ala | Cys | Xaa' | Xaa' | Gly | Gly | Cys | (SEQ ID NO: 3634) |
| Pro | Gly | Thr | Cys | Gly | Glu | Xaa' | Ile | Cys | Ala | Xaa' | Tyr | Ala | Ala | Cys | Xaa' | Thr | Xaa' | Gly | Cys | (SEQ ID NO: 3635) |
| Pro | Gly | Thr | Cys | Gly | Glu | Xaa' | Ile | Cys | Ala | Xaa' | Tyr | Ala | Ala | Cys | Xaa' | Thr | Gly | Xaa' | Cys | (SEQ ID NO: 3636) |
| Pro | Gly | Thr | Cys | Gly | Glu | Xaa' | Ile | Cys | Ala | Xaa' | Tyr | Ala | Ala | Cys | Xaa' | Thr | Gly | Gly | Xaa' | (SEQ ID NO: 3637) |
| Pro | Gly | Thr | Cys | Gly | Glu | Xaa' | Ile | Cys | Ala | Xaa' | Tyr | Ala | Ala | Cys | Thr | Xaa' | Xaa' | Gly | Cys | (SEQ ID NO: 3638) |
| Pro | Gly | Thr | Cys | Gly | Glu | Xaa' | Ile | Cys | Ala | Xaa' | Tyr | Ala | Ala | Cys | Thr | Xaa' | Gly | Xaa' | Cys | (SEQ ID NO: 3639) |
| Pro | Gly | Thr | Cys | Gly | Glu | Xaa' | Ile | Cys | Ala | Xaa' | Tyr | Ala | Ala | Cys | Thr | Xaa' | Gly | Cys | Xaa' | (SEQ ID NO: 3640) |
| Pro | Gly | Thr | Cys | Gly | Glu | Xaa' | Ile | Cys | Ala | Xaa' | Tyr | Ala | Ala | Cys | Thr | Gly | Xaa' | Xaa' | Cys | (SEQ ID NO: 3641) |
| Pro | Gly | Thr | Cys | Gly | Glu | Xaa' | Ile | Cys | Ala | Xaa' | Tyr | Ala | Ala | Cys | Thr | Gly | Xaa' | Cys | Xaa' | (SEQ ID NO: 3642) |

FIG. 2CC

FIG. 2CD

| Pro Gly Thr Cys Gly Glu Xaa' Ile Cys Ala Tyr Xaa' Ala Ala Cys Thr Gly Xaa' Xaa' Cys | (SEQ ID NO: 3677) |
|---|---|
| Pro Gly Thr Cys Gly Glu Xaa' Ile Cys Ala Tyr Xaa' Ala Ala Cys Thr Gly Xaa' Cys Xaa' | (SEQ ID NO: 3678) |
| Pro Gly Thr Cys Gly Glu Xaa' Ile Cys Ala Tyr Xaa' Ala Ala Cys Thr Gly Cys Xaa' | (SEQ ID NO: 3679) |
| Pro Gly Thr Cys Gly Glu Xaa' Ile Cys Ala Tyr Xaa' Ala Ala Cys Thr Gly Cys Xaa' Xaa' | (SEQ ID NO: 3680) |
| Pro Gly Thr Cys Gly Glu Xaa' Ile Cys Ala Tyr Ala Ala Xaa' Cys Thr Gly Cys | (SEQ ID NO: 3681) |
| Pro Gly Thr Cys Gly Glu Xaa' Ile Cys Ala Tyr Ala Ala Xaa' Cys Ala Cys Thr Gly Cys | (SEQ ID NO: 3682) |
| Pro Gly Thr Cys Gly Glu Xaa' Ile Cys Ala Tyr Ala Ala Xaa' Xaa' Ala Cys Thr Gly Cys | (SEQ ID NO: 3683) |
| Pro Gly Thr Cys Gly Glu Xaa' Ile Cys Ala Tyr Ala Ala Xaa' Xaa' Ala Cys Thr Gly Cys | (SEQ ID NO: 3684) |
| Pro Gly Thr Cys Gly Glu Xaa' Ile Cys Ala Tyr Ala Ala Xaa' Xaa' Ala Cys Thr Gly Cys | (SEQ ID NO: 3685) |
| Pro Gly Thr Cys Gly Glu Xaa' Ile Cys Ala Tyr Ala Ala Xaa' Xaa' Ala Cys Thr Gly Xaa' Cys | (SEQ ID NO: 3686) |
| Pro Gly Thr Cys Gly Glu Xaa' Ile Cys Ala Tyr Ala Ala Xaa' Xaa' Ala Cys Thr Gly Xaa' Cys | (SEQ ID NO: 3687) |
| Pro Gly Thr Cys Gly Glu Xaa' Ile Cys Ala Tyr Ala Ala Xaa' Xaa' Ala Cys Thr Gly Cys | (SEQ ID NO: 3688) |
| Pro Gly Thr Cys Gly Glu Xaa' Ile Cys Ala Tyr Ala Ala Xaa' Xaa' Xaa' Cys Thr Gly Cys | (SEQ ID NO: 3689) |
| Pro Gly Thr Cys Gly Glu Xaa' Ile Cys Ala Tyr Ala Ala Xaa' Xaa' Cys Xaa' Cys Thr Gly Cys | (SEQ ID NO: 3690) |
| Pro Gly Thr Cys Gly Glu Xaa' Ile Cys Ala Tyr Ala Ala Xaa' Xaa' Cys Xaa' Thr Gly Cys | (SEQ ID NO: 3691) |
| Pro Gly Thr Cys Gly Glu Xaa' Ile Cys Ala Tyr Ala Ala Xaa' Xaa' Cys Thr Xaa' Gly Cys | (SEQ ID NO: 3692) |
| Pro Gly Thr Cys Gly Glu Xaa' Ile Cys Ala Tyr Ala Ala Xaa' Xaa' Cys Thr Gly Xaa' Cys | (SEQ ID NO: 3693) |
| Pro Gly Thr Cys Gly Glu Xaa' Ile Cys Ala Tyr Ala Ala Xaa' Xaa' Cys Thr Gly Cys Xaa' | (SEQ ID NO: 3694) |
| Pro Gly Thr Cys Gly Glu Xaa' Ile Cys Ala Tyr Ala Ala Xaa' Cys Thr Xaa' Gly Cys | (SEQ ID NO: 3695) |
| Pro Gly Thr Cys Gly Glu Xaa' Ile Cys Ala Tyr Ala Ala Xaa' Cys Xaa' Thr Gly Cys | (SEQ ID NO: 3696) |
| Pro Gly Thr Cys Gly Glu Xaa' Ile Cys Ala Tyr Ala Ala Xaa' Cys Thr Xaa' Gly Cys | (SEQ ID NO: 3697) |
| Pro Gly Thr Cys Gly Glu Xaa' Ile Cys Ala Tyr Ala Ala Xaa' Cys Thr Gly Xaa' Gly Cys | (SEQ ID NO: 3698) |
| Pro Gly Thr Cys Gly Glu Xaa' Ile Cys Ala Tyr Ala Ala Xaa' Cys Thr Gly Xaa' Cys Xaa' | (SEQ ID NO: 3699) |
| Pro Gly Thr Cys Gly Glu Xaa' Ile Cys Ala Tyr Ala Ala Ala Cys Thr Xaa' Gly Cys | (SEQ ID NO: 3700) |
| Pro Gly Thr Cys Gly Glu Xaa' Ile Cys Ala Tyr Ala Ala Ala Cys Thr Xaa' Xaa' Gly Cys | (SEQ ID NO: 3701) |
| Pro Gly Thr Cys Gly Glu Xaa' Ile Cys Ala Tyr Ala Ala Ala Cys Thr Xaa' Gly Xaa' Cys | (SEQ ID NO: 3702) |
| Pro Gly Thr Cys Gly Glu Xaa' Ile Cys Ala Tyr Ala Ala Ala Cys Thr Xaa' Gly Cys Xaa' | (SEQ ID NO: 3703) |
| Pro Gly Thr Cys Gly Glu Xaa' Ile Cys Ala Tyr Ala Ala Ala Cys Thr Gly Xaa' Cys | (SEQ ID NO: 3704) |
| Pro Gly Thr Cys Gly Glu Xaa' Ile Cys Ala Tyr Ala Ala Ala Cys Thr Gly Xaa' Xaa' Cys | (SEQ ID NO: 3705) |
| Pro Gly Thr Cys Gly Glu Xaa' Ile Cys Ala Tyr Ala Ala Ala Cys Thr Gly Xaa' Cys Xaa' | (SEQ ID NO: 3706) |
| Pro Gly Thr Cys Gly Glu Xaa' Ile Cys Ala Tyr Ala Ala Ala Cys Thr Gly Cys Xaa' | (SEQ ID NO: 3707) |
| Pro Gly Thr Cys Gly Glu Xaa' Ile Cys Ala Tyr Ala Ala Xaa' Xaa' Cys Thr Gly Cys | (SEQ ID NO: 3708) |
| Pro Gly Thr Cys Gly Glu Xaa' Ile Cys Ala Tyr Ala Ala Xaa' Cys Thr Gly Cys | (SEQ ID NO: 3709) |
| Pro Gly Thr Cys Gly Glu Xaa' Ile Cys Ala Tyr Ala Ala Xaa' Xaa' Cys Thr Gly Cys | (SEQ ID NO: 3710) |

FIG. 2CE

| | | | | | | | | | | | | |
|---|---|---|---|---|---|---|---|---|---|---|---|---|
| Pro | Gly | Thr | Cys | Gly | Glu | Xaa' | Ile | Cys | Ala | Tyr | Ala | Ala | Xaa' | Xaa' | Cys | Thr | Gly | Cys | (SEQ ID NO: 3711) |
| Pro | Gly | Thr | Cys | Gly | Glu | Xaa' | Ile | Cys | Ala | Tyr | Ala | Ala | Xaa' | Xaa' | Cys | Xaa' | Thr | Gly | Cys | (SEQ ID NO: 3712) |
| Pro | Gly | Thr | Cys | Gly | Glu | Xaa' | Ile | Cys | Ala | Tyr | Ala | Ala | Xaa' | Xaa' | Cys | Thr | Xaa' | Gly | Cys | (SEQ ID NO: 3713) |
| Pro | Gly | Thr | Cys | Gly | Glu | Xaa' | Ile | Cys | Ala | Tyr | Ala | Ala | Xaa' | Xaa' | Cys | Thr | Gly | Xaa' | Cys | (SEQ ID NO: 3714) |
| Pro | Gly | Thr | Cys | Gly | Glu | Xaa' | Ile | Cys | Ala | Tyr | Ala | Ala | Xaa' | Xaa' | Cys | Thr | Gly | Cys | Xaa' | (SEQ ID NO: 3715) |
| Pro | Gly | Thr | Cys | Gly | Glu | Xaa' | Ile | Cys | Ala | Tyr | Ala | Ala | Xaa' | Cys | Xaa' | Thr | Gly | Cys | (SEQ ID NO: 3716) |
| Pro | Gly | Thr | Cys | Gly | Glu | Xaa' | Ile | Cys | Ala | Tyr | Ala | Ala | Xaa' | Cys | Xaa' | Xaa' | Thr | Gly | Cys | (SEQ ID NO: 3717) |
| Pro | Gly | Thr | Cys | Gly | Glu | Xaa' | Ile | Cys | Ala | Tyr | Ala | Ala | Xaa' | Cys | Xaa' | Thr | Xaa' | Gly | Cys | (SEQ ID NO: 3718) |
| Pro | Gly | Thr | Cys | Gly | Glu | Xaa' | Ile | Cys | Ala | Tyr | Ala | Ala | Xaa' | Cys | Xaa' | Thr | Gly | Xaa' | Cys | (SEQ ID NO: 3719) |
| Pro | Gly | Thr | Cys | Gly | Glu | Xaa' | Ile | Cys | Ala | Tyr | Ala | Ala | Xaa' | Cys | Xaa' | Thr | Gly | Cys | Xaa' | (SEQ ID NO: 3720) |
| Pro | Gly | Thr | Cys | Gly | Glu | Xaa' | Ile | Cys | Ala | Tyr | Ala | Ala | Xaa' | Cys | Thr | Gly | Cys | (SEQ ID NO: 3721) |
| Pro | Gly | Thr | Cys | Gly | Glu | Xaa' | Ile | Cys | Ala | Tyr | Ala | Ala | Xaa' | Cys | Thr | Xaa' | Gly | Cys | (SEQ ID NO: 3722) |
| Pro | Gly | Thr | Cys | Gly | Glu | Xaa' | Ile | Cys | Ala | Tyr | Ala | Ala | Xaa' | Cys | Thr | Xaa' | Xaa' | Gly | Cys | (SEQ ID NO: 3723) |
| Pro | Gly | Thr | Cys | Gly | Glu | Xaa' | Ile | Cys | Ala | Tyr | Ala | Ala | Xaa' | Cys | Thr | Xaa' | Gly | Xaa' | Cys | (SEQ ID NO: 3724) |
| Pro | Gly | Thr | Cys | Gly | Glu | Xaa' | Ile | Cys | Ala | Tyr | Ala | Ala | Xaa' | Cys | Thr | Xaa' | Gly | Cys | Xaa' | (SEQ ID NO: 3725) |
| Pro | Gly | Thr | Cys | Gly | Glu | Xaa' | Ile | Cys | Ala | Tyr | Ala | Ala | Xaa' | Cys | Thr | Gly | Xaa' | Cys | (SEQ ID NO: 3726) |
| Pro | Gly | Thr | Cys | Gly | Glu | Xaa' | Ile | Cys | Ala | Tyr | Ala | Ala | Xaa' | Cys | Thr | Gly | Xaa' | Xaa' | Cys | (SEQ ID NO: 3727) |
| Pro | Gly | Thr | Cys | Gly | Glu | Xaa' | Ile | Cys | Ala | Tyr | Ala | Ala | Xaa' | Cys | Thr | Gly | Xaa' | Cys | Xaa' | (SEQ ID NO: 3728) |
| Pro | Gly | Thr | Cys | Gly | Glu | Xaa' | Ile | Cys | Ala | Tyr | Ala | Ala | Xaa' | Cys | Thr | Gly | Cys | Xaa' | (SEQ ID NO: 3729) |
| Pro | Gly | Thr | Cys | Gly | Glu | Xaa' | Ile | Cys | Ala | Tyr | Ala | Ala | Xaa' | Cys | Thr | Gly | Cys | Xaa' | Xaa' | (SEQ ID NO: 3730) |
| Pro | Gly | Thr | Cys | Gly | Glu | Xaa' | Ile | Cys | Ala | Tyr | Ala | Ala | Cys | Xaa' | Xaa' | Thr | Gly | Cys | (SEQ ID NO: 3731) |
| Pro | Gly | Thr | Cys | Gly | Glu | Xaa' | Ile | Cys | Ala | Tyr | Ala | Ala | Cys | Xaa' | Xaa' | Xaa' | Thr | Gly | Cys | (SEQ ID NO: 3732) |
| Pro | Gly | Thr | Cys | Gly | Glu | Xaa' | Ile | Cys | Ala | Tyr | Ala | Ala | Cys | Xaa' | Xaa' | Thr | Xaa' | Gly | Cys | (SEQ ID NO: 3733) |
| Pro | Gly | Thr | Cys | Gly | Glu | Xaa' | Ile | Cys | Ala | Tyr | Ala | Ala | Cys | Xaa' | Xaa' | Thr | Gly | Xaa' | Cys | (SEQ ID NO: 3734) |
| Pro | Gly | Thr | Cys | Gly | Glu | Xaa' | Ile | Cys | Ala | Tyr | Ala | Ala | Cys | Xaa' | Xaa' | Thr | Gly | Cys | Xaa' | (SEQ ID NO: 3735) |
| Pro | Gly | Thr | Cys | Gly | Glu | Xaa' | Ile | Cys | Ala | Tyr | Ala | Ala | Cys | Xaa' | Thr | Gly | Cys | (SEQ ID NO: 3736) |
| Pro | Gly | Thr | Cys | Gly | Glu | Xaa' | Ile | Cys | Ala | Tyr | Ala | Ala | Cys | Xaa' | Thr | Xaa' | Gly | Cys | (SEQ ID NO: 3737) |
| Pro | Gly | Thr | Cys | Gly | Glu | Xaa' | Ile | Cys | Ala | Tyr | Ala | Ala | Cys | Xaa' | Thr | Xaa' | Xaa' | Gly | Cys | (SEQ ID NO: 3738) |
| Pro | Gly | Thr | Cys | Gly | Glu | Xaa' | Ile | Cys | Ala | Tyr | Ala | Ala | Cys | Xaa' | Thr | Xaa' | Gly | Xaa' | Cys | (SEQ ID NO: 3739) |
| Pro | Gly | Thr | Cys | Gly | Glu | Xaa' | Ile | Cys | Ala | Tyr | Ala | Ala | Cys | Xaa' | Thr | Xaa' | Gly | Cys | Xaa' | (SEQ ID NO: 3740) |
| Pro | Gly | Thr | Cys | Gly | Glu | Xaa' | Ile | Cys | Ala | Tyr | Ala | Ala | Cys | Xaa' | Thr | Gly | Xaa' | Cys | (SEQ ID NO: 3741) |
| Pro | Gly | Thr | Cys | Gly | Glu | Xaa' | Ile | Cys | Ala | Tyr | Ala | Ala | Cys | Xaa' | Thr | Gly | Xaa' | Xaa' | Cys | (SEQ ID NO: 3742) |
| Pro | Gly | Thr | Cys | Gly | Glu | Xaa' | Ile | Cys | Ala | Tyr | Ala | Ala | Cys | Xaa' | Thr | Gly | Xaa' | Cys | Xaa' | (SEQ ID NO: 3743) |
| Pro | Gly | Thr | Cys | Gly | Glu | Xaa' | Ile | Cys | Ala | Tyr | Ala | Ala | Cys | Xaa' | Thr | Gly | Cys | Xaa' | Xaa' | (SEQ ID NO: 3744) |

FIG. 2CF

| | | |
|---|---|---|
| Pro Gly Thr Cys Gly Glu Xaa' Ile Cys Ala Ala Tyr Ala Ala Cys Thr Xaa' Gly Cys | | (SEQ ID NO: 3745) |
| Pro Gly Thr Cys Gly Glu Xaa' Ile Cys Ala Ala Tyr Ala Ala Cys Thr Xaa' Gly Cys | | (SEQ ID NO: 3746) |
| Pro Gly Thr Cys Gly Glu Xaa' Ile Cys Ala Ala Tyr Ala Ala Cys Thr Xaa' Xaa' Gly Cys | | (SEQ ID NO: 3747) |
| Pro Gly Thr Cys Gly Glu Xaa' Ile Cys Ala Ala Tyr Ala Ala Cys Thr Xaa' Xaa' Gly Xaa' Cys | | (SEQ ID NO: 3748) |
| Pro Gly Thr Cys Gly Glu Xaa' Ile Cys Ala Ala Tyr Ala Ala Cys Thr Xaa' Xaa' Gly Cys Xaa' | | (SEQ ID NO: 3749) |
| Pro Gly Thr Cys Gly Glu Xaa' Ile Cys Ala Ala Tyr Ala Ala Cys Thr Xaa' Gly Xaa' Cys | | (SEQ ID NO: 3750) |
| Pro Gly Thr Cys Gly Glu Xaa' Ile Cys Ala Ala Tyr Ala Ala Cys Thr Xaa' Gly Xaa' Xaa' Cys | | (SEQ ID NO: 3751) |
| Pro Gly Thr Cys Gly Glu Xaa' Ile Cys Ala Ala Tyr Ala Ala Cys Thr Xaa' Gly Xaa' Cys Xaa' | | (SEQ ID NO: 3752) |
| Pro Gly Thr Cys Gly Glu Xaa' Ile Cys Ala Ala Tyr Ala Ala Cys Thr Xaa' Gly Cys Xaa' | | (SEQ ID NO: 3753) |
| Pro Gly Thr Cys Gly Glu Xaa' Ile Cys Ala Ala Tyr Ala Ala Cys Thr Xaa' Gly Cys Xaa' Xaa' | | (SEQ ID NO: 3754) |
| Pro Gly Thr Cys Gly Glu Xaa' Ile Cys Ala Ala Tyr Ala Ala Cys Thr Gly Xaa' Cys | | (SEQ ID NO: 3755) |
| Pro Gly Thr Cys Gly Glu Xaa' Ile Cys Ala Ala Tyr Ala Ala Cys Thr Gly Xaa' Xaa' Cys | | (SEQ ID NO: 3756) |
| Pro Gly Thr Cys Gly Glu Xaa' Ile Cys Ala Ala Tyr Ala Ala Cys Thr Gly Xaa' Xaa' Cys Xaa' | | (SEQ ID NO: 3757) |
| Pro Gly Thr Cys Gly Glu Xaa' Ile Cys Ala Ala Tyr Ala Ala Cys Thr Gly Xaa' Cys Xaa' | | (SEQ ID NO: 3758) |
| Pro Gly Thr Cys Gly Glu Xaa' Ile Cys Ala Ala Tyr Ala Ala Cys Thr Gly Xaa' Cys Xaa' Xaa' | | (SEQ ID NO: 3759) |
| Pro Gly Thr Cys Gly Glu Xaa' Ile Cys Ala Ala Tyr Ala Ala Cys Thr Gly Cys Xaa' | | (SEQ ID NO: 3760) |
| Pro Gly Thr Cys Gly Glu Xaa' Ile Xaa' Xaa' Xaa' Xaa' Cys Xaa' Cys Thr Gly Cys Xaa' | | (SEQ ID NO: 3761) |
| Pro Gly Thr Cys Gly Glu Xaa' Ile Xaa' Xaa' Xaa' Xaa' Xaa' Xaa' Cys Thr Gly Cys Xaa' Xaa' | | (SEQ ID NO: 3762) |
| Pro Gly Thr Cys Gly Glu Xaa' Ile Xaa' Xaa' Xaa' Xaa' Xaa' Xaa' Cys Thr Gly Cys Xaa' Xaa' Cys | | (SEQ ID NO: 3763) |
| Pro Gly Thr Cys Gly Glu Xaa' Ile Xaa' Xaa' Xaa' Xaa' Xaa' Xaa' Cys Thr Gly Cys | | (SEQ ID NO: 3764) |
| Pro Gly Thr Cys Gly Glu Xaa' Ile Xaa' Xaa' Xaa' Xaa' Ala Tyr Ala Ala Cys Thr Gly Cys | | (SEQ ID NO: 3765) |
| Pro Gly Thr Cys Gly Glu Xaa' Ile Xaa' Xaa' Xaa' Cys Ala Tyr Ala Ala Cys Thr Gly Cys | | (SEQ ID NO: 3766) |
| Pro Gly Thr Cys Gly Glu Xaa' Ile Xaa' Xaa' Xaa' Cys Ala Xaa' Ala Ala Cys Thr Gly Cys | | (SEQ ID NO: 3767) |
| Pro Gly Thr Cys Gly Glu Xaa' Ile Xaa' Xaa' Xaa' Cys Ala Tyr Ala Ala Cys Thr Gly Cys | | (SEQ ID NO: 3768) |
| Pro Gly Thr Cys Gly Glu Xaa' Ile Xaa' Xaa' Xaa' Cys Ala Tyr Ala Ala Cys Thr Gly Cys | | (SEQ ID NO: 3769) |
| Pro Gly Thr Cys Gly Glu Xaa' Ile Xaa' Xaa' Xaa' Cys Ala Tyr Xaa' Ala Cys Thr Gly Cys | | (SEQ ID NO: 3770) |
| Pro Gly Thr Cys Gly Glu Xaa' Ile Xaa' Xaa' Xaa' Cys Ala Tyr Ala Xaa' Cys Thr Gly Cys | | (SEQ ID NO: 3771) |
| Pro Gly Thr Cys Gly Glu Xaa' Ile Xaa' Xaa' Xaa' Cys Ala Tyr Ala Ala Xaa' Thr Gly Cys | | (SEQ ID NO: 3772) |
| Pro Gly Thr Cys Gly Glu Xaa' Ile Xaa' Xaa' Xaa' Cys Ala Tyr Ala Ala Cys Xaa' Gly Cys | | (SEQ ID NO: 3773) |
| Pro Gly Thr Cys Gly Glu Xaa' Ile Xaa' Xaa' Xaa' Cys Ala Tyr Ala Ala Cys Thr Xaa' Gly Cys | | (SEQ ID NO: 3774) |
| Pro Gly Thr Cys Gly Glu Xaa' Ile Xaa' Xaa' Xaa' Cys Ala Tyr Ala Ala Cys Thr Gly Xaa' Cys | | (SEQ ID NO: 3775) |
| Pro Gly Thr Cys Gly Glu Xaa' Ile Xaa' Xaa' Cys Xaa' Ala Tyr Ala Ala Cys Thr Gly Cys Xaa' | | (SEQ ID NO: 3776) |
| Pro Gly Thr Cys Gly Glu Xaa' Ile Xaa' Cys Xaa' Xaa' Ala Tyr Ala Ala Cys Thr Gly Cys | | (SEQ ID NO: 3777) |
| Pro Gly Thr Cys Gly Glu Xaa' Ile Xaa' Cys Xaa' Xaa' Ala Tyr Ala Ala Cys Thr Gly Cys | | (SEQ ID NO: 3778) |

FIG. 2CG

```
Pro Gly Thr Cys Gly Glu Ile Xaa' Xaa' Ala Xaa' Tyr Ala Ala Cys Thr Gly Cys   (SEQ ID NO: 3779)
Pro Gly Thr Cys Gly Glu Ile Xaa' Xaa' Cys Xaa' Ala Tyr Xaa' Ala Cys Thr Gly Cys   (SEQ ID NO: 3780)
Pro Gly Thr Cys Gly Glu Ile Xaa' Xaa' Cys Xaa' Ala Tyr Ala Ala Xaa' Thr Gly Cys   (SEQ ID NO: 3781)
Pro Gly Thr Cys Gly Glu Ile Xaa' Xaa' Cys Xaa' Ala Tyr Ala Ala Cys Xaa' Gly Cys   (SEQ ID NO: 3782)
Pro Gly Thr Cys Gly Glu Ile Xaa' Xaa' Cys Xaa' Ala Tyr Ala Ala Cys Thr Xaa' Cys   (SEQ ID NO: 3783)
Pro Gly Thr Cys Gly Glu Ile Xaa' Xaa' Cys Xaa' Ala Tyr Ala Ala Cys Thr Gly Xaa'   (SEQ ID NO: 3784)
Pro Gly Thr Cys Gly Glu Ile Xaa' Xaa' Cys Xaa' Ala Tyr Ala Ala Cys Thr Gly Cys   (SEQ ID NO: 3785)
Pro Gly Thr Cys Gly Glu Ile Xaa' Xaa' Cys Ala Xaa' Tyr Ala Ala Cys Thr Gly Cys   (SEQ ID NO: 3786)
Pro Gly Thr Cys Gly Glu Ile Xaa' Xaa' Cys Ala Xaa' Xaa' Ala Ala Cys Thr Gly Cys   (SEQ ID NO: 3787)
Pro Gly Thr Cys Gly Glu Ile Xaa' Xaa' Cys Ala Xaa' Tyr Xaa' Ala Cys Thr Gly Cys   (SEQ ID NO: 3788)
Pro Gly Thr Cys Gly Glu Ile Xaa' Xaa' Cys Ala Xaa' Tyr Ala Xaa' Cys Thr Gly Cys   (SEQ ID NO: 3789)
Pro Gly Thr Cys Gly Glu Ile Xaa' Xaa' Cys Ala Xaa' Tyr Ala Ala Xaa' Thr Gly Cys   (SEQ ID NO: 3790)
Pro Gly Thr Cys Gly Glu Ile Xaa' Xaa' Cys Ala Xaa' Tyr Ala Ala Cys Xaa' Gly Cys   (SEQ ID NO: 3791)
Pro Gly Thr Cys Gly Glu Ile Xaa' Xaa' Cys Ala Xaa' Tyr Ala Ala Cys Thr Xaa' Cys   (SEQ ID NO: 3792)
Pro Gly Thr Cys Gly Glu Ile Xaa' Xaa' Cys Ala Xaa' Tyr Ala Ala Cys Thr Gly Xaa'   (SEQ ID NO: 3793)
Pro Gly Thr Cys Gly Glu Ile Xaa' Xaa' Cys Ala Xaa' Tyr Ala Ala Cys Thr Gly Cys   (SEQ ID NO: 3794)
Pro Gly Thr Cys Gly Glu Ile Xaa' Xaa' Cys Ala Tyr Xaa' Ala Ala Cys Thr Gly Cys   (SEQ ID NO: 3795)
Pro Gly Thr Cys Gly Glu Ile Xaa' Xaa' Cys Ala Tyr Xaa' Xaa' Ala Cys Thr Gly Cys   (SEQ ID NO: 3796)
Pro Gly Thr Cys Gly Glu Ile Xaa' Xaa' Cys Ala Tyr Xaa' Ala Xaa' Cys Thr Gly Cys   (SEQ ID NO: 3797)
Pro

| | | | | | | | | | | |
|---|---|---|---|---|---|---|---|---|---|---|
| Pro Gly Thr Cys Gly Glu Ile | Xaa' | Xaa' | Cys | Ala | Tyr | Ala | Ala | Xaa' | Cys | Xaa' Thr Gly Cys | (SEQ ID NO: 3813) |
| Pro Gly Thr Cys Gly Glu Ile | Xaa' | Xaa' | Cys | Ala | Tyr | Ala | Ala | Xaa' | Cys | Thr Xaa' Gly Cys | (SEQ ID NO: 3814) |
| Pro Gly Thr Cys Gly Glu Ile | Xaa' | Xaa' | Cys | Ala | Tyr | Ala | Ala | Xaa' | Cys | Thr Gly Xaa' Cys | (SEQ ID NO: 3815) |
| Pro Gly Thr Cys Gly Glu Ile | Xaa' | Xaa' | Cys | Ala | Tyr | Ala | Ala | Xaa' | Cys | Thr Gly Cys Xaa' | (SEQ ID NO: 3816) |
| Pro Gly Thr Cys Gly Glu Ile | Xaa' | Xaa' | Cys | Ala | Tyr | Ala | Ala | Cys | Xaa' | Thr Gly Cys | (SEQ ID NO: 3817) |
| Pro Gly Thr Cys Gly Glu Ile | Xaa' | Xaa' | Cys | Ala | Tyr | Ala | Ala | Cys | Xaa' | Xaa' Thr Gly Cys | (SEQ ID NO: 3818) |
| Pro Gly Thr Cys Gly Glu Ile | Xaa' | Xaa' | Cys | Ala | Tyr | Ala | Ala | Cys | Xaa' | Thr Xaa' Gly Cys | (SEQ ID NO: 3819) |
| Pro Gly Thr Cys Gly Glu Ile | Xaa' | Xaa' | Cys | Ala | Tyr | Ala | Ala | Cys | Xaa' | Thr Gly Xaa' Cys | (SEQ ID NO: 3820) |
| Pro Gly Thr Cys Gly Glu Ile | Xaa' | Xaa' | Cys | Ala | Tyr | Ala | Ala | Cys | Xaa' | Thr Gly Cys Xaa' | (SEQ ID NO: 3821) |
| Pro Gly Thr Cys Gly Glu Ile | Xaa' | Xaa' | Cys | Ala | Tyr | Ala | Ala | Cys | Thr | Xaa' Gly Cys | (SEQ ID NO: 3822) |
| Pro Gly Thr Cys Gly Glu Ile | Xaa' | Xaa' | Cys | Ala | Tyr | Ala | Ala | Cys | Thr | Xaa' Xaa' Gly Cys | (SEQ ID NO: 3823) |
| Pro Gly Thr Cys Gly Glu Ile | Xaa' | Xaa' | Cys | Ala | Tyr | Ala | Ala | Cys | Thr | Xaa' Gly Xaa' Cys | (SEQ ID NO: 3824) |
| Pro Gly Thr Cys Gly Glu Ile | Xaa' | Xaa' | Cys | Ala | Tyr | Ala | Ala | Cys | Thr | Xaa' Gly Cys Xaa' | (SEQ ID NO: 3825) |
| Pro Gly Thr Cys Gly Glu Ile | Xaa' | Xaa' | Cys | Ala | Tyr | Ala | Ala | Cys | Thr | Gly Xaa' Cys | (SEQ ID NO: 3826) |
| Pro Gly Thr Cys Gly Glu Ile | Xaa' | Xaa' | Cys | Ala | Tyr | Ala | Ala | Cys | Thr | Gly Xaa' Xaa' Cys | (SEQ ID NO: 3827) |
| Pro Gly Thr Cys Gly Glu Ile | Xaa' | Xaa' | Cys | Ala | Tyr | Ala | Ala | Cys | Thr | Gly Xaa' Cys Xaa' | (SEQ ID NO: 3828) |
| Pro Gly Thr Cys Gly Glu Ile | Xaa' | Xaa' | Cys | Ala | Tyr | Ala | Ala | Cys | Thr | Gly Cys Xaa' | (SEQ ID NO: 3829) |
| Pro Gly Thr Cys Gly Glu Ile | Xaa' | Xaa' | Cys | Ala | Tyr | Ala | Ala | Cys | Thr | Gly Cys Xaa' Xaa' | (SEQ ID NO: 3830) |
| Pro Gly Thr Cys Gly Glu Ile | Xaa' | Cys | Xaa' | Ala | Tyr | Ala | Ala | Cys | Thr | Gly Cys | (SEQ ID NO: 3831) |
| Pro Gly Thr Cys Gly Glu Ile | Xaa' | Cys | Xaa' | Xaa' | Ala | Tyr | Ala | Ala | Cys | Thr Gly Cys | (SEQ ID NO: 3832) |
| Pro Gly Thr Cys Gly Glu Ile | Xaa' | Cys | Xaa' | Ala | Xaa' | Tyr | Ala | Ala | Cys | Thr Gly Cys | (SEQ ID NO: 3833) |
| Pro Gly Thr Cys Gly Glu Ile | Xaa' | Cys | Xaa' | Ala | Tyr | Xaa' | Ala | Ala | Cys | Thr Gly Cys | (SEQ ID NO: 3834) |
| Pro Gly Thr Cys Gly Gln Ile | Xaa' | Cys | Xaa' | Ala | Tyr | Ala | Xaa' | Ala | Cys | Thr Gly Cys | (SEQ ID NO: 3835) |
| Pro Gly Thr Cys Gly Glu Ile | Xaa' | Cys | Xaa' | Ala | Tyr | Ala | Ala | Xaa' | Cys | Thr Gly Cys | (SEQ ID NO: 3836) |
| Pro Gly Thr Cys Gly Glu Ile | Xaa' | Cys | Xaa' | Ala | Tyr | Ala | Ala | Cys | Xaa' | Thr Gly Cys | (SEQ ID NO: 3837) |
| Pro Gly Thr Cys Gly Glu Ile | Xaa' | Cys | Xaa' | Ala | Tyr | Ala | Ala | Cys | Thr | Xaa' Gly Cys | (SEQ ID NO: 3838) |
| Pro Gly Thr Cys Gly Glu Ile | Xaa' | Cys | Xaa' | Ala | Tyr | Ala | Ala | Cys | Thr | Gly Xaa' Cys | (SEQ ID NO: 3839) |
| Pro Gly Thr Cys Gly Glu Ile | Xaa' | Cys | Xaa' | Ala | Tyr | Ala | Ala | Cys | Thr | Gly Cys Xaa' | (SEQ ID NO: 3840) |
| Pro Gly Thr Cys Gly Glu Ile | Xaa' | Cys | Ala | Xaa' | Tyr | Ala | Ala | Cys | Thr | Gly Cys | (SEQ ID NO: 3841) |
| Pro Gly Thr Cys Gly Glu Ile | Xaa' | Cys | Ala | Xaa' | Xaa' | Tyr | Ala | Ala | Cys | Thr Gly Cys | (SEQ ID NO: 3842) |
| Pro Gly Thr Cys Gly Glu Ile | Xaa' | Cys | Ala | Xaa' | Tyr | Xaa' | Ala | Ala | Cys | Thr Gly Cys | (SEQ ID NO: 3843) |
| Pro Gly Thr Cys Gly Glu Ile | Xaa' | Cys | Ala | Xaa' | Tyr | Ala | Xaa' | Ala | Cys | Thr Gly Cys | (SEQ ID NO: 3844) |
| Pro Gly Thr Cys Gly Glu Ile | Xaa' | Cys | Ala | Xaa' | Tyr | Ala | Ala | Xaa' | Cys | Thr Gly Cys | (SEQ ID NO: 3845) |
| Pro Gly Thr Cys Gly Glu Ile | Xaa' | Cys | Ala | Xaa' | Tyr | Ala | Ala | Cys | Xaa' | Thr Gly Cys | (SEQ ID NO: 3846) |

FIG. 2CI

| | | | | | | | | | | |
|---|---|---|---|---|---|---|---|---|---|---|
| Pro Gly Thr Cys Gly Glu Ile Xaa' Cys Xaa' Ala Xaa' Tyr Ala Ala Cys Xaa' Thr Gly Cys | (SEQ ID NO: 3847) |
| Pro Gly Thr Cys Gly Glu Ile Xaa' Cys Xaa' Ala Xaa' Tyr Ala Ala Cys Thr Thr Gly Cys | (SEQ ID NO: 3848) |
| Pro Gly Thr Cys Gly Glu Ile Xaa' Cys Xaa' Ala Xaa' Tyr Ala Ala Cys Thr Gly Xaa' Cys | (SEQ ID NO: 3849) |
| Pro Gly Thr Cys Gly Glu Ile Xaa' Cys Xaa' Ala Xaa' Tyr Ala Ala Cys Thr Gly Cys Xaa' | (SEQ ID NO: 3850) |
| Pro Gly Thr Cys Gly Glu Ile Xaa' Cys Xaa' Ala Xaa' Tyr Ala Ala Cys Thr Gly Cys | (SEQ ID NO: 3851) |
| Pro Gly Thr Cys Gly Glu Ile Xaa' Cys Xaa' Ala Tyr Xaa' Ala Ala Cys Thr Thr Gly Cys | (SEQ ID NO: 3852) |
| Pro Gly Thr Cys Gly Glu Ile Xaa' Cys Xaa' Ala Tyr Xaa' Ala Ala Cys Thr Thr Gly Cys | (SEQ ID NO: 3853) |
| Pro Gly Thr Cys Gly Glu Ile Xaa' Cys Xaa' Ala Tyr Xaa' Ala Ala Xaa' Cys Thr Gly Cys | (SEQ ID NO: 3854) |
| Pro Gly Thr Cys Gly Glu Ile Xaa' Cys Xaa' Ala Tyr Xaa' Ala Ala Cys Thr Gly Cys | (SEQ ID NO: 3855) |
| Pro Gly Thr Cys Gly Glu Ile Xaa' Cys Xaa' Ala Tyr Xaa' Ala Ala Cys Thr Gly Xaa' Cys | (SEQ ID NO: 3856) |
| Pro Gly Thr Cys Gly Glu Ile Xaa' Cys Xaa' Ala Tyr Xaa' Ala Ala Cys Thr Gly Cys Xaa' | (SEQ ID NO: 3857) |
| Pro Gly Thr Cys Gly Glu Ile Xaa' Cys Xaa' Ala Tyr Ala Xaa' Ala Cys Thr Gly Cys | (SEQ ID NO: 3858) |
| Pro Gly Thr Cys Gly Glu Ile Xaa' Cys Xaa' Ala Tyr Ala Xaa' Ala Cys Thr Gly Cys | (SEQ ID NO: 3859) |
| Pro Gly Thr Cys Gly Glu Ile Xaa' Cys Xaa' Ala Tyr Ala Xaa' Ala Cys Thr Gly Cys | (SEQ ID NO: 3860) |
| Pro Gly Thr Cys Gly Glu Ile Xaa' Cys Xaa' Ala Tyr Ala Xaa' Ala Cys Thr Gly Xaa' Cys | (SEQ ID NO: 3861) |
| Pro Gly Thr Cys Gly Glu Ile Xaa' Cys Xaa' Ala Tyr Ala Xaa' Ala Cys Thr Gly Cys Xaa' | (SEQ ID NO: 3862) |
| Pro Gly Thr Cys Gly Glu Ile Xaa' Cys Xaa' Ala Tyr Ala Ala Xaa' Cys Thr Gly Cys | (SEQ ID NO: 3863) |
| Pro Gly Thr Cys Gly Glu Ile Xaa' Cys Xaa' Ala Tyr Ala Ala Xaa' Cys Thr Gly Cys | (SEQ ID NO: 3864) |
| Pro Gly Thr Cys Gly Glu Ile Xaa' Cys Xaa' Ala Tyr Ala Ala Xaa' Cys Thr Gly Xaa' Cys | (SEQ ID NO: 3865) |
| Pro Gly Thr Cys Gly Glu Ile Xaa' Cys Xaa' Ala Tyr Ala Ala Xaa' Cys Thr Gly Cys Xaa' | (SEQ ID NO: 3866) |
| Pro Gly Thr Cys Gly Glu Ile Xaa' Cys Xaa' Ala Tyr Ala Ala Ala Xaa' Thr Gly Cys | (SEQ ID NO: 3867) |
| Pro Gly Thr Cys Gly Glu Ile Xaa' Cys Xaa' Ala Tyr Ala Ala Ala Xaa' Cys Thr Gly Cys | (SEQ ID NO: 3868) |
| Pro Gly Thr Cys Gly Glu Ile Xaa' Cys Xaa' Ala Tyr Ala Ala Ala Xaa' Cys Thr Gly Xaa' Cys | (SEQ ID NO: 3869) |
| Pro Gly Thr Cys Gly Glu Ile Xaa' Cys Xaa' Ala Tyr Ala Ala Ala Xaa' Cys Thr Gly Cys Xaa' | (SEQ ID NO: 3870) |
| Pro Gly Thr Cys Gly Glu Ile Xaa' Cys Xaa' Ala Tyr Ala Ala Ala Cys Xaa' Thr Gly Cys | (SEQ ID NO: 3871) |
| Pro Gly Thr Cys Gly Glu Ile Xaa' Cys Xaa' Ala Tyr Ala Ala Ala Cys Xaa' Thr Gly Cys Xaa' | (SEQ ID NO: 3872) |
| Pro Gly Thr Cys Gly Glu Ile Xaa' Cys Xaa' Ala Tyr Ala Ala Ala Cys Xaa' Thr Gly Xaa' Cys | (SEQ ID NO: 3873) |
| Pro Gly Thr Cys Gly Glu Ile Xaa' Cys Xaa' Ala Tyr Ala Ala Ala Cys Xaa' Xaa' Thr Gly Cys | (SEQ ID NO: 3874) |
| Pro Gly Thr Cys Gly Glu Ile Xaa' Cys Xaa' Ala Tyr Ala Ala Ala Cys Xaa' Gly Cys Xaa' | (SEQ ID NO: 3875) |
| Pro Gly Thr Cys Gly Glu Ile Xaa' Cys Xaa' Ala Tyr Ala Ala Ala Cys Thr Xaa' Gly Cys Xaa' | (SEQ ID NO: 3876) |
| Pro Gly Thr Cys Gly Glu Ile Xaa' Cys Xaa' Ala Tyr Ala Ala Ala Cys Thr Xaa' Gly Cys | (SEQ ID NO: 3877) |
| Pro Gly Thr Cys Gly Glu Ile Xaa' Cys Xaa' Ala Tyr Ala Ala Ala Cys Thr Xaa' Gly Xaa' Cys | (SEQ ID NO: 3878) |
| Pro Gly Thr Cys Gly Glu Ile Xaa' Cys Xaa' Ala Tyr Ala Ala Ala Cys Thr Xaa' Gly Cys Xaa' | (SEQ ID NO: 3879) |
| Pro Gly Thr Cys Gly Glu Ile Xaa' Cys Xaa' Ala Tyr Ala Ala Ala Cys Thr Thr Xaa' Gly Cys Xaa' | (SEQ ID NO: 3880) |

FIG. 2CJ

| | | | | | | | | | | | | | |
|---|---|---|---|---|---|---|---|---|---|---|---|---|---|
|Pro|Gly|Thr|Cys|Gly|Glu|Ile|Xaa'|Cys|Xaa'|Ala|Tyr|Ala|Ala|Cys|Thr|Gly|Xaa'|Cys|(SEQ ID NO: 3881)|
|Pro|Gly|Thr|Cys|Gly|Glu|Ile|Xaa'|Cys|Xaa'|Ala|Tyr|Ala|Ala|Cys|Thr|Gly|Xaa'|Xaa'|Cys|(SEQ ID NO: 3882)|
|Pro|Gly|Thr|Cys|Gly|Glu|Ile|Xaa'|Cys|Xaa'|Ala|Tyr|Ala|Ala|Cys|Thr|Gly|Xaa'|Cys|Xaa'|(SEQ ID NO: 3883)|
|Pro|Gly|Thr|Cys|Gly|Glu|Ile|Xaa'|Cys|Xaa'|Ala|Tyr|Ala|Ala|Cys|Thr|Gly|Cys|Xaa'|(SEQ ID NO: 3884)|
|Pro|Gly|Thr|Cys|Gly|Glu|Ile|Xaa'|Cys|Xaa'|Ala|Tyr|Ala|Ala|Cys|Thr|Gly|Cys|Xaa'|Xaa'|(SEQ ID NO: 3885)|
|Pro|Gly|Thr|Cys|Gly|Glu|Ile|Xaa'|Cys|Ala|Ala|Tyr|Ala|Ala|Cys|Thr|Gly|Cys|(SEQ ID NO: 3886)|
|Pro|Gly|Thr|Cys|Gly|Glu|Ile|Xaa'|Cys|Xaa'|Ala|Tyr|Ala|Ala|Cys|Thr|Gly|Cys|(SEQ ID NO: 3887)|
|Pro|Gly|Thr|Cys|Gly|Glu|Ile|Xaa'|Cys|Ala|Ala|Xaa'|Tyr|Ala|Ala|Cys|Thr|Gly|Cys|(SEQ ID NO: 3888)|
|Pro|Gly|Thr|Cys|Gly|Glu|Ile|Xaa'|Cys|Ala|Ala|Xaa'|Tyr|Ala|Ala|Cys|Thr|Gly|Xaa'|Cys|(SEQ ID NO: 3889)|
|Pro|Gly|Thr|Cys|Gly|Glu|Ile|Xaa'|Cys|Ala|Ala|Xaa'|Tyr|Xaa'|Ala|Ala|Cys|Thr|Gly|Xaa'|Cys|(SEQ ID NO: 3890)|
|Pro|Gly|Thr|Cys|Gly|Glu|Ile|Xaa'|Cys|Ala|Ala|Xaa'|Tyr|Xaa'|Ala|Ala|Cys|Thr|Gly|Cys|Xaa'|(SEQ ID NO: 3891)|
|Pro|Gly|Thr|Cys|Gly|Glu|Ile|Xaa'|Cys|Ala|Ala|Xaa'|Tyr|Xaa'|Ala|Ala|Cys|Xaa'|Thr|Gly|Cys|(SEQ ID NO: 3892)|
|Pro|Gly|Thr|Cys|Gly|Glu|Ile|Xaa'|Cys|Ala|Ala|Xaa'|Tyr|Xaa'|Ala|Ala|Cys|Xaa'|Thr|Gly|Xaa'|Cys|(SEQ ID NO: 3893)|
|Pro|Gly|Thr|Cys|Gly|Glu|Ile|Xaa'|Cys|Ala|Ala|Xaa'|Tyr|Xaa'|Ala|Ala|Cys|Xaa'|Thr|Gly|Cys|Xaa'|(SEQ ID NO: 3894)|
|Pro|Gly|Thr|Cys|Gly|Glu|Ile|Xaa'|Cys|Ala|Ala|Xaa'|Tyr|Xaa'|Ala|Ala|Cys|Thr|Gly|Cys|(SEQ ID NO: 3895)|
|Pro|Gly|Thr|Cys|Gly|Glu|Ile|Xaa'|Cys|Ala|Ala|Xaa'|Tyr|Xaa'|Xaa'|Ala|Ala|Cys|Thr|Gly|Cys|(SEQ ID NO: 3896)|
|Pro|Gly|Thr|Cys|Gly|Glu|Ile|Xaa'|Cys|Ala|Ala|Xaa'|Tyr|Xaa'|Xaa'|Ala|Ala|Cys|Thr|Gly|Xaa'|Cys|(SEQ ID NO: 3897)|
|Pro|Gly|Thr|Cys|Gly|Glu|Ile|Xaa'|Cys|Ala|Ala|Xaa'|Tyr|Xaa'|Xaa'|Ala|Ala|Cys|Thr|Gly|Cys|Xaa'|(SEQ ID NO: 3898)|
|Pro|Gly|Thr|Cys|Gly|Glu|Ile|Xaa'|Cys|Ala|Ala|Xaa'|Tyr|Xaa'|Xaa'|Ala|Ala|Cys|Xaa'|Thr|Gly|Cys|(SEQ ID NO: 3899)|
|Pro|Gly|Thr|Cys|Gly|Glu|Ile|Xaa'|Cys|Ala|Ala|Xaa'|Tyr|Xaa'|Xaa'|Ala|Ala|Cys|Xaa'|Thr|Gly|Xaa'|Cys|(SEQ ID NO: 3900)|
|Pro|Gly|Thr|Cys|Gly|Glu|Ile|Xaa'|Cys|Ala|Ala|Xaa'|Tyr|Xaa'|Xaa'|Ala|Ala|Cys|Xaa'|Thr|Gly|Cys|Xaa'|(SEQ ID NO: 3901)|
|Pro|Gly|Thr|Cys|Gly|Glu|Ile|Xaa'|Cys|Ala|Ala|Xaa'|Tyr|Xaa'|Xaa'|Ala|Xaa'|Cys|Thr|Gly|Cys|(SEQ ID NO: 3902)|
|Pro|Gly|Thr|Cys|Gly|Glu|Ile|Xaa'|Cys|Ala|Ala|Xaa'|Tyr|Xaa'|Xaa'|Ala|Xaa'|Cys|Thr|Gly|Xaa'|Cys|(SEQ ID NO: 3903)|
|Pro|Gly|Thr|Cys|Gly|Glu|Ile|Xaa'|Cys|Ala|Ala|Xaa'|Tyr|Xaa'|Xaa'|Ala|Xaa'|Cys|Thr|Gly|Cys|Xaa'|(SEQ ID NO: 3904)|
|Pro|Gly|Thr|Cys|Gly|Glu|Ile|Xaa'|Cys|Ala|Ala|Tyr|Ala|Xaa'|Cys|Thr|Gly|Cys|(SEQ ID NO: 3905)|
|Pro|Gly|Thr|Cys|Gly|Glu|Ile|Xaa'|Cys|Ala|Ala|Tyr|Ala|Xaa'|Cys|Thr|Gly|Xaa'|Cys|(SEQ ID NO: 3906)|
|Pro|Gly|Thr|Cys|Gly|Glu|Ile|Xaa'|Cys|Ala|Ala|Xaa'|Tyr|Ala|Xaa'|Cys|Thr|Gly|Cys|(SEQ ID NO: 3907)|
|Pro|Gly|Thr|Cys|Gly|Glu|Ile|Xaa'|Cys|Ala|Ala|Xaa'|Tyr|Ala|Xaa'|Cys|Thr|Gly|Xaa'|Cys|(SEQ ID NO: 3908)|
|Pro|Gly|Thr|Cys|Gly|Glu|Ile|Xaa'|Cys|Ala|Ala|Xaa'|Tyr|Ala|Xaa'|Cys|Thr|Gly|Cys|Xaa'|(SEQ ID NO: 3909)|
|Pro|Gly|Thr|Cys|Gly|Glu|Ile|Xaa'|Cys|Ala|Ala|Xaa'|Tyr|Xaa'|Ala|Xaa'|Cys|Thr|Gly|Cys|(SEQ ID NO: 3910)|
|Pro|Gly|Thr|Cys|Gly|Glu|Ile|Xaa'|Cys|Ala|Ala|Xaa'|Tyr|Xaa'|Ala|Xaa'|Cys|Thr|Gly|Xaa'|Cys|(SEQ ID NO: 3911)|
|Pro|Gly|Thr|Cys|Gly|Glu|Ile|Xaa'|Cys|Ala|Ala|Xaa'|Tyr|Xaa'|Ala|Xaa'|Cys|Thr|Gly|Cys|Xaa'|(SEQ ID NO: 3912)|
|Pro|Gly|Thr|Cys|Gly|Glu|Ile|Xaa'|Cys|Ala|Ala|Xaa'|Tyr|Xaa'|Ala|Xaa'|Xaa'|Cys|Thr|Gly|Cys|(SEQ ID NO: 3913)|
|Pro|Gly|Thr|Cys|Gly|Glu|Ile|Xaa'|Cys|Ala|Ala|Xaa'|Tyr|Xaa'|Ala|Xaa'|Xaa'|Cys|Thr|Gly|Xaa'|Cys|(SEQ ID NO: 3914)|

FIG. 2CK

| | | | | | | | | | | | |
|---|---|---|---|---|---|---|---|---|---|---|---|
| Pro Gly Thr Cys Gly Glu Ile Xaa' Cys Ala Xaa' Tyr Ala Ala Xaa' Cys Thr Gly Xaa' Cys | (SEQ ID NO: 3915) |
| Pro Gly Thr Cys Gly Glu Ile Xaa' Cys Ala Xaa' Tyr Ala Ala Xaa' Cys Thr Gly Cys Xaa' | (SEQ ID NO: 3916) |
| Pro Gly Thr Cys Gly Glu Ile Xaa' Cys Ala Xaa' Tyr Ala Ala Xaa' Cys Thr Gly Cys Cys | (SEQ ID NO: 3917) |
| Pro Gly Thr Cys Gly Glu Ile Xaa' Cys Ala Xaa' Tyr Ala Ala Xaa' Cys Xaa' Thr Gly Cys | (SEQ ID NO: 3918) |
| Pro Gly Thr Cys Gly Glu Ile Xaa' Cys Ala Xaa' Tyr Ala Ala Xaa' Cys Xaa' Thr Gly Cys | (SEQ ID NO: 3919) |
| Pro Gly Thr Cys Gly Glu Ile Xaa' Cys Ala Xaa' Tyr Ala Ala Xaa' Cys Xaa' Thr Gly Xaa' | (SEQ ID NO: 3920) |
| Pro Gly Thr Cys Gly Glu Ile Xaa' Cys Ala Xaa' Tyr Ala Ala Xaa' Cys Xaa' Thr Cys Xaa' | (SEQ ID NO: 3921) |
| Pro Gly Thr Cys Gly Glu Ile Xaa' Cys Ala Xaa' Tyr Ala Ala Xaa' Cys Thr Xaa' Gly Cys | (SEQ ID NO: 3922) |
| Pro Gly Thr Cys Gly Glu Ile Xaa' Cys Ala Xaa' Tyr Ala Ala Xaa' Cys Thr Xaa' Gly Cys | (SEQ ID NO: 3923) |
| Pro Gly Thr Cys Gly Glu Ile Xaa' Cys Ala Xaa' Tyr Ala Ala Xaa' Cys Thr Xaa' Cys Xaa' | (SEQ ID NO: 3924) |
| Pro Gly Thr Cys Gly Glu Ile Xaa' Cys Ala Xaa' Tyr Ala Ala Xaa' Cys Thr Gly Xaa' Cys | (SEQ ID NO: 3925) |
| Pro Gly Thr Cys Gly Glu Ile Xaa' Cys Ala Xaa' Tyr Ala Ala Xaa' Cys Thr Gly Xaa' Cys | (SEQ ID NO: 3926) |
| Pro Gly Thr Cys Gly Glu Ile Xaa' Cys Ala Xaa' Tyr Ala Ala Xaa' Cys Thr Gly Xaa' Cys | (SEQ ID NO: 3927) |
| Pro Gly Thr Cys Gly Glu Ile Xaa' Cys Ala Xaa' Tyr Ala Ala Xaa' Cys Thr Gly Cys Xaa' | (SEQ ID NO: 3928) |
| Pro Gly Thr Cys Gly Glu Ile Xaa' Cys Ala Xaa' Tyr Ala Ala Xaa' Cys Thr Gly Cys Xaa' | (SEQ ID NO: 3929) |
| Pro Gly Thr Cys Gly Glu Ile Xaa' Cys Ala Xaa' Tyr Ala Ala Tyr Cys Thr Gly Cys | (SEQ ID NO: 3930) |
| Pro Gly Thr Cys Gly Glu Ile Xaa' Cys Ala Xaa' Tyr Ala Ala Tyr Cys Thr Gly Cys | (SEQ ID NO: 3931) |
| Pro Gly Thr Cys Gly Glu Ile Xaa' Cys Ala Xaa' Tyr Xaa' Ala Ala Cys Thr Gly Cys | (SEQ ID NO: 3932) |
| Pro Gly Thr Cys Gly Glu Ile Xaa' Cys Ala Xaa' Tyr Xaa' Ala Ala Cys Thr Gly Cys | (SEQ ID NO: 3933) |
| Pro Gly Thr Cys Gly Glu Ile Xaa' Cys Ala Xaa' Tyr Xaa' Ala Ala Cys Thr Gly Cys | (SEQ ID NO: 3934) |
| Pro Gly Thr Cys Gly Glu Ile Xaa' Cys Ala Xaa' Tyr Xaa' Ala Ala Cys Thr Gly Cys | (SEQ ID NO: 3935) |
| Pro Gly Thr Cys Gly Glu Ile Xaa' Cys Ala Xaa' Tyr Xaa' Ala Ala Cys Thr Gly Cys | (SEQ ID NO: 3936) |
| Pro Gly Thr Cys Gly Glu Ile Xaa' Cys Ala Xaa' Tyr Xaa' Ala Ala Cys Thr Gly Cys | (SEQ ID NO: 3937) |
| Pro Gly Thr Cys Gly Glu Ile Xaa' Cys Ala Xaa' Tyr Xaa' Ala Ala Cys Thr Gly Cys | (SEQ ID NO: 3938) |
| Pro Gly Thr Cys Gly Glu Ile Xaa' Cys Ala Xaa' Tyr Xaa' Ala Xaa' Cys Thr Gly Cys | (SEQ ID NO: 3939) |
| Pro Gly Thr Cys Gly Glu Ile Xaa' Cys Ala Xaa' Tyr Xaa' Ala Xaa' Cys Thr Gly Cys | (SEQ ID NO: 3940) |
| Pro Gly Thr Cys Gly Glu Ile Xaa' Cys Ala Xaa' Tyr Xaa' Ala Xaa' Cys Thr Gly Cys | (SEQ ID NO: 3941) |
| Pro Gly Thr Cys Gly Glu Ile Xaa' Cys Ala Xaa' Tyr Xaa' Ala Xaa' Cys Thr Gly Cys | (SEQ ID NO: 3942) |
| Pro Gly Thr Cys Gly Glu Ile Xaa' Cys Ala Xaa' Tyr Xaa' Ala Xaa' Cys Thr Gly Cys | (SEQ ID NO: 3943) |
| Pro Gly Thr Cys Gly Glu Ile Xaa' Cys Ala Xaa' Tyr Xaa' Ala Xaa' Cys Thr Gly Cys | (SEQ ID NO: 3944) |
| Pro Gly Thr Cys Gly Glu Ile Xaa' Cys Ala Xaa' Tyr Xaa' Ala Xaa' Cys Thr Gly Cys | (SEQ ID NO: 3945) |
| Pro Gly Thr Cys Gly Glu Ile Xaa' Cys Ala Xaa' Tyr Xaa' Ala Xaa' Cys Thr Gly Cys | (SEQ ID NO: 3946) |
| Pro Gly Thr Cys Gly Glu Ile Xaa' Cys Ala Xaa' Tyr Xaa' Ala Ala Xaa' Cys Thr Gly Cys | (SEQ ID NO: 3947) |
| Pro Gly Thr Cys Gly Glu Ile Xaa' Cys Ala Xaa' Tyr Xaa' Ala Ala Xaa' Cys Thr Gly Cys | (SEQ ID NO: 3948) |

FIG. 2CL

| | | | | | | | | | | | |
|---|---|---|---|---|---|---|---|---|---|---|---|
| Pro | Gly | Thr | Cys | Gly | Glu | Ile | Xaa' | Cys | Ala | Tyr | Xaa' | Ala | Ala | Xaa' | Cys | Xaa' | Thr | Gly | Cys | (SEQ ID NO: 3949) |
| Pro | Gly | Thr | Cys | Gly | Glu | Ile | Xaa' | Cys | Ala | Tyr | Xaa' | Ala | Ala | Xaa' | Cys | Thr | Xaa' | Gly | Cys | (SEQ ID NO: 3950) |
| Pro | Gly | Thr | Cys | Gly | Glu | Ile | Xaa' | Cys | Ala | Tyr | Xaa' | Ala | Ala | Xaa' | Cys | Thr | Gly | Xaa' | Cys | (SEQ ID NO: 3951) |
| Pro | Gly | Thr | Cys | Gly | Glu | Ile | Xaa' | Cys | Ala | Tyr | Xaa' | Ala | Ala | Xaa' | Cys | Thr | Gly | Cys | Xaa' | (SEQ ID NO: 3952) |
| Pro | Gly | Thr | Cys | Gly | Glu | Ile | Xaa' | Cys | Ala | Tyr | Xaa' | Ala | Ala | Cys | Xaa' | Xaa' | Thr | Gly | Cys | (SEQ ID NO: 3953) |
| Pro | Gly | Thr | Cys | Gly | Glu | Ile | Xaa' | Cys | Ala | Tyr | Xaa' | Ala | Ala | Cys | Xaa' | Thr | Xaa' | Gly | Cys | (SEQ ID NO: 3954) |
| Pro | Gly | Thr | Cys | Gly | Glu | Ile | Xaa' | Cys | Ala | Tyr | Xaa' | Ala | Ala | Cys | Xaa' | Thr | Gly | Xaa' | Cys | (SEQ ID NO: 3955) |
| Pro | Gly | Thr | Cys | Gly | Glu | Ile | Xaa' | Cys | Ala | Tyr | Xaa' | Ala | Ala | Cys | Xaa' | Thr | Gly | Cys | Xaa' | (SEQ ID NO: 3956) |
| Pro | Gly | Thr | Cys | Gly | Glu | Ile | Xaa' | Cys | Ala | Tyr | Xaa' | Ala | Ala | Cys | Thr | Xaa' | Xaa' | Gly | Cys | (SEQ ID NO: 3957) |
| Pro | Gly | Thr | Cys | Gly | Glu | Ile | Xaa' | Cys | Ala | Tyr | Xaa' | Ala | Ala | Cys | Thr | Xaa' | Gly | Xaa' | Cys | (SEQ ID NO: 3958) |
| Pro | Gly | Thr | Cys | Gly | Glu | Ile | Xaa' | Cys | Ala | Tyr | Xaa' | Ala | Ala | Cys | Thr | Xaa' | Gly | Cys | Xaa' | (SEQ ID NO: 3959) |
| Pro | Gly | Thr | Cys | Gly | Glu | Ile | Xaa' | Cys | Ala | Tyr | Xaa' | Ala | Ala | Cys | Thr | Gly | Xaa' | Xaa' | Cys | (SEQ ID NO: 3960) |
| Pro | Gly | Thr | Cys | Gly | Glu | Ile | Xaa' | Cys | Ala | Tyr | Xaa' | Ala | Ala | Cys | Thr | Gly | Xaa' | Cys | Xaa' | (SEQ ID NO: 3961) |
| Pro | Gly | Thr | Cys | Gly | Glu | Ile | Xaa' | Cys | Ala | Tyr | Xaa' | Ala | Ala | Cys | Thr | Gly | Cys | Xaa' | Xaa' | (SEQ ID NO: 3962) |
| Pro | Gly | Thr | Cys | Gly | Glu | Ile | Xaa' | Cys | Ala | Tyr | Ala | Xaa' | Xaa' | Xaa' | Cys | Thr | Gly | Cys | | (SEQ ID NO: 3963) |
| Pro | Gly | Thr | Cys | Gly | Glu | Ile | Xaa' | Cys | Ala | Tyr | Ala | Xaa' | Xaa' | Cys | Xaa' | Thr | Gly | Cys | | (SEQ ID NO: 3964) |
| Pro | Gly | Thr | Cys | Gly | Glu | Ile | Xaa' | Cys | Ala | Tyr | Ala | Xaa' | Xaa' | Cys | Thr | Xaa' | Gly | Cys | | (SEQ ID NO: 3965) |
| Pro | Gly | Thr | Cys | Gly | Glu | Ile | Xaa' | Cys | Ala | Tyr | Ala | Xaa' | Xaa' | Cys | Thr | Gly | Xaa' | Cys | | (SEQ ID NO: 3966) |
| Pro | Gly | Thr | Cys | Gly | Glu | Ile | Xaa' | Cys | Ala | Tyr | Ala | Xaa' | Xaa' | Cys | Thr | Gly | Cys | Xaa' | | (SEQ ID NO: 3967) |
| Pro | Gly | Thr | Cys | Gly | Glu | Ile | Xaa' | Cys | Ala | Tyr | Ala | Xaa' | Ala | Xaa' | Cys | Thr | Gly | Cys | | (SEQ ID NO: 3968) |
| Pro | Gly | Thr | Cys | Gly | Glu | Ile | Xaa' | Cys | Ala | Tyr | Ala | Xaa' | Ala | Cys | Xaa' | Thr | Gly | Cys | | (SEQ ID NO: 3969) |
| Pro | Gly | Thr | Cys | Gly | Glu | Ile | Xaa' | Cys | Ala | Tyr | Ala | Xaa' | Ala | Cys | Thr | Xaa' | Gly | Cys | | (SEQ ID NO: 3970) |
| Pro | Gly | Thr | Cys | Gly | Glu | Ile | Xaa' | Cys | Ala | Tyr | Ala | Xaa' | Ala | Cys | Thr | Gly | Xaa' | Cys | | (SEQ ID NO: 3971) |
| Pro | Gly | Thr | Cys | Gly | Glu | Ile | Xaa' | Cys | Ala | Tyr | Ala | Xaa' | Ala | Cys | Thr | Gly | Cys | Xaa' | | (SEQ ID NO: 3972) |
| Pro | Gly | Thr | Cys | Gly | Glu | Ile | Xaa' | Cys | Ala | Tyr | Ala | Ala | Xaa' | Xaa' | Cys | Thr | Gly | Cys | | (SEQ ID NO: 3973) |
| Pro | Gly | Thr | Cys | Gly | Glu | Ile | Xaa' | Cys | Ala | Tyr | Ala | Ala | Xaa' | Cys | Xaa' | Thr | Gly | Cys | | (SEQ ID NO: 3974) |
| Pro | Gly | Thr | Cys | Gly | Glu | Ile | Xaa' | Cys | Ala | Tyr | Ala | Ala | Xaa' | Cys | Thr | Xaa' | Gly | Cys | | (SEQ ID NO: 3975) |
| Pro | Gly | Thr | Cys | Gly | Glu | Ile | Xaa' | Cys | Ala | Tyr | Ala | Ala | Xaa' | Cys | Thr | Gly | Xaa' | Cys | | (SEQ ID NO: 3976) |
| Pro | Gly | Thr | Cys | Gly | Glu | Ile | Xaa' | Cys | Ala | Tyr | Ala | Ala | Xaa' | Cys | Thr | Gly | Cys | Xaa' | | (SEQ ID NO: 3977) |
| Pro | Gly | Thr | Cys | Gly | Glu | Ile | Xaa' | Cys | Ala | Tyr | Ala | Ala | Cys | Xaa' | Xaa' | Thr | Gly | Cys | | (SEQ ID NO: 3978) |
| Pro | Gly | Thr | Cys | Gly | Glu | Ile | Xaa' | Cys | Ala | Tyr | Ala | Ala | Cys | Xaa' | Thr | Xaa' | Gly | Cys | | (SEQ ID NO: 3979) |
| Pro | Gly | Thr | Cys | Gly | Glu | Ile | Xaa' | Cys | Ala | Tyr | Ala | Ala | Cys | Xaa' | Thr | Gly | Xaa' | Cys | | (SEQ ID NO: 3980) |
| Pro | Gly | Thr | Cys | Gly | Glu | Ile | Xaa' | Cys | Ala | Tyr | Ala | Ala | Cys | Xaa' | Thr | Gly | Cys | Xaa' | | (SEQ ID NO: 3981) |
| Pro | Gly | Thr | Cys | Gly | Glu | Ile | Xaa' | Cys | Ala | Tyr | Ala | Ala | Cys | Thr | Xaa' | Xaa' | Thr | Gly | Cys | (SEQ ID NO: 3982) |

FIG. 2CM

| | | | | | | | | | | | | |
|---|---|---|---|---|---|---|---|---|---|---|---|---|
| Pro | Gly | Thr | Cys | Gly | Glu | Ile | Xaa' | Cys | Ala | Tyr | Ala | Xaa' | Ala | Cys | Xaa' | Xaa' | Thr | Xaa' | Gly | Cys | (SEQ ID NO: 3983) |
| Pro | Gly | Thr | Cys | Gly | Glu | Ile | Xaa' | Cys | Ala | Tyr | Ala | Xaa' | Ala | Cys | Xaa' | Xaa' | Thr | Gly | Xaa' | Cys | (SEQ ID NO: 3984) |
| Pro | Gly | Thr | Cys | Gly | Glu | Ile | Xaa' | Cys | Ala | Tyr | Ala | Xaa' | Ala | Cys | Xaa' | Thr | Gly | Xaa' | Cys | Xaa' | (SEQ ID NO: 3985) |
| Pro | Gly | Thr | Cys | Gly | Glu | Ile | Xaa' | Cys | Ala | Tyr | Ala | Xaa' | Ala | Cys | Xaa' | Thr | Gly | Cys | Xaa' | | (SEQ ID NO: 3986) |
| Pro | Gly | Thr | Cys | Gly | Glu | Ile | Xaa' | Cys | Ala | Tyr | Ala | Xaa' | Ala | Cys | Xaa' | Thr | Xaa' | Gly | Cys | | (SEQ ID NO: 3987) |
| Pro | Gly | Thr | Cys | Gly | Glu | Ile | Xaa' | Cys | Ala | Tyr | Ala | Xaa' | Ala | Cys | Thr | Xaa' | Xaa' | Gly | Cys | | (SEQ ID NO: 3988) |
| Pro | Gly | Thr | Cys | Gly | Glu | Ile | Xaa' | Cys | Ala | Tyr | Ala | Xaa' | Ala | Cys | Thr | Xaa' | Gly | Xaa' | Cys | | (SEQ ID NO: 3989) |
| Pro | Gly | Thr | Cys | Gly | Glu | Ile | Xaa' | Cys | Ala | Tyr | Ala | Xaa' | Ala | Cys | Thr | Gly | Xaa' | Cys | | | (SEQ ID NO: 3990) |
| Pro | Gly | Thr | Cys | Gly | Glu | Ile | Xaa' | Cys | Ala | Tyr | Ala | Xaa' | Ala | Cys | Thr | Gly | Xaa' | Xaa' | Cys | | (SEQ ID NO: 3991) |
| Pro | Gly | Thr | Cys | Gly | Glu | Ile | Xaa' | Cys | Ala | Tyr | Ala | Xaa' | Ala | Cys | Thr | Gly | Cys | Xaa' | | | (SEQ ID NO: 3992) |
| Pro | Gly | Thr | Cys | Gly | Glu | Ile | Xaa' | Cys | Ala | Tyr | Ala | Xaa' | Ala | Cys | Thr | Gly | Cys | Xaa' | Xaa' | | (SEQ ID NO: 3993) |
| Pro | Gly | Thr | Cys | Gly | Glu | Ile | Xaa' | Cys | Ala | Tyr | Ala | Xaa' | Ala | Cys | Cys | Thr | Gly | Cys | | | (SEQ ID NO: 3994) |
| Pro | Gly | Thr | Cys | Gly | Glu | Ile | Xaa' | Cys | Ala | Tyr | Ala | Xaa' | Ala | Xaa' | Cys | Thr | Gly | Cys | | | (SEQ ID NO: 3995) |
| Pro | Gly | Thr | Cys | Gly | Glu | Ile | Xaa' | Cys | Ala | Tyr | Ala | Ala | Xaa' | Xaa' | Cys | Thr | Gly | Cys | | | (SEQ ID NO: 3996) |
| Pro | Gly | Thr | Cys | Gly | Glu | Ile | Xaa' | Cys | Ala | Tyr | Ala | Ala | Xaa' | Xaa' | Xaa' | Cys | Thr | Gly | Cys | | (SEQ ID NO: 3997) |
| Pro | Gly | Thr | Cys | Gly | Glu | Ile | Xaa' | Cys | Ala | Tyr | Ala | Ala | Xaa' | Xaa' | Cys | Thr | Xaa' | Gly | Cys | | (SEQ ID NO: 3998) |
| Pro | Gly | Thr | Cys | Gly | Glu | Ile | Xaa' | Cys | Ala | Tyr | Ala | Ala | Xaa' | Xaa' | Cys | Thr | Gly | Xaa' | Cys | | (SEQ ID NO: 3999) |
| Pro | Gly | Thr | Cys | Gly | Glu | Ile | Xaa' | Cys | Ala | Tyr | Ala | Ala | Xaa' | Xaa' | Cys | Thr | Gly | Cys | Xaa' | | (SEQ ID NO: 4000) |
| Pro | Gly | Thr | Cys | Gly | Glu | Ile | Xaa' | Cys | Ala | Tyr | Ala | Ala | Xaa' | Cys | Xaa' | Thr | Gly | Cys | | | (SEQ ID NO: 4001) |
| Pro | Gly | Thr | Cys | Gly | Glu | Ile | Xaa' | Cys | Ala | Tyr | Ala | Ala | Xaa' | Cys | Xaa' | Xaa' | Thr | Gly | Cys | | (SEQ ID NO: 4002) |
| Pro | Gly | Thr | Cys | Gly | Glu | Ile | Xaa' | Cys | Ala | Tyr | Ala | Ala | Xaa' | Cys | Xaa' | Thr | Xaa' | Gly | Cys | | (SEQ ID NO: 4003) |
| Pro | Gly | Thr | Cys | Gly | Glu | Ile | Xaa' | Cys | Ala | Tyr | Ala | Ala | Xaa' | Cys | Xaa' | Thr | Gly | Xaa' | Cys | | (SEQ ID NO: 4004) |
| Pro | Gly | Thr | Cys | Gly | Glu | Ile | Xaa' | Cys | Ala | Tyr | Ala | Ala | Xaa' | Cys | Xaa' | Thr | Gly | Cys | Xaa' | | (SEQ ID NO: 4005) |
| Pro | Gly | Thr | Cys | Gly | Glu | Ile | Xaa' | Cys | Ala | Tyr | Ala | Ala | Xaa' | Cys | Thr | Xaa' | Gly | Cys | | | (SEQ ID NO: 4006) |
| Pro | Gly | Thr | Cys | Gly | Glu | Ile | Xaa' | Cys | Ala | Tyr | Ala | Ala | Xaa' | Cys | Thr | Xaa' | Xaa' | Gly | Cys | | (SEQ ID NO: 4007) |
| Pro | Gly | Thr | Cys | Gly | Glu | Ile | Xaa' | Cys | Ala | Tyr | Ala | Ala | Xaa' | Cys | Thr | Xaa' | Gly | Xaa' | Cys | | (SEQ ID NO: 4008) |
| Pro | Gly | Thr | Cys | Gly | Glu | Ile | Xaa' | Cys | Ala | Tyr | Ala | Ala | Xaa' | Cys | Thr | Gly | Xaa' | Cys | | | (SEQ ID NO: 4009) |
| Pro | Gly | Thr | Cys | Gly | Glu | Ile | Xaa' | Cys | Ala | Tyr | Ala | Ala | Xaa' | Cys | Thr | Gly | Xaa' | Xaa' | Cys | | (SEQ ID NO: 4010) |
| Pro | Gly | Thr | Cys | Gly | Glu | Ile | Xaa' | Cys | Ala | Tyr | Ala | Ala | Xaa' | Cys | Thr | Gly | Cys | Xaa' | | | (SEQ ID NO: 4011) |
| Pro | Gly | Thr | Cys | Gly | Glu | Ile | Xaa' | Cys | Ala | Tyr | Ala | Ala | Xaa' | Cys | Thr | Gly | Xaa' | Cys | Xaa' | | (SEQ ID NO: 4012) |
| Pro | Gly | Thr | Cys | Gly | Glu | Ile | Xaa' | Cys | Ala | Tyr | Ala | Ala | Ala | Xaa' | Cys | Thr | Gly | Cys | | | (SEQ ID NO: 4013) |
| Pro | Gly | Thr | Cys | Gly | Glu | Ile | Ile | Xaa' | Cys | Ala | Tyr | Ala | Ala | Xaa' | Cys | Thr | Gly | Cys | Xaa' | | (SEQ ID NO: 4014) |
| Pro | Gly | Thr | Cys | Gly | Glu | Ile | Xaa' | Cys | Ala | Tyr | Ala | Ala | Ala | Xaa' | Cys | Thr | Gly | Cys | Xaa' | Xaa' | (SEQ ID NO: 4015) |
| Pro | Gly | Thr | Cys | Gly | Glu | Ile | Xaa' | Cys | Ala | Tyr | Ala | Ala | Cys | Xaa' | Thr | Gly | Cys | | | | (SEQ ID NO: 4016) |

FIG. 2CN

| | | | | | | | | | | | | | | |
|---|---|---|---|---|---|---|---|---|---|---|---|---|---|---|
| Pro | Gly | Thr | Cys | Gly | Glu | Ile | Xaa | Cys | Ala | Tyr | Ala | Cys | Xaa' | Xaa' Xaa' Thr Gly Cys | (SEQ ID NO: 4017) |
| Pro | Gly | Thr | Cys | Gly | Glu | Ile | Xaa | Cys | Ala | Tyr | Ala | Cys | Xaa' | Xaa' Xaa' Thr Gly Cys | (SEQ ID NO: 4018) |
| Pro | Gly | Thr | Cys | Gly | Glu | Ile | Xaa | Cys | Ala | Tyr | Ala | Cys | Xaa' | Xaa' Thr Xaa' Gly Cys | (SEQ ID NO: 4019) |
| Pro | Gly | Thr | Cys | Gly | Glu | Ile | Xaa | Cys | Ala | Tyr | Ala | Cys | Xaa' | Xaa' Thr Gly Xaa' Cys | (SEQ ID NO: 4020) |
| Pro | Gly | Thr | Cys | Gly | Glu | Ile | Xaa | Cys | Ala | Tyr | Ala | Cys | Xaa' | Xaa' Thr Gly Cys Xaa' | (SEQ ID NO: 4021) |
| Pro | Gly | Thr | Cys | Gly | Glu | Ile | Xaa | Cys | Ala | Tyr | Ala | Cys | Xaa' | Thr Xaa' Xaa' Gly Cys | (SEQ ID NO: 4022) |
| Pro | Gly | Thr | Cys | Gly | Glu | Ile | Xaa | Cys | Ala | Tyr | Ala | Cys | Xaa' | Thr Xaa' Gly Xaa' Cys | (SEQ ID NO: 4023) |
| Pro | Gly | Thr | Cys | Gly | Glu | Ile | Xaa | Cys | Ala | Tyr | Ala | Cys | Xaa' | Thr Xaa' Gly Cys Xaa' | (SEQ ID NO: 4024) |
| Pro | Gly | Thr | Cys | Gly | Glu | Ile | Xaa | Cys | Ala | Tyr | Ala | Cys | Xaa' | Thr Gly Xaa' Cys Xaa' | (SEQ ID NO: 4025) |
| Pro | Gly | Thr | Cys | Gly | Glu | Ile | Xaa | Cys | Ala | Tyr | Ala | Cys | Xaa' | Thr Gly Xaa' Xaa' Cys | (SEQ ID NO: 4026) |
| Pro | Gly | Thr | Cys | Gly | Glu | Ile | Xaa | Cys | Ala | Tyr | Ala | Cys | Xaa' | Thr Gly Cys Xaa' Xaa' | (SEQ ID NO: 4027) |
| Pro | Gly | Thr | Cys | Gly | Glu | Ile | Xaa | Cys | Ala | Tyr | Ala | Cys | Xaa' | Thr Gly Cys Xaa' | (SEQ ID NO: 4028) |
| Pro | Gly | Thr | Cys | Gly | Glu | Ile | Xaa | Cys | Ala | Tyr | Ala | Cys | Xaa' | Thr Gly Cys Xaa' | (SEQ ID NO: 4029) |
| Pro | Gly | Thr | Cys | Gly | Glu | Ile | Xaa | Cys | Ala | Tyr | Ala | Cys | Xaa' | Thr Gly Cys Xaa' | (SEQ ID NO: 4030) |
| Pro | Gly | Thr | Cys | Gly | Glu | Ile | Xaa | Cys | Ala | Tyr | Ala | Cys | Xaa' | Thr Xaa' Gly Cys | (SEQ ID NO: 4031) |
| Pro | Gly | Thr | Cys | Gly | Glu | Ile | Xaa | Cys | Ala | Tyr | Ala | Cys | Thr | Xaa' Xaa' Xaa' Gly Cys | (SEQ ID NO: 4032) |
| Pro | Gly | Thr | Cys | Gly | Glu | Ile | Xaa | Cys | Ala | Tyr | Ala | Cys | Thr | Xaa' Xaa' Gly Xaa' Cys | (SEQ ID NO: 4033) |
| Pro | Gly | Thr | Cys | Gly | Glu | Ile | Xaa | Cys | Ala | Tyr | Ala | Cys | Thr | Xaa' Xaa' Gly Cys Xaa' | (SEQ ID NO: 4034) |
| Pro | Gly | Thr | Cys | Gly | Glu | Ile | Xaa | Cys | Ala | Tyr | Ala | Cys | Thr | Xaa' Gly Xaa' Xaa' Cys | (SEQ ID NO: 4035) |
| Pro | Gly | Thr | Cys | Gly | Glu | Ile | Xaa | Cys | Ala | Tyr | Ala | Cys | Thr | Xaa' Gly Xaa' Cys Xaa' | (SEQ ID NO: 4036) |
| Pro | Gly | Thr | Cys | Gly | Glu | Ile | Xaa | Cys | Ala | Tyr | Ala | Cys | Thr | Xaa' Gly Cys Xaa' Xaa' | (SEQ ID NO: 4037) |
| Pro | Gly | Thr | Cys | Gly | Glu | Ile | Xaa | Cys | Ala | Tyr | Ala | Cys | Thr | Gly Xaa' Xaa' Cys Xaa' | (SEQ ID NO: 4038) |
| Pro | Gly | Thr | Cys | Gly | Glu | Ile | Xaa | Cys | Ala | Tyr | Ala | Cys | Thr | Gly Xaa' Xaa' Xaa' Cys | (SEQ ID NO: 4039) |
| Pro | Gly | Thr | Cys | Gly | Glu | Ile | Xaa | Cys | Ala | Tyr | Ala | Cys | Thr | Gly Xaa' Cys Xaa' Xaa' | (SEQ ID NO: 4040) |
| Pro | Gly | Thr | Cys | Gly | Glu | Ile | Xaa | Cys | Ala | Tyr | Ala | Cys | Thr | Gly Xaa' Cys | (SEQ ID NO: 4041) |
| Pro | Gly | Thr | Cys | Gly | Glu | Ile | Xaa | Cys | Ala | Tyr | Ala | Cys | Thr | Gly Cys Xaa' Xaa' Cys | (SEQ ID NO: 4042) |
| Pro | Gly | Thr | Cys | Gly | Glu | Ile | Xaa | Cys | Ala | Tyr | Ala | Cys | Thr | Gly Cys Xaa' Xaa' Xaa' | (SEQ ID NO: 4043) |
| Pro | Gly | Thr | Cys | Gly | Glu | Ile | Xaa | Cys | Ala | Tyr | Ala | Cys | Thr | Gly Cys Xaa' Xaa' | (SEQ ID NO: 4044) |
| Pro | Gly | Thr | Cys | Gly | Glu | Ile | Xaa | Cys | Ala | Tyr | Ala | Cys | Thr | Gly Cys Xaa' Xaa' | (SEQ ID NO: 4045) |
| Pro | Gly | Thr | Cys | Gly | Glu | Ile | Xaa | Cys | Ala | Tyr | Ala | Cys | Thr | Gly Cys Xaa' | (SEQ ID NO: 4046) |
| Pro | Gly | Thr | Cys | Gly | Glu | Ile | Xaa | Cys | Ala | Tyr | Ala | Cys | Thr | Gly Cys Xaa' Xaa' | (SEQ ID NO: 4047) |
| Pro | Gly | Thr | Cys | Gly | Glu | Ile | Xaa | Cys Xaa' | Ala | Tyr | Ala | Cys | Thr | Gly Cys Xaa' Xaa' | (SEQ ID NO: 4048) |
| Pro | Gly | Thr | Cys | Gly | Glu | Ile | Cys | Xaa' | Ala | Tyr | Ala | Cys | Thr | Gly Cys Xaa' Xaa' | (SEQ ID NO: 4049) |
| Pro | Gly | Thr | Cys | Gly | Glu | Ile | Cys | Xaa' | Ala | Tyr | Ala | Cys | Thr | Gly Cys | (SEQ ID NO: 4050) |

FIG. 2CO

| | | | | | | | | | | | | | |
|---|---|---|---|---|---|---|---|---|---|---|---|---|---|
| Pro | Gly | Thr | Cys | Gly | Glu | Ile | Cys | Xaa' | Ala | Tyr | Ala | Ala | Cys | Thr | Gly | Cys | (SEQ ID NO: 4051) |
| Pro | Gly | Thr | Cys | Gly | Glu | Ile | Cys | Xaa' | Xaa' | Tyr | Ala | Ala | Cys | Thr | Gly | Cys | (SEQ ID NO: 4052) |
| Pro | Gly | Thr | Cys | Gly | Glu | Ile | Cys | Xaa' | Xaa' | Ala | Tyr | Ala | Ala | Cys | Thr | Gly | Cys | (SEQ ID NO: 4053) |
| Pro | Gly | Thr | Cys | Gly | Glu | Ile | Cys | Xaa' | Xaa' | Xaa' | Tyr | Ala | Ala | Cys | Thr | Gly | Cys | (SEQ ID NO: 4054) |
| Pro | Gly | Thr | Cys | Gly | Glu | Ile | Cys | Xaa' | Xaa' | Ala | Xaa' | Tyr | Ala | Ala | Cys | Thr | Gly | Cys | (SEQ ID NO: 4055) |
| Pro | Gly | Thr | Cys | Gly | Glu | Ile | Cys | Xaa' | Xaa' | Ala | Tyr | Xaa' | Ala | Cys | Thr | Gly | Cys | (SEQ ID NO: 4056) |
| Pro | Gly | Thr | Cys | Gly | Glu | Ile | Cys | Xaa' | Xaa' | Ala | Tyr | Ala | Xaa' | Cys | Thr | Gly | Cys | (SEQ ID NO: 4057) |
| Pro | Gly | Thr | Cys | Gly | Glu | Ile | Cys | Xaa' | Xaa' | Ala | Tyr | Ala | Xaa' | Cys | Thr | Gly | Cys | (SEQ ID NO: 4058) |
| Pro | Gly | Thr | Cys | Gly | Glu | Ile | Cys | Xaa' | Xaa' | Ala | Tyr | Ala | Ala | Cys | Xaa' | Gly | Cys | (SEQ ID NO: 4059) |
| Pro | Gly | Thr | Cys | Gly | Glu | Ile | Cys | Xaa' | Xaa' | Ala | Tyr | Ala | Ala | Cys | Thr | Xaa' | Cys | (SEQ ID NO: 4060) |
| Pro | Gly | Thr | Cys | Gly | Glu | Ile | Cys | Xaa' | Xaa' | Ala | Tyr | Ala | Ala | Cys | Thr | Gly | Xaa' | (SEQ ID NO: 4061) |
| Pro | Gly | Thr | Cys | Gly | Glu | Ile | Cys | Xaa' | Xaa' | Ala | Xaa' | Ala | Ala | Cys | Thr | Gly | Cys | (SEQ ID NO: 4062) |
| Pro | Gly | Thr | Cys | Gly | Glu | Ile | Cys | Xaa' | Ala | Xaa' | Tyr | Ala | Ala | Cys | Thr | Gly | Cys | (SEQ ID NO: 4063) |
| Pro | Gly | Thr | Cys | Gly | Glu | Ile | Cys | Xaa' | Xaa' | Tyr | Xaa' | Ala | Ala | Cys | Thr | Gly | Cys | (SEQ ID NO: 4064) |
| Pro | Gly | Thr | Cys | Gly | Glu | Ile | Cys | Xaa' | Xaa' | Tyr | Ala | Xaa' | Ala | Cys | Thr | Gly | Cys | (SEQ ID NO: 4065) |
| Pro | Gly | Thr | Cys | Gly | Glu | Ile | Cys | Xaa' | Xaa' | Tyr | Ala | Ala | Xaa' | Cys | Thr | Gly | Cys | (SEQ ID NO: 4066) |
| Pro | Gly | Thr | Cys | Gly | Glu | Ile | Cys | Xaa' | Xaa' | Tyr | Ala | Ala | Xaa' | Cys | Thr | Gly | Cys | (SEQ ID NO: 4067) |
| Pro | Gly | Thr | Cys | Gly | Glu | Ile | Cys | Xaa' | Xaa' | Tyr | Ala | Ala | Ala | Cys | Xaa' | Gly | Cys | (SEQ ID NO: 4068) |
| Pro | Gly | Thr | Cys | Gly | Glu | Ile | Cys | Xaa' | Xaa' | Tyr | Ala | Ala | Ala | Cys | Thr | Xaa' | Cys | (SEQ ID NO: 4069) |
| Pro | Gly | Thr | Cys | Gly | Glu | Ile | Cys | Xaa' | Xaa' | Tyr | Ala | Ala | Ala | Cys | Thr | Gly | Xaa' | (SEQ ID NO: 4070) |
| Pro | Gly | Thr | Cys | Gly | Glu | Ile | Cys | Xaa' | Ala | Tyr | Xaa' | Ala | Ala | Cys | Thr | Gly | Cys | (SEQ ID NO: 4071) |
| Pro | Gly | Thr | Cys | Gly | Glu | Ile | Cys | Xaa' | Ala | Tyr | Ala | Xaa' | Ala | Cys | Thr | Gly | Cys | (SEQ ID NO: 4072) |
| Pro | Gly | Thr | Cys | Gly | Glu | Ile | Cys | Xaa' | Ala | Tyr | Ala | Ala | Xaa' | Cys | Thr | Gly | Cys | (SEQ ID NO: 4073) |
| Pro | Gly | Thr | Cys | Gly | Glu | Ile | Cys | Xaa' | Ala | Tyr | Ala | Ala | Xaa' | Cys | Thr | Gly | Cys | (SEQ ID NO: 4074) |
| Pro | Gly | Thr | Cys | Gly | Glu | Ile | Cys | Xaa' | Ala | Tyr | Ala | Ala | Ala | Cys | Xaa' | Gly | Cys | (SEQ ID NO: 4075) |
| Pro | Gly | Thr | Cys | Gly | Glu | Ile | Cys | Xaa' | Ala | Tyr | Ala | Ala | Ala | Cys | Thr | Xaa' | Cys | (SEQ ID NO: 4076) |
| Pro | Gly | Thr | Cys | Gly | Glu | Ile | Cys | Xaa' | Ala | Tyr | Ala | Ala | Ala | Cys | Thr | Gly | Xaa' | (SEQ ID NO: 4077) |
| Pro | Gly | Thr | Cys | Gly | Glu | Ile | Cys | Xaa' | Xaa' | Ala | Xaa' | Ala | Ala | Cys | Thr | Gly | Cys | (SEQ ID NO: 4078) |
| Pro | Gly | Thr | Cys | Gly | Glu | Ile | Cys | Xaa' | Xaa' | Ala | Tyr | Ala | Ala | Cys | Thr | Gly | Cys | (SEQ ID NO: 4079) |
| Pro | Gly | Thr | Cys | Gly | Glu | Ile | Cys | Xaa' | Xaa' | Ala | Xaa' | Ala | Cys | Thr | Gly | Cys | (SEQ ID NO: 4080) |
| Pro | Gly | Thr | Cys | Gly | Glu | Ile | Cys | Xaa' | Xaa' | Ala | Xaa' | Ala | Ala | Cys | Thr | Gly | Cys | (SEQ ID NO: 4081) |
| Pro | Gly | Thr | Cys | Gly | Glu | Ile | Cys | Xaa' | Ala | Xaa' | Xaa' | Ala | Ala | Cys | Thr | Gly | Cys | (SEQ ID NO: 4082) |
| Pro | Gly | Thr | Cys | Gly | Glu | Ile | Cys | Xaa' | Ala | Tyr | Ala | Cys | Thr | Xaa' | Gly | Cys | (SEQ ID NO: 4083) |
| Pro | Gly | Thr | Cys | Gly | Glu | Ile | Cys | Xaa' | Ala | Tyr | Ala | Cys | Thr | Gly | Xaa' | Cys | (SEQ ID NO: 4084) |

FIG. 2CP

FIG. 2CQ

| | | | | | | | | | | | | | | |
|---|---|---|---|---|---|---|---|---|---|---|---|---|---|---|
| Pro | Gly | Thr | Cys | Gly | Glu | Ile | Cys | Xaa' | Ala | Xaa' | Tyr | Xaa' | Ala | Ala | Xaa' | Cys | Thr | Gly | Cys | (SEQ ID NO: 4119) |
| Pro | Gly | Thr | Cys | Gly | Glu | Ile | Cys | Xaa' | Ala | Xaa' | Tyr | Xaa' | Ala | Ala | Xaa' | Cys | Thr | Gly | Cys | (SEQ ID NO: 4120) |
| Pro | Gly | Thr | Cys | Gly | Glu | Ile | Cys | Xaa' | Ala | Xaa' | Tyr | Xaa' | Ala | Ala | Xaa' | Cys | Thr | Xaa' | Gly | Cys | (SEQ ID NO: 4121) |
| Pro | Gly | Thr | Cys | Gly | Glu | Ile | Cys | Xaa' | Ala | Xaa' | Tyr | Xaa' | Ala | Ala | Xaa' | Cys | Thr | Gly | Xaa' | Cys | (SEQ ID NO: 4122) |
| Pro | Gly | Thr | Cys | Gly | Glu | Ile | Cys | Xaa' | Ala | Xaa' | Tyr | Xaa' | Ala | Ala | Xaa' | Cys | Thr | Gly | Cys | Xaa' | (SEQ ID NO: 4123) |
| Pro | Gly | Thr | Cys | Gly | Glu | Ile | Cys | Xaa' | Ala | Xaa' | Tyr | Ala | Ala | Xaa' | Ala | Cys | Thr | Gly | Cys | (SEQ ID NO: 4124) |
| Pro | Gly | Thr | Cys | Gly | Glu | Ile | Cys | Xaa' | Ala | Xaa' | Tyr | Ala | Xaa' | Xaa' | Ala | Cys | Thr | Gly | Cys | (SEQ ID NO: 4125) |
| Pro | Gly | Thr | Cys | Gly | Glu | Ile | Cys | Xaa' | Ala | Xaa' | Tyr | Ala | Xaa' | Ala | Xaa' | Cys | Thr | Gly | Cys | (SEQ ID NO: 4126) |
| Pro | Gly | Thr | Cys | Gly | Glu | Ile | Cys | Xaa' | Ala | Xaa' | Tyr | Ala | Xaa' | Ala | Ala | Cys | Xaa' | Thr | Gly | Cys | (SEQ ID NO: 4127) |
| Pro | Gly | Thr | Cys | Gly | Glu | Ile | Cys | Xaa' | Ala | Xaa' | Tyr | Ala | Xaa' | Ala | Ala | Cys | Thr | Xaa' | Gly | Cys | (SEQ ID NO: 4128) |
| Pro | Gly | Thr | Cys | Gly | Glu | Ile | Cys | Xaa' | Ala | Xaa' | Tyr | Ala | Xaa' | Ala | Ala | Cys | Thr | Gly | Xaa' | Cys | (SEQ ID NO: 4129) |
| Pro | Gly | Thr | Cys | Gly | Glu | Ile | Cys | Xaa' | Ala | Xaa' | Tyr | Ala | Xaa' | Ala | Ala | Cys | Thr | Gly | Cys | Xaa' | (SEQ ID NO: 4130) |
| Pro | Gly | Thr | Cys | Gly | Glu | Ile | Cys | Xaa' | Ala | Xaa' | Tyr | Ala | Ala | Xaa' | Xaa' | Cys | Thr | Gly | Cys | (SEQ ID NO: 4131) |
| Pro | Gly | Thr | Cys | Gly | Glu | Ile | Cys | Xaa' | Ala | Xaa' | Tyr | Ala | Ala | Xaa' | Ala | Cys | Xaa' | Thr | Gly | Cys | (SEQ ID NO: 4132) |
| Pro | Gly | Thr | Cys | Gly | Glu | Ile | Cys | Xaa' | Ala | Xaa' | Tyr | Ala | Ala | Xaa' | Ala | Cys | Thr | Xaa' | Gly | Cys | (SEQ ID NO: 4133) |
| Pro | Gly | Thr | Cys | Gly | Glu | Ile | Cys | Xaa' | Ala | Xaa' | Tyr | Ala | Ala | Xaa' | Ala | Cys | Thr | Gly | Xaa' | Cys | (SEQ ID NO: 4134) |
| Pro | Gly | Thr | Cys | Gly | Glu | Ile | Cys | Xaa' | Ala | Xaa' | Tyr | Ala | Ala | Xaa' | Ala | Cys | Thr | Gly | Cys | Xaa' | (SEQ ID NO: 4135) |
| Pro | Gly | Thr | Cys | Gly | Glu | Ile | Cys | Xaa' | Ala | Xaa' | Tyr | Ala | Ala | Ala | Xaa' | Cys | Xaa' | Thr | Gly | Cys | (SEQ ID NO: 4136) |
| Pro | Gly | Thr | Cys | Gly | Glu | Ile | Cys | Xaa' | Ala | Xaa' | Tyr | Ala | Ala | Ala | Xaa' | Cys | Thr | Xaa' | Gly | Cys | (SEQ ID NO: 4137) |
| Pro | Gly | Thr | Cys | Gly | Glu | Ile | Cys | Xaa' | Ala | Xaa' | Tyr | Ala | Ala | Ala | Xaa' | Cys | Thr | Gly | Xaa' | Cys | (SEQ ID NO: 4138) |
| Pro | Gly | Thr | Cys | Gly | Glu | Ile | Cys | Xaa' | Ala | Xaa' | Tyr | Ala | Ala | Ala | Xaa' | Cys | Thr | Gly | Cys | Xaa' | (SEQ ID NO: 4139) |
| Pro | Gly | Thr | Cys | Gly | Glu | Ile | Cys | Xaa' | Ala | Xaa' | Tyr | Ala | Ala | Ala | Ala | Cys | Xaa' | Thr | Gly | Cys | (SEQ ID NO: 4140) |
| Pro | Gly | Thr | Cys | Gly | Glu | Ile | Cys | Xaa' | Ala | Xaa' | Tyr | Ala | Ala | Ala | Ala | Cys | Xaa' | Thr | Gly | Xaa' | Cys | (SEQ ID NO: 4141) |
| Pro | Gly | Thr | Cys | Gly | Glu | Ile | Cys | Xaa' | Ala | Xaa' | Tyr | Ala | Ala | Ala | Ala | Cys | Xaa' | Thr | Gly | Cys | Xaa' | (SEQ ID NO: 4142) |
| Pro | Gly | Thr | Cys | Gly | Glu | Ile | Cys | Xaa' | Ala | Xaa' | Tyr | Ala | Ala | Ala | Ala | Cys | Thr | Xaa' | Gly | Xaa' | Cys | (SEQ ID NO: 4143) |
| Pro | Gly | Thr | Cys | Gly | Glu | Ile | Cys | Xaa' | Ala | Xaa' | Tyr | Ala | Ala | Ala | Ala | Cys | Thr | Xaa' | Gly | Cys | Xaa' | (SEQ ID NO: 4144) |
| Pro | Gly | Thr | Cys | Gly | Glu | Ile | Cys | Xaa' | Ala | Xaa' | Tyr | Ala | Ala | Ala | Ala | Cys | Thr | Gly | Xaa' | Cys | Xaa' | (SEQ ID NO: 4145) |
| Pro | Gly | Thr | Cys | Gly | Glu | Ile | Cys | Xaa' | Ala | Xaa' | Tyr | Ala | Ala | Ala | Ala | Cys | Thr | Gly | Cys | Xaa' | (SEQ ID NO: 4146) |
| Pro | Gly | Thr | Cys | Gly | Glu | Ile | Cys | Xaa' | Ala | Ala | Xaa' | Xaa' | Ala | Ala | Xaa' | Cys | Thr | Gly | Cys | (SEQ ID NO: 4147) |
| Pro | Gly | Thr | Cys | Gly | Glu | Ile | Cys | Xaa' | Ala | Ala | Xaa' | Xaa' | Ala | Xaa' | Ala | Cys | Thr | Gly | Cys | (SEQ ID NO: 4148) |
| Pro | Gly | Thr | Cys | Gly | Glu | Ile | Cys | Xaa' | Ala | Ala | Xaa' | Xaa' | Xaa' | Ala | Ala | Cys | Thr | Gly | Cys | (SEQ ID NO: 4149) |
| Pro | Gly | Thr | Cys | Gly | Glu | Ile | Cys | Xaa' | Ala | Ala | Tyr | Xaa' | Ala | Ala | Xaa' | Cys | Thr | Gly | Cys | Xaa' | (SEQ ID NO: 4150) |
| Pro | Gly | Thr | Cys | Gly | Glu | Ile | Cys | Xaa' | Ala | Ala | Tyr | Xaa' | Ala | Ala | Xaa' | Cys | Thr | Gly | Cys | (SEQ ID NO: 4151) |
| Pro | Gly | Thr | Cys | Gly | Glu | Ile | Cys | Xaa' | Ala | Tyr | Xaa' | Xaa' | Ala | Ala | Ala | Cys | Thr | Gly | Cys | (SEQ ID NO: 4152) |

FIG. 2CR

| | | | | | | | | | | | |
|---|---|---|---|---|---|---|---|---|---|---|---|
| Pro | Gly | Thr | Cys | Gly | Glu | Ile | Cys | Xaa' | Ala | Tyr | Xaa' | Xaa' | Ala | Ala | Cys | Thr | Gly | Cys | (SEQ ID NO: 4153) |
| Pro | Gly | Thr | Cys | Gly | Glu | Ile | Cys | Xaa' | Ala | Tyr | Xaa' | Xaa' | Ala | Xaa' | Cys | Thr | Gly | Cys | (SEQ ID NO: 4154) |
| Pro | Gly | Thr | Cys | Gly | Glu | Ile | Cys | Xaa' | Ala | Tyr | Xaa' | Xaa' | Ala | Ala | Xaa' | Cys | Thr | Gly | Cys | (SEQ ID NO: 4155) |
| Pro | Gly | Thr | Cys | Gly | Glu | Ile | Cys | Xaa' | Ala | Tyr | Xaa' | Xaa' | Ala | Ala | Cys | Xaa' | Thr | Gly | Cys | (SEQ ID NO: 4156) |
| Pro | Gly | Thr | Cys | Gly | Glu | Ile | Cys | Xaa' | Ala | Tyr | Xaa' | Xaa' | Ala | Ala | Cys | Thr | Xaa' | Gly | Cys | (SEQ ID NO: 4157) |
| Pro | Gly | Thr | Cys | Gly | Glu | Ile | Cys | Xaa' | Ala | Tyr | Xaa' | Xaa' | Ala | Ala | Cys | Thr | Gly | Xaa' | Cys | (SEQ ID NO: 4158) |
| Pro | Gly | Thr | Cys | Gly | Glu | Ile | Cys | Xaa' | Ala | Tyr | Xaa' | Xaa' | Ala | Ala | Cys | Thr | Gly | Xaa' | Cys | (SEQ ID NO: 4159) |
| Pro | Gly | Thr | Cys | Gly | Glu | Ile | Cys | Xaa' | Ala | Tyr | Xaa' | Ala | Ala | Ala | Cys | Thr | Gly | Cys | (SEQ ID NO: 4160) |
| Pro | Gly | Thr | Cys | Gly | Glu | Ile | Cys | Xaa' | Ala | Tyr | Xaa' | Ala | Xaa' | Ala | Cys | Thr | Gly | Cys | (SEQ ID NO: 4161) |
| Pro | Gly | Thr | Cys | Gly | Glu | Ile | Cys | Xaa' | Ala | Tyr | Xaa' | Ala | Ala | Xaa' | Cys | Thr | Gly | Cys | (SEQ ID NO: 4162) |
| Pro | Gly | Thr | Cys | Gly | Glu | Ile | Cys | Xaa' | Ala | Tyr | Xaa' | Ala | Ala | Ala | Xaa' | Thr | Gly | Cys | (SEQ ID NO: 4163) |
| Pro | Gly | Thr | Cys | Gly | Glu | Ile | Cys | Xaa' | Ala | Tyr | Xaa' | Ala | Ala | Ala | Cys | Xaa' | Gly | Cys | (SEQ ID NO: 4164) |
| Pro | Gly | Thr | Cys | Gly | Glu | Ile | Cys | Xaa' | Ala | Tyr | Xaa' | Ala | Ala | Ala | Cys | Thr | Xaa' | Cys | (SEQ ID NO: 4165) |
| Pro | Gly | Thr | Cys | Gly | Glu | Ile | Cys | Xaa' | Ala | Tyr | Xaa' | Ala | Ala | Ala | Cys | Thr | Gly | Xaa' | (SEQ ID NO: 4166) |
| Pro | Gly | Thr | Cys | Gly | Glu | Ile | Cys | Xaa' | Ala | Tyr | Xaa' | Xaa' | Xaa' | Ala | Cys | Thr | Gly | Cys | (SEQ ID NO: 4167) |
| Pro | Gly | Thr | Cys | Gly | Glu | Ile | Cys | Xaa' | Ala | Tyr | Xaa' | Xaa' | Ala | Xaa' | Cys | Thr | Gly | Cys | (SEQ ID NO: 4168) |
| Pro | Gly | Thr | Cys | Gly | Glu | Ile | Cys | Xaa' | Ala | Tyr | Xaa' | Xaa' | Ala | Ala | Xaa' | Thr | Gly | Cys | (SEQ ID NO: 4169) |
| Pro | Gly | Thr | Cys | Gly | Glu | Ile | Cys | Xaa' | Ala | Tyr | Xaa' | Xaa' | Ala | Ala | Cys | Xaa' | Gly | Cys | (SEQ ID NO: 4170) |
| Pro | Gly | Thr | Cys | Gly | Glu | Ile | Cys | Xaa' | Ala | Tyr | Xaa' | Xaa' | Ala | Ala | Cys | Thr | Xaa' | Cys | (SEQ ID NO: 4171) |
| Pro | Gly | Thr | Cys | Gly | Glu | Ile | Cys | Xaa' | Ala | Tyr | Xaa' | Xaa' | Ala | Ala | Cys | Thr | Gly | Xaa' | (SEQ ID NO: 4172) |
| Pro | Gly | Thr | Cys | Gly | Glu | Ile | Cys | Xaa' | Ala | Tyr | Xaa' | Xaa' | Xaa' | Xaa' | Cys | Thr | Gly | Cys | (SEQ ID NO: 4173) |
| Pro | Gly | Thr | Cys | Gly | Glu | Ile | Cys | Xaa' | Ala | Tyr | Xaa' | Xaa' | Xaa' | Ala | Xaa' | Thr | Gly | Cys | (SEQ ID NO: 4174) |
| Pro | Gly | Thr | Cys | Gly | Glu | Ile | Cys | Xaa' | Ala | Tyr | Xaa' | Xaa' | Xaa' | Ala | Cys | Xaa' | Gly | Cys | (SEQ ID NO: 4175) |
| Pro | Gly | Thr | Cys | Gly | Glu | Ile | Cys | Xaa' | Ala | Tyr | Xaa' | Xaa' | Xaa' | Ala | Cys | Thr | Xaa' | Cys | (SEQ ID NO: 4176) |
| Pro | Gly | Thr | Cys | Gly | Glu | Ile | Cys | Xaa' | Ala | Tyr | Xaa' | Xaa' | Xaa' | Ala | Cys | Thr | Gly | Xaa' | (SEQ ID NO: 4177) |
| Pro | Gly | Thr | Cys | Gly | Glu | Ile | Cys | Xaa' | Ala | Tyr | Xaa' | Xaa' | Ala | Xaa' | Xaa' | Thr | Gly | Cys | (SEQ ID NO: 4178) |
| Pro | Gly | Thr | Cys | Gly | Glu | Ile | Cys | Xaa' | Ala | Tyr | Xaa' | Xaa' | Ala | Xaa' | Cys | Xaa' | Gly | Cys | (SEQ ID NO: 4179) |
| Pro | Gly | Thr | Cys | Gly | Glu | Ile | Cys | Xaa' | Ala | Tyr | Xaa' | Xaa' | Ala | Xaa' | Cys | Thr | Xaa' | Cys | (SEQ ID NO: 4180) |
| Pro | Gly | Thr | Cys | Gly | Glu | Ile | Cys | Xaa' | Ala | Tyr | Xaa' | Xaa' | Ala | Xaa' | Cys | Thr | Gly | Xaa' | (SEQ ID NO: 4181) |
| Pro | Gly | Thr | Cys | Gly | Glu | Ile | Cys | Xaa' | Ala | Tyr | Xaa' | Xaa' | Ala | Ala | Xaa' | Xaa' | Gly | Cys | (SEQ ID NO: 4182) |
| Pro | Gly | Thr | Cys | Gly | Glu | Ile | Cys | Xaa' | Ala | Tyr | Xaa' | Xaa' | Ala | Ala | Xaa' | Thr | Xaa' | Cys | (SEQ ID NO: 4183) |
| Pro | Gly | Thr | Cys | Gly | Glu | Ile | Cys | Xaa' | Ala | Tyr | Xaa' | Xaa' | Ala | Ala | Xaa' | Thr | Gly | Xaa' | (SEQ ID NO: 4184) |
| Pro | Gly | Thr | Cys | Gly | Glu | Ile | Cys | Xaa' | Ala | Tyr | Xaa' | Xaa' | Ala | Ala | Cys | Xaa' | Xaa' | Cys | (SEQ ID NO: 4185) |
| Pro | Gly | Thr | Cys | Gly | Glu | Ile | Cys | Xaa' | Ala | Tyr | Xaa' | Xaa' | Ala | Ala | Cys | Thr | Gly | Xaa' | (SEQ ID NO: 4186) |

FIG. 2CS

| | | | | | | | | | | | | |
|---|---|---|---|---|---|---|---|---|---|---|---|---|
| Pro | Gly | Thr | Cys | Gly | Glu | Ile | Cys | Xaa' | Ala | Tyr | Ala | Xaa' | Ala | Cys | Thr | Gly | Cys | (SEQ ID NO: 4187) |
| Pro | Gly | Thr | Cys | Gly | Glu | Ile | Cys | Xaa' | Ala | Tyr | Ala | Xaa' | Xaa' | Ala | Cys | Thr | Gly | Cys | (SEQ ID NO: 4188) |
| Pro | Gly | Thr | Cys | Gly | Glu | Ile | Cys | Xaa' | Ala | Tyr | Ala | Xaa' | Xaa' | Ala | Cys | Thr | Gly | Cys | (SEQ ID NO: 4189) |
| Pro | Gly | Thr | Cys | Gly | Glu | Ile | Cys | Xaa' | Ala | Tyr | Ala | Xaa' | Xaa' | Ala | Cys | Xaa' | Thr | Gly | Cys | (SEQ ID NO: 4190) |
| Pro | Gly | Thr | Cys | Gly | Glu | Ile | Cys | Xaa' | Ala | Tyr | Ala | Xaa' | Xaa' | Ala | Cys | Xaa' | Thr | Gly | Cys | (SEQ ID NO: 4191) |
| Pro | Gly | Thr | Cys | Gly | Glu | Ile | Cys | Xaa' | Ala | Tyr | Ala | Xaa' | Xaa' | Ala | Cys | Xaa' | Thr | Gly | Cys | (SEQ ID NO: 4192) |
| Pro | Gly | Thr | Cys | Gly | Glu | Ile | Cys | Xaa' | Ala | Tyr | Ala | Xaa' | Xaa' | Ala | Cys | Thr | Gly | Cys | Xaa' | (SEQ ID NO: 4193) |
| Pro | Gly | Thr | Cys | Gly | Glu | Ile | Cys | Xaa' | Ala | Tyr | Ala | Xaa' | Xaa' | Ala | Cys | Thr | Gly | Cys | Xaa' | (SEQ ID NO: 4194) |
| Pro | Gly | Thr | Cys | Gly | Glu | Ile | Cys | Xaa' | Ala | Tyr | Ala | Xaa' | Ala | Xaa' | Cys | Thr | Gly | Cys | (SEQ ID NO: 4195) |
| Pro | Gly | Thr | Cys | Gly | Glu | Ile | Cys | Xaa' | Ala | Tyr | Ala | Xaa' | Ala | Xaa' | Cys | Xaa' | Thr | Gly | Cys | (SEQ ID NO: 4196) |
| Pro | Gly | Thr | Cys | Gly | Glu | Ile | Cys | Xaa' | Ala | Tyr | Ala | Xaa' | Ala | Xaa' | Cys | Xaa' | Thr | Gly | Cys | (SEQ ID NO: 4197) |
| Pro | Gly | Thr | Cys | Gly | Glu | Ile | Cys | Xaa' | Ala | Tyr | Ala | Xaa' | Ala | Xaa' | Cys | Xaa' | Thr | Gly | Cys | (SEQ ID NO: 4198) |
| Pro | Gly | Thr | Cys | Gly | Glu | Ile | Cys | Xaa' | Ala | Tyr | Ala | Xaa' | Ala | Xaa' | Cys | Thr | Gly | Cys | Xaa' | (SEQ ID NO: 4199) |
| Pro | Gly | Thr | Cys | Gly | Glu | Ile | Cys | Xaa' | Ala | Tyr | Ala | Xaa' | Ala | Xaa' | Cys | Thr | Gly | Cys | Xaa' | (SEQ ID NO: 4200) |
| Pro | Gly | Thr | Cys | Gly | Glu | Ile | Cys | Xaa' | Ala | Tyr | Ala | Xaa' | Ala | Cys | Xaa' | Thr | Gly | Cys | (SEQ ID NO: 4201) |
| Pro | Gly | Thr | Cys | Gly | Glu | Ile | Cys | Xaa' | Ala | Tyr | Ala | Xaa' | Ala | Cys | Xaa' | Thr | Gly | Cys | (SEQ ID NO: 4202) |
| Pro | Gly | Thr | Cys | Gly | Glu | Ile | Cys | Xaa' | Ala | Tyr | Ala | Xaa' | Ala | Cys | Xaa' | Thr | Gly | Cys | (SEQ ID NO: 4203) |
| Pro | Gly | Thr | Cys | Gly | Glu | Ile | Cys | Xaa' | Ala | Tyr | Ala | Xaa' | Ala | Cys | Xaa' | Thr | Gly | Cys | Xaa' | (SEQ ID NO: 4204) |
| Pro | Gly | Thr | Cys | Gly | Glu | Ile | Cys | Xaa' | Ala | Tyr | Ala | Xaa' | Ala | Cys | Xaa' | Thr | Gly | Cys | Xaa' | (SEQ ID NO: 4205) |
| Pro | Gly | Thr | Cys | Gly | Glu | Ile | Cys | Xaa' | Ala | Tyr | Ala | Xaa' | Ala | Cys | Thr | Gly | Cys | Xaa' | (SEQ ID NO: 4206) |
| Pro | Gly | Thr | Cys | Gly | Glu | Ile | Cys | Xaa' | Ala | Tyr | Ala | Xaa' | Ala | Cys | Thr | Gly | Cys | Xaa' | (SEQ ID NO: 4207) |
| Pro | Gly | Thr | Cys | Gly | Glu | Ile | Cys | Xaa' | Ala | Tyr | Ala | Xaa' | Ala | Cys | Xaa' | Gly | Cys | Xaa' | (SEQ ID NO: 4208) |
| Pro | Gly | Thr | Cys | Gly | Glu | Ile | Cys | Xaa' | Ala | Tyr | Ala | Xaa' | Ala | Cys | Xaa' | Thr | Gly | Cys | Xaa' | (SEQ ID NO: 4209) |
| Pro | Gly | Thr | Cys | Gly | Glu | Ile | Cys | Xaa' | Ala | Tyr | Ala | Xaa' | Ala | Cys | Thr | Gly | Cys | (SEQ ID NO: 4210) |
| Pro | Gly | Thr | Cys | Gly | Glu | Ile | Cys | Xaa' | Ala | Tyr | Ala | Xaa' | Ala | Cys | Thr | Gly | Xaa' | Cys | (SEQ ID NO: 4211) |
| Pro | Gly | Thr | Cys | Gly | Glu | Ile | Cys | Xaa' | Ala | Tyr | Ala | Xaa' | Ala | Cys | Xaa' | Thr | Gly | Cys | Xaa' | (SEQ ID NO: 4212) |
| Pro | Gly | Thr | Cys | Gly | Glu | Ile | Cys | Xaa' | Ala | Tyr | Ala | Xaa' | Ala | Cys | Xaa' | Gly | Cys | Xaa' | (SEQ ID NO: 4213) |
| Pro | Gly | Thr | Cys | Gly | Glu | Ile | Cys | Xaa' | Ala | Tyr | Ala | Ala | Xaa' | Cys | Thr | Gly | Cys | Xaa' | (SEQ ID NO: 4214) |
| Pro | Gly | Thr | Cys | Gly | Glu | Ile | Cys | Xaa' | Ala | Tyr | Ala | Ala | Xaa' | Cys | Thr | Gly | Cys | (SEQ ID NO: 4215) |
| Pro | Gly | Thr | Cys | Gly | Glu | Ile | Cys | Xaa' | Ala | Tyr | Ala | Ala | Xaa' | Xaa' | Cys | Thr | Gly | Cys | (SEQ ID NO: 4216) |
| Pro | Gly | Thr | Cys | Gly | Glu | Ile | Cys | Xaa' | Ala | Tyr | Ala | Ala | Xaa' | Xaa' | Cys | Xaa' | Thr | Gly | Cys | (SEQ ID NO: 4217) |
| Pro | Gly | Thr | Cys | Gly | Glu | Ile | Cys | Xaa' | Ala | Tyr | Ala | Ala | Xaa' | Xaa' | Cys | Thr | Gly | Cys | (SEQ ID NO: 4218) |
| Pro | Gly | Thr | Cys | Gly | Glu | Ile | Cys | Xaa' | Ala | Tyr | Ala | Ala | Xaa' | Xaa' | Cys | Thr | Gly | Xaa' | Cys | (SEQ ID NO: 4219) |
| Pro | Gly | Thr | Cys | Gly | Glu | Ile | Cys | Xaa' | Ala | Tyr | Ala | Ala | Xaa' | Xaa' | Cys | Thr | Gly | Xaa' | Cys | (SEQ ID NO: 4220) |

FIG. 2CT

| | | | | | | | | | | |
|---|---|---|---|---|---|---|---|---|---|---|
| Pro Gly Thr Cys Gly Glu Ile Cys Xaa' Ala Tyr Ala Ala Xaa' Xaa' Cys Thr Gly Cys Xaa' | (SEQ ID NO: 4221) |
| Pro Gly Thr Cys Gly Glu Ile Cys Xaa' Ala Tyr Ala Ala Xaa' Xaa' Cys Xaa' Thr Gly Cys | (SEQ ID NO: 4222) |
| Pro Gly Thr Cys Gly Glu Ile Cys Xaa' Ala Tyr Ala Ala Xaa' Xaa' Cys Xaa' Thr Xaa' Gly Cys | (SEQ ID NO: 4223) |
| Pro Gly Thr Cys Gly Glu Ile Cys Xaa' Ala Tyr Ala Ala Xaa' Xaa' Cys Xaa' Thr Xaa' Gly Cys | (SEQ ID NO: 4224) |
| Pro Gly Thr Cys Gly Glu Ile Cys Xaa' Ala Tyr Ala Ala Xaa' Xaa' Cys Xaa' Thr Gly Xaa' Cys | (SEQ ID NO: 4225) |
| Pro Gly Thr Cys Gly Glu Ile Cys Xaa' Ala Tyr Ala Ala Xaa' Xaa' Cys Xaa' Thr Gly Cys Xaa' | (SEQ ID NO: 4226) |
| Pro Gly Thr Cys Gly Glu Ile Cys Xaa' Ala Tyr Ala Ala Xaa' Xaa' Cys Thr Xaa' Gly Cys | (SEQ ID NO: 4227) |
| Pro Gly Thr Cys Gly Glu Ile Cys Xaa' Ala Tyr Ala Ala Xaa' Xaa' Cys Thr Xaa' Gly Cys | (SEQ ID NO: 4228) |
| Pro Gly Thr Cys Gly Glu Ile Cys Xaa' Ala Tyr Ala Ala Xaa' Xaa' Cys Thr Xaa' Gly Xaa' Cys | (SEQ ID NO: 4229) |
| Pro Gly Thr Cys Gly Glu Ile Cys Xaa' Ala Tyr Ala Ala Xaa' Xaa' Cys Thr Xaa' Gly Cys Xaa' | (SEQ ID NO: 4230) |
| Pro Gly Thr Cys Gly Glu Ile Cys Xaa' Ala Tyr Ala Ala Xaa' Xaa' Cys Thr Gly Xaa' Cys | (SEQ ID NO: 4231) |
| Pro Gly Thr Cys Gly Glu Ile Cys Xaa' Ala Tyr Ala Ala Xaa' Xaa' Cys Thr Gly Xaa' Cys Xaa' | (SEQ ID NO: 4232) |
| Pro Gly Thr Cys Gly Glu Ile Cys Xaa' Ala Tyr Ala Ala Xaa' Xaa' Cys Thr Gly Cys Xaa' | (SEQ ID NO: 4233) |
| Pro Gly Thr Cys Gly Glu Ile Cys Xaa' Ala Tyr Ala Ala Xaa' Cys Xaa' Xaa' Thr Gly Cys Xaa' | (SEQ ID NO: 4234) |
| Pro Gly Thr Cys Gly Glu Ile Cys Xaa' Ala Tyr Ala Ala Xaa' Cys Xaa' Xaa' Thr Gly Cys | (SEQ ID NO: 4235) |
| Pro Gly Thr Cys Gly Glu Ile Cys Xaa' Ala Tyr Ala Ala Xaa' Cys Xaa' Xaa' Thr Gly Cys | (SEQ ID NO: 4236) |
| Pro Gly Thr Cys Gly Glu Ile Cys Xaa' Ala Tyr Ala Ala Xaa' Cys Xaa' Thr Xaa' Gly Cys | (SEQ ID NO: 4237) |
| Pro Gly Thr Cys Gly Glu Ile Cys Xaa' Ala Tyr Ala Ala Xaa' Cys Xaa' Thr Xaa' Gly Cys | (SEQ ID NO: 4238) |
| Pro Gly Thr Cys Gly Glu Ile Cys Xaa' Ala Tyr Ala Ala Xaa' Cys Xaa' Thr Gly Xaa' Cys | (SEQ ID NO: 4239) |
| Pro Gly Thr Cys Gly Glu Ile Cys Xaa' Ala Tyr Ala Ala Xaa' Cys Xaa' Thr Gly Cys Xaa' | (SEQ ID NO: 4240) |
| Pro Gly Thr Cys Gly Glu Ile Cys Xaa' Ala Tyr Ala Ala Xaa' Cys Thr Xaa' Xaa' Gly Cys | (SEQ ID NO: 4241) |
| Pro Gly Thr Cys Gly Glu Ile Cys Xaa' Ala Tyr Ala Ala Xaa' Cys Thr Xaa' Xaa' Gly Cys | (SEQ ID NO: 4242) |
| Pro Gly Thr Cys Gly Glu Ile Cys Xaa' Ala Tyr Ala Ala Xaa' Cys Thr Xaa' Gly Xaa' Cys | (SEQ ID NO: 4243) |
| Pro Gly Thr Cys Gly Glu Ile Cys Xaa' Ala Tyr Ala Ala Xaa' Cys Thr Xaa' Gly Cys Xaa' | (SEQ ID NO: 4244) |
| Pro Gly Thr Cys Gly Glu Ile Cys Xaa' Ala Tyr Ala Ala Xaa' Cys Thr Gly Xaa' Xaa' Cys | (SEQ ID NO: 4245) |
| Pro Gly Thr Cys Gly Glu Ile Cys Xaa' Ala Tyr Ala Ala Xaa' Cys Thr Gly Xaa' Cys Xaa' | (SEQ ID NO: 4246) |
| Pro Gly Thr Cys Gly Glu Ile Cys Xaa' Ala Tyr Ala Ala Xaa' Cys Thr Gly Cys Xaa' | (SEQ ID NO: 4247) |
| Pro Gly Thr Cys Gly Glu Ile Cys Xaa' Ala Tyr Ala Ala Cys Xaa' Xaa' Thr Gly Cys Xaa' | (SEQ ID NO: 4248) |
| Pro Gly Thr Cys Gly Glu Ile Cys Xaa' Ala Tyr Ala Ala Cys Xaa' Thr Xaa' Xaa' Gly Cys Xaa' | (SEQ ID NO: 4249) |
| Pro Gly Thr Cys Gly Glu Ile Cys Xaa' Ala Tyr Ala Ala Cys Xaa' Thr Xaa' Gly Xaa' Cys Xaa' | (SEQ ID NO: 4250) |
| Pro Gly Thr Cys Gly Glu Ile Cys Xaa' Ala Tyr Ala Ala Cys Xaa' Thr Gly Xaa' Xaa' Cys Xaa' | (SEQ ID NO: 4251) |
| Pro Gly Thr Cys Gly Glu Ile Cys Xaa' Ala Tyr Ala Ala Cys Thr Xaa' Xaa' Xaa' Gly Cys | (SEQ ID NO: 4252) |
| Pro Gly Thr Cys Gly Glu Ile Cys Xaa' Ala Tyr Ala Ala Cys Thr Xaa' Xaa' Gly Xaa' Cys | (SEQ ID NO: 4253) |
| Pro Gly Thr Cys Gly Glu Ile Cys Xaa' Ala Tyr.Ala Ala Cys Thr Ala Xaa' Xaa' Gly Xaa' Cys | (SEQ ID NO: 4254) |

FIG. 2CU

Pro Gly Thr Cys Gly Glu Ile Cys Xaa' Ala Xaa' Ala Tyr Ala Ala Cys Thr Xaa' Xaa' Gly Cys Xaa' (SEQ ID NO: 4255)
Pro Gly Thr Cys Gly Glu Ile Cys Xaa' Ala Xaa' Ala Tyr Ala Ala Cys Thr Xaa' Cys Gly Xaa' Cys (SEQ ID NO: 4256)
Pro Gly Thr Cys Gly Glu Ile Cys Xaa' Ala Xaa' Ala Tyr Ala Ala Cys Thr Xaa' Gly Xaa' Xaa' Cys (SEQ ID NO: 4257)
Pro Gly Thr Cys Gly Glu Ile Cys Xaa' Ala Xaa' Ala Tyr Ala Ala Cys Thr Xaa' Gly Cys Xaa' (SEQ ID NO: 4258)
Pro Gly Thr Cys Gly Glu Ile Cys Xaa' Ala Xaa' Ala Tyr Ala Ala Cys Thr Xaa' Gly Cys Xaa' (SEQ ID NO: 4259)
Pro Gly Thr Cys Gly Glu Ile Cys Xaa' Ala Xaa' Ala Tyr Ala Ala Cys Thr Xaa' Gly Cys Xaa' Xaa' (SEQ ID NO: 4260)
Pro Gly Thr Cys Gly Glu Ile Cys Xaa' Ala Xaa' Ala Tyr Ala Ala Cys Thr Gly Xaa' Xaa' Cys (SEQ ID NO: 4261)
Pro Gly Thr Cys Gly Glu Ile Cys Xaa' Ala Xaa' Ala Tyr Ala Ala Cys Thr Gly Xaa' Xaa' Cys (SEQ ID NO: 4262)
Pro Gly Thr Cys Gly Glu Ile Cys Xaa' Ala Xaa' Ala Tyr Ala Ala Cys Thr Gly Xaa' Xaa' Xaa' Cys (SEQ ID NO: 4263)
Pro Gly Thr Cys Gly Glu Ile Cys Xaa' Ala Xaa' Ala Tyr Ala Ala Cys Thr Gly Xaa' Cys Xaa' (SEQ ID NO: 4264)
Pro Gly Thr Cys Gly Glu Ile Cys Xaa' Ala Xaa' Ala Tyr Ala Ala Cys Thr Gly Xaa' Cys Xaa' (SEQ ID NO: 4265)
Pro Gly Thr Cys Gly Glu Ile Cys Xaa' Ala Xaa' Ala Tyr Ala Ala Cys Thr Gly Cys Xaa' Xaa' (SEQ ID NO: 4266)
Pro Gly Thr Cys Gly Glu Ile Cys Xaa' Ala Xaa' Ala Tyr Ala Ala Cys Thr Gly Cys Xaa' (SEQ ID NO: 4267)
Pro Gly Thr Cys Gly Glu Ile Cys Xaa' Ala Xaa' Ala Tyr Ala Ala Cys Thr Gly Cys Xaa' (SEQ ID NO: 4268)
Pro Gly Thr Cys Gly Glu Ile Cys Xaa' Ala Xaa' Ala Tyr Ala Ala Cys Thr Gly Cys Xaa' Xaa' (SEQ ID NO: 4269)
Pro Gly Thr Cys Gly Glu Ile Cys Xaa' Ala Xaa' Ala Tyr Ala Ala Cys Thr Gly Cys Xaa' (SEQ ID NO: 4270)
Pro Gly Thr Cys Gly Glu Ile Cys Xaa' Ala Xaa' Ala Tyr Ala Ala Cys Thr Gly Cys . (SEQ ID NO: 4271)
Pro Gly Thr Cys Gly Glu Ile Cys Ala Xaa' Xaa' Tyr Ala Ala Cys Thr Gly Cys (SEQ ID NO: 4272)
Pro Gly Thr Cys Gly Glu Ile Cys Ala Xaa' Xaa' Tyr Ala Ala Cys Thr Gly Cys (SEQ ID NO: 4273)
Pro Gly Thr Cys Gly Glu Ile Cys Ala Xaa' Xaa' Tyr Ala Ala Cys Thr Gly Cys (SEQ ID NO: 4274)
Pro Gly Thr Cys Gly Glu Ile Cys Ala Xaa' Xaa' Tyr Xaa' Ala Ala Cys Thr Gly Cys (SEQ ID NO: 4275)
Pro Gly Thr Cys Gly Glu Ile Cys Ala Xaa' Xaa' Tyr Ala Xaa' Ala Cys Thr Gly Cys (SEQ ID NO: 4276)
Pro Gly Thr Cys Gly Glu Ile Cys Ala Xaa' Xaa' Tyr Ala Ala Xaa' Cys Thr Gly Cys (SEQ ID NO: 4277)
Pro Gly Thr Cys Gly Glu Ile Cys Ala Xaa' Xaa' Tyr Ala Ala Cys Xaa' Thr Gly Cys (SEQ ID NO: 4278)
Pro Gly Thr Cys Gly Glu Ile Cys Ala Xaa' Xaa' Tyr Ala Ala Cys Thr Xaa' Gly Cys Xaa' (SEQ ID NO: 4279)
Pro Gly Thr Cys Gly Glu Ile Cys Ala Xaa' Xaa' Tyr Ala Ala Cys Thr Gly Cys Xaa' (SEQ ID NO: 4280)
Pro Gly Thr Cys Gly Glu Ile Cys Ala Xaa' Xaa' Tyr Xaa' Ala Ala Cys Thr Gly Cys (SEQ ID NO: 4281)
Pro Gly Thr Cys Gly Glu Ile Cys Ala Xaa' Xaa' Tyr Xaa' Ala Ala Cys Thr Gly Cys (SEQ ID NO: 4282)
Pro Gly Thr Cys Gly Glu Ile Cys Ala Xaa' Xaa' Tyr Xaa' Ala Ala Cys Thr Gly Cys (SEQ ID NO: 4283)
Pro Gly Thr Cys Gly Glu Ile Cys Ala Xaa' Xaa' Tyr Xaa' Ala Ala Cys Xaa' Thr Gly Cys (SEQ ID NO: 4284)
Pro Gly Thr Cys Gly Glu Ile Cys Ala Xaa' Xaa' Tyr Xaa' Ala Ala Cys Thr Xaa' Gly Cys (SEQ ID NO: 4285)
Pro Gly Thr Cys Gly Glu Ile Cys Ala Xaa' Xaa' Tyr Xaa' Ala Ala Cys Thr Gly Xaa' Cys (SEQ ID NO: 4286)
Pro Gly Thr Cys Gly Glu Ile Cys Ala Xaa' Xaa' Tyr Xaa' Ala Ala Cys Thr Gly Xaa' Cys (SEQ ID NO: 4287)
Pro Gly Thr Cys Gly Glu Ile Cys Ala Xaa' Xaa' Tyr Xaa' Ala Ala Cys Thr Gly Cys Xaa' (SEQ ID NO: 4288)

FIG. 2CV

| Sequence | SEQ ID NO |
|---|---|
| Pro Gly Thr Cys Gly Glu Ile Cys Ala Xaa' Tyr Ala Xaa' Ala Cys Thr Gly Cys | (SEQ ID NO: 4289) |
| Pro Gly Thr Cys Gly Glu Ile Cys Ala Xaa' Tyr Ala Xaa' Ala Cys Thr Gly Cys | (SEQ ID NO: 4290) |
| Pro Gly Thr Cys Gly Glu Ile Cys Ala Xaa' Tyr Ala Xaa' Ala Cys Thr Gly Cys | (SEQ ID NO: 4291) |
| Pro Gly Thr Cys Gly Glu Ile Cys Ala Xaa' Tyr Ala Xaa' Ala Cys Thr Gly Cys | (SEQ ID NO: 4292) |
| Pro Gly Thr Cys Gly Glu Ile Cys Ala Xaa' Tyr Ala Xaa' Ala Cys Thr Gly Cys | (SEQ ID NO: 4293) |
| Pro Gly Thr Cys Gly Glu Ile Cys Ala Xaa' Tyr Ala Xaa' Ala Cys Thr Gly Cys | (SEQ ID NO: 4294) |
| Pro Gly Thr Cys Gly Glu Ile Cys Ala Xaa' Tyr Ala Xaa' Ala Cys Thr Gly Xaa' | (SEQ ID NO: 4295) |
| Pro Gly Thr Cys Gly Glu Ile Cys Ala Xaa' Tyr Ala Xaa' Ala Cys Thr Gly Cys | (SEQ ID NO: 4296) |
| Pro Gly Thr Cys Gly Glu Ile Cys Ala Xaa' Tyr Ala Xaa' Xaa' Cys Thr Gly Cys | (SEQ ID NO: 4297) |
| Pro Gly Thr Cys Gly Glu Ile Cys Ala Xaa' Tyr Ala Xaa' Cys Xaa' Thr Gly Cys | (SEQ ID NO: 4298) |
| Pro Gly Thr Cys Gly Glu Ile Cys Ala Xaa' Tyr Ala Xaa' Cys Xaa' Thr Gly Cys | (SEQ ID NO: 4299) |
| Pro Gly Thr Cys Gly Glu Ile Cys Ala Xaa' Tyr Ala Xaa' Cys Xaa' Thr Gly Cys | (SEQ ID NO: 4300) |
| Pro Gly Thr Cys Gly Glu Ile Cys Ala Xaa' Tyr Ala Xaa' Cys Xaa' Thr Gly Xaa' | (SEQ ID NO: 4301) |
| Pro Gly Thr Cys Gly Glu Ile Cys Ala Xaa' Tyr Ala Xaa' Cys Xaa' Thr Gly Cys | (SEQ ID NO: 4302) |
| Pro Gly Thr Cys Gly Glu Ile Cys Ala Xaa' Tyr Ala Xaa' Cys Xaa' Thr Gly Cys | (SEQ ID NO: 4303) |
| Pro Gly Thr Cys Gly Glu Ile Cys Ala Xaa' Tyr Ala Xaa' Cys Xaa' Thr Gly Cys | (SEQ ID NO: 4304) |
| Pro Gly Thr Cys Gly Glu Ile Cys Ala Xaa' Tyr Ala Xaa' Cys Xaa' Gly Xaa' Cys | (SEQ ID NO: 4305) |
| Pro Gly Thr Cys Gly Glu Ile Cys Ala Xaa' Tyr Ala Xaa' Cys Xaa' Thr Gly Xaa' | (SEQ ID NO: 4306) |
| Pro Gly Thr Cys Gly Glu Ile Cys Ala Xaa' Tyr Xaa' Xaa' Cys Xaa' Gly Cys | (SEQ ID NO: 4307) |
| Pro Gly Thr Cys Gly Glu Ile Cys Ala Xaa' Tyr Xaa' Xaa' Cys Xaa' Gly Xaa' Cys | (SEQ ID NO: 4308) |
| Pro Gly Thr Cys Gly Glu Ile Cys Ala Xaa' Tyr Xaa' Xaa' Cys Xaa' Gly Xaa' Cys | (SEQ ID NO: 4309) |
| Pro Gly Thr Cys Gly Glu Ile Cys Ala Xaa' Tyr Xaa' Xaa' Cys Xaa' Gly Cys Xaa' | (SEQ ID NO: 4310) |
| Pro Gly Thr Cys Gly Glu Ile Cys Ala Xaa' Tyr Xaa' Xaa' Cys Thr Gly Xaa' Cys | (SEQ ID NO: 4311) |
| Pro Gly Thr Cys Gly Glu Ile Cys Ala Xaa' Tyr Xaa' Xaa' Cys Thr Gly Xaa' Cys | (SEQ ID NO: 4312) |
| Pro Gly Thr Cys Gly Glu Ile Cys Ala Xaa' Tyr Xaa' Ala Cys Thr Gly Cys Xaa' | (SEQ ID NO: 4313) |
| Pro Gly Thr Cys Gly Glu Ile Cys Ala Xaa' Tyr Xaa' Ala Cys Thr Gly Cys Xaa' | (SEQ ID NO: 4314) |
| Pro Gly Thr Cys Gly Glu Ile Cys Ala Xaa' Tyr Xaa' Ala Cys Thr Gly Cys Xaa' | (SEQ ID NO: 4315) |
| Pro Gly Thr Cys Gly Glu Ile Cys Ala Xaa' Tyr Xaa' Ala Cys Thr Gly Cys Xaa' | (SEQ ID NO: 4316) |
| Pro Gly Thr Cys Gly Glu Ile Cys Ala Xaa' Tyr Xaa' Ala Ala Cys Thr Gly Cys | (SEQ ID NO: 4317) |
| Pro Gly Thr Cys Gly Glu Ile Cys Ala Xaa' Tyr Xaa' Ala Ala Cys Thr Gly Cys | (SEQ ID NO: 4318) |
| Pro Gly Thr Cys Gly Glu Ile Cys Ala Xaa' Tyr Xaa' Ala Ala Cys Thr Gly Cys | (SEQ ID NO: 4319) |
| Pro Gly Thr Cys Gly Glu Ile Cys Ala Xaa' Tyr Xaa' Ala Ala Cys Thr Gly Cys | (SEQ ID NO: 4320) |
| Pro Gly Thr Cys Gly Glu Ile Cys Ala Xaa' Tyr Xaa' Ala Ala Xaa' Thr Gly Cys | (SEQ ID NO: 4321) |
| Pro Gly Thr Cys Gly Glu Ile Cys Ala Xaa' Tyr Xaa' Ala Ala Cys Thr Gly Cys | (SEQ ID NO: 4322) |

FIG. 2CW

| | | | | | | | | | | | |
|---|---|---|---|---|---|---|---|---|---|---|---|
| Pro | Gly | Thr | Cys | Gly | Glu | Ile | Cys | Ala | Xaa' | Tyr | Xaa' | Xaa' | Ala | Ala | Cys | Thr | Gly | Xaa' | Cys | (SEQ ID NO: 4323) |
| Pro | Gly | Thr | Cys | Gly | Glu | Ile | Cys | Ala | Xaa' | Tyr | Xaa' | Xaa' | Ala | Ala | Cys | Thr | Gly | Cys | Xaa' | (SEQ ID NO: 4324) |
| Pro | Gly | Thr | Cys | Gly | Glu | Ile | Cys | Ala | Xaa' | Tyr | Xaa' | Ala | Ala | Xaa' | Cys | Thr | Gly | Cys | | (SEQ ID NO: 4325) |
| Pro | Gly | Thr | Cys | Gly | Glu | Ile | Cys | Ala | Xaa' | Tyr | Xaa' | Ala | Xaa' | Ala | Cys | Thr | Gly | Cys | | (SEQ ID NO: 4326) |
| Pro | Gly | Thr | Cys | Gly | Glu | Ile | Cys | Ala | Xaa' | Tyr | Xaa' | Ala | Xaa' | Xaa' | Cys | Thr | Gly | Gly | Cys | (SEQ ID NO: 4327) |
| Pro | Gly | Thr | Cys | Gly | Glu | Ile | Cys | Ala | Xaa' | Tyr | Xaa' | Ala | Xaa' | Ala | Cys | Xaa' | Thr | Gly | Cys | (SEQ ID NO: 4328) |
| Pro | Gly | Thr | Cys | Gly | Glu | Ile | Cys | Ala | Xaa' | Tyr | Xaa' | Ala | Ala | Xaa' | Cys | Thr | Gly | Xaa' | Cys | (SEQ ID NO: 4329) |
| Pro | Gly | Thr | Cys | Gly | Glu | Ile | Cys | Ala | Xaa' | Tyr | Xaa' | Ala | Ala | Xaa' | Cys | Thr | Gly | Cys | Xaa' | (SEQ ID NO: 4330) |
| Pro | Gly | Thr | Cys | Gly | Glu | Ile | Cys | Ala | Xaa' | Tyr | Xaa' | Ala | Ala | Xaa' | Cys | Thr | Gly | Cys | | (SEQ ID NO: 4331) |
| Pro | Gly | Thr | Cys | Gly | Glu | Ile | Cys | Ala | Xaa' | Tyr | Xaa' | Ala | Ala | Xaa' | Cys | Thr | Gly | Cys | Xaa' | (SEQ ID NO: 4332) |
| Pro | Gly | Thr | Cys | Gly | Glu | Ile | Cys | Ala | Xaa' | Tyr | Xaa' | Ala | Ala | Xaa' | Xaa' | Cys | Thr | Gly | Cys | (SEQ ID NO: 4333) |
| Pro | Gly | Thr | Cys | Gly | Glu | Ile | Cys | Ala | Xaa' | Tyr | Xaa' | Ala | Ala | Xaa' | Cys | Xaa' | Thr | Gly | Cys | (SEQ ID NO: 4334) |
| Pro | Gly | Thr | Cys | Gly | Glu | Ile | Cys | Ala | Xaa' | Tyr | Xaa' | Ala | Ala | Xaa' | Cys | Thr | Xaa' | Gly | Cys | (SEQ ID NO: 4335) |
| Pro | Gly | Thr | Cys | Gly | Glu | Ile | Cys | Ala | Xaa' | Tyr | Xaa' | Ala | Ala | Xaa' | Cys | Thr | Gly | Xaa' | Cys | (SEQ ID NO: 4336) |
| Pro | Gly | Thr | Cys | Gly | Glu | Ile | Cys | Ala | Xaa' | Tyr | Xaa' | Ala | Ala | Xaa' | Cys | Thr | Gly | Cys | Xaa' | (SEQ ID NO: 4337) |
| Pro | Gly | Thr | Cys | Gly | Glu | Ile | Cys | Ala | Xaa' | Tyr | Xaa' | Ala | Ala | Cys | Xaa' | Thr | Gly | Cys | | (SEQ ID NO: 4338) |
| Pro | Gly | Thr | Cys | Gly | Glu | Ile | Cys | Ala | Xaa' | Tyr | Xaa' | Ala | Ala | Cys | Xaa' | Xaa' | Thr | Gly | Cys | (SEQ ID NO: 4339) |
| Pro | Gly | Thr | Cys | Gly | Glu | Ile | Cys | Ala | Xaa' | Tyr | Xaa' | Ala | Ala | Cys | Xaa' | Thr | Xaa' | Gly | Cys | (SEQ ID NO: 4340) |
| Pro | Gly | Thr | Cys | Gly | Glu | Ile | Cys | Ala | Xaa' | Tyr | Xaa' | Ala | Ala | Cys | Xaa' | Thr | Gly | Xaa' | Cys | (SEQ ID NO: 4341) |
| Pro | Gly | Thr | Cys | Gly | Glu | Ile | Cys | Ala | Xaa' | Tyr | Xaa' | Ala | Ala | Cys | Xaa' | Thr | Gly | Cys | Xaa' | (SEQ ID NO: 4342) |
| Pro | Gly | Thr | Cys | Gly | Glu | Ile | Cys | Ala | Xaa' | Tyr | Xaa' | Ala | Ala | Cys | Thr | Xaa' | Gly | Cys | | (SEQ ID NO: 4343) |
| Pro | Gly | Thr | Cys | Gly | Glu | Ile | Cys | Ala | Xaa' | Tyr | Xaa' | Ala | Ala | Cys | Thr | Xaa' | Xaa' | Gly | Cys | (SEQ ID NO: 4344) |
| Pro | Gly | Thr | Cys | Gly | Glu | Ile | Cys | Ala | Xaa' | Tyr | Xaa' | Ala | Ala | Cys | Thr | Xaa' | Gly | Xaa' | Cys | (SEQ ID NO: 4345) |
| Pro | Gly | Thr | Cys | Gly | Glu | Ile | Cys | Ala | Xaa' | Tyr | Xaa' | Ala | Ala | Cys | Thr | Xaa' | Gly | Cys | Xaa' | (SEQ ID NO: 4346) |
| Pro | Gly | Thr | Cys | Gly | Glu | Ile | Cys | Ala | Xaa' | Tyr | Xaa' | Ala | Ala | Cys | Thr | Gly | Xaa' | Cys | | (SEQ ID NO: 4347) |
| Pro | Gly | Thr | Cys | Gly | Glu | Ile | Cys | Ala | Xaa' | Tyr | Xaa' | Ala | Ala | Cys | Thr | Gly | Xaa' | Xaa' | Cys | (SEQ ID NO: 4348) |
| Pro | Gly | Thr | Cys | Gly | Glu | Ile | Cys | Ala | Xaa' | Tyr | Xaa' | Ala | Ala | Cys | Thr | Gly | Xaa' | Cys | Xaa' | (SEQ ID NO: 4349) |
| Pro | Gly | Thr | Cys | Gly | Glu | Ile | Cys | Ala | Xaa' | Tyr | Xaa' | Ala | Ala | Cys | Thr | Gly | Cys | Xaa' | | (SEQ ID NO: 4350) |
| Pro | Gly | Thr | Cys | Gly | Glu | Ile | Cys | Ala | Xaa' | Tyr | Xaa' | Ala | Ala | Cys | Thr | Gly | Cys | Xaa' | Xaa' | (SEQ ID NO: 4351) |
| Pro | Gly | Thr | Cys | Gly | Glu | Ile | Cys | Ala | Xaa' | Tyr | Ala | Xaa' | Ala | Cys | Thr | Gly | Cys | | | (SEQ ID NO: 4352) |
| Pro | Gly | Thr | Cys | Gly | Glu | Ile | Cys | Ala | Xaa' | Tyr | Ala | Xaa' | Xaa' | Ala | Cys | Thr | Gly | Cys | | (SEQ ID NO: 4353) |
| Pro | Gly | Thr | Cys | Gly | Glu | Ile | Cys | Ala | Xaa' | Tyr | Ala | Xaa' | Ala | Cys | Xaa' | Thr | Gly | Cys | | (SEQ ID NO: 4354) |
| Pro | Gly | Thr | Cys | Gly | Glu | Ile | Cys | Ala | Xaa' | Tyr | Ala | Xaa' | Ala | Cys | Thr | Xaa' | Gly | Cys | | (SEQ ID NO: 4355) |
| Pro | Gly | Thr | Cys | Gly | Glu | Ile | Cys | Ala | Xaa' | Tyr | Ala | Xaa' | Ala | Cys | Thr | Gly | Xaa' | Cys | | (SEQ ID NO: 4356) |

FIG. 2CX

FIG. 2CY

| | | | | | | | | | | | |
|---|---|---|---|---|---|---|---|---|---|---|---|
| Pro Gly Thr Cys Gly Glu Ile Cys Ala Xaa Tyr Ala Ala Xaa Cys Xaa Thr Gly Cys Xaa | (SEQ ID NO: 4391) |
| Pro Gly Thr Cys Gly Glu Ile Cys Ala Xaa Tyr Ala Ala Xaa Cys Thr Xaa Gly Cys Xaa | (SEQ ID NO: 4392) |
| Pro Gly Thr Cys Gly Glu Ile Cys Ala Xaa Tyr Ala Ala Xaa Cys Xaa Thr Gly Cys Cys | (SEQ ID NO: 4393) |
| Pro Gly Thr Cys Gly Glu Ile Cys Ala Xaa Tyr Ala Ala Xaa Cys Thr Xaa Xaa Gly Cys | (SEQ ID NO: 4394) |
| Pro Gly Thr Cys Gly Glu Ile Cys Ala Xaa Tyr Ala Ala Xaa Cys Thr Xaa Gly Xaa Cys | (SEQ ID NO: 4395) |
| Pro Gly Thr Cys Gly Glu Ile Cys Ala Xaa Tyr Ala Ala Xaa Cys Thr Xaa Gly Cys Xaa | (SEQ ID NO: 4396) |
| Pro Gly Thr Cys Gly Glu Ile Cys Ala Xaa Tyr Ala Ala Xaa Cys Thr Gly Xaa Cys Xaa | (SEQ ID NO: 4397) |
| Pro Gly Thr Cys Gly Glu Ile Cys Ala Xaa Tyr Ala Ala Xaa Cys Thr Gly Xaa Cys Xaa | (SEQ ID NO: 4398) |
| Pro Gly Thr Cys Gly Glu Ile Cys Ala Xaa Tyr Ala Ala Xaa Cys Thr Gly Cys Xaa Xaa | (SEQ ID NO: 4399) |
| Pro Gly Thr Cys Gly Glu Ile Cys Ala Xaa Tyr Ala Ala Cys Xaa Thr Gly Cys Xaa | (SEQ ID NO: 4400) |
| Pro Gly Thr Cys Gly Glu Ile Cys Ala Xaa Tyr Ala Ala Cys Xaa Thr Gly Cys | (SEQ ID NO: 4401) |
| Pro Gly Thr Cys Gly Glu Ile Cys Ala Xaa Tyr Ala Ala Cys Xaa Xaa Thr Gly Cys | (SEQ ID NO: 4402) |
| Pro Gly Thr Cys Gly Glu Ile Cys Ala Xaa Tyr Ala Ala Cys Xaa Xaa Thr Xaa Gly Cys | (SEQ ID NO: 4403) |
| Pro Gly Thr Cys Gly Glu Ile Cys Ala Xaa Tyr Ala Ala Cys Xaa Xaa Thr Gly Xaa Cys | (SEQ ID NO: 4404) |
| Pro Gly Thr Cys Gly Glu Ile Cys Ala Xaa Tyr Ala Ala Cys Xaa Xaa Thr Gly Cys Xaa | (SEQ ID NO: 4405) |
| Pro Gly Thr Cys Gly Glu Ile Cys Ala Xaa Tyr Ala Ala Cys Xaa Xaa Gly Cys Xaa | (SEQ ID NO: 4406) |
| Pro Gly Thr Cys Gly Glu Ile Cys Ala Xaa Tyr Ala Ala Cys Xaa Thr Xaa Gly Cys Xaa | (SEQ ID NO: 4407) |
| Pro Gly Thr Cys Gly Glu Ile Cys Ala Xaa Tyr Ala Ala Cys Xaa Thr Xaa Gly Cys | (SEQ ID NO: 4408) |
| Pro Gly Thr Cys Gly Glu Ile Cys Ala Xaa Tyr Ala Ala Cys Xaa Thr Xaa Xaa Gly Cys | (SEQ ID NO: 4409) |
| Pro Gly Thr Cys Gly Glu Ile Cys Ala Xaa Tyr Ala Ala Cys Xaa Thr Xaa Gly Xaa Cys | (SEQ ID NO: 4410) |
| Pro Gly Thr Cys Gly Glu Ile Cys Ala Xaa Tyr Ala Ala Cys Xaa Thr Xaa Gly Cys Xaa | (SEQ ID NO: 4411) |
| Pro Gly Thr Cys Gly Glu Ile Cys Ala Xaa Tyr Ala Ala Cys Xaa Thr Gly Xaa Cys Xaa | (SEQ ID NO: 4412) |
| Pro Gly Thr Cys Gly Glu Ile Cys Ala Xaa Tyr Ala Ala Cys Xaa Thr Gly Xaa Cys | (SEQ ID NO: 4413) |
| Pro Gly Thr Cys Gly Glu Ile Cys Ala Xaa Tyr Ala Ala Cys Xaa Thr Gly Xaa Cys Xaa | (SEQ ID NO: 4414) |
| Pro Gly Thr Cys Gly Glu Ile Cys Ala Xaa Tyr Ala Ala Cys Xaa Thr Gly Cys Xaa Xaa | (SEQ ID NO: 4415) |
| Pro Gly Thr Cys Gly Glu Ile Cys Ala Xaa Tyr Ala Ala Cys Thr Xaa Xaa Gly Cys | (SEQ ID NO: 4416) |
| Pro Gly Thr Cys Gly Glu Ile Cys Ala Xaa Tyr Ala Ala Cys Thr Xaa Xaa Gly Cys | (SEQ ID NO: 4417) |
| Pro Gly Thr Cys Gly Glu Ile Cys Ala Xaa Tyr Ala Ala Cys Thr Xaa Xaa Xaa Gly Cys | (SEQ ID NO: 4418) |
| Pro Gly Thr Cys Gly Glu Ile Cys Ala Xaa Tyr Ala Ala Cys Thr Xaa Xaa Gly Xaa Cys | (SEQ ID NO: 4419) |
| Pro Gly Thr Cys Gly Glu Ile Cys Ala Xaa Tyr Ala Ala Cys Thr Xaa Xaa Gly Cys Xaa | (SEQ ID NO: 4420) |
| Pro Gly Thr Cys Gly Glu Ile Cys Ala Xaa Tyr Ala Ala Cys Thr Xaa Gly Xaa Cys | (SEQ ID NO: 4421) |
| Pro Gly Thr Cys Gly Glu Ile Cys Ala Xaa Tyr Ala Ala Cys Thr Xaa Gly Xaa Xaa Cys | (SEQ ID NO: 4422) |
| Pro Gly Thr Cys Gly Glu Ile Cys Ala Xaa Tyr Ala Ala Cys Thr Xaa Gly Xaa Cys Xaa | (SEQ ID NO: 4423) |
| Pro Gly Thr Cys Gly Glu Ile Cys Ala Xaa Tyr Ala Ala Cys Thr Xaa Gly Cys Xaa | (SEQ ID NO: 4424) |

FIG. 2CZ

FIG. 2DA

| | | | | | | | | | | | | | | |
|---|---|---|---|---|---|---|---|---|---|---|---|---|---|---|
| Pro Gly Thr Cys Gly Glu Ile Cys Ala Xaa' Tyr Ala Ala Cys Thr Xaa' Gly Cys Xaa' Xaa' | (SEQ ID NO: 4425) |
| Pro Gly Thr Cys Gly Glu Ile Cys Ala Xaa' Tyr Ala Ala Cys Thr Gly Xaa' Cys | (SEQ ID NO: 4426) |
| Pro Gly Thr Cys Gly Glu Ile Cys Ala Xaa' Tyr Ala Ala Cys Thr Gly Xaa' Xaa' Cys | (SEQ ID NO: 4427) |
| Pro Gly Thr Cys Gly Glu Ile Cys Ala Xaa' Tyr Ala Ala Cys Thr Gly Xaa' Xaa' Xaa' Cys | (SEQ ID NO: 4428) |
| Pro Gly Thr Cys Gly Glu Ile Cys Ala Xaa' Tyr Ala Ala Cys Thr Gly Xaa' Xaa' Cys Xaa' | (SEQ ID NO: 4429) |
| Pro Gly Thr Cys Gly Glu Ile Cys Ala Xaa' Tyr Ala Ala Cys Thr Gly Xaa' Cys Xaa' | (SEQ ID NO: 4430) |
| Pro Gly Thr Cys Gly Glu Ile Cys Ala Xaa' Tyr Ala Ala Cys Thr Gly Xaa' Cys Xaa' Xaa' | (SEQ ID NO: 4431) |
| Pro Gly Thr Cys Gly Glu Ile Cys Ala Xaa' Tyr Ala Ala Cys Thr Gly Cys Xaa' | (SEQ ID NO: 4432) |
| Pro Gly Thr Cys Gly Glu Ile Cys Ala Xaa' Tyr Ala Ala Cys Thr Gly Cys Xaa' Xaa' | (SEQ ID NO: 4433) |
| Pro Gly Thr Cys Gly Glu Ile Cys Ala Xaa' Tyr Ala Ala Cys Thr Gly Cys Xaa' Xaa' Xaa' | (SEQ ID NO: 4434) |
| Pro Gly Thr Cys Gly Glu Ile Cys Ala Tyr Xaa' Ala Ala Cys Thr Gly Cys | (SEQ ID NO: 4435) |
| Pro Gly Thr Cys Gly Glu Ile Cys Ala Tyr Xaa' Xaa' Ala Ala Cys Thr Gly Cys | (SEQ ID NO: 4436) |
| Pro Gly Thr Cys Gly Glu Ile Cys Ala Tyr Xaa' Xaa' Xaa' Ala Ala Cys Thr Gly Cys | (SEQ ID NO: 4437) |
| Pro Gly Thr Cys Gly Glu Ile Cys Ala Tyr Xaa' Xaa' Xaa' Ala Ala Cys Thr Gly Cys Cys | (SEQ ID NO: 4438) |
| Pro Gly Thr Cys Gly Glu Ile Cys Ala Tyr Xaa' Xaa' Xaa' Ala Xaa' Cys Thr Gly Cys Cys | (SEQ ID NO: 4439) |
| Pro Gly Thr Cys Gly Glu Ile Cys Ala Tyr Xaa' Xaa' Xaa' Ala Ala Xaa' Cys Thr Gly Cys Cys | (SEQ ID NO: 4440) |
| Pro Gly Thr Cys Gly Glu Ile Cys Ala Tyr Xaa' Xaa' Xaa' Ala Ala Cys Xaa' Thr Gly Cys Cys | (SEQ ID NO: 4441) |
| Pro Gly Thr Cys Gly Glu Ile Cys Ala Tyr Xaa' Xaa' Xaa' Ala Ala Cys Thr Xaa' Gly Cys Cys | (SEQ ID NO: 4442) |
| Pro Gly Thr Cys Gly Glu Ile Cys Ala Tyr Xaa' Xaa' Xaa' Ala Ala Cys Thr Gly Xaa' Cys Cys | (SEQ ID NO: 4443) |
| Pro Gly Thr Cys Gly Glu Ile Cys Ala Tyr Xaa' Xaa' Xaa' Ala Ala Cys Thr Gly Cys Xaa' Cys | (SEQ ID NO: 4444) |
| Pro Gly Thr Cys Gly Glu Ile Cys Ala Tyr Xaa' Xaa' Xaa' Ala Ala Cys Thr Gly Cys Xaa' | (SEQ ID NO: 4445) |
| Pro Gly Thr Cys Gly Glu Ile Cys Ala Tyr Xaa' Xaa' Xaa' Ala Xaa' Ala Cys Thr Gly Cys | (SEQ ID NO: 4446) |
| Pro Gly Thr Cys Gly Glu Ile Cys Ala Tyr Xaa' Xaa' Xaa' Xaa' Ala Ala Cys Thr Gly Cys Cys | (SEQ ID NO: 4447) |
| Pro Gly Thr Cys Gly Glu Ile Cys Ala Tyr Xaa' Xaa' Xaa' Ala Xaa' Ala Cys Thr Gly Cys Cys | (SEQ ID NO: 4448) |
| Pro Gly Thr Cys Gly Glu Ile Cys Ala Tyr Xaa' Xaa' Xaa' Ala Ala Xaa' Cys Thr Gly Cys Cys | (SEQ ID NO: 4449) |
| Pro Gly Thr Cys Gly Glu Ile Cys Ala Tyr Xaa' Xaa' Xaa' Ala Ala Cys Xaa' Thr Gly Cys Cys | (SEQ ID NO: 4450) |
| Pro Gly Thr Cys Gly Glu Ile Cys Ala Tyr Xaa' Xaa' Xaa' Ala Ala Cys Thr Xaa' Gly Cys Cys | (SEQ ID NO: 4451) |
| Pro Gly Thr Cys Gly Glu Ile Cys Ala Tyr Xaa' Xaa' Xaa' Ala Ala Cys Thr Gly Xaa' Cys Xaa' | (SEQ ID NO: 4452) |
| Pro Gly Thr Cys Gly Glu Ile Cys Ala Tyr Xaa' Xaa' Xaa' Ala Ala Cys Thr Gly Cys Cys | (SEQ ID NO: 4453) |
| Pro Gly Thr Cys Gly Glu Ile Cys Ala Tyr Xaa' Xaa' Xaa' Ala Xaa' Cys Thr Xaa' Gly Cys Cys | (SEQ ID NO: 4454) |
| Pro Gly Thr Cys Gly Glu Ile Cys Ala Tyr Xaa' Xaa' Xaa' Ala Xaa' Cys Thr Gly Xaa' Cys Cys | (SEQ ID NO: 4455) |
| Pro Gly Thr Cys Gly Glu Ile Cys Ala Tyr Xaa' Xaa' Xaa' Ala Ala Cys Xaa' Thr Gly Xaa' Cys Cys | (SEQ ID NO: 4456) |
| Pro Gly Thr Cys Gly Glu Ile Cys Ala Tyr Xaa' Xaa' Xaa' Ala Ala Cys Thr Xaa' Gly Cys Xaa' | (SEQ ID NO: 4457) |
| Pro Gly Thr Cys Gly Glu Ile Cys Ala Tyr Xaa' Ala Ala Cys Thr Gly Cys | (SEQ ID NO: 4458) |

| | | | | | | | | | | | |
|---|---|---|---|---|---|---|---|---|---|---|---|
| Pro Gly Thr Cys Gly Glu Ile Cys Ala Tyr Xaa' Xaa' Ala Cys Xaa' Xaa' Thr Gly Cys | (SEQ ID NO: 4459) |
| Pro Gly Thr Cys Gly Glu Ile Cys Ala Tyr Xaa' Xaa' Ala Cys Xaa' Thr Xaa' Gly Cys | (SEQ ID NO: 4460) |
| Pro Gly Thr Cys Gly Glu Ile Cys Ala Tyr Xaa' Xaa' Ala Cys Xaa' Thr Gly Xaa' Cys | (SEQ ID NO: 4461) |
| Pro Gly Thr Cys Gly Glu Ile Cys Ala Tyr Xaa' Xaa' Ala Cys Xaa' Thr Gly Cys Xaa' | (SEQ ID NO: 4462) |
| Pro Gly Thr Cys Gly Glu Ile Cys Ala Tyr Xaa' Xaa' Ala Cys Thr Xaa' Gly Cys | (SEQ ID NO: 4463) |
| Pro Gly Thr Cys Gly Glu Ile Cys Ala Tyr Xaa' Xaa' Ala Cys Thr Xaa' Xaa' Gly Cys | (SEQ ID NO: 4464) |
| Pro Gly Thr Cys Gly Glu Ile Cys Ala Tyr Xaa' Xaa' Ala Cys Thr Xaa' Gly Xaa' Cys | (SEQ ID NO: 4465) |
| Pro Gly Thr Cys Gly Glu Ile Cys Ala Tyr Xaa' Xaa' Ala Cys Thr Xaa' Gly Cys Xaa' | (SEQ ID NO: 4466) |
| Pro Gly Thr Cys Gly Glu Ile Cys Ala Tyr Xaa' Xaa' Ala Cys Thr Gly Xaa' Cys | (SEQ ID NO: 4467) |
| Pro Gly Thr Cys Gly Glu Ile Cys Ala Tyr Xaa' Xaa' Ala Cys Thr Gly Xaa' Xaa' Cys | (SEQ ID NO: 4468) |
| Pro Gly Thr Cys Gly Glu Ile Cys Ala Tyr Xaa' Xaa' Ala Cys Thr Gly Xaa' Cys Xaa' | (SEQ ID NO: 4469) |
| Pro Gly Thr Cys Gly Glu Ile Cys Ala Tyr Xaa' Xaa' Ala Cys Thr Gly Cys Xaa' | (SEQ ID NO: 4470) |
| Pro Gly Thr Cys Gly Glu Ile Cys Ala Tyr Xaa' Xaa' Ala Cys Thr Gly Cys Xaa' Xaa' | (SEQ ID NO: 4471) |
| Pro Gly Thr Cys Gly Glu Ile Cys Ala Tyr Xaa' Ala Xaa' Xaa' Ala Cys Thr Gly Cys | (SEQ ID NO: 4472) |
| Pro Gly Thr Cys Gly Glu Ile Cys Ala Tyr Xaa' Ala Xaa' Ala Cys Xaa' Ala Cys Thr Gly Cys | (SEQ ID NO: 4473) |
| Pro Gly Thr Cys Gly Glu Ile Cys Ala Tyr Xaa' Ala Xaa' Ala Cys Xaa' Ala Xaa' Cys Thr Gly Cys | (SEQ ID NO: 4474) |
| Pro Gly Thr Cys Gly Glu Ile Cys Ala Tyr Xaa' Ala Xaa' Ala Cys Xaa' Ala Cys Xaa' Thr Gly Cys | (SEQ ID NO: 4475) |
| Pro Gly Thr Cys Gly Glu Ile Cys Ala Tyr Xaa' Ala Xaa' Ala Cys Xaa' Ala Cys Thr Xaa' Gly Cys | (SEQ ID NO: 4476) |
| Pro Gly Thr Cys Gly Glu Ile Cys Ala Tyr Xaa' Ala Xaa' Ala Cys Xaa' Ala Cys Thr Gly Xaa' Cys | (SEQ ID NO: 4477) |
| Pro Gly Thr Cys Gly Glu Ile Cys Ala Tyr Xaa' Ala Xaa' Ala Cys Xaa' Ala Cys Thr Gly Cys Xaa' | (SEQ ID NO: 4478) |
| Pro Gly Thr Cys Gly Glu Ile Cys Ala Tyr Xaa' Ala Xaa' Ala Xaa' Ala Cys Thr Gly Cys | (SEQ ID NO: 4479) |
| Pro Gly Thr Cys Gly Glu Ile Cys Ala Tyr Xaa' Ala Xaa' Ala Xaa' Ala Cys Xaa' Cys Thr Gly Cys | (SEQ ID NO: 4480) |
| Pro Gly Thr Cys Gly Glu Ile Cys Ala Tyr Xaa' Ala Xaa' Ala Xaa' Ala Cys Cys Thr Gly Cys | (SEQ ID NO: 4481) |
| Pro Gly Thr Cys Gly Glu Ile Cys Ala Tyr Xaa' Ala Xaa' Ala Xaa' Ala Cys Xaa' Cys Thr · Thr Gly Cys | (SEQ ID NO: 4482) |
| Pro Gly Thr Cys Gly Glu Ile Cys Ala Tyr Xaa' Ala Xaa' Ala Xaa' Ala Cys Cys Thr Xaa' Gly Cys | (SEQ ID NO: 4483) |
| Pro Gly Thr Cys Gly Glu Ile Cys Ala Tyr Xaa' Ala Xaa' Ala Xaa' Ala Cys Cys Thr Gly Xaa' Cys | (SEQ ID NO: 4484) |
| Pro Gly Thr Cys Gly Glu Ile Cys Ala Tyr Xaa' Ala Xaa' Ala Xaa' Ala Cys Cys Thr Gly Cys Xaa' | (SEQ ID NO: 4485) |
| Pro Gly Thr Cys Gly Glu Ile Cys Ala Tyr Xaa' Ala Xaa' Ala Cys Xaa' Thr Gly Cys | (SEQ ID NO: 4486) |
| Pro Gly Thr Cys Gly Glu Ile Cys Ala Tyr Xaa' Ala Xaa' Ala Cys Xaa' Xaa' Thr Gly Cys | (SEQ ID NO: 4487) |
| Pro Gly Thr Cys Gly Glu Ile Cys Ala Tyr Xaa' Ala Xaa' Ala Cys Xaa' Thr Xaa' Gly Cys | (SEQ ID NO: 4488) |
| Pro Gly Thr Cys Gly Glu Ile Cys Ala Tyr Xaa' Ala Xaa' Ala Cys Xaa' Thr Gly Xaa' Cys | (SEQ ID NO: 4489) |
| Pro Gly Thr Cys Gly Glu Ile Cys Ala Tyr Xaa' Ala Xaa' Ala Cys Xaa' Thr Gly Cys Xaa' | (SEQ ID NO: 4490) |
| Pro Gly Thr Cys Gly Glu Ile Cys Ala Tyr Xaa' Ala Xaa' Ala Cys Thr Gly Cys | (SEQ ID NO: 4491) |
| Pro Gly Thr Cys Gly Glu Ile Cys Ala Tyr Xaa' Ala Xaa' Ala Cys Thr Xaa' Xaa' Gly Cys | (SEQ ID NO: 4492) |

FIG. 2DB

| | | | | | | | | | | | | |
|---|---|---|---|---|---|---|---|---|---|---|---|---|
| Pro | Gly | Thr | Cys | Gly | Glu | Ile | Cys | Ala | Tyr | Xaa' | Ala | Cys | Thr | Xaa' | Gly | Xaa' | Cys | (SEQ ID NO: 4493) |
| Pro | Gly | Thr | Cys | Gly | Glu | Ile | Cys | Ala | Tyr | Xaa' | Ala | Cys | Thr | Xaa' | Gly | Cys | Xaa' | (SEQ ID NO: 4494) |
| Pro | Gly | Thr | Cys | Gly | Glu | Ile | Cys | Ala | Tyr | Xaa' | Ala | Cys | Thr | Gly | Xaa' | Cys | | (SEQ ID NO: 4495) |
| Pro | Gly | Thr | Cys | Gly | Glu | Ile | Cys | Ala | Tyr | Xaa' | Ala | Cys | Xaa' | Thr | Gly | Xaa' | Cys | (SEQ ID NO: 4496) |
| Pro | Gly | Thr | Cys | Gly | Glu | Ile | Cys | Ala | Tyr | Xaa' | Ala | Cys | Xaa' | Thr | Gly | Cys | Xaa' | (SEQ ID NO: 4497) |
| Pro | Gly | Thr | Cys | Gly | Glu | Ile | Cys | Ala | Tyr | Xaa' | Ala | Cys | Xaa' | Thr | Cys | Xaa' | Xaa' | (SEQ ID NO: 4498) |
| Pro | Gly | Thr | Cys | Gly | Glu | Ile | Cys | Ala | Tyr | Xaa' | Ala | Cys | Xaa' | Thr | Cys | Xaa' | | (SEQ ID NO: 4499) |
| Pro | Gly | Thr | Cys | Gly | Glu | Ile | Cys | Ala | Tyr | Xaa' | Ala | Ala | Xaa' | Cys | Thr | Gly | Cys | (SEQ ID NO: 4500) |
| Pro | Gly | Thr | Cys | Gly | Glu | Ile | Cys | Ala | Tyr | Xaa' | Ala | Ala | Xaa' | Cys | Thr | Gly | Cys | (SEQ ID NO: 4501) |
| Pro | Gly | Thr | Cys | Gly | Glu | Ile | Cys | Ala | Tyr | Xaa' | Ala | Xaa' | Xaa' | Cys | Xaa' | Thr | Gly | Cys | (SEQ ID NO: 4502) |
| Pro | Gly | Thr | Cys | Gly | Glu | Ile | Cys | Ala | Tyr | Xaa' | Ala | Xaa' | Xaa' | Cys | Xaa' | Thr | Gly | Cys | (SEQ ID NO: 4503) |
| Pro | Gly | Thr | Cys | Gly | Glu | Ile | Cys | Ala | Tyr | Xaa' | Ala | Xaa' | Xaa' | Cys | Thr | Xaa' | Gly | Cys | (SEQ ID NO: 4504) |
| Pro | Gly | Thr | Cys | Gly | Glu | Ile | Cys | Ala | Tyr | Xaa' | Ala | Xaa' | Xaa' | Cys | Thr | Gly | Xaa' | Cys | (SEQ ID NO: 4505) |
| Pro | Gly | Thr | Cys | Gly | Glu | Ile | Cys | Ala | Tyr | Xaa' | Ala | Xaa' | Xaa' | Cys | Thr | Gly | Cys | Xaa' | (SEQ ID NO: 4506) |
| Pro | Gly | Thr | Cys | Gly | Glu | Ile | Cys | Ala | Tyr | Xaa' | Ala | Xaa' | Xaa' | Cys | Thr | Gly | Cys | | (SEQ ID NO: 4507) |
| Pro | Gly | Thr | Cys | Gly | Glu | Ile | Cys | Ala | Tyr | Xaa' | Ala | Xaa' | Xaa' | Cys | Xaa' | Thr | Gly | Cys | (SEQ ID NO: 4508) |
| Pro | Gly | Thr | Cys | Gly | Glu | Ile | Cys | Ala | Tyr | Xaa' | Ala | Xaa' | Xaa' | Cys | Xaa' | Thr | Gly | Cys | (SEQ ID NO: 4509) |
| Pro | Gly | Thr | Cys | Gly | Glu | Ile | Cys | Ala | Tyr | Xaa' | Ala | Xaa' | Xaa' | Cys | Thr | Xaa' | Gly | Cys | (SEQ ID NO: 4510) |
| Pro | Gly | Thr | Cys | Gly | Glu | Ile | Cys | Ala | Tyr | Xaa' | Ala | Xaa' | Xaa' | Cys | Thr | Gly | Xaa' | Cys | (SEQ ID NO: 4511) |
| Pro | Gly | Thr | Cys | Gly | Glu | Ile | Cys | Ala | Tyr | Xaa' | Ala | Xaa' | Xaa' | Cys | Thr | Gly | Cys | Xaa' | (SEQ ID NO: 4512) |
| Pro | Gly | Thr | Cys | Gly | Glu | Ile | Cys | Ala | Tyr | Xaa' | Ala | Xaa' | Xaa' | Cys | Thr | Xaa' | Gly | Cys | (SEQ ID NO: 4513) |
| Pro | Gly | Thr | Cys | Gly | Glu | Ile | Cys | Ala | Tyr | Xaa' | Ala | Xaa' | Xaa' | Cys | Thr | Xaa' | Gly | Cys | (SEQ ID NO: 4514) |
| Pro | Gly | Thr | Cys | Gly | Glu | Ile | Cys | Ala | Tyr | Xaa' | Ala | Xaa' | Xaa' | Cys | Thr | Gly | Xaa' | Cys | (SEQ ID NO: 4515) |
| Pro | Gly | Thr | Cys | Gly | Glu | Ile | Cys | Ala | Tyr | Xaa' | Ala | Xaa' | Xaa' | Cys | Thr | Gly | Cys | Xaa' | (SEQ ID NO: 4516) |
| Pro | Gly | Thr | Cys | Gly | Glu | Ile | Cys | Ala | Tyr | Xaa' | Ala | Xaa' | Xaa' | Cys | Thr | Gly | Cys | | (SEQ ID NO: 4517) |
| Pro | Gly | Thr | Cys | Gly | Glu | Ile | Cys | Ala | Tyr | Xaa' | Ala | Xaa' | Cys | Xaa' | Thr | Gly | Cys | Xaa' | (SEQ ID NO: 4518) |
| Pro | Gly | Thr | Cys | Gly | Glu | Ile | Cys | Ala | Tyr | Xaa' | Ala | Xaa' | Cys | Xaa' | Thr | Gly | Cys | | (SEQ ID NO: 4519) |
| Pro | Gly | Thr | Cys | Gly | Glu | Ile | Cys | Ala | Tyr | Xaa' | Ala | Xaa' | Cys | Xaa' | Thr | Gly | Cys | Xaa' | (SEQ ID NO: 4520) |
| Pro | Gly | Thr | Cys | Gly | Glu | Ile | Cys | Ala | Tyr | Xaa' | Ala | Xaa' | Cys | Xaa' | Thr | Gly | Cys | | (SEQ ID NO: 4521) |
| Pro | Gly | Thr | Cys | Gly | Glu | Ile | Cys | Ala | Tyr | Xaa' | Ala | Ala | Cys | Xaa' | Xaa' | Thr | Gly | Cys | (SEQ ID NO: 4522) |
| Pro | Gly | Thr | Cys | Gly | Glu | Ile | Cys | Ala | Tyr | Xaa' | Ala | Ala | Cys | Xaa' | Xaa' | Thr | Gly | Cys | (SEQ ID NO: 4523) |
| Pro | Gly | Thr | Cys | Gly | Glu | Ile | Cys | Ala | Tyr | Xaa' | Ala | Ala | Cys | Xaa' | Thr | Xaa' | Gly | Cys | (SEQ ID NO: 4524) |
| Pro | Gly | Thr | Cys | Gly | Glu | Ile | Cys | Ala | Tyr | Xaa' | Ala | Ala | Cys | Xaa' | Thr | Gly | Xaa' | Cys | (SEQ ID NO: 4525) |
| Pro | Gly | Thr | Cys | Gly | Glu | Ile | Cys | Ala | Tyr | Xaa' | Ala | Ala | Cys | Xaa' | Thr | Gly | Cys | Xaa' | (SEQ ID NO: 4526) |

FIG. 2DC

Pro Gly Thr Cys Gly Glu Ile Cys Ala Tyr Xaa' Ala Ala Cys Xaa' Thr Xaa' Gly Cys                       (SEQ ID NO: 4527)
Pro Gly Thr Cys Gly Glu Ile Cys Ala Tyr Xaa' Ala Ala Cys Xaa' Thr Xaa' Xaa' Gly Cys                  (SEQ ID NO: 4528)
Pro Gly Thr Cys Gly Glu Ile Cys Ala Tyr Xaa' Ala Ala Cys Xaa' Thr Xaa' Gly Xaa' Cys                  (SEQ ID NO: 4529)
Pro Gly Thr Cys Gly Glu Ile Cys Ala Tyr Xaa' Ala Ala Cys Xaa' Thr Xaa' Xaa' Gly Xaa' Cys             (SEQ ID NO: 4530)
Pro Gly Thr Cys Gly Glu Ile Cys Ala Tyr Xaa' Ala Ala Cys Xaa' Thr Xaa' Gly Xaa' Xaa' Cys             (SEQ ID NO: 4531)
Pro Gly Thr Cys Gly Glu Ile Cys Ala Tyr Xaa' Ala Ala Cys Xaa' Thr Xaa' Gly Xaa' Xaa' Cys             (SEQ ID NO: 4532)
Pro Gly Thr Cys Gly Glu Ile Cys Ala Tyr Xaa' Ala Ala Cys Xaa' Thr Xaa' Gly Cys Xaa'                  (SEQ ID NO: 4533)
Pro Gly Thr Cys Gly Glu Ile Cys Ala Tyr Xaa' Ala Ala Cys Xaa' Thr Xaa' Xaa' Gly Cys Xaa'             (SEQ ID NO: 4534)
Pro Gly Thr Cys Gly Glu Ile Cys Ala Tyr Xaa' Ala Ala Cys Xaa' Thr Xaa' Gly Cys Xaa' Xaa'             (SEQ ID NO: 4535)
Pro Gly Thr Cys Gly Glu Ile Cys Ala Tyr Xaa' Ala Ala Cys Thr Xaa' Gly Cys                            (SEQ ID NO: 4536)
Pro Gly Thr Cys Gly Glu Ile Cys Ala Tyr Xaa' Ala Ala Cys Thr Xaa' Xaa' Gly Cys                       (SEQ ID NO: 4537)
Pro Gly Thr Cys Gly Glu Ile Cys Ala Tyr Xaa' Ala Ala Cys Thr Xaa' Xaa' Xaa' Gly Cys                  (SEQ ID NO: 4538)
Pro Gly Thr Cys Gly Glu Ile Cys Ala Tyr Xaa' Ala Ala Cys Thr Xaa' Gly Xaa' Cys                       (SEQ ID NO: 4539)
Pro Gly Thr Cys Gly Glu Ile Cys Ala Tyr Xaa' Ala Ala Cys Thr Xaa' Xaa' Gly Xaa' Cys                  (SEQ ID NO: 4540)
Pro Gly Thr Cys Gly Glu Ile Cys Ala Tyr Xaa' Ala Ala Cys Thr Xaa' Gly Xaa' Xaa' Cys                  (SEQ ID NO: 4541)
Pro Gly Thr Cys Gly Glu Ile Cys Ala Tyr Xaa' Ala Ala Cys Thr Xaa' Gly Cys Xaa'                       (SEQ ID NO: 4542)
Pro Gly Thr Cys Gly Glu Ile Cys Ala Tyr Xaa' Ala Ala Cys Thr Xaa' Xaa' Gly Cys Xaa'                  (SEQ ID NO: 4543)
Pro Gly Thr Cys Gly Glu Ile Cys Ala Tyr Xaa' Ala Ala Cys Thr Xaa' Gly Cys Xaa' Xaa'                  (SEQ ID NO: 4544)
Pro Gly Thr Cys Gly Glu Ile Cys Ala Tyr Xaa' Ala Ala Cys Xaa' Thr Gly Xaa' Cys                       (SEQ ID NO: 4545)
Pro Gly Thr Cys Gly Glu Ile Cys Ala Tyr Xaa' Ala Ala Cys Xaa' Thr Gly Xaa' Xaa' Cys                  (SEQ ID NO: 4546)
Pro Gly Thr Cys Gly Glu Ile Cys Ala Tyr Xaa' Ala Ala Cys Xaa' Thr Gly Xaa' Cys                       (SEQ ID NO: 4547)
Pro Gly Thr Cys Gly Glu Ile Cys Ala Tyr Xaa' Ala Ala Cys Xaa' Thr Gly Xaa' Xaa' Cys                  (SEQ ID NO: 4548)
Pro Gly Thr Cys Gly Glu Ile Cys Ala Tyr Xaa' Ala Ala Cys Xaa' Thr Gly Xaa' Xaa' Cys Xaa'             (SEQ ID NO: 4549)
Pro Gly Thr Cys Gly Glu Ile Cys Ala Tyr Xaa' Ala Ala Cys Xaa' Thr Gly Cys Xaa'                       (SEQ ID NO: 4550)
Pro Gly Thr Cys Gly Glu Ile Cys Ala Tyr Xaa' Ala Ala Cys Xaa' Thr Gly Cys Xaa' Xaa'                  (SEQ ID NO: 4551)
Pro Gly Thr Cys Gly Glu Ile Cys Ala Tyr Ala Ala Xaa' Cys Thr Gly Xaa'                                (SEQ ID NO: 4552)
Pro Gly Thr Cys Gly Glu Ile Cys Ala Tyr Ala Ala Xaa' Cys Thr Gly Cys                                 (SEQ ID NO: 4553)
Pro Gly Thr Cys Gly Glu Ile Cys Ala Tyr Ala Ala Xaa' Cys Thr Gly Cys                                 (SEQ ID NO: 4554)
Pro Gly Thr Cys Gly Glu Ile Cys Ala Tyr Ala Ala Xaa' Cys Ala Thr Gly Cys                             (SEQ ID NO: 4555)
Pro Gly Thr Cys Gly Glu Ile Cys Ala Tyr Ala Ala Xaa' Cys Ala Thr Gly Cys                             (SEQ ID NO: 4556)
Pro Gly Thr Cys Gly Glu Ile Cys Ala Tyr Ala Ala Xaa' Cys Xaa' Ala Cys Thr Gly Cys                    (SEQ ID NO: 4557)
Pro Gly Thr Cys Gly Glu Ile Cys Ala Tyr Ala Ala Xaa' Cys Xaa' Ala Cys Thr Gly Cys                    (SEQ ID NO: 4558)
Pro Gly Thr Cys Gly Glu Ile Cys Ala Tyr Ala Ala Xaa' Cys Xaa' Ala Xaa' Cys Thr Gly Cys               (SEQ ID NO: 4559)
Pro Gly Thr Cys Gly Glu Ile Cys Ala Tyr Ala Ala Xaa' Cys Xaa' Ala Xaa' Cys Thr Gly Cys               (SEQ ID NO: 4560)

FIG. 2DD

FIG. 2DE

| | | |
|---|---|---|
| Pro Gly Thr Cys Gly Glu Ile Cys Ala Tyr Ala Xaa' Cys Xaa' Thr Gly Cys Xaa' | (SEQ ID NO: 4595) |
| Pro Gly Thr Cys Gly Glu Ile Cys Ala Tyr Ala Xaa' Cys Xaa' Thr Xaa' Gly Cys | (SEQ ID NO: 4596) |
| Pro Gly Thr Cys Gly Glu Ile Cys Ala Tyr Ala Xaa' Cys Xaa' Thr Xaa' Gly Cys | (SEQ ID NO: 4597) |
| Pro Gly Thr Cys Gly Glu Ile Cys Ala Tyr Ala Xaa' Cys Xaa' Thr Xaa' Gly Cys | (SEQ ID NO: 4598) |
| Pro Gly Thr Cys Gly Glu Ile Cys Ala Tyr Ala Xaa' Cys Xaa' Thr Xaa' Gly Cys | (SEQ ID NO: 4599) |
| Pro Gly Thr Cys Gly Glu Ile Cys Ala Tyr Ala Xaa' Cys Xaa' Thr Gly Cys Xaa' | (SEQ ID NO: 4600) |
| Pro Gly Thr Cys Gly Glu Ile Cys Ala Tyr Ala Xaa' Cys Xaa' Thr Gly Xaa' Cys | (SEQ ID NO: 4601) |
| Pro Gly Thr Cys Gly Glu Ile Cys Ala Tyr Ala Xaa' Cys Xaa' Thr Gly Xaa' Cys | (SEQ ID NO: 4602) |
| Pro Gly Thr Cys Gly Glu Ile Cys Ala Tyr Ala Xaa' Cys Xaa' Thr Gly Cys Xaa' | (SEQ ID NO: 4603) |
| Pro Gly Thr Cys Gly Glu Ile Cys Ala Tyr Ala Xaa' Cys Xaa' Thr Gly Cys Xaa' | (SEQ ID NO: 4604) |
| Pro Gly Thr Cys Gly Glu Ile Cys Ala Tyr Ala Xaa' Cys Xaa' Thr Gly Cys | (SEQ ID NO: 4605) |
| Pro Gly Thr Cys Gly Glu Ile Cys Ala Tyr Ala Cys Xaa' Xaa' Thr Gly Cys | (SEQ ID NO: 4606) |
| Pro Gly Thr Cys Gly Glu Ile Cys Ala Tyr Ala Cys Xaa' Xaa' Thr Xaa' Gly Cys | (SEQ ID NO: 4607) |
| Pro Gly Thr Cys Gly Glu Ile Cys Ala Tyr Ala Cys Xaa' Xaa' Thr Xaa' Gly Cys | (SEQ ID NO: 4608) |
| Pro Gly Thr Cys Gly Glu Ile Cys Ala Tyr Ala Cys Xaa' Xaa' Thr Gly Xaa' Cys | (SEQ ID NO: 4609) |
| Pro Gly Thr Cys Gly Glu Ile Cys Ala Tyr Ala Cys Xaa' Xaa" Thr Gly Cys Xaa' | (SEQ ID NO: 4610) |
| Pro Gly Thr Cys Gly Glu Ile Cys Ala Tyr Ala Cys Xaa' Thr Xaa' Gly Cys | (SEQ ID NO: 4611) |
| Pro Gly Thr Cys Gly Glu Ile Cys Ala Tyr Ala Cys Xaa' Thr Xaa' Xaa' Gly Cys | (SEQ ID NO: 4612) |
| Pro Gly Thr Cys Gly Glu Ile Cys Ala Tyr Ala Cys Xaa' Thr Xaa' Xaa' Gly Cys | (SEQ ID NO: 4613) |
| Pro Gly Thr Cys Gly Glu Ile Cys Ala Tyr Ala Cys Xaa' Thr Xaa' Gly Xaa' Cys | (SEQ ID NO: 4614) |
| Pro Gly Thr Cys Gly Glu Ile Cys Ala Tyr Ala Cys Xaa' Thr Xaa' Gly Cys Xaa' | (SEQ ID NO: 4615) |
| Pro Gly Thr Cys Gly Glu Ile Cys Ala Tyr Ala Cys Xaa' Thr Gly Xaa' Xaa' Cys | (SEQ ID NO: 4616) |
| Pro Gly Thr Cys Gly Glu Ile Cys Ala Tyr Ala Cys Xaa' Thr Gly Xaa' Cys Xaa' | (SEQ ID NO: 4617) |
| Pro Gly Thr Cys Gly Glu Ile Cys Ala Tyr Ala Cys Xaa' Thr Gly Cys Xaa' Xaa' | (SEQ ID NO: 4618) |
| Pro Gly Thr Cys Gly Glu Ile Cys Ala Tyr Ala Cys Xaa' Thr Gly Cys Xaa' Xaa' | (SEQ ID NO: 4619) |
| Pro Gly Thr Cys Gly Glu Ile Cys Ala Tyr Ala Cys Xaa' Thr Xaa' Gly Cys | (SEQ ID NO: 4620) |
| Pro Gly Thr Cys Gly Glu Ile Cys Ala Tyr Ala Xaa' Thr Xaa' Xaa' Gly Cys | (SEQ ID NO: 4621) |
| Pro Gly Thr Cys Gly Glu Ile Cys Ala Tyr Ala Xaa' Thr Xaa' Xaa' Xaa' Gly Cys | (SEQ ID NO: 4622) |
| Pro Gly Thr Cys Gly Glu Ile Cys Ala Tyr Ala Xaa' Thr Xaa' Xaa' Gly Xaa' Cys | (SEQ ID NO: 4623) |
| Pro Gly Thr Cys Gly Glu Ile Cys Ala Tyr Ala Xaa' Thr Xaa' Xaa' Gly Cys Xaa' | (SEQ ID NO: 4624) |
| Pro Gly Thr Cys Gly Glu Ile Cys Ala Tyr Ala Xaa' Thr Xaa' Gly Xaa' Cys | (SEQ ID NO: 4625) |
| Pro Gly Thr Cys Gly Glu Ile Cys Ala Tyr Ala Xaa' Thr Xaa' Gly Xaa' Xaa' Cys | (SEQ ID NO: 4626) |
| Pro Gly Thr Cys Gly Glu Ile Cys Ala Tyr Ala Xaa' Thr Xaa' Gly Xaa' Cys Xaa' | (SEQ ID NO: 4627) |
| Pro Gly Thr Cys Gly Glu Ile Cys Ala Tyr Ala Xaa' Thr Xaa' Gly Cys Xaa' | (SEQ ID NO: 4628) |

FIG. 2DF

| | | | | | | | | | | | | | |
|---|---|---|---|---|---|---|---|---|---|---|---|---|---|
| Pro Gly Thr Cys Gly Glu Ile Cys Ala Tyr Ala Xaa' Ala Cys Thr Xaa' Gly Cys Xaa' Xaa' | (SEQ ID NO: 4629) |
| Pro Gly Thr Cys Gly Glu Ile Cys Ala Tyr Ala Xaa' Ala Cys Thr Gly Xaa' Cys | (SEQ ID NO: 4630) |
| Pro Gly Thr Cys Gly Glu Ile Cys Ala Tyr Ala Xaa' Ala Cys Thr Gly Xaa' Xaa' Cys | (SEQ ID NO: 4631) |
| Pro Gly Thr Cys Gly Glu Ile Cys Ala Tyr Ala Xaa' Ala Cys Thr Gly Xaa' Xaa' Xaa' Cys | (SEQ ID NO: 4632) |
| Pro Gly Thr Cys Gly Glu Ile Cys Ala Tyr Ala Xaa' Ala Cys Thr Gly Xaa' Xaa' Cys Xaa' | (SEQ ID NO: 4633) |
| Pro Gly Thr Cys Gly Glu Ile Cys Ala Tyr Ala Xaa' Ala Cys Thr Gly Xaa' Cys Xaa' | (SEQ ID NO: 4634) |
| Pro Gly Thr Cys Gly Glu Ile Cys Ala Tyr Ala Xaa' Ala Cys Thr Gly Xaa' Cys Xaa' Xaa' | (SEQ ID NO: 4635) |
| Pro Gly Thr Cys Gly Glu Ile Cys Ala Tyr Ala Xaa' Ala Cys Thr Gly Cys Xaa' Xaa' | (SEQ ID NO: 4636) |
| Pro Gly Thr Cys Gly Glu Ile Cys Ala Tyr Ala Xaa' Ala Cys Thr Gly Cys Xaa' Xaa' | (SEQ ID NO: 4637) |
| Pro Gly Thr Cys Gly Glu Ile Cys Ala Tyr Ala Xaa' Ala Cys Thr Gly Cys Xaa' Xaa' Xaa' | (SEQ ID NO: 4638) |
| Pro Gly Thr Cys Gly Glu Ile Cys Ala Tyr Ala Ala Xaa' Cys Thr Gly Cys | (SEQ ID NO: 4639) |
| Pro Gly Thr Cys Gly Glu Ile Cys Ala Tyr Ala Ala Xaa' Cys Xaa' Thr Gly Cys | (SEQ ID NO: 4640) |
| Pro Gly Thr Cys Gly Glu Ile Cys Ala Tyr Ala Ala Xaa' Xaa' Cys Thr Gly Cys | (SEQ ID NO: 4641) |
| Pro Gly Thr Cys Gly Glu Ile Cys Ala Tyr Ala Ala Xaa' Xaa' Cys Xaa' Thr Gly Cys | (SEQ ID NO: 4642) |
| Pro Gly Thr Cys Gly Glu Ile Cys Ala Tyr Ala Ala Xaa' Xaa' Xaa' Cys Thr Gly Cys | (SEQ ID NO: 4643) |
| Pro Gly Thr Cys Gly Glu Ile Cys Ala Tyr Ala Ala Xaa' Xaa' Cys Thr Xaa' Gly Cys | (SEQ ID NO: 4644) |
| Pro Gly Thr Cys Gly Glu Ile Cys Ala Tyr Ala Ala Xaa' Xaa' Cys Thr Gly Xaa' Cys | (SEQ ID NO: 4645) |
| Pro Gly Thr Cys Gly Glu Ile Cys Ala Tyr Ala Ala Xaa' Xaa' Cys Thr Gly Xaa' Xaa' Cys | (SEQ ID NO: 4646) |
| Pro Gly Thr Cys Gly Glu Ile Cys Ala Tyr Ala Ala Xaa' Xaa' Cys Thr Gly Cys Xaa' | (SEQ ID NO: 4647) |
| Pro Gly Thr Cys Gly Glu Ile Cys Ala Tyr Ala Ala Xaa' Xaa' Cys Xaa' Thr Gly Cys | (SEQ ID NO: 4648) |
| Pro Gly Thr Cys Gly Glu Ile Cys Ala Tyr Ala Ala Xaa' Xaa' Cys Xaa' Thr Xaa' Gly Cys | (SEQ ID NO: 4649) |
| Pro Gly Thr Cys Gly Glu Ile Cys Ala Tyr Ala Ala Xaa' Xaa' Cys Xaa' Thr Gly Xaa' Cys | (SEQ ID NO: 4650) |
| Pro Gly Thr Cys Gly Glu Ile Cys Ala Tyr Ala Ala Xaa' Xaa' Cys Xaa' Thr Gly Xaa' Xaa' Cys | (SEQ ID NO: 4651) |
| Pro Gly Thr Cys Gly Glu Ile Cys Ala Tyr Ala Ala Xaa' Xaa' Cys Xaa' Thr Gly Cys Xaa' | (SEQ ID NO: 4652) |
| Pro Gly Thr Cys Gly Glu Ile Cys Ala Tyr Ala Ala Xaa' Xaa' Cys Thr Xaa' Gly Cys | (SEQ ID NO: 4653) |
| Pro Gly Thr Cys Gly Glu Ile Cys Ala Tyr Ala Ala Xaa' Xaa' Cys Thr Xaa' Xaa' Gly Cys | (SEQ ID NO: 4654) |
| Pro Gly Thr Cys Gly Glu Ile Cys Ala Tyr Ala Ala Xaa' Xaa' Cys Thr Xaa' Gly Xaa' Cys | (SEQ ID NO: 4655) |
| Pro Gly Thr Cys Gly Glu Ile Cys Ala Tyr Ala Ala Xaa' Xaa' Cys Thr Xaa' Gly Xaa' Xaa' Cys | (SEQ ID NO: 4656) |
| Pro Gly Thr Cys Gly Glu Ile Cys Ala Tyr Ala Ala Xaa' Xaa' Cys Thr Xaa' Gly Cys | (SEQ ID NO: 4657) |
| Pro Gly Thr Cys Gly Glu Ile Cys Ala Tyr Ala Ala Xaa' Xaa' Cys Thr Gly Xaa' Cys Xaa' | (SEQ ID NO: 4658) |
| Pro Gly Thr Cys Gly Glu Ile Cys Ala Tyr Ala Ala Xaa' Xaa' Cys Thr Gly Cys Xaa' | (SEQ ID NO: 4659) |
| Pro Gly Thr Cys Gly Glu Ile Cys Ala Tyr Ala Ala Xaa' Cys Xaa' Xaa' Thr Gly Cys | (SEQ ID NO: 4660) |
| Pro Gly Thr Cys Gly Glu Ile Cys Ala Tyr Ala Ala Xaa' Cys Xaa' Thr Gly Cys | (SEQ ID NO: 4661) |
| Pro Gly Thr Cys Gly Glu Ile Cys Ala Tyr Ala Ala Xaa' Cys Xaa' Xaa' Thr Gly Cys | (SEQ ID NO: 4662) |

FIG. 2DG

| | | | | | | | | | | | | |
|---|---|---|---|---|---|---|---|---|---|---|---|---|
| Pro | Gly | Thr | Cys | Gly | Glu | Ile | Cys | Ala | Tyr | Ala | Ala | Xaa | Cys | Thr | Xaa' | Xaa' | Xaa' | Thr | Gly | Cys | (SEQ ID NO: 4663) |
| Pro | Gly | Thr | Cys | Gly | Glu | Ile | Cys | Ala | Tyr | Ala | Ala | Xaa | Cys | Thr | Xaa' | Xaa' | Xaa' | Xaa' | Gly | Cys | (SEQ ID NO: 4664) |
| Pro | Gly | Thr | Cys | Gly | Glu | Ile | Cys | Ala | Tyr | Ala | Ala | Xaa | Cys | Thr | Xaa' | Xaa' | Thr | Gly | Xaa' | Cys | (SEQ ID NO: 4665) |
| Pro | Gly | Thr | Cys | Gly | Glu | Ile | Cys | Ala | Tyr | Ala | Ala | Xaa | Cys | Thr | Xaa' | Xaa' | Thr | Xaa' | Gly | Cys | (SEQ ID NO: 4666) |
| Pro | Gly | Thr | Cys | Gly | Glu | Ile | Cys | Ala | Tyr | Ala | Ala | Xaa | Cys | Thr | Xaa' | Xaa' | Thr | Gly | Cys | Xaa' | (SEQ ID NO: 4667) |
| Pro | Gly | Thr | Cys | Gly | Glu | Ile | Cys | Ala | Tyr | Ala | Ala | Xaa | Cys | Thr | Xaa' | Xaa' | Xaa' | Gly | Cys | Xaa' | (SEQ ID NO: 4668) |
| Pro | Gly | Thr | Cys | Gly | Glu | Ile | Cys | Ala | Tyr | Ala | Ala | Xaa | Cys | Thr | Xaa' | Xaa' | Gly | Xaa' | Cys | Xaa' | (SEQ ID NO: 4669) |
| Pro | Gly | Thr | Cys | Gly | Glu | Ile | Cys | Ala | Tyr | Ala | Ala | Xaa | Cys | Thr | Xaa' | Xaa' | Gly | Cys | Xaa' | Xaa' | (SEQ ID NO: 4670) |
| Pro | Gly | Thr | Cys | Gly | Glu | Ile | Cys | Ala | Tyr | Ala | Ala | Xaa | Cys | Thr | Xaa' | Gly | Xaa' | Cys | Xaa' | Xaa' | (SEQ ID NO: 4671) |
| Pro | Gly | Thr | Cys | Gly | Glu | Ile | Cys | Ala | Tyr | Ala | Ala | Xaa | Cys | Thr | Gly | Xaa' | Cys | Xaa' | Xaa' | Xaa' | (SEQ ID NO: 4672) |
| Pro | Gly | Thr | Cys | Gly | Glu | Ile | Cys | Ala | Tyr | Ala | Ala | Xaa | Cys | Thr | Gly | Xaa' | Cys | Xaa' | Xaa' | Xaa' | (SEQ ID NO: 4673) |
| Pro | Gly | Thr | Cys | Gly | Glu | Ile | Cys | Ala | Tyr | Ala | Ala | Xaa | Cys | Thr | Gly | Cys | Xaa' | Xaa' | Xaa' | Xaa' | (SEQ ID NO: 4674) |
| Pro | Gly | Thr | Cys | Gly | Glu | Ile | Cys | Ala | Tyr | Ala | Ala | Xaa | Cys | Thr | Gly | Cys | Xaa' | Xaa' | Xaa' | Xaa' | (SEQ ID NO: 4675) |
| Pro | Gly | Thr | Cys | Gly | Glu | Ile | Cys | Ala | Tyr | Ala | Ala | Xaa | Cys | Thr | Xaa' | Gly | Cys | | | | (SEQ ID NO: 4676) |
| Pro | Gly | Thr | Cys | Gly | Glu | Ile | Cys | Ala | Tyr | Ala | Ala | Xaa | Cys | Thr | Thr | Xaa' | Xaa' | Xaa' | Gly | Cys | (SEQ ID NO: 4677) |
| Pro | Gly | Thr | Cys | Gly | Glu | Ile | Cys | Ala | Tyr | Ala | Ala | Xaa | Cys | Thr | Thr | Xaa' | Xaa' | Gly | Xaa' | Cys | (SEQ ID NO: 4678) |
| Pro | Gly | Thr | Cys | Gly | Glu | Ile | Cys | Ala | Tyr | Ala | Ala | Xaa | Cys | Thr | Thr | Xaa' | Xaa' | Gly | Cys | Xaa' | (SEQ ID NO: 4679) |
| Pro | Gly | Thr | Cys | Gly | Glu | Ile | Cys | Ala | Tyr | Ala | Ala | Xaa | Cys | Thr | Thr | Xaa' | Gly | Xaa' | Cys | Xaa' | (SEQ ID NO: 4680) |
| Pro | Gly | Thr | Cys | Gly | Glu | Ile | Cys | Ala | Tyr | Ala | Ala | Xaa | Cys | Thr | Thr | Gly | Xaa' | Cys | Xaa' | Xaa' | (SEQ ID NO: 4681) |
| Pro | Gly | Thr | Cys | Gly | Glu | Ile | Cys | Ala | Tyr | Ala | Ala | Xaa | Cys | Thr | Thr | Gly | Cys | Xaa' | Xaa' | Xaa' | (SEQ ID NO: 4682) |
| Pro | Gly | Thr | Cys | Gly | Glu | Ile | Cys | Ala | Tyr | Ala | Ala | Xaa | Cys | Thr | Thr | Xaa' | Gly | Cys | Xaa' | Xaa' | (SEQ ID NO: 4683) |
| Pro | Gly | Thr | Cys | Gly | Glu | Ile | Cys | Ala | Tyr | Ala | Ala | Xaa | Cys | Thr | Thr | Gly | Cys | Xaa' | Xaa' | Xaa' | (SEQ ID NO: 4684) |
| Pro | Gly | Thr | Cys | Gly | Glu | Ile | Cys | Ala | Tyr | Ala | Ala | Xaa | Cys | Thr | Thr | Xaa' | Gly | Cys | Xaa' | Xaa' | (SEQ ID NO: 4685) |
| Pro | Gly | Thr | Cys | Gly | Glu | Ile | Cys | Ala | Tyr | Ala | Ala | Xaa | Cys | Thr | Thr | Gly | Cys | Xaa' | | | (SEQ ID NO: 4686) |
| Pro | Gly | Thr | Cys | Gly | Glu | Ile | Cys | Ala | Tyr | Ala | Ala | Xaa | Cys | Thr | Gly | Xaa' | Xaa' | Xaa' | Xaa' | Cys | (SEQ ID NO: 4687) |
| Pro | Gly | Thr | Cys | Gly | Glu | Ile | Cys | Ala | Tyr | Ala | Ala | Xaa | Cys | Thr | Gly | Xaa' | Xaa' | Xaa' | Cys | Xaa' | (SEQ ID NO: 4688) |
| Pro | Gly | Thr | Cys | Gly | Glu | Ile | Cys | Ala | Tyr | Ala | Ala | Xaa | Cys | Thr | Gly | Xaa' | Xaa' | Cys | Xaa' | Xaa' | (SEQ ID NO: 4689) |
| Pro | Gly | Thr | Cys | Gly | Glu | Ile | Cys | Ala | Tyr | Ala | Ala | Xaa | Cys | Thr | Gly | Xaa' | Cys | Xaa' | Xaa' | Xaa' | (SEQ ID NO: 4690) |
| Pro | Gly | Thr | Cys | Gly | Glu | Ile | Cys | Ala | Tyr | Ala | Ala | Xaa | Cys | Thr | Gly | Cys | Xaa' | Xaa' | Xaa' | Xaa' | (SEQ ID NO: 4691) |
| Pro | Gly | Thr | Cys | Gly | Glu | Ile | Cys | Ala | Tyr | Ala | Ala | Xaa | Cys | Thr | Gly | Cys | Xaa' | Xaa' | Xaa' | | (SEQ ID NO: 4692) |
| Pro | Gly | Thr | Cys | Gly | Glu | Ile | Cys | Ala | Tyr | Ala | Ala | Xaa | Cys | Thr | Gly | Cys | Xaa' | Xaa' | | | (SEQ ID NO: 4693) |
| Pro | Gly | Thr | Cys | Gly | Glu | Ile | Cys | Ala | Tyr | Ala | Ala | Cys | Xaa' | Xaa' | Xaa' | Xaa' | Xaa' | | | | (SEQ ID NO: 4694) |
| Pro | Gly | Thr | Cys | Gly | Glu | Ile | Cys | Ala | Tyr | Ala | Ala | Cys | Xaa' | Xaa' | Xaa' | Thr | Gly | Cys | | | (SEQ ID NO: 4695) |
| Pro | Gly | Thr | Cys | Gly | Glu | Ile | Cys | Ala | Tyr | Ala | Ala | Cys | Xaa' | Xaa' | Thr | Gly | Cys | | | | (SEQ ID NO: 4696) |

FIG. 2DH

| | | | | | | | | | | | | | | | |
|---|---|---|---|---|---|---|---|---|---|---|---|---|---|---|---|
| Pro | Gly | Thr | Cys | Gly | Glu | Ile | Cys | Ala | Tyr | Ala | Ala | Cys | Xaa' | Xaa' | Thr Gly Cys (SEQID NO:4697) |
| Pro | Gly | Thr | Cys | Gly | Glu | Ile | Cys | Ala | Tyr | Ala | Ala | Cys | Xaa' | Xaa' | Xaa' Thr Gly Cys (SEQID NO:4698) |
| Pro | Gly | Thr | Cys | Gly | Glu | Ile | Cys | Ala | Tyr | Ala | Ala | Cys | Xaa' | Xaa' | Thr Xaa' Gly Cys (SEQID NO:4699) |
| Pro | Gly | Thr | Cys | Gly | Glu | Ile | Cys | Ala | Tyr | Ala | Ala | Cys | Xaa' | Xaa' | Xaa' Thr Gly Xaa' Cys (SEQID NO:4700) |
| Pro | Gly | Thr | Cys | Gly | Glu | Ile | Cys | Ala | Tyr | Ala | Ala | Cys | Xaa' | Xaa' | Xaa' Thr Gly Cys Xaa' (SEQID NO:4701) |
| Pro | Gly | Thr | Cys | Gly | Glu | Ile | Cys | Ala | Tyr | Ala | Ala | Cys | Xaa' | Xaa' | Thr Xaa' Gly Cys (SEQID NO:4702) |
| Pro | Gly | Thr | Cys | Gly | Glu | Ile | Cys | Ala | Tyr | Ala | Ala | Cys | Xaa' | Xaa' | Thr Xaa' Xaa' Gly Cys (SEQID NO:4703) |
| Pro | Gly | Thr | Cys | Gly | Glu | Ile | Cys | Ala | Tyr | Ala | Ala | Cys | Xaa' | Xaa' | Thr Xaa' Gly Xaa' Cys (SEQID NO:4704) |
| Pro | Gly | Thr | Cys | Gly | Glu | Ile | Cys | Ala | Tyr | Ala | Ala | Cys | Xaa' | Xaa' | Thr Xaa' Gly Cys Xaa' (SEQID NO:4705) |
| Pro | Gly | Thr | Cys | Gly | Glu | Ile | Cys | Ala | Tyr | Ala | Ala | Cys | Xaa' | Xaa' | Thr Gly Xaa' Cys (SEQID NO:4706) |
| Pro | Gly | Thr | Cys | Gly | Glu | Ile | Cys | Ala | Tyr | Ala | Ala | Cys | Xaa' | Xaa' | Thr Gly Xaa' Xaa' Cys (SEQID NO:4707) |
| Pro | Gly | Thr | Cys | Gly | Glu | Ile | Cys | Ala | Tyr | Ala | Ala | Cys | Xaa' | Xaa' | Thr Gly Xaa' Cys Xaa' (SEQID NO:4708) |
| Pro | Gly | Thr | Cys | Gly | Glu | Ile | Cys | Ala | Tyr | Ala | Ala | Cys | Xaa' | Xaa' | Thr Gly Cys Xaa' (SEQID NO:4709) |
| Pro | Gly | Thr | Cys | Gly | Glu | Ile | Cys | Ala | Tyr | Ala | Ala | Cys | Xaa' | Xaa' | Thr Gly Cys Xaa' Xaa' (SEQID NO:4710) |
| Pro | Gly | Thr | Cys | Gly | Glu | Ile | Cys | Ala | Tyr | Ala | Ala | Cys | Xaa' | Thr | Xaa' Gly Cys (SEQID NO:4711) |
| Pro | Gly | Thr | Cys | Gly | Glu | Ile | Cys | Ala | Tyr | Ala | Ala | Cys | Xaa' | Thr | Gly Cys (SEQID NO:4712) |
| Pro | Gly | Thr | Cys | Gly | Glu | Ile | Cys | Ala | Tyr | Ala | Ala | Cys | Xaa' | Thr | Xaa' Xaa' Gly Cys (SEQID NO:4713) |
| Pro | Gly | Thr | Cys | Gly | Glu | Ile | Cys | Ala | Tyr | Ala | Ala | Cys | Xaa' | Thr | Xaa' Gly Xaa' Cys (SEQID NO:4714) |
| Pro | Gly | Thr | Cys | Gly | Glu | Ile | Cys | Ala | Tyr | Ala | Ala | Cys | Xaa' | Thr | Xaa' Gly Cys Xaa' (SEQID NO:4715) |
| Pro | Gly | Thr | Cys | Gly | Glu | Ile | Cys | Ala | Tyr | Ala | Ala | Cys | Xaa' | Thr | Gly Xaa' Cys (SEQID NO:4716) |
| Pro | Gly | Thr | Cys | Gly | Glu | Ile | Cys | Ala | Tyr | Ala | Ala | Cys | Xaa' | Thr | Gly Xaa' Xaa' Cys (SEQID NO:4717) |
| Pro | Gly | Thr | Cys | Gly | Glu | Ile | Cys | Ala | Tyr | Ala | Ala | Cys | Xaa' | Thr | Gly Xaa' Cys Xaa' (SEQID NO:4718) |
| Pro | Gly | Thr | Cys | Gly | Glu | Ile | Cys | Ala | Tyr | Ala | Ala | Cys | Xaa' | Thr | Gly Cys Xaa' (SEQID NO:4719) |
| Pro | Gly | Thr | Cys | Gly | Glu | Ile | Cys | Ala | Tyr | Ala | Ala | Cys | Xaa' | Thr | Gly Cys Xaa' Xaa' (SEQID NO:4720) |
| Pro | Gly | Thr | Cys | Gly | Glu | Ile | Cys | Ala | Tyr | Ala | Ala | Cys | Xaa' | Thr | Gly Cys Xaa' (SEQID NO:4721) |
| Pro | Gly | Thr | Cys | Gly | Glu | Ile | Cys | Ala | Tyr | Ala | Ala | Cys | Xaa' | Thr | Gly Xaa' Xaa' Cys (SEQID NO:4722) |
| Pro | Gly | Thr | Cys | Gly | Glu | Ile | Cys | Ala | Tyr | Ala | Ala | Cys | Xaa' | Thr | Gly Xaa' Cys Xaa' (SEQID NO:4723) |
| Pro | Gly | Thr | Cys | Gly | Glu | Ile | Cys | Ala | Tyr | Ala | Ala | Cys | Xaa' | Thr | Gly Xaa' Xaa' Cys Xaa' (SEQID NO:4724) |
| Pro | Gly | Thr | Cys | Gly | Glu | Ile | Cys | Ala | Tyr | Ala | Ala | Cys | Xaa' | Thr | Gly Cys Xaa' Xaa' (SEQID NO:4725) |
| Pro | Gly | Thr | Cys | Gly | Glu | Ile | Cys | Ala | Tyr | Ala | Ala | Cys | Xaa' | Thr | Gly Xaa' Cys Xaa' (SEQID NO:4726) |
| Pro | Gly | Thr | Cys | Gly | Glu | Ile | Cys | Ala | Tyr | Ala | Ala | Cys | Xaa' | Thr | Gly Cys Xaa' (SEQID NO:4727) |
| Pro | Gly | Thr | Cys | Gly | Glu | Ile | Cys | Ala | Tyr | Ala | Ala | Cys | Xaa' | Thr | Gly Cys Xaa' Xaa' (SEQID NO:4728) |
| Pro | Gly | Thr | Cys | Gly | Glu | Ile | Cys | Ala | Tyr | Ala | Ala | Cys | Xaa' | Thr | Gly Cys Xaa' Xaa' Xaa' (SEQID NO:4729) |
| Pro | Gly | Thr | Cys | Gly | Glu | Ile | Cys | Ala | Tyr | Ala | Ala | Cys | Thr | Gly | Cys (SEQID NO:4730) |

FIG. 2DI

```
Pro Gly Thr Cys Gly Glu Ile Cys Ala Tyr Ala Ala Cys Thr Xaa' Xaa' Gly Cys                          (SEQ ID NO: 4731)
Pro Gly Thr Cys Gly Glu Ile Cys Ala Tyr Ala Ala Cys Thr Xaa' Xaa' Xaa' Gly Cys                     (SEQ ID NO: 4732)
Pro Gly Thr Cys Gly Glu Ile Cys Ala Tyr Ala Ala Cys Thr Xaa' Xaa' Xaa' Xaa' Gly Cys                (SEQ ID NO: 4733)
Pro Gly Thr Cys Gly Glu Ile Cys Ala Tyr Ala Ala Cys Thr Xaa' Xaa' Xaa' Xaa' Xaa' Gly Cys           (SEQ ID NO: 4734)
Pro Gly Thr Cys Gly Glu Ile Cys Ala Tyr Ala Ala Cys Thr Xaa' Xaa' Xaa' Xaa' Xaa' Gly Xaa' Cys      (SEQ ID NO: 4735)
Pro Gly Thr Cys Gly Glu Ile Cys Ala Tyr Ala Ala Cys Thr Xaa' Xaa' Xaa' Xaa' Xaa' Gly Xaa' Cys      (SEQ ID NO: 4736)
Pro Gly Thr Cys Gly Glu Ile Cys Ala Tyr Ala Ala Cys Thr Xaa' Xaa' Xaa' Xaa' Gly Xaa' Xaa' Cys      (SEQ ID NO: 4737)
Pro Gly Thr Cys Gly Glu Ile Cys Ala Tyr Ala Ala Cys Thr Xaa' Xaa' Xaa' Gly Xaa' Xaa' Cys Xaa'      (SEQ ID NO: 4738)
Pro Gly Thr Cys Gly Glu Ile Cys Ala Tyr Ala Ala Cys Thr Xaa' Xaa' Gly Xaa' Xaa' Cys Xaa'           (SEQ ID NO: 4739)
Pro Gly Thr Cys Gly Glu Ile Cys Ala Tyr Ala Ala Cys Thr Xaa' Gly Xaa' Gly Cys Xaa'                 (SEQ ID NO: 4740)
Pro Gly Thr Cys Gly Glu Ile Cys Ala Tyr Ala Ala Cys Thr Xaa' Gly Xaa' Cys                          (SEQ ID NO: 4741)
Pro Gly Thr Cys Gly Glu Ile Cys Ala Tyr Ala Ala Cys Thr Gly Xaa' Xaa' Cys                          (SEQ ID NO: 4742)
Pro Gly Thr Cys Gly Glu Ile Cys Ala Tyr Ala Ala Cys Thr Gly Xaa' Xaa' Xaa' Cys                     (SEQ ID NO: 4743)
Pro Gly Thr Cys Gly Glu Ile Cys Ala Tyr Ala Ala Cys Thr Gly Xaa' Xaa' Xaa' Xaa' Cys                (SEQ ID NO: 4744)
Pro Gly Thr Cys Gly Glu Ile Cys Ala Tyr Ala Ala Cys Thr Gly Xaa' Xaa' Xaa' Cys Xaa'                (SEQ ID NO: 4745)
Pro Gly Thr Cys Gly Glu Ile Cys Ala Tyr Ala Ala Cys Thr Gly Xaa' Xaa' Cys Xaa' Xaa'                (SEQ ID NO: 4746)
Pro Gly Thr Cys Gly Glu Ile Cys Ala Tyr Ala Ala Cys Thr Gly Xaa' Cys Xaa' Xaa' Xaa'                (SEQ ID NO: 4747)
Pro Gly Thr Cys Gly Glu Ile Cys Ala Tyr Ala Ala Cys Thr Gly Cys Xaa' Xaa' Xaa' Xaa'                (SEQ ID NO: 4748)
Pro Gly Thr Cys Gly Glu Ile Cys Ala Tyr Ala Ala Cys Thr Gly Cys Xaa' Xaa' Xaa'                     (SEQ ID NO: 4749)
Pro Gly Thr Cys Gly Glu Ile Cys Ala Tyr Ala Ala Cys Thr Gly Xaa' Cys                               (SEQ ID NO: 4750)
Pro Gly Thr Cys Gly Glu Ile Cys Ala Tyr Ala Ala Cys Thr Gly Xaa' Xaa' Cys                          (SEQ ID NO: 4751)
Pro Gly Thr Cys Gly Glu Ile Cys Ala Tyr Ala Ala Cys Thr Gly Xaa' Xaa' Xaa' Cys                     (SEQ ID NO: 4752)
Pro Gly Thr Cys Gly Glu Ile Cys Ala Tyr Ala Ala Cys Thr Gly Xaa' Xaa' Xaa' Xaa' Cys                (SEQ ID NO: 4753)
Pro Gly Thr Cys Gly Glu Ile Cys Ala Tyr Ala Ala Cys Thr Gly Xaa' Xaa' Xaa' Xaa' Xaa' Cys           (SEQ ID NO: 4754)
Pro Gly Thr Cys Gly Glu Ile Cys Ala Tyr Ala Ala Cys Thr Gly Xaa' Xaa' Xaa' Xaa' Cys Xaa'           (SEQ ID NO: 4755)
Pro Gly Thr Cys Gly Glu Ile Cys Ala Tyr Ala Ala Cys Thr Gly Xaa' Xaa' Xaa' Cys Xaa' Xaa'           (SEQ ID NO: 4756)
Pro Gly Thr Cys Gly Glu Ile Cys Ala Tyr Ala Ala Cys Thr Gly Xaa' Xaa' Cys Xaa' Xaa' Xaa'           (SEQ ID NO: 4757)
Pro Gly Thr Cys Gly Glu Ile Cys Ala Tyr Ala Ala Cys Thr Gly Xaa' Cys Xaa' Xaa' Xaa' Xaa'           (SEQ ID NO: 4758)
Pro Gly Thr Cys Gly Glu Ile Cys Ala Tyr Ala Ala Cys Thr Gly Cys Xaa' Xaa' Xaa' Xaa' Xaa'           (SEQ ID NO: 4759)
Pro Gly Thr Cys Gly Glu Ile Cys Ala Tyr Ala Ala Cys Thr Gly Cys Xaa' Xaa'                          (SEQ ID NO: 4760)
Pro Gly Thr Cys Gly Glu Ile Cys Ala Tyr Ala Ala Cys Thr Gly Cys Xaa' Xaa' Xaa'                     (SEQ ID NO: 4761)
Pro Gly Thr Cys Gly Glu Ile Cys Ala Tyr Ala Ala Cys Thr Gly Cys Xaa' Xaa' Xaa' Xaa'                (SEQ ID NO: 4762)
Pro Gly Thr Cys Gly Glu Ile Cys Ala Tyr Ala Ala Cys Thr Gly Cys Xaa' Xaa' Xaa' Xaa' Xaa'           (SEQ ID NO: 4763)
```

FIG. 2DJ

| | |
|---|---|
| (SEQ ID NO: 4764) | Cys Glu Tyr Cys Ala Asn Pro Ala Cys Thr Gly Cys Tyr |
| (SEQ ID NO: 4765) | Cys Glu Tyr Cys Ala Asn Pro Ala Cys Thr Ala Cys Tyr |
| (SEQ ID NO: 4766) | Cys Glu Tyr Cys Ala Asn Pro Ala Cys Val Gly Cys Tyr |
| (SEQ ID NO: 4767) | Cys Glu Tyr Cys Ala Asn Pro Ala Cys Val Ala Cys Tyr |
| (SEQ ID NO: 4768) | Cys Glu Tyr Cys Ala Asn Pro Ala Cys Gly Gly Cys Tyr |
| (SEQ ID NO: 4769) | Cys Glu Tyr Cys Ala Asn Pro Ala Cys Gly Ala Cys Tyr |
| (SEQ ID NO: 4770) | Cys Glu Tyr Cys Ala Asn Pro Thr Cys Thr Gly Cys Tyr |
| (SEQ ID NO: 4771) | Cys Glu Tyr Cys Ala Asn Pro Thr Cys Thr Ala Cys Tyr |
| (SEQ ID NO: 4772) | Cys Glu Tyr Cys Ala Asn Pro Thr Cys Val Gly Cys Tyr |
| (SEQ ID NO: 4773) | Cys Glu Tyr Cys Ala Asn Pro Thr Cys Val Ala Cys Tyr |
| (SEQ ID NO: 4774) | Cys Glu Tyr Cys Ala Asn Pro Thr Cys Gly Gly Cys Tyr |
| (SEQ ID NO: 4775) | Cys Glu Tyr Cys Ala Asn Pro Thr Cys Gly Ala Cys Tyr |
| (SEQ ID NO: 4776) | Cys Glu Tyr Cys Ala Asn Gly Ala Cys Thr Gly Cys Tyr |
| (SEQ ID NO: 4777) | Cys Glu Tyr Cys Ala Asn Gly Ala Cys Thr Ala Cys Tyr |
| (SEQ ID NO: 4778) | Cys Glu Tyr Cys Ala Asn Gly Ala Cys Val Gly Cys Tyr |
| (SEQ ID NO: 4779) | Cys Glu Tyr Cys Ala Asn Gly Ala Cys Val Ala Cys Tyr |
| (SEQ ID NO: 4780) | Cys Glu Tyr Cys Ala Asn Gly Ala Cys Gly Gly Cys Tyr |
| (SEQ ID NO: 4781) | Cys Glu Tyr Cys Ala Asn Gly Ala Cys Gly Ala Cys Tyr |
| (SEQ ID NO: 4782) | Cys Glu Tyr Cys Ala Asn Gly Thr Cys Thr Gly Cys Tyr |
| (SEQ ID NO: 4783) | Cys Glu Tyr Cys Ala Asn Gly Thr Cys Thr Ala Cys Tyr |
| (SEQ ID NO: 4784) | Cys Glu Tyr Cys Ala Asn Gly Thr Cys Val Gly Cys Tyr |
| (SEQ ID NO: 4785) | Cys Glu Tyr Cys Ala Asn Gly Thr Cys Val Ala Cys Tyr |
| (SEQ ID NO: 4786) | Cys Glu Tyr Cys Ala Asn Gly Thr Cys Gly Gly Cys Tyr |
| (SEQ ID NO: 4787) | Cys Glu Tyr Cys Ala Asn Gly Thr Cys Gly Ala Cys Tyr |
| (SEQ ID NO: 4788) | Cys Glu Tyr Cys Arg Asn Pro Ala Cys Thr Gly Cys Tyr |
| (SEQ ID NO: 4789) | Cys Glu Tyr Cys Arg Asn Pro Ala Cys Thr Ala Cys Tyr |
| (SEQ ID NO: 4790) | Cys Glu Tyr Cys Arg Asn Pro Ala Cys Val Gly Cys Tyr |
| (SEQ ID NO: 4791) | Cys Glu Tyr Cys Arg Asn Pro Ala Cys Val Ala Cys Tyr |
| (SEQ ID NO: 4792) | Cys Glu Tyr Cys Arg Asn Pro Ala Cys Gly Gly Cys Tyr |
| (SEQ ID NO: 4793) | Cys Glu Tyr Cys Arg Asn Pro Ala Cys Gly Ala Cys Tyr |
| (SEQ ID NO: 4794) | Cys Glu Tyr Cys Arg Asn Pro Thr Cys Thr Gly Cys Tyr |
| (SEQ ID NO: 4795) | Cys Glu Tyr Cys Arg Asn Pro Thr Cys Thr Ala Cys Tyr |
| (SEQ ID NO: 4796) | Cys Glu Tyr Cys Arg Asn Pro Thr Cys Val Gly Cys Tyr |
| (SEQ ID NO: 4797) | Cys Glu Tyr Cys Arg Asn Pro Thr Cys Val Ala Cys Tyr |
| (SEQ ID NO: 4798) | Cys Glu Tyr Cys Arg Asn Pro Thr Cys Gly Gly Cys Tyr |
| (SEQ ID NO: 4799) | Cys Glu Tyr Cys Arg Asn Pro Thr Cys Gly Ala Cys Tyr |
| (SEQ ID NO: 4800) | Cys Glu Tyr Cys Arg Asn Gly Ala Cys Thr Gly Cys Tyr |
| (SEQ ID NO: 4801) | Cys Glu Tyr Cys Arg Asn Gly Ala Cys Thr Ala Cys Tyr |
| (SEQ ID NO: 4802) | Cys Glu Tyr Cys Arg Asn Gly Ala Cys Val Gly Cys Tyr |
| (SEQ ID NO: 4803) | Cys Glu Tyr Cys Arg Asn Gly Ala Cys Val Ala Cys Tyr |
| (SEQ ID NO: 4804) | Cys Glu Tyr Cys Arg Asn Gly Ala Cys Gly Gly Cys Tyr |
| (SEQ ID NO: 4805) | Cys Glu Tyr Cys Arg Asn Gly Ala Cys Gly Ala Cys Tyr |
| (SEQ ID NO: 4806) | Cys Glu Tyr Cys Arg Asn Gly Thr Cys Thr Gly Cys Tyr |

FIG. 3A

| | |
|---|---|
| (SEQ ID NO: 4807 ) | Cys Glu Tyr Cys Arg Asn Gly Thr Cys Thr Ala Cys Tyr |
| (SEQ ID NO: 4808 ) | Cys Glu Tyr Cys Arg Asn Gly Thr Cys Val Gly Cys Tyr |
| (SEQ ID NO: 4809 ) | Cys Glu Tyr Cys Arg Asn Gly Thr Cys Val Ala Cys Tyr |
| (SEQ ID NO: 4810 ) | Cys Glu Tyr Cys Arg Asn Gly Thr Cys Gly Gly Cys Tyr |
| (SEQ ID NO: 4811 ) | Cys Glu Tyr Cys Arg Asn Gly Thr Cys Gly Ala Cys Tyr |
| (SEQ ID NO: 4812 ) | Cys Glu Tyr Cys Asn Asn Pro Ala Cys Thr Gly Cys Tyr |
| (SEQ ID NO: 4813 ) | Cys Glu Tyr Cys Asn Asn Pro Ala Cys Thr Ala Cys Tyr |
| (SEQ ID NO: 4814 ) | Cys Glu Tyr Cys Asn Asn Pro Ala Cys Val Gly Cys Tyr |
| (SEQ ID NO: 4815 ) | Cys Glu Tyr Cys Asn Asn Pro Ala Cys Val Ala Cys Tyr |
| (SEQ ID NO: 4816 ) | Cys Glu Tyr Cys Asn Asn Pro Ala Cys Gly Gly Cys Tyr |
| (SEQ ID NO: 4817 ) | Cys Glu Tyr Cys Asn Asn Pro Ala Cys Gly Ala Cys Tyr |
| (SEQ ID NO: 4818 ) | Cys Glu Tyr Cys Asn Asn Pro Thr Cys Thr Gly Cys Tyr |
| (SEQ ID NO: 4819 ) | Cys Glu Tyr Cys Asn Asn Pro Thr Cys Thr Ala Cys Tyr |
| (SEQ ID NO: 4820 ) | Cys Glu Tyr Cys Asn Asn Pro Thr Cys Val Gly Cys Tyr |
| (SEQ ID NO: 4821 ) | Cys Glu Tyr Cys Asn Asn Pro Thr Cys Val Ala Cys Tyr |
| (SEQ ID NO: 4822 ) | Cys Glu Tyr Cys Asn Asn Pro Thr Cys Gly Gly Cys Tyr |
| (SEQ ID NO: 4823 ) | Cys Glu Tyr Cys Asn Asn Pro Thr Cys Gly Ala Cys Tyr |
| (SEQ ID NO: 4824 ) | Cys Glu Tyr Cys Asn Asn Gly Ala Cys Thr Gly Cys Tyr |
| (SEQ ID NO: 4825 ) | Cys Glu Tyr Cys Asn Asn Gly Ala Cys Thr Ala Cys Tyr |
| (SEQ ID NO: 4826 ) | Cys Glu Tyr Cys Asn Asn Gly Ala Cys Val Gly Cys Tyr |
| (SEQ ID NO: 4827 ) | Cys Glu Tyr Cys Asn Asn Gly Ala Cys Val Ala Cys Tyr |
| (SEQ ID NO: 4828 ) | Cys Glu Tyr Cys Asn Asn Gly Ala Cys Gly Gly Cys Tyr |
| (SEQ ID NO: 4829 ) | Cys Glu Tyr Cys Asn Asn Gly Ala Cys Gly Ala Cys Tyr |
| (SEQ ID NO: 4830 ) | Cys Glu Tyr Cys Asn Asn Gly Thr Cys Thr Gly Cys Tyr |
| (SEQ ID NO: 4831 ) | Cys Glu Tyr Cys Asn Asn Gly Thr Cys Thr Ala Cys Tyr |
| (SEQ ID NO: 4832 ) | Cys Glu Tyr Cys Asn Asn Gly Thr Cys Val Gly Cys Tyr |
| (SEQ ID NO: 4833 ) | Cys Glu Tyr Cys Asn Asn Gly Thr Cys Val Ala Cys Tyr |
| (SEQ ID NO: 4834 ) | Cys Glu Tyr Cys Asn Asn Gly Thr Cys Gly Gly Cys Tyr |
| (SEQ ID NO: 4835 ) | Cys Glu Tyr Cys Asn Asn Gly Thr Cys Gly Ala Cys Tyr |
| (SEQ ID NO: 4836 ) | Cys Glu Tyr Cys Asp Asn Pro Ala Cys Thr Gly Cys Tyr |
| (SEQ ID NO: 4837 ) | Cys Glu Tyr Cys Asp Asn Pro Ala Cys Thr Ala Cys Tyr |
| (SEQ ID NO: 4838 ) | Cys Glu Tyr Cys Asp Asn Pro Ala Cys Val Gly Cys Tyr |
| (SEQ ID NO: 4839 ) | Cys Glu Tyr Cys Asp Asn Pro Ala Cys Val Ala Cys Tyr |
| (SEQ ID NO: 4840 ) | Cys Glu Tyr Cys Asp Asn Pro Ala Cys Gly Gly Cys Tyr |
| (SEQ ID NO: 4841 ) | Cys Glu Tyr Cys Asp Asn Pro Ala Cys Gly Ala Cys Tyr |
| (SEQ ID NO: 4842 ) | Cys Glu Tyr Cys Asp Asn Pro Thr Cys Thr Gly Cys Tyr |
| (SEQ ID NO: 4843 ) | Cys Glu Tyr Cys Asp Asn Pro Thr Cys Thr Ala Cys Tyr |
| (SEQ ID NO: 4844 ) | Cys Glu Tyr Cys Asp Asn Pro Thr Cys Val Gly Cys Tyr |
| (SEQ ID NO: 4845 ) | Cys Glu Tyr Cys Asp Asn Pro Thr Cys Val Ala Cys Tyr |
| (SEQ ID NO: 4846 ) | Cys Glu Tyr Cys Asp Asn Pro Thr Cys Gly Gly Cys Tyr |
| (SEQ ID NO: 4847 ) | Cys Glu Tyr Cys Asp Asn Pro Thr Cys Gly Ala Cys Tyr |
| (SEQ ID NO: 4848 ) | Cys Glu Tyr Cys Asp Asn Gly Ala Cys Thr Gly Cys Tyr |
| (SEQ ID NO: 4849 ) | Cys Glu Tyr Cys Asp Asn Gly Ala Cys Thr Ala Cys Tyr |

FIG. 3B (SEQ ID NO: 4850) Cys Glu Tyr Cys Asp Asn Gly Ala Cys Val Gly Cys Tyr
(SEQ ID NO: 4851) Cys Glu Tyr Cys Asp Asn Gly Ala Cys Val Ala Cys Tyr
(SEQ ID NO: 4852) Cys Glu Tyr Cys Asp Asn Gly Ala Cys Gly Gly Cys Tyr
(SEQ ID NO: 4853) Cys Glu Tyr Cys Asp Asn Gly Ala Cys Gly Ala Cys Tyr
(SEQ ID NO: 4854) Cys Glu Tyr Cys Asp Asn Gly Thr Cys Thr Gly Cys Tyr
(SEQ ID NO: 4855) Cys Glu Tyr Cys Asp Asn Gly Thr Cys Thr Ala Cys Tyr
(SEQ ID NO: 4856) Cys Glu Tyr Cys Asp Asn Gly Thr Cys Val Gly Cys Tyr
(SEQ ID NO: 4857) Cys Glu Tyr Cys Asp Asn Gly Thr Cys Val Ala Cys Tyr
(SEQ ID NO: 4858) Cys Glu Tyr Cys Asp Asn Gly Thr Cys Gly Gly Cys Tyr
(SEQ ID NO: 4859) Cys Glu Tyr Cys Asp Asn Gly Thr Cys Gly Ala Cys Tyr
(SEQ ID NO: 4860) Cys Glu Tyr Cys Gln Asn Pro Ala Cys Thr Gly Cys Tyr
(SEQ ID NO: 4861) Cys Glu Tyr Cys Gln Asn Pro Ala Cys Thr Ala Cys Tyr
(SEQ ID NO: 4862) Cys Glu Tyr Cys Gln Asn Pro Ala Cys Val Gly Cys Tyr
(SEQ ID NO: 4863) Cys Glu Tyr Cys Gln Asn Pro Ala Cys Val Ala Cys Tyr
(SEQ ID NO: 4864) Cys Glu Tyr Cys Gln Asn Pro Ala Cys Gly Gly Cys Tyr
(SEQ ID NO: 4865) Cys Glu Tyr Cys Gln Asn Pro Ala Cys Gly Ala Cys Tyr
(SEQ ID NO: 4866) Cys Glu Tyr Cys Gln Asn Pro Thr Cys Thr Gly Cys Tyr
(SEQ ID NO: 4867) Cys Glu Tyr Cys Gln Asn Pro Thr Cys Thr Ala Cys Tyr
(SEQ ID NO: 4868) Cys Glu Tyr Cys Gln Asn Pro Thr Cys Val Gly Cys Tyr
(SEQ ID NO: 4869) Cys Glu Tyr Cys Gln Asn Pro Thr Cys Val Ala Cys Tyr
(SEQ ID NO: 4870) Cys Glu Tyr Cys Gln Asn Pro Thr Cys Gly Gly Cys Tyr
(SEQ ID NO: 4871) Cys Glu Tyr Cys Gln Asn Pro Thr Cys Gly Ala Cys Tyr
(SEQ ID NO: 4872) Cys Glu Tyr Cys Gln Asn Gly Ala Cys Thr Gly Cys Tyr
(SEQ ID NO: 4873) Cys Glu Tyr Cys Gln Asn Gly Ala Cys Thr Ala Cys Tyr
(SEQ ID NO: 4874) Cys Glu Tyr Cys Gln Asn Gly Ala Cys Val Gly Cys Tyr
(SEQ ID NO: 4875) Cys Glu Tyr Cys Gln Asn Gly Ala Cys Val Ala Cys Tyr
(SEQ ID NO: 4876) Cys Glu Tyr Cys Gln Asn Gly Ala Cys Gly Gly Cys Tyr
(SEQ ID NO: 4877) Cys Glu Tyr Cys Gln Asn Gly Ala Cys Gly Ala Cys Tyr
(SEQ ID NO: 4878) Cys Glu Tyr Cys Gln Asn Gly Thr Cys Thr Gly Cys Tyr
(SEQ ID NO: 4879) Cys Glu Tyr Cys Gln Asn Gly Thr Cys Thr Ala Cys Tyr
(SEQ ID NO: 4880) Cys Glu Tyr Cys Gln Asn Gly Thr Cys Val Gly Cys Tyr
(SEQ ID NO: 4881) Cys Glu Tyr Cys Gln Asn Gly Thr Cys Val Ala Cys Tyr
(SEQ ID NO: 4882) Cys Glu Tyr Cys Gln Asn Gly Thr Cys Gly Gly Cys Tyr
(SEQ ID NO: 4883) Cys Glu Tyr Cys Gln Asn Gly Thr Cys Gly Ala Cys Tyr
(SEQ ID NO: 4884) Cys Glu Tyr Cys Glu Asn Pro Ala Cys Thr Gly Cys Tyr
(SEQ ID NO: 4885) Cys Glu Tyr Cys Glu Asn Pro Ala Cys Thr Ala Cys Tyr
(SEQ ID NO: 4886) Cys Glu Tyr Cys Glu Asn Pro Ala Cys Val Gly Cys Tyr
(SEQ ID NO: 4887) Cys Glu Tyr Cys Glu Asn Pro Ala Cys Val Ala Cys Tyr
(SEQ ID NO: 4888) Cys Glu Tyr Cys Glu Asn Pro Ala Cys Gly Gly Cys Tyr
(SEQ ID NO: 4889) Cys Glu Tyr Cys Glu Asn Pro Ala Cys Gly Ala Cys Tyr
(SEQ ID NO: 4890) Cys Glu Tyr Cys Glu Asn Pro Thr Cys Thr Gly Cys Tyr
(SEQ ID NO: 4891) Cys Glu Tyr Cys Glu Asn Pro Thr Cys Thr Ala Cys Tyr
(SEQ ID NO: 4892) Cys Glu Tyr Cys Glu Asn Pro Thr Cys Val Gly Cys Tyr

FIG. 3C (SEQ ID NO: 4893)  Cys Glu Tyr Cys Glu Asn Pro Thr Cys Val Ala Cys Tyr
(SEQ ID NO: 4894)  Cys Glu Tyr Cys Glu Asn Pro Thr Cys Gly Gly Cys Tyr
(SEQ ID NO: 4895)  Cys Glu Tyr Cys Glu Asn Pro Thr Cys Gly Ala Cys Tyr
(SEQ ID NO: 4896)  Cys Glu Tyr Cys Glu Asn Gly Ala Cys Thr Gly Cys Tyr
(SEQ ID NO: 4897)  Cys Glu Tyr Cys Glu Asn Gly Ala Cys Thr Ala Cys Tyr
(SEQ ID NO: 4898)  Cys Glu Tyr Cys Glu Asn Gly Ala Cys Val Gly Cys Tyr
(SEQ ID NO: 4899)  Cys Glu Tyr Cys Glu Asn Gly Ala Cys Val Ala Cys Tyr
(SEQ ID NO: 4900)  Cys Glu Tyr Cys Glu Asn Gly Ala Cys Gly Gly Cys Tyr
(SEQ ID NO: 4901)  Cys Glu Tyr Cys Glu Asn Gly Ala Cys Gly Ala Cys Tyr
(SEQ ID NO: 4902)  Cys Glu Tyr Cys Glu Asn Gly Thr Cys Thr Gly Cys Tyr
(SEQ ID NO: 4903)  Cys Glu Tyr Cys Glu Asn Gly Thr Cys Thr Ala Cys Tyr
(SEQ ID NO: 4904)  Cys Glu Tyr Cys Glu Asn Gly Thr Cys Val Gly Cys Tyr
(SEQ ID NO: 4905)  Cys Glu Tyr Cys Glu Asn Gly Thr Cys Val Ala Cys Tyr
(SEQ ID NO: 4906)  Cys Glu Tyr Cys Glu Asn Gly Thr Cys Gly Gly Cys Tyr
(SEQ ID NO: 4907)  Cys Glu Tyr Cys Glu Asn Gly Thr Cys Gly Ala Cys Tyr
(SEQ ID NO: 4908)  Cys Glu Tyr Cys Gly Asn Pro Ala Cys Thr Gly Cys Tyr
(SEQ ID NO: 4909)  Cys Glu Tyr Cys Gly Asn Pro Ala Cys Thr Ala Cys Tyr
(SEQ ID NO: 4910)  Cys Glu Tyr Cys Gly Asn Pro Ala Cys Val Gly Cys Tyr
(SEQ ID NO: 4911)  Cys Glu Tyr Cys Gly Asn Pro Ala Cys Val Ala Cys Tyr
(SEQ ID NO: 4912)  Cys Glu Tyr Cys Gly Asn Pro Ala Cys Gly Gly Cys Tyr
(SEQ ID NO: 4913)  Cys Glu Tyr Cys Gly Asn Pro Ala Cys Gly Ala Cys Tyr
(SEQ ID NO: 4914)  Cys Glu Tyr Cys Gly Asn Pro Thr Cys Thr Gly Cys Tyr
(SEQ ID NO: 4915)  Cys Glu Tyr Cys Gly Asn Pro Thr Cys Thr Ala Cys Tyr
(SEQ ID NO: 4916)  Cys Glu Tyr Cys Gly Asn Pro Thr Cys Val Gly Cys Tyr
(SEQ ID NO: 4917)  Cys Glu Tyr Cys Gly Asn Pro Thr Cys Val Ala Cys Tyr
(SEQ ID NO: 4918)  Cys Glu Tyr Cys Gly Asn Pro Thr Cys Gly Gly Cys Tyr
(SEQ ID NO: 4919)  Cys Glu Tyr Cys Gly Asn Pro Thr Cys Gly Ala Cys Tyr
(SEQ ID NO: 4920)  Cys Glu Tyr Cys Gly Asn Gly Ala Cys Thr Gly Cys Tyr
(SEQ ID NO: 4921)  Cys Glu Tyr Cys Gly Asn Gly Ala Cys Thr Ala Cys Tyr
(SEQ ID NO: 4922)  Cys Glu Tyr Cys Gly Asn Gly Ala Cys Val Gly Cys Tyr
(SEQ ID NO: 4923)  Cys Glu Tyr Cys Gly Asn Gly Ala Cys Val Ala Cys Tyr
(SEQ ID NO: 4924)  Cys Glu Tyr Cys Gly Asn Gly Ala Cys Gly Gly Cys Tyr
(SEQ ID NO: 4925)  Cys Glu Tyr Cys Gly Asn Gly Ala Cys Gly Ala Cys Tyr
(SEQ ID NO: 4926)  Cys Glu Tyr Cys Gly Asn Gly Thr Cys Thr Gly Cys Tyr
(SEQ ID NO: 4927)  Cys Glu Tyr Cys Gly Asn Gly Thr Cys Thr Ala Cys Tyr
(SEQ ID NO: 4928)  Cys Glu Tyr Cys Gly Asn Gly Thr Cys Val Gly Cys Tyr
(SEQ ID NO: 4929)  Cys Glu Tyr Cys Gly Asn Gly Thr Cys Val Ala Cys Tyr
(SEQ ID NO: 4930)  Cys Glu Tyr Cys Gly Asn Gly Thr Cys Gly Gly Cys Tyr
(SEQ ID NO: 4931)  Cys Glu Tyr Cys Gly Asn Gly Thr Cys Gly Ala Cys Tyr
(SEQ ID NO: 4932)  Cys Glu Tyr Cys His Asn Pro Ala Cys Thr Gly Cys Tyr
(SEQ ID NO: 4933)  Cys Glu Tyr Cys His Asn Pro Ala Cys Thr Ala Cys Tyr
(SEQ ID NO: 4934)  Cys Glu Tyr Cys His Asn Pro Ala Cys Val Gly Cys Tyr
(SEQ ID NO: 4935)  Cys Glu Tyr Cys His Asn Pro Ala Cys Val Ala Cys Tyr

FIG. 3D

| | |
|---|---|
| (SEQ ID NO: 4936 ) | Cys Glu Tyr Cys His Asn Pro Ala Cys Gly Gly Cys Tyr |
| (SEQ ID NO: 4937 ) | Cys Glu Tyr Cys His Asn Pro Ala Cys Gly Ala Cys Tyr |
| (SEQ ID NO: 4938 ) | Cys Glu Tyr Cys His Asn Pro Thr Cys Thr Gly Cys Tyr |
| (SEQ ID NO: 4939 ) | Cys Glu Tyr Cys His Asn Pro Thr Cys Thr Ala Cys Tyr |
| (SEQ ID NO: 4940 ) | Cys Glu Tyr Cys His Asn Pro Thr Cys Val Gly Cys Tyr |
| (SEQ ID NO: 4941 ) | Cys Glu Tyr Cys His Asn Pro Thr Cys Val Ala Cys Tyr |
| (SEQ ID NO: 4942 ) | Cys Glu Tyr Cys His Asn Pro Thr Cys Gly Gly Cys Tyr |
| (SEQ ID NO: 4943 ) | Cys Glu Tyr Cys His Asn Pro Thr Cys Gly Ala Cys Tyr |
| (SEQ ID NO: 4944 ) | Cys Glu Tyr Cys His Asn Gly Ala Cys Thr Gly Cys Tyr |
| (SEQ ID NO: 4945 ) | Cys Glu Tyr Cys His Asn Gly Ala Cys Thr Ala Cys Tyr |
| (SEQ ID NO: 4946 ) | Cys Glu Tyr Cys His Asn Gly Ala Cys Val Gly Cys Tyr |
| (SEQ ID NO: 4947 ) | Cys Glu Tyr Cys His Asn Gly Ala Cys Val Ala Cys Tyr |
| (SEQ ID NO: 4948 ) | Cys Glu Tyr Cys His Asn Gly Ala Cys Gly Gly Cys Tyr |
| (SEQ ID NO: 4949 ) | Cys Glu Tyr Cys His Asn Gly Ala Cys Gly Ala Cys Tyr |
| (SEQ ID NO: 4950 ) | Cys Glu Tyr Cys His Asn Gly Thr Cys Thr Gly Cys Tyr |
| (SEQ ID NO: 4951 ) | Cys Glu Tyr Cys His Asn Gly Thr Cys Thr Ala Cys Tyr |
| (SEQ ID NO: 4952 ) | Cys Glu Tyr Cys His Asn Gly Thr Cys Val Gly Cys Tyr |
| (SEQ ID NO: 4953 ) | Cys Glu Tyr Cys His Asn Gly Thr Cys Val Ala Cys Tyr |
| (SEQ ID NO: 4954 ) | Cys Glu Tyr Cys His Asn Gly Thr Cys Gly Gly Cys Tyr |
| (SEQ ID NO: 4955 ) | Cys Glu Tyr Cys His Asn Gly Thr Cys Gly Ala Cys Tyr |
| (SEQ ID NO: 4956 ) | Cys Glu Tyr Cys Ile Asn Pro Ala Cys Thr Gly Cys Tyr |
| (SEQ ID NO: 4957 ) | Cys Glu Tyr Cys Ile Asn Pro Ala Cys Thr Ala Cys Tyr |
| (SEQ ID NO: 4958 ) | Cys Glu Tyr Cys Ile Asn Pro Ala Cys Val Gly Cys Tyr |
| (SEQ ID NO: 4959 ) | Cys Glu Tyr Cys. Ile Asn Pro Ala Cys Val Ala Cys Tyr |
| (SEQ ID NO: 4960 ) | Cys Glu Tyr Cys Ile Asn Pro Ala Cys Gly Gly Cys Tyr |
| (SEQ ID NO: 4961 ) | Cys Glu Tyr Cys Ile Asn Pro Ala Cys Gly Ala Cys Tyr |
| (SEQ ID NO: 4962 ) | Cys Glu Tyr Cys Ile Asn Pro Thr Cys Thr Gly Cys Tyr |
| (SEQ ID NO: 4963 ) | Cys Glu Tyr Cys Ile Asn Pro Thr Cys Thr Ala Cys Tyr |
| (SEQ ID NO: 4964 ) | Cys Glu Tyr Cys Ile Asn Pro Thr Cys Val Gly Cys Tyr |
| (SEQ ID NO: 4965 ) | Cys Glu Tyr Cys Ile Asn Pro Thr Cys Val Ala Cys Tyr |
| (SEQ ID NO: 4966 ) | Cys Glu Tyr Cys Ile Asn Pro Thr Cys Gly Gly Cys Tyr |
| (SEQ ID NO: 4967 ) | Cys Glu Tyr Cys Ile Asn Pro Thr Cys Gly Ala Cys Tyr |
| (SEQ ID NO: 4968 ) | Cys Glu Tyr Cys Ile Asn Gly Ala Cys Thr Gly Cys Tyr |
| (SEQ ID NO: 4969 ) | Cys Glu Tyr Cys Ile Asn Gly Ala Cys Thr Ala Cys Tyr |
| (SEQ ID NO: 4970 ) | Cys Glu Tyr Cys Ile Asn Gly Ala Cys Val Gly Cys Tyr |
| (SEQ ID NO: 4971 ) | Cys Glu Tyr Cys Ile Asn Gly Ala Cys Val Ala Cys Tyr |
| (SEQ ID NO: 4972 ) | Cys Glu Tyr Cys Ile Asn Gly Ala Cys Gly Gly Cys Tyr |
| (SEQ ID NO: 4973 ) | Cys Glu Tyr Cys Ile Asn Gly Ala Cys Gly Ala Cys Tyr |
| (SEQ ID NO: 4974 ) | Cys Glu Tyr Cys Ile Asn Gly Thr Cys Thr Gly Cys Tyr |
| (SEQ ID NO: 4975 ) | Cys Glu Tyr Cys Ile Asn Gly Thr Cys Thr Ala Cys Tyr |
| (SEQ ID NO: 4976 ) | Cys Glu Tyr Cys Ile Asn Gly Thr Cys Val Gly Cys Tyr |
| (SEQ ID NO: 4977 ) | Cys Glu Tyr Cys Ile Asn Gly Thr Cys Val Ala Cys Tyr |
| (SEQ ID NO: 4978 ) | Cys Glu Tyr Cys Ile Asn Gly Thr Cys Gly Gly Cys Tyr |

FIG. 3E

(SEQ ID NO: 4979)  Cys Glu Tyr Cys Ile Asn Gly Thr Cys Gly Ala Cys Tyr
(SEQ ID NO: 4980)  Cys Glu Tyr Cys Leu Asn Pro Ala Cys Thr Gly Cys Tyr
(SEQ ID NO: 4981)  Cys Glu Tyr Cys Leu Asn Pro Ala Cys Thr Ala Cys Tyr
(SEQ ID NO: 4982)  Cys Glu Tyr Cys Leu Asn Pro Ala Cys Val Gly Cys Tyr
(SEQ ID NO: 4983)  Cys Glu Tyr Cys Leu Asn Pro Ala Cys Val Ala Cys Tyr
(SEQ ID NO: 4984)  Cys Glu Tyr Cys Leu Asn Pro Ala Cys Gly Gly Cys Tyr
(SEQ ID NO: 4985)  Cys Glu Tyr Cys Leu Asn Pro Ala Cys Gly Ala Cys Tyr
(SEQ ID NO: 4986)  Cys Glu Tyr Cys Leu Asn Pro Thr Cys Thr Gly Cys Tyr
(SEQ ID NO: 4987)  Cys Glu Tyr Cys Leu Asn Pro Thr Cys Thr Ala Cys Tyr
(SEQ ID NO: 4988)  Cys Glu Tyr Cys Leu Asn Pro Thr Cys Val Gly Cys Tyr
(SEQ ID NO: 4989)  Cys Glu Tyr Cys Leu Asn Pro Thr Cys Val Ala Cys Tyr
(SEQ ID NO: 4990)  Cys Glu Tyr Cys Leu Asn Pro Thr Cys Gly Gly Cys Tyr
(SEQ ID NO: 4991)  Cys Glu Tyr Cys Leu Asn Pro Thr Cys Gly Ala Cys Tyr
(SEQ ID NO: 4992)  Cys Glu Tyr Cys Leu Asn Gly Ala Cys Thr Gly Cys Tyr
(SEQ ID NO: 4993)  Cys Glu Tyr Cys Leu Asn Gly Ala Cys Thr Ala Cys Tyr
(SEQ ID NO: 4994)  Cys Glu Tyr Cys Leu Asn Gly Ala Cys Val Gly Cys Tyr
(SEQ ID NO: 4995)  Cys Glu Tyr Cys Leu Asn Gly Ala Cys Val Ala Cys Tyr
(SEQ ID NO: 4996)  Cys Glu Tyr Cys Leu Asn Gly Ala Cys Gly Gly Cys Tyr
(SEQ ID NO: 4997)  Cys Glu Tyr Cys Leu Asn Gly Ala Cys Gly Ala Cys Tyr
(SEQ ID NO: 4998)  Cys Glu Tyr Cys Leu Asn Gly Thr Cys Thr Gly Cys Tyr
(SEQ ID NO: 4999)  Cys Glu Tyr Cys Leu Asn Gly Thr Cys Thr Ala Cys Tyr
(SEQ ID NO: 5000)  Cys Glu Tyr Cys Leu Asn Gly Thr Cys Val Gly Cys Tyr
(SEQ ID NO: 5001)  Cys Glu Tyr Cys Leu Asn Gly Thr Cys Val Ala Cys Tyr
(SEQ ID NO: 5002)  Cys Glu Tyr Cys Leu Asn Gly Thr Cys Gly Gly Cys Tyr
(SEQ ID NO: 5003)  Cys Glu Tyr Cys Leu Asn Gly Thr Cys Gly Ala Cys Tyr
(SEQ ID NO: 5004)  Cys Glu Tyr Cys Lys Asn Pro Ala Cys Thr Gly Cys Tyr
(SEQ ID NO: 5005)  Cys Glu Tyr Cys Lys Asn Pro Ala Cys Thr Ala Cys Tyr
(SEQ ID NO: 5006)  Cys Glu Tyr Cys Lys Asn Pro Ala Cys Val Gly Cys Tyr
(SEQ ID NO: 5007)  Cys Glu Tyr Cys Lys Asn Pro Ala Cys Val Ala Cys Tyr
(SEQ ID NO: 5008)  Cys Glu Tyr Cys Lys Asn Pro Ala Cys Gly Gly Cys Tyr
(SEQ ID NO: 5009)  Cys Glu Tyr Cys Lys Asn Pro Ala Cys Gly Ala Cys Tyr
(SEQ ID NO: 5010)  Cys Glu Tyr Cys Lys Asn Pro Thr Cys Thr Gly Cys Tyr
(SEQ ID NO: 5011)  Cys Glu Tyr Cys Lys Asn Pro Thr Cys Thr Ala Cys Tyr
(SEQ ID NO: 5012)  Cys Glu Tyr Cys Lys Asn Pro Thr Cys Val Gly Cys Tyr
(SEQ ID NO: 5013)  Cys Glu Tyr Cys Lys Asn Pro Thr Cys Val Ala Cys Tyr
(SEQ ID NO: 5014)  Cys Glu Tyr Cys Lys Asn Pro Thr Cys Gly Gly Cys Tyr
(SEQ ID NO: 5015)  Cys Glu Tyr Cys Lys Asn Pro Thr Cys Gly Ala Cys Tyr
(SEQ ID NO: 5016)  Cys Glu Tyr Cys Lys Asn Gly Ala Cys Thr Gly Cys Tyr
(SEQ ID NO: 5017)  Cys Glu Tyr Cys Lys Asn Gly Ala Cys Thr Ala Cys Tyr
(SEQ ID NO: 5018)  Cys Glu Tyr Cys Lys Asn Gly Ala Cys Val Gly Cys Tyr
(SEQ ID NO: 5019)  Cys Glu Tyr Cys Lys Asn Gly Ala Cys Val Ala Cys Tyr
(SEQ ID NO: 5020)  Cys Glu Tyr Cys Lys Asn Gly Ala Cys Gly Gly Cys Tyr
(SEQ ID NO: 5021)  Cys Glu Tyr Cys Lys Asn Gly Ala Cys Gly Ala Cys Tyr

FIG. 3F

| | |
|---|---|
| (SEQ ID NO: 5022) | Cys Glu Tyr Cys Lys Asn Gly Thr Cys Thr Gly Cys Tyr |
| (SEQ ID NO: 5023) | Cys Glu Tyr Cys Lys Asn Gly Thr Cys Thr Ala Cys Tyr |
| (SEQ ID NO: 5024) | Cys Glu Tyr Cys Lys Asn Gly Thr Cys Val Gly Cys Tyr |
| (SEQ ID NO: 5025) | Cys Glu Tyr Cys Lys Asn Gly Thr Cys Val Ala Cys Tyr |
| (SEQ ID NO: 5026) | Cys Glu Tyr Cys Lys Asn Gly Thr Cys Gly Gly Cys Tyr |
| (SEQ ID NO: 5027) | Cys Glu Tyr Cys Lys Asn Gly Thr Cys Gly Ala Cys Tyr |
| (SEQ ID NO: 5028) | Cys Glu Tyr Cys Met Asn Pro Ala Cys Thr Gly Cys Tyr |
| (SEQ ID NO: 5029) | Cys Glu Tyr Cys Met Asn Pro Ala Cys Thr Ala Cys Tyr |
| (SEQ ID NO: 5030) | Cys Glu Tyr Cys Met Asn Pro Ala Cys Val Gly Cys Tyr |
| (SEQ ID NO: 5031) | Cys Glu Tyr Cys Met Asn Pro Ala Cys Val Ala Cys Tyr |
| (SEQ ID NO: 5032) | Cys Glu Tyr Cys Met Asn Pro Ala Cys Gly Gly Cys Tyr |
| (SEQ ID NO: 5033) | Cys Glu Tyr Cys Met Asn Pro Ala Cys Gly Ala Cys Tyr |
| (SEQ ID NO: 5034) | Cys Glu Tyr Cys Met Asn Pro Thr Cys Thr Gly Cys Tyr |
| (SEQ ID NO: 5035) | Cys Glu Tyr Cys Met Asn Pro Thr Cys Thr Ala Cys Tyr |
| (SEQ ID NO: 5036) | Cys Glu Tyr Cys Met Asn Pro Thr Cys Val Gly Cys Tyr |
| (SEQ ID NO: 5037) | Cys Glu Tyr Cys Met Asn Pro Thr Cys Val Ala Cys Tyr |
| (SEQ ID NO: 5038) | Cys Glu Tyr Cys Met Asn Pro Thr Cys Gly Gly Cys Tyr |
| (SEQ ID NO: 5039) | Cys Glu Tyr Cys Met Asn Pro Thr Cys Gly Ala Cys Tyr |
| (SEQ ID NO: 5040) | Cys Glu Tyr Cys Met Asn Gly Ala Cys Thr Gly Cys Tyr |
| (SEQ ID NO: 5041) | Cys Glu Tyr Cys Met Asn Gly Ala Cys Thr Ala Cys Tyr |
| (SEQ ID NO: 5042) | Cys Glu Tyr Cys Met Asn Gly Ala Cys Val Gly Cys Tyr |
| (SEQ ID NO: 5043) | Cys Glu Tyr Cys Met Asn Gly Ala Cys Val Ala Cys Tyr |
| (SEQ ID NO: 5044) | Cys Glu Tyr Cys Met Asn Gly Ala Cys Gly Gly Cys Tyr |
| (SEQ ID NO: 5045) | Cys Glu Tyr Cys Met Asn Gly Ala Cys Gly Ala Cys Tyr |
| (SEQ ID NO: 5046) | Cys Glu Tyr Cys Met Asn Gly Thr Cys Thr Gly Cys Tyr |
| (SEQ ID NO: 5047) | Cys Glu Tyr Cys Met Asn Gly Thr Cys Thr Ala Cys Tyr |
| (SEQ ID NO: 5048) | Cys Glu Tyr Cys Met Asn Gly Thr Cys Val Gly Cys Tyr |
| (SEQ ID NO: 5049) | Cys Glu Tyr Cys Met Asn Gly Thr Cys Val Ala Cys Tyr |
| (SEQ ID NO: 5050) | Cys Glu Tyr Cys Met Asn Gly Thr Cys Gly Gly Cys Tyr |
| (SEQ ID NO: 5051) | Cys Glu Tyr Cys Met Asn Gly Thr Cys Gly Ala Cys Tyr |
| (SEQ ID NO: 5052) | Cys Glu Tyr Cys Phe Asn Pro Ala Cys Thr Gly Cys Tyr |
| (SEQ ID NO: 5053) | Cys Glu Tyr Cys Phe Asn Pro Ala Cys Thr Ala Cys Tyr |
| (SEQ ID NO: 5054) | Cys Glu Tyr Cys Phe Asn Pro Ala Cys Val Gly Cys Tyr |
| (SEQ ID NO: 5055) | Cys Glu Tyr Cys Phe Asn Pro Ala Cys Val Ala Cys Tyr |
| (SEQ ID NO: 5056) | Cys Glu Tyr Cys Phe Asn Pro Ala Cys Gly Gly Cys Tyr |
| (SEQ ID NO: 5057) | Cys Glu Tyr Cys Phe Asn Pro Ala Cys Gly Ala Cys Tyr |
| (SEQ ID NO: 5058) | Cys Glu Tyr Cys Phe Asn Pro Thr Cys Thr Gly Cys Tyr |
| (SEQ ID NO: 5059) | Cys Glu Tyr Cys Phe Asn Pro Thr Cys Thr Ala Cys Tyr |
| (SEQ ID NO: 5060) | Cys Glu Tyr Cys Phe Asn Pro Thr Cys Val Gly Cys Tyr |
| (SEQ ID NO: 5061) | Cys Glu Tyr Cys Phe Asn Pro Thr Cys Val Ala Cys Tyr |
| (SEQ ID NO: 5062) | Cys Glu Tyr Cys Phe Asn Pro Thr Cys Gly Gly Cys Tyr |
| (SEQ ID NO: 5063) | Cys Glu Tyr Cys Phe Asn Pro Thr Cys Gly Ala Cys Tyr |
| (SEQ ID NO: 5064) | Cys Glu Tyr Cys Phe Asn Gly Ala Cys Thr Gly Cys Tyr |

FIG. 3G

| | |
|---|---|
| (SEQ ID NO: 5065) | Cys Glu Tyr Cys Phe Asn Gly Ala Cys Thr Ala Cys Tyr |
| (SEQ ID NO: 5066) | Cys Glu Tyr Cys Phe Asn Gly Ala Cys Val Gly Cys Tyr |
| (SEQ ID NO: 5067) | Cys Glu Tyr Cys Phe Asn Gly Ala Cys Val Ala Cys Tyr |
| (SEQ ID NO: 5068) | Cys Glu Tyr Cys Phe Asn Gly Ala Cys Gly Gly Cys Tyr |
| (SEQ ID NO: 5069) | Cys Glu Tyr Cys Phe Asn Gly Ala Cys Gly Ala Cys Tyr |
| (SEQ ID NO: 5070) | Cys Glu Tyr Cys Phe Asn Gly Thr Cys Thr Gly Cys Tyr |
| (SEQ ID NO: 5071) | Cys Glu Tyr Cys Phe Asn Gly Thr Cys Thr Ala Cys Tyr |
| (SEQ ID NO: 5072) | Cys Glu Tyr Cys Phe Asn Gly Thr Cys Val Gly Cys Tyr |
| (SEQ ID NO: 5073) | Cys Glu Tyr Cys Phe Asn Gly Thr Cys Val Ala Cys Tyr |
| (SEQ ID NO: 5074) | Cys Glu Tyr Cys Phe Asn Gly Thr Cys Gly Gly Cys Tyr |
| (SEQ ID NO: 5075) | Cys Glu Tyr Cys Phe Asn Gly Thr Cys Gly Ala Cys Tyr |
| (SEQ ID NO: 5076) | Cys Glu Tyr Cys Pro Asn Pro Ala Cys Thr Gly Cys Tyr |
| (SEQ ID NO: 5077) | Cys Glu Tyr Cys Pro Asn Pro Ala Cys Thr Ala Cys Tyr |
| (SEQ ID NO: 5078) | Cys Glu Tyr Cys Pro Asn Pro Ala Cys Val Gly Cys Tyr |
| (SEQ ID NO: 5079) | Cys Glu Tyr Cys Pro Asn Pro Ala Cys Val Ala Cys Tyr |
| (SEQ ID NO: 5080) | Cys Glu Tyr Cys Pro Asn Pro Ala Cys Gly Gly Cys Tyr |
| (SEQ ID NO: 5081) | Cys Glu Tyr Cys Pro Asn Pro Ala Cys Gly Ala Cys Tyr |
| (SEQ ID NO: 5082) | Cys Glu Tyr Cys Pro Asn Pro Thr Cys Thr Gly Cys Tyr |
| (SEQ ID NO: 5083) | Cys Glu Tyr Cys Pro Asn Pro Thr Cys Thr Ala Cys Tyr |
| (SEQ ID NO: 5084) | Cys Glu Tyr Cys Pro Asn Pro Thr Cys Val Gly Cys Tyr |
| (SEQ ID NO: 5085) | Cys Glu Tyr Cys Pro Asn Pro Thr Cys Val Ala Cys Tyr |
| (SEQ ID NO: 5086) | Cys Glu Tyr Cys Pro Asn Pro Thr Cys Gly Gly Cys Tyr |
| (SEQ ID NO: 5087) | Cys Glu Tyr Cys Pro Asn Pro Thr Cys Gly Ala Cys Tyr |
| (SEQ ID NO: 5088) | Cys Glu Tyr Cys Pro Asn Gly Ala Cys Thr Gly Cys Tyr |
| (SEQ ID NO: 5089) | Cys Glu Tyr Cys Pro Asn Gly Ala Cys Thr Ala Cys Tyr |
| (SEQ ID NO: 5090) | Cys Glu Tyr Cys Pro Asn Gly Ala Cys Val Gly Cys Tyr |
| (SEQ ID NO: 5091) | Cys Glu Tyr Cys Pro Asn Gly Ala Cys Val Ala Cys Tyr |
| (SEQ ID NO: 5092) | Cys Glu Tyr Cys Pro Asn Gly Ala Cys Gly Gly Cys Tyr |
| (SEQ ID NO: 5093) | Cys Glu Tyr Cys Pro Asn Gly Ala Cys Gly Ala Cys Tyr |
| (SEQ ID NO: 5094) | Cys Glu Tyr Cys Pro Asn Gly Thr Cys Thr Gly Cys Tyr |
| (SEQ ID NO: 5095) | Cys Glu Tyr Cys Pro Asn Gly Thr Cys Thr Ala Cys Tyr |
| (SEQ ID NO: 5096) | Cys Glu Tyr Cys Pro Asn Gly Thr Cys Val Gly Cys Tyr |
| (SEQ ID NO: 5097) | Cys Glu Tyr Cys Pro Asn Gly Thr Cys Val Ala Cys Tyr |
| (SEQ ID NO: 5098) | Cys Glu Tyr Cys Pro Asn Gly Thr Cys Gly Gly Cys Tyr |
| (SEQ ID NO: 5099) | Cys Glu Tyr Cys Pro Asn Gly Thr Cys Gly Ala Cys Tyr |
| (SEQ ID NO: 5100) | Cys Glu Tyr Cys Ser Asn Pro Ala Cys Thr Gly Cys Tyr |
| (SEQ ID NO: 5101) | Cys Glu Tyr Cys Ser Asn Pro Ala Cys Thr Ala Cys Tyr |
| (SEQ ID NO: 5102) | Cys Glu Tyr Cys Ser Asn Pro Ala Cys Val Gly Cys Tyr |
| (SEQ ID NO: 5103) | Cys Glu Tyr Cys Ser Asn Pro Ala Cys Val Ala Cys Tyr |
| (SEQ ID NO: 5104) | Cys Glu Tyr Cys Ser Asn Pro Ala Cys Gly Gly Cys Tyr |
| (SEQ ID NO: 5105) | Cys Glu Tyr Cys Ser Asn Pro Ala Cys Gly Ala Cys Tyr |
| (SEQ ID NO: 5106) | Cys Glu Tyr Cys Ser Asn Pro Thr Cys Thr Gly Cys Tyr |
| (SEQ ID NO: 5107) | Cys Glu Tyr Cys Ser Asn Pro Thr Cys Thr Ala Cys Tyr |

FIG. 3H (SEQ ID NO: 5108 )   Cys Glu Tyr Cys Ser Asn Pro Thr Cys Val Gly Cys Tyr
(SEQ ID NO: 5109 )   Cys Glu Tyr Cys Ser Asn Pro Thr Cys Val Ala Cys Tyr
(SEQ ID NO: 5110 )   Cys Glu Tyr Cys Ser Asn Pro Thr Cys Gly Gly Cys Tyr
(SEQ ID NO: 5111 )   Cys Glu Tyr Cys Ser Asn Pro Thr Cys Gly Ala Cys Tyr
(SEQ ID NO: 5112 )   Cys Glu Tyr Cys Ser Asn Gly Ala Cys Thr Gly Cys Tyr
(SEQ ID NO: 5113 )   Cys Glu Tyr Cys Ser Asn Gly Ala Cys Thr Ala Cys Tyr
(SEQ ID NO: 5114 )   Cys Glu Tyr Cys Ser Asn Gly Ala Cys Val Gly Cys Tyr
(SEQ ID NO: 5115 )   Cys Glu Tyr Cys Ser Asn Gly Ala Cys Val Ala Cys Tyr
(SEQ ID NO: 5116 )   Cys Glu Tyr Cys Ser Asn Gly Ala Cys Gly Gly Cys Tyr
(SEQ ID NO: 5117 )   Cys Glu Tyr Cys Ser Asn Gly Ala Cys Gly Ala Cys Tyr
(SEQ ID NO: 5118 )   Cys Glu Tyr Cys Ser Asn Gly Thr Cys Thr Gly Cys Tyr
(SEQ ID NO: 5119 )   Cys Glu Tyr Cys Ser Asn Gly Thr Cys Thr Ala Cys Tyr
(SEQ ID NO: 5120 )   Cys Glu Tyr Cys Ser Asn Gly Thr Cys Val Gly Cys Tyr
(SEQ ID NO: 5121 )   Cys Glu Tyr Cys Ser Asn Gly Thr Cys Val Ala Cys Tyr
(SEQ ID NO: 5122 )   Cys Glu Tyr Cys Ser Asn Gly Thr Cys Gly Gly Cys Tyr
(SEQ ID NO: 5123 )   Cys Glu Tyr Cys Ser Asn Gly Thr Cys Gly Ala Cys Tyr
(SEQ ID NO: 5124 )   Cys Glu Tyr Cys Thr Asn Pro Ala Cys Thr Gly Cys Tyr
(SEQ ID NO: 5125 )   Cys Glu Tyr Cys Thr Asn Pro Ala Cys Thr Ala Cys Tyr
(SEQ ID NO: 5126 )   Cys Glu Tyr Cys Thr Asn Pro Ala Cys Val Gly Cys Tyr
(SEQ ID NO: 5127 )   Cys Glu Tyr Cys Thr Asn Pro Ala Cys Val Ala Cys Tyr
(SEQ ID NO: 5128 )   Cys Glu Tyr Cys Thr Asn Pro Ala Cys Gly Gly Cys Tyr
(SEQ ID NO: 5129 )   Cys Glu Tyr Cys Thr Asn Pro Ala Cys Gly Ala Cys Tyr
(SEQ ID NO: 5130 )   Cys Glu Tyr Cys Thr Asn Pro Thr Cys Thr Gly Cys Tyr
(SEQ ID NO: 5131 )   Cys Glu Tyr Cys Thr Asn Pro Thr Cys Thr Ala Cys Tyr
(SEQ ID NO: 5132 )   Cys Glu Tyr Cys Thr Asn Pro Thr Cys Val Gly Cys Tyr
(SEQ ID NO: 5133 )   Cys Glu Tyr Cys Thr Asn Pro Thr Cys Val Ala Cys Tyr
(SEQ ID NO: 5134 )   Cys Glu Tyr Cys Thr Asn Pro Thr Cys Gly Gly Cys Tyr
(SEQ ID NO: 5135 )   Cys Glu Tyr Cys Thr Asn Pro Thr Cys Gly Ala Cys Tyr
(SEQ ID NO: 5136 )   Cys Glu Tyr Cys Thr Asn Gly Ala Cys Thr Gly Cys Tyr
(SEQ ID NO: 5137 )   Cys Glu Tyr Cys Thr Asn Gly Ala Cys Thr Ala Cys Tyr
(SEQ ID NO: 5138 )   Cys Glu Tyr Cys Thr Asn Gly Ala Cys Val Gly Cys Tyr
(SEQ ID NO: 5139 )   Cys Glu Tyr Cys Thr Asn Gly Ala Cys Val Ala Cys Tyr
(SEQ ID NO: 5140 )   Cys Glu Tyr Cys Thr Asn Gly Ala Cys Gly Gly Cys Tyr
(SEQ ID NO: 5141 )   Cys Glu Tyr Cys Thr Asn Gly Ala Cys Gly Ala Cys Tyr
(SEQ ID NO: 5142 )   Cys Glu Tyr Cys Thr Asn Gly Thr Cys Thr Gly Cys Tyr
(SEQ ID NO: 5143 )   Cys Glu Tyr Cys Thr Asn Gly Thr Cys Thr Ala Cys Tyr
(SEQ ID NO: 5144 )   Cys Glu Tyr Cys Thr Asn Gly Thr Cys Val Gly Cys Tyr
(SEQ ID NO: 5145 )   Cys Glu Tyr Cys Thr Asn Gly Thr Cys Val Ala Cys Tyr
(SEQ ID NO: 5146 )   Cys Glu Tyr Cys Thr Asn Gly Thr Cys Gly Gly Cys Tyr
(SEQ ID NO: 5147 )   Cys Glu Tyr Cys Thr Asn Gly Thr Cys Gly Ala Cys Tyr
(SEQ ID NO: 5148 )   Cys Glu Tyr Cys Trp Asn Pro Ala Cys Thr Gly Cys Tyr
(SEQ ID NO: 5149 )   Cys Glu Tyr Cys Trp Asn Pro Ala Cys Thr Ala Cys Tyr
(SEQ ID NO: 5150 )   Cys Glu Tyr Cys Trp Asn Pro Ala Cys Val Gly Cys Tyr

FIG. 3I

| SEQ ID NO | Sequence |
|---|---|
| (SEQ ID NO: 5151) | Cys Glu Tyr Cys Trp Asn Pro Ala Cys Val Ala Cys Tyr |
| (SEQ ID NO: 5152) | Cys Glu Tyr Cys Trp Asn Pro Ala Cys Gly Gly Cys Tyr |
| (SEQ ID NO: 5153) | Cys Glu Tyr Cys Trp Asn Pro Ala Cys Gly Ala Cys Tyr |
| (SEQ ID NO: 5154) | Cys Glu Tyr Cys Trp Asn Pro Thr Cys Thr Gly Cys Tyr |
| (SEQ ID NO: 5155) | Cys Glu Tyr Cys Trp Asn Pro Thr Cys Thr Ala Cys Tyr |
| (SEQ ID NO: 5156) | Cys Glu Tyr Cys Trp Asn Pro Thr Cys Val Gly Cys Tyr |
| (SEQ ID NO: 5157) | Cys Glu Tyr Cys Trp Asn Pro Thr Cys Val Ala Cys Tyr |
| (SEQ ID NO: 5158) | Cys Glu Tyr Cys Trp Asn Pro Thr Cys Gly Gly Cys Tyr |
| (SEQ ID NO: 5159) | Cys Glu Tyr Cys Trp Asn Pro Thr Cys Gly Ala Cys Tyr |
| (SEQ ID NO: 5160) | Cys Glu Tyr Cys Trp Asn Gly Ala Cys Thr Gly Cys Tyr |
| (SEQ ID NO: 5161) | Cys Glu Tyr Cys Trp Asn Gly Ala Cys Thr Ala Cys Tyr |
| (SEQ ID NO: 5162) | Cys Glu Tyr Cys Trp Asn Gly Ala Cys Val Gly Cys Tyr |
| (SEQ ID NO: 5163) | Cys Glu Tyr Cys Trp Asn Gly Ala Cys Val Ala Cys Tyr |
| (SEQ ID NO: 5164) | Cys Glu Tyr Cys Trp Asn Gly Ala Cys Gly Gly Cys Tyr |
| (SEQ ID NO: 5165) | Cys Glu Tyr Cys Trp Asn Gly Ala Cys Gly Ala Cys Tyr |
| (SEQ ID NO: 5166) | Cys Glu Tyr Cys Trp Asn Gly Thr Cys Thr Gly Cys Tyr |
| (SEQ ID NO: 5167) | Cys Glu Tyr Cys Trp Asn Gly Thr Cys Thr Ala Cys Tyr |
| (SEQ ID NO: 5168) | Cys Glu Tyr Cys Trp Asn Gly Thr Cys Val Gly Cys Tyr |
| (SEQ ID NO: 5169) | Cys Glu Tyr Cys Trp Asn Gly Thr Cys Val Ala Cys Tyr |
| (SEQ ID NO: 5170) | Cys Glu Tyr Cys Trp Asn Gly Thr Cys Gly Gly Cys Tyr |
| (SEQ ID NO: 5171) | Cys Glu Tyr Cys Trp Asn Gly Thr Cys Gly Ala Cys Tyr |
| (SEQ ID NO: 5172) | Cys Glu Tyr Cys Tyr Asn Pro Ala Cys Thr Gly Cys Tyr |
| (SEQ ID NO: 5173) | Cys Glu Tyr Cys Tyr Asn Pro Ala Cys Thr Ala Cys Tyr |
| (SEQ ID NO: 5174) | Cys Glu Tyr Cys Tyr Asn Pro Ala Cys Val Gly Cys Tyr |
| (SEQ ID NO: 5175) | Cys Glu Tyr Cys Tyr Asn Pro Ala Cys Val Ala Cys Tyr |
| (SEQ ID NO: 5176) | Cys Glu Tyr Cys Tyr Asn Pro Ala Cys Gly Gly Cys Tyr |
| (SEQ ID NO: 5177) | Cys Glu Tyr Cys Tyr Asn Pro Ala Cys Gly Ala Cys Tyr |
| (SEQ ID NO: 5178) | Cys Glu Tyr Cys Tyr Asn Pro Thr Cys Thr Gly Cys Tyr |
| (SEQ ID NO: 5179) | Cys Glu Tyr Cys Tyr Asn Pro Thr Cys Thr Ala Cys Tyr |
| (SEQ ID NO: 5180) | Cys Glu Tyr Cys Tyr Asn Pro Thr Cys Val Gly Cys Tyr |
| (SEQ ID NO: 5181) | Cys Glu Tyr Cys Tyr Asn Pro Thr Cys Val Ala Cys Tyr |
| (SEQ ID NO: 5182) | Cys Glu Tyr Cys Tyr Asn Pro Thr Cys Gly Gly Cys Tyr |
| (SEQ ID NO: 5183) | Cys Glu Tyr Cys Tyr Asn Pro Thr Cys Gly Ala Cys Tyr |
| (SEQ ID NO: 5184) | Cys Glu Tyr Cys Tyr Asn Gly Ala Cys Thr Gly Cys Tyr |
| (SEQ ID NO: 5185) | Cys Glu Tyr Cys Tyr Asn Gly Ala Cys Thr Ala Cys Tyr |
| (SEQ ID NO: 5186) | Cys Glu Tyr Cys Tyr Asn Gly Ala Cys Val Gly Cys Tyr |
| (SEQ ID NO: 5187) | Cys Glu Tyr Cys Tyr Asn Gly Ala Cys Val Ala Cys Tyr |
| (SEQ ID NO: 5188) | Cys Glu Tyr Cys Tyr Asn Gly Ala Cys Gly Gly Cys Tyr |
| (SEQ ID NO: 5189) | Cys Glu Tyr Cys Tyr Asn Gly Ala Cys Gly Ala Cys Tyr |
| (SEQ ID NO: 5190) | Cys Glu Tyr Cys Tyr Asn Gly Thr Cys Thr Gly Cys Tyr |
| (SEQ ID NO: 5191) | Cys Glu Tyr Cys Tyr Asn Gly Thr Cys Thr Ala Cys Tyr |
| (SEQ ID NO: 5192) | Cys Glu Tyr Cys Tyr Asn Gly Thr Cys Val Gly Cys Tyr |
| (SEQ ID NO: 5193) | Cys Glu Tyr Cys Tyr Asn Gly Thr Cys Val Ala Cys Tyr |

FIG. 3J

| | |
|---|---|
| (SEQ ID NO: 5194) | Cys Glu Tyr Cys Tyr Asn Gly Thr Cys Gly Gly Cys Tyr |
| (SEQ ID NO: 5195) | Cys Glu Tyr Cys Tyr Asn Gly Thr Cys Gly Ala Cys Tyr |
| (SEQ ID NO: 5196) | Cys Glu Tyr Cys Val Asn Pro Ala Cys Thr Gly Cys Tyr |
| (SEQ ID NO: 5197) | Cys Glu Tyr Cys Val Asn Pro Ala Cys Thr Ala Cys Tyr |
| (SEQ ID NO: 5198) | Cys Glu Tyr Cys Val Asn Pro Ala Cys Val Gly Cys Tyr |
| (SEQ ID NO: 5199) | Cys Glu Tyr Cys Val Asn Pro Ala Cys Val Ala Cys Tyr |
| (SEQ ID NO: 5200) | Cys Glu Tyr Cys Val Asn Pro Ala Cys Gly Gly Cys Tyr |
| (SEQ ID NO: 5201) | Cys Glu Tyr Cys Val Asn Pro Ala Cys Gly Ala Cys Tyr |
| (SEQ ID NO: 5202) | Cys Glu Tyr Cys Val Asn Pro Thr Cys Thr Gly Cys Tyr |
| (SEQ ID NO: 5203) | Cys Glu Tyr Cys Val Asn Pro Thr Cys Thr Ala Cys Tyr |
| (SEQ ID NO: 5204) | Cys Glu Tyr Cys Val Asn Pro Thr Cys Val Gly Cys Tyr |
| (SEQ ID NO: 5205) | Cys Glu Tyr Cys Val Asn Pro Thr Cys Val Ala Cys Tyr |
| (SEQ ID NO: 5206) | Cys Glu Tyr Cys Val Asn Pro Thr Cys Gly Gly Cys Tyr |
| (SEQ ID NO: 5207) | Cys Glu Tyr Cys Val Asn Pro Thr Cys Gly Ala Cys Tyr |
| (SEQ ID NO: 5208) | Cys Glu Tyr Cys Val Asn Gly Ala Cys Thr Gly Cys Tyr |
| (SEQ ID NO: 5209) | Cys Glu Tyr Cys Val Asn Gly Ala Cys Thr Ala Cys Tyr |
| (SEQ ID NO: 5210) | Cys Glu Tyr Cys Val Asn Gly Ala Cys Val Gly Cys Tyr |
| (SEQ ID NO: 5211) | Cys Glu Tyr Cys Val Asn Gly Ala Cys Val Ala Cys Tyr |
| (SEQ ID NO: 5212) | Cys Glu Tyr Cys Val Asn Gly Ala Cys Gly Gly Cys Tyr |
| (SEQ ID NO: 5213) | Cys Glu Tyr Cys Val Asn Gly Ala Cys Gly Ala Cys Tyr |
| (SEQ ID NO: 5214) | Cys Glu Tyr Cys Val Asn Gly Thr Cys Thr Gly Cys Tyr |
| (SEQ ID NO: 5215) | Cys Glu Tyr Cys Val Asn Gly Thr Cys Thr Ala Cys Tyr |
| (SEQ ID NO: 5216) | Cys Glu Tyr Cys Val Asn Gly Thr Cys Val Gly Cys Tyr |
| (SEQ ID NO: 5217) | Cys Glu Tyr Cys Val Asn Gly Thr Cys Val Ala Cys Tyr |
| (SEQ ID NO: 5218) | Cys Glu Tyr Cys Val Asn Gly Thr Cys Gly Gly Cys Tyr |
| (SEQ ID NO: 5219) | Cys Glu Tyr Cys Val Asn Gly Thr Cys Gly Ala Cys Tyr |
| (SEQ ID NO: 5220) | Cys Glu Tyr Cys --- Asn Pro Ala Cys Thr Gly Cys Tyr |
| (SEQ ID NO: 5221) | Cys Glu Tyr Cys --- Asn Pro Ala Cys Thr Ala Cys Tyr |
| (SEQ ID NO: 5222) | Cys Glu Tyr Cys --- Asn Pro Ala Cys Val Gly Cys Tyr |
| (SEQ ID NO: 5223) | Cys Glu Tyr Cys --- Asn Pro Ala Cys Val Ala Cys Tyr |
| (SEQ ID NO: 5224) | Cys Glu Tyr Cys --- Asn Pro Ala Cys Gly Gly Cys Tyr |
| (SEQ ID NO: 5225) | Cys Glu Tyr Cys --- Asn Pro Ala Cys Gly Ala Cys Tyr |
| (SEQ ID NO: 5226) | Cys Glu Tyr Cys --- Asn Pro Thr Cys Thr Gly Cys Tyr |
| (SEQ ID NO: 5227) | Cys Glu Tyr Cys --- Asn Pro Thr Cys Thr Ala Cys Tyr |
| (SEQ ID NO: 5228) | Cys Glu Tyr Cys --- Asn Pro Thr Cys Val Gly Cys Tyr |
| (SEQ ID NO: 5229) | Cys Glu Tyr Cys --- Asn Pro Thr Cys Val Ala Cys Tyr |
| (SEQ ID NO: 5230) | Cys Glu Tyr Cys --- Asn Pro Thr Cys Gly Gly Cys Tyr |
| (SEQ ID NO: 5231) | Cys Glu Tyr Cys --- Asn Pro Thr Cys Gly Ala Cys Tyr |
| (SEQ ID NO: 5232) | Cys Glu Tyr Cys --- Asn Gly Ala Cys Thr Gly Cys Tyr |
| (SEQ ID NO: 5233) | Cys Glu Tyr Cys --- Asn Gly Ala Cys Thr Ala Cys Tyr |
| (SEQ ID NO: 5234) | Cys Glu Tyr Cys --- Asn Gly Ala Cys Val Gly Cys Tyr |
| (SEQ ID NO: 5235) | Cys Glu Tyr Cys --- Asn Gly Ala Cys Val Ala Cys Tyr |
| (SEQ ID NO: 5236) | Cys Glu Tyr Cys --- Asn Gly Ala Cys Gly Gly Cys Tyr |

FIG. 3K

| | | | | | | | | | | |
|---|---|---|---|---|---|---|---|---|---|---|
| (SEQ ID NO: 5237) | Cys | Glu | Tyr | Cys | --- | Asn | Gly | Ala | Cys | Gly | Ala | Cys | Tyr |
| (SEQ ID NO: 5238) | Cys | Glu | Tyr | Cys | --- | Asn | Gly | Thr | Cys | Thr | Gly | Cys | Tyr |
| (SEQ ID NO: 5239) | Cys | Glu | Tyr | Cys | --- | Asn | Gly | Thr | Cys | Thr | Ala | Cys | Tyr |
| (SEQ ID NO: 5240) | Cys | Glu | Tyr | Cys | --- | Asn | Gly | Thr | Cys | Val | Gly | Cys | Tyr |
| (SEQ ID NO: 5241) | Cys | Glu | Tyr | Cys | --- | Asn | Gly | Thr | Cys | Val | Ala | Cys | Tyr |
| (SEQ ID NO: 5242) | Cys | Glu | Tyr | Cys | --- | Asn | Gly | Thr | Cys | Gly | Gly | Cys | Tyr |
| (SEQ ID NO: 5243) | Cys | Glu | Tyr | Cys | --- | Asn | Gly | Thr | Cys | Gly | Ala | Cys | Tyr |
| (SEQ ID NO: 5244) | Cys | Glu | Trp | Cys | Ala | Asn | Pro | Ala | Cys | Thr | Gly | Cys | Tyr |
| (SEQ ID NO: 5245) | Cys | Glu | Trp | Cys | Ala | Asn | Pro | Ala | Cys | Thr | Ala | Cys | Tyr |
| (SEQ ID NO: 5246) | Cys | Glu | Trp | Cys | Ala | Asn | Pro | Ala | Cys | Val | Gly | Cys | Tyr |
| (SEQ ID NO: 5247) | Cys | Glu | Trp | Cys | Ala | Asn | Pro | Ala | Cys | Val | Ala | Cys | Tyr |
| (SEQ ID NO: 5248) | Cys | Glu | Trp | Cys | Ala | Asn | Pro | Ala | Cys | Gly | Gly | Cys | Tyr |
| (SEQ ID NO: 5249) | Cys | Glu | Trp | Cys | Ala | Asn | Pro | Ala | Cys | Gly | Ala | Cys | Tyr |
| (SEQ ID NO: 5250) | Cys | Glu | Trp | Cys | Ala | Asn | Pro | Thr | Cys | Thr | Gly | Cys | Tyr |
| (SEQ ID NO: 5251) | Cys | Glu | Trp | Cys | Ala | Asn | Pro | Thr | Cys | Thr | Ala | Cys | Tyr |
| (SEQ ID NO: 5252) | Cys | Glu | Trp | Cys | Ala | Asn | Pro | Thr | Cys | Val | Gly | Cys | Tyr |
| (SEQ ID NO: 5253) | Cys | Glu | Trp | Cys | Ala | Asn | Pro | Thr | Cys | Val | Ala | Cys | Tyr |
| (SEQ ID NO: 5254) | Cys | Glu | Trp | Cys | Ala | Asn | Pro | Thr | Cys | Gly | Gly | Cys | Tyr |
| (SEQ ID NO: 5255) | Cys | Glu | Trp | Cys | Ala | Asn | Pro | Thr | Cys | Gly | Ala | Cys | Tyr |
| (SEQ ID NO: 5256) | Cys | Glu | Trp | Cys | Ala | Asn | Gly | Ala | Cys | Thr | Gly | Cys | Tyr |
| (SEQ ID NO: 5257) | Cys | Glu | Trp | Cys | Ala | Asn | Gly | Ala | Cys | Thr | Ala | Cys | Tyr |
| (SEQ ID NO: 5258) | Cys | Glu | Trp | Cys | Ala | Asn | Gly | Ala | Cys | Val | Gly | Cys | Tyr |
| (SEQ ID NO: 5259) | Cys | Glu | Trp | Cys | Ala | Asn | Gly | Ala | Cys | Val | Ala | Cys | Tyr |
| (SEQ ID NO: 5260) | Cys | Glu | Trp | Cys | Ala | Asn | Gly | Ala | Cys | Gly | Gly | Cys | Tyr |
| (SEQ ID NO: 5261) | Cys | Glu | Trp | Cys | Ala | Asn | Gly | Ala | Cys | Gly | Ala | Cys | Tyr |
| (SEQ ID NO: 5262) | Cys | Glu | Trp | Cys | Ala | Asn | Gly | Thr | Cys | Thr | Gly | Cys | Tyr |
| (SEQ ID NO: 5263) | Cys | Glu | Trp | Cys | Ala | Asn | Gly | Thr | Cys | Thr | Ala | Cys | Tyr |
| (SEQ ID NO: 5264) | Cys | Glu | Trp | Cys | Ala | Asn | Gly | Thr | Cys | Val | Gly | Cys | Tyr |
| (SEQ ID NO: 5265) | Cys | Glu | Trp | Cys | Ala | Asn | Gly | Thr | Cys | Val | Ala | Cys | Tyr |
| (SEQ ID NO: 5266) | Cys | Glu | Trp | Cys | Ala | Asn | Gly | Thr | Cys | Gly | Gly | Cys | Tyr |
| (SEQ ID NO: 5267) | Cys | Glu | Trp | Cys | Ala | Asn | Gly | Thr | Cys | Gly | Ala | Cys | Tyr |
| (SEQ ID NO: 5268) | Cys | Glu | Trp | Cys | Arg | Asn | Pro | Ala | Cys | Thr | Gly | Cys | Tyr |
| (SEQ ID NO: 5269) | Cys | Glu | Trp | Cys | Arg | Asn | Pro | Ala | Cys | Thr | Ala | Cys | Tyr |
| (SEQ ID NO: 5270) | Cys | Glu | Trp | Cys | Arg | Asn | Pro | Ala | Cys | Val | Gly | Cys | Tyr |
| (SEQ ID NO: 5271) | Cys | Glu | Trp | Cys | Arg | Asn | Pro | Ala | Cys | Val | Ala | Cys | Tyr |
| (SEQ ID NO: 5272) | Cys | Glu | Trp | Cys | Arg | Asn | Pro | Ala | Cys | Gly | Gly | Cys | Tyr |
| (SEQ ID NO: 5273) | Cys | Glu | Trp | Cys | Arg | Asn | Pro | Ala | Cys | Gly | Ala | Cys | Tyr |
| (SEQ ID NO: 5274) | Cys | Glu | Trp | Cys | Arg | Asn | Pro | Thr | Cys | Thr | Gly | Cys | Tyr |
| (SEQ ID NO: 5275) | Cys | Glu | Trp | Cys | Arg | Asn | Pro | Thr | Cys | Thr | Ala | Cys | Tyr |
| (SEQ ID NO: 5276) | Cys | Glu | Trp | Cys | Arg | Asn | Pro | Thr | Cys | Val | Gly | Cys | Tyr |
| (SEQ ID NO: 5277) | Cys | Glu | Trp | Cys | Arg | Asn | Pro | Thr | Cys | Val | Ala | Cys | Tyr |
| (SEQ ID NO: 5278) | Cys | Glu | Trp | Cys | Arg | Asn | Pro | Thr | Cys | Gly | Gly | Cys | Tyr |
| (SEQ ID NO: 5279) | Cys | Glu | Trp | Cys | Arg | Asn | Pro | Thr | Cys | Gly | Ala | Cys | Tyr |

FIG. 3L (SEQ ID NO: 5280)  Cys Glu Trp Cys Arg Asn Gly Ala Cys Thr Gly Cys Tyr
(SEQ ID NO: 5281)  Cys Glu Trp Cys Arg Asn Gly Ala Cys Thr Ala Cys Tyr
(SEQ ID NO: 5282)  Cys Glu Trp Cys Arg Asn Gly Ala Cys Val Gly Cys Tyr
(SEQ ID NO: 5283)  Cys Glu Trp Cys Arg Asn Gly Ala Cys Val Ala Cys Tyr
(SEQ ID NO: 5284)  Cys Glu Trp Cys Arg Asn Gly Ala Cys Gly Gly Cys Tyr
(SEQ ID NO: 5285)  Cys Glu Trp Cys Arg Asn Gly Ala Cys Gly Ala Cys Tyr
(SEQ ID NO: 5286)  Cys Glu Trp Cys Arg Asn Gly Thr Cys Thr Gly Cys Tyr
(SEQ ID NO: 5287)  Cys Glu Trp Cys Arg Asn Gly Thr Cys Thr Ala Cys Tyr
(SEQ ID NO: 5288)  Cys Glu Trp Cys Arg Asn Gly Thr Cys Val Gly Cys Tyr
(SEQ ID NO: 5289)  Cys Glu Trp Cys Arg Asn Gly Thr Cys Val Ala Cys Tyr
(SEQ ID NO: 5290)  Cys Glu Trp Cys Arg Asn Gly Thr Cys Gly Gly Cys Tyr
(SEQ ID NO: 5291)  Cys Glu Trp Cys Arg Asn Gly Thr Cys Gly Ala Cys Tyr
(SEQ ID NO: 5292)  Cys Glu Trp Cys Asn Asn Pro Ala Cys Thr Gly Cys Tyr
(SEQ ID NO: 5293)  Cys Glu Trp Cys Asn Asn Pro Ala Cys Thr Ala Cys Tyr
(SEQ ID NO: 5294)  Cys Glu Trp Cys Asn Asn Pro Ala Cys Val Gly Cys Tyr
(SEQ ID NO: 5295)  Cys Glu Trp Cys Asn Asn Pro Ala Cys Val Ala Cys Tyr
(SEQ ID NO: 5296)  Cys Glu Trp Cys Asn Asn Pro Ala Cys Gly Gly Cys Tyr
(SEQ ID NO: 5297)  Cys Glu Trp Cys Asn Asn Pro Ala Cys Gly Ala Cys Tyr
(SEQ ID NO: 5298)  Cys Glu Trp Cys Asn Asn Pro Thr Cys Thr Gly Cys Tyr
(SEQ ID NO: 5299)  Cys Glu Trp Cys Asn Asn Pro Thr Cys Thr Ala Cys Tyr
(SEQ ID NO: 5300)  Cys Glu Trp Cys Asn Asn Pro Thr Cys Val Gly Cys Tyr
(SEQ ID NO: 5301)  Cys Glu Trp Cys Asn Asn Pro Thr Cys Val Ala Cys Tyr
(SEQ ID NO: 5302)  Cys Glu Trp Cys Asn Asn Pro Thr Cys Gly Gly Cys Tyr
(SEQ ID NO: 5303)  Cys Glu Trp Cys Asn Asn Pro Thr Cys Gly Ala Cys Tyr
(SEQ ID NO: 5304)  Cys Glu Trp Cys Asn Asn Gly Ala Cys Thr Gly Cys Tyr
(SEQ ID NO: 5305)  Cys Glu Trp Cys Asn Asn Gly Ala Cys Thr Ala Cys Tyr
(SEQ ID NO: 5306)  Cys Glu Trp Cys Asn Asn Gly Ala Cys Val Gly Cys Tyr
(SEQ ID NO: 5307)  Cys Glu Trp Cys Asn Asn Gly Ala Cys Val Ala Cys Tyr
(SEQ ID NO: 5308)  Cys Glu Trp Cys Asn Asn Gly Ala Cys Gly Gly Cys Tyr
(SEQ ID NO: 5309)  Cys Glu Trp Cys Asn Asn Gly Ala Cys Gly Ala Cys Tyr
(SEQ ID NO: 5310)  Cys Glu Trp Cys Asn Asn Gly Thr Cys Thr Gly Cys Tyr
(SEQ ID NO: 5311)  Cys Glu Trp Cys Asn Asn Gly Thr Cys Thr Ala Cys Tyr
(SEQ ID NO: 5312)  Cys Glu Trp Cys Asn Asn Gly Thr Cys Val Gly Cys Tyr
(SEQ ID NO: 5313)  Cys Glu Trp Cys Asn Asn Gly Thr Cys Val Ala Cys Tyr
(SEQ ID NO: 5314)  Cys Glu Trp Cys Asn Asn Gly Thr Cys Gly Gly Cys Tyr
(SEQ ID NO: 5315)  Cys Glu Trp Cys Asn Asn Gly Thr Cys Gly Ala Cys Tyr
(SEQ ID NO: 5316)  Cys Glu Trp Cys Asp Asn Pro Ala Cys Thr Gly Cys Tyr
(SEQ ID NO: 5317)  Cys Glu Trp Cys Asp Asn Pro Ala Cys Thr Ala Cys Tyr
(SEQ ID NO: 5318)  Cys Glu Trp Cys Asp Asn Pro Ala Cys Val Gly Cys Tyr
(SEQ ID NO: 5319)  Cys Glu Trp Cys Asp Asn Pro Ala Cys Val Ala Cys Tyr
(SEQ ID NO: 5320)  Cys Glu Trp Cys Asp Asn Pro Ala Cys Gly Gly Cys Tyr
(SEQ ID NO: 5321)  Cys Glu Trp Cys Asp Asn Pro Ala Cys Gly Ala Cys Tyr
(SEQ ID NO: 5322)  Cys Glu Trp Cys Asp Asn Pro Thr Cys Thr Gly Cys Tyr

FIG. 3M

| SEQ ID NO | Sequence |
|---|---|
| (SEQ ID NO: 5323) | Cys Glu Trp Cys Asp Asn Pro Thr Cys Thr Ala Cys Tyr |
| (SEQ ID NO: 5324) | Cys Glu Trp Cys Asp Asn Pro Thr Cys Val Gly Cys Tyr |
| (SEQ ID NO: 5325) | Cys Glu Trp Cys Asp Asn Pro Thr Cys Val Ala Cys Tyr |
| (SEQ ID NO: 5326) | Cys Glu Trp Cys Asp Asn Pro Thr Cys Gly Gly Cys Tyr |
| (SEQ ID NO: 5327) | Cys Glu Trp Cys Asp Asn Pro Thr Cys Gly Ala Cys Tyr |
| (SEQ ID NO: 5328) | Cys Glu Trp Cys Asp Asn Gly Ala Cys Thr Gly Cys Tyr |
| (SEQ ID NO: 5329) | Cys Glu Trp Cys Asp Asn Gly Ala Cys Thr Ala Cys Tyr |
| (SEQ ID NO: 5330) | Cys Glu Trp Cys Asp Asn Gly Ala Cys Val Gly Cys Tyr |
| (SEQ ID NO: 5331) | Cys Glu Trp Cys Asp Asn Gly Ala Cys Val Ala Cys Tyr |
| (SEQ ID NO: 5332) | Cys Glu Trp Cys Asp Asn Gly Ala Cys Gly Gly Cys Tyr |
| (SEQ ID NO: 5333) | Cys Glu Trp Cys Asp Asn Gly Ala Cys Gly Ala Cys Tyr |
| (SEQ ID NO: 5334) | Cys Glu Trp Cys Asp Asn Gly Thr Cys Thr Gly Cys Tyr |
| (SEQ ID NO: 5335) | Cys Glu Trp Cys Asp Asn Gly Thr Cys Thr Ala Cys Tyr |
| (SEQ ID NO: 5336) | Cys Glu Trp Cys Asp Asn Gly Thr Cys Val Gly Cys Tyr |
| (SEQ ID NO: 5337) | Cys Glu Trp Cys Asp Asn Gly Thr Cys Val Ala Cys Tyr |
| (SEQ ID NO: 5338) | Cys Glu Trp Cys Asp Asn Gly Thr Cys Gly Gly Cys Tyr |
| (SEQ ID NO: 5339) | Cys Glu Trp Cys Asp Asn Gly Thr Cys Gly Ala Cys Tyr |
| (SEQ ID NO: 5340) | Cys Glu Trp Cys Gln Asn Pro Ala Cys Thr Gly Cys Tyr |
| (SEQ ID NO: 5341) | Cys Glu Trp Cys Gln Asn Pro Ala Cys Thr Ala Cys Tyr |
| (SEQ ID NO: 5342) | Cys Glu Trp Cys Gln Asn Pro Ala Cys Val Gly Cys Tyr |
| (SEQ ID NO: 5343) | Cys Glu Trp Cys Gln Asn Pro Ala Cys Val Ala Cys Tyr |
| (SEQ ID NO: 5344) | Cys Glu Trp Cys Gln Asn Pro Ala Cys Gly Gly Cys Tyr |
| (SEQ ID NO: 5345) | Cys Glu Trp Cys Gln Asn Pro Ala Cys Gly Ala Cys Tyr |
| (SEQ ID NO: 5346) | Cys Glu Trp Cys Gln Asn Pro Thr Cys Thr Gly Cys Tyr |
| (SEQ ID NO: 5347) | Cys Glu Trp Cys Gln Asn Pro Thr Cys Thr Ala Cys Tyr |
| (SEQ ID NO: 5348) | Cys Glu Trp Cys Gln Asn Pro Thr Cys Val Gly Cys Tyr |
| (SEQ ID NO: 5349) | Cys Glu Trp Cys Gln Asn Pro Thr Cys Val Ala Cys Tyr |
| (SEQ ID NO: 5350) | Cys Glu Trp Cys Gln Asn Pro Thr Cys Gly Gly Cys Tyr |
| (SEQ ID NO: 5351) | Cys Glu Trp Cys Gln Asn Pro Thr Cys Gly Ala Cys Tyr |
| (SEQ ID NO: 5352) | Cys Glu Trp Cys Gln Asn Gly Ala Cys Thr Gly Cys Tyr |
| (SEQ ID NO: 5353) | Cys Glu Trp Cys Gln Asn Gly Ala Cys Thr Ala Cys Tyr |
| (SEQ ID NO: 5354) | Cys Glu Trp Cys Gln Asn Gly Ala Cys Val Gly Cys Tyr |
| (SEQ ID NO: 5355) | Cys Glu Trp Cys Gln Asn Gly Ala Cys Val Ala Cys Tyr |
| (SEQ ID NO: 5356) | Cys Glu Trp Cys Gln Asn Gly Ala Cys Gly Gly Cys Tyr |
| (SEQ ID NO: 5357) | Cys Glu Trp Cys Gln Asn Gly Ala Cys Gly Ala Cys Tyr |
| (SEQ ID NO: 5358) | Cys Glu Trp Cys Gln Asn Gly Thr Cys Thr Gly Cys Tyr |
| (SEQ ID NO: 5359) | Cys Glu Trp Cys Gln Asn Gly Thr Cys Thr Ala Cys Tyr |
| (SEQ ID NO: 5360) | Cys Glu Trp Cys Gln Asn Gly Thr Cys Val Gly Cys Tyr |
| (SEQ ID NO: 5361) | Cys Glu Trp Cys Gln Asn Gly Thr Cys Val Ala Cys Tyr |
| (SEQ ID NO: 5362) | Cys Glu Trp Cys Gln Asn Gly Thr Cys Gly Gly Cys Tyr |
| (SEQ ID NO: 5363) | Cys Glu Trp Cys Gln Asn Gly Thr Cys Gly Ala Cys Tyr |
| (SEQ ID NO: 5364) | Cys Glu Trp Cys Glu Asn Pro Ala Cys Thr Gly Cys Tyr |
| (SEQ ID NO: 5365) | Cys Glu Trp Cys Glu Asn Pro Ala Cys Thr Ala Cys Tyr |

FIG. 3N

| | |
|---|---|
| (SEQ ID NO: 5366) | Cys Glu Trp Cys Glu Asn Pro Ala Cys Val Gly Cys Tyr |
| (SEQ ID NO: 5367) | Cys Glu Trp Cys Glu Asn Pro Ala Cys Val Ala Cys Tyr |
| (SEQ ID NO: 5368) | Cys Glu Trp Cys Glu Asn Pro Ala Cys Gly Gly Cys Tyr |
| (SEQ ID NO: 5369) | Cys Glu Trp Cys Glu Asn Pro Ala Cys Gly Ala Cys Tyr |
| (SEQ ID NO: 5370) | Cys Glu Trp Cys Glu Asn Pro Thr Cys Thr Gly Cys Tyr |
| (SEQ ID NO: 5371) | Cys Glu Trp Cys Glu Asn Pro Thr Cys Thr Ala Cys Tyr |
| (SEQ ID NO: 5372) | Cys Glu Trp Cys Glu Asn Pro Thr Cys Val Gly Cys Tyr |
| (SEQ ID NO: 5373) | Cys Glu Trp Cys Glu Asn Pro Thr Cys Val Ala Cys Tyr |
| (SEQ ID NO: 5374) | Cys Glu Trp Cys Glu Asn Pro Thr Cys Gly Gly Cys Tyr |
| (SEQ ID NO: 5375) | Cys Glu Trp Cys Glu Asn Pro Thr Cys Gly Ala Cys Tyr |
| (SEQ ID NO: 5376) | Cys Glu Trp Cys Glu Asn Gly Ala Cys Thr Gly Cys Tyr |
| (SEQ ID NO: 5377) | Cys Glu Trp Cys Glu Asn Gly Ala Cys Thr Ala Cys Tyr |
| (SEQ ID NO: 5378) | Cys Glu Trp Cys Glu Asn Gly Ala Cys Val Gly Cys Tyr |
| (SEQ ID NO: 5379) | Cys Glu Trp Cys Glu Asn Gly Ala Cys Val Ala Cys Tyr |
| (SEQ ID NO: 5380) | Cys Glu Trp Cys Glu Asn Gly Ala Cys Gly Gly Cys Tyr |
| (SEQ ID NO: 5381) | Cys Glu Trp Cys Glu Asn Gly Ala Cys Gly Ala Cys Tyr |
| (SEQ ID NO: 5382) | Cys Glu Trp Cys Glu Asn Gly Thr Cys Thr Gly Cys Tyr |
| (SEQ ID NO: 5383) | Cys Glu Trp Cys Glu Asn Gly Thr Cys Thr Ala Cys Tyr |
| (SEQ ID NO: 5384) | Cys Glu Trp Cys Glu Asn Gly Thr Cys Val Gly Cys Tyr |
| (SEQ ID NO: 5385) | Cys Glu Trp Cys Glu Asn Gly Thr Cys Val Ala Cys Tyr |
| (SEQ ID NO: 5386) | Cys Glu Trp Cys Glu Asn Gly Thr Cys Gly Gly Cys Tyr |
| (SEQ ID NO: 5387) | Cys Glu Trp Cys Glu Asn Gly Thr Cys Gly Ala Cys Tyr |
| (SEQ ID NO: 5388) | Cys Glu Trp Cys Gly Asn Pro Ala Cys Thr Gly Cys Tyr |
| (SEQ ID NO: 5389) | Cys Glu Trp Cys Gly Asn Pro Ala Cys Thr Ala Cys Tyr |
| (SEQ ID NO: 5390) | Cys Glu Trp Cys Gly Asn Pro Ala Cys Val Gly Cys Tyr |
| (SEQ ID NO: 5391) | Cys Glu Trp Cys Gly Asn Pro Ala Cys Val Ala Cys Tyr |
| (SEQ ID NO: 5392) | Cys Glu Trp Cys Gly Asn Pro Ala Cys Gly Gly Cys Tyr |
| (SEQ ID NO: 5393) | Cys Glu Trp Cys Gly Asn Pro Ala Cys Gly Ala Cys Tyr |
| (SEQ ID NO: 5394) | Cys Glu Trp Cys Gly Asn Pro Thr Cys Thr Gly Cys Tyr |
| (SEQ ID NO: 5395) | Cys Glu Trp Cys Gly Asn Pro Thr Cys Thr Ala Cys Tyr |
| (SEQ ID NO: 5396) | Cys Glu Trp Cys Gly Asn Pro Thr Cys Val Gly Cys Tyr |
| (SEQ ID NO: 5397) | Cys Glu Trp Cys Gly Asn Pro Thr Cys Val Ala Cys Tyr |
| (SEQ ID NO: 5398) | Cys Glu Trp Cys Gly Asn Pro Thr Cys Gly Gly Cys Tyr |
| (SEQ ID NO: 5399) | Cys Glu Trp Cys Gly Asn Pro Thr Cys Gly Ala Cys Tyr |
| (SEQ ID NO: 5400) | Cys Glu Trp Cys Gly Asn Gly Ala Cys Thr Gly Cys Tyr |
| (SEQ ID NO: 5401) | Cys Glu Trp Cys Gly Asn Gly Ala Cys Thr Ala Cys Tyr |
| (SEQ ID NO: 5402) | Cys Glu Trp Cys Gly Asn Gly Ala Cys Val Gly Cys Tyr |
| (SEQ ID NO: 5403) | Cys Glu Trp Cys Gly Asn Gly Ala Cys Val Ala Cys Tyr |
| (SEQ ID NO: 5404) | Cys Glu Trp Cys Gly Asn Gly Ala Cys Gly Gly Cys Tyr |
| (SEQ ID NO: 5405) | Cys Glu Trp Cys Gly Asn Gly Ala Cys Gly Ala Cys Tyr |
| (SEQ ID NO: 5406) | Cys Glu Trp Cys Gly Asn Gly Thr Cys Thr Gly Cys Tyr |
| (SEQ ID NO: 5407) | Cys Glu Trp Cys Gly Asn Gly Thr Cys Thr Ala Cys Tyr |
| (SEQ ID NO: 5408) | Cys Glu Trp Cys Gly Asn Gly Thr Cys Val Gly Cys Tyr |

FIG. 3O

| | |
|---|---|
| (SEQ ID NO: 5409) | Cys Glu Trp Cys Gly Asn Gly Thr Cys Val Ala Cys Tyr |
| (SEQ ID NO: 5410) | Cys Glu Trp Cys Gly Asn Gly Thr Cys Gly Gly Cys Tyr |
| (SEQ ID NO: 5411) | Cys Glu Trp Cys Gly Asn Gly Thr Cys Gly Ala Cys Tyr |
| (SEQ ID NO: 5412) | Cys Glu Trp Cys His Asn Pro Ala Cys Thr Gly Cys Tyr |
| (SEQ ID NO: 5413) | Cys Glu Trp Cys His Asn Pro Ala Cys Thr Ala Cys Tyr |
| (SEQ ID NO: 5414) | Cys Glu Trp Cys His Asn Pro Ala Cys Val Gly Cys Tyr |
| (SEQ ID NO: 5415) | Cys Glu Trp Cys His Asn Pro Ala Cys Val Ala Cys Tyr |
| (SEQ ID NO: 5416) | Cys Glu Trp Cys His Asn Pro Ala Cys Gly Gly Cys Tyr |
| (SEQ ID NO: 5417) | Cys Glu Trp Cys His Asn Pro Ala Cys Gly Ala Cys Tyr |
| (SEQ ID NO: 5418) | Cys Glu Trp Cys His Asn Pro Thr Cys Thr Gly Cys Tyr |
| (SEQ ID NO: 5419) | Cys Glu Trp Cys His Asn Pro Thr Cys Thr Ala Cys Tyr |
| (SEQ ID NO: 5420) | Cys Glu Trp Cys His Asn Pro Thr Cys Val Gly Cys Tyr |
| (SEQ ID NO: 5421) | Cys Glu Trp Cys His Asn Pro Thr Cys Val Ala Cys Tyr |
| (SEQ ID NO: 5422) | Cys Glu Trp Cys His Asn Pro Thr Cys Gly Gly Cys Tyr |
| (SEQ ID NO: 5423) | Cys Glu Trp Cys His Asn Pro Thr Cys Gly Ala Cys Tyr |
| (SEQ ID NO: 5424) | Cys Glu Trp Cys His Asn Gly Ala Cys Thr Gly Cys Tyr |
| (SEQ ID NO: 5425) | Cys Glu Trp Cys His Asn Gly Ala Cys Thr Ala Cys Tyr |
| (SEQ ID NO: 5426) | Cys Glu Trp Cys His Asn Gly Ala Cys Val Gly Cys Tyr |
| (SEQ ID NO: 5427) | Cys Glu Trp Cys His Asn Gly Ala Cys Val Ala Cys Tyr |
| (SEQ ID NO: 5428) | Cys Glu Trp Cys His Asn Gly Ala Cys Gly Gly Cys Tyr |
| (SEQ ID NO: 5429) | Cys Glu Trp Cys His Asn Gly Ala Cys Gly Ala Cys Tyr |
| (SEQ ID NO: 5430) | Cys Glu Trp Cys His Asn Gly Thr Cys Thr Gly Cys Tyr |
| (SEQ ID NO: 5431) | Cys Glu Trp Cys His Asn Gly Thr Cys Thr Ala Cys Tyr |
| (SEQ ID NO: 5432) | Cys Glu Trp Cys His Asn Gly Thr Cys Val Gly Cys Tyr |
| (SEQ ID NO: 5433) | Cys Glu Trp Cys His Asn Gly Thr Cys Val Ala Cys Tyr |
| (SEQ ID NO: 5434) | Cys Glu Trp Cys His Asn Gly Thr Cys Gly Gly Cys Tyr |
| (SEQ ID NO: 5435) | Cys Glu Trp Cys His Asn Gly Thr Cys Gly Ala Cys Tyr |
| (SEQ ID NO: 5436) | Cys Glu Trp Cys Ile Asn Pro Ala Cys Thr Gly Cys Tyr |
| (SEQ ID NO: 5437) | Cys Glu Trp Cys Ile Asn Pro Ala Cys Thr Ala Cys Tyr |
| (SEQ ID NO: 5438) | Cys Glu Trp Cys Ile Asn Pro Ala Cys Val Gly Cys Tyr |
| (SEQ ID NO: 5439) | Cys Glu Trp Cys Ile Asn Pro Ala Cys Val Ala Cys Tyr |
| (SEQ ID NO: 5440) | Cys Glu Trp Cys Ile Asn Pro Ala Cys Gly Gly Cys Tyr |
| (SEQ ID NO: 5441) | Cys Glu Trp Cys Ile Asn Pro Ala Cys Gly Ala Cys Tyr |
| (SEQ ID NO: 5442) | Cys Glu Trp Cys Ile Asn Pro Thr Cys Thr Gly Cys Tyr |
| (SEQ ID NO: 5443) | Cys Glu Trp Cys Ile Asn Pro Thr Cys Thr Ala Cys Tyr |
| (SEQ ID NO: 5444) | Cys Glu Trp Cys Ile Asn Pro Thr Cys Val Gly Cys Tyr |
| (SEQ ID NO: 5445) | Cys Glu Trp Cys Ile Asn Pro Thr Cys Val Ala Cys Tyr |
| (SEQ ID NO: 5446) | Cys Glu Trp Cys Ile Asn Pro Thr Cys Gly Gly Cys Tyr |
| (SEQ ID NO: 5447) | Cys Glu Trp Cys Ile Asn Pro Thr Cys Gly Ala Cys Tyr |
| (SEQ ID NO: 5448) | Cys Glu Trp Cys Ile Asn Gly Ala Cys Thr Gly Cys Tyr |
| (SEQ ID NO: 5449) | Cys Glu Trp Cys Ile Asn Gly Ala Cys Thr Ala Cys Tyr |
| (SEQ ID NO: 5450) | Cys Glu Trp Cys Ile Asn Gly Ala Cys Val Gly Cys Tyr |
| (SEQ ID NO: 5451) | Cys Glu Trp Cys Ile Asn Gly Ala Cys Val Ala Cys Tyr |

FIG. 3P (SEQ ID NO: 5452)  Cys Glu Trp Cys Ile Asn Gly Ala Cys Gly Gly Cys Tyr
(SEQ ID NO: 5453)  Cys Glu Trp Cys Ile Asn Gly Ala Cys Gly Ala Cys Tyr
(SEQ ID NO: 5454)  Cys Glu Trp Cys Ile Asn Gly Thr Cys Thr Gly Cys Tyr
(SEQ ID NO: 5455)  Cys Glu Trp Cys Ile Asn Gly Thr Cys Thr Ala Cys Tyr
(SEQ ID NO: 5456)  Cys Glu Trp Cys Ile Asn Gly Thr Cys Val Gly Cys Tyr
(SEQ ID NO: 5457)  Cys Glu Trp Cys Ile Asn Gly Thr Cys Val Ala Cys Tyr
(SEQ ID NO: 5458)  Cys Glu Trp Cys Ile Asn Gly Thr Cys Gly Gly Cys Tyr
(SEQ ID NO: 5459)  Cys Glu Trp Cys Ile Asn Gly Thr Cys Gly Ala Cys Tyr
(SEQ ID NO: 5460)  Cys Glu Trp Cys Leu Asn Pro Ala Cys Thr Gly Cys Tyr
(SEQ ID NO: 5461)  Cys Glu Trp Cys Leu Asn Pro Ala Cys Thr Ala Cys Tyr
(SEQ ID NO: 5462)  Cys Glu Trp Cys Leu Asn Pro Ala Cys Val Gly Cys Tyr
(SEQ ID NO: 5463)  Cys Glu Trp Cys Leu Asn Pro Ala Cys Val Ala Cys Tyr
(SEQ ID NO: 5464)  Cys Glu Trp Cys Leu Asn Pro Ala Cys Gly Gly Cys Tyr
(SEQ ID NO: 5465)  Cys Glu Trp Cys Leu Asn Pro Ala Cys Gly Ala Cys Tyr
(SEQ ID NO: 5466)  Cys Glu Trp Cys Leu Asn Pro Thr Cys Thr Gly Cys Tyr
(SEQ ID NO: 5467)  Cys Glu Trp Cys Leu Asn Pro Thr Cys Thr Ala Cys Tyr
(SEQ ID NO: 5468)  Cys Glu Trp Cys Leu Asn Pro Thr Cys Val Gly Cys Tyr
(SEQ ID NO: 5469)  Cys Glu Trp Cys Leu Asn Pro Thr Cys Val Ala Cys Tyr
(SEQ ID NO: 5470)  Cys Glu Trp Cys Leu Asn Pro Thr Cys Gly Gly Cys Tyr
(SEQ ID NO: 5471)  Cys Glu Trp Cys Leu Asn Pro Thr Cys Gly Ala Cys Tyr
(SEQ ID NO: 5472)  Cys Glu Trp Cys Leu Asn Gly Ala Cys Thr Gly Cys Tyr
(SEQ ID NO: 5473)  Cys Glu Trp Cys Leu Asn Gly Ala Cys Thr Ala Cys Tyr
(SEQ ID NO: 5474)  Cys Glu Trp Cys Leu Asn Gly Ala Cys Val Gly Cys Tyr
(SEQ ID NO: 5475)  Cys Glu Trp Cys Leu Asn Gly Ala Cys Val Ala Cys Tyr
(SEQ ID NO: 5476)  Cys Glu Trp Cys Leu Asn Gly Ala Cys Gly Gly Cys Tyr
(SEQ ID NO: 5477)  Cys Glu Trp Cys Leu Asn Gly Ala Cys Gly Ala Cys Tyr
(SEQ ID NO: 5478)  Cys Glu Trp Cys Leu Asn Gly Thr Cys Thr Gly Cys Tyr
(SEQ ID NO: 5479)  Cys Glu Trp Cys Leu Asn Gly Thr Cys Thr Ala Cys Tyr
(SEQ ID NO: 5480)  Cys Glu Trp Cys Leu Asn Gly Thr Cys Val Gly Cys Tyr
(SEQ ID NO: 5481)  Cys Glu Trp Cys Leu Asn Gly Thr Cys Val Ala Cys Tyr
(SEQ ID NO: 5482)  Cys Glu Trp Cys Leu Asn Gly Thr Cys Gly Gly Cys Tyr
(SEQ ID NO: 5483)  Cys Glu Trp Cys Leu Asn Gly Thr Cys Gly Ala Cys Tyr
(SEQ ID NO: 5484)  Cys Glu Trp Cys Lys Asn Pro Ala Cys Thr Gly Cys Tyr
(SEQ ID NO: 5485)  Cys Glu Trp Cys Lys Asn Pro Ala Cys Thr Ala Cys Tyr
(SEQ ID NO: 5486)  Cys Glu Trp Cys Lys Asn Pro Ala Cys Val Gly Cys Tyr
(SEQ ID NO: 5487)  Cys Glu Trp Cys Lys Asn Pro Ala Cys Val Ala Cys Tyr
(SEQ ID NO: 5488)  Cys Glu Trp Cys Lys Asn Pro Ala Cys Gly Gly Cys Tyr
(SEQ ID NO: 5489)  Cys Glu Trp Cys Lys Asn Pro Ala Cys Gly Ala Cys Tyr
(SEQ ID NO: 5490)  Cys Glu Trp Cys Lys Asn Pro Thr Cys Thr Gly Cys Tyr
(SEQ ID NO: 5491)  Cys Glu Trp Cys Lys Asn Pro Thr Cys Thr Ala Cys Tyr
(SEQ ID NO: 5492)  Cys Glu Trp Cys Lys Asn Pro Thr Cys Val Gly Cys Tyr
(SEQ ID NO: 5493)  Cys Glu Trp Cys Lys Asn Pro Thr Cys Val Ala Cys Tyr
(SEQ ID NO: 5494)  Cys Glu Trp Cys Lys Asn Pro Thr Cys Gly Gly Cys Tyr

FIG. 3Q

| | |
|---|---|
| (SEQ ID NO: 5495) | Cys Glu Trp Cys Lys Asn Pro Thr Cys Gly Ala Cys Tyr |
| (SEQ ID NO: 5496) | Cys Glu Trp Cys Lys Asn Gly Ala Cys Thr Gly Cys Tyr |
| (SEQ ID NO: 5497) | Cys Glu Trp Cys Lys Asn Gly Ala Cys Thr Ala Cys Tyr |
| (SEQ ID NO: 5498) | Cys Glu Trp Cys Lys Asn Gly Ala Cys Val Gly Cys Tyr |
| (SEQ ID NO: 5499) | Cys Glu Trp Cys Lys Asn Gly Ala Cys Val Ala Cys Tyr |
| (SEQ ID NO: 5500) | Cys Glu Trp Cys Lys Asn Gly Ala Cys Gly Gly Cys Tyr |
| (SEQ ID NO: 5501) | Cys Glu Trp Cys Lys Asn Gly Ala Cys Gly Ala Cys Tyr |
| (SEQ ID NO: 5502) | Cys Glu Trp Cys Lys Asn Gly Thr Cys Thr Gly Cys Tyr |
| (SEQ ID NO: 5503) | Cys Glu Trp Cys Lys Asn Gly Thr Cys Thr Ala Cys Tyr |
| (SEQ ID NO: 5504) | Cys Glu Trp Cys Lys Asn Gly Thr Cys Val Gly Cys Tyr |
| (SEQ ID NO: 5505) | Cys Glu Trp Cys Lys Asn Gly Thr Cys Val Ala Cys Tyr |
| (SEQ ID NO: 5506) | Cys Glu Trp Cys Lys Asn Gly Thr Cys Gly Gly Cys Tyr |
| (SEQ ID NO: 5507) | Cys Glu Trp Cys Lys Asn Gly Thr Cys Gly Ala Cys Tyr |
| (SEQ ID NO: 5508) | Cys Glu Trp Cys Met Asn Pro Ala Cys Thr Gly Cys Tyr |
| (SEQ ID NO: 5509) | Cys Glu Trp Cys Met Asn Pro Ala Cys Thr Ala Cys Tyr |
| (SEQ ID NO: 5510) | Cys Glu Trp Cys Met Asn Pro Ala Cys Val Gly Cys Tyr |
| (SEQ ID NO: 5511) | Cys Glu Trp Cys Met Asn Pro Ala Cys Val Ala Cys Tyr |
| (SEQ ID NO: 5512) | Cys Glu Trp Cys Met Asn Pro Ala Cys Gly Gly Cys Tyr |
| (SEQ ID NO: 5513) | Cys Glu Trp Cys Met Asn Pro Ala Cys Gly Ala Cys Tyr |
| (SEQ ID NO: 5514) | Cys Glu Trp Cys Met Asn Pro Thr Cys Thr Gly Cys Tyr |
| (SEQ ID NO: 5515) | Cys Glu Trp Cys Met Asn Pro Thr Cys Thr Ala Cys Tyr |
| (SEQ ID NO: 5516) | Cys Glu Trp Cys Met Asn Pro Thr Cys Val Gly Cys Tyr |
| (SEQ ID NO: 5517) | Cys Glu Trp Cys Met Asn Pro Thr Cys Val Ala Cys Tyr |
| (SEQ ID NO: 5518) | Cys Glu Trp Cys Met Asn Pro Thr Cys Gly Gly Cys Tyr |
| (SEQ ID NO: 5519) | Cys Glu Trp Cys Met Asn Pro Thr Cys Gly Ala Cys Tyr |
| (SEQ ID NO: 5520) | Cys Glu Trp Cys Met Asn Gly Ala Cys Thr Gly Cys Tyr |
| (SEQ ID NO: 5521) | Cys Glu Trp Cys Met Asn Gly Ala Cys Thr Ala Cys Tyr |
| (SEQ ID NO: 5522) | Cys Glu Trp Cys Met Asn Gly Ala Cys Val Gly Cys Tyr |
| (SEQ ID NO: 5523) | Cys Glu Trp Cys Met Asn Gly Ala Cys Val Ala Cys Tyr |
| (SEQ ID NO: 5524) | Cys Glu Trp Cys Met Asn Gly Ala Cys Gly Gly Cys Tyr |
| (SEQ ID NO: 5525) | Cys Glu Trp Cys Met Asn Gly Ala Cys Gly Ala Cys Tyr |
| (SEQ ID NO: 5526) | Cys Glu Trp Cys Met Asn Gly Thr Cys Thr Gly Cys Tyr |
| (SEQ ID NO: 5527) | Cys Glu Trp Cys Met Asn Gly Thr Cys Thr Ala Cys Tyr |
| (SEQ ID NO: 5528) | Cys Glu Trp Cys Met Asn Gly Thr Cys Val Gly Cys Tyr |
| (SEQ ID NO: 5529) | Cys Glu Trp Cys Met Asn Gly Thr Cys Val Ala Cys Tyr |
| (SEQ ID NO: 5530) | Cys Glu Trp Cys Met Asn Gly Thr Cys Gly Gly Cys Tyr |
| (SEQ ID NO: 5531) | Cys Glu Trp Cys Met Asn Gly Thr Cys Gly Ala Cys Tyr |
| (SEQ ID NO: 5532) | Cys Glu Trp Cys Phe Asn Pro Ala Cys Thr Gly Cys Tyr |
| (SEQ ID NO: 5533) | Cys Glu Trp Cys Phe Asn Pro Ala Cys Thr Ala Cys Tyr |
| (SEQ ID NO: 5534) | Cys Glu Trp Cys Phe Asn Pro Ala Cys Val Gly Cys Tyr |
| (SEQ ID NO: 5535) | Cys Glu Trp Cys Phe Asn Pro Ala Cys Val Ala Cys Tyr |
| (SEQ ID NO: 5536) | Cys Glu Trp Cys Phe Asn Pro Ala Cys Gly Gly Cys Tyr |
| (SEQ ID NO: 5537) | Cys Glu Trp Cys Phe Asn Pro Ala Cys Gly Ala Cys Tyr |

FIG. 3R

| | |
|---|---|
| (SEQ ID NO: 5538) | Cys Glu Trp Cys Phe Asn Pro Thr Cys Thr Gly Cys Tyr |
| (SEQ ID NO: 5539) | Cys Glu Trp Cys Phe Asn Pro Thr Cys Thr Ala Cys Tyr |
| (SEQ ID NO: 5540) | Cys Glu Trp Cys Phe Asn Pro Thr Cys Val Gly Cys Tyr |
| (SEQ ID NO: 5541) | Cys Glu Trp Cys Phe Asn Pro Thr Cys Val Ala Cys Tyr |
| (SEQ ID NO: 5542) | Cys Glu Trp Cys Phe Asn Pro Thr Cys Gly Gly Cys Tyr |
| (SEQ ID NO: 5543) | Cys Glu Trp Cys Phe Asn Pro Thr Cys Gly Ala Cys Tyr |
| (SEQ ID NO: 5544) | Cys Glu Trp Cys Phe Asn Gly Ala Cys Thr Gly Cys Tyr |
| (SEQ ID NO: 5545) | Cys Glu Trp Cys Phe Asn Gly Ala Cys Thr Ala Cys Tyr |
| (SEQ ID NO: 5546) | Cys Glu Trp Cys Phe Asn Gly Ala Cys Val Gly Cys Tyr |
| (SEQ ID NO: 5547) | Cys Glu Trp Cys Phe Asn Gly Ala Cys Val Ala Cys Tyr |
| (SEQ ID NO: 5548) | Cys Glu Trp Cys Phe Asn Gly Ala Cys Gly Gly Cys Tyr |
| (SEQ ID NO: 5549) | Cys Glu Trp Cys Phe Asn Gly Ala Cys Gly Ala Cys Tyr |
| (SEQ ID NO: 5550) | Cys Glu Trp Cys Phe Asn Gly Thr Cys Thr Gly Cys Tyr |
| (SEQ ID NO: 5551) | Cys Glu Trp Cys Phe Asn Gly Thr Cys Thr Ala Cys Tyr |
| (SEQ ID NO: 5552) | Cys Glu Trp Cys Phe Asn Gly Thr Cys Val Gly Cys Tyr |
| (SEQ ID NO: 5553) | Cys Glu Trp Cys Phe Asn Gly Thr Cys Val Ala Cys Tyr |
| (SEQ ID NO: 5554) | Cys Glu Trp Cys Phe Asn Gly Thr Cys Gly Gly Cys Tyr |
| (SEQ ID NO: 5555) | Cys Glu Trp Cys Phe Asn Gly Thr Cys Gly Ala Cys Tyr |
| (SEQ ID NO: 5556) | Cys Glu Trp Cys Pro Asn Pro Ala Cys Thr Gly Cys Tyr |
| (SEQ ID NO: 5557) | Cys Glu Trp Cys Pro Asn Pro Ala Cys Thr Ala Cys Tyr |
| (SEQ ID NO: 5558) | Cys Glu Trp Cys Pro Asn Pro Ala Cys Val Gly Cys Tyr |
| (SEQ ID NO: 5559) | Cys Glu Trp Cys Pro Asn Pro Ala Cys Val Ala Cys Tyr |
| (SEQ ID NO: 5560) | Cys Glu Trp Cys Pro Asn Pro Ala Cys Gly Gly Cys Tyr |
| (SEQ ID NO: 5561) | Cys Glu Trp Cys Pro Asn Pro Ala Cys Gly Ala Cys Tyr |
| (SEQ ID NO: 5562) | Cys Glu Trp Cys Pro Asn Pro Thr Cys Thr Gly Cys Tyr |
| (SEQ ID NO: 5563) | Cys Glu Trp Cys Pro Asn Pro Thr Cys Thr Ala Cys Tyr |
| (SEQ ID NO: 5564) | Cys Glu Trp Cys Pro Asn Pro Thr Cys Val Gly Cys Tyr |
| (SEQ ID NO: 5565) | Cys Glu Trp Cys Pro Asn Pro Thr Cys Val Ala Cys Tyr |
| (SEQ ID NO: 5566) | Cys Glu Trp Cys Pro Asn Pro Thr Cys Gly Gly Cys Tyr |
| (SEQ ID NO: 5567) | Cys Glu Trp Cys Pro Asn Pro Thr Cys Gly Ala Cys Tyr |
| (SEQ ID NO: 5568) | Cys Glu Trp Cys Pro Asn Gly Ala Cys Thr Gly Cys Tyr |
| (SEQ ID NO: 5569) | Cys Glu Trp Cys Pro Asn Gly Ala Cys Thr Ala Cys Tyr |
| (SEQ ID NO: 5570) | Cys Glu Trp Cys Pro Asn Gly Ala Cys Val Gly Cys Tyr |
| (SEQ ID NO: 5571) | Cys Glu Trp Cys Pro Asn Gly Ala Cys Val Ala Cys Tyr |
| (SEQ ID NO: 5572) | Cys Glu Trp Cys Pro Asn Gly Ala Cys Gly Gly Cys Tyr |
| (SEQ ID NO: 5573) | Cys Glu Trp Cys Pro Asn Gly Ala Cys Gly Ala Cys Tyr |
| (SEQ ID NO: 5574) | Cys Glu Trp Cys Pro Asn Gly Thr Cys Thr Gly Cys Tyr |
| (SEQ ID NO: 5575) | Cys Glu Trp Cys Pro Asn Gly Thr Cys Thr Ala Cys Tyr |
| (SEQ ID NO: 5576) | Cys Glu Trp Cys Pro Asn Gly Thr Cys Val Gly Cys Tyr |
| (SEQ ID NO: 5577) | Cys Glu Trp Cys Pro Asn Gly Thr Cys Val Ala Cys Tyr |
| (SEQ ID NO: 5578) | Cys Glu Trp Cys Pro Asn Gly Thr Cys Gly Gly Cys Tyr |
| (SEQ ID NO: 5579) | Cys Glu Trp Cys Pro Asn Gly Thr Cys Gly Ala Cys Tyr |
| (SEQ ID NO: 5580) | Cys Glu Trp Cys Ser Asn Pro Ala Cys Thr Gly Cys Tyr |

FIG. 3S

| | |
|---|---|
| (SEQ ID NO: 5581) | Cys Glu Trp Cys Ser Asn Pro Ala Cys Thr Ala Cys Tyr |
| (SEQ ID NO: 5582) | Cys Glu Trp Cys Ser Asn Pro Ala Cys Val Gly Cys Tyr |
| (SEQ ID NO: 5583) | Cys Glu Trp Cys Ser Asn Pro Ala Cys Val Ala Cys Tyr |
| (SEQ ID NO: 5584) | Cys Glu Trp Cys Ser Asn Pro Ala Cys Gly Gly Cys Tyr |
| (SEQ ID NO: 5585) | Cys Glu Trp Cys Ser Asn Pro Ala Cys Gly Ala Cys Tyr |
| (SEQ ID NO: 5586) | Cys Glu Trp Cys Ser Asn Pro Thr Cys Thr Gly Cys Tyr |
| (SEQ ID NO: 5587) | Cys Glu Trp Cys Ser Asn Pro Thr Cys Thr Ala Cys Tyr |
| (SEQ ID NO: 5588) | Cys Glu Trp Cys Ser Asn Pro Thr Cys Val Gly Cys Tyr |
| (SEQ ID NO: 5589) | Cys Glu Trp Cys Ser Asn Pro Thr Cys Val Ala Cys Tyr |
| (SEQ ID NO: 5590) | Cys Glu Trp Cys Ser Asn Pro Thr Cys Gly Gly Cys Tyr |
| (SEQ ID NO: 5591) | Cys Glu Trp Cys Ser Asn Pro Thr Cys Gly Ala Cys Tyr |
| (SEQ ID NO: 5592) | Cys Glu Trp Cys Ser Asn Gly Ala Cys Thr Gly Cys Tyr |
| (SEQ ID NO: 5593) | Cys Glu Trp Cys Ser Asn Gly Ala Cys Thr Ala Cys Tyr |
| (SEQ ID NO: 5594) | Cys Glu Trp Cys Ser Asn Gly Ala Cys Val Gly Cys Tyr |
| (SEQ ID NO: 5595) | Cys Glu Trp Cys Ser Asn Gly Ala Cys Val Ala Cys Tyr |
| (SEQ ID NO: 5596) | Cys Glu Trp Cys Ser Asn Gly Ala Cys Gly Gly Cys Tyr |
| (SEQ ID NO: 5597) | Cys Glu Trp Cys Ser Asn Gly Ala Cys Gly Ala Cys Tyr |
| (SEQ ID NO: 5598) | Cys Glu Trp Cys Ser Asn Gly Thr Cys Thr Gly Cys Tyr |
| (SEQ ID NO: 5599) | Cys Glu Trp Cys Ser Asn Gly Thr Cys Thr Ala Cys Tyr |
| (SEQ ID NO: 5600) | Cys Glu Trp Cys Ser Asn Gly Thr Cys Val Gly Cys Tyr |
| (SEQ ID NO: 5601) | Cys Glu Trp Cys Ser Asn Gly Thr Cys Val Ala Cys Tyr |
| (SEQ ID NO: 5602) | Cys Glu Trp Cys Ser Asn Gly Thr Cys Gly Gly Cys Tyr |
| (SEQ ID NO: 5603) | Cys Glu Trp Cys Ser Asn Gly Thr Cys Gly Ala Cys Tyr |
| (SEQ ID NO: 5604) | Cys Glu Trp Cys Thr Asn Pro Ala Cys Thr Gly Cys Tyr |
| (SEQ ID NO: 5605) | Cys Glu Trp Cys Thr Asn Pro Ala Cys Thr Ala Cys Tyr |
| (SEQ ID NO: 5606) | Cys Glu Trp Cys Thr Asn Pro Ala Cys Val Gly Cys Tyr |
| (SEQ ID NO: 5607) | Cys Glu Trp Cys Thr Asn Pro Ala Cys Val Ala Cys Tyr |
| (SEQ ID NO: 5608) | Cys Glu Trp Cys Thr Asn Pro Ala Cys Gly Gly Cys Tyr |
| (SEQ ID NO: 5609) | Cys Glu Trp Cys Thr Asn Pro Ala Cys Gly Ala Cys Tyr |
| (SEQ ID NO: 5610) | Cys Glu Trp Cys Thr Asn Pro Thr Cys Thr Gly Cys Tyr |
| (SEQ ID NO: 5611) | Cys Glu Trp Cys Thr Asn Pro Thr Cys Thr Ala Cys Tyr |
| (SEQ ID NO: 5612) | Cys Glu Trp Cys Thr Asn Pro Thr Cys Val Gly Cys Tyr |
| (SEQ ID NO: 5613) | Cys Glu Trp Cys Thr Asn Pro Thr Cys Val Ala Cys Tyr |
| (SEQ ID NO: 5614) | Cys Glu Trp Cys Thr Asn Pro Thr Cys Gly Gly Cys Tyr |
| (SEQ ID NO: 5615) | Cys Glu Trp Cys Thr Asn Pro Thr Cys Gly Ala Cys Tyr |
| (SEQ ID NO: 5616) | Cys Glu Trp Cys Thr Asn Gly Ala Cys Thr Gly Cys Tyr |
| (SEQ ID NO: 5617) | Cys Glu Trp Cys Thr Asn Gly Ala Cys Thr Ala Cys Tyr |
| (SEQ ID NO: 5618) | Cys Glu Trp Cys Thr Asn Gly Ala Cys Val Gly Cys Tyr |
| (SEQ ID NO: 5619) | Cys Glu Trp Cys Thr Asn Gly Ala Cys Val Ala Cys Tyr |
| (SEQ ID NO: 5620) | Cys Glu Trp Cys Thr Asn Gly Ala Cys Gly Gly Cys Tyr |
| (SEQ ID NO: 5621) | Cys Glu Trp Cys Thr Asn Gly Ala Cys Gly Ala Cys Tyr |
| (SEQ ID NO: 5622) | Cys Glu Trp Cys Thr Asn Gly Thr Cys Thr Gly Cys Tyr |
| (SEQ ID NO: 5623) | Cys Glu Trp Cys Thr Asn Gly Thr Cys Thr Ala Cys Tyr |

FIG. 3T (SEQ ID NO: 5624 )   Cys Glu Trp Cys Thr Asn Gly Thr Cys Val Gly Cys Tyr
(SEQ ID NO: 5625 )   Cys Glu Trp Cys Thr Asn Gly Thr Cys Val Ala Cys Tyr
(SEQ ID NO: 5626 )   Cys Glu Trp Cys Thr Asn Gly Thr Cys Gly Gly Cys Tyr
(SEQ ID NO: 5627 )   Cys Glu Trp Cys Thr Asn Gly Thr Cys Gly Ala Cys Tyr
(SEQ ID NO: 5628 )   Cys Glu Trp Cys Trp Asn Pro Ala Cys Thr Gly Cys Tyr
(SEQ ID NO: 5629 )   Cys Glu Trp Cys Trp Asn Pro Ala Cys Thr Ala Cys Tyr
(SEQ ID NO: 5630 )   Cys Glu Trp Cys Trp Asn Pro Ala Cys Val Gly Cys Tyr
(SEQ ID NO: 5631 )   Cys Glu Trp Cys Trp Asn Pro Ala Cys Val Ala Cys Tyr
(SEQ ID NO: 5632 )   Cys Glu Trp Cys Trp Asn Pro Ala Cys Gly Gly Cys Tyr
(SEQ ID NO: 5633 )   Cys Glu Trp Cys Trp Asn Pro Ala Cys Gly Ala Cys Tyr
(SEQ ID NO: 5634 )   Cys Glu Trp Cys Trp Asn Pro Thr Cys Thr Gly Cys Tyr
(SEQ ID NO: 5635 )   Cys Glu Trp Cys Trp Asn Pro Thr Cys Thr Ala Cys Tyr
(SEQ ID NO: 5636 )   Cys Glu Trp Cys Trp Asn Pro Thr Cys Val Gly Cys Tyr
(SEQ ID NO: 5637 )   Cys Glu Trp Cys Trp Asn Pro Thr Cys Val Ala Cys Tyr
(SEQ ID NO: 5638 )   Cys Glu Trp Cys Trp Asn Pro Thr Cys Gly Gly Cys Tyr
(SEQ ID NO: 5639 )   Cys Glu Trp Cys Trp Asn Pro Thr Cys Gly Ala Cys Tyr
(SEQ ID NO: 5640 )   Cys Glu Trp Cys Trp Asn Gly Ala Cys Thr Gly Cys Tyr
(SEQ ID NO: 5641 )   Cys Glu Trp Cys Trp Asn Gly Ala Cys Thr Ala Cys Tyr
(SEQ ID NO: 5642 )   Cys Glu Trp Cys Trp Asn Gly Ala Cys Val Gly Cys Tyr
(SEQ ID NO: 5643 )   Cys Glu Trp Cys Trp Asn Gly Ala Cys Val Ala Cys Tyr
(SEQ ID NO: 5644 )   Cys Glu Trp Cys Trp Asn Gly Ala Cys Gly Gly Cys Tyr
(SEQ ID NO: 5645 )   Cys Glu Trp Cys Trp Asn Gly Ala Cys Gly Ala Cys Tyr
(SEQ ID NO: 5646 )   Cys Glu Trp Cys Trp Asn Gly Thr Cys Thr Gly Cys Tyr
(SEQ ID NO: 5647 )   Cys Glu Trp Cys Trp Asn Gly Thr Cys Thr Ala Cys Tyr
(SEQ ID NO: 5648 )   Cys Glu Trp Cys Trp Asn Gly Thr Cys Val Gly Cys Tyr
(SEQ ID NO: 5649 )   Cys Glu Trp Cys Trp Asn Gly Thr Cys Val Ala Cys Tyr
(SEQ ID NO: 5650 )   Cys Glu Trp Cys Trp Asn Gly Thr Cys Gly Gly Cys Tyr
(SEQ ID NO: 5651 )   Cys Glu Trp Cys Trp Asn Gly Thr Cys Gly Ala Cys Tyr
(SEQ ID NO: 5652 )   Cys Glu Trp Cys Tyr Asn Pro Ala Cys Thr Gly Cys Tyr
(SEQ ID NO: 5653 )   Cys Glu Trp Cys Tyr Asn Pro Ala Cys Thr Ala Cys Tyr
(SEQ ID NO: 5654 )   Cys Glu Trp Cys Tyr Asn Pro Ala Cys Val Gly Cys Tyr
(SEQ ID NO: 5655 )   Cys Glu Trp Cys Tyr Asn Pro Ala Cys Val Ala Cys Tyr
(SEQ ID NO: 5656 )   Cys Glu Trp Cys Tyr Asn Pro Ala Cys Gly Gly Cys Tyr
(SEQ ID NO: 5657 )   Cys Glu Trp Cys Tyr Asn Pro Ala Cys Gly Ala Cys Tyr
(SEQ ID NO: 5658 )   Cys Glu Trp Cys Tyr Asn Pro Thr Cys Thr Gly Cys Tyr
(SEQ ID NO: 5659 )   Cys Glu Trp Cys Tyr Asn Pro Thr Cys Thr Ala Cys Tyr
(SEQ ID NO: 5660 )   Cys Glu Trp Cys Tyr Asn Pro Thr Cys Val Gly Cys Tyr
(SEQ ID NO: 5661 )   Cys Glu Trp Cys Tyr Asn Pro Thr Cys Val Ala Cys Tyr
(SEQ ID NO: 5662 )   Cys Glu Trp Cys Tyr Asn Pro Thr Cys Gly Gly Cys Tyr
(SEQ ID NO: 5663 )   Cys Glu Trp Cys Tyr Asn Pro Thr Cys Gly Ala Cys Tyr
(SEQ ID NO: 5664 )   Cys Glu Trp Cys Tyr Asn Gly Ala Cys Thr Gly Cys Tyr
(SEQ ID NO: 5665 )   Cys Glu Trp Cys Tyr Asn Gly Ala Cys Thr Ala Cys Tyr
(SEQ ID NO: 5666 )   Cys Glu Trp Cys Tyr Asn Gly Ala Cys Val Gly Cys Tyr

FIG. 3U (SEQ ID NO: 5667)  Cys Glu Trp Cys Tyr Asn Gly Ala Cys Val Ala Cys Tyr
(SEQ ID NO: 5668)  Cys Glu Trp Cys Tyr Asn Gly Ala Cys Gly Gly Cys Tyr
(SEQ ID NO: 5669)  Cys Glu Trp Cys Tyr Asn Gly Ala Cys Gly Ala Cys Tyr
(SEQ ID NO: 5670)  Cys Glu Trp Cys Tyr Asn Gly Thr Cys Thr Gly Cys Tyr
(SEQ ID NO: 5671)  Cys Glu Trp Cys Tyr Asn Gly Thr Cys Thr Ala Cys Tyr
(SEQ ID NO: 5672)  Cys Glu Trp Cys Tyr Asn Gly Thr Cys Val Gly Cys Tyr
(SEQ ID NO: 5673)  Cys Glu Trp Cys Tyr Asn Gly Thr Cys Val Ala Cys Tyr
(SEQ ID NO: 5674)  Cys Glu Trp Cys Tyr Asn Gly Thr Cys Gly Gly Cys Tyr
(SEQ ID NO: 5675)  Cys Glu Trp Cys Tyr Asn Gly Thr Cys Gly Ala Cys Tyr
(SEQ ID NO: 5676)  Cys Glu Trp Cys Val Asn Pro Ala Cys Thr Gly Cys Tyr
(SEQ ID NO: 5677)  Cys Glu Trp Cys Val Asn Pro Ala Cys Thr Ala Cys Tyr
(SEQ ID NO: 5678)  Cys Glu Trp Cys Val Asn Pro Ala Cys Val Gly Cys Tyr
(SEQ ID NO: 5679)  Cys Glu Trp Cys Val Asn Pro Ala Cys Val Ala Cys Tyr
(SEQ ID NO: 5680)  Cys Glu Trp Cys Val Asn Pro Ala Cys Gly Gly Cys Tyr
(SEQ ID NO: 5681)  Cys Glu Trp Cys Val Asn Pro Ala Cys Gly Ala Cys Tyr
(SEQ ID NO: 5682)  Cys Glu Trp Cys Val Asn Pro Thr Cys Thr Gly Cys Tyr
(SEQ ID NO: 5683)  Cys Glu Trp Cys Val Asn Pro Thr Cys Thr Ala Cys Tyr
(SEQ ID NO: 5684)  Cys Glu Trp Cys Val Asn Pro Thr Cys Val Gly Cys Tyr
(SEQ ID NO: 5685)  Cys Glu Trp Cys Val Asn Pro Thr Cys Val Ala Cys Tyr
(SEQ ID NO: 5686)  Cys Glu Trp Cys Val Asn Pro Thr Cys Gly Gly Cys Tyr
(SEQ ID NO: 5687)  Cys Glu Trp Cys Val Asn Pro Thr Cys Gly Ala Cys Tyr
(SEQ ID NO: 5688)  Cys Glu Trp Cys Val Asn Gly Ala Cys Thr Gly Cys Tyr
(SEQ ID NO: 5689)  Cys Glu Trp Cys Val Asn Gly Ala Cys Thr Ala Cys Tyr
(SEQ ID NO: 5690)  Cys Glu Trp Cys Val Asn Gly Ala Cys Val Gly Cys Tyr
(SEQ ID NO: 5691)  Cys Glu Trp Cys Val Asn Gly Ala Cys Val Ala Cys Tyr
(SEQ ID NO: 5692)  Cys Glu Trp Cys Val Asn Gly Ala Cys Gly Gly Cys Tyr
(SEQ ID NO: 5693)  Cys Glu Trp Cys Val Asn Gly Ala Cys Gly Ala Cys Tyr
(SEQ ID NO: 5694)  Cys Glu Trp Cys Val Asn Gly Thr Cys Thr Gly Cys Tyr
(SEQ ID NO: 5695)  Cys Glu Trp Cys Val Asn Gly Thr Cys Thr Ala Cys Tyr
(SEQ ID NO: 5696)  Cys Glu Trp Cys Val Asn Gly Thr Cys Val Gly Cys Tyr
(SEQ ID NO: 5697)  Cys Glu Trp Cys Val Asn Gly Thr Cys Val Ala Cys Tyr
(SEQ ID NO: 5698)  Cys Glu Trp Cys Val Asn Gly Thr Cys Gly Gly Cys Tyr
(SEQ ID NO: 5699)  Cys Glu Trp Cys Val Asn Gly Thr Cys Gly Ala Cys Tyr
(SEQ ID NO: 5700)  Cys Glu Trp Cys --- Asn Pro Ala Cys Thr Gly Cys Tyr
(SEQ ID NO: 5701)  Cys Glu Trp Cys --- Asn Pro Ala Cys Thr Ala Cys Tyr
(SEQ ID NO: 5702)  Cys Glu Trp Cys --- Asn Pro Ala Cys Val Gly Cys Tyr
(SEQ ID NO: 5703)  Cys Glu Trp Cys --- Asn Pro Ala Cys Val Ala Cys Tyr
(SEQ ID NO: 5704)  Cys Glu Trp Cys --- Asn Pro Ala Cys Gly Gly Cys Tyr
(SEQ ID NO: 5705)  Cys Glu Trp Cys --- Asn Pro Ala Cys Gly Ala Cys Tyr
(SEQ ID NO: 5706)  Cys Glu Trp Cys --- Asn Pro Thr Cys Thr Gly Cys Tyr
(SEQ ID NO: 5707)  Cys Glu Trp Cys --- Asn Pro Thr Cys Thr Ala Cys Tyr
(SEQ ID NO: 5708)  Cys Glu Trp Cys --- Asn Pro Thr Cys Val Gly Cys Tyr
(SEQ ID NO: 5709)  Cys Glu Trp Cys --- Asn Pro Thr Cys Val Ala Cys Tyr

FIG. 3V

| | | | | | | | | | | | |
|---|---|---|---|---|---|---|---|---|---|---|---|
| (SEQ ID NO: 5710) | Cys | Glu | Trp | Cys | --- | Asn | Pro | Thr | Cys | Gly | Gly | Cys | Tyr |
| (SEQ ID NO: 5711) | Cys | Glu | Trp | Cys | --- | Asn | Pro | Thr | Cys | Gly | Ala | Cys | Tyr |
| (SEQ ID NO: 5712) | Cys | Glu | Trp | Cys | --- | Asn | Gly | Ala | Cys | Thr | Gly | Cys | Tyr |
| (SEQ ID NO: 5713) | Cys | Glu | Trp | Cys | --- | Asn | Gly | Ala | Cys | Thr | Ala | Cys | Tyr |
| (SEQ ID NO: 5714) | Cys | Glu | Trp | Cys | --- | Asn | Gly | Ala | Cys | Val | Gly | Cys | Tyr |
| (SEQ ID NO: 5715) | Cys | Glu | Trp | Cys | --- | Asn | Gly | Ala | Cys | Val | Ala | Cys | Tyr |
| (SEQ ID NO: 5716) | Cys | Glu | Trp | Cys | --- | Asn | Gly | Ala | Cys | Gly | Gly | Cys | Tyr |
| (SEQ ID NO: 5717) | Cys | Glu | Trp | Cys | --- | Asn | Gly | Ala | Cys | Gly | Ala | Cys | Tyr |
| (SEQ ID NO: 5718) | Cys | Glu | Trp | Cys | --- | Asn | Gly | Thr | Cys | Thr | Gly | Cys | Tyr |
| (SEQ ID NO: 5719) | Cys | Glu | Trp | Cys | --- | Asn | Gly | Thr | Cys | Thr | Ala | Cys | Tyr |
| (SEQ ID NO: 5720) | Cys | Glu | Trp | Cys | --- | Asn | Gly | Thr | Cys | Val | Gly | Cys | Tyr |
| (SEQ ID NO: 5721) | Cys | Glu | Trp | Cys | --- | Asn | Gly | Thr | Cys | Val | Ala | Cys | Tyr |
| (SEQ ID NO: 5722) | Cys | Glu | Trp | Cys | --- | Asn | Gly | Thr | Cys | Gly | Gly | Cys | Tyr |
| (SEQ ID NO: 5723) | Cys | Glu | Trp | Cys | --- | Asn | Gly | Thr | Cys | Gly | Ala | Cys | Tyr |
| (SEQ ID NO: 5724) | Cys | Glu | Phe | Cys | Ala | Asn | Pro | Ala | Cys | Thr | Gly | Cys | Tyr |
| (SEQ ID NO: 5725) | Cys | Glu | Phe | Cys | Ala | Asn | Pro | Ala | Cys | Thr | Ala | Cys | Tyr |
| (SEQ ID NO: 5726) | Cys | Glu | Phe | Cys | Ala | Asn | Pro | Ala | Cys | Val | Gly | Cys | Tyr |
| (SEQ ID NO: 5727) | Cys | Glu | Phe | Cys | Ala | Asn | Pro | Ala | Cys | Val | Ala | Cys | Tyr |
| (SEQ ID NO: 5728) | Cys | Glu | Phe | Cys | Ala | Asn | Pro | Ala | Cys | Gly | Gly | Cys | Tyr |
| (SEQ ID NO: 5729) | Cys | Glu | Phe | Cys | Ala | Asn | Pro | Ala | Cys | Gly | Ala | Cys | Tyr |
| (SEQ ID NO: 5730) | Cys | Glu | Phe | Cys | Ala | Asn | Pro | Thr | Cys | Thr | Gly | Cys | Tyr |
| (SEQ ID NO: 5731) | Cys | Glu | Phe | Cys | Ala | Asn | Pro | Thr | Cys | Thr | Ala | Cys | Tyr |
| (SEQ ID NO: 5732) | Cys | Glu | Phe | Cys | Ala | Asn | Pro | Thr | Cys | Val | Gly | Cys | Tyr |
| (SEQ ID NO: 5733) | Cys | Glu | Phe | Cys | Ala | Asn | Pro | Thr | Cys | Val | Ala | Cys | Tyr |
| (SEQ ID NO: 5734) | Cys | Glu | Phe | Cys | Ala | Asn | Pro | Thr | Cys | Gly | Gly | Cys | Tyr |
| (SEQ ID NO: 5735) | Cys | Glu | Phe | Cys | Ala | Asn | Pro | Thr | Cys | Gly | Ala | Cys | Tyr |
| (SEQ ID NO: 5736) | Cys | Glu | Phe | Cys | Ala | Asn | Gly | Ala | Cys | Thr | Gly | Cys | Tyr |
| (SEQ ID NO: 5737) | Cys | Glu | Phe | Cys | Ala | Asn | Gly | Ala | Cys | Thr | Ala | Cys | Tyr |
| (SEQ ID NO: 5738) | Cys | Glu | Phe | Cys | Ala | Asn | Gly | Ala | Cys | Val | Gly | Cys | Tyr |
| (SEQ ID NO: 5739) | Cys | Glu | Phe | Cys | Ala | Asn | Gly | Ala | Cys | Val | Ala | Cys | Tyr |
| (SEQ ID NO: 5740) | Cys | Glu | Phe | Cys | Ala | Asn | Gly | Ala | Cys | Gly | Gly | Cys | Tyr |
| (SEQ ID NO: 5741) | Cys | Glu | Phe | Cys | Ala | Asn | Gly | Ala | Cys | Gly | Ala | Cys | Tyr |
| (SEQ ID NO: 5742) | Cys | Glu | Phe | Cys | Ala | Asn | Gly | Thr | Cys | Thr | Gly | Cys | Tyr |
| (SEQ ID NO: 5743) | Cys | Glu | Phe | Cys | Ala | Asn | Gly | Thr | Cys | Thr | Ala | Cys | Tyr |
| (SEQ ID NO: 5744) | Cys | Glu | Phe | Cys | Ala | Asn | Gly | Thr | Cys | Val | Gly | Cys | Tyr |
| (SEQ ID NO: 5745) | Cys | Glu | Phe | Cys | Ala | Asn | Gly | Thr | Cys | Val | Ala | Cys | Tyr |
| (SEQ ID NO: 5746) | Cys | Glu | Phe | Cys | Ala | Asn | Gly | Thr | Cys | Gly | Gly | Cys | Tyr |
| (SEQ ID NO: 5747) | Cys | Glu | Phe | Cys | Ala | Asn | Gly | Thr | Cys | Gly | Ala | Cys | Tyr |
| (SEQ ID NO: 5748) | Cys | Glu | Phe | Cys | Arg | Asn | Pro | Ala | Cys | Thr | Gly | Cys | Tyr |
| (SEQ ID NO: 5749) | Cys | Glu | Phe | Cys | Arg | Asn | Pro | Ala | Cys | Thr | Ala | Cys | Tyr |
| (SEQ ID NO: 5750) | Cys | Glu | Phe | Cys | Arg | Asn | Pro | Ala | Cys | Val | Gly | Cys | Tyr |
| (SEQ ID NO: 5751) | Cys | Glu | Phe | Cys | Arg | Asn | Pro | Ala | Cys | Val | Ala | Cys | Tyr |
| (SEQ ID NO: 5752) | Cys | Glu | Phe | Cys | Arg | Asn | Pro | Ala | Cys | Gly | Gly | Cys | Tyr |

FIG. 3W

| | |
|---|---|
| (SEQ ID NO: 5753) | Cys Glu Phe Cys Arg Asn Pro Ala Cys Gly Ala Cys Tyr |
| (SEQ ID NO: 5754) | Cys Glu Phe Cys Arg Asn Pro Thr Cys Thr Gly Cys Tyr |
| (SEQ ID NO: 5755) | Cys Glu Phe Cys Arg Asn Pro Thr Cys Thr Ala Cys Tyr |
| (SEQ ID NO: 5756) | Cys Glu Phe Cys Arg Asn Pro Thr Cys Val Gly Cys Tyr |
| (SEQ ID NO: 5757) | Cys Glu Phe Cys Arg Asn Pro Thr Cys Val Ala Cys Tyr |
| (SEQ ID NO: 5758) | Cys Glu Phe Cys Arg Asn Pro Thr Cys Gly Gly Cys Tyr |
| (SEQ ID NO: 5759) | Cys Glu Phe Cys Arg Asn Pro Thr Cys Gly Ala Cys Tyr |
| (SEQ ID NO: 5760) | Cys Glu Phe Cys Arg Asn Gly Ala Cys Thr Gly Cys Tyr |
| (SEQ ID NO: 5761) | Cys Glu Phe Cys Arg Asn Gly Ala Cys Thr Ala Cys Tyr |
| (SEQ ID NO: 5762) | Cys Glu Phe Cys Arg Asn Gly Ala Cys Val Gly Cys Tyr |
| (SEQ ID NO: 5763) | Cys Glu Phe Cys Arg Asn Gly Ala Cys Val Ala Cys Tyr |
| (SEQ ID NO: 5764) | Cys Glu Phe Cys Arg Asn Gly Ala Cys Gly Gly Cys Tyr |
| (SEQ ID NO: 5765) | Cys Glu Phe Cys Arg Asn Gly Ala Cys Gly Ala Cys Tyr |
| (SEQ ID NO: 5766) | Cys Glu Phe Cys Arg Asn Gly Thr Cys Thr Gly Cys Tyr |
| (SEQ ID NO: 5767) | Cys Glu Phe Cys Arg Asn Gly Thr Cys Thr Ala Cys Tyr |
| (SEQ ID NO: 5768) | Cys Glu Phe Cys Arg Asn Gly Thr Cys Val Gly Cys Tyr |
| (SEQ ID NO: 5769) | Cys Glu Phe Cys Arg Asn Gly Thr Cys Val Ala Cys Tyr |
| (SEQ ID NO: 5770) | Cys Glu Phe Cys Arg Asn Gly Thr Cys Gly Gly Cys Tyr |
| (SEQ ID NO: 5771) | Cys Glu Phe Cys Arg Asn Gly Thr Cys Gly Ala Cys Tyr |
| (SEQ ID NO: 5772) | Cys Glu Phe Cys Asn Asn Pro Ala Cys Thr Gly Cys Tyr |
| (SEQ ID NO: 5773) | Cys Glu Phe Cys Asn Asn Pro Ala Cys Thr Ala Cys Tyr |
| (SEQ ID NO: 5774) | Cys Glu Phe Cys Asn Asn Pro Ala Cys Val Gly Cys Tyr |
| (SEQ ID NO: 5775) | Cys Glu Phe Cys Asn Asn Pro Ala Cys Val Ala Cys Tyr |
| (SEQ ID NO: 5776) | Cys Glu Phe Cys Asn Asn Pro Ala Cys Gly Gly Cys Tyr |
| (SEQ ID NO: 5777) | Cys Glu Phe Cys Asn Asn Pro Ala Cys Gly Ala Cys Tyr |
| (SEQ ID NO: 5778) | Cys Glu Phe Cys Asn Asn Pro Thr Cys Thr Gly Cys Tyr |
| (SEQ ID NO: 5779) | Cys Glu Phe Cys Asn Asn Pro Thr Cys Thr Ala Cys Tyr |
| (SEQ ID NO: 5780) | Cys Glu Phe Cys Asn Asn Pro Thr Cys Val Gly Cys Tyr |
| (SEQ ID NO: 5781) | Cys Glu Phe Cys Asn Asn Pro Thr Cys Val Ala Cys Tyr |
| (SEQ ID NO: 5782) | Cys Glu Phe Cys Asn Asn Pro Thr Cys Gly Gly Cys Tyr |
| (SEQ ID NO: 5783) | Cys Glu Phe Cys Asn Asn Pro Thr Cys Gly Ala Cys Tyr |
| (SEQ ID NO: 5784) | Cys Glu Phe Cys Asn Asn Gly Ala Cys Thr Gly Cys Tyr |
| (SEQ ID NO: 5785) | Cys Glu Phe Cys Asn Asn Gly Ala Cys Thr Ala Cys Tyr |
| (SEQ ID NO: 5786) | Cys Glu Phe Cys Asn Asn Gly Ala Cys Val Gly Cys Tyr |
| (SEQ ID NO: 5787) | Cys Glu Phe Cys Asn Asn Gly Ala Cys Val Ala Cys Tyr |
| (SEQ ID NO: 5788) | Cys Glu Phe Cys Asn Asn Gly Ala Cys Gly Gly Cys Tyr |
| (SEQ ID NO: 5789) | Cys Glu Phe Cys Asn Asn Gly Ala Cys Gly Ala Cys Tyr |
| (SEQ ID NO: 5790) | Cys Glu Phe Cys Asn Asn Gly Thr Cys Thr Gly Cys Tyr |
| (SEQ ID NO: 5791) | Cys Glu Phe Cys Asn Asn Gly Thr Cys Thr Ala Cys Tyr |
| (SEQ ID NO: 5792) | Cys Glu Phe Cys Asn Asn Gly Thr Cys Val Gly Cys Tyr |
| (SEQ ID NO: 5793) | Cys Glu Phe Cys Asn Asn Gly Thr Cys Val Ala Cys Tyr |
| (SEQ ID NO: 5794) | Cys Glu Phe Cys Asn Asn Gly Thr Cys Gly Gly Cys Tyr |
| (SEQ ID NO: 5795) | Cys Glu Phe Cys Asn Asn Gly Thr Cys Gly Ala Cys Tyr |

FIG. 3X (SEQ ID NO: 5796 )   Cys Glu Phe Cys Asp Asn Pro Ala Cys Thr Gly Cys Tyr
(SEQ ID NO: 5797 )   Cys Glu Phe Cys Asp Asn Pro Ala Cys Thr Ala Cys Tyr
(SEQ ID NO: 5798 )   Cys Glu Phe Cys Asp Asn Pro Ala Cys Val Gly Cys Tyr
(SEQ ID NO: 5799 )   Cys Glu Phe Cys Asp Asn Pro Ala Cys Val Ala Cys Tyr
(SEQ ID NO: 5800 )   Cys Glu Phe Cys Asp Asn Pro Ala Cys Gly Gly Cys Tyr
(SEQ ID NO: 5801 )   Cys Glu Phe Cys Asp Asn Pro Ala Cys Gly Ala Cys Tyr
(SEQ ID NO: 5802 )   Cys Glu Phe Cys Asp Asn Pro Thr Cys Thr Gly Cys Tyr
(SEQ ID NO: 5803 )   Cys Glu Phe Cys Asp Asn Pro Thr Cys Thr Ala Cys Tyr
(SEQ ID NO: 5804 )   Cys Glu Phe Cys Asp Asn Pro Thr Cys Val Gly Cys Tyr
(SEQ ID NO: 5805 )   Cys Glu Phe Cys Asp Asn Pro Thr Cys Val Ala Cys Tyr
(SEQ ID NO: 5806 )   Cys Glu Phe Cys Asp Asn Pro Thr Cys Gly Gly Cys Tyr
(SEQ ID NO: 5807 )   Cys Glu Phe Cys Asp Asn Pro Thr Cys Gly Ala Cys Tyr
(SEQ ID NO: 5808 )   Cys Glu Phe Cys Asp Asn Gly Ala Cys Thr Gly Cys Tyr
(SEQ ID NO: 5809 )   Cys Glu Phe Cys Asp Asn Gly Ala Cys Thr Ala Cys Tyr
(SEQ ID NO: 5810 )   Cys Glu Phe Cys Asp Asn Gly Ala Cys Val Gly Cys Tyr
(SEQ ID NO: 5811 )   Cys Glu Phe Cys Asp Asn Gly Ala Cys Val Ala Cys Tyr
(SEQ ID NO: 5812 )   Cys Glu Phe Cys Asp Asn Gly Ala Cys Gly Gly Cys Tyr
(SEQ ID NO: 5813 )   Cys Glu Phe Cys Asp Asn Gly Ala Cys Gly Ala Cys Tyr
(SEQ ID NO: 5814 )   Cys Glu Phe Cys Asp Asn Gly Thr Cys Thr Gly Cys Tyr
(SEQ ID NO: 5815 )   Cys Glu Phe Cys Asp Asn Gly Thr Cys Thr Ala Cys Tyr
(SEQ ID NO: 5816 )   Cys Glu Phe Cys Asp Asn Gly Thr Cys Val Gly Cys Tyr
(SEQ ID NO: 5817 )   Cys Glu Phe Cys Asp Asn Gly Thr Cys Val Ala Cys Tyr
(SEQ ID NO: 5818 )   Cys Glu Phe Cys Asp Asn Gly Thr Cys Gly Gly Cys Tyr
(SEQ ID NO: 5819 )   Cys Glu Phe Cys Asp Asn Gly Thr Cys Gly Ala Cys Tyr
(SEQ ID NO: 5820 )   Cys Glu Phe Cys Gln Asn Pro Ala Cys Thr Gly Cys Tyr
(SEQ ID NO: 5821 )   Cys Glu Phe Cys Gln Asn Pro Ala Cys Thr Ala Cys Tyr
(SEQ ID NO: 5822 )   Cys Glu Phe Cys Gln Asn Pro Ala Cys Val Gly Cys Tyr
(SEQ ID NO: 5823 )   Cys Glu Phe Cys Gln Asn Pro Ala Cys Val Ala Cys Tyr
(SEQ ID NO: 5824 )   Cys Glu Phe Cys Gln Asn Pro Ala Cys Gly Gly Cys Tyr
(SEQ ID NO: 5825 )   Cys Glu Phe Cys Gln Asn Pro Ala Cys Gly Ala Cys Tyr
(SEQ ID NO: 5826 )   Cys Glu Phe Cys Gln Asn Pro Thr Cys Thr Gly Cys Tyr
(SEQ ID NO: 5827 )   Cys Glu Phe Cys Gln Asn Pro Thr Cys Thr Ala Cys Tyr
(SEQ ID NO: 5828 )   Cys Glu Phe Cys Gln Asn Pro Thr Cys Val Gly Cys Tyr
(SEQ ID NO: 5829 )   Cys Glu Phe Cys Gln Asn Pro Thr Cys Val Ala Cys Tyr
(SEQ ID NO: 5830 )   Cys Glu Phe Cys Gln Asn Pro Thr Cys Gly Gly Cys Tyr
(SEQ ID NO: 5831 )   Cys Glu Phe Cys Gln Asn Pro Thr Cys Gly Ala Cys Tyr
(SEQ ID NO: 5832 )   Cys Glu Phe Cys Gln Asn Gly Ala Cys Thr Gly Cys Tyr
(SEQ ID NO: 5833 )   Cys Glu Phe Cys Gln Asn Gly Ala Cys Thr Ala Cys Tyr
(SEQ ID NO: 5834 )   Cys Glu Phe Cys Gln Asn Gly Ala Cys Val Gly Cys Tyr
(SEQ ID NO: 5835 )   Cys Glu Phe Cys Gln Asn Gly Ala Cys Val Ala Cys Tyr
(SEQ ID NO: 5836 )   Cys Glu Phe Cys Gln Asn Gly Ala Cys Gly Gly Cys Tyr
(SEQ ID NO: 5837 )   Cys Glu Phe Cys Gln Asn Gly Ala Cys Gly Ala Cys Tyr
(SEQ ID NO: 5838 )   Cys Glu Phe Cys Gln Asn Gly Thr Cys Thr Gly Cys Tyr

FIG. 3Y

| | |
|---|---|
| (SEQ ID NO: 5839) | Cys Glu Phe Cys Gln Asn Gly Thr Cys Thr Ala Cys Tyr |
| (SEQ ID NO: 5840) | Cys Glu Phe Cys Gln Asn Gly Thr Cys Val Gly Cys Tyr |
| (SEQ ID NO: 5841) | Cys Glu Phe Cys Gln Asn Gly Thr Cys Val Ala Cys Tyr |
| (SEQ ID NO: 5842) | Cys Glu Phe Cys Gln Asn Gly Thr Cys Gly Gly Cys Tyr |
| (SEQ ID NO: 5843) | Cys Glu Phe Cys Gln Asn Gly Thr Cys Gly Ala Cys Tyr |
| (SEQ ID NO: 5844) | Cys Glu Phe Cys Glu Asn Pro Ala Cys Thr Gly Cys Tyr |
| (SEQ ID NO: 5845) | Cys Glu Phe Cys Glu Asn Pro Ala Cys Thr Ala Cys Tyr |
| (SEQ ID NO: 5846) | Cys Glu Phe Cys Glu Asn Pro Ala Cys Val Gly Cys Tyr |
| (SEQ ID NO: 5847) | Cys Glu Phe Cys Glu Asn Pro Ala Cys Val Ala Cys Tyr |
| (SEQ ID NO: 5848) | Cys Glu Phe Cys Glu Asn Pro Ala Cys Gly Gly Cys Tyr |
| (SEQ ID NO: 5849) | Cys Glu Phe Cys Glu Asn Pro Ala Cys Gly Ala Cys Tyr |
| (SEQ ID NO: 5850) | Cys Glu Phe Cys Glu Asn Pro Thr Cys Thr Gly Cys Tyr |
| (SEQ ID NO: 5851) | Cys Glu Phe Cys Glu Asn Pro Thr Cys Thr Ala Cys Tyr |
| (SEQ ID NO: 5852) | Cys Glu Phe Cys Glu Asn Pro Thr Cys Val Gly Cys Tyr |
| (SEQ ID NO: 5853) | Cys Glu Phe Cys Glu Asn Pro Thr Cys Val Ala Cys Tyr |
| (SEQ ID NO: 5854) | Cys Glu Phe Cys Glu Asn Pro Thr Cys Gly Gly Cys Tyr |
| (SEQ ID NO: 5855) | Cys Glu Phe Cys Glu Asn Pro Thr Cys Gly Ala Cys Tyr |
| (SEQ ID NO: 5856) | Cys Glu Phe Cys Glu Asn Gly Ala Cys Thr Gly Cys Tyr |
| (SEQ ID NO: 5857) | Cys Glu Phe Cys Glu Asn Gly Ala Cys Thr Ala Cys Tyr |
| (SEQ ID NO: 5858) | Cys Glu Phe Cys Glu Asn Gly Ala Cys Val Gly Cys Tyr |
| (SEQ ID NO: 5859) | Cys Glu Phe Cys Glu Asn Gly Ala Cys Val Ala Cys Tyr |
| (SEQ ID NO: 5860) | Cys Glu Phe Cys Glu Asn Gly Ala Cys Gly Gly Cys Tyr |
| (SEQ ID NO: 5861) | Cys Glu Phe Cys Glu Asn Gly Ala Cys Gly Ala Cys Tyr |
| (SEQ ID NO: 5862) | Cys Glu Phe Cys Glu Asn Gly Thr Cys Thr Gly Cys Tyr |
| (SEQ ID NO: 5863) | Cys Glu Phe Cys Glu Asn Gly Thr Cys Thr Ala Cys Tyr |
| (SEQ ID NO: 5864) | Cys Glu Phe Cys Glu Asn Gly Thr Cys Val Gly Cys Tyr |
| (SEQ ID NO: 5865) | Cys Glu Phe Cys Glu Asn Gly Thr Cys Val Ala Cys Tyr |
| (SEQ ID NO: 5866) | Cys Glu Phe Cys Glu Asn Gly Thr Cys Gly Gly Cys Tyr |
| (SEQ ID NO: 5867) | Cys Glu Phe Cys Glu Asn Gly Thr Cys Gly Ala Cys Tyr |
| (SEQ ID NO: 5868) | Cys Glu Phe Cys Gly Asn Pro Ala Cys Thr Gly Cys Tyr |
| (SEQ ID NO: 5869) | Cys Glu Phe Cys Gly Asn Pro Ala Cys Thr Ala Cys Tyr |
| (SEQ ID NO: 5870) | Cys Glu Phe Cys Gly Asn Pro Ala Cys Val Gly Cys Tyr |
| (SEQ ID NO: 5871) | Cys Glu Phe Cys Gly Asn Pro Ala Cys Val Ala Cys Tyr |
| (SEQ ID NO: 5872) | Cys Glu Phe Cys Gly Asn Pro Ala Cys Gly Gly Cys Tyr |
| (SEQ ID NO: 5873) | Cys Glu Phe Cys Gly Asn Pro Ala Cys Gly Ala Cys Tyr |
| (SEQ ID NO: 5874) | Cys Glu Phe Cys Gly Asn Pro Thr Cys Thr Gly Cys Tyr |
| (SEQ ID NO: 5875) | Cys Glu Phe Cys Gly Asn Pro Thr Cys Thr Ala Cys Tyr |
| (SEQ ID NO: 5876) | Cys Glu Phe Cys Gly Asn Pro Thr Cys Val Gly Cys Tyr |
| (SEQ ID NO: 5877) | Cys Glu Phe Cys Gly Asn Pro Thr Cys Val Ala Cys Tyr |
| (SEQ ID NO: 5878) | Cys Glu Phe Cys Gly Asn Pro Thr Cys Gly Gly Cys Tyr |
| (SEQ ID NO: 5879) | Cys Glu Phe Cys Gly Asn Pro Thr Cys Gly Ala Cys Tyr |
| (SEQ ID NO: 5880) | Cys Glu Phe Cys Gly Asn Gly Ala Cys Thr Gly Cys Tyr |
| (SEQ ID NO: 5881) | Cys Glu Phe Cys Gly Asn Gly Ala Cys Thr Ala Cys Tyr |

FIG. 3Z

| | |
|---|---|
| (SEQ ID NO: 5882) | Cys Glu Phe Cys Gly Asn Gly Ala Cys Val Gly Cys Tyr |
| (SEQ ID NO: 5883) | Cys Glu Phe Cys Gly Asn Gly Ala Cys Val Ala Cys Tyr |
| (SEQ ID NO: 5884) | Cys Glu Phe Cys Gly Asn Gly Ala Cys Gly Gly Cys Tyr |
| (SEQ ID NO: 5885) | Cys Glu Phe Cys Gly Asn Gly Ala Cys Gly Ala Cys Tyr |
| (SEQ ID NO: 5886) | Cys Glu Phe Cys Gly Asn Gly Thr Cys Thr Gly Cys Tyr |
| (SEQ ID NO: 5887) | Cys Glu Phe Cys Gly Asn Gly Thr Cys Thr Ala Cys Tyr |
| (SEQ ID NO: 5888) | Cys Glu Phe Cys Gly Asn Gly Thr Cys Val Gly Cys Tyr |
| (SEQ ID NO: 5889) | Cys Glu Phe Cys Gly Asn Gly Thr Cys Val Ala Cys Tyr |
| (SEQ ID NO: 5890) | Cys Glu Phe Cys Gly Asn Gly Thr Cys Gly Gly Cys Tyr |
| (SEQ ID NO: 5891) | Cys Glu Phe Cys Gly Asn Gly Thr Cys Gly Ala Cys Tyr |
| (SEQ ID NO: 5892) | Cys Glu Phe Cys His Asn Pro Ala Cys Thr Gly Cys Tyr |
| (SEQ ID NO: 5893) | Cys Glu Phe Cys His Asn Pro Ala Cys Thr Ala Cys Tyr |
| (SEQ ID NO: 5894) | Cys Glu Phe Cys His Asn Pro Ala Cys Val Gly Cys Tyr |
| (SEQ ID NO: 5895) | Cys Glu Phe Cys His Asn Pro Ala Cys Val Ala Cys Tyr |
| (SEQ ID NO: 5896) | Cys Glu Phe Cys His Asn Pro Ala Cys Gly Gly Cys Tyr |
| (SEQ ID NO: 5897) | Cys Glu Phe Cys His Asn Pro Ala Cys Gly Ala Cys Tyr |
| (SEQ ID NO: 5898) | Cys Glu Phe Cys His Asn Pro Thr Cys Thr Gly Cys Tyr |
| (SEQ ID NO: 5899) | Cys Glu Phe Cys His Asn Pro Thr Cys Thr Ala Cys Tyr |
| (SEQ ID NO: 5900) | Cys Glu Phe Cys His Asn Pro Thr Cys Val Gly Cys Tyr |
| (SEQ ID NO: 5901) | Cys Glu Phe Cys His Asn Pro Thr Cys Val Ala Cys Tyr |
| (SEQ ID NO: 5902) | Cys Glu Phe Cys His Asn Pro Thr Cys Gly Gly Cys Tyr |
| (SEQ ID NO: 5903) | Cys Glu Phe Cys His Asn Pro Thr Cys Gly Ala Cys Tyr |
| (SEQ ID NO: 5904) | Cys Glu Phe Cys His Asn Gly Ala Cys Thr Gly Cys Tyr |
| (SEQ ID NO: 5905) | Cys Glu Phe Cys His Asn Gly Ala Cys Thr Ala Cys Tyr |
| (SEQ ID NO: 5906) | Cys Glu Phe Cys His Asn Gly Ala Cys Val Gly Cys Tyr |
| (SEQ ID NO: 5907) | Cys Glu Phe Cys His Asn Gly Ala Cys Val Ala Cys Tyr |
| (SEQ ID NO: 5908) | Cys Glu Phe Cys His Asn Gly Ala Cys Gly Gly Cys Tyr |
| (SEQ ID NO: 5909) | Cys Glu Phe Cys His Asn Gly Ala Cys Gly Ala Cys Tyr |
| (SEQ ID NO: 5910) | Cys Glu Phe Cys His Asn Gly Thr Cys Thr Gly Cys Tyr |
| (SEQ ID NO: 5911) | Cys Glu Phe Cys His Asn Gly Thr Cys Thr Ala Cys Tyr |
| (SEQ ID NO: 5912) | Cys Glu Phe Cys His Asn Gly Thr Cys Val Gly Cys Tyr |
| (SEQ ID NO: 5913) | Cys Glu Phe Cys His Asn Gly Thr Cys Val Ala Cys Tyr |
| (SEQ ID NO: 5914) | Cys Glu Phe Cys His Asn Gly Thr Cys Gly Gly Cys Tyr |
| (SEQ ID NO: 5915) | Cys Glu Phe Cys His Asn Gly Thr Cys Gly Ala Cys Tyr |
| (SEQ ID NO: 5916) | Cys Glu Phe Cys Ile Asn Pro Ala Cys Thr Gly Cys Tyr |
| (SEQ ID NO: 5917) | Cys Glu Phe Cys Ile Asn Pro Ala Cys Thr Ala Cys Tyr |
| (SEQ ID NO: 5918) | Cys Glu Phe Cys Ile Asn Pro Ala Cys Val Gly Cys Tyr |
| (SEQ ID NO: 5919) | Cys Glu Phe Cys Ile Asn Pro Ala Cys Val Ala Cys Tyr |
| (SEQ ID NO: 5920) | Cys Glu Phe Cys Ile Asn Pro Ala Cys Gly Gly Cys Tyr |
| (SEQ ID NO: 5921) | Cys Glu Phe Cys Ile Asn Pro Ala Cys Gly Ala Cys Tyr |
| (SEQ ID NO: 5922) | Cys Glu Phe Cys Ile Asn Pro Thr Cys Thr Gly Cys Tyr |
| (SEQ ID NO: 5923) | Cys Glu Phe Cys Ile Asn Pro Thr Cys Thr Ala Cys Tyr |
| (SEQ ID NO: 5924) | Cys Glu Phe Cys Ile Asn Pro Thr Cys Val Gly Cys Tyr |

FIG. 3AA

| | |
|---|---|
| (SEQ ID NO: 5925) | Cys Glu Phe Cys Ile Asn Pro Thr Cys Val Ala Cys Tyr |
| (SEQ ID NO: 5926) | Cys Glu Phe Cys Ile Asn Pro Thr Cys Gly Gly Cys Tyr |
| (SEQ ID NO: 5927) | Cys Glu Phe Cys Ile Asn Pro Thr Cys Gly Ala Cys Tyr |
| (SEQ ID NO: 5928) | Cys Glu Phe Cys Ile Asn Gly Ala Cys Thr Gly Cys Tyr |
| (SEQ ID NO: 5929) | Cys Glu Phe Cys Ile Asn Gly Ala Cys Thr Ala Cys Tyr |
| (SEQ ID NO: 5930) | Cys Glu Phe Cys Ile Asn Gly Ala Cys Val Gly Cys Tyr |
| (SEQ ID NO: 5931) | Cys Glu Phe Cys Ile Asn Gly Ala Cys Val Ala Cys Tyr |
| (SEQ ID NO: 5932) | Cys Glu Phe Cys Ile Asn Gly Ala Cys Gly Gly Cys Tyr |
| (SEQ ID NO: 5933) | Cys Glu Phe Cys Ile Asn Gly Ala Cys Gly Ala Cys Tyr |
| (SEQ ID NO: 5934) | Cys Glu Phe Cys Ile Asn Gly Thr Cys Thr Gly Cys Tyr |
| (SEQ ID NO: 5935) | Cys Glu Phe Cys Ile Asn Gly Thr Cys Thr Ala Cys Tyr |
| (SEQ ID NO: 5936) | Cys Glu Phe Cys Ile Asn Gly Thr Cys Val Gly Cys Tyr |
| (SEQ ID NO: 5937) | Cys Glu Phe Cys Ile Asn Gly Thr Cys Val Ala Cys Tyr |
| (SEQ ID NO: 5938) | Cys Glu Phe Cys Ile Asn Gly Thr Cys Gly Gly Cys Tyr |
| (SEQ ID NO: 5939) | Cys Glu Phe Cys Ile Asn Gly Thr Cys Gly Ala Cys Tyr |
| (SEQ ID NO: 5940) | Cys Glu Phe Cys Leu Asn Pro Ala Cys Thr Gly Cys Tyr |
| (SEQ ID NO: 5941) | Cys Glu Phe Cys Leu Asn Pro Ala Cys Thr Ala Cys Tyr |
| (SEQ ID NO: 5942) | Cys Glu Phe Cys Leu Asn Pro Ala Cys Val Gly Cys Tyr |
| (SEQ ID NO: 5943) | Cys Glu Phe Cys Leu Asn Pro Ala Cys Val Ala Cys Tyr |
| (SEQ ID NO: 5944) | Cys Glu Phe Cys Leu Asn Pro Ala Cys Gly Gly Cys Tyr |
| (SEQ ID NO: 5945) | Cys Glu Phe Cys Leu Asn Pro Ala Cys Gly Ala Cys Tyr |
| (SEQ ID NO: 5946) | Cys Glu Phe Cys Leu Asn Pro Thr Cys Thr Gly Cys Tyr |
| (SEQ ID NO: 5947) | Cys Glu Phe Cys Leu Asn Pro Thr Cys Thr Ala Cys Tyr |
| (SEQ ID NO: 5948) | Cys Glu Phe Cys Leu Asn Pro Thr Cys Val Gly Cys Tyr |
| (SEQ ID NO: 5949) | Cys Glu Phe Cys Leu Asn Pro Thr Cys Val Ala Cys Tyr |
| (SEQ ID NO: 5950) | Cys Glu Phe Cys Leu Asn Pro Thr Cys Gly Gly Cys Tyr |
| (SEQ ID NO: 5951) | Cys Glu Phe Cys Leu Asn Pro Thr Cys Gly Ala Cys Tyr |
| (SEQ ID NO: 5952) | Cys Glu Phe Cys Leu Asn Gly Ala Cys Thr Gly Cys Tyr |
| (SEQ ID NO: 5953) | Cys Glu Phe Cys Leu Asn Gly Ala Cys Thr Ala Cys Tyr |
| (SEQ ID NO: 5954) | Cys Glu Phe Cys Leu Asn Gly Ala Cys Val Gly Cys Tyr |
| (SEQ ID NO: 5955) | Cys Glu Phe Cys Leu Asn Gly Ala Cys Val Ala Cys Tyr |
| (SEQ ID NO: 5956) | Cys Glu Phe Cys Leu Asn Gly Ala Cys Gly Gly Cys Tyr |
| (SEQ ID NO: 5957) | Cys Glu Phe Cys Leu Asn Gly Ala Cys Gly Ala Cys Tyr |
| (SEQ ID NO: 5958) | Cys Glu Phe Cys Leu Asn Gly Thr Cys Thr Gly Cys Tyr |
| (SEQ ID NO: 5959) | Cys Glu Phe Cys Leu Asn Gly Thr Cys Thr Ala Cys Tyr |
| (SEQ ID NO: 5960) | Cys Glu Phe Cys Leu Asn Gly Thr Cys Val Gly Cys Tyr |
| (SEQ ID NO: 5961) | Cys Glu Phe Cys Leu Asn Gly Thr Cys Val Ala Cys Tyr |
| (SEQ ID NO: 5962) | Cys Glu Phe Cys Leu Asn Gly Thr Cys Gly Gly Cys Tyr |
| (SEQ ID NO: 5963) | Cys Glu Phe Cys Leu Asn Gly Thr Cys Gly Ala Cys Tyr |
| (SEQ ID NO: 5964) | Cys Glu Phe Cys Lys Asn Pro Ala Cys Thr Gly Cys Tyr |
| (SEQ ID NO: 5965) | Cys Glu Phe Cys Lys Asn Pro Ala Cys Thr Ala Cys Tyr |
| (SEQ ID NO: 5966) | Cys Glu Phe Cys Lys Asn Pro Ala Cys Val Gly Cys Tyr |
| (SEQ ID NO: 5967) | Cys Glu Phe Cys Lys Asn Pro Ala Cys Val Ala Cys Tyr |

FIG. 3AB

| | |
|---|---|
| (SEQ ID NO: 5968) | Cys Glu Phe Cys Lys Asn Pro Ala Cys Gly Gly Cys Tyr |
| (SEQ ID NO: 5969) | Cys Glu Phe Cys Lys Asn Pro Ala Cys Gly Ala Cys Tyr |
| (SEQ ID NO: 5970) | Cys Glu Phe Cys Lys Asn Pro Thr Cys Thr Gly Cys Tyr |
| (SEQ ID NO: 5971) | Cys Glu Phe Cys Lys Asn Pro Thr Cys Thr Ala Cys Tyr |
| (SEQ ID NO: 5972) | Cys Glu Phe Cys Lys Asn Pro Thr Cys Val Gly Cys Tyr |
| (SEQ ID NO: 5973) | Cys Glu Phe Cys Lys Asn Pro Thr Cys Val Ala Cys Tyr |
| (SEQ ID NO: 5974) | Cys Glu Phe Cys Lys Asn Pro Thr Cys Gly Gly Cys Tyr |
| (SEQ ID NO: 5975) | Cys Glu Phe Cys Lys Asn Pro Thr Cys Gly Ala Cys Tyr |
| (SEQ ID NO: 5976) | Cys Glu Phe Cys Lys Asn Gly Ala Cys Thr Gly Cys Tyr |
| (SEQ ID NO: 5977) | Cys Glu Phe Cys Lys Asn Gly Ala Cys Thr Ala Cys Tyr |
| (SEQ ID NO: 5978) | Cys Glu Phe Cys Lys Asn Gly Ala Cys Val Gly Cys Tyr |
| (SEQ ID NO: 5979) | Cys Glu Phe Cys Lys Asn Gly Ala Cys Val Ala Cys Tyr |
| (SEQ ID NO: 5980) | Cys Glu Phe Cys Lys Asn Gly Ala Cys Gly Gly Cys Tyr |
| (SEQ ID NO: 5981) | Cys Glu Phe Cys Lys Asn Gly Ala Cys Gly Ala Cys Tyr |
| (SEQ ID NO: 5982) | Cys Glu Phe Cys Lys Asn Gly Thr Cys Thr Gly Cys Tyr |
| (SEQ ID NO: 5983) | Cys Glu Phe Cys Lys Asn Gly Thr Cys Thr Ala Cys Tyr |
| (SEQ ID NO: 5984) | Cys Glu Phe Cys Lys Asn Gly Thr Cys Val Gly Cys Tyr |
| (SEQ ID NO: 5985) | Cys Glu Phe Cys Lys Asn Gly Thr Cys Val Ala Cys Tyr |
| (SEQ ID NO: 5986) | Cys Glu Phe Cys Lys Asn Gly Thr Cys Gly Gly Cys Tyr |
| (SEQ ID NO: 5987) | Cys Glu Phe Cys Lys Asn Gly Thr Cys Gly Ala Cys Tyr |
| (SEQ ID NO: 5988) | Cys Glu Phe Cys Met Asn Pro Ala Cys Thr Gly Cys Tyr |
| (SEQ ID NO: 5989) | Cys Glu Phe Cys Met Asn Pro Ala Cys Thr Ala Cys Tyr |
| (SEQ ID NO: 5990) | Cys Glu Phe Cys Met Asn Pro Ala Cys Val Gly Cys Tyr |
| (SEQ ID NO: 5991) | Cys Glu Phe Cys Met Asn Pro Ala Cys Val Ala Cys Tyr |
| (SEQ ID NO: 5992) | Cys Glu Phe Cys Met Asn Pro Ala Cys Gly Gly Cys Tyr |
| (SEQ ID NO: 5993) | Cys Glu Phe Cys Met Asn Pro Ala Cys Gly Ala Cys Tyr |
| (SEQ ID NO: 5994) | Cys Glu Phe Cys Met Asn Pro Thr Cys Thr Gly Cys Tyr |
| (SEQ ID NO: 5995) | Cys Glu Phe Cys Met Asn Pro Thr Cys Thr Ala Cys Tyr |
| (SEQ ID NO: 5996) | Cys Glu Phe Cys Met Asn Pro Thr Cys Val Gly Cys Tyr |
| (SEQ ID NO: 5997) | Cys Glu Phe Cys Met Asn Pro Thr Cys Val Ala Cys Tyr |
| (SEQ ID NO: 5998) | Cys Glu Phe Cys Met Asn Pro Thr Cys Gly Gly Cys Tyr |
| (SEQ ID NO: 5999) | Cys Glu Phe Cys Met Asn Pro Thr Cys Gly Ala Cys Tyr |
| (SEQ ID NO: 6000) | Cys Glu Phe Cys Met Asn Gly Ala Cys Thr Gly Cys Tyr |
| (SEQ ID NO: 6001) | Cys Glu Phe Cys Met Asn Gly Ala Cys Thr Ala Cys Tyr |
| (SEQ ID NO: 6002) | Cys Glu Phe Cys Met Asn Gly Ala Cys Val Gly Cys Tyr |
| (SEQ ID NO: 6003) | Cys Glu Phe Cys Met Asn Gly Ala Cys Val Ala Cys Tyr |
| (SEQ ID NO: 6004) | Cys Glu Phe Cys Met Asn Gly Ala Cys Gly Gly Cys Tyr |
| (SEQ ID NO: 6005) | Cys Glu Phe Cys Met Asn Gly Ala Cys Gly Ala Cys Tyr |
| (SEQ ID NO: 6006) | Cys Glu Phe Cys Met Asn Gly Thr Cys Thr Gly Cys Tyr |
| (SEQ ID NO: 6007) | Cys Glu Phe Cys Met Asn Gly Thr Cys Thr Ala Cys Tyr |
| (SEQ ID NO: 6008) | Cys Glu Phe Cys Met Asn Gly Thr Cys Val Gly Cys Tyr |
| (SEQ ID NO: 6009) | Cys Glu Phe Cys Met Asn Gly Thr Cys Val Ala Cys Tyr |
| (SEQ ID NO: 6010) | Cys Glu Phe Cys Met Asn Gly Thr Cys Gly Gly Cys Tyr |

FIG. 3AC

| | |
|---|---|
| (SEQ ID NO: 6011) | Cys Glu Phe Cys Met Asn Gly Thr Cys Gly Ala Cys Tyr |
| (SEQ ID NO: 6012) | Cys Glu Phe Cys Phe Asn Pro Ala Cys Thr Gly Cys Tyr |
| (SEQ ID NO: 6013) | Cys Glu Phe Cys Phe Asn Pro Ala Cys Thr Ala Cys Tyr |
| (SEQ ID NO: 6014) | Cys Glu Phe Cys Phe Asn Pro Ala Cys Val Gly Cys Tyr |
| (SEQ ID NO: 6015) | Cys Glu Phe Cys Phe Asn Pro Ala Cys Val Ala Cys Tyr |
| (SEQ ID NO: 6016) | Cys Glu Phe Cys Phe Asn Pro Ala Cys Gly Gly Cys Tyr |
| (SEQ ID NO: 6017) | Cys Glu Phe Cys Phe Asn Pro Ala Cys Gly Ala Cys Tyr |
| (SEQ ID NO: 6018) | Cys Glu Phe Cys Phe Asn Pro Thr Cys Thr Gly Cys Tyr |
| (SEQ ID NO: 6019) | Cys Glu Phe Cys Phe Asn Pro Thr Cys Thr Ala Cys Tyr |
| (SEQ ID NO: 6020) | Cys Glu Phe Cys Phe Asn Pro Thr Cys Val Gly Cys Tyr |
| (SEQ ID NO: 6021) | Cys Glu Phe Cys Phe Asn Pro Thr Cys Val Ala Cys Tyr |
| (SEQ ID NO: 6022) | Cys Glu Phe Cys Phe Asn Pro Thr Cys Gly Gly Cys Tyr |
| (SEQ ID NO: 6023) | Cys Glu Phe Cys Phe Asn Pro Thr Cys Gly Ala Cys Tyr |
| (SEQ ID NO: 6024) | Cys Glu Phe Cys Phe Asn Gly Ala Cys Thr Gly Cys Tyr |
| (SEQ ID NO: 6025) | Cys Glu Phe Cys Phe Asn Gly Ala Cys Thr Ala Cys Tyr |
| (SEQ ID NO: 6026) | Cys Glu Phe Cys Phe Asn Gly Ala Cys Val Gly Cys Tyr |
| (SEQ ID NO: 6027) | Cys Glu Phe Cys Phe Asn Gly Ala Cys Val Ala Cys Tyr |
| (SEQ ID NO: 6028) | Cys Glu Phe Cys Phe Asn Gly Ala Cys Gly Gly Cys Tyr |
| (SEQ ID NO: 6029) | Cys Glu Phe Cys Phe Asn Gly Ala Cys Gly Ala Cys Tyr |
| (SEQ ID NO: 6030) | Cys Glu Phe Cys Phe Asn Gly Thr Cys Thr Gly Cys Tyr |
| (SEQ ID NO: 6031) | Cys Glu Phe Cys Phe Asn Gly Thr Cys Thr Ala Cys Tyr |
| (SEQ ID NO: 6032) | Cys Glu Phe Cys Phe Asn Gly Thr Cys Val Gly Cys Tyr |
| (SEQ ID NO: 6033) | Cys Glu Phe Cys Phe Asn Gly Thr Cys Val Ala Cys Tyr |
| (SEQ ID NO: 6034) | Cys Glu Phe Cys Phe Asn Gly Thr Cys Gly Gly Cys Tyr |
| (SEQ ID NO: 6035) | Cys Glu Phe Cys Phe Asn Gly Thr Cys Gly Ala Cys Tyr |
| (SEQ ID NO: 6036) | Cys Glu Phe Cys Pro Asn Pro Ala Cys Thr Gly Cys Tyr |
| (SEQ ID NO: 6037) | Cys Glu Phe Cys Pro Asn Pro Ala Cys Thr Ala Cys Tyr |
| (SEQ ID NO: 6038) | Cys Glu Phe Cys Pro Asn Pro Ala Cys Val Gly Cys Tyr |
| (SEQ ID NO: 6039) | Cys Glu Phe Cys Pro Asn Pro Ala Cys Val Ala Cys Tyr |
| (SEQ ID NO: 6040) | Cys Glu Phe Cys Pro Asn Pro Ala Cys Gly Gly Cys Tyr |
| (SEQ ID NO: 6041) | Cys Glu Phe Cys Pro Asn Pro Ala Cys Gly Ala Cys Tyr |
| (SEQ ID NO: 6042) | Cys Glu Phe Cys Pro Asn Pro Thr Cys Thr Gly Cys Tyr |
| (SEQ ID NO: 6043) | Cys Glu Phe Cys Pro Asn Pro Thr Cys Thr Ala Cys Tyr |
| (SEQ ID NO: 6044) | Cys Glu Phe Cys Pro Asn Pro Thr Cys Val Gly Cys Tyr |
| (SEQ ID NO: 6045) | Cys Glu Phe Cys Pro Asn Pro Thr Cys Val Ala Cys Tyr |
| (SEQ ID NO: 6046) | Cys Glu Phe Cys Pro Asn Pro Thr Cys Gly Gly Cys Tyr |
| (SEQ ID NO: 6047) | Cys Glu Phe Cys Pro Asn Pro Thr Cys Gly Ala Cys Tyr |
| (SEQ ID NO: 6048) | Cys Glu Phe Cys Pro Asn Gly Ala Cys Thr Gly Cys Tyr |
| (SEQ ID NO: 6049) | Cys Glu Phe Cys Pro Asn Gly Ala Cys Thr Ala Cys Tyr |
| (SEQ ID NO: 6050) | Cys Glu Phe Cys Pro Asn Gly Ala Cys Val Gly Cys Tyr |
| (SEQ ID NO: 6051) | Cys Glu Phe Cys Pro Asn Gly Ala Cys Val Ala Cys Tyr |
| (SEQ ID NO: 6052) | Cys Glu Phe Cys Pro Asn Gly Ala Cys Gly Gly Cys Tyr |
| (SEQ ID NO: 6053) | Cys Glu Phe Cys Pro Asn Gly Ala Cys Gly Ala Cys Tyr |

FIG. 3AD

| | |
|---|---|
| (SEQ ID NO: 6054) | Cys Glu Phe Cys Pro Asn Gly Thr Cys Thr Gly Cys Tyr |
| (SEQ ID NO: 6055) | Cys Glu Phe Cys Pro Asn Gly Thr Cys Thr Ala Cys Tyr |
| (SEQ ID NO: 6056) | Cys Glu Phe Cys Pro Asn Gly Thr Cys Val Gly Cys Tyr |
| (SEQ ID NO: 6057) | Cys Glu Phe Cys Pro Asn Gly Thr Cys Val Ala Cys Tyr |
| (SEQ ID NO: 6058) | Cys Glu Phe Cys Pro Asn Gly Thr Cys Gly Gly Cys Tyr |
| (SEQ ID NO: 6059) | Cys Glu Phe Cys Pro Asn Gly Thr Cys Gly Ala Cys Tyr |
| (SEQ ID NO: 6060) | Cys Glu Phe Cys Ser Asn Pro Ala Cys Thr Gly Cys Tyr |
| (SEQ ID NO: 6061) | Cys Glu Phe Cys Ser Asn Pro Ala Cys Thr Ala Cys Tyr |
| (SEQ ID NO: 6062) | Cys Glu Phe Cys Ser Asn Pro Ala Cys Val Gly Cys Tyr |
| (SEQ ID NO: 6063) | Cys Glu Phe Cys Ser Asn Pro Ala Cys Val Ala Cys Tyr |
| (SEQ ID NO: 6064) | Cys Glu Phe Cys Ser Asn Pro Ala Cys Gly Gly Cys Tyr |
| (SEQ ID NO: 6065) | Cys Glu Phe Cys Ser Asn Pro Ala Cys Gly Ala Cys Tyr |
| (SEQ ID NO: 6066) | Cys Glu Phe Cys Ser Asn Pro Thr Cys Thr Gly Cys Tyr |
| (SEQ ID NO: 6067) | Cys Glu Phe Cys Ser Asn Pro Thr Cys Thr Ala Cys Tyr |
| (SEQ ID NO: 6068) | Cys Glu Phe Cys Ser Asn Pro Thr Cys Val Gly Cys Tyr |
| (SEQ ID NO: 6069) | Cys Glu Phe Cys Ser Asn Pro Thr Cys Val Ala Cys Tyr |
| (SEQ ID NO: 6070) | Cys Glu Phe Cys Ser Asn Pro Thr Cys Gly Gly Cys Tyr |
| (SEQ ID NO: 6071) | Cys Glu Phe Cys Ser Asn Pro Thr Cys Gly Ala Cys Tyr |
| (SEQ ID NO: 6072) | Cys Glu Phe Cys Ser Asn Gly Ala Cys Thr Gly Cys Tyr |
| (SEQ ID NO: 6073) | Cys Glu Phe Cys Ser Asn Gly Ala Cys Thr Ala Cys Tyr |
| (SEQ ID NO: 6074) | Cys Glu Phe Cys Ser Asn Gly Ala Cys Val Gly Cys Tyr |
| (SEQ ID NO: 6075) | Cys Glu Phe Cys Ser Asn Gly Ala Cys Val Ala Cys Tyr |
| (SEQ ID NO: 6076) | Cys Glu Phe Cys Ser Asn Gly Ala Cys Gly Gly Cys Tyr |
| (SEQ ID NO: 6077) | Cys Glu Phe Cys Ser Asn Gly Ala Cys Gly Ala Cys Tyr |
| (SEQ ID NO: 6078) | Cys Glu Phe Cys Ser Asn Gly Thr Cys Thr Gly Cys Tyr |
| (SEQ ID NO: 6079) | Cys Glu Phe Cys Ser Asn Gly Thr Cys Thr Ala Cys Tyr |
| (SEQ ID NO: 6080) | Cys Glu Phe Cys Ser Asn Gly Thr Cys Val Gly Cys Tyr |
| (SEQ ID NO: 6081) | Cys Glu Phe Cys Ser Asn Gly Thr Cys Val Ala Cys Tyr |
| (SEQ ID NO: 6082) | Cys Glu Phe Cys Ser Asn Gly Thr Cys Gly Gly Cys Tyr |
| (SEQ ID NO: 6083) | Cys Glu Phe Cys Ser Asn Gly Thr Cys Gly Ala Cys Tyr |
| (SEQ ID NO: 6084) | Cys Glu Phe Cys Thr Asn Pro Ala Cys Thr Gly Cys Tyr |
| (SEQ ID NO: 6085) | Cys Glu Phe Cys Thr Asn Pro Ala Cys Thr Ala Cys Tyr |
| (SEQ ID NO: 6086) | Cys Glu Phe Cys Thr Asn Pro Ala Cys Val Gly Cys Tyr |
| (SEQ ID NO: 6087) | Cys Glu Phe Cys Thr Asn Pro Ala Cys Val Ala Cys Tyr |
| (SEQ ID NO: 6088) | Cys Glu Phe Cys Thr Asn Pro Ala Cys Gly Gly Cys Tyr |
| (SEQ ID NO: 6089) | Cys Glu Phe Cys Thr Asn Pro Ala Cys Gly Ala Cys Tyr |
| (SEQ ID NO: 6090) | Cys Glu Phe Cys Thr Asn Pro Thr Cys Thr Gly Cys Tyr |
| (SEQ ID NO: 6091) | Cys Glu Phe Cys Thr Asn Pro Thr Cys Thr Ala Cys Tyr |
| (SEQ ID NO: 6092) | Cys Glu Phe Cys Thr Asn Pro Thr Cys Val Gly Cys Tyr |
| (SEQ ID NO: 6093) | Cys Glu Phe Cys Thr Asn Pro Thr Cys Val Ala Cys Tyr |
| (SEQ ID NO: 6094) | Cys Glu Phe Cys Thr Asn Pro Thr Cys Gly Gly Cys Tyr |
| (SEQ ID NO: 6095) | Cys Glu Phe Cys Thr Asn Pro Thr Cys Gly Ala Cys Tyr |
| (SEQ ID NO: 6096) | Cys Glu Phe Cys Thr Asn Gly Ala Cys Thr Gly Cys Tyr |

FIG. 3AE

| | |
|---|---|
| (SEQ ID NO: 6097) | Cys Glu Phe Cys Thr Asn Gly Ala Cys Thr Ala Cys Tyr |
| (SEQ ID NO: 6098) | Cys Glu Phe Cys Thr Asn Gly Ala Cys Val Gly Cys Tyr |
| (SEQ ID NO: 6099) | Cys Glu Phe Cys Thr Asn Gly Ala Cys Val Ala Cys Tyr |
| (SEQ ID NO: 6100) | Cys Glu Phe Cys Thr Asn Gly Ala Cys Gly Gly Cys Tyr |
| (SEQ ID NO: 6101) | Cys Glu Phe Cys Thr Asn Gly Ala Cys Gly Ala Cys Tyr |
| (SEQ ID NO: 6102) | Cys Glu Phe Cys Thr Asn Gly Thr Cys Thr Gly Cys Tyr |
| (SEQ ID NO: 6103) | Cys Glu Phe Cys Thr Asn Gly Thr Cys Thr Ala Cys Tyr |
| (SEQ ID NO: 6104) | Cys Glu Phe Cys Thr Asn Gly Thr Cys Val Gly Cys Tyr |
| (SEQ ID NO: 6105) | Cys Glu Phe Cys Thr Asn Gly Thr Cys Val Ala Cys Tyr |
| (SEQ ID NO: 6106) | Cys Glu Phe Cys Thr Asn Gly Thr Cys Gly Gly Cys Tyr |
| (SEQ ID NO: 6107) | Cys Glu Phe Cys Thr Asn Gly Thr Cys Gly Ala Cys Tyr |
| (SEQ ID NO: 6108) | Cys Glu Phe Cys Trp Asn Pro Ala Cys Thr Gly Cys Tyr |
| (SEQ ID NO: 6109) | Cys Glu Phe Cys Trp Asn Pro Ala Cys Thr Ala Cys Tyr |
| (SEQ ID NO: 6110) | Cys Glu Phe Cys Trp Asn Pro Ala Cys Val Gly Cys Tyr |
| (SEQ ID NO: 6111) | Cys Glu Phe Cys Trp Asn Pro Ala Cys Val Ala Cys Tyr |
| (SEQ ID NO: 6112) | Cys Glu Phe Cys Trp Asn Pro Ala Cys Gly Gly Cys Tyr |
| (SEQ ID NO: 6113) | Cys Glu Phe Cys Trp Asn Pro Ala Cys Gly Ala Cys Tyr |
| (SEQ ID NO: 6114) | Cys Glu Phe Cys Trp Asn Pro Thr Cys Thr Gly Cys Tyr |
| (SEQ ID NO: 6115) | Cys Glu Phe Cys Trp Asn Pro Thr Cys Thr Ala Cys Tyr |
| (SEQ ID NO: 6116) | Cys Glu Phe Cys Trp Asn Pro Thr Cys Val Gly Cys Tyr |
| (SEQ ID NO: 6117) | Cys Glu Phe Cys Trp Asn Pro Thr Cys Val Ala Cys Tyr |
| (SEQ ID NO: 6118) | Cys Glu Phe Cys Trp Asn Pro Thr Cys Gly Gly Cys Tyr |
| (SEQ ID NO: 6119) | Cys Glu Phe Cys Trp Asn Pro Thr Cys Gly Ala Cys Tyr |
| (SEQ ID NO: 6120) | Cys Glu Phe Cys Trp Asn Gly Ala Cys Thr Gly Cys Tyr |
| (SEQ ID NO: 6121) | Cys Glu Phe Cys Trp Asn Gly Ala Cys Thr Ala Cys Tyr |
| (SEQ ID NO: 6122) | Cys Glu Phe Cys Trp Asn Gly Ala Cys Val Gly Cys Tyr |
| (SEQ ID NO: 6123) | Cys Glu Phe Cys Trp Asn Gly Ala Cys Val Ala Cys Tyr |
| (SEQ ID NO: 6124) | Cys Glu Phe Cys Trp Asn Gly Ala Cys Gly Gly Cys Tyr |
| (SEQ ID NO: 6125) | Cys Glu Phe Cys Trp Asn Gly Ala Cys Gly Ala Cys Tyr |
| (SEQ ID NO: 6126) | Cys Glu Phe Cys Trp Asn Gly Thr Cys Thr Gly Cys Tyr |
| (SEQ ID NO: 6127) | Cys Glu Phe Cys Trp Asn Gly Thr Cys Thr Ala Cys Tyr |
| (SEQ ID NO: 6128) | Cys Glu Phe Cys Trp Asn Gly Thr Cys Val Gly Cys Tyr |
| (SEQ ID NO: 6129) | Cys Glu Phe Cys Trp Asn Gly Thr Cys Val Ala Cys Tyr |
| (SEQ ID NO: 6130) | Cys Glu Phe Cys Trp Asn Gly Thr Cys Gly Gly Cys Tyr |
| (SEQ ID NO: 6131) | Cys Glu Phe Cys Trp Asn Gly Thr Cys Gly Ala Cys Tyr |
| (SEQ ID NO: 6132) | Cys Glu Phe Cys Tyr Asn Pro Ala Cys Thr Gly Cys Tyr |
| (SEQ ID NO: 6133) | Cys Glu Phe Cys Tyr Asn Pro Ala Cys Thr Ala Cys Tyr |
| (SEQ ID NO: 6134) | Cys Glu Phe Cys Tyr Asn Pro Ala Cys Val Gly Cys Tyr |
| (SEQ ID NO: 6135) | Cys Glu Phe Cys Tyr Asn Pro Ala Cys Val Ala Cys Tyr |
| (SEQ ID NO: 6136) | Cys Glu Phe Cys Tyr Asn Pro Ala Cys Gly Gly Cys Tyr |
| (SEQ ID NO: 6137) | Cys Glu Phe Cys Tyr Asn Pro Ala Cys Gly Ala Cys Tyr |
| (SEQ ID NO: 6138) | Cys Glu Phe Cys Tyr Asn Pro Thr Cys Thr Gly Cys Tyr |
| (SEQ ID NO: 6139) | Cys Glu Phe Cys Tyr Asn Pro Thr Cys Thr Ala Cys Tyr |

FIG. 3AF

| | |
|---|---|
| (SEQ ID NO: 6140) | Cys Glu Phe Cys Tyr Asn Pro Thr Cys Val Gly Cys Tyr |
| (SEQ ID NO: 6141) | Cys Glu Phe Cys Tyr Asn Pro Thr Cys Val Ala Cys Tyr |
| (SEQ ID NO: 6142) | Cys Glu Phe Cys Tyr Asn Pro Thr Cys Gly Gly Cys Tyr |
| (SEQ ID NO: 6143) | Cys Glu Phe Cys Tyr Asn Pro Thr Cys Gly Ala Cys Tyr |
| (SEQ ID NO: 6144) | Cys Glu Phe Cys Tyr Asn Gly Ala Cys Thr Gly Cys Tyr |
| (SEQ ID NO: 6145) | Cys Glu Phe Cys Tyr Asn Gly Ala Cys Thr Ala Cys Tyr |
| (SEQ ID NO: 6146) | Cys Glu Phe Cys Tyr Asn Gly Ala Cys Val Gly Cys Tyr |
| (SEQ ID NO: 6147) | Cys Glu Phe Cys Tyr Asn Gly Ala Cys Val Ala Cys Tyr |
| (SEQ ID NO: 6148) | Cys Glu Phe Cys Tyr Asn Gly Ala Cys Gly Gly Cys Tyr |
| (SEQ ID NO: 6149) | Cys Glu Phe Cys Tyr Asn Gly Ala Cys Gly Ala Cys Tyr |
| (SEQ ID NO: 6150) | Cys Glu Phe Cys Tyr Asn Gly Thr Cys Thr Gly Cys Tyr |
| (SEQ ID NO: 6151) | Cys Glu Phe Cys Tyr Asn Gly Thr Cys Thr Ala Cys Tyr |
| (SEQ ID NO: 6152) | Cys Glu Phe Cys Tyr Asn Gly Thr Cys Val Gly Cys Tyr |
| (SEQ ID NO: 6153) | Cys Glu Phe Cys Tyr Asn Gly Thr Cys Val Ala Cys Tyr |
| (SEQ ID NO: 6154) | Cys Glu Phe Cys Tyr Asn Gly Thr Cys Gly Gly Cys Tyr |
| (SEQ ID NO: 6155) | Cys Glu Phe Cys Tyr Asn Gly Thr Cys Gly Ala Cys Tyr |
| (SEQ ID NO: 6156) | Cys Glu Phe Cys Val Asn Pro Ala Cys Thr Gly Cys Tyr |
| (SEQ ID NO: 6157) | Cys Glu Phe Cys Val Asn Pro Ala Cys Thr Ala Cys Tyr |
| (SEQ ID NO: 6158) | Cys Glu Phe Cys Val Asn Pro Ala Cys Val Gly Cys Tyr |
| (SEQ ID NO: 6159) | Cys Glu Phe Cys Val Asn Pro Ala Cys Val Ala Cys Tyr |
| (SEQ ID NO: 6160) | Cys Glu Phe Cys Val Asn Pro Ala Cys Gly Gly Cys Tyr |
| (SEQ ID NO: 6161) | Cys Glu Phe Cys Val Asn Pro Ala Cys Gly Ala Cys Tyr |
| (SEQ ID NO: 6162) | Cys Glu Phe Cys Val Asn Pro Thr Cys Thr Gly Cys Tyr |
| (SEQ ID NO: 6163) | Cys Glu Phe Cys Val Asn Pro Thr Cys Thr Ala Cys Tyr |
| (SEQ ID NO: 6164) | Cys Glu Phe Cys Val Asn Pro Thr Cys Val Gly Cys Tyr |
| (SEQ ID NO: 6165) | Cys Glu Phe Cys Val Asn Pro Thr Cys Val Ala Cys Tyr |
| (SEQ ID NO: 6166) | Cys Glu Phe Cys Val Asn Pro Thr Cys Gly Gly Cys Tyr |
| (SEQ ID NO: 6167) | Cys Glu Phe Cys Val Asn Pro Thr Cys Gly Ala Cys Tyr |
| (SEQ ID NO: 6168) | Cys Glu Phe Cys Val Asn Gly Ala Cys Thr Gly Cys Tyr |
| (SEQ ID NO: 6169) | Cys Glu Phe Cys Val Asn Gly Ala Cys Thr Ala Cys Tyr |
| (SEQ ID NO: 6170) | Cys Glu Phe Cys Val Asn Gly Ala Cys Val Gly Cys Tyr |
| (SEQ ID NO: 6171) | Cys Glu Phe Cys Val Asn Gly Ala Cys Val Ala Cys Tyr |
| (SEQ ID NO: 6172) | Cys Glu Phe Cys Val Asn Gly Ala Cys Gly Gly Cys Tyr |
| (SEQ ID NO: 6173) | Cys Glu Phe Cys Val Asn Gly Ala Cys Gly Ala Cys Tyr |
| (SEQ ID NO: 6174) | Cys Glu Phe Cys Val Asn Gly Thr Cys Thr Gly Cys Tyr |
| (SEQ ID NO: 6175) | Cys Glu Phe Cys Val Asn Gly Thr Cys Thr Ala Cys Tyr |
| (SEQ ID NO: 6176) | Cys Glu Phe Cys Val Asn Gly Thr Cys Val Gly Cys Tyr |
| (SEQ ID NO: 6177) | Cys Glu Phe Cys Val Asn Gly Thr Cys Val Ala Cys Tyr |
| (SEQ ID NO: 6178) | Cys Glu Phe Cys Val Asn Gly Thr Cys Gly Gly Cys Tyr |
| (SEQ ID NO: 6179) | Cys Glu Phe Cys Val Asn Gly Thr Cys Gly Ala Cys Tyr |
| (SEQ ID NO: 6180) | Cys Glu Phe Cys --- Asn Pro Ala Cys Thr Gly Cys Tyr |
| (SEQ ID NO: 6181) | Cys Glu Phe Cys --- Asn Pro Ala Cys Thr Ala Cys Tyr |
| (SEQ ID NO: 6182) | Cys Glu Phe Cys --- Asn Pro Ala Cys Val Gly Cys Tyr |

FIG. 3AG

| | |
|---|---|
| (SEQ ID NO: 6183) | Cys Glu Phe Cys --- Asn Pro Ala Cys Val Ala Cys Tyr |
| (SEQ ID NO: 6184) | Cys Glu Phe Cys --- Asn Pro Ala Cys Gly Gly Cys Tyr |
| (SEQ ID NO: 6185) | Cys Glu Phe Cys --- Asn Pro Ala Cys Gly Ala Cys Tyr |
| (SEQ ID NO: 6186) | Cys Glu Phe Cys --- Asn Pro Thr Cys Thr Gly Cys Tyr |
| (SEQ ID NO: 6187) | Cys Glu Phe Cys --- Asn Pro Thr Cys Thr Ala Cys Tyr |
| (SEQ ID NO: 6188) | Cys Glu Phe Cys --- Asn Pro Thr Cys Val Gly Cys Tyr |
| (SEQ ID NO: 6189) | Cys Glu Phe Cys --- Asn Pro Thr Cys Val Ala Cys Tyr |
| (SEQ ID NO: 6190) | Cys Glu Phe Cys --- Asn Pro Thr Cys Gly Gly Cys Tyr |
| (SEQ ID NO: 6191) | Cys Glu Phe Cys --- Asn Pro Thr Cys Gly Ala Cys Tyr |
| (SEQ ID NO: 6192) | Cys Glu Phe Cys --- Asn Gly Ala Cys Thr Gly Cys Tyr |
| (SEQ ID NO: 6193) | Cys Glu Phe Cys --- Asn Gly Ala Cys Thr Ala Cys Tyr |
| (SEQ ID NO: 6194) | Cys Glu Phe Cys --- Asn Gly Ala Cys Val Gly Cys Tyr |
| (SEQ ID NO: 6195) | Cys Glu Phe Cys --- Asn Gly Ala Cys Val Ala Cys Tyr |
| (SEQ ID NO: 6196) | Cys Glu Phe Cys --- Asn Gly Ala Cys Gly Gly Cys Tyr |
| (SEQ ID NO: 6197) | Cys Glu Phe Cys --- Asn Gly Ala Cys Gly Ala Cys Tyr |
| (SEQ ID NO: 6198) | Cys Glu Phe Cys --- Asn Gly Thr Cys Thr Gly Cys Tyr |
| (SEQ ID NO: 6199) | Cys Glu Phe Cys --- Asn Gly Thr Cys Thr Ala Cys Tyr |
| (SEQ ID NO: 6200) | Cys Glu Phe Cys --- Asn Gly Thr Cys Val Gly Cys Tyr |
| (SEQ ID NO: 6201) | Cys Glu Phe Cys --- Asn Gly Thr Cys Val Ala Cys Tyr |
| (SEQ ID NO: 6202) | Cys Glu Phe Cys --- Asn Gly Thr Cys Gly Gly Cys Tyr |
| (SEQ ID NO: 6203) | Cys Glu Phe Cys --- Asn Gly Thr Cys Gly Ala Cys Tyr |
| (SEQ ID NO: 6204) | Cys Glu Leu Cys Ala Asn Pro Ala Cys Thr Gly Cys Tyr |
| (SEQ ID NO: 6205) | Cys Glu Leu Cys Ala Asn Pro Ala Cys Thr Ala Cys Tyr |
| (SEQ ID NO: 6206) | Cys Glu Leu Cys Ala Asn Pro Ala Cys Val Gly Cys Tyr |
| (SEQ ID NO: 6207) | Cys Glu Leu Cys Ala Asn Pro Ala Cys Val Ala Cys Tyr |
| (SEQ ID NO: 6208) | Cys Glu Leu Cys Ala Asn Pro Ala Cys Gly Gly Cys Tyr |
| (SEQ ID NO: 6209) | Cys Glu Leu Cys Ala Asn Pro Ala Cys Gly Ala Cys Tyr |
| (SEQ ID NO: 6210) | Cys Glu Leu Cys Ala Asn Pro Thr Cys Thr Gly Cys Tyr |
| (SEQ ID NO: 6211) | Cys Glu Leu Cys Ala Asn Pro Thr Cys Thr Ala Cys Tyr |
| (SEQ ID NO: 6212) | Cys Glu Leu Cys Ala Asn Pro Thr Cys Val Gly Cys Tyr |
| (SEQ ID NO: 6213) | Cys Glu Leu Cys Ala Asn Pro Thr Cys Val Ala Cys Tyr |
| (SEQ ID NO: 6214) | Cys Glu Leu Cys Ala Asn Pro Thr Cys Gly Gly Cys Tyr |
| (SEQ ID NO: 6215) | Cys Glu Leu Cys Ala Asn Pro Thr Cys Gly Ala Cys Tyr |
| (SEQ ID NO: 6216) | Cys Glu Leu Cys Ala Asn Gly Ala Cys Thr Gly Cys Tyr |
| (SEQ ID NO: 6217) | Cys Glu Leu Cys Ala Asn Gly Ala Cys Thr Ala Cys Tyr |
| (SEQ ID NO: 6218) | Cys Glu Leu Cys Ala Asn Gly Ala Cys Val Gly Cys Tyr |
| (SEQ ID NO: 6219) | Cys Glu Leu Cys Ala Asn Gly Ala Cys Val Ala Cys Tyr |
| (SEQ ID NO: 6220) | Cys Glu Leu Cys Ala Asn Gly Ala Cys Gly Gly Cys Tyr |
| (SEQ ID NO: 6221) | Cys Glu Leu Cys Ala Asn Gly Ala Cys Gly Ala Cys Tyr |
| (SEQ ID NO: 6222) | Cys Glu Leu Cys Ala Asn Gly Thr Cys Thr Gly Cys Tyr |
| (SEQ ID NO: 6223) | Cys Glu Leu Cys Ala Asn Gly Thr Cys Thr Ala Cys Tyr |
| (SEQ ID NO: 6224) | Cys Glu Leu Cys Ala Asn Gly Thr Cys Val Gly Cys Tyr |
| (SEQ ID NO: 6225) | Cys Glu Leu Cys Ala Asn Gly Thr Cys Val Ala Cys Tyr |

FIG. 3AH (SEQ ID NO: 6226) Cys Glu Leu Cys Ala Asn Gly Thr Cys Gly Gly Cys Tyr
(SEQ ID NO: 6227) Cys Glu Leu Cys Ala Asn Gly Thr Cys Gly Ala Cys Tyr
(SEQ ID NO: 6228) Cys Glu Leu Cys Arg Asn Pro Ala Cys Thr Gly Cys Tyr
(SEQ ID NO: 6229) Cys Glu Leu Cys Arg Asn Pro Ala Cys Thr Ala Cys Tyr
(SEQ ID NO: 6230) Cys Glu Leu Cys Arg Asn Pro Ala Cys Val Gly Cys Tyr
(SEQ ID NO: 6231) Cys Glu Leu Cys Arg Asn Pro Ala Cys Val Ala Cys Tyr
(SEQ ID NO: 6232) Cys Glu Leu Cys Arg Asn Pro Ala Cys Gly Gly Cys Tyr
(SEQ ID NO: 6233) Cys Glu Leu Cys Arg Asn Pro Ala Cys Gly Ala Cys Tyr
(SEQ ID NO: 6234) Cys Glu Leu Cys Arg Asn Pro Thr Cys Thr Gly Cys Tyr
(SEQ ID NO: 6235) Cys Glu Leu Cys Arg Asn Pro Thr Cys Thr Ala Cys Tyr
(SEQ ID NO: 6236) Cys Glu Leu Cys Arg Asn Pro Thr Cys Val Gly Cys Tyr
(SEQ ID NO: 6237) Cys Glu Leu Cys Arg Asn Pro Thr Cys Val Ala Cys Tyr
(SEQ ID NO: 6238) Cys Glu Leu Cys Arg Asn Pro Thr Cys Gly Gly Cys Tyr
(SEQ ID NO: 6239) Cys Glu Leu Cys Arg Asn Pro Thr Cys Gly Ala Cys Tyr
(SEQ ID NO: 6240) Cys Glu Leu Cys Arg Asn Gly Ala Cys Thr Gly Cys Tyr
(SEQ ID NO: 6241) Cys Glu Leu Cys Arg Asn Gly Ala Cys Thr Ala Cys Tyr
(SEQ ID NO: 6242) Cys Glu Leu Cys Arg Asn Gly Ala Cys Val Gly Cys Tyr
(SEQ ID NO: 6243) Cys Glu Leu Cys Arg Asn Gly Ala Cys Val Ala Cys Tyr
(SEQ ID NO: 6244) Cys Glu Leu Cys Arg Asn Gly Ala Cys Gly Gly Cys Tyr
(SEQ ID NO: 6245) Cys Glu Leu Cys Arg Asn Gly Ala Cys Gly Ala Cys Tyr
(SEQ ID NO: 6246) Cys Glu Leu Cys Arg Asn Gly Thr Cys Thr Gly Cys Tyr
(SEQ ID NO: 6247) Cys Glu Leu Cys Arg Asn Gly Thr Cys Thr Ala Cys Tyr
(SEQ ID NO: 6248) Cys Glu Leu Cys Arg Asn Gly Thr Cys Val Gly Cys Tyr
(SEQ ID NO: 6249) Cys Glu Leu Cys Arg Asn Gly Thr Cys Val Ala Cys Tyr
(SEQ ID NO: 6250) Cys Glu Leu Cys Arg Asn Gly Thr Cys Gly Gly Cys Tyr
(SEQ ID NO: 6251) Cys Glu Leu Cys Arg Asn Gly Thr Cys Gly Ala Cys Tyr
(SEQ ID NO: 6252) Cys Glu Leu Cys Asn Asn Pro Ala Cys Thr Gly Cys Tyr
(SEQ ID NO: 6253) Cys Glu Leu Cys Asn Asn Pro Ala Cys Thr Ala Cys Tyr
(SEQ ID NO: 6254) Cys Glu Leu Cys Asn Asn Pro Ala Cys Val Gly Cys Tyr
(SEQ ID NO: 6255) Cys Glu Leu Cys Asn Asn Pro Ala Cys Val Ala Cys Tyr
(SEQ ID NO: 6256) Cys Glu Leu Cys Asn Asn Pro Ala Cys Gly Gly Cys Tyr
(SEQ ID NO: 6257) Cys Glu Leu Cys Asn Asn Pro Ala Cys Gly Ala Cys Tyr
(SEQ ID NO: 6258) Cys Glu Leu Cys Asn Asn Pro Thr Cys Thr Gly Cys Tyr
(SEQ ID NO: 6259) Cys Glu Leu Cys Asn Asn Pro Thr Cys Thr Ala Cys Tyr
(SEQ ID NO: 6260) Cys Glu Leu Cys Asn Asn Pro Thr Cys Val Gly Cys Tyr
(SEQ ID NO: 6261) Cys Glu Leu Cys Asn Asn Pro Thr Cys Val Ala Cys Tyr
(SEQ ID NO: 6262) Cys Glu Leu Cys Asn Asn Pro Thr Cys Gly Gly Cys Tyr
(SEQ ID NO: 6263) Cys Glu Leu Cys Asn Asn Pro Thr Cys Gly Ala Cys Tyr
(SEQ ID NO: 6264) Cys Glu Leu Cys Asn Asn Gly Ala Cys Thr Gly Cys Tyr
(SEQ ID NO: 6265) Cys Glu Leu Cys Asn Asn Gly Ala Cys Thr Ala Cys Tyr
(SEQ ID NO: 6266) Cys Glu Leu Cys Asn Asn Gly Ala Cys Val Gly Cys Tyr
(SEQ ID NO: 6267) Cys Glu Leu Cys Asn Asn Gly Ala Cys Val Ala Cys Tyr
(SEQ ID NO: 6268) Cys Glu Leu Cys Asn Asn Gly Ala Cys Gly Gly Cys Tyr

FIG. 3AI (SEQ ID NO: 6269)  Cys Glu Leu Cys Asn Asn Gly Ala Cys Gly Ala Cys Tyr
(SEQ ID NO: 6270)  Cys Glu Leu Cys Asn Asn Gly Thr Cys Thr Gly Cys Tyr
(SEQ ID NO: 6271)  Cys Glu Leu Cys Asn Asn Gly Thr Cys Thr Ala Cys Tyr
(SEQ ID NO: 6272)  Cys Glu Leu Cys Asn Asn Gly Thr Cys Val Gly Cys Tyr
(SEQ ID NO: 6273)  Cys Glu Leu Cys Asn Asn Gly Thr Cys Val Ala Cys Tyr
(SEQ ID NO: 6274)  Cys Glu Leu Cys Asn Asn Gly Thr Cys Gly Gly Cys Tyr
(SEQ ID NO: 6275)  Cys Glu Leu Cys Asn Asn Gly Thr Cys Gly Ala Cys Tyr
(SEQ ID NO: 6276)  Cys Glu Leu Cys Asp Asn Pro Ala Cys Thr Gly Cys Tyr
(SEQ ID NO: 6277)  Cys Glu Leu Cys Asp Asn Pro Ala Cys Thr Ala Cys Tyr
(SEQ ID NO: 6278)  Cys Glu Leu Cys Asp Asn Pro Ala Cys Val Gly Cys Tyr
(SEQ ID NO: 6279)  Cys Glu Leu Cys Asp Asn Pro Ala Cys Val Ala Cys Tyr
(SEQ ID NO: 6280)  Cys Glu Leu Cys Asp Asn Pro Ala Cys Gly Gly Cys Tyr
(SEQ ID NO: 6281)  Cys Glu Leu Cys Asp Asn Pro Ala Cys Gly Ala Cys Tyr
(SEQ ID NO: 6282)  Cys Glu Leu Cys Asp Asn Pro Thr Cys Thr Gly Cys Tyr
(SEQ ID NO: 6283)  Cys Glu Leu Cys Asp Asn Pro Thr Cys Thr Ala Cys Tyr
(SEQ ID NO: 6284)  Cys Glu Leu Cys Asp Asn Pro Thr Cys Val Gly Cys Tyr
(SEQ ID NO: 6285)  Cys Glu Leu Cys Asp Asn Pro Thr Cys Val Ala Cys Tyr
(SEQ ID NO: 6286)  Cys Glu Leu Cys Asp Asn Pro Thr Cys Gly Gly Cys Tyr
(SEQ ID NO: 6287)  Cys Glu Leu Cys Asp Asn Pro Thr Cys Gly Ala Cys Tyr
(SEQ ID NO: 6288)  Cys Glu Leu Cys Asp Asn Gly Ala Cys Thr Gly Cys Tyr
(SEQ ID NO: 6289)  Cys Glu Leu Cys Asp Asn Gly Ala Cys Thr Ala Cys Tyr
(SEQ ID NO: 6290)  Cys Glu Leu Cys Asp Asn Gly Ala Cys Val Gly Cys Tyr
(SEQ ID NO: 6291)  Cys Glu Leu Cys Asp Asn Gly Ala Cys Val Ala Cys Tyr
(SEQ ID NO: 6292)  Cys Glu Leu Cys Asp Asn Gly Ala Cys Gly Gly Cys Tyr
(SEQ ID NO: 6293)  Cys Glu Leu Cys Asp Asn Gly Ala Cys Gly Ala Cys Tyr
(SEQ ID NO: 6294)  Cys Glu Leu Cys Asp Asn Gly Thr Cys Thr Gly Cys Tyr
(SEQ ID NO: 6295)  Cys Glu Leu Cys Asp Asn Gly Thr Cys Thr Ala Cys Tyr
(SEQ ID NO: 6296)  Cys Glu Leu Cys Asp Asn Gly Thr Cys Val Gly Cys Tyr
(SEQ ID NO: 6297)  Cys Glu Leu Cys Asp Asn Gly Thr Cys Val Ala Cys Tyr
(SEQ ID NO: 6298)  Cys Glu Leu Cys Asp Asn Gly Thr Cys Gly Gly Cys Tyr
(SEQ ID NO: 6299)  Cys Glu Leu Cys Asp Asn Gly Thr Cys Gly Ala Cys Tyr
(SEQ ID NO: 6300)  Cys Glu Leu Cys Gln Asn Pro Ala Cys Thr Gly Cys Tyr
(SEQ ID NO: 6301)  Cys Glu Leu Cys Gln Asn Pro Ala Cys Thr Ala Cys Tyr
(SEQ ID NO: 6302)  Cys Glu Leu Cys Gln Asn Pro Ala Cys Val Gly Cys Tyr
(SEQ ID NO: 6303)  Cys Glu Leu Cys Gln Asn Pro Ala Cys Val Ala Cys Tyr
(SEQ ID NO: 6304)  Cys Glu Leu Cys Gln Asn Pro Ala Cys Gly Gly Cys Tyr
(SEQ ID NO: 6305)  Cys Glu Leu Cys Gln Asn Pro Ala Cys Gly Ala Cys Tyr
(SEQ ID NO: 6306)  Cys Glu Leu Cys Gln Asn Pro Thr Cys Thr Gly Cys Tyr
(SEQ ID NO: 6307)  Cys Glu Leu Cys Gln Asn Pro Thr Cys Thr Ala Cys Tyr
(SEQ ID NO: 6308)  Cys Glu Leu Cys Gln Asn Pro Thr Cys Val Gly Cys Tyr
(SEQ ID NO: 6309)  Cys Glu Leu Cys Gln Asn Pro Thr Cys Val Ala Cys Tyr
(SEQ ID NO: 6310)  Cys Glu Leu Cys Gln Asn Pro Thr Cys Gly Gly Cys Tyr
(SEQ ID NO: 6311)  Cys Glu Leu Cys Gln Asn Pro Thr Cys Gly Ala Cys Tyr

FIG. 3AJ

| | |
|---|---|
| (SEQ ID NO: 6312) | Cys Glu Leu Cys Gln Asn Gly Ala Cys Thr Gly Cys Tyr |
| (SEQ ID NO: 6313) | Cys Glu Leu Cys Gln Asn Gly Ala Cys Thr Ala Cys Tyr |
| (SEQ ID NO: 6314) | Cys Glu Leu Cys Gln Asn Gly Ala Cys Val Gly Cys Tyr |
| (SEQ ID NO: 6315) | Cys Glu Leu Cys Gln Asn Gly Ala Cys Val Ala Cys Tyr |
| (SEQ ID NO: 6316) | Cys Glu Leu Cys Gln Asn Gly Ala Cys Gly Gly Cys Tyr |
| (SEQ ID NO: 6317) | Cys Glu Leu Cys Gln Asn Gly Ala Cys Gly Ala Cys Tyr |
| (SEQ ID NO: 6318) | Cys Glu Leu Cys Gln Asn Gly Thr Cys Thr Gly Cys Tyr |
| (SEQ ID NO: 6319) | Cys Glu Leu Cys Gln Asn Gly Thr Cys Thr Ala Cys Tyr |
| (SEQ ID NO: 6320) | Cys Glu Leu Cys Gln Asn Gly Thr Cys Val Gly Cys Tyr |
| (SEQ ID NO: 6321) | Cys Glu Leu Cys Gln Asn Gly Thr Cys Val Ala Cys Tyr |
| (SEQ ID NO: 6322) | Cys Glu Leu Cys Gln Asn Gly Thr Cys Gly Gly Cys Tyr |
| (SEQ ID NO: 6323) | Cys Glu Leu Cys Gln Asn Gly Thr Cys Gly Ala Cys Tyr |
| (SEQ ID NO: 6324) | Cys Glu Leu Cys Glu Asn Pro Ala Cys Thr Gly Cys Tyr |
| (SEQ ID NO: 6325) | Cys Glu Leu Cys Glu Asn Pro Ala Cys Thr Ala Cys Tyr |
| (SEQ ID NO: 6326) | Cys Glu Leu Cys Glu Asn Pro Ala Cys Val Gly Cys Tyr |
| (SEQ ID NO: 6327) | Cys Glu Leu Cys Glu Asn Pro Ala Cys Val Ala Cys Tyr |
| (SEQ ID NO: 6328) | Cys Glu Leu Cys Glu Asn Pro Ala Cys Gly Gly Cys Tyr |
| (SEQ ID NO: 6329) | Cys Glu Leu Cys Glu Asn Pro Ala Cys Gly Ala Cys Tyr |
| (SEQ ID NO: 6330) | Cys Glu Leu Cys Glu Asn Pro Thr Cys Thr Gly Cys Tyr |
| (SEQ ID NO: 6331) | Cys Glu Leu Cys Glu Asn Pro Thr Cys Thr Ala Cys Tyr |
| (SEQ ID NO: 6332) | Cys Glu Leu Cys Glu Asn Pro Thr Cys Val Gly Cys Tyr |
| (SEQ ID NO: 6333) | Cys Glu Leu Cys Glu Asn Pro Thr Cys Val Ala Cys Tyr |
| (SEQ ID NO: 6334) | Cys Glu Leu Cys Glu Asn Pro Thr Cys Gly Gly Cys Tyr |
| (SEQ ID NO: 6335) | Cys Glu Leu Cys Glu Asn Pro Thr Cys Gly Ala Cys Tyr |
| (SEQ ID NO: 6336) | Cys Glu Leu Cys Glu Asn Gly Ala Cys Thr Gly Cys Tyr |
| (SEQ ID NO: 6337) | Cys Glu Leu Cys Glu Asn Gly Ala Cys Thr Ala Cys Tyr |
| (SEQ ID NO: 6338) | Cys Glu Leu Cys Glu Asn Gly Ala Cys Val Gly Cys Tyr |
| (SEQ ID NO: 6339) | Cys Glu Leu Cys Glu Asn Gly Ala Cys Val Ala Cys Tyr |
| (SEQ ID NO: 6340) | Cys Glu Leu Cys Glu Asn Gly Ala Cys Gly Gly Cys Tyr |
| (SEQ ID NO: 6341) | Cys Glu Leu Cys Glu Asn Gly Ala Cys Gly Ala Cys Tyr |
| (SEQ ID NO: 6342) | Cys Glu Leu Cys Glu Asn Gly Thr Cys Thr Gly Cys Tyr |
| (SEQ ID NO: 6343) | Cys Glu Leu Cys Glu Asn Gly Thr Cys Thr Ala Cys Tyr |
| (SEQ ID NO: 6344) | Cys Glu Leu Cys Glu Asn Gly Thr Cys Val Gly Cys Tyr |
| (SEQ ID NO: 6345) | Cys Glu Leu Cys Glu Asn Gly Thr Cys Val Ala Cys Tyr |
| (SEQ ID NO: 6346) | Cys Glu Leu Cys Glu Asn Gly Thr Cys Gly Gly Cys Tyr |
| (SEQ ID NO: 6347) | Cys Glu Leu Cys Glu Asn Gly Thr Cys Gly Ala Cys Tyr |
| (SEQ ID NO: 6348) | Cys Glu Leu Cys Gly Asn Pro Ala Cys Thr Gly Cys Tyr |
| (SEQ ID NO: 6349) | Cys Glu Leu Cys Gly Asn Pro Ala Cys Thr Ala Cys Tyr |
| (SEQ ID NO: 6350) | Cys Glu Leu Cys Gly Asn Pro Ala Cys Val Gly Cys Tyr |
| (SEQ ID NO: 6351) | Cys Glu Leu Cys Gly Asn Pro Ala Cys Val Ala Cys Tyr |
| (SEQ ID NO: 6352) | Cys Glu Leu Cys Gly Asn Pro Ala Cys Gly Gly Cys Tyr |
| (SEQ ID NO: 6353) | Cys Glu Leu Cys Gly Asn Pro Ala Cys Gly Ala Cys Tyr |
| (SEQ ID NO: 6354) | Cys Glu Leu Cys Gly Asn Pro Thr Cys Thr Gly Cys Tyr |

FIG. 3AK

| | | |
|---|---|---|
| (SEQ ID NO: 6355) | Cys Glu Leu Cys Gly Asn Pro Thr Cys Thr Ala Cys Tyr |
| (SEQ ID NO: 6356) | Cys Glu Leu Cys Gly Asn Pro Thr Cys Val Gly Cys Tyr |
| (SEQ ID NO: 6357) | Cys Glu Leu Cys Gly Asn Pro Thr Cys Val Ala Cys Tyr |
| (SEQ ID NO: 6358) | Cys Glu Leu Cys Gly Asn Pro Thr Cys Gly Gly Cys Tyr |
| (SEQ ID NO: 6359) | Cys Glu Leu Cys Gly Asn Pro Thr Cys Gly Ala Cys Tyr |
| (SEQ ID NO: 6360) | Cys Glu Leu Cys Gly Asn Gly Ala Cys Thr Gly Cys Tyr |
| (SEQ ID NO: 6361) | Cys Glu Leu Cys Gly Asn Gly Ala Cys Thr Ala Cys Tyr |
| (SEQ ID NO: 6362) | Cys Glu Leu Cys Gly Asn Gly Ala Cys Val Gly Cys Tyr |
| (SEQ ID NO: 6363) | Cys Glu Leu Cys Gly Asn Gly Ala Cys Val Ala Cys Tyr |
| (SEQ ID NO: 6364) | Cys Glu Leu Cys Gly Asn Gly Ala Cys Gly Gly Cys Tyr |
| (SEQ ID NO: 6365) | Cys Glu Leu Cys Gly Asn Gly Ala Cys Gly Ala Cys Tyr |
| (SEQ ID NO: 6366) | Cys Glu Leu Cys Gly Asn Gly Thr Cys Thr Gly Cys Tyr |
| (SEQ ID NO: 6367) | Cys Glu Leu Cys Gly Asn Gly Thr Cys Thr Ala Cys Tyr |
| (SEQ ID NO: 6368) | Cys Glu Leu Cys Gly Asn Gly Thr Cys Val Gly Cys Tyr |
| (SEQ ID NO: 6369) | Cys Glu Leu Cys Gly Asn Gly Thr Cys Val Ala Cys Tyr |
| (SEQ ID NO: 6370) | Cys Glu Leu Cys Gly Asn Gly Thr Cys Gly Gly Cys Tyr |
| (SEQ ID NO: 6371) | Cys Glu Leu Cys Gly Asn Gly Thr Cys Gly Ala Cys Tyr |
| (SEQ ID NO: 6372) | Cys Glu Leu Cys His Asn Pro Ala Cys Thr Gly Cys Tyr |
| (SEQ ID NO: 6373) | Cys Glu Leu Cys His Asn Pro Ala Cys Thr Ala Cys Tyr |
| (SEQ ID NO: 6374) | Cys Glu Leu Cys His Asn Pro Ala Cys Val Gly Cys Tyr |
| (SEQ ID NO: 6375) | Cys Glu Leu Cys His Asn Pro Ala Cys Val Ala Cys Tyr |
| (SEQ ID NO: 6376) | Cys Glu Leu Cys His Asn Pro Ala Cys Gly Gly Cys Tyr |
| (SEQ ID NO: 6377) | Cys Glu Leu Cys His Asn Pro Ala Cys Gly Ala Cys Tyr |
| (SEQ ID NO: 6378) | Cys Glu Leu Cys His Asn Pro Thr Cys Thr Gly Cys Tyr |
| (SEQ ID NO: 6379) | Cys Glu Leu Cys His Asn Pro Thr Cys Thr Ala Cys Tyr |
| (SEQ ID NO: 6380) | Cys Glu Leu Cys His Asn Pro Thr Cys Val Gly Cys Tyr |
| (SEQ ID NO: 6381) | Cys Glu Leu Cys His Asn Pro Thr Cys Val Ala Cys Tyr |
| (SEQ ID NO: 6382) | Cys Glu Leu Cys His Asn Pro Thr Cys Gly Gly Cys Tyr |
| (SEQ ID NO: 6383) | Cys Glu Leu Cys His Asn Pro Thr Cys Gly Ala Cys Tyr |
| (SEQ ID NO: 6384) | Cys Glu Leu Cys His Asn Gly Ala Cys Thr Gly Cys Tyr |
| (SEQ ID NO: 6385) | Cys Glu Leu Cys His Asn Gly Ala Cys Thr Ala Cys Tyr |
| (SEQ ID NO: 6386) | Cys Glu Leu Cys His Asn Gly Ala Cys Val Gly Cys Tyr |
| (SEQ ID NO: 6387) | Cys Glu Leu Cys His Asn Gly Ala Cys Val Ala Cys Tyr |
| (SEQ ID NO: 6388) | Cys Glu Leu Cys His Asn Gly Ala Cys Gly Gly Cys Tyr |
| (SEQ ID NO: 6389) | Cys Glu Leu Cys His Asn Gly Ala Cys Gly Ala Cys Tyr |
| (SEQ ID NO: 6390) | Cys Glu Leu Cys His Asn Gly Thr Cys Thr Gly Cys Tyr |
| (SEQ ID NO: 6391) | Cys Glu Leu Cys His Asn Gly Thr Cys Thr Ala Cys Tyr |
| (SEQ ID NO: 6392) | Cys Glu Leu Cys His Asn Gly Thr Cys Val Gly Cys Tyr |
| (SEQ ID NO: 6393) | Cys Glu Leu Cys His Asn Gly Thr Cys Val Ala Cys Tyr |
| (SEQ ID NO: 6394) | Cys Glu Leu Cys His Asn Gly Thr Cys Gly Gly Cys Tyr |
| (SEQ ID NO: 6395) | Cys Glu Leu Cys His Asn Gly Thr Cys Gly Ala Cys Tyr |
| (SEQ ID NO: 6396) | Cys Glu Leu Cys Ile Asn Pro Ala Cys Thr Gly Cys Tyr |
| (SEQ ID NO: 6397) | Cys Glu Leu Cys Ile Asn Pro Ala Cys Thr Ala Cys Tyr |

FIG. 3AL (SEQ ID NO: 6398)  Cys Glu Leu Cys Ile Asn Pro Ala Cys Val Gly Cys Tyr
(SEQ ID NO: 6399)  Cys Glu Leu Cys Ile Asn Pro Ala Cys Val Ala Cys Tyr
(SEQ ID NO: 6400)  Cys Glu Leu Cys Ile Asn Pro Ala Cys Gly Gly Cys Tyr
(SEQ ID NO: 6401)  Cys Glu Leu Cys Ile Asn Pro Ala Cys Gly Ala Cys Tyr
(SEQ ID NO: 6402)  Cys Glu Leu Cys Ile Asn Pro Thr Cys Thr Gly Cys Tyr
(SEQ ID NO: 6403)  Cys Glu Leu Cys Ile Asn Pro Thr Cys Thr Ala Cys Tyr
(SEQ ID NO: 6404)  Cys Glu Leu Cys Ile Asn Pro Thr Cys Val Gly Cys Tyr
(SEQ ID NO: 6405)  Cys Glu Leu Cys Ile Asn Pro Thr Cys Val Ala Cys Tyr
(SEQ ID NO: 6406)  Cys Glu Leu Cys Ile Asn Pro Thr Cys Gly Gly Cys Tyr
(SEQ ID NO: 6407)  Cys Glu Leu Cys Ile Asn Pro Thr Cys Gly Ala Cys Tyr
(SEQ ID NO: 6408)  Cys Glu Leu Cys Ile Asn Gly Ala Cys Thr Gly Cys Tyr
(SEQ ID NO: 6409)  Cys Glu Leu Cys Ile Asn Gly Ala Cys Thr Ala Cys Tyr
(SEQ ID NO: 6410)  Cys Glu Leu Cys Ile Asn Gly Ala Cys Val Gly Cys Tyr
(SEQ ID NO: 6411)  Cys Glu Leu Cys Ile Asn Gly Ala Cys Val Ala Cys Tyr
(SEQ ID NO: 6412)  Cys Glu Leu Cys Ile Asn Gly Ala Cys Gly Gly Cys Tyr
(SEQ ID NO: 6413)  Cys Glu Leu Cys Ile Asn Gly Ala Cys Gly Ala Cys Tyr
(SEQ ID NO: 6414)  Cys Glu Leu Cys Ile Asn Gly Thr Cys Thr Gly Cys Tyr
(SEQ ID NO: 6415)  Cys Glu Leu Cys Ile Asn Gly Thr Cys Thr Ala Cys Tyr
(SEQ ID NO: 6416)  Cys Glu Leu Cys Ile Asn Gly Thr Cys Val Gly Cys Tyr
(SEQ ID NO: 6417)  Cys Glu Leu Cys Ile Asn Gly Thr Cys Val Ala Cys Tyr
(SEQ ID NO: 6418)  Cys Glu Leu Cys Ile Asn Gly Thr Cys Gly Gly Cys Tyr
(SEQ ID NO: 6419)  Cys Glu Leu Cys Ile Asn Gly Thr Cys Gly Ala Cys Tyr
(SEQ ID NO: 6420)  Cys Glu Leu Cys Leu Asn Pro Ala Cys Thr Gly Cys Tyr
(SEQ ID NO: 6421)  Cys Glu Leu Cys Leu Asn Pro Ala Cys Thr Ala Cys Tyr
(SEQ ID NO: 6422)  Cys Glu Leu Cys Leu Asn Pro Ala Cys Val Gly Cys Tyr
(SEQ ID NO: 6423)  Cys Glu Leu Cys Leu Asn Pro Ala Cys Val Ala Cys Tyr
(SEQ ID NO: 6424)  Cys Glu Leu Cys Leu Asn Pro Ala Cys Gly Gly Cys Tyr
(SEQ ID NO: 6425)  Cys Glu Leu Cys Leu Asn Pro Ala Cys Gly Ala Cys Tyr
(SEQ ID NO: 6426)  Cys Glu Leu Cys Leu Asn Pro Thr Cys Thr Gly Cys Tyr
(SEQ ID NO: 6427)  Cys Glu Leu Cys Leu Asn Pro Thr Cys Thr Ala Cys Tyr
(SEQ ID NO: 6428)  Cys Glu Leu Cys Leu Asn Pro Thr Cys Val Gly Cys Tyr
(SEQ ID NO: 6429)  Cys Glu Leu Cys Leu Asn Pro Thr Cys Val Ala Cys Tyr
(SEQ ID NO: 6430)  Cys Glu Leu Cys Leu Asn Pro Thr Cys Gly Gly Cys Tyr
(SEQ ID NO: 6431)  Cys Glu Leu Cys Leu Asn Pro Thr Cys Gly Ala Cys Tyr
(SEQ ID NO: 6432)  Cys Glu Leu Cys Leu Asn Gly Ala Cys Thr Gly Cys Tyr
(SEQ ID NO: 6433)  Cys Glu Leu Cys Leu Asn Gly Ala Cys Thr Ala Cys Tyr
(SEQ ID NO: 6434)  Cys Glu Leu Cys Leu Asn Gly Ala Cys Val Gly Cys Tyr
(SEQ ID NO: 6435)  Cys Glu Leu Cys Leu Asn Gly Ala Cys Val Ala Cys Tyr
(SEQ ID NO: 6436)  Cys Glu Leu Cys Leu Asn Gly Ala Cys Gly Gly Cys Tyr
(SEQ ID NO: 6437)  Cys Glu Leu Cys Leu Asn Gly Ala Cys Gly Ala Cys Tyr
(SEQ ID NO: 6438)  Cys Glu Leu Cys Leu Asn Gly Thr Cys Thr Gly Cys Tyr
(SEQ ID NO: 6439)  Cys Glu Leu Cys Leu Asn Gly Thr Cys Thr Ala Cys Tyr
(SEQ ID NO: 6440)  Cys Glu Leu Cys Leu Asn Gly Thr Cys Val Gly Cys Tyr

FIG. 3AM

| | |
|---|---|
| (SEQ ID NO: 6441) | Cys Glu Leu Cys Leu Asn Gly Thr Cys Val Ala Cys Tyr |
| (SEQ ID NO: 6442) | Cys Glu Leu Cys Leu Asn Gly Thr Cys Gly Gly Cys Tyr |
| (SEQ ID NO: 6443) | Cys Glu Leu Cys Leu Asn Gly Thr Cys Gly Ala Cys Tyr |
| (SEQ ID NO: 6444) | Cys Glu Leu Cys Lys Asn Pro Ala Cys Thr Gly Cys Tyr |
| (SEQ ID NO: 6445) | Cys Glu Leu Cys Lys Asn Pro Ala Cys Thr Ala Cys Tyr |
| (SEQ ID NO: 6446) | Cys Glu Leu Cys Lys Asn Pro Ala Cys Val Gly Cys Tyr |
| (SEQ ID NO: 6447) | Cys Glu Leu Cys Lys Asn Pro Ala Cys Val Ala Cys Tyr |
| (SEQ ID NO: 6448) | Cys Glu Leu Cys Lys Asn Pro Ala Cys Gly Gly Cys Tyr |
| (SEQ ID NO: 6449) | Cys Glu Leu Cys Lys Asn Pro Ala Cys Gly Ala Cys Tyr |
| (SEQ ID NO: 6450) | Cys Glu Leu Cys Lys Asn Pro Thr Cys Thr Gly Cys Tyr |
| (SEQ ID NO: 6451) | Cys Glu Leu Cys Lys Asn Pro Thr Cys Thr Ala Cys Tyr |
| (SEQ ID NO: 6452) | Cys Glu Leu Cys Lys Asn Pro Thr Cys Val Gly Cys Tyr |
| (SEQ ID NO: 6453) | Cys Glu Leu Cys Lys Asn Pro Thr Cys Val Ala Cys Tyr |
| (SEQ ID NO: 6454) | Cys Glu Leu Cys Lys Asn Pro Thr Cys Gly Gly Cys Tyr |
| (SEQ ID NO: 6455) | Cys Glu Leu Cys Lys Asn Pro Thr Cys Gly Ala Cys Tyr |
| (SEQ ID NO: 6456) | Cys Glu Leu Cys Lys Asn Gly Ala Cys Thr Gly Cys Tyr |
| (SEQ ID NO: 6457) | Cys Glu Leu Cys Lys Asn Gly Ala Cys Thr Ala Cys Tyr |
| (SEQ ID NO: 6458) | Cys Glu Leu Cys Lys Asn Gly Ala Cys Val Gly Cys Tyr |
| (SEQ ID NO: 6459) | Cys Glu Leu Cys Lys Asn Gly Ala Cys Val Ala Cys Tyr |
| (SEQ ID NO: 6460) | Cys Glu Leu Cys Lys Asn Gly Ala Cys Gly Gly Cys Tyr |
| (SEQ ID NO: 6461) | Cys Glu Leu Cys Lys Asn Gly Ala Cys Gly Ala Cys Tyr |
| (SEQ ID NO: 6462) | Cys Glu Leu Cys Lys Asn Gly Thr Cys Thr Gly Cys Tyr |
| (SEQ ID NO: 6463) | Cys Glu Leu Cys Lys Asn Gly Thr Cys Thr Ala Cys Tyr |
| (SEQ ID NO: 6464) | Cys Glu Leu Cys Lys Asn Gly Thr Cys Val Gly Cys Tyr |
| (SEQ ID NO: 6465) | Cys Glu Leu Cys Lys Asn Gly Thr Cys Val Ala Cys Tyr |
| (SEQ ID NO: 6466) | Cys Glu Leu Cys Lys Asn Gly Thr Cys Gly Gly Cys Tyr |
| (SEQ ID NO: 6467) | Cys Glu Leu Cys Lys Asn Gly Thr Cys Gly Ala Cys Tyr |
| (SEQ ID NO: 6468) | Cys Glu Leu Cys Met Asn Pro Ala Cys Thr Gly Cys Tyr |
| (SEQ ID NO: 6469) | Cys Glu Leu Cys Met Asn Pro Ala Cys Thr Ala Cys Tyr |
| (SEQ ID NO: 6470) | Cys Glu Leu Cys Met Asn Pro Ala Cys Val Gly Cys Tyr |
| (SEQ ID NO: 6471) | Cys Glu Leu Cys Met Asn Pro Ala Cys Val Ala Cys Tyr |
| (SEQ ID NO: 6472) | Cys Glu Leu Cys Met Asn Pro Ala Cys Gly Gly Cys Tyr |
| (SEQ ID NO: 6473) | Cys Glu Leu Cys Met Asn Pro Ala Cys Gly Ala Cys Tyr |
| (SEQ ID NO: 6474) | Cys Glu Leu Cys Met Asn Pro Thr Cys Thr Gly Cys Tyr |
| (SEQ ID NO: 6475) | Cys Glu Leu Cys Met Asn Pro Thr Cys Thr Ala Cys Tyr |
| (SEQ ID NO: 6476) | Cys Glu Leu Cys Met Asn Pro Thr Cys Val Gly Cys Tyr |
| (SEQ ID NO: 6477) | Cys Glu Leu Cys Met Asn Pro Thr Cys Val Ala Cys Tyr |
| (SEQ ID NO: 6478) | Cys Glu Leu Cys Met Asn Pro Thr Cys Gly Gly Cys Tyr |
| (SEQ ID NO: 6479) | Cys Glu Leu Cys Met Asn Pro Thr Cys Gly Ala Cys Tyr |
| (SEQ ID NO: 6480) | Cys Glu Leu Cys Met Asn Gly Ala Cys Thr Gly Cys Tyr |
| (SEQ ID NO: 6481) | Cys Glu Leu Cys Met Asn Gly Ala Cys Thr Ala Cys Tyr |
| (SEQ ID NO: 6482) | Cys Glu Leu Cys Met Asn Gly Ala Cys Val Gly Cys Tyr |
| (SEQ ID NO: 6483) | Cys Glu Leu Cys Met Asn Gly Ala Cys Val Ala Cys Tyr |

FIG. 3AN

| | |
|---|---|
| (SEQ ID NO: 6484) | Cys Glu Leu Cys Met Asn Gly Ala Cys Gly Gly Cys Tyr |
| (SEQ ID NO: 6485) | Cys Glu Leu Cys Met Asn Gly Ala Cys Gly Ala Cys Tyr |
| (SEQ ID NO: 6486) | Cys Glu Leu Cys Met Asn Gly Thr Cys Thr Gly Cys Tyr |
| (SEQ ID NO: 6487) | Cys Glu Leu Cys Met Asn Gly Thr Cys Thr Ala Cys Tyr |
| (SEQ ID NO: 6488) | Cys Glu Leu Cys Met Asn Gly Thr Cys Val Gly Cys Tyr |
| (SEQ ID NO: 6489) | Cys Glu Leu Cys Met Asn Gly Thr Cys Val Ala Cys Tyr |
| (SEQ ID NO: 6490) | Cys Glu Leu Cys Met Asn Gly Thr Cys Gly Gly Cys Tyr |
| (SEQ ID NO: 6491) | Cys Glu Leu Cys Met Asn Gly Thr Cys Gly Ala Cys Tyr |
| (SEQ ID NO: 6492) | Cys Glu Leu Cys Phe Asn Pro Ala Cys Thr Gly Cys Tyr |
| (SEQ ID NO: 6493) | Cys Glu Leu Cys Phe Asn Pro Ala Cys Thr Ala Cys Tyr |
| (SEQ ID NO: 6494) | Cys Glu Leu Cys Phe Asn Pro Ala Cys Val Gly Cys Tyr |
| (SEQ ID NO: 6495) | Cys Glu Leu Cys Phe Asn Pro Ala Cys Val Ala Cys Tyr |
| (SEQ ID NO: 6496) | Cys Glu Leu Cys Phe Asn Pro Ala Cys Gly Gly Cys Tyr |
| (SEQ ID NO: 6497) | Cys Glu Leu Cys Phe Asn Pro Ala Cys Gly Ala Cys Tyr |
| (SEQ ID NO: 6498) | Cys Glu Leu Cys Phe Asn Pro Thr Cys Thr Gly Cys Tyr |
| (SEQ ID NO: 6499) | Cys Glu Leu Cys Phe Asn Pro Thr Cys Thr Ala Cys Tyr |
| (SEQ ID NO: 6500) | Cys Glu Leu Cys Phe Asn Pro Thr Cys Val Gly Cys Tyr |
| (SEQ ID NO: 6501) | Cys Glu Leu Cys Phe Asn Pro Thr Cys Val Ala Cys Tyr |
| (SEQ ID NO: 6502) | Cys Glu Leu Cys Phe Asn Pro Thr Cys Gly Gly Cys Tyr |
| (SEQ ID NO: 6503) | Cys Glu Leu Cys Phe Asn Pro Thr Cys Gly Ala Cys Tyr |
| (SEQ ID NO: 6504) | Cys Glu Leu Cys Phe Asn Gly Ala Cys Thr Gly Cys Tyr |
| (SEQ ID NO: 6505) | Cys Glu Leu Cys Phe Asn Gly Ala Cys Thr Ala Cys Tyr |
| (SEQ ID NO: 6506) | Cys Glu Leu Cys Phe Asn Gly Ala Cys Val Gly Cys Tyr |
| (SEQ ID NO: 6507) | Cys Glu Leu Cys Phe Asn Gly Ala Cys Val Ala Cys Tyr |
| (SEQ ID NO: 6508) | Cys Glu Leu Cys Phe Asn Gly Ala Cys Gly Gly Cys Tyr |
| (SEQ ID NO: 6509) | Cys Glu Leu Cys Phe Asn Gly Ala Cys Gly Ala Cys Tyr |
| (SEQ ID NO: 6510) | Cys Glu Leu Cys Phe Asn Gly Thr Cys Thr Gly Cys Tyr |
| (SEQ ID NO: 6511) | Cys Glu Leu Cys Phe Asn Gly Thr Cys Thr Ala Cys Tyr |
| (SEQ ID NO: 6512) | Cys Glu Leu Cys Phe Asn Gly Thr Cys Val Gly Cys Tyr |
| (SEQ ID NO: 6513) | Cys Glu Leu Cys Phe Asn Gly Thr Cys Val Ala Cys Tyr |
| (SEQ ID NO: 6514) | Cys Glu Leu Cys Phe Asn Gly Thr Cys Gly Gly Cys Tyr |
| (SEQ ID NO: 6515) | Cys Glu Leu Cys Phe Asn Gly Thr Cys Gly Ala Cys Tyr |
| (SEQ ID NO: 6516) | Cys Glu Leu Cys Pro Asn Pro Ala Cys Thr Gly Cys Tyr |
| (SEQ ID NO: 6517) | Cys Glu Leu Cys Pro Asn Pro Ala Cys Thr Ala Cys Tyr |
| (SEQ ID NO: 6518) | Cys Glu Leu Cys Pro Asn Pro Ala Cys Val Gly Cys Tyr |
| (SEQ ID NO: 6519) | Cys Glu Leu Cys Pro Asn Pro Ala Cys Val Ala Cys Tyr |
| (SEQ ID NO: 6520) | Cys Glu Leu Cys Pro Asn Pro Ala Cys Gly Gly Cys Tyr |
| (SEQ ID NO: 6521) | Cys Glu Leu Cys Pro Asn Pro Ala Cys Gly Ala Cys Tyr |
| (SEQ ID NO: 6522) | Cys Glu Leu Cys Pro Asn Pro Thr Cys Thr Gly Cys Tyr |
| (SEQ ID NO: 6523) | Cys Glu Leu Cys Pro Asn Pro Thr Cys Thr Ala Cys Tyr |
| (SEQ ID NO: 6524) | Cys Glu Leu Cys Pro Asn Pro Thr Cys Val Gly Cys Tyr |
| (SEQ ID NO: 6525) | Cys Glu Leu Cys Pro Asn Pro Thr Cys Val Ala Cys Tyr |
| (SEQ ID NO: 6526) | Cys Glu Leu Cys Pro Asn Pro Thr Cys Gly Gly Cys Tyr |

FIG. 3AO

| | |
|---|---|
| (SEQ ID NO: 6527) | Cys Glu Leu Cys Pro Asn Pro Thr Cys Gly Ala Cys Tyr |
| (SEQ ID NO: 6528) | Cys Glu Leu Cys Pro Asn Gly Ala Cys Thr Gly Cys Tyr |
| (SEQ ID NO: 6529) | Cys Glu Leu Cys Pro Asn Gly Ala Cys Thr Ala Cys Tyr |
| (SEQ ID NO: 6530) | Cys Glu Leu Cys Pro Asn Gly Ala Cys Val Gly Cys Tyr |
| (SEQ ID NO: 6531) | Cys Glu Leu Cys Pro Asn Gly Ala Cys Val Ala Cys Tyr |
| (SEQ ID NO: 6532) | Cys Glu Leu Cys Pro Asn Gly Ala Cys Gly Gly Cys Tyr |
| (SEQ ID NO: 6533) | Cys Glu Leu Cys Pro Asn Gly Ala Cys Gly Ala Cys Tyr |
| (SEQ ID NO: 6534) | Cys Glu Leu Cys Pro Asn Gly Thr Cys Thr Gly Cys Tyr |
| (SEQ ID NO: 6535) | Cys Glu Leu Cys Pro Asn Gly Thr Cys Thr Ala Cys Tyr |
| (SEQ ID NO: 6536) | Cys Glu Leu Cys Pro Asn Gly Thr Cys Val Gly Cys Tyr |
| (SEQ ID NO: 6537) | Cys Glu Leu Cys Pro Asn Gly Thr Cys Val Ala Cys Tyr |
| (SEQ ID NO: 6538) | Cys Glu Leu Cys Pro Asn Gly Thr Cys Gly Gly Cys Tyr |
| (SEQ ID NO: 6539) | Cys Glu Leu Cys Pro Asn Gly Thr Cys Gly Ala Cys Tyr |
| (SEQ ID NO: 6540) | Cys Glu Leu Cys Ser Asn Pro Ala Cys Thr Gly Cys Tyr |
| (SEQ ID NO: 6541) | Cys Glu Leu Cys Ser Asn Pro Ala Cys Thr Ala Cys Tyr |
| (SEQ ID NO: 6542) | Cys Glu Leu Cys Ser Asn Pro Ala Cys Val Gly Cys Tyr |
| (SEQ ID NO: 6543) | Cys Glu Leu Cys Ser Asn Pro Ala Cys Val Ala Cys Tyr |
| (SEQ ID NO: 6544) | Cys Glu Leu Cys Ser Asn Pro Ala Cys Gly Gly Cys Tyr |
| (SEQ ID NO: 6545) | Cys Glu Leu Cys Ser Asn Pro Ala Cys Gly Ala Cys Tyr |
| (SEQ ID NO: 6546) | Cys Glu Leu Cys Ser Asn Pro Thr Cys Thr Gly Cys Tyr |
| (SEQ ID NO: 6547) | Cys Glu Leu Cys Ser Asn Pro Thr Cys Thr Ala Cys Tyr |
| (SEQ ID NO: 6548) | Cys Glu Leu Cys Ser Asn Pro Thr Cys Val Gly Cys Tyr |
| (SEQ ID NO: 6549) | Cys Glu Leu Cys Ser Asn Pro Thr Cys Val Ala Cys Tyr |
| (SEQ ID NO: 6550) | Cys Glu Leu Cys Ser Asn Pro Thr Cys Gly Gly Cys Tyr |
| (SEQ ID NO: 6551) | Cys Glu Leu Cys Ser Asn Pro Thr Cys Gly Ala Cys Tyr |
| (SEQ ID NO: 6552) | Cys Glu Leu Cys Ser Asn Gly Ala Cys Thr Gly Cys Tyr |
| (SEQ ID NO: 6553) | Cys Glu Leu Cys Ser Asn Gly Ala Cys Thr Ala Cys Tyr |
| (SEQ ID NO: 6554) | Cys Glu Leu Cys Ser Asn Gly Ala Cys Val Gly Cys Tyr |
| (SEQ ID NO: 6555) | Cys Glu Leu Cys Ser Asn Gly Ala Cys Val Ala Cys Tyr |
| (SEQ ID NO: 6556) | Cys Glu Leu Cys Ser Asn Gly Ala Cys Gly Gly Cys Tyr |
| (SEQ ID NO: 6557) | Cys Glu Leu Cys Ser Asn Gly Ala Cys Gly Ala Cys Tyr |
| (SEQ ID NO: 6558) | Cys Glu Leu Cys Ser Asn Gly Thr Cys Thr Gly Cys Tyr |
| (SEQ ID NO: 6559) | Cys Glu Leu Cys Ser Asn Gly Thr Cys Thr Ala Cys Tyr |
| (SEQ ID NO: 6560) | Cys Glu Leu Cys Ser Asn Gly Thr Cys Val Gly Cys Tyr |
| (SEQ ID NO: 6561) | Cys Glu Leu Cys Ser Asn Gly Thr Cys Val Ala Cys Tyr |
| (SEQ ID NO: 6562) | Cys Glu Leu Cys Ser Asn Gly Thr Cys Gly Gly Cys Tyr |
| (SEQ ID NO: 6563) | Cys Glu Leu Cys Ser Asn Gly Thr Cys Gly Ala Cys Tyr |
| (SEQ ID NO: 6564) | Cys Glu Leu Cys Thr Asn Pro Ala Cys Thr Gly Cys Tyr |
| (SEQ ID NO: 6565) | Cys Glu Leu Cys Thr Asn Pro Ala Cys Thr Ala Cys Tyr |
| (SEQ ID NO: 6566) | Cys Glu Leu Cys Thr Asn Pro Ala Cys Val Gly Cys Tyr |
| (SEQ ID NO: 6567) | Cys Glu Leu Cys Thr Asn Pro Ala Cys Val Ala Cys Tyr |
| (SEQ ID NO: 6568) | Cys Glu Leu Cys Thr Asn Pro Ala Cys Gly Gly Cys Tyr |
| (SEQ ID NO: 6569) | Cys Glu Leu Cys Thr Asn Pro Ala Cys Gly Ala Cys Tyr |

FIG. 3AP

| | |
|---|---|
| (SEQ ID NO: 6570) | Cys Glu Leu Cys Thr Asn Pro Thr Cys Thr Gly Cys Tyr |
| (SEQ ID NO: 6571) | Cys Glu Leu Cys Thr Asn Pro Thr Cys Thr Ala Cys Tyr |
| (SEQ ID NO: 6572) | Cys Glu Leu Cys Thr Asn Pro Thr Cys Val Gly Cys Tyr |
| (SEQ ID NO: 6573) | Cys Glu Leu Cys Thr Asn Pro Thr Cys Val Ala Cys Tyr |
| (SEQ ID NO: 6574) | Cys Glu Leu Cys Thr Asn Pro Thr Cys Gly Gly Cys Tyr |
| (SEQ ID NO: 6575) | Cys Glu Leu Cys Thr Asn Pro Thr Cys Gly Ala Cys Tyr |
| (SEQ ID NO: 6576) | Cys Glu Leu Cys Thr Asn Gly Ala Cys Thr Gly Cys Tyr |
| (SEQ ID NO: 6577) | Cys Glu Leu Cys Thr Asn Gly Ala Cys Thr Ala Cys Tyr |
| (SEQ ID NO: 6578) | Cys Glu Leu Cys Thr Asn Gly Ala Cys Val Gly Cys Tyr |
| (SEQ ID NO: 6579) | Cys Glu Leu Cys Thr Asn Gly Ala Cys Val Ala Cys Tyr |
| (SEQ ID NO: 6580) | Cys Glu Leu Cys Thr Asn Gly Ala Cys Gly Gly Cys Tyr |
| (SEQ ID NO: 6581) | Cys Glu Leu Cys Thr Asn Gly Ala Cys Gly Ala Cys Tyr |
| (SEQ ID NO: 6582) | Cys Glu Leu Cys Thr Asn Gly Thr Cys Thr Gly Cys Tyr |
| (SEQ ID NO: 6583) | Cys Glu Leu Cys Thr Asn Gly Thr Cys Thr Ala Cys Tyr |
| (SEQ ID NO: 6584) | Cys Glu Leu Cys Thr Asn Gly Thr Cys Val Gly Cys Tyr |
| (SEQ ID NO: 6585) | Cys Glu Leu Cys Thr Asn Gly Thr Cys Val Ala Cys Tyr |
| (SEQ ID NO: 6586) | Cys Glu Leu Cys Thr Asn Gly Thr Cys Gly Gly Cys Tyr |
| (SEQ ID NO: 6587) | Cys Glu Leu Cys Thr Asn Gly Thr Cys Gly Ala Cys Tyr |
| (SEQ ID NO: 6588) | Cys Glu Leu Cys Trp Asn Pro Ala Cys Thr Gly Cys Tyr |
| (SEQ ID NO: 6589) | Cys Glu Leu Cys Trp Asn Pro Ala Cys Thr Ala Cys Tyr |
| (SEQ ID NO: 6590) | Cys Glu Leu Cys Trp Asn Pro Ala Cys Val Gly Cys Tyr |
| (SEQ ID NO: 6591) | Cys Glu Leu Cys Trp Asn Pro Ala Cys Val Ala Cys Tyr |
| (SEQ ID NO: 6592) | Cys Glu Leu Cys Trp Asn Pro Ala Cys Gly Gly Cys Tyr |
| (SEQ ID NO: 6593) | Cys Glu Leu Cys Trp Asn Pro Ala Cys Gly Ala Cys Tyr |
| (SEQ ID NO: 6594) | Cys Glu Leu Cys Trp Asn Pro Thr Cys Thr Gly Cys Tyr |
| (SEQ ID NO: 6595) | Cys Glu Leu Cys Trp Asn Pro Thr Cys Thr Ala Cys Tyr |
| (SEQ ID NO: 6596) | Cys Glu Leu Cys Trp Asn Pro Thr Cys Val Gly Cys Tyr |
| (SEQ ID NO: 6597) | Cys Glu Leu Cys Trp Asn Pro Thr Cys Val Ala Cys Tyr |
| (SEQ ID NO: 6598) | Cys Glu Leu Cys Trp Asn Pro Thr Cys Gly Gly Cys Tyr |
| (SEQ ID NO: 6599) | Cys Glu Leu Cys Trp Asn Pro Thr Cys Gly Ala Cys Tyr |
| (SEQ ID NO: 6600) | Cys Glu Leu Cys Trp Asn Gly Ala Cys Thr Gly Cys Tyr |
| (SEQ ID NO: 6601) | Cys Glu Leu Cys Trp Asn Gly Ala Cys Thr Ala Cys Tyr |
| (SEQ ID NO: 6602) | Cys Glu Leu Cys Trp Asn Gly Ala Cys Val Gly Cys Tyr |
| (SEQ ID NO: 6603) | Cys Glu Leu Cys Trp Asn Gly Ala Cys Val Ala Cys Tyr |
| (SEQ ID NO: 6604) | Cys Glu Leu Cys Trp Asn Gly Ala Cys Gly Gly Cys Tyr |
| (SEQ ID NO: 6605) | Cys Glu Leu Cys Trp Asn Gly Ala Cys Gly Ala Cys Tyr |
| (SEQ ID NO: 6606) | Cys Glu Leu Cys Trp Asn Gly Thr Cys Thr Gly Cys Tyr |
| (SEQ ID NO: 6607) | Cys Glu Leu Cys Trp Asn Gly Thr Cys Thr Ala Cys Tyr |
| (SEQ ID NO: 6608) | Cys Glu Leu Cys Trp Asn Gly Thr Cys Val Gly Cys Tyr |
| (SEQ ID NO: 6609) | Cys Glu Leu Cys Trp Asn Gly Thr Cys Val Ala Cys Tyr |
| (SEQ ID NO: 6610) | Cys Glu Leu Cys Trp Asn Gly Thr Cys Gly Gly Cys Tyr |
| (SEQ ID NO: 6611) | Cys Glu Leu Cys Trp Asn Gly Thr Cys Gly Ala Cys Tyr |
| (SEQ ID NO: 6612) | Cys Glu Leu Cys Tyr Asn Pro Ala Cys Thr Gly Cys Tyr |

FIG. 3AQ

| | |
|---|---|
| (SEQ ID NO: 6613) | Cys Glu Leu Cys Tyr Asn Pro Ala Cys Thr Ala Cys Tyr |
| (SEQ ID NO: 6614) | Cys Glu Leu Cys Tyr Asn Pro Ala Cys Val Gly Cys Tyr |
| (SEQ ID NO: 6615) | Cys Glu Leu Cys Tyr Asn Pro Ala Cys Val Ala Cys Tyr |
| (SEQ ID NO: 6616) | Cys Glu Leu Cys Tyr Asn Pro Ala Cys Gly Gly Cys Tyr |
| (SEQ ID NO: 6617) | Cys Glu Leu Cys Tyr Asn Pro Ala Cys Gly Ala Cys Tyr |
| (SEQ ID NO: 6618) | Cys Glu Leu Cys Tyr Asn Pro Thr Cys Thr Gly Cys Tyr |
| (SEQ ID NO: 6619) | Cys Glu Leu Cys Tyr Asn Pro Thr Cys Thr Ala Cys Tyr |
| (SEQ ID NO: 6620) | Cys Glu Leu Cys Tyr Asn Pro Thr Cys Val Gly Cys Tyr |
| (SEQ ID NO: 6621) | Cys Glu Leu Cys Tyr Asn Pro Thr Cys Val Ala Cys Tyr |
| (SEQ ID NO: 6622) | Cys Glu Leu Cys Tyr Asn Pro Thr Cys Gly Gly Cys Tyr |
| (SEQ ID NO: 6623) | Cys Glu Leu Cys Tyr Asn Pro Thr Cys Gly Ala Cys Tyr |
| (SEQ ID NO: 6624) | Cys Glu Leu Cys Tyr Asn Gly Ala Cys Thr Gly Cys Tyr |
| (SEQ ID NO: 6625) | Cys Glu Leu Cys Tyr Asn Gly Ala Cys Thr Ala Cys Tyr |
| (SEQ ID NO: 6626) | Cys Glu Leu Cys Tyr Asn Gly Ala Cys Val Gly Cys Tyr |
| (SEQ ID NO: 6627) | Cys Glu Leu Cys Tyr Asn Gly Ala Cys Val Ala Cys Tyr |
| (SEQ ID NO: 6628) | Cys Glu Leu Cys Tyr Asn Gly Ala Cys Gly Gly Cys Tyr |
| (SEQ ID NO: 6629) | Cys Glu Leu Cys Tyr Asn Gly Ala Cys Gly Ala Cys Tyr |
| (SEQ ID NO: 6630) | Cys Glu Leu Cys Tyr Asn Gly Thr Cys Thr Gly Cys Tyr |
| (SEQ ID NO: 6631) | Cys Glu Leu Cys Tyr Asn Gly Thr Cys Thr Ala Cys Tyr |
| (SEQ ID NO: 6632) | Cys Glu Leu Cys Tyr Asn Gly Thr Cys Val Gly Cys Tyr |
| (SEQ ID NO: 6633) | Cys Glu Leu Cys Tyr Asn Gly Thr Cys Val Ala Cys Tyr |
| (SEQ ID NO: 6634) | Cys Glu Leu Cys Tyr Asn Gly Thr Cys Gly Gly Cys Tyr |
| (SEQ ID NO: 6635) | Cys Glu Leu Cys Tyr Asn Gly Thr Cys Gly Ala Cys Tyr |
| (SEQ ID NO: 6636) | Cys Glu Leu Cys Val Asn Pro Ala Cys Thr Gly Cys Tyr |
| (SEQ ID NO: 6637) | Cys Glu Leu Cys Val Asn Pro Ala Cys Thr Ala Cys Tyr |
| (SEQ ID NO: 6638) | Cys Glu Leu Cys Val Asn Pro Ala Cys Val Gly Cys Tyr |
| (SEQ ID NO: 6639) | Cys Glu Leu Cys Val Asn Pro Ala Cys Val Ala Cys Tyr |
| (SEQ ID NO: 6640) | Cys Glu Leu Cys Val Asn Pro Ala Cys Gly Gly Cys Tyr |
| (SEQ ID NO: 6641) | Cys Glu Leu Cys Val Asn Pro Ala Cys Gly Ala Cys Tyr |
| (SEQ ID NO: 6642) | Cys Glu Leu Cys Val Asn Pro Thr Cys Thr Gly Cys Tyr |
| (SEQ ID NO: 6643) | Cys Glu Leu Cys Val Asn Pro Thr Cys Thr Ala Cys Tyr |
| (SEQ ID NO: 6644) | Cys Glu Leu Cys Val Asn Pro Thr Cys Val Gly Cys Tyr |
| (SEQ ID NO: 6645) | Cys Glu Leu Cys Val Asn Pro Thr Cys Val Ala Cys Tyr |
| (SEQ ID NO: 6646) | Cys Glu Leu Cys Val Asn Pro Thr Cys Gly Gly Cys Tyr |
| (SEQ ID NO: 6647) | Cys Glu Leu Cys Val Asn Pro Thr Cys Gly Ala Cys Tyr |
| (SEQ ID NO: 6648) | Cys Glu Leu Cys Val Asn Gly Ala Cys Thr Gly Cys Tyr |
| (SEQ ID NO: 6649) | Cys Glu Leu Cys Val Asn Gly Ala Cys Thr Ala Cys Tyr |
| (SEQ ID NO: 6650) | Cys Glu Leu Cys Val Asn Gly Ala Cys Val Gly Cys Tyr |
| (SEQ ID NO: 6651) | Cys Glu Leu Cys Val Asn Gly Ala Cys Val Ala Cys Tyr |
| (SEQ ID NO: 6652) | Cys Glu Leu Cys Val Asn Gly Ala Cys Gly Gly Cys Tyr |
| (SEQ ID NO: 6653) | Cys Glu Leu Cys Val Asn Gly Ala Cys Gly Ala Cys Tyr |
| (SEQ ID NO: 6654) | Cys Glu Leu Cys Val Asn Gly Thr Cys Thr Gly Cys Tyr |
| (SEQ ID NO: 6655) | Cys Glu Leu Cys Val Asn Gly Thr Cys Thr Ala Cys Tyr |

FIG. 3AR

| | |
|---|---|
| (SEQ ID NO: 6656) | Cys Glu Leu Cys Val Asn Gly Thr Cys Val Gly Cys Tyr |
| (SEQ ID NO: 6657) | Cys Glu Leu Cys Val Asn Gly Thr Cys Val Ala Cys Tyr |
| (SEQ ID NO: 6658) | Cys Glu Leu Cys Val Asn Gly Thr Cys Gly Gly Cys Tyr |
| (SEQ ID NO: 6659) | Cys Glu Leu Cys Val Asn Gly Thr Cys Gly Ala Cys Tyr |
| (SEQ ID NO: 6660) | Cys Glu Leu Cys --- Asn Pro Ala Cys Thr Gly Cys Tyr |
| (SEQ ID NO: 6661) | Cys Glu Leu Cys --- Asn Pro Ala Cys Thr Ala Cys Tyr |
| (SEQ ID NO: 6662) | Cys Glu Leu Cys --- Asn Pro Ala Cys Val Gly Cys Tyr |
| (SEQ ID NO: 6663) | Cys Glu Leu Cys --- Asn Pro Ala Cys Val Ala Cys Tyr |
| (SEQ ID NO: 6664) | Cys Glu Leu Cys --- Asn Pro Ala Cys Gly Gly Cys Tyr |
| (SEQ ID NO: 6665) | Cys Glu Leu Cys --- Asn Pro Ala Cys Gly Ala Cys Tyr |
| (SEQ ID NO: 6666) | Cys Glu Leu Cys --- Asn Pro Thr Cys Thr Gly Cys Tyr |
| (SEQ ID NO: 6667) | Cys Glu Leu Cys --- Asn Pro Thr Cys Thr Ala Cys Tyr |
| (SEQ ID NO: 6668) | Cys Glu Leu Cys --- Asn Pro Thr Cys Val Gly Cys Tyr |
| (SEQ ID NO: 6669) | Cys Glu Leu Cys --- Asn Pro Thr Cys Val Ala Cys Tyr |
| (SEQ ID NO: 6670) | Cys Glu Leu Cys --- Asn Pro Thr Cys Gly Gly Cys Tyr |
| (SEQ ID NO: 6671) | Cys Glu Leu Cys --- Asn Pro Thr Cys Gly Ala Cys Tyr |
| (SEQ ID NO: 6672) | Cys Glu Leu Cys --- Asn Gly Ala Cys Thr Gly Cys Tyr |
| (SEQ ID NO: 6673) | Cys Glu Leu Cys --- Asn Gly Ala Cys Thr Ala Cys Tyr |
| (SEQ ID NO: 6674) | Cys Glu Leu Cys --- Asn Gly Ala Cys Val Gly Cys Tyr |
| (SEQ ID NO: 6675) | Cys Glu Leu Cys --- Asn Gly Ala Cys Val Ala Cys Tyr |
| (SEQ ID NO: 6676) | Cys Glu Leu Cys --- Asn Gly Ala Cys Gly Gly Cys Tyr |
| (SEQ ID NO: 6677) | Cys Glu Leu Cys --- Asn Gly Ala Cys Gly Ala Cys Tyr |
| (SEQ ID NO: 6678) | Cys Glu Leu Cys --- Asn Gly Thr Cys Thr Gly Cys Tyr |
| (SEQ ID NO: 6679) | Cys Glu Leu Cys --- Asn Gly Thr Cys Thr Ala Cys Tyr |
| (SEQ ID NO: 6680) | Cys Glu Leu Cys --- Asn Gly Thr Cys Val Gly Cys Tyr |
| (SEQ ID NO: 6681) | Cys Glu Leu Cys --- Asn Gly Thr Cys Val Ala Cys Tyr |
| (SEQ ID NO: 6682) | Cys Glu Leu Cys --- Asn Gly Thr Cys Gly Gly Cys Tyr |
| (SEQ ID NO: 6683) | Cys Glu Leu Cys --- Asn Gly Thr Cys Gly Ala Cys Tyr |
| (SEQ ID NO: 6684) | Cys Glu Tyr Cys Ala Asn Pro Ala Cys Thr Gly Cys |
| (SEQ ID NO: 6685) | Cys Glu Tyr Cys Ala Asn Pro Ala Cys Thr Ala Cys |
| (SEQ ID NO: 6686) | Cys Glu Tyr Cys Ala Asn Pro Ala Cys Val Gly Cys |
| (SEQ ID NO: 6687) | Cys Glu Tyr Cys Ala Asn Pro Ala Cys Val Ala Cys |
| (SEQ ID NO: 6688) | Cys Glu Tyr Cys Ala Asn Pro Ala Cys Gly Gly Cys |
| (SEQ ID NO: 6689) | Cys Glu Tyr Cys Ala Asn Pro Ala Cys Gly Ala Cys |
| (SEQ ID NO: 6690) | Cys Glu Tyr Cys Ala Asn Pro Thr Cys Thr Gly Cys |
| (SEQ ID NO: 6691) | Cys Glu Tyr Cys Ala Asn Pro Thr Cys Thr Ala Cys |
| (SEQ ID NO: 6692) | Cys Glu Tyr Cys Ala Asn Pro Thr Cys Val Gly Cys |
| (SEQ ID NO: 6693) | Cys Glu Tyr Cys Ala Asn Pro Thr Cys Val Ala Cys |
| (SEQ ID NO: 6694) | Cys Glu Tyr Cys Ala Asn Pro Thr Cys Gly Gly Cys |
| (SEQ ID NO: 6695) | Cys Glu Tyr Cys Ala Asn Pro Thr Cys Gly Ala Cys |
| (SEQ ID NO: 6696) | Cys Glu Tyr Cys Ala Asn Gly Ala Cys Thr Gly Cys |
| (SEQ ID NO: 6697) | Cys Glu Tyr Cys Ala Asn Gly Ala Cys Thr Ala Cys |
| (SEQ ID NO: 6698) | Cys Glu Tyr Cys Ala Asn Gly Ala Cys Val Gly Cys |

FIG. 3AS

| | | | | | | | | | | |
|---|---|---|---|---|---|---|---|---|---|---|
| (SEQ ID NO: 6699 ) | Cys | Glu | Tyr | Cys | Ala | Asn | Gly | Ala | Cys | Val | Ala | Cys |
| (SEQ ID NO: 6700 ) | Cys | Glu | Tyr | Cys | Ala | Asn | Gly | Ala | Cys | Gly | Gly | Cys |
| (SEQ ID NO: 6701 ) | Cys | Glu | Tyr | Cys | Ala | Asn | Gly | Ala | Cys | Gly | Ala | Cys |
| (SEQ ID NO: 6702 ) | Cys | Glu | Tyr | Cys | Ala | Asn | Gly | Thr | Cys | Thr | Gly | Cys |
| (SEQ ID NO: 6703 ) | Cys | Glu | Tyr | Cys | Ala | Asn | Gly | Thr | Cys | Thr | Ala | Cys |
| (SEQ ID NO: 6704 ) | Cys | Glu | Tyr | Cys | Ala | Asn | Gly | Thr | Cys | Val | Gly | Cys |
| (SEQ ID NO: 6705 ) | Cys | Glu | Tyr | Cys | Ala | Asn | Gly | Thr | Cys | Val | Ala | Cys |
| (SEQ ID NO: 6706 ) | Cys | Glu | Tyr | Cys | Ala | Asn | Gly | Thr | Cys | Gly | Gly | Cys |
| (SEQ ID NO: 6707 ) | Cys | Glu | Tyr | Cys | Ala | Asn | Gly | Thr | Cys | Gly | Ala | Cys |
| (SEQ ID NO: 6708 ) | Cys | Glu | Tyr | Cys | Arg | Asn | Pro | Ala | Cys | Thr | Gly | Cys |
| (SEQ ID NO: 6709 ) | Cys | Glu | Tyr | Cys | Arg | Asn | Pro | Ala | Cys | Thr | Ala | Cys |
| (SEQ ID NO: 6710 ) | Cys | Glu | Tyr | Cys | Arg | Asn | Pro | Ala | Cys | Val | Gly | Cys |
| (SEQ ID NO: 6711 ) | Cys | Glu | Tyr | Cys | Arg | Asn | Pro | Ala | Cys | Val | Ala | Cys |
| (SEQ ID NO: 6712 ) | Cys | Glu | Tyr | Cys | Arg | Asn | Pro | Ala | Cys | Gly | Gly | Cys |
| (SEQ ID NO: 6713 ) | Cys | Glu | Tyr | Cys | Arg | Asn | Pro | Ala | Cys | Gly | Ala | Cys |
| (SEQ ID NO: 6714 ) | Cys | Glu | Tyr | Cys | Arg | Asn | Pro | Thr | Cys | Thr | Gly | Cys |
| (SEQ ID NO: 6715 ) | Cys | Glu | Tyr | Cys | Arg | Asn | Pro | Thr | Cys | Thr | Ala | Cys |
| (SEQ ID NO: 6716 ) | Cys | Glu | Tyr | Cys | Arg | Asn | Pro | Thr | Cys | Val | Gly | Cys |
| (SEQ ID NO: 6717 ) | Cys | Glu | Tyr | Cys | Arg | Asn | Pro | Thr | Cys | Val | Ala | Cys |
| (SEQ ID NO: 6718 ) | Cys | Glu | Tyr | Cys | Arg | Asn | Pro | Thr | Cys | Gly | Gly | Cys |
| (SEQ ID NO: 6719 ) | Cys | Glu | Tyr | Cys | Arg | Asn | Pro | Thr | Cys | Gly | Ala | Cys |
| (SEQ ID NO: 6720 ) | Cys | Glu | Tyr | Cys | Arg | Asn | Gly | Ala | Cys | Thr | Gly | Cys |
| (SEQ ID NO: 6721 ) | Cys | Glu | Tyr | Cys | Arg | Asn | Gly | Ala | Cys | Thr | Ala | Cys |
| (SEQ ID NO: 6722 ) | Cys | Glu | Tyr | Cys | Arg | Asn | Gly | Ala | Cys | Val | Gly | Cys |
| (SEQ ID NO: 6723 ) | Cys | Glu | Tyr | Cys | Arg | Asn | Gly | Ala | Cys | Val | Ala | Cys |
| (SEQ ID NO: 6724 ) | Cys | Glu | Tyr | Cys | Arg | Asn | Gly | Ala | Cys | Gly | Gly | Cys |
| (SEQ ID NO: 6725 ) | Cys | Glu | Tyr | Cys | Arg | Asn | Gly | Ala | Cys | Gly | Ala | Cys |
| (SEQ ID NO: 6726 ) | Cys | Glu | Tyr | Cys | Arg | Asn | Gly | Thr | Cys | Thr | Gly | Cys |
| (SEQ ID NO: 6727 ) | Cys | Glu | Tyr | Cys | Arg | Asn | Gly | Thr | Cys | Thr | Ala | Cys |
| (SEQ ID NO: 6728 ) | Cys | Glu | Tyr | Cys | Arg | Asn | Gly | Thr | Cys | Val | Gly | Cys |
| (SEQ ID NO: 6729 ) | Cys | Glu | Tyr | Cys | Arg | Asn | Gly | Thr | Cys | Val | Ala | Cys |
| (SEQ ID NO: 6730 ) | Cys | Glu | Tyr | Cys | Arg | Asn | Gly | Thr | Cys | Gly | Gly | Cys |
| (SEQ ID NO: 6731 ) | Cys | Glu | Tyr | Cys | Arg | Asn | Gly | Thr | Cys | Gly | Ala | Cys |
| (SEQ ID NO: 6732 ) | Cys | Glu | Tyr | Cys | Asn | Asn | Pro | Ala | Cys | Thr | Gly | Cys |
| (SEQ ID NO: 6733 ) | Cys | Glu | Tyr | Cys | Asn | Asn | Pro | Ala | Cys | Thr | Ala | Cys |
| (SEQ ID NO: 6734 ) | Cys | Glu | Tyr | Cys | Asn | Asn | Pro | Ala | Cys | Val | Gly | Cys |
| (SEQ ID NO: 6735 ) | Cys | Glu | Tyr | Cys | Asn | Asn | Pro | Ala | Cys | Val | Ala | Cys |
| (SEQ ID NO: 6736 ) | Cys | Glu | Tyr | Cys | Asn | Asn | Pro | Ala | Cys | Gly | Gly | Cys |
| (SEQ ID NO: 6737 ) | Cys | Glu | Tyr | Cys | Asn | Asn | Pro | Ala | Cys | Gly | Ala | Cys |
| (SEQ ID NO: 6738 ) | Cys | Glu | Tyr | Cys | Asn | Asn | Pro | Thr | Cys | Thr | Gly | Cys |
| (SEQ ID NO: 6739 ) | Cys | Glu | Tyr | Cys | Asn | Asn | Pro | Thr | Cys | Thr | Ala | Cys |
| (SEQ ID NO: 6740 ) | Cys | Glu | Tyr | Cys | Asn | Asn | Pro | Thr | Cys | Val | Gly | Cys |
| (SEQ ID NO: 6741 ) | Cys | Glu | Tyr | Cys | Asn | Asn | Pro | Thr | Cys | Val | Ala | Cys |

FIG. 3AT

| | |
|---|---|
| (SEQ ID NO: 6742) | Cys Glu Tyr Cys Asn Asn Pro Thr Cys Gly Gly Cys |
| (SEQ ID NO: 6743) | Cys Glu Tyr Cys Asn Asn Pro Thr Cys Gly Ala Cys |
| (SEQ ID NO: 6744) | Cys Glu Tyr Cys Asn Asn Gly Ala Cys Thr Gly Cys |
| (SEQ ID NO: 6745) | Cys Glu Tyr Cys Asn Asn Gly Ala Cys Thr Ala Cys |
| (SEQ ID NO: 6746) | Cys Glu Tyr Cys Asn Asn Gly Ala Cys Val Gly Cys |
| (SEQ ID NO: 6747) | Cys Glu Tyr Cys Asn Asn Gly Ala Cys Val Ala Cys |
| (SEQ ID NO: 6748) | Cys Glu Tyr Cys Asn Asn Gly Ala Cys Gly Gly Cys |
| (SEQ ID NO: 6749) | Cys Glu Tyr Cys Asn Asn Gly Ala Cys Gly Ala Cys |
| (SEQ ID NO: 6750) | Cys Glu Tyr Cys Asn Asn Gly Thr Cys Thr Gly Cys |
| (SEQ ID NO: 6751) | Cys Glu Tyr Cys Asn Asn Gly Thr Cys Thr Ala Cys |
| (SEQ ID NO: 6752) | Cys Glu Tyr Cys Asn Asn Gly Thr Cys Val Gly Cys |
| (SEQ ID NO: 6753) | Cys Glu Tyr Cys Asn Asn Gly Thr Cys Val Ala Cys |
| (SEQ ID NO: 6754) | Cys Glu Tyr Cys Asn Asn Gly Thr Cys Gly Gly Cys |
| (SEQ ID NO: 6755) | Cys Glu Tyr Cys Asn Asn Gly Thr Cys Gly Ala Cys |
| (SEQ ID NO: 6756) | Cys Glu Tyr Cys Asp Asn Pro Ala Cys Thr Gly Cys |
| (SEQ ID NO: 6757) | Cys Glu Tyr Cys Asp Asn Pro Ala Cys Thr Ala Cys |
| (SEQ ID NO: 6758) | Cys Glu Tyr Cys Asp Asn Pro Ala Cys Val Gly Cys |
| (SEQ ID NO: 6759) | Cys Glu Tyr Cys Asp Asn Pro Ala Cys Val Ala Cys |
| (SEQ ID NO: 6760) | Cys Glu Tyr Cys Asp Asn Pro Ala Cys Gly Gly Cys |
| (SEQ ID NO: 6761) | Cys Glu Tyr Cys Asp Asn Pro Ala Cys Gly Ala Cys |
| (SEQ ID NO: 6762) | Cys Glu Tyr Cys Asp Asn Pro Thr Cys Thr Gly Cys |
| (SEQ ID NO: 6763) | Cys Glu Tyr Cys Asp Asn Pro Thr Cys Thr Ala Cys |
| (SEQ ID NO: 6764) | Cys Glu Tyr Cys Asp Asn Pro Thr Cys Val Gly Cys |
| (SEQ ID NO: 6765) | Cys Glu Tyr Cys Asp Asn Pro Thr Cys Val Ala Cys |
| (SEQ ID NO: 6766) | Cys Glu Tyr Cys Asp Asn Pro Thr Cys Gly Gly Cys |
| (SEQ ID NO: 6767) | Cys Glu Tyr Cys Asp Asn Pro Thr Cys Gly Ala Cys |
| (SEQ ID NO: 6768) | Cys Glu Tyr Cys Asp Asn Gly Ala Cys Thr Gly Cys |
| (SEQ ID NO: 6769) | Cys Glu Tyr Cys Asp Asn Gly Ala Cys Thr Ala Cys |
| (SEQ ID NO: 6770) | Cys Glu Tyr Cys Asp Asn Gly Ala Cys Val Gly Cys |
| (SEQ ID NO: 6771) | Cys Glu Tyr Cys Asp Asn Gly Ala Cys Val Ala Cys |
| (SEQ ID NO: 6772) | Cys Glu Tyr Cys Asp Asn Gly Ala Cys Gly Gly Cys |
| (SEQ ID NO: 6773) | Cys Glu Tyr Cys Asp Asn Gly Ala Cys Gly Ala Cys |
| (SEQ ID NO: 6774) | Cys Glu Tyr Cys Asp Asn Gly Thr Cys Thr Gly Cys |
| (SEQ ID NO: 6775) | Cys Glu Tyr Cys Asp Asn Gly Thr Cys Thr Ala Cys |
| (SEQ ID NO: 6776) | Cys Glu Tyr Cys Asp Asn Gly Thr Cys Val Gly Cys |
| (SEQ ID NO: 6777) | Cys Glu Tyr Cys Asp Asn Gly Thr Cys Val Ala Cys |
| (SEQ ID NO: 6778) | Cys Glu Tyr Cys Asp Asn Gly Thr Cys Gly Gly Cys |
| (SEQ ID NO: 6779) | Cys Glu Tyr Cys Asp Asn Gly Thr Cys Gly Ala Cys |
| (SEQ ID NO: 6780) | Cys Glu Tyr Cys Gln Asn Pro Ala Cys Thr Gly Cys |
| (SEQ ID NO: 6781) | Cys Glu Tyr Cys Gln Asn Pro Ala Cys Thr Ala Cys |
| (SEQ ID NO: 6782) | Cys Glu Tyr Cys Gln Asn Pro Ala Cys Val Gly Cys |
| (SEQ ID NO: 6783) | Cys Glu Tyr Cys Gln Asn Pro Ala Cys Val Ala Cys |
| (SEQ ID NO: 6784) | Cys Glu Tyr Cys Gln Asn Pro Ala Cys Gly Gly Cys |

FIG. 3AU

| | |
|---|---|
| (SEQ ID NO: 6785) | Cys Glu Tyr Cys Gln Asn Pro Ala Cys Gly Ala Cys |
| (SEQ ID NO: 6786) | Cys Glu Tyr Cys Gln Asn Pro Thr Cys Thr Gly Cys |
| (SEQ ID NO: 6787) | Cys Glu Tyr Cys Gln Asn Pro Thr Cys Thr Ala Cys |
| (SEQ ID NO: 6788) | Cys Glu Tyr Cys Gln Asn Pro Thr Cys Val Gly Cys |
| (SEQ ID NO: 6789) | Cys Glu Tyr Cys Gln Asn Pro Thr Cys Val Ala Cys |
| (SEQ ID NO: 6790) | Cys Glu Tyr Cys Gln Asn Pro Thr Cys Gly Gly Cys |
| (SEQ ID NO: 6791) | Cys Glu Tyr Cys Gln Asn Pro Thr Cys Gly Ala Cys |
| (SEQ ID NO: 6792) | Cys Glu Tyr Cys Gln Asn Gly Ala Cys Thr Gly Cys |
| (SEQ ID NO: 6793) | Cys Glu Tyr Cys Gln Asn Gly Ala Cys Thr Ala Cys |
| (SEQ ID NO: 6794) | Cys Glu Tyr Cys Gln Asn Gly Ala Cys Val Gly Cys |
| (SEQ ID NO: 6795) | Cys Glu Tyr Cys Gln Asn Gly Ala Cys Val Ala Cys |
| (SEQ ID NO: 6796) | Cys Glu Tyr Cys Gln Asn Gly Ala Cys Gly Gly Cys |
| (SEQ ID NO: 6797) | Cys Glu Tyr Cys Gln Asn Gly Ala Cys Gly Ala Cys |
| (SEQ ID NO: 6798) | Cys Glu Tyr Cys Gln Asn Gly Thr Cys Thr Gly Cys |
| (SEQ ID NO: 6799) | Cys Glu Tyr Cys Gln Asn Gly Thr Cys Thr Ala Cys |
| (SEQ ID NO: 6800) | Cys Glu Tyr Cys Gln Asn Gly Thr Cys Val Gly Cys |
| (SEQ ID NO: 6801) | Cys Glu Tyr Cys Gln Asn Gly Thr Cys Val Ala Cys |
| (SEQ ID NO: 6802) | Cys Glu Tyr Cys Gln Asn Gly Thr Cys Gly Gly Cys |
| (SEQ ID NO: 6803) | Cys Glu Tyr Cys Gln Asn Gly Thr Cys Gly Ala Cys |
| (SEQ ID NO: 6804) | Cys Glu Tyr Cys Glu Asn Pro Ala Cys Thr Gly Cys |
| (SEQ ID NO: 6805) | Cys Glu Tyr Cys Glu Asn Pro Ala Cys Thr Ala Cys |
| (SEQ ID NO: 6806) | Cys Glu Tyr Cys Glu Asn Pro Ala Cys Val Gly Cys |
| (SEQ ID NO: 6807) | Cys Glu Tyr Cys Glu Asn Pro Ala Cys Val Ala Cys |
| (SEQ ID NO: 6808) | Cys Glu Tyr Cys Glu Asn Pro Ala Cys Gly Gly Cys |
| (SEQ ID NO: 6809) | Cys Glu Tyr Cys Glu Asn Pro Ala Cys Gly Ala Cys |
| (SEQ ID NO: 6810) | Cys Glu Tyr Cys Glu Asn Pro Thr Cys Thr Gly Cys |
| (SEQ ID NO: 6811) | Cys Glu Tyr Cys Glu Asn Pro Thr Cys Thr Ala Cys |
| (SEQ ID NO: 6812) | Cys Glu Tyr Cys Glu Asn Pro Thr Cys Val Gly Cys |
| (SEQ ID NO: 6813) | Cys Glu Tyr Cys Glu Asn Pro Thr Cys Val Ala Cys |
| (SEQ ID NO: 6814) | Cys Glu Tyr Cys Glu Asn Pro Thr Cys Gly Gly Cys |
| (SEQ ID NO: 6815) | Cys Glu Tyr Cys Glu Asn Pro Thr Cys Gly Ala Cys |
| (SEQ ID NO: 6816) | Cys Glu Tyr Cys Glu Asn Gly Ala Cys Thr Gly Cys |
| (SEQ ID NO: 6817) | Cys Glu Tyr Cys Glu Asn Gly Ala Cys Thr Ala Cys |
| (SEQ ID NO: 6818) | Cys Glu Tyr Cys Glu Asn Gly Ala Cys Val Gly Cys |
| (SEQ ID NO: 6819) | Cys Glu Tyr Cys Glu Asn Gly Ala Cys Val Ala Cys |
| (SEQ ID NO: 6820) | Cys Glu Tyr Cys Glu Asn Gly Ala Cys Gly Gly Cys |
| (SEQ ID NO: 6821) | Cys Glu Tyr Cys Glu Asn Gly Ala Cys Gly Ala Cys |
| (SEQ ID NO: 6822) | Cys Glu Tyr Cys Glu Asn Gly Thr Cys Thr Gly Cys |
| (SEQ ID NO: 6823) | Cys Glu Tyr Cys Glu Asn Gly Thr Cys Thr Ala Cys |
| (SEQ ID NO: 6824) | Cys Glu Tyr Cys Glu Asn Gly Thr Cys Val Gly Cys |
| (SEQ ID NO: 6825) | Cys Glu Tyr Cys Glu Asn Gly Thr Cys Val Ala Cys |
| (SEQ ID NO: 6826) | Cys Glu Tyr Cys Glu Asn Gly Thr Cys Gly Gly Cys |
| (SEQ ID NO: 6827) | Cys Glu Tyr Cys Glu Asn Gly Thr Cys Gly Ala Cys |

FIG. 3AV

| SEQ ID NO | Sequence |
|---|---|
| (SEQ ID NO: 6828) | Cys Glu Tyr Cys Gly Asn Pro Ala Cys Thr Gly Cys |
| (SEQ ID NO: 6829) | Cys Glu Tyr Cys Gly Asn Pro Ala Cys Thr Ala Cys |
| (SEQ ID NO: 6830) | Cys Glu Tyr Cys Gly Asn Pro Ala Cys Val Gly Cys |
| (SEQ ID NO: 6831) | Cys Glu Tyr Cys Gly Asn Pro Ala Cys Val Ala Cys |
| (SEQ ID NO: 6832) | Cys Glu Tyr Cys Gly Asn Pro Ala Cys Gly Gly Cys |
| (SEQ ID NO: 6833) | Cys Glu Tyr Cys Gly Asn Pro Ala Cys Gly Ala Cys |
| (SEQ ID NO: 6834) | Cys Glu Tyr Cys Gly Asn Pro Thr Cys Thr Gly Cys |
| (SEQ ID NO: 6835) | Cys Glu Tyr Cys Gly Asn Pro Thr Cys Thr Ala Cys |
| (SEQ ID NO: 6836) | Cys Glu Tyr Cys Gly Asn Pro Thr Cys Val Gly Cys |
| (SEQ ID NO: 6837) | Cys Glu Tyr Cys Gly Asn Pro Thr Cys Val Ala Cys |
| (SEQ ID NO: 6838) | Cys Glu Tyr Cys Gly Asn Pro Thr Cys Gly Gly Cys |
| (SEQ ID NO: 6839) | Cys Glu Tyr Cys Gly Asn Pro Thr Cys Gly Ala Cys |
| (SEQ ID NO: 6840) | Cys Glu Tyr Cys Gly Asn Gly Ala Cys Thr Gly Cys |
| (SEQ ID NO: 6841) | Cys Glu Tyr Cys Gly Asn Gly Ala Cys Thr Ala Cys |
| (SEQ ID NO: 6842) | Cys Glu Tyr Cys Gly Asn Gly Ala Cys Val Gly Cys |
| (SEQ ID NO: 6843) | Cys Glu Tyr Cys Gly Asn Gly Ala Cys Val Ala Cys |
| (SEQ ID NO: 6844) | Cys Glu Tyr Cys Gly Asn Gly Ala Cys Gly Gly Cys |
| (SEQ ID NO: 6845) | Cys Glu Tyr Cys Gly Asn Gly Ala Cys Gly Ala Cys |
| (SEQ ID NO: 6846) | Cys Glu Tyr Cys Gly Asn Gly Thr Cys Thr Gly Cys |
| (SEQ ID NO: 6847) | Cys Glu Tyr Cys Gly Asn Gly Thr Cys Thr Ala Cys |
| (SEQ ID NO: 6848) | Cys Glu Tyr Cys Gly Asn Gly Thr Cys Val Gly Cys |
| (SEQ ID NO: 6849) | Cys Glu Tyr Cys Gly Asn Gly Thr Cys Val Ala Cys |
| (SEQ ID NO: 6850) | Cys Glu Tyr Cys Gly Asn Gly Thr Cys Gly Gly Cys |
| (SEQ ID NO: 6851) | Cys Glu Tyr Cys Gly Asn Gly Thr Cys Gly Ala Cys |
| (SEQ ID NO: 6852) | Cys Glu Tyr Cys His Asn Pro Ala Cys Thr Gly Cys |
| (SEQ ID NO: 6853) | Cys Glu Tyr Cys His Asn Pro Ala Cys Thr Ala Cys |
| (SEQ ID NO: 6854) | Cys Glu Tyr Cys His Asn Pro Ala Cys Val Gly Cys |
| (SEQ ID NO: 6855) | Cys Glu Tyr Cys His Asn Pro Ala Cys Val Ala Cys |
| (SEQ ID NO: 6856) | Cys Glu Tyr Cys His Asn Pro Ala Cys Gly Gly Cys |
| (SEQ ID NO: 6857) | Cys Glu Tyr Cys His Asn Pro Ala Cys Gly Ala Cys |
| (SEQ ID NO: 6858) | Cys Glu Tyr Cys His Asn Pro Thr Cys Thr Gly Cys |
| (SEQ ID NO: 6859) | Cys Glu Tyr Cys His Asn Pro Thr Cys Thr Ala Cys |
| (SEQ ID NO: 6860) | Cys Glu Tyr Cys His Asn Pro Thr Cys Val Gly Cys |
| (SEQ ID NO: 6861) | Cys Glu Tyr Cys His Asn Pro Thr Cys Val Ala Cys |
| (SEQ ID NO: 6862) | Cys Glu Tyr Cys His Asn Pro Thr Cys Gly Gly Cys |
| (SEQ ID NO: 6863) | Cys Glu Tyr Cys His Asn Pro Thr Cys Gly Ala Cys |
| (SEQ ID NO: 6864) | Cys Glu Tyr Cys His Asn Gly Ala Cys Thr Gly Cys |
| (SEQ ID NO: 6865) | Cys Glu Tyr Cys His Asn Gly Ala Cys Thr Ala Cys |
| (SEQ ID NO: 6866) | Cys Glu Tyr Cys His Asn Gly Ala Cys Val Gly Cys |
| (SEQ ID NO: 6867) | Cys Glu Tyr Cys His Asn Gly Ala Cys Val Ala Cys |
| (SEQ ID NO: 6868) | Cys Glu Tyr Cys His Asn Gly Ala Cys Gly Gly Cys |
| (SEQ ID NO: 6869) | Cys Glu Tyr Cys His Asn Gly Ala Cys Gly Ala Cys |
| (SEQ ID NO: 6870) | Cys Glu Tyr Cys His Asn Gly Thr Cys Thr Gly Cys |

FIG. 3AW (SEQ ID NO: 6871) Cys Glu Tyr Cys His Asn Gly Thr Cys Thr Ala Cys
(SEQ ID NO: 6872) Cys Glu Tyr Cys His Asn Gly Thr Cys Val Gly Cys
(SEQ ID NO: 6873) Cys Glu Tyr Cys His Asn Gly Thr Cys Val Ala Cys
(SEQ ID NO: 6874) Cys Glu Tyr Cys His Asn Gly Thr Cys Gly Gly Cys
(SEQ ID NO: 6875) Cys Glu Tyr Cys His Asn Gly Thr Cys Gly Ala Cys
(SEQ ID NO: 6876) Cys Glu Tyr Cys Ile Asn Pro Ala Cys Thr Gly Cys
(SEQ ID NO: 6877) Cys Glu Tyr Cys Ile Asn Pro Ala Cys Thr Ala Cys
(SEQ ID NO: 6878) Cys Glu Tyr Cys Ile Asn Pro Ala Cys Val Gly Cys
(SEQ ID NO: 6879) Cys Glu Tyr Cys Ile Asn Pro Ala Cys Val Ala Cys
(SEQ ID NO: 6880) Cys Glu Tyr Cys Ile Asn Pro Ala Cys Gly Gly Cys
(SEQ ID NO: 6881) Cys Glu Tyr Cys Ile Asn Pro Ala Cys Gly Ala Cys
(SEQ ID NO: 6882) Cys Glu Tyr Cys Ile Asn Pro Thr Cys Thr Gly Cys
(SEQ ID NO: 6883) Cys Glu Tyr Cys Ile Asn Pro Thr Cys Thr Ala Cys
(SEQ ID NO: 6884) Cys Glu Tyr Cys Ile Asn Pro Thr Cys Val Gly Cys
(SEQ ID NO: 6885) Cys Glu Tyr Cys Ile Asn Pro Thr Cys Val Ala Cys
(SEQ ID NO: 6886) Cys Glu Tyr Cys Ile Asn Pro Thr Cys Gly Gly Cys
(SEQ ID NO: 6887) Cys Glu Tyr Cys Ile Asn Pro Thr Cys Gly Ala Cys
(SEQ ID NO: 6888) Cys Glu Tyr Cys Ile Asn Gly Ala Cys Thr Gly Cys
(SEQ ID NO: 6889) Cys Glu Tyr Cys Ile Asn Gly Ala Cys Thr Ala Cys
(SEQ ID NO: 6890) Cys Glu Tyr Cys Ile Asn Gly Ala Cys Val Gly Cys
(SEQ ID NO: 6891) Cys Glu Tyr Cys Ile Asn Gly Ala Cys Val Ala Cys
(SEQ ID NO: 6892) Cys Glu Tyr Cys Ile Asn Gly Ala Cys Gly Gly Cys
(SEQ ID NO: 6893) Cys Glu Tyr Cys Ile Asn Gly Ala Cys Gly Ala Cys
(SEQ ID NO: 6894) Cys Glu Tyr Cys Ile Asn Gly Thr Cys Thr Gly Cys
(SEQ ID NO: 6895) Cys Glu Tyr Cys Ile Asn Gly Thr Cys Thr Ala Cys
(SEQ ID NO: 6896) Cys Glu Tyr Cys Ile Asn Gly Thr Cys Val Gly Cys
(SEQ ID NO: 6897) Cys Glu Tyr Cys Ile Asn Gly Thr Cys Val Ala Cys
(SEQ ID NO: 6898) Cys Glu Tyr Cys Ile Asn Gly Thr Cys Gly Gly Cys
(SEQ ID NO: 6899) Cys Glu Tyr Cys Ile Asn Gly Thr Cys Gly Ala Cys
(SEQ ID NO: 6900) Cys Glu Tyr Cys Leu Asn Pro Ala Cys Thr Gly Cys
(SEQ ID NO: 6901) Cys Glu Tyr Cys Leu Asn Pro Ala Cys Thr Ala Cys
(SEQ ID NO: 6902) Cys Glu Tyr Cys Leu Asn Pro Ala Cys Val Gly Cys
(SEQ ID NO: 6903) Cys Glu Tyr Cys Leu Asn Pro Ala Cys Val Ala Cys
(SEQ ID NO: 6904) Cys Glu Tyr Cys Leu Asn Pro Ala Cys Gly Gly Cys
(SEQ ID NO: 6905) Cys Glu Tyr Cys Leu Asn Pro Ala Cys Gly Ala Cys
(SEQ ID NO: 6906) Cys Glu Tyr Cys Leu Asn Pro Thr Cys Thr Gly Cys
(SEQ ID NO: 6907) Cys Glu Tyr Cys Leu Asn Pro Thr Cys Thr Ala Cys
(SEQ ID NO: 6908) Cys Glu Tyr Cys Leu Asn Pro Thr Cys Val Gly Cys
(SEQ ID NO: 6909) Cys Glu Tyr Cys Leu Asn Pro Thr Cys Val Ala Cys
(SEQ ID NO: 6910) Cys Glu Tyr Cys Leu Asn Pro Thr Cys Gly Gly Cys
(SEQ ID NO: 6911) Cys Glu Tyr Cys Leu Asn Pro Thr Cys Gly Ala Cys
(SEQ ID NO: 6912) Cys Glu Tyr Cys Leu Asn Gly Ala Cys Thr Gly Cys
(SEQ ID NO: 6913) Cys Glu Tyr Cys Leu Asn Gly Ala Cys Thr Ala Cys

FIG. 3AX (SEQ ID NO: 6914)  Cys Glu Tyr Cys Leu Asn Gly Ala Cys Val Gly Cys
(SEQ ID NO: 6915)  Cys Glu Tyr Cys Leu Asn Gly Ala Cys Val Ala Cys
(SEQ ID NO: 6916)  Cys Glu Tyr Cys Leu Asn Gly Ala Cys Gly Gly Cys
(SEQ ID NO: 6917)  Cys Glu Tyr Cys Leu Asn Gly Ala Cys Gly Ala Cys
(SEQ ID NO: 6918)  Cys Glu Tyr Cys Leu Asn Gly Thr Cys Thr Gly Cys
(SEQ ID NO: 6919)  Cys Glu Tyr Cys Leu Asn Gly Thr Cys Thr Ala Cys
(SEQ ID NO: 6920)  Cys Glu Tyr Cys Leu Asn Gly Thr Cys Val Gly Cys
(SEQ ID NO: 6921)  Cys Glu Tyr Cys Leu Asn Gly Thr Cys Val Ala Cys
(SEQ ID NO: 6922)  Cys Glu Tyr Cys Leu Asn Gly Thr Cys Gly Gly Cys
(SEQ ID NO: 6923)  Cys Glu Tyr Cys Leu Asn Gly Thr Cys Gly Ala Cys
(SEQ ID NO: 6924)  Cys Glu Tyr Cys Lys Asn Pro Ala Cys Thr Gly Cys
(SEQ ID NO: 6925)  Cys Glu Tyr Cys Lys Asn Pro Ala Cys Thr Ala Cys
(SEQ ID NO: 6926)  Cys Glu Tyr Cys Lys Asn Pro Ala Cys Val Gly Cys
(SEQ ID NO: 6927)  Cys Glu Tyr Cys Lys Asn Pro Ala Cys Val Ala Cys
(SEQ ID NO: 6928)  Cys Glu Tyr Cys Lys Asn Pro Ala Cys Gly Gly Cys
(SEQ ID NO: 6929)  Cys Glu Tyr Cys Lys Asn Pro Ala Cys Gly Ala Cys
(SEQ ID NO: 6930)  Cys Glu Tyr Cys Lys Asn Pro Thr Cys Thr Gly Cys
(SEQ ID NO: 6931)  Cys Glu Tyr Cys Lys Asn Pro Thr Cys Thr Ala Cys
(SEQ ID NO: 6932)  Cys Glu Tyr Cys Lys Asn Pro Thr Cys Val Gly Cys
(SEQ ID NO: 6933)  Cys Glu Tyr Cys Lys Asn Pro Thr Cys Val Ala Cys
(SEQ ID NO: 6934)  Cys Glu Tyr Cys Lys Asn Pro Thr Cys Gly Gly Cys
(SEQ ID NO: 6935)  Cys Glu Tyr Cys Lys Asn Pro Thr Cys Gly Ala Cys
(SEQ ID NO: 6936)  Cys Glu Tyr Cys Lys Asn Gly Ala Cys Thr Gly Cys
(SEQ ID NO: 6937)  Cys Glu Tyr Cys Lys Asn Gly Ala Cys Thr Ala Cys
(SEQ ID NO: 6938)  Cys Glu Tyr Cys Lys Asn Gly Ala Cys Val Gly Cys
(SEQ ID NO: 6939)  Cys Glu Tyr Cys Lys Asn Gly Ala Cys Val Ala Cys
(SEQ ID NO: 6940)  Cys Glu Tyr Cys Lys Asn Gly Ala Cys Gly Gly Cys
(SEQ ID NO: 6941)  Cys Glu Tyr Cys Lys Asn Gly Ala Cys Gly Ala Cys
(SEQ ID NO: 6942)  Cys Glu Tyr Cys Lys Asn Gly Thr Cys Thr Gly Cys
(SEQ ID NO: 6943)  Cys Glu Tyr Cys Lys Asn Gly Thr Cys Thr Ala Cys
(SEQ ID NO: 6944)  Cys Glu Tyr Cys Lys Asn Gly Thr Cys Val Gly Cys
(SEQ ID NO: 6945)  Cys Glu Tyr Cys Lys Asn Gly Thr Cys Val Ala Cys
(SEQ ID NO: 6946)  Cys Glu Tyr Cys Lys Asn Gly Thr Cys Gly Gly Cys
(SEQ ID NO: 6947)  Cys Glu Tyr Cys Lys Asn Gly Thr Cys Gly Ala Cys
(SEQ ID NO: 6948)  Cys Glu Tyr Cys Met Asn Pro Ala Cys Thr Gly Cys
(SEQ ID NO: 6949)  Cys Glu Tyr Cys Met Asn Pro Ala Cys Thr Ala Cys
(SEQ ID NO: 6950)  Cys Glu Tyr Cys Met Asn Pro Ala Cys Val Gly Cys
(SEQ ID NO: 6951)  Cys Glu Tyr Cys Met Asn Pro Ala Cys Val Ala Cys
(SEQ ID NO: 6952)  Cys Glu Tyr Cys Met Asn Pro Ala Cys Gly Gly Cys
(SEQ ID NO: 6953)  Cys Glu Tyr Cys Met Asn Pro Ala Cys Gly Ala Cys
(SEQ ID NO: 6954)  Cys Glu Tyr Cys Met Asn Pro Thr Cys Thr Gly Cys
(SEQ ID NO: 6955)  Cys Glu Tyr Cys Met Asn Pro Thr Cys Thr Ala Cys
(SEQ ID NO: 6956)  Cys Glu Tyr Cys Met Asn Pro Thr Cys Val Gly Cys

FIG. 3AY

| | |
|---|---|
| (SEQ ID NO: 6957) | Cys Glu Tyr Cys Met Asn Pro Thr Cys Val Ala Cys |
| (SEQ ID NO: 6958) | Cys Glu Tyr Cys Met Asn Pro Thr Cys Gly Gly Cys |
| (SEQ ID NO: 6959) | Cys Glu Tyr Cys Met Asn Pro Thr Cys Gly Ala Cys |
| (SEQ ID NO: 6960) | Cys Glu Tyr Cys Met Asn Gly Ala Cys Thr Gly Cys |
| (SEQ ID NO: 6961) | Cys Glu Tyr Cys Met Asn Gly Ala Cys Thr Ala Cys |
| (SEQ ID NO: 6962) | Cys Glu Tyr Cys Met Asn Gly Ala Cys Val Gly Cys |
| (SEQ ID NO: 6963) | Cys Glu Tyr Cys Met Asn Gly Ala Cys Val Ala Cys |
| (SEQ ID NO: 6964) | Cys Glu Tyr Cys Met Asn Gly Ala Cys Gly Gly Cys |
| (SEQ ID NO: 6965) | Cys Glu Tyr Cys Met Asn Gly Ala Cys Gly Ala Cys |
| (SEQ ID NO: 6966) | Cys Glu Tyr Cys Met Asn Gly Thr Cys Thr Gly Cys |
| (SEQ ID NO: 6967) | Cys Glu Tyr Cys Met Asn Gly Thr Cys Thr Ala Cys |
| (SEQ ID NO: 6968) | Cys Glu Tyr Cys Met Asn Gly Thr Cys Val Gly Cys |
| (SEQ ID NO: 6969) | Cys Glu Tyr Cys Met Asn Gly Thr Cys Val Ala Cys |
| (SEQ ID NO: 6970) | Cys Glu Tyr Cys Met Asn Gly Thr Cys Gly Gly Cys |
| (SEQ ID NO: 6971) | Cys Glu Tyr Cys Met Asn Gly Thr Cys Gly Ala Cys |
| (SEQ ID NO: 6972) | Cys Glu Tyr Cys Phe Asn Pro Ala Cys Thr Gly Cys |
| (SEQ ID NO: 6973) | Cys Glu Tyr Cys Phe Asn Pro Ala Cys Thr Ala Cys |
| (SEQ ID NO: 6974) | Cys Glu Tyr Cys Phe Asn Pro Ala Cys Val Gly Cys |
| (SEQ ID NO: 6975) | Cys Glu Tyr Cys Phe Asn Pro Ala Cys Val Ala Cys |
| (SEQ ID NO: 6976) | Cys Glu Tyr Cys Phe Asn Pro Ala Cys Gly Gly Cys |
| (SEQ ID NO: 6977) | Cys Glu Tyr Cys Phe Asn Pro Ala Cys Gly Ala Cys |
| (SEQ ID NO: 6978) | Cys Glu Tyr Cys Phe Asn Pro Thr Cys Thr Gly Cys |
| (SEQ ID NO: 6979) | Cys Glu Tyr Cys Phe Asn Pro Thr Cys Thr Ala Cys |
| (SEQ ID NO: 6980) | Cys Glu Tyr Cys Phe Asn Pro Thr Cys Val Gly Cys |
| (SEQ ID NO: 6981) | Cys Glu Tyr Cys Phe Asn Pro Thr Cys Val Ala Cys |
| (SEQ ID NO: 6982) | Cys Glu Tyr Cys Phe Asn Pro Thr Cys Gly Gly Cys |
| (SEQ ID NO: 6983) | Cys Glu Tyr Cys Phe Asn Pro Thr Cys Gly Ala Cys |
| (SEQ ID NO: 6984) | Cys Glu Tyr Cys Phe Asn Gly Ala Cys Thr Gly Cys |
| (SEQ ID NO: 6985) | Cys Glu Tyr Cys Phe Asn Gly Ala Cys Thr Ala Cys |
| (SEQ ID NO: 6986) | Cys Glu Tyr Cys Phe Asn Gly Ala Cys Val Gly Cys |
| (SEQ ID NO: 6987) | Cys Glu Tyr Cys Phe Asn Gly Ala Cys Val Ala Cys |
| (SEQ ID NO: 6988) | Cys Glu Tyr Cys Phe Asn Gly Ala Cys Gly Gly Cys |
| (SEQ ID NO: 6989) | Cys Glu Tyr Cys Phe Asn Gly Ala Cys Gly Ala Cys |
| (SEQ ID NO: 6990) | Cys Glu Tyr Cys Phe Asn Gly Thr Cys Thr Gly Cys |
| (SEQ ID NO: 6991) | Cys Glu Tyr Cys Phe Asn Gly Thr Cys Thr Ala Cys |
| (SEQ ID NO: 6992) | Cys Glu Tyr Cys Phe Asn Gly Thr Cys Val Gly Cys |
| (SEQ ID NO: 6993) | Cys Glu Tyr Cys Phe Asn Gly Thr Cys Val Ala Cys |
| (SEQ ID NO: 6994) | Cys Glu Tyr Cys Phe Asn Gly Thr Cys Gly Gly Cys |
| (SEQ ID NO: 6995) | Cys Glu Tyr Cys Phe Asn Gly Thr Cys Gly Ala Cys |
| (SEQ ID NO: 6996) | Cys Glu Tyr Cys Pro Asn Pro Ala Cys Thr Gly Cys |
| (SEQ ID NO: 6997) | Cys Glu Tyr Cys Pro Asn Pro Ala Cys Thr Ala Cys |
| (SEQ ID NO: 6998) | Cys Glu Tyr Cys Pro Asn Pro Ala Cys Val Gly Cys |
| (SEQ ID NO: 6999) | Cys Glu Tyr Cys Pro Asn Pro Ala Cys Val Ala Cys |

FIG. 3AZ

| | |
|---|---|
| (SEQ ID NO: 7000) | Cys Glu Tyr Cys Pro Asn Pro Ala Cys Gly Gly Cys |
| (SEQ ID NO: 7001) | Cys Glu Tyr Cys Pro Asn Pro Ala Cys Gly Ala Cys |
| (SEQ ID NO: 7002) | Cys Glu Tyr Cys Pro Asn Pro Thr Cys Thr Gly Cys |
| (SEQ ID NO: 7003) | Cys Glu Tyr Cys Pro Asn Pro Thr Cys Thr Ala Cys |
| (SEQ ID NO: 7004) | Cys Glu Tyr Cys Pro Asn Pro Thr Cys Val Gly Cys |
| (SEQ ID NO: 7005) | Cys Glu Tyr Cys Pro Asn Pro Thr Cys Val Ala Cys |
| (SEQ ID NO: 7006) | Cys Glu Tyr Cys Pro Asn Pro Thr Cys Gly Gly Cys |
| (SEQ ID NO: 7007) | Cys Glu Tyr Cys Pro Asn Pro Thr Cys Gly Ala Cys |
| (SEQ ID NO: 7008) | Cys Glu Tyr Cys Pro Asn Gly Ala Cys Thr Gly Cys |
| (SEQ ID NO: 7009) | Cys Glu Tyr Cys Pro Asn Gly Ala Cys Thr Ala Cys |
| (SEQ ID NO: 7010) | Cys Glu Tyr Cys Pro Asn Gly Ala Cys Val Gly Cys |
| (SEQ ID NO: 7011) | Cys Glu Tyr Cys Pro Asn Gly Ala Cys Val Ala Cys |
| (SEQ ID NO: 7012) | Cys Glu Tyr Cys Pro Asn Gly Ala Cys Gly Gly Cys |
| (SEQ ID NO: 7013) | Cys Glu Tyr Cys Pro Asn Gly Ala Cys Gly Ala Cys |
| (SEQ ID NO: 7014) | Cys Glu Tyr Cys Pro Asn Gly Thr Cys Thr Gly Cys |
| (SEQ ID NO: 7015) | Cys Glu Tyr Cys Pro Asn Gly Thr Cys Thr Ala Cys |
| (SEQ ID NO: 7016) | Cys Glu Tyr Cys Pro Asn Gly Thr Cys Val Gly Cys |
| (SEQ ID NO: 7017) | Cys Glu Tyr Cys Pro Asn Gly Thr Cys Val Ala Cys |
| (SEQ ID NO: 7018) | Cys Glu Tyr Cys Pro Asn Gly Thr Cys Gly Gly Cys |
| (SEQ ID NO: 7019) | Cys Glu Tyr Cys Pro Asn Gly Thr Cys Gly Ala Cys |
| (SEQ ID NO: 7020) | Cys Glu Tyr Cys Ser Asn Pro Ala Cys Thr Gly Cys |
| (SEQ ID NO: 7021) | Cys Glu Tyr Cys Ser Asn Pro Ala Cys Thr Ala Cys |
| (SEQ ID NO: 7022) | Cys Glu Tyr Cys Ser Asn Pro Ala Cys Val Gly Cys |
| (SEQ ID NO: 7023) | Cys Glu Tyr Cys Ser Asn Pro Ala Cys Val Ala Cys |
| (SEQ ID NO: 7024) | Cys Glu Tyr Cys Ser Asn Pro Ala Cys Gly Gly Cys |
| (SEQ ID NO: 7025) | Cys Glu Tyr Cys Ser Asn Pro Ala Cys Gly Ala Cys |
| (SEQ ID NO: 7026) | Cys Glu Tyr Cys Ser Asn Pro Thr Cys Thr Gly Cys |
| (SEQ ID NO: 7027) | Cys Glu Tyr Cys Ser Asn Pro Thr Cys Thr Ala Cys |
| (SEQ ID NO: 7028) | Cys Glu Tyr Cys Ser Asn Pro Thr Cys Val Gly Cys |
| (SEQ ID NO: 7029) | Cys Glu Tyr Cys Ser Asn Pro Thr Cys Val Ala Cys |
| (SEQ ID NO: 7030) | Cys Glu Tyr Cys Ser Asn Pro Thr Cys Gly Gly Cys |
| (SEQ ID NO: 7031) | Cys Glu Tyr Cys Ser Asn Pro Thr Cys Gly Ala Cys |
| (SEQ ID NO: 7032) | Cys Glu Tyr Cys Ser Asn Gly Ala Cys Thr Gly Cys |
| (SEQ ID NO: 7033) | Cys Glu Tyr Cys Ser Asn Gly Ala Cys Thr Ala Cys |
| (SEQ ID NO: 7034) | Cys Glu Tyr Cys Ser Asn Gly Ala Cys Val Gly Cys |
| (SEQ ID NO: 7035) | Cys Glu Tyr Cys Ser Asn Gly Ala Cys Val Ala Cys |
| (SEQ ID NO: 7036) | Cys Glu Tyr Cys Ser Asn Gly Ala Cys Gly Gly Cys |
| (SEQ ID NO: 7037) | Cys Glu Tyr Cys Ser Asn Gly Ala Cys Gly Ala Cys |
| (SEQ ID NO: 7038) | Cys Glu Tyr Cys Ser Asn Gly Thr Cys Thr Gly Cys |
| (SEQ ID NO: 7039) | Cys Glu Tyr Cys Ser Asn Gly Thr Cys Thr Ala Cys |
| (SEQ ID NO: 7040) | Cys Glu Tyr Cys Ser Asn Gly Thr Cys Val Gly Cys |
| (SEQ ID NO: 7041) | Cys Glu Tyr Cys Ser Asn Gly Thr Cys Val Ala Cys |
| (SEQ ID NO: 7042) | Cys Glu Tyr Cys Ser Asn Gly Thr Cys Gly Gly Cys |

FIG. 3BA

| | |
|---|---|
| (SEQ ID NO: 7043) | Cys Glu Tyr Cys Ser Asn Gly Thr Cys Gly Ala Cys |
| (SEQ ID NO: 7044) | Cys Glu Tyr Cys Thr Asn Pro Ala Cys Thr Gly Cys |
| (SEQ ID NO: 7045) | Cys Glu Tyr Cys Thr Asn Pro Ala Cys Thr Ala Cys |
| (SEQ ID NO: 7046) | Cys Glu Tyr Cys Thr Asn Pro Ala Cys Val Gly Cys |
| (SEQ ID NO: 7047) | Cys Glu Tyr Cys Thr Asn Pro Ala Cys Val Ala Cys |
| (SEQ ID NO: 7048) | Cys Glu Tyr Cys Thr Asn Pro Ala Cys Gly Gly Cys |
| (SEQ ID NO: 7049) | Cys Glu Tyr Cys Thr Asn Pro Ala Cys Gly Ala Cys |
| (SEQ ID NO: 7050) | Cys Glu Tyr Cys Thr Asn Pro Thr Cys Thr Gly Cys |
| (SEQ ID NO: 7051) | Cys Glu Tyr Cys Thr Asn Pro Thr Cys Thr Ala Cys |
| (SEQ ID NO: 7052) | Cys Glu Tyr Cys Thr Asn Pro Thr Cys Val Gly Cys |
| (SEQ ID NO: 7053) | Cys Glu Tyr Cys Thr Asn Pro Thr Cys Val Ala Cys |
| (SEQ ID NO: 7054) | Cys Glu Tyr Cys Thr Asn Pro Thr Cys Gly Gly Cys |
| (SEQ ID NO: 7055) | Cys Glu Tyr Cys Thr Asn Pro Thr Cys Gly Ala Cys |
| (SEQ ID NO: 7056) | Cys Glu Tyr Cys Thr Asn Gly Ala Cys Thr Gly Cys |
| (SEQ ID NO: 7057) | Cys Glu Tyr Cys Thr Asn Gly Ala Cys Thr Ala Cys |
| (SEQ ID NO: 7058) | Cys Glu Tyr Cys Thr Asn Gly Ala Cys Val Gly Cys |
| (SEQ ID NO: 7059) | Cys Glu Tyr Cys Thr Asn Gly Ala Cys Val Ala Cys |
| (SEQ ID NO: 7060) | Cys Glu Tyr Cys Thr Asn Gly Ala Cys Gly Gly Cys |
| (SEQ ID NO: 7061) | Cys Glu Tyr Cys Thr Asn Gly Ala Cys Gly Ala Cys |
| (SEQ ID NO: 7062) | Cys Glu Tyr Cys Thr Asn Gly Thr Cys Thr Gly Cys |
| (SEQ ID NO: 7063) | Cys Glu Tyr Cys Thr Asn Gly Thr Cys Thr Ala Cys |
| (SEQ ID NO: 7064) | Cys Glu Tyr Cys Thr Asn Gly Thr Cys Val Gly Cys |
| (SEQ ID NO: 7065) | Cys Glu Tyr Cys Thr Asn Gly Thr Cys Val Ala Cys |
| (SEQ ID NO: 7066) | Cys Glu Tyr Cys Thr Asn Gly Thr Cys Gly Gly Cys |
| (SEQ ID NO: 7067) | Cys Glu Tyr Cys Thr Asn Gly Thr Cys Gly Ala Cys |
| (SEQ ID NO: 7068) | Cys Glu Tyr Cys Trp Asn Pro Ala Cys Thr Gly Cys |
| (SEQ ID NO: 7069) | Cys Glu Tyr Cys Trp Asn Pro Ala Cys Thr Ala Cys |
| (SEQ ID NO: 7070) | Cys Glu Tyr Cys Trp Asn Pro Ala Cys Val Gly Cys |
| (SEQ ID NO: 7071) | Cys Glu Tyr Cys Trp Asn Pro Ala Cys Val Ala Cys |
| (SEQ ID NO: 7072) | Cys Glu Tyr Cys Trp Asn Pro Ala Cys Gly Gly Cys |
| (SEQ ID NO: 7073) | Cys Glu Tyr Cys Trp Asn Pro Ala Cys Gly Ala Cys |
| (SEQ ID NO: 7074) | Cys Glu Tyr Cys Trp Asn Pro Thr Cys Thr Gly Cys |
| (SEQ ID NO: 7075) | Cys Glu Tyr Cys Trp Asn Pro Thr Cys Thr Ala Cys |
| (SEQ ID NO: 7076) | Cys Glu Tyr Cys Trp Asn Pro Thr Cys Val Gly Cys |
| (SEQ ID NO: 7077) | Cys Glu Tyr Cys Trp Asn Pro Thr Cys Val Ala Cys |
| (SEQ ID NO: 7078) | Cys Glu Tyr Cys Trp Asn Pro Thr Cys Gly Gly Cys |
| (SEQ ID NO: 7079) | Cys Glu Tyr Cys Trp Asn Pro Thr Cys Gly Ala Cys |
| (SEQ ID NO: 7080) | Cys Glu Tyr Cys Trp Asn Gly Ala Cys Thr Gly Cys |
| (SEQ ID NO: 7081) | Cys Glu Tyr Cys Trp Asn Gly Ala Cys Thr Ala Cys |
| (SEQ ID NO: 7082) | Cys Glu Tyr Cys Trp Asn Gly Ala Cys Val Gly Cys |
| (SEQ ID NO: 7083) | Cys Glu Tyr Cys Trp Asn Gly Ala Cys Val Ala Cys |
| (SEQ ID NO: 7084) | Cys Glu Tyr Cys Trp Asn Gly Ala Cys Gly Gly Cys |
| (SEQ ID NO: 7085) | Cys Glu Tyr Cys Trp Asn Gly Ala Cys Gly Ala Cys |

FIG. 3BB

| | |
|---|---|
| (SEQ ID NO: 7086) | Cys Glu Tyr Cys Trp Asn Gly Thr Cys Thr Gly Cys |
| (SEQ ID NO: 7087) | Cys Glu Tyr Cys Trp Asn Gly Thr Cys Thr Ala Cys |
| (SEQ ID NO: 7088) | Cys Glu Tyr Cys Trp Asn Gly Thr Cys Val Gly Cys |
| (SEQ ID NO: 7089) | Cys Glu Tyr Cys Trp Asn Gly Thr Cys Val Ala Cys |
| (SEQ ID NO: 7090) | Cys Glu Tyr Cys Trp Asn Gly Thr Cys Gly Gly Cys |
| (SEQ ID NO: 7091) | Cys Glu Tyr Cys Trp Asn Gly Thr Cys Gly Ala Cys |
| (SEQ ID NO: 7092) | Cys Glu Tyr Cys Tyr Asn Pro Ala Cys Thr Gly Cys |
| (SEQ ID NO: 7093) | Cys Glu Tyr Cys Tyr Asn Pro Ala Cys Thr Ala Cys |
| (SEQ ID NO: 7094) | Cys Glu Tyr Cys Tyr Asn Pro Ala Cys Val Gly Cys |
| (SEQ ID NO: 7095) | Cys Glu Tyr Cys Tyr Asn Pro Ala Cys Val Ala Cys |
| (SEQ ID NO: 7096) | Cys Glu Tyr Cys Tyr Asn Pro Ala Cys Gly Gly Cys |
| (SEQ ID NO: 7097) | Cys Glu Tyr Cys Tyr Asn Pro Ala Cys Gly Ala Cys |
| (SEQ ID NO: 7098) | Cys Glu Tyr Cys Tyr Asn Pro Thr Cys Thr Gly Cys |
| (SEQ ID NO: 7099) | Cys Glu Tyr Cys Tyr Asn Pro Thr Cys Thr Ala Cys |
| (SEQ ID NO: 7100) | Cys Glu Tyr Cys Tyr Asn Pro Thr Cys Val Gly Cys |
| (SEQ ID NO: 7101) | Cys Glu Tyr Cys Tyr Asn Pro Thr Cys Val Ala Cys |
| (SEQ ID NO: 7102) | Cys Glu Tyr Cys Tyr Asn Pro Thr Cys Gly Gly Cys |
| (SEQ ID NO: 7103) | Cys Glu Tyr Cys Tyr Asn Pro Thr Cys Gly Ala Cys |
| (SEQ ID NO: 7104) | Cys Glu Tyr Cys Tyr Asn Gly Ala Cys Thr Gly Cys |
| (SEQ ID NO: 7105) | Cys Glu Tyr Cys Tyr Asn Gly Ala Cys Thr Ala Cys |
| (SEQ ID NO: 7106) | Cys Glu Tyr Cys Tyr Asn Gly Ala Cys Val Gly Cys |
| (SEQ ID NO: 7107) | Cys Glu Tyr Cys Tyr Asn Gly Ala Cys Val Ala Cys |
| (SEQ ID NO: 7108) | Cys Glu Tyr Cys Tyr Asn Gly Ala Cys Gly Gly Cys |
| (SEQ ID NO: 7109) | Cys Glu Tyr Cys Tyr Asn Gly Ala Cys Gly Ala Cys |
| (SEQ ID NO: 7110) | Cys Glu Tyr Cys Tyr Asn Gly Thr Cys Thr Gly Cys |
| (SEQ ID NO: 7111) | Cys Glu Tyr Cys Tyr Asn Gly Thr Cys Thr Ala Cys |
| (SEQ ID NO: 7112) | Cys Glu Tyr Cys Tyr Asn Gly Thr Cys Val Gly Cys |
| (SEQ ID NO: 7113) | Cys Glu Tyr Cys Tyr Asn Gly Thr Cys Val Ala Cys |
| (SEQ ID NO: 7114) | Cys Glu Tyr Cys Tyr Asn Gly Thr Cys Gly Gly Cys |
| (SEQ ID NO: 7115) | Cys Glu Tyr Cys Tyr Asn Gly Thr Cys Gly Ala Cys |
| (SEQ ID NO: 7116) | Cys Glu Tyr Cys Val Asn Pro Ala Cys Thr Gly Cys |
| (SEQ ID NO: 7117) | Cys Glu Tyr Cys Val Asn Pro Ala Cys Thr Ala Cys |
| (SEQ ID NO: 7118) | Cys Glu Tyr Cys Val Asn Pro Ala Cys Val Gly Cys |
| (SEQ ID NO: 7119) | Cys Glu Tyr Cys Val Asn Pro Ala Cys Val Ala Cys |
| (SEQ ID NO: 7120) | Cys Glu Tyr Cys Val Asn Pro Ala Cys Gly Gly Cys |
| (SEQ ID NO: 7121) | Cys Glu Tyr Cys Val Asn Pro Ala Cys Gly Ala Cys |
| (SEQ ID NO: 7122) | Cys Glu Tyr Cys Val Asn Pro Thr Cys Thr Gly Cys |
| (SEQ ID NO: 7123) | Cys Glu Tyr Cys Val Asn Pro Thr Cys Thr Ala Cys |
| (SEQ ID NO: 7124) | Cys Glu Tyr Cys Val Asn Pro Thr Cys Val Gly Cys |
| (SEQ ID NO: 7125) | Cys Glu Tyr Cys Val Asn Pro Thr Cys Val Ala Cys |
| (SEQ ID NO: 7126) | Cys Glu Tyr Cys Val Asn Pro Thr Cys Gly Gly Cys |
| (SEQ ID NO: 7127) | Cys Glu Tyr Cys Val Asn Pro Thr Cys Gly Ala Cys |
| (SEQ ID NO: 7128) | Cys Glu Tyr Cys Val Asn Gly Ala Cys Thr Gly Cys |

FIG. 3BC

| | |
|---|---|
| (SEQ ID NO: 7129) | Cys Glu Tyr Cys Val Asn Gly Ala Cys Thr Ala Cys |
| (SEQ ID NO: 7130) | Cys Glu Tyr Cys Val Asn Gly Ala Cys Val Gly Cys |
| (SEQ ID NO: 7131) | Cys Glu Tyr Cys Val Asn Gly Ala Cys Val Ala Cys |
| (SEQ ID NO: 7132) | Cys Glu Tyr Cys Val Asn Gly Ala Cys Gly Gly Cys |
| (SEQ ID NO: 7133) | Cys Glu Tyr Cys Val Asn Gly Ala Cys Gly Ala Cys |
| (SEQ ID NO: 7134) | Cys Glu Tyr Cys Val Asn Gly Thr Cys Thr Gly Cys |
| (SEQ ID NO: 7135) | Cys Glu Tyr Cys Val Asn Gly Thr Cys Thr Ala Cys |
| (SEQ ID NO: 7136) | Cys Glu Tyr Cys Val Asn Gly Thr Cys Val Gly Cys |
| (SEQ ID NO: 7137) | Cys Glu Tyr Cys Val Asn Gly Thr Cys Val Ala Cys |
| (SEQ ID NO: 7138) | Cys Glu Tyr Cys Val Asn Gly Thr Cys Gly Gly Cys |
| (SEQ ID NO: 7139) | Cys Glu Tyr Cys Val Asn Gly Thr Cys Gly Ala Cys |
| (SEQ ID NO: 7140) | Cys Glu Tyr Cys --- Asn Pro Ala Cys Thr Gly Cys |
| (SEQ ID NO: 7141) | Cys Glu Tyr Cys --- Asn Pro Ala Cys Thr Ala Cys |
| (SEQ ID NO: 7142) | Cys Glu Tyr Cys --- Asn Pro Ala Cys Val Gly Cys |
| (SEQ ID NO: 7143) | Cys Glu Tyr Cys --- Asn Pro Ala Cys Val Ala Cys |
| (SEQ ID NO: 7144) | Cys Glu Tyr Cys --- Asn Pro Ala Cys Gly Gly Cys |
| (SEQ ID NO: 7145) | Cys Glu Tyr Cys --- Asn Pro Ala Cys Gly Ala Cys |
| (SEQ ID NO: 7146) | Cys Glu Tyr Cys --- Asn Pro Thr Cys Thr Gly Cys |
| (SEQ ID NO: 7147) | Cys Glu Tyr Cys --- Asn Pro Thr Cys Thr Ala Cys |
| (SEQ ID NO: 7148) | Cys Glu Tyr Cys --- Asn Pro Thr Cys Val Gly Cys |
| (SEQ ID NO: 7149) | Cys Glu Tyr Cys --- Asn Pro Thr Cys Val Ala Cys |
| (SEQ ID NO: 7150) | Cys Glu Tyr Cys --- Asn Pro Thr Cys Gly Gly Cys |
| (SEQ ID NO: 7151) | Cys Glu Tyr Cys --- Asn Pro Thr Cys Gly Ala Cys |
| (SEQ ID NO: 7152) | Cys Glu Tyr Cys --- Asn Gly Ala Cys Thr Gly Cys |
| (SEQ ID NO: 7153) | Cys Glu Tyr Cys --- Asn Gly Ala Cys Thr Ala Cys |
| (SEQ ID NO: 7154) | Cys Glu Tyr Cys --- Asn Gly Ala Cys Val Gly Cys |
| (SEQ ID NO: 7155) | Cys Glu Tyr Cys --- Asn Gly Ala Cys Val Ala Cys |
| (SEQ ID NO: 7156) | Cys Glu Tyr Cys --- Asn Gly Ala Cys Gly Gly Cys |
| (SEQ ID NO: 7157) | Cys Glu Tyr Cys --- Asn Gly Ala Cys Gly Ala Cys |
| (SEQ ID NO: 7158) | Cys Glu Tyr Cys --- Asn Gly Thr Cys Thr Gly Cys |
| (SEQ ID NO: 7159) | Cys Glu Tyr Cys --- Asn Gly Thr Cys Thr Ala Cys |
| (SEQ ID NO: 7160) | Cys Glu Tyr Cys --- Asn Gly Thr Cys Val Gly Cys |
| (SEQ ID NO: 7161) | Cys Glu Tyr Cys --- Asn Gly Thr Cys Val Ala Cys |
| (SEQ ID NO: 7162) | Cys Glu Tyr Cys --- Asn Gly Thr Cys Gly Gly Cys |
| (SEQ ID NO: 7163) | Cys Glu Tyr Cys --- Asn Gly Thr Cys Gly Ala Cys |
| (SEQ ID NO: 7164) | Cys Glu Trp Cys Ala Asn Pro Ala Cys Thr Gly Cys |
| (SEQ ID NO: 7165) | Cys Glu Trp Cys Ala Asn Pro Ala Cys Thr Ala Cys |
| (SEQ ID NO: 7166) | Cys Glu Trp Cys Ala Asn Pro Ala Cys Val Gly Cys |
| (SEQ ID NO: 7167) | Cys Glu Trp Cys Ala Asn Pro Ala Cys Val Ala Cys |
| (SEQ ID NO: 7168) | Cys Glu Trp Cys Ala Asn Pro Ala Cys Gly Gly Cys |
| (SEQ ID NO: 7169) | Cys Glu Trp Cys Ala Asn Pro Ala Cys Gly Ala Cys |
| (SEQ ID NO: 7170) | Cys Glu Trp Cys Ala Asn Pro Thr Cys Thr Gly Cys |
| (SEQ ID NO: 7171) | Cys Glu Trp Cys Ala Asn Pro Thr Cys Thr Ala Cys |

FIG. 3BD

| | |
|---|---|
| (SEQ ID NO: 7172) | Cys Glu Trp Cys Ala Asn Pro Thr Cys Val Gly Cys |
| (SEQ ID NO: 7173) | Cys Glu Trp Cys Ala Asn Pro Thr Cys Val Ala Cys |
| (SEQ ID NO: 7174) | Cys Glu Trp Cys Ala Asn Pro Thr Cys Gly Gly Cys |
| (SEQ ID NO: 7175) | Cys Glu Trp Cys Ala Asn Pro Thr Cys Gly Ala Cys |
| (SEQ ID NO: 7176) | Cys Glu Trp Cys Ala Asn Gly Ala Cys Thr Gly Cys |
| (SEQ ID NO: 7177) | Cys Glu Trp Cys Ala Asn Gly Ala Cys Thr Ala Cys |
| (SEQ ID NO: 7178) | Cys Glu Trp Cys Ala Asn Gly Ala Cys Val Gly Cys |
| (SEQ ID NO: 7179) | Cys Glu Trp Cys Ala Asn Gly Ala Cys Val Ala Cys |
| (SEQ ID NO: 7180) | Cys Glu Trp Cys Ala Asn Gly Ala Cys Gly Gly Cys |
| (SEQ ID NO: 7181) | Cys Glu Trp Cys Ala Asn Gly Ala Cys Gly Ala Cys |
| (SEQ ID NO: 7182) | Cys Glu Trp Cys Ala Asn Gly Thr Cys Thr Gly Cys |
| (SEQ ID NO: 7183) | Cys Glu Trp Cys Ala Asn Gly Thr Cys Thr Ala Cys |
| (SEQ ID NO: 7184) | Cys Glu Trp Cys Ala Asn Gly Thr Cys Val Gly Cys |
| (SEQ ID NO: 7185) | Cys Glu Trp Cys Ala Asn Gly Thr Cys Val Ala Cys |
| (SEQ ID NO: 7186) | Cys Glu Trp Cys Ala Asn Gly Thr Cys Gly Gly Cys |
| (SEQ ID NO: 7187) | Cys Glu Trp Cys Ala Asn Gly Thr Cys Gly Ala Cys |
| (SEQ ID NO: 7188) | Cys Glu Trp Cys Arg Asn Pro Ala Cys Thr Gly Cys |
| (SEQ ID NO: 7189) | Cys Glu Trp Cys Arg Asn Pro Ala Cys Thr Ala Cys |
| (SEQ ID NO: 7190) | Cys Glu Trp Cys Arg Asn Pro Ala Cys Val Gly Cys |
| (SEQ ID NO: 7191) | Cys Glu Trp Cys Arg Asn Pro Ala Cys Val Ala Cys |
| (SEQ ID NO: 7192) | Cys Glu Trp Cys Arg Asn Pro Ala Cys Gly Gly Cys |
| (SEQ ID NO: 7193) | Cys Glu Trp Cys Arg Asn Pro Ala Cys Gly Ala Cys |
| (SEQ ID NO: 7194) | Cys Glu Trp Cys Arg Asn Pro Thr Cys Thr Gly Cys |
| (SEQ ID NO: 7195) | Cys Glu Trp Cys Arg Asn Pro Thr Cys Thr Ala Cys |
| (SEQ ID NO: 7196) | Cys Glu Trp Cys Arg Asn Pro Thr Cys Val Gly Cys |
| (SEQ ID NO: 7197) | Cys Glu Trp Cys Arg Asn Pro Thr Cys Val Ala Cys |
| (SEQ ID NO: 7198) | Cys Glu Trp Cys Arg Asn Pro Thr Cys Gly Gly Cys |
| (SEQ ID NO: 7199) | Cys Glu Trp Cys Arg Asn Pro Thr Cys Gly Ala Cys |
| (SEQ ID NO: 7200) | Cys Glu Trp Cys Arg Asn Gly Ala Cys Thr Gly Cys |
| (SEQ ID NO: 7201) | Cys Glu Trp Cys Arg Asn Gly Ala Cys Thr Ala Cys |
| (SEQ ID NO: 7202) | Cys Glu Trp Cys Arg Asn Gly Ala Cys Val Gly Cys |
| (SEQ ID NO: 7203) | Cys Glu Trp Cys Arg Asn Gly Ala Cys Val Ala Cys |
| (SEQ ID NO: 7204) | Cys Glu Trp Cys Arg Asn Gly Ala Cys Gly Gly Cys |
| (SEQ ID NO: 7205) | Cys Glu Trp Cys Arg Asn Gly Ala Cys Gly Ala Cys |
| (SEQ ID NO: 7206) | Cys Glu Trp Cys Arg Asn Gly Thr Cys Thr Gly Cys |
| (SEQ ID NO: 7207) | Cys Glu Trp Cys Arg Asn Gly Thr Cys Thr Ala Cys |
| (SEQ ID NO: 7208) | Cys Glu Trp Cys Arg Asn Gly Thr Cys Val Gly Cys |
| (SEQ ID NO: 7209) | Cys Glu Trp Cys Arg Asn Gly Thr Cys Val Ala Cys |
| (SEQ ID NO: 7210) | Cys Glu Trp Cys Arg Asn Gly Thr Cys Gly Gly Cys |
| (SEQ ID NO: 7211) | Cys Glu Trp Cys Arg Asn Gly Thr Cys Gly Ala Cys |
| (SEQ ID NO: 7212) | Cys Glu Trp Cys Asn Asn Pro Ala Cys Thr Gly Cys |
| (SEQ ID NO: 7213) | Cys Glu Trp Cys Asn Asn Pro Ala Cys Thr Ala Cys |
| (SEQ ID NO: 7214) | Cys Glu Trp Cys Asn Asn Pro Ala Cys Val Gly Cys |

FIG. 3BE (SEQ ID NO: 7215 )  Cys Glu Trp Cys Asn Asn Pro Ala Cys Val Ala Cys
(SEQ ID NO: 7216 )  Cys Glu Trp Cys Asn Asn Pro Ala Cys Gly Gly Cys
(SEQ ID NO: 7217 )  Cys Glu Trp Cys Asn Asn Pro Ala Cys Gly Ala Cys
(SEQ ID NO: 7218 )  Cys Glu Trp Cys Asn Asn Pro Thr Cys Thr Gly Cys
(SEQ ID NO: 7219 )  Cys Glu Trp Cys Asn Asn Pro Thr Cys Thr Ala Cys
(SEQ ID NO: 7220 )  Cys Glu Trp Cys Asn Asn Pro Thr Cys Val Gly Cys
(SEQ ID NO: 7221 )  Cys Glu Trp Cys Asn Asn Pro Thr Cys Val Ala Cys
(SEQ ID NO: 7222 )  Cys Glu Trp Cys Asn Asn Pro Thr Cys Gly Gly Cys
(SEQ ID NO: 7223 )  Cys Glu Trp Cys Asn Asn Pro Thr Cys Gly Ala Cys
(SEQ ID NO: 7224 )  Cys Glu Trp Cys Asn Asn Gly Ala Cys Thr Gly Cys
(SEQ ID NO: 7225 )  Cys Glu Trp Cys Asn Asn Gly Ala Cys Thr Ala Cys
(SEQ ID NO: 7226 )  Cys Glu Trp Cys Asn Asn Gly Ala Cys Val Gly Cys
(SEQ ID NO: 7227 )  Cys Glu Trp Cys Asn Asn Gly Ala Cys Val Ala Cys
(SEQ ID NO: 7228 )  Cys Glu Trp Cys Asn Asn Gly Ala Cys Gly Gly Cys
(SEQ ID NO: 7229 )  Cys Glu Trp Cys Asn Asn Gly Ala Cys Gly Ala Cys
(SEQ ID NO: 7230 )  Cys Glu Trp Cys Asn Asn Gly Thr Cys Thr Gly Cys
(SEQ ID NO: 7231 )  Cys Glu Trp Cys Asn Asn Gly Thr Cys Thr Ala Cys
(SEQ ID NO: 7232 )  Cys Glu Trp Cys Asn Asn Gly Thr Cys Val Gly Cys
(SEQ ID NO: 7233 )  Cys Glu Trp Cys Asn Asn Gly Thr Cys Val Ala Cys
(SEQ ID NO: 7234 )  Cys Glu Trp Cys Asn Asn Gly Thr Cys Gly Gly Cys
(SEQ ID NO: 7235 )  Cys Glu Trp Cys Asn Asn Gly Thr Cys Gly Ala Cys
(SEQ ID NO: 7236 )  Cys Glu Trp Cys Asp Asn Pro Ala Cys Thr Gly Cys
(SEQ ID NO: 7237 )  Cys Glu Trp Cys Asp Asn Pro Ala Cys Thr Ala Cys
(SEQ ID NO: 7238 )  Cys Glu Trp Cys Asp Asn Pro Ala Cys Val Gly Cys
(SEQ ID NO: 7239 )  Cys Glu Trp Cys Asp Asn Pro Ala Cys Val Ala Cys
(SEQ ID NO: 7240 )  Cys Glu Trp Cys Asp Asn Pro Ala Cys Gly Gly Cys
(SEQ ID NO: 7241 )  Cys Glu Trp Cys Asp Asn Pro Ala Cys Gly Ala Cys
(SEQ ID NO: 7242 )  Cys Glu Trp Cys Asp Asn Pro Thr Cys Thr Gly Cys
(SEQ ID NO: 7243 )  Cys Glu Trp Cys Asp Asn Pro Thr Cys Thr Ala Cys
(SEQ ID NO: 7244 )  Cys Glu Trp Cys Asp Asn Pro Thr Cys Val Gly Cys
(SEQ ID NO: 7245 )  Cys Glu Trp Cys Asp Asn Pro Thr Cys Val Ala Cys
(SEQ ID NO: 7246 )  Cys Glu Trp Cys Asp Asn Pro Thr Cys Gly Gly Cys
(SEQ ID NO: 7247 )  Cys Glu Trp Cys Asp Asn Pro Thr Cys Gly Ala Cys
(SEQ ID NO: 7248 )  Cys Glu Trp Cys Asp Asn Gly Ala Cys Thr Gly Cys
(SEQ ID NO: 7249 )  Cys Glu Trp Cys Asp Asn Gly Ala Cys Thr Ala Cys
(SEQ ID NO: 7250 )  Cys Glu Trp Cys Asp Asn Gly Ala Cys Val Gly Cys
(SEQ ID NO: 7251 )  Cys Glu Trp Cys Asp Asn Gly Ala Cys Val Ala Cys
(SEQ ID NO: 7252 )  Cys Glu Trp Cys Asp Asn Gly Ala Cys Gly Gly Cys
(SEQ ID NO: 7253 )  Cys Glu Trp Cys Asp Asn Gly Ala Cys Gly Ala Cys
(SEQ ID NO: 7254 )  Cys Glu Trp Cys Asp Asn Gly Thr Cys Thr Gly Cys
(SEQ ID NO: 7255 )  Cys Glu Trp Cys Asp Asn Gly Thr Cys Thr Ala Cys
(SEQ ID NO: 7256 )  Cys Glu Trp Cys Asp Asn Gly Thr Cys Val Gly Cys
(SEQ ID NO: 7257 )  Cys Glu Trp Cys Asp Asn Gly Thr Cys Val Ala Cys

FIG. 3BF

| | | | | | | | | | | |
|---|---|---|---|---|---|---|---|---|---|---|
| (SEQ ID NO: 7258) | Cys | Glu | Trp | Cys | Asp | Asn | Gly | Thr | Cys | Gly | Gly | Cys |
| (SEQ ID NO: 7259) | Cys | Glu | Trp | Cys | Asp | Asn | Gly | Thr | Cys | Gly | Ala | Cys |
| (SEQ ID NO: 7260) | Cys | Glu | Trp | Cys | Gln | Asn | Pro | Ala | Cys | Thr | Gly | Cys |
| (SEQ ID NO: 7261) | Cys | Glu | Trp | Cys | Gln | Asn | Pro | Ala | Cys | Thr | Ala | Cys |
| (SEQ ID NO: 7262) | Cys | Glu | Trp | Cys | Gln | Asn | Pro | Ala | Cys | Val | Gly | Cys |
| (SEQ ID NO: 7263) | Cys | Glu | Trp | Cys | Gln | Asn | Pro | Ala | Cys | Val | Ala | Cys |
| (SEQ ID NO: 7264) | Cys | Glu | Trp | Cys | Gln | Asn | Pro | Ala | Cys | Gly | Gly | Cys |
| (SEQ ID NO: 7265) | Cys | Glu | Trp | Cys | Gln | Asn | Pro | Ala | Cys | Gly | Ala | Cys |
| (SEQ ID NO: 7266) | Cys | Glu | Trp | Cys | Gln | Asn | Pro | Thr | Cys | Thr | Gly | Cys |
| (SEQ ID NO: 7267) | Cys | Glu | Trp | Cys | Gln | Asn | Pro | Thr | Cys | Thr | Ala | Cys |
| (SEQ ID NO: 7268) | Cys | Glu | Trp | Cys | Gln | Asn | Pro | Thr | Cys | Val | Gly | Cys |
| (SEQ ID NO: 7269) | Cys | Glu | Trp | Cys | Gln | Asn | Pro | Thr | Cys | Val | Ala | Cys |
| (SEQ ID NO: 7270) | Cys | Glu | Trp | Cys | Gln | Asn | Pro | Thr | Cys | Gly | Gly | Cys |
| (SEQ ID NO: 7271) | Cys | Glu | Trp | Cys | Gln | Asn | Pro | Thr | Cys | Gly | Ala | Cys |
| (SEQ ID NO: 7272) | Cys | Glu | Trp | Cys | Gln | Asn | Gly | Ala | Cys | Thr | Gly | Cys |
| (SEQ ID NO: 7273) | Cys | Glu | Trp | Cys | Gln | Asn | Gly | Ala | Cys | Thr | Ala | Cys |
| (SEQ ID NO: 7274) | Cys | Glu | Trp | Cys | Gln | Asn | Gly | Ala | Cys | Val | Gly | Cys |
| (SEQ ID NO: 7275) | Cys | Glu | Trp | Cys | Gln | Asn | Gly | Ala | Cys | Val | Ala | Cys |
| (SEQ ID NO: 7276) | Cys | Glu | Trp | Cys | Gln | Asn | Gly | Ala | Cys | Gly | Gly | Cys |
| (SEQ ID NO: 7277) | Cys | Glu | Trp | Cys | Gln | Asn | Gly | Ala | Cys | Gly | Ala | Cys |
| (SEQ ID NO: 7278) | Cys | Glu | Trp | Cys | Gln | Asn | Gly | Thr | Cys | Thr | Gly | Cys |
| (SEQ ID NO: 7279) | Cys | Glu | Trp | Cys | Gln | Asn | Gly | Thr | Cys | Thr | Ala | Cys |
| (SEQ ID NO: 7280) | Cys | Glu | Trp | Cys | Gln | Asn | Gly | Thr | Cys | Val | Gly | Cys |
| (SEQ ID NO: 7281) | Cys | Glu | Trp | Cys | Gln | Asn | Gly | Thr | Cys | Val | Ala | Cys |
| (SEQ ID NO: 7282) | Cys | Glu | Trp | Cys | Gln | Asn | Gly | Thr | Cys | Gly | Gly | Cys |
| (SEQ ID NO: 7283) | Cys | Glu | Trp | Cys | Gln | Asn | Gly | Thr | Cys | Gly | Ala | Cys |
| (SEQ ID NO: 7284) | Cys | Glu | Trp | Cys | Glu | Asn | Pro | Ala | Cys | Thr | Gly | Cys |
| (SEQ ID NO: 7285) | Cys | Glu | Trp | Cys | Glu | Asn | Pro | Ala | Cys | Thr | Ala | Cys |
| (SEQ ID NO: 7286) | Cys | Glu | Trp | Cys | Glu | Asn | Pro | Ala | Cys | Val | Gly | Cys |
| (SEQ ID NO: 7287) | Cys | Glu | Trp | Cys | Glu | Asn | Pro | Ala | Cys | Val | Ala | Cys |
| (SEQ ID NO: 7288) | Cys | Glu | Trp | Cys | Glu | Asn | Pro | Ala | Cys | Gly | Gly | Cys |
| (SEQ ID NO: 7289) | Cys | Glu | Trp | Cys | Glu | Asn | Pro | Ala | Cys | Gly | Ala | Cys |
| (SEQ ID NO: 7290) | Cys | Glu | Trp | Cys | Glu | Asn | Pro | Thr | Cys | Thr | Gly | Cys |
| (SEQ ID NO: 7291) | Cys | Glu | Trp | Cys | Glu | Asn | Pro | Thr | Cys | Thr | Ala | Cys |
| (SEQ ID NO: 7292) | Cys | Glu | Trp | Cys | Glu | Asn | Pro | Thr | Cys | Val | Gly | Cys |
| (SEQ ID NO: 7293) | Cys | Glu | Trp | Cys | Glu | Asn | Pro | Thr | Cys | Val | Ala | Cys |
| (SEQ ID NO: 7294) | Cys | Glu | Trp | Cys | Glu | Asn | Pro | Thr | Cys | Gly | Gly | Cys |
| (SEQ ID NO: 7295) | Cys | Glu | Trp | Cys | Glu | Asn | Pro | Thr | Cys | Gly | Ala | Cys |
| (SEQ ID NO: 7296) | Cys | Glu | Trp | Cys | Glu | Asn | Gly | Ala | Cys | Thr | Gly | Cys |
| (SEQ ID NO: 7297) | Cys | Glu | Trp | Cys | Glu | Asn | Gly | Ala | Cys | Thr | Ala | Cys |
| (SEQ ID NO: 7298) | Cys | Glu | Trp | Cys | Glu | Asn | Gly | Ala | Cys | Val | Gly | Cys |
| (SEQ ID NO: 7299) | Cys | Glu | Trp | Cys | Glu | Asn | Gly | Ala | Cys | Val | Ala | Cys |
| (SEQ ID NO: 7300) | Cys | Glu | Trp | Cys | Glu | Asn | Gly | Ala | Cys | Gly | Gly | Cys |

FIG. 3BG (SEQ ID NO: 7301) Cys Glu Trp Cys Glu Asn Gly Ala Cys Gly Ala Cys
(SEQ ID NO: 7302) Cys Glu Trp Cys Glu Asn Gly Thr Cys Thr Gly Cys
(SEQ ID NO: 7303) Cys Glu Trp Cys Glu Asn Gly Thr Cys Thr Ala Cys
(SEQ ID NO: 7304) Cys Glu Trp Cys Glu Asn Gly Thr Cys Val Gly Cys
(SEQ ID NO: 7305) Cys Glu Trp Cys Glu Asn Gly Thr Cys Val Ala Cys
(SEQ ID NO: 7306) Cys Glu Trp Cys Glu Asn Gly Thr Cys Gly Gly Cys
(SEQ ID NO: 7307) Cys Glu Trp Cys Glu Asn Gly Thr Cys Gly Ala Cys
(SEQ ID NO: 7308) Cys Glu Trp Cys Gly Asn Pro Ala Cys Thr Gly Cys
(SEQ ID NO: 7309) Cys Glu Trp Cys Gly Asn Pro Ala Cys Thr Ala Cys
(SEQ ID NO: 7310) Cys Glu Trp Cys Gly Asn Pro Ala Cys Val Gly Cys
(SEQ ID NO: 7311) Cys Glu Trp Cys Gly Asn Pro Ala Cys Val Ala Cys
(SEQ ID NO: 7312) Cys Glu Trp Cys Gly Asn Pro Ala Cys Gly Gly Cys
(SEQ ID NO: 7313) Cys Glu Trp Cys Gly Asn Pro Ala Cys Gly Ala Cys
(SEQ ID NO: 7314) Cys Glu Trp Cys Gly Asn Pro Thr Cys Thr Gly Cys
(SEQ ID NO: 7315) Cys Glu Trp Cys Gly Asn Pro Thr Cys Thr Ala Cys
(SEQ ID NO: 7316) Cys Glu Trp Cys Gly Asn Pro Thr Cys Val Gly Cys
(SEQ ID NO: 7317) Cys Glu Trp Cys Gly Asn Pro Thr Cys Val Ala Cys
(SEQ ID NO: 7318) Cys Glu Trp Cys Gly Asn Pro Thr Cys Gly Gly Cys
(SEQ ID NO: 7319) Cys Glu Trp Cys Gly Asn Pro Thr Cys Gly Ala Cys
(SEQ ID NO: 7320) Cys Glu Trp Cys Gly Asn Gly Ala Cys Thr Gly Cys
(SEQ ID NO: 7321) Cys Glu Trp Cys Gly Asn Gly Ala Cys Thr Ala Cys
(SEQ ID NO: 7322) Cys Glu Trp Cys Gly Asn Gly Ala Cys Val Gly Cys
(SEQ ID NO: 7323) Cys Glu Trp Cys Gly Asn Gly Ala Cys Val Ala Cys
(SEQ ID NO: 7324) Cys Glu Trp Cys Gly Asn Gly Ala Cys Gly Gly Cys
(SEQ ID NO: 7325) Cys Glu Trp Cys Gly Asn Gly Ala Cys Gly Ala Cys
(SEQ ID NO: 7326) Cys Glu Trp Cys Gly Asn Gly Thr Cys Thr Gly Cys
(SEQ ID NO: 7327) Cys Glu Trp Cys Gly Asn Gly Thr Cys Thr Ala Cys
(SEQ ID NO: 7328) Cys Glu Trp Cys Gly Asn Gly Thr Cys Val Gly Cys
(SEQ ID NO: 7329) Cys Glu Trp Cys Gly Asn Gly Thr Cys Val Ala Cys
(SEQ ID NO: 7330) Cys Glu Trp Cys Gly Asn Gly Thr Cys Gly Gly Cys
(SEQ ID NO: 7331) Cys Glu Trp Cys Gly Asn Gly Thr Cys Gly Ala Cys
(SEQ ID NO: 7332) Cys Glu Trp Cys His Asn Pro Ala Cys Thr Gly Cys
(SEQ ID NO: 7333) Cys Glu Trp Cys His Asn Pro Ala Cys Thr Ala Cys
(SEQ ID NO: 7334) Cys Glu Trp Cys His Asn Pro Ala Cys Val Gly Cys
(SEQ ID NO: 7335) Cys Glu Trp Cys His Asn Pro Ala Cys Val Ala Cys
(SEQ ID NO: 7336) Cys Glu Trp Cys His Asn Pro Ala Cys Gly Gly Cys
(SEQ ID NO: 7337) Cys Glu Trp Cys His Asn Pro Ala Cys Gly Ala Cys
(SEQ ID NO: 7338) Cys Glu Trp Cys His Asn Pro Thr Cys Thr Gly Cys
(SEQ ID NO: 7339) Cys Glu Trp Cys His Asn Pro Thr Cys Thr Ala Cys
(SEQ ID NO: 7340) Cys Glu Trp Cys His Asn Pro Thr Cys Val Gly Cys
(SEQ ID NO: 7341) Cys Glu Trp Cys His Asn Pro Thr Cys Val Ala Cys
(SEQ ID NO: 7342) Cys Glu Trp Cys His Asn Pro Thr Cys Gly Gly Cys
(SEQ ID NO: 7343) Cys Glu Trp Cys His Asn Pro Thr Cys Gly Ala Cys

FIG. 3BH

| | |
|---|---|
| (SEQ ID NO: 7344) | Cys Glu Trp Cys His Asn Gly Ala Cys Thr Gly Cys |
| (SEQ ID NO: 7345) | Cys Glu Trp Cys His Asn Gly Ala Cys Thr Ala Cys |
| (SEQ ID NO: 7346) | Cys Glu Trp Cys His Asn Gly Ala Cys Val Gly Cys |
| (SEQ ID NO: 7347) | Cys Glu Trp Cys His Asn Gly Ala Cys Val Ala Cys |
| (SEQ ID NO: 7348) | Cys Glu Trp Cys His Asn Gly Ala Cys Gly Gly Cys |
| (SEQ ID NO: 7349) | Cys Glu Trp Cys His Asn Gly Ala Cys Gly Ala Cys |
| (SEQ ID NO: 7350) | Cys Glu Trp Cys His Asn Gly Thr Cys Thr Gly Cys |
| (SEQ ID NO: 7351) | Cys Glu Trp Cys His Asn Gly Thr Cys Thr Ala Cys |
| (SEQ ID NO: 7352) | Cys Glu Trp Cys His Asn Gly Thr Cys Val Gly Cys |
| (SEQ ID NO: 7353) | Cys Glu Trp Cys His Asn Gly Thr Cys Val Ala Cys |
| (SEQ ID NO: 7354) | Cys Glu Trp Cys His Asn Gly Thr Cys Gly Gly Cys |
| (SEQ ID NO: 7355) | Cys Glu Trp Cys His Asn Gly Thr Cys Gly Ala Cys |
| (SEQ ID NO: 7356) | Cys Glu Trp Cys Ile Asn Pro Ala Cys Thr Gly Cys |
| (SEQ ID NO: 7357) | Cys Glu Trp Cys Ile Asn Pro Ala Cys Thr Ala Cys |
| (SEQ ID NO: 7358) | Cys Glu Trp Cys Ile Asn Pro Ala Cys Val Gly Cys |
| (SEQ ID NO: 7359) | Cys Glu Trp Cys Ile Asn Pro Ala Cys Val Ala Cys |
| (SEQ ID NO: 7360) | Cys Glu Trp Cys Ile Asn Pro Ala Cys Gly Gly Cys |
| (SEQ ID NO: 7361) | Cys Glu Trp Cys Ile Asn Pro Ala Cys Gly Ala Cys |
| (SEQ ID NO: 7362) | Cys Glu Trp Cys Ile Asn Pro Thr Cys Thr Gly Cys |
| (SEQ ID NO: 7363) | Cys Glu Trp Cys Ile Asn Pro Thr Cys Thr Ala Cys |
| (SEQ ID NO: 7364) | Cys Glu Trp Cys Ile Asn Pro Thr Cys Val Gly Cys |
| (SEQ ID NO: 7365) | Cys Glu Trp Cys Ile Asn Pro Thr Cys Val Ala Cys |
| (SEQ ID NO: 7366) | Cys Glu Trp Cys Ile Asn Pro Thr Cys Gly Gly Cys |
| (SEQ ID NO: 7367) | Cys Glu Trp Cys Ile Asn Pro Thr Cys Gly Ala Cys |
| (SEQ ID NO: 7368) | Cys Glu Trp Cys Ile Asn Gly Ala Cys Thr Gly Cys |
| (SEQ ID NO: 7369) | Cys Glu Trp Cys Ile Asn Gly Ala Cys Thr Ala Cys |
| (SEQ ID NO: 7370) | Cys Glu Trp Cys Ile Asn Gly Ala Cys Val Gly Cys |
| (SEQ ID NO: 7371) | Cys Glu Trp Cys Ile Asn Gly Ala Cys Val Ala Cys |
| (SEQ ID NO: 7372) | Cys Glu Trp Cys Ile Asn Gly Ala Cys Gly Gly Cys |
| (SEQ ID NO: 7373) | Cys Glu Trp Cys Ile Asn Gly Ala Cys Gly Ala Cys |
| (SEQ ID NO: 7374) | Cys Glu Trp Cys Ile Asn Gly Thr Cys Thr Gly Cys |
| (SEQ ID NO: 7375) | Cys Glu Trp Cys Ile Asn Gly Thr Cys Thr Ala Cys |
| (SEQ ID NO: 7376) | Cys Glu Trp Cys Ile Asn Gly Thr Cys Val Gly Cys |
| (SEQ ID NO: 7377) | Cys Glu Trp Cys Ile Asn Gly Thr Cys Val Ala Cys |
| (SEQ ID NO: 7378) | Cys Glu Trp Cys Ile Asn Gly Thr Cys Gly Gly Cys |
| (SEQ ID NO: 7379) | Cys Glu Trp Cys Ile Asn Gly Thr Cys Gly Ala Cys |
| (SEQ ID NO: 7380) | Cys Glu Trp Cys Leu Asn Pro Ala Cys Thr Gly Cys |
| (SEQ ID NO: 7381) | Cys Glu Trp Cys Leu Asn Pro Ala Cys Thr Ala Cys |
| (SEQ ID NO: 7382) | Cys Glu Trp Cys Leu Asn Pro Ala Cys Val Gly Cys |
| (SEQ ID NO: 7383) | Cys Glu Trp Cys Leu Asn Pro Ala Cys Val Ala Cys |
| (SEQ ID NO: 7384) | Cys Glu Trp Cys Leu Asn Pro Ala Cys Gly Gly Cys |
| (SEQ ID NO: 7385) | Cys Glu Trp Cys Leu Asn Pro Ala Cys Gly Ala Cys |
| (SEQ ID NO: 7386) | Cys Glu Trp Cys Leu Asn Pro Thr Cys Thr Gly Cys |

FIG. 3BI

| | |
|---|---|
| (SEQ ID NO: 7387) | Cys Glu Trp Cys Leu Asn Pro Thr Cys Thr Ala Cys |
| (SEQ ID NO: 7388) | Cys Glu Trp Cys Leu Asn Pro Thr Cys Val Gly Cys |
| (SEQ ID NO: 7389) | Cys Glu Trp Cys Leu Asn Pro Thr Cys Val Ala Cys |
| (SEQ ID NO: 7390) | Cys Glu Trp Cys Leu Asn Pro Thr Cys Gly Gly Cys |
| (SEQ ID NO: 7391) | Cys Glu Trp Cys Leu Asn Pro Thr Cys Gly Ala Cys |
| (SEQ ID NO: 7392) | Cys Glu Trp Cys Leu Asn Gly Ala Cys Thr Gly Cys |
| (SEQ ID NO: 7393) | Cys Glu Trp Cys Leu Asn Gly Ala Cys Thr Ala Cys |
| (SEQ ID NO: 7394) | Cys Glu Trp Cys Leu Asn Gly Ala Cys Val Gly Cys |
| (SEQ ID NO: 7395) | Cys Glu Trp Cys Leu Asn Gly Ala Cys Val Ala Cys |
| (SEQ ID NO: 7396) | Cys Glu Trp Cys Leu Asn Gly Ala Cys Gly Gly Cys |
| (SEQ ID NO: 7397) | Cys Glu Trp Cys Leu Asn Gly Ala Cys Gly Ala Cys |
| (SEQ ID NO: 7398) | Cys Glu Trp Cys Leu Asn Gly Thr Cys Thr Gly Cys |
| (SEQ ID NO: 7399) | Cys Glu Trp Cys Leu Asn Gly Thr Cys Thr Ala Cys |
| (SEQ ID NO: 7400) | Cys Glu Trp Cys Leu Asn Gly Thr Cys Val Gly Cys |
| (SEQ ID NO: 7401) | Cys Glu Trp Cys Leu Asn Gly Thr Cys Val Ala Cys |
| (SEQ ID NO: 7402) | Cys Glu Trp Cys Leu Asn Gly Thr Cys Gly Gly Cys |
| (SEQ ID NO: 7403) | Cys Glu Trp Cys Leu Asn Gly Thr Cys Gly Ala Cys |
| (SEQ ID NO: 7404) | Cys Glu Trp Cys Lys Asn Pro Ala Cys Thr Gly Cys |
| (SEQ ID NO: 7405) | Cys Glu Trp Cys Lys Asn Pro Ala Cys Thr Ala Cys |
| (SEQ ID NO: 7406) | Cys Glu Trp Cys Lys Asn Pro Ala Cys Val Gly Cys |
| (SEQ ID NO: 7407) | Cys Glu Trp Cys Lys Asn Pro Ala Cys Val Ala Cys |
| (SEQ ID NO: 7408) | Cys Glu Trp Cys Lys Asn Pro Ala Cys Gly Gly Cys |
| (SEQ ID NO: 7409) | Cys Glu Trp Cys Lys Asn Pro Ala Cys Gly Ala Cys |
| (SEQ ID NO: 7410) | Cys Glu Trp Cys Lys Asn Pro Thr Cys Thr Gly Cys |
| (SEQ ID NO: 7411) | Cys Glu Trp Cys Lys Asn Pro Thr Cys Thr Ala Cys |
| (SEQ ID NO: 7412) | Cys Glu Trp Cys Lys Asn Pro Thr Cys Val Gly Cys |
| (SEQ ID NO: 7413) | Cys Glu Trp Cys Lys Asn Pro Thr Cys Val Ala Cys |
| (SEQ ID NO: 7414) | Cys Glu Trp Cys Lys Asn Pro Thr Cys Gly Gly Cys |
| (SEQ ID NO: 7415) | Cys Glu Trp Cys Lys Asn Pro Thr Cys Gly Ala Cys |
| (SEQ ID NO: 7416) | Cys Glu Trp Cys Lys Asn Gly Ala Cys Thr Gly Cys |
| (SEQ ID NO: 7417) | Cys Glu Trp Cys Lys Asn Gly Ala Cys Thr Ala Cys |
| (SEQ ID NO: 7418) | Cys Glu Trp Cys Lys Asn Gly Ala Cys Val Gly Cys |
| (SEQ ID NO: 7419) | Cys Glu Trp Cys Lys Asn Gly Ala Cys Val Ala Cys |
| (SEQ ID NO: 7420) | Cys Glu Trp Cys Lys Asn Gly Ala Cys Gly Gly Cys |
| (SEQ ID NO: 7421) | Cys Glu Trp Cys Lys Asn Gly Ala Cys Gly Ala Cys |
| (SEQ ID NO: 7422) | Cys Glu Trp Cys Lys Asn Gly Thr Cys Thr Gly Cys |
| (SEQ ID NO: 7423) | Cys Glu Trp Cys Lys Asn Gly Thr Cys Thr Ala Cys |
| (SEQ ID NO: 7424) | Cys Glu Trp Cys Lys Asn Gly Thr Cys Val Gly Cys |
| (SEQ ID NO: 7425) | Cys Glu Trp Cys Lys Asn Gly Thr Cys Val Ala Cys |
| (SEQ ID NO: 7426) | Cys Glu Trp Cys Lys Asn Gly Thr Cys Gly Gly Cys |
| (SEQ ID NO: 7427) | Cys Glu Trp Cys Lys Asn Gly Thr Cys Gly Ala Cys |
| (SEQ ID NO: 7428) | Cys Glu Trp Cys Met Asn Pro Ala Cys Thr Gly Cys |
| (SEQ ID NO: 7429) | Cys Glu Trp Cys Met Asn Pro Ala Cys Thr Ala Cys |

FIG. 3BJ

| | |
|---|---|
| (SEQ ID NO: 7430) | Cys Glu Trp Cys Met Asn Pro Ala Cys Val Gly Cys |
| (SEQ ID NO: 7431) | Cys Glu Trp Cys Met Asn Pro Ala Cys Val Ala Cys |
| (SEQ ID NO: 7432) | Cys Glu Trp Cys Met Asn Pro Ala Cys Gly Gly Cys |
| (SEQ ID NO: 7433) | Cys Glu Trp Cys Met Asn Pro Ala Cys Gly Ala Cys |
| (SEQ ID NO: 7434) | Cys Glu Trp Cys Met Asn Pro Thr Cys Thr Gly Cys |
| (SEQ ID NO: 7435) | Cys Glu Trp Cys Met Asn Pro Thr Cys Thr Ala Cys |
| (SEQ ID NO: 7436) | Cys Glu Trp Cys Met Asn Pro Thr Cys Val Gly Cys |
| (SEQ ID NO: 7437) | Cys Glu Trp Cys Met Asn Pro Thr Cys Val Ala Cys |
| (SEQ ID NO: 7438) | Cys Glu Trp Cys Met Asn Pro Thr Cys Gly Gly Cys |
| (SEQ ID NO: 7439) | Cys Glu Trp Cys Met Asn Pro Thr Cys Gly Ala Cys |
| (SEQ ID NO: 7440) | Cys Glu Trp Cys Met Asn Gly Ala Cys Thr Gly Cys |
| (SEQ ID NO: 7441) | Cys Glu Trp Cys Met Asn Gly Ala Cys Thr Ala Cys |
| (SEQ ID NO: 7442) | Cys Glu Trp Cys Met Asn Gly Ala Cys Val Gly Cys |
| (SEQ ID NO: 7443) | Cys Glu Trp Cys Met Asn Gly Ala Cys Val Ala Cys |
| (SEQ ID NO: 7444) | Cys Glu Trp Cys Met Asn Gly Ala Cys Gly Gly Cys |
| (SEQ ID NO: 7445) | Cys Glu Trp Cys Met Asn Gly Ala Cys Gly Ala Cys |
| (SEQ ID NO: 7446) | Cys Glu Trp Cys Met Asn Gly Thr Cys Thr Gly Cys |
| (SEQ ID NO: 7447) | Cys Glu Trp Cys Met Asn Gly Thr Cys Thr Ala Cys |
| (SEQ ID NO: 7448) | Cys Glu Trp Cys Met Asn Gly Thr Cys Val Gly Cys |
| (SEQ ID NO: 7449) | Cys Glu Trp Cys Met Asn Gly Thr Cys Val Ala Cys |
| (SEQ ID NO: 7450) | Cys Glu Trp Cys Met Asn Gly Thr Cys Gly Gly Cys |
| (SEQ ID NO: 7451) | Cys Glu Trp Cys Met Asn Gly Thr Cys Gly Ala Cys |
| (SEQ ID NO: 7452) | Cys Glu Trp Cys Phe Asn Pro Ala Cys Thr Gly Cys |
| (SEQ ID NO: 7453) | Cys Glu Trp Cys Phe Asn Pro Ala Cys Thr Ala Cys |
| (SEQ ID NO: 7454) | Cys Glu Trp Cys Phe Asn Pro Ala Cys Val Gly Cys |
| (SEQ ID NO: 7455) | Cys Glu Trp Cys Phe Asn Pro Ala Cys Val Ala Cys |
| (SEQ ID NO: 7456) | Cys Glu Trp Cys Phe Asn Pro Ala Cys Gly Gly Cys |
| (SEQ ID NO: 7457) | Cys Glu Trp Cys Phe Asn Pro Ala Cys Gly Ala Cys |
| (SEQ ID NO: 7458) | Cys Glu Trp Cys Phe Asn Pro Thr Cys Thr Gly Cys |
| (SEQ ID NO: 7459) | Cys Glu Trp Cys Phe Asn Pro Thr Cys Thr Ala Cys |
| (SEQ ID NO: 7460) | Cys Glu Trp Cys Phe Asn Pro Thr Cys Val Gly Cys |
| (SEQ ID NO: 7461) | Cys Glu Trp Cys Phe Asn Pro Thr Cys Val Ala Cys |
| (SEQ ID NO: 7462) | Cys Glu Trp Cys Phe Asn Pro Thr Cys Gly Gly Cys |
| (SEQ ID NO: 7463) | Cys Glu Trp Cys Phe Asn Pro Thr Cys Gly Ala Cys |
| (SEQ ID NO: 7464) | Cys Glu Trp Cys Phe Asn Gly Ala Cys Thr Gly Cys |
| (SEQ ID NO: 7465) | Cys Glu Trp Cys Phe Asn Gly Ala Cys Thr Ala Cys |
| (SEQ ID NO: 7466) | Cys Glu Trp Cys Phe Asn Gly Ala Cys Val Gly Cys |
| (SEQ ID NO: 7467) | Cys Glu Trp Cys Phe Asn Gly Ala Cys Val Ala Cys |
| (SEQ ID NO: 7468) | Cys Glu Trp Cys Phe Asn Gly Ala Cys Gly Gly Cys |
| (SEQ ID NO: 7469) | Cys Glu Trp Cys Phe Asn Gly Ala Cys Gly Ala Cys |
| (SEQ ID NO: 7470) | Cys Glu Trp Cys Phe Asn Gly Thr Cys Thr Gly Cys |
| (SEQ ID NO: 7471) | Cys Glu Trp Cys Phe Asn Gly Thr Cys Thr Ala Cys |
| (SEQ ID NO: 7472) | Cys Glu Trp Cys Phe Asn Gly Thr Cys Val Gly Cys |

FIG. 3BK

| | |
|---|---|
| (SEQ ID NO: 7473) | Cys Glu Trp Cys Phe Asn Gly Thr Cys Val Ala Cys |
| (SEQ ID NO: 7474) | Cys Glu Trp Cys Phe Asn Gly Thr Cys Gly Gly Cys |
| (SEQ ID NO: 7475) | Cys Glu Trp Cys Phe Asn Gly Thr Cys Gly Ala Cys |
| (SEQ ID NO: 7476) | Cys Glu Trp Cys Pro Asn Pro Ala Cys Thr Gly Cys |
| (SEQ ID NO: 7477) | Cys Glu Trp Cys Pro Asn Pro Ala Cys Thr Ala Cys |
| (SEQ ID NO: 7478) | Cys Glu Trp Cys Pro Asn Pro Ala Cys Val Gly Cys |
| (SEQ ID NO: 7479) | Cys Glu Trp Cys Pro Asn Pro Ala Cys Val Ala Cys |
| (SEQ ID NO: 7480) | Cys Glu Trp Cys Pro Asn Pro Ala Cys Gly Gly Cys |
| (SEQ ID NO: 7481) | Cys Glu Trp Cys Pro Asn Pro Ala Cys Gly Ala Cys |
| (SEQ ID NO: 7482) | Cys Glu Trp Cys Pro Asn Pro Thr Cys Thr Gly Cys |
| (SEQ ID NO: 7483) | Cys Glu Trp Cys Pro Asn Pro Thr Cys Thr Ala Cys |
| (SEQ ID NO: 7484) | Cys Glu Trp Cys Pro Asn Pro Thr Cys Val Gly Cys |
| (SEQ ID NO: 7485) | Cys Glu Trp Cys Pro Asn Pro Thr Cys Val Ala Cys |
| (SEQ ID NO: 7486) | Cys Glu Trp Cys Pro Asn Pro Thr Cys Gly Gly Cys |
| (SEQ ID NO: 7487) | Cys Glu Trp Cys Pro Asn Pro Thr Cys Gly Ala Cys |
| (SEQ ID NO: 7488) | Cys Glu Trp Cys Pro Asn Gly Ala Cys Thr Gly Cys |
| (SEQ ID NO: 7489) | Cys Glu Trp Cys Pro Asn Gly Ala Cys Thr Ala Cys |
| (SEQ ID NO: 7490) | Cys Glu Trp Cys Pro Asn Gly Ala Cys Val Gly Cys |
| (SEQ ID NO: 7491) | Cys Glu Trp Cys Pro Asn Gly Ala Cys Val Ala Cys |
| (SEQ ID NO: 7492) | Cys Glu Trp Cys Pro Asn Gly Ala Cys Gly Gly Cys |
| (SEQ ID NO: 7493) | Cys Glu Trp Cys Pro Asn Gly Ala Cys Gly Ala Cys |
| (SEQ ID NO: 7494) | Cys Glu Trp Cys Pro Asn Gly Thr Cys Thr Gly Cys |
| (SEQ ID NO: 7495) | Cys Glu Trp Cys Pro Asn Gly Thr Cys Thr Ala Cys |
| (SEQ ID NO: 7496) | Cys Glu Trp Cys Pro Asn Gly Thr Cys Val Gly Cys |
| (SEQ ID NO: 7497) | Cys Glu Trp Cys Pro Asn Gly Thr Cys Val Ala Cys |
| (SEQ ID NO: 7498) | Cys Glu Trp Cys Pro Asn Gly Thr Cys Gly Gly Cys |
| (SEQ ID NO: 7499) | Cys Glu Trp Cys Pro Asn Gly Thr Cys Gly Ala Cys |
| (SEQ ID NO: 7500) | Cys Glu Trp Cys Ser Asn Pro Ala Cys Thr Gly Cys |
| (SEQ ID NO: 7501) | Cys Glu Trp Cys Ser Asn Pro Ala Cys Thr Ala Cys |
| (SEQ ID NO: 7502) | Cys Glu Trp Cys Ser Asn Pro Ala Cys Val Gly Cys |
| (SEQ ID NO: 7503) | Cys Glu Trp Cys Ser Asn Pro Ala Cys Val Ala Cys |
| (SEQ ID NO: 7504) | Cys Glu Trp Cys Ser Asn Pro Ala Cys Gly Gly Cys |
| (SEQ ID NO: 7505) | Cys Glu Trp Cys Ser Asn Pro Ala Cys Gly Ala Cys |
| (SEQ ID NO: 7506) | Cys Glu Trp Cys Ser Asn Pro Thr Cys Thr Gly Cys |
| (SEQ ID NO: 7507) | Cys Glu Trp Cys Ser Asn Pro Thr Cys Thr Ala Cys |
| (SEQ ID NO: 7508) | Cys Glu Trp Cys Ser Asn Pro Thr Cys Val Gly Cys |
| (SEQ ID NO: 7509) | Cys Glu Trp Cys Ser Asn Pro Thr Cys Val Ala Cys |
| (SEQ ID NO: 7510) | Cys Glu Trp Cys Ser Asn Pro Thr Cys Gly Gly Cys |
| (SEQ ID NO: 7511) | Cys Glu Trp Cys Ser Asn Pro Thr Cys Gly Ala Cys |
| (SEQ ID NO: 7512) | Cys Glu Trp Cys Ser Asn Gly Ala Cys Thr Gly Cys |
| (SEQ ID NO: 7513) | Cys Glu Trp Cys Ser Asn Gly Ala Cys Thr Ala Cys |
| (SEQ ID NO: 7514) | Cys Glu Trp Cys Ser Asn Gly Ala Cys Val Gly Cys |
| (SEQ ID NO: 7515) | Cys Glu Trp Cys Ser Asn Gly Ala Cys Val Ala Cys |

FIG. 3BL

| | |
|---|---|
| (SEQ ID NO: 7516) | Cys Glu Trp Cys Ser Asn Gly Ala Cys Gly Gly Cys |
| (SEQ ID NO: 7517) | Cys Glu Trp Cys Ser Asn Gly Ala Cys Gly Ala Cys |
| (SEQ ID NO: 7518) | Cys Glu Trp Cys Ser Asn Gly Thr Cys Thr Gly Cys |
| (SEQ ID NO: 7519) | Cys Glu Trp Cys Ser Asn Gly Thr Cys Thr Ala Cys |
| (SEQ ID NO: 7520) | Cys Glu Trp Cys Ser Asn Gly Thr Cys Val Gly Cys |
| (SEQ ID NO: 7521) | Cys Glu Trp Cys Ser Asn Gly Thr Cys Val Ala Cys |
| (SEQ ID NO: 7522) | Cys Glu Trp Cys Ser Asn Gly Thr Cys Gly Gly Cys |
| (SEQ ID NO: 7523) | Cys Glu Trp Cys Ser Asn Gly Thr Cys Gly Ala Cys |
| (SEQ ID NO: 7524) | Cys Glu Trp Cys Thr Asn Pro Ala Cys Thr Gly Cys |
| (SEQ ID NO: 7525) | Cys Glu Trp Cys Thr Asn Pro Ala Cys Thr Ala Cys |
| (SEQ ID NO: 7526) | Cys Glu Trp Cys Thr Asn Pro Ala Cys Val Gly Cys |
| (SEQ ID NO: 7527) | Cys Glu Trp Cys Thr Asn Pro Ala Cys Val Ala Cys |
| (SEQ ID NO: 7528) | Cys Glu Trp Cys Thr Asn Pro Ala Cys Gly Gly Cys |
| (SEQ ID NO: 7529) | Cys Glu Trp Cys Thr Asn Pro Ala Cys Gly Ala Cys |
| (SEQ ID NO: 7530) | Cys Glu Trp Cys Thr Asn Pro Thr Cys Thr Gly Cys |
| (SEQ ID NO: 7531) | Cys Glu Trp Cys Thr Asn Pro Thr Cys Thr Ala Cys |
| (SEQ ID NO: 7532) | Cys Glu Trp Cys Thr Asn Pro Thr Cys Val Gly Cys |
| (SEQ ID NO: 7533) | Cys Glu Trp Cys Thr Asn Pro Thr Cys Val Ala Cys |
| (SEQ ID NO: 7534) | Cys Glu Trp Cys Thr Asn Pro Thr Cys Gly Gly Cys |
| (SEQ ID NO: 7535) | Cys Glu Trp Cys Thr Asn Pro Thr Cys Gly Ala Cys |
| (SEQ ID NO: 7536) | Cys Glu Trp Cys Thr Asn Gly Ala Cys Thr Gly Cys |
| (SEQ ID NO: 7537) | Cys Glu Trp Cys Thr Asn Gly Ala Cys Thr Ala Cys |
| (SEQ ID NO: 7538) | Cys Glu Trp Cys Thr Asn Gly Ala Cys Val Gly Cys |
| (SEQ ID NO: 7539) | Cys Glu Trp Cys Thr Asn Gly Ala Cys Val Ala Cys |
| (SEQ ID NO: 7540) | Cys Glu Trp Cys Thr Asn Gly Ala Cys Gly Gly Cys |
| (SEQ ID NO: 7541) | Cys Glu Trp Cys Thr Asn Gly Ala Cys Gly Ala Cys |
| (SEQ ID NO: 7542) | Cys Glu Trp Cys Thr Asn Gly Thr Cys Thr Gly Cys |
| (SEQ ID NO: 7543) | Cys Glu Trp Cys Thr Asn Gly Thr Cys Thr Ala Cys |
| (SEQ ID NO: 7544) | Cys Glu Trp Cys Thr Asn Gly Thr Cys Val Gly Cys |
| (SEQ ID NO: 7545) | Cys Glu Trp Cys Thr Asn Gly Thr Cys Val Ala Cys |
| (SEQ ID NO: 7546) | Cys Glu Trp Cys Thr Asn Gly Thr Cys Gly Gly Cys |
| (SEQ ID NO: 7547) | Cys Glu Trp Cys Thr Asn Gly Thr Cys Gly Ala Cys |
| (SEQ ID NO: 7548) | Cys Glu Trp Cys Trp Asn Pro Ala Cys Thr Gly Cys |
| (SEQ ID NO: 7549) | Cys Glu Trp Cys Trp Asn Pro Ala Cys Thr Ala Cys |
| (SEQ ID NO: 7550) | Cys Glu Trp Cys Trp Asn Pro Ala Cys Val Gly Cys |
| (SEQ ID NO: 7551) | Cys Glu Trp Cys Trp Asn Pro Ala Cys Val Ala Cys |
| (SEQ ID NO: 7552) | Cys Glu Trp Cys Trp Asn Pro Ala Cys Gly Gly Cys |
| (SEQ ID NO: 7553) | Cys Glu Trp Cys Trp Asn Pro Ala Cys Gly Ala Cys |
| (SEQ ID NO: 7554) | Cys Glu Trp Cys Trp Asn Pro Thr Cys Thr Gly Cys |
| (SEQ ID NO: 7555) | Cys Glu Trp Cys Trp Asn Pro Thr Cys Thr Ala Cys |
| (SEQ ID NO: 7556) | Cys Glu Trp Cys Trp Asn Pro Thr Cys Val Gly Cys |
| (SEQ ID NO: 7557) | Cys Glu Trp Cys Trp Asn Pro Thr Cys Val Ala Cys |
| (SEQ ID NO: 7558) | Cys Glu Trp Cys Trp Asn Pro Thr Cys Gly Gly Cys |

FIG. 3BM

| | |
|---|---|
| (SEQ ID NO: 7559) | Cys Glu Trp Cys Trp Asn Pro Thr Cys Gly Ala Cys |
| (SEQ ID NO: 7560) | Cys Glu Trp Cys Trp Asn Gly Ala Cys Thr Gly Cys |
| (SEQ ID NO: 7561) | Cys Glu Trp Cys Trp Asn Gly Ala Cys Thr Ala Cys |
| (SEQ ID NO: 7562) | Cys Glu Trp Cys Trp Asn Gly Ala Cys Val Gly Cys |
| (SEQ ID NO: 7563) | Cys Glu Trp Cys Trp Asn Gly Ala Cys Val Ala Cys |
| (SEQ ID NO: 7564) | Cys Glu Trp Cys Trp Asn Gly Ala Cys Gly Gly Cys |
| (SEQ ID NO: 7565) | Cys Glu Trp Cys Trp Asn Gly Ala Cys Gly Ala Cys |
| (SEQ ID NO: 7566) | Cys Glu Trp Cys Trp Asn Gly Thr Cys Thr Gly Cys |
| (SEQ ID NO: 7567) | Cys Glu Trp Cys Trp Asn Gly Thr Cys Thr Ala Cys |
| (SEQ ID NO: 7568) | Cys Glu Trp Cys Trp Asn Gly Thr Cys Val Gly Cys |
| (SEQ ID NO: 7569) | Cys Glu Trp Cys Trp Asn Gly Thr Cys Val Ala Cys |
| (SEQ ID NO: 7570) | Cys Glu Trp Cys Trp Asn Gly Thr Cys Gly Gly Cys |
| (SEQ ID NO: 7571) | Cys Glu Trp Cys Trp Asn Gly Thr Cys Gly Ala Cys |
| (SEQ ID NO: 7572) | Cys Glu Trp Cys Tyr Asn Pro Ala Cys Thr Gly Cys |
| (SEQ ID NO: 7573) | Cys Glu Trp Cys Tyr Asn Pro Ala Cys Thr Ala Cys |
| (SEQ ID NO: 7574) | Cys Glu Trp Cys Tyr Asn Pro Ala Cys Val Gly Cys |
| (SEQ ID NO: 7575) | Cys Glu Trp Cys Tyr Asn Pro Ala Cys Val Ala Cys |
| (SEQ ID NO: 7576) | Cys Glu Trp Cys Tyr Asn Pro Ala Cys Gly Gly Cys |
| (SEQ ID NO: 7577) | Cys Glu Trp Cys Tyr Asn Pro Ala Cys Gly Ala Cys |
| (SEQ ID NO: 7578) | Cys Glu Trp Cys Tyr Asn Pro Thr Cys Thr Gly Cys |
| (SEQ ID NO: 7579) | Cys Glu Trp Cys Tyr Asn Pro Thr Cys Thr Ala Cys |
| (SEQ ID NO: 7580) | Cys Glu Trp Cys Tyr Asn Pro Thr Cys Val Gly Cys |
| (SEQ ID NO: 7581) | Cys Glu Trp Cys Tyr Asn Pro Thr Cys Val Ala Cys |
| (SEQ ID NO: 7582) | Cys Glu Trp Cys Tyr Asn Pro Thr Cys Gly Gly Cys |
| (SEQ ID NO: 7583) | Cys Glu Trp Cys Tyr Asn Pro Thr Cys Gly Ala Cys |
| (SEQ ID NO: 7584) | Cys Glu Trp Cys Tyr Asn Gly Ala Cys Thr Gly Cys |
| (SEQ ID NO: 7585) | Cys Glu Trp Cys Tyr Asn Gly Ala Cys Thr Ala Cys |
| (SEQ ID NO: 7586) | Cys Glu Trp Cys Tyr Asn Gly Ala Cys Val Gly Cys |
| (SEQ ID NO: 7587) | Cys Glu Trp Cys Tyr Asn Gly Ala Cys Val Ala Cys |
| (SEQ ID NO: 7588) | Cys Glu Trp Cys Tyr Asn Gly Ala Cys Gly Gly Cys |
| (SEQ ID NO: 7589) | Cys Glu Trp Cys Tyr Asn Gly Ala Cys Gly Ala Cys |
| (SEQ ID NO: 7590) | Cys Glu Trp Cys Tyr Asn Gly Thr Cys Thr Gly Cys |
| (SEQ ID NO: 7591) | Cys Glu Trp Cys Tyr Asn Gly Thr Cys Thr Ala Cys |
| (SEQ ID NO: 7592) | Cys Glu Trp Cys Tyr Asn Gly Thr Cys Val Gly Cys |
| (SEQ ID NO: 7593) | Cys Glu Trp Cys Tyr Asn Gly Thr Cys Val Ala Cys |
| (SEQ ID NO: 7594) | Cys Glu Trp Cys Tyr Asn Gly Thr Cys Gly Gly Cys |
| (SEQ ID NO: 7595) | Cys Glu Trp Cys Tyr Asn Gly Thr Cys Gly Ala Cys |
| (SEQ ID NO: 7596) | Cys Glu Trp Cys Val Asn Pro Ala Cys Thr Gly Cys |
| (SEQ ID NO: 7597) | Cys Glu Trp Cys Val Asn Pro Ala Cys Thr Ala Cys |
| (SEQ ID NO: 7598) | Cys Glu Trp Cys Val Asn Pro Ala Cys Val Gly Cys |
| (SEQ ID NO: 7599) | Cys Glu Trp Cys Val Asn Pro Ala Cys Val Ala Cys |
| (SEQ ID NO: 7600) | Cys Glu Trp Cys Val Asn Pro Ala Cys Gly Gly Cys |
| (SEQ ID NO: 7601) | Cys Glu Trp Cys Val Asn Pro Ala Cys Gly Ala Cys |

FIG. 3BN

| | | | | | | | | | | |
|---|---|---|---|---|---|---|---|---|---|---|
| (SEQ ID NO: 7602 ) | Cys | Glu | Trp | Cys | Val | Asn | Pro | Thr | Cys | Thr | Gly | Cys |
| (SEQ ID NO: 7603 ) | Cys | Glu | Trp | Cys | Val | Asn | Pro | Thr | Cys | Thr | Ala | Cys |
| (SEQ ID NO: 7604 ) | Cys | Glu | Trp | Cys | Val | Asn | Pro | Thr | Cys | Val | Gly | Cys |
| (SEQ ID NO: 7605 ) | Cys | Glu | Trp | Cys | Val | Asn | Pro | Thr | Cys | Val | Ala | Cys |
| (SEQ ID NO: 7606 ) | Cys | Glu | Trp | Cys | Val | Asn | Pro | Thr | Cys | Gly | Gly | Cys |
| (SEQ ID NO: 7607 ) | Cys | Glu | Trp | Cys | Val | Asn | Pro | Thr | Cys | Gly | Ala | Cys |
| (SEQ ID NO: 7608 ) | Cys | Glu | Trp | Cys | Val | Asn | Gly | Ala | Cys | Thr | Gly | Cys |
| (SEQ ID NO: 7609 ) | Cys | Glu | Trp | Cys | Val | Asn | Gly | Ala | Cys | Thr | Ala | Cys |
| (SEQ ID NO: 7610 ) | Cys | Glu | Trp | Cys | Val | Asn | Gly | Ala | Cys | Val | Gly | Cys |
| (SEQ ID NO: 7611 ) | Cys | Glu | Trp | Cys | Val | Asn | Gly | Ala | Cys | Val | Ala | Cys |
| (SEQ ID NO: 7612 ) | Cys | Glu | Trp | Cys | Val | Asn | Gly | Ala | Cys | Gly | Gly | Cys |
| (SEQ ID NO: 7613 ) | Cys | Glu | Trp | Cys | Val | Asn | Gly | Ala | Cys | Gly | Ala | Cys |
| (SEQ ID NO: 7614 ) | Cys | Glu | Trp | Cys | Val | Asn | Gly | Thr | Cys | Thr | Gly | Cys |
| (SEQ ID NO: 7615 ) | Cys | Glu | Trp | Cys | Val | Asn | Gly | Thr | Cys | Thr | Ala | Cys |
| (SEQ ID NO: 7616 ) | Cys | Glu | Trp | Cys | Val | Asn | Gly | Thr | Cys | Val | Gly | Cys |
| (SEQ ID NO: 7617 ) | Cys | Glu | Trp | Cys | Val | Asn | Gly | Thr | Cys | Val | Ala | Cys |
| (SEQ ID NO: 7618 ) | Cys | Glu | Trp | Cys | Val | Asn | Gly | Thr | Cys | Gly | Gly | Cys |
| (SEQ ID NO: 7619 ) | Cys | Glu | Trp | Cys | Val | Asn | Gly | Thr | Cys | Gly | Ala | Cys |
| (SEQ ID NO: 7620 ) | Cys | Glu | Trp | Cys | --- | Asn | Pro | Ala | Cys | Thr | Gly | Cys |
| (SEQ ID NO: 7621 ) | Cys | Glu | Trp | Cys | --- | Asn | Pro | Ala | Cys | Thr | Ala | Cys |
| (SEQ ID NO: 7622 ) | Cys | Glu | Trp | Cys | --- | Asn | Pro | Ala | Cys | Val | Gly | Cys |
| (SEQ ID NO: 7623 ) | Cys | Glu | Trp | Cys | --- | Asn | Pro | Ala | Cys | Val | Ala | Cys |
| (SEQ ID NO: 7624 ) | Cys | Glu | Trp | Cys | --- | Asn | Pro | Ala | Cys | Gly | Gly | Cys |
| (SEQ ID NO: 7625 ) | Cys | Glu | Trp | Cys | --- | Asn | Pro | Ala | Cys | Gly | Ala | Cys |
| (SEQ ID NO: 7626 ) | Cys | Glu | Trp | Cys | --- | Asn | Pro | Thr | Cys | Thr | Gly | Cys |
| (SEQ ID NO: 7627 ) | Cys | Glu | Trp | Cys | --- | Asn | Pro | Thr | Cys | Thr | Ala | Cys |
| (SEQ ID NO: 7628 ) | Cys | Glu | Trp | Cys | --- | Asn | Pro | Thr | Cys | Val | Gly | Cys |
| (SEQ ID NO: 7629 ) | Cys | Glu | Trp | Cys | --- | Asn | Pro | Thr | Cys | Val | Ala | Cys |
| (SEQ ID NO: 7630 ) | Cys | Glu | Trp | Cys | --- | Asn | Pro | Thr | Cys | Gly | Gly | Cys |
| (SEQ ID NO: 7631 ) | Cys | Glu | Trp | Cys | --- | Asn | Pro | Thr | Cys | Gly | Ala | Cys |
| (SEQ ID NO: 7632 ) | Cys | Glu | Trp | Cys | --- | Asn | Gly | Ala | Cys | Thr | Gly | Cys |
| (SEQ ID NO: 7633 ) | Cys | Glu | Trp | Cys | --- | Asn | Gly | Ala | Cys | Thr | Ala | Cys |
| (SEQ ID NO: 7634 ) | Cys | Glu | Trp | Cys | --- | Asn | Gly | Ala | Cys | Val | Gly | Cys |
| (SEQ ID NO: 7635 ) | Cys | Glu | Trp | Cys | --- | Asn | Gly | Ala | Cys | Val | Ala | Cys |
| (SEQ ID NO: 7636 ) | Cys | Glu | Trp | Cys | --- | Asn | Gly | Ala | Cys | Gly | Gly | Cys |
| (SEQ ID NO: 7637 ) | Cys | Glu | Trp | Cys | --- | Asn | Gly | Ala | Cys | Gly | Ala | Cys |
| (SEQ ID NO: 7638 ) | Cys | Glu | Trp | Cys | --- | Asn | Gly | Thr | Cys | Thr | Gly | Cys |
| (SEQ ID NO: 7639 ) | Cys | Glu | Trp | Cys | --- | Asn | Gly | Thr | Cys | Thr | Ala | Cys |
| (SEQ ID NO: 7640 ) | Cys | Glu | Trp | Cys | --- | Asn | Gly | Thr | Cys | Val | Gly | Cys |
| (SEQ ID NO: 7641 ) | Cys | Glu | Trp | Cys | --- | Asn | Gly | Thr | Cys | Val | Ala | Cys |
| (SEQ ID NO: 7642 ) | Cys | Glu | Trp | Cys | --- | Asn | Gly | Thr | Cys | Gly | Gly | Cys |
| (SEQ ID NO: 7643 ) | Cys | Glu | Trp | Cys | --- | Asn | Gly | Thr | Cys | Gly | Ala | Cys |
| (SEQ ID NO: 7644 ) | Cys | Glu | Phe | Cys | Ala | Asn | Pro | Ala | Cys | Thr | Gly | Cys |

FIG. 3BO

| | |
|---|---|
| (SEQ ID NO: 7645) | Cys Glu Phe Cys Ala Asn Pro Ala Cys Thr Ala Cys |
| (SEQ ID NO: 7646) | Cys Glu Phe Cys Ala Asn Pro Ala Cys Val Gly Cys |
| (SEQ ID NO: 7647) | Cys Glu Phe Cys Ala Asn Pro Ala Cys Val Ala Cys |
| (SEQ ID NO: 7648) | Cys Glu Phe Cys Ala Asn Pro Ala Cys Gly Gly Cys |
| (SEQ ID NO: 7649) | Cys Glu Phe Cys Ala Asn Pro Ala Cys Gly Ala Cys |
| (SEQ ID NO: 7650) | Cys Glu Phe Cys Ala Asn Pro Thr Cys Thr Gly Cys |
| (SEQ ID NO: 7651) | Cys Glu Phe Cys Ala Asn Pro Thr Cys Thr Ala Cys |
| (SEQ ID NO: 7652) | Cys Glu Phe Cys Ala Asn Pro Thr Cys Val Gly Cys |
| (SEQ ID NO: 7653) | Cys Glu Phe Cys Ala Asn Pro Thr Cys Val Ala Cys |
| (SEQ ID NO: 7654) | Cys Glu Phe Cys Ala Asn Pro Thr Cys Gly Gly Cys |
| (SEQ ID NO: 7655) | Cys Glu Phe Cys Ala Asn Pro Thr Cys Gly Ala Cys |
| (SEQ ID NO: 7656) | Cys Glu Phe Cys Ala Asn Gly Ala Cys Thr Gly Cys |
| (SEQ ID NO: 7657) | Cys Glu Phe Cys Ala Asn Gly Ala Cys Thr Ala Cys |
| (SEQ ID NO: 7658) | Cys Glu Phe Cys Ala Asn Gly Ala Cys Val Gly Cys |
| (SEQ ID NO: 7659) | Cys Glu Phe Cys Ala Asn Gly Ala Cys Val Ala Cys |
| (SEQ ID NO: 7660) | Cys Glu Phe Cys Ala Asn Gly Ala Cys Gly Gly Cys |
| (SEQ ID NO: 7661) | Cys Glu Phe Cys Ala Asn Gly Ala Cys Gly Ala Cys |
| (SEQ ID NO: 7662) | Cys Glu Phe Cys Ala Asn Gly Thr Cys Thr Gly Cys |
| (SEQ ID NO: 7663) | Cys Glu Phe Cys Ala Asn Gly Thr Cys Thr Ala Cys |
| (SEQ ID NO: 7664) | Cys Glu Phe Cys Ala Asn Gly Thr Cys Val Gly Cys |
| (SEQ ID NO: 7665) | Cys Glu Phe Cys Ala Asn Gly Thr Cys Val Ala Cys |
| (SEQ ID NO: 7666) | Cys Glu Phe Cys Ala Asn Gly Thr Cys Gly Gly Cys |
| (SEQ ID NO: 7667) | Cys Glu Phe Cys Ala Asn Gly Thr Cys Gly Ala Cys |
| (SEQ ID NO: 7668) | Cys Glu Phe Cys Arg Asn Pro Ala Cys Thr Gly Cys |
| (SEQ ID NO: 7669) | Cys Glu Phe Cys Arg Asn Pro Ala Cys Thr Ala Cys |
| (SEQ ID NO: 7670) | Cys Glu Phe Cys Arg Asn Pro Ala Cys Val Gly Cys |
| (SEQ ID NO: 7671) | Cys Glu Phe Cys Arg Asn Pro Ala Cys Val Ala Cys |
| (SEQ ID NO: 7672) | Cys Glu Phe Cys Arg Asn Pro Ala Cys Gly Gly Cys |
| (SEQ ID NO: 7673) | Cys Glu Phe Cys Arg Asn Pro Ala Cys Gly Ala Cys |
| (SEQ ID NO: 7674) | Cys Glu Phe Cys Arg Asn Pro Thr Cys Thr Gly Cys |
| (SEQ ID NO: 7675) | Cys Glu Phe Cys Arg Asn Pro Thr Cys Thr Ala Cys |
| (SEQ ID NO: 7676) | Cys Glu Phe Cys Arg Asn Pro Thr Cys Val Gly Cys |
| (SEQ ID NO: 7677) | Cys Glu Phe Cys Arg Asn Pro Thr Cys Val Ala Cys |
| (SEQ ID NO: 7678) | Cys Glu Phe Cys Arg Asn Pro Thr Cys Gly Gly Cys |
| (SEQ ID NO: 7679) | Cys Glu Phe Cys Arg Asn Pro Thr Cys Gly Ala Cys |
| (SEQ ID NO: 7680) | Cys Glu Phe Cys Arg Asn Gly Ala Cys Thr Gly Cys |
| (SEQ ID NO: 7681) | Cys Glu Phe Cys Arg Asn Gly Ala Cys Thr Ala Cys |
| (SEQ ID NO: 7682) | Cys Glu Phe Cys Arg Asn Gly Ala Cys Val Gly Cys |
| (SEQ ID NO: 7683) | Cys Glu Phe Cys Arg Asn Gly Ala Cys Val Ala Cys |
| (SEQ ID NO: 7684) | Cys Glu Phe Cys Arg Asn Gly Ala Cys Gly Gly Cys |
| (SEQ ID NO: 7685) | Cys Glu Phe Cys Arg Asn Gly Ala Cys Gly Ala Cys |
| (SEQ ID NO: 7686) | Cys Glu Phe Cys Arg Asn Gly Thr Cys Thr Gly Cys |
| (SEQ ID NO: 7687) | Cys Glu Phe Cys Arg Asn Gly Thr Cys Thr Ala Cys |

FIG. 3BP

| | |
|---|---|
| (SEQ ID NO: 7688) | Cys Glu Phe Cys Arg Asn Gly Thr Cys Val Gly Cys |
| (SEQ ID NO: 7689) | Cys Glu Phe Cys Arg Asn Gly Thr Cys Val Ala Cys |
| (SEQ ID NO: 7690) | Cys Glu Phe Cys Arg Asn Gly Thr Cys Gly Gly Cys |
| (SEQ ID NO: 7691) | Cys Glu Phe Cys Arg Asn Gly Thr Cys Gly Ala Cys |
| (SEQ ID NO: 7692) | Cys Glu Phe Cys Asn Asn Pro Ala Cys Thr Gly Cys |
| (SEQ ID NO: 7693) | Cys Glu Phe Cys Asn Asn Pro Ala Cys Thr Ala Cys |
| (SEQ ID NO: 7694) | Cys Glu Phe Cys Asn Asn Pro Ala Cys Val Gly Cys |
| (SEQ ID NO: 7695) | Cys Glu Phe Cys Asn Asn Pro Ala Cys Val Ala Cys |
| (SEQ ID NO: 7696) | Cys Glu Phe Cys Asn Asn Pro Ala Cys Gly Gly Cys |
| (SEQ ID NO: 7697) | Cys Glu Phe Cys Asn Asn Pro Ala Cys Gly Ala Cys |
| (SEQ ID NO: 7698) | Cys Glu Phe Cys Asn Asn Pro Thr Cys Thr Gly Cys |
| (SEQ ID NO: 7699) | Cys Glu Phe Cys Asn Asn Pro Thr Cys Thr Ala Cys |
| (SEQ ID NO: 7700) | Cys Glu Phe Cys Asn Asn Pro Thr Cys Val Gly Cys |
| (SEQ ID NO: 7701) | Cys Glu Phe Cys Asn Asn Pro Thr Cys Val Ala Cys |
| (SEQ ID NO: 7702) | Cys Glu Phe Cys Asn Asn Pro Thr Cys Gly Gly Cys |
| (SEQ ID NO: 7703) | Cys Glu Phe Cys Asn Asn Pro Thr Cys Gly Ala Cys |
| (SEQ ID NO: 7704) | Cys Glu Phe Cys Asn Asn Gly Ala Cys Thr Gly Cys |
| (SEQ ID NO: 7705) | Cys Glu Phe Cys Asn Asn Gly Ala Cys Thr Ala Cys |
| (SEQ ID NO: 7706) | Cys Glu Phe Cys Asn Asn Gly Ala Cys Val Gly Cys |
| (SEQ ID NO: 7707) | Cys Glu Phe Cys Asn Asn Gly Ala Cys Val Ala Cys |
| (SEQ ID NO: 7708) | Cys Glu Phe Cys Asn Asn Gly Ala Cys Gly Gly Cys |
| (SEQ ID NO: 7709) | Cys Glu Phe Cys Asn Asn Gly Ala Cys Gly Ala Cys |
| (SEQ ID NO: 7710) | Cys Glu Phe Cys Asn Asn Gly Thr Cys Thr Gly Cys |
| (SEQ ID NO: 7711) | Cys Glu Phe Cys Asn Asn Gly Thr Cys Thr Ala Cys |
| (SEQ ID NO: 7712) | Cys Glu Phe Cys Asn Asn Gly Thr Cys Val Gly Cys |
| (SEQ ID NO: 7713) | Cys Glu Phe Cys Asn Asn Gly Thr Cys Val Ala Cys |
| (SEQ ID NO: 7714) | Cys Glu Phe Cys Asn Asn Gly Thr Cys Gly Gly Cys |
| (SEQ ID NO: 7715) | Cys Glu Phe Cys Asn Asn Gly Thr Cys Gly Ala Cys |
| (SEQ ID NO: 7716) | Cys Glu Phe Cys Asp Asn Pro Ala Cys Thr Gly Cys |
| (SEQ ID NO: 7717) | Cys Glu Phe Cys Asp Asn Pro Ala Cys Thr Ala Cys |
| (SEQ ID NO: 7718) | Cys Glu Phe Cys Asp Asn Pro Ala Cys Val Gly Cys |
| (SEQ ID NO: 7719) | Cys Glu Phe Cys Asp Asn Pro Ala Cys Val Ala Cys |
| (SEQ ID NO: 7720) | Cys Glu Phe Cys Asp Asn Pro Ala Cys Gly Gly Cys |
| (SEQ ID NO: 7721) | Cys Glu Phe Cys Asp Asn Pro Ala Cys Gly Ala Cys |
| (SEQ ID NO: 7722) | Cys Glu Phe Cys Asp Asn Pro Thr Cys Thr Gly Cys |
| (SEQ ID NO: 7723) | Cys Glu Phe Cys Asp Asn Pro Thr Cys Thr Ala Cys |
| (SEQ ID NO: 7724) | Cys Glu Phe Cys Asp Asn Pro Thr Cys Val Gly Cys |
| (SEQ ID NO: 7725) | Cys Glu Phe Cys Asp Asn Pro Thr Cys Val Ala Cys |
| (SEQ ID NO: 7726) | Cys Glu Phe Cys Asp Asn Pro Thr Cys Gly Gly Cys |
| (SEQ ID NO: 7727) | Cys Glu Phe Cys Asp Asn Pro Thr Cys Gly Ala Cys |
| (SEQ ID NO: 7728) | Cys Glu Phe Cys Asp Asn Gly Ala Cys Thr Gly Cys |
| (SEQ ID NO: 7729) | Cys Glu Phe Cys Asp Asn Gly Ala Cys Thr Ala Cys |
| (SEQ ID NO: 7730) | Cys Glu Phe Cys Asp Asn Gly Ala Cys Val Gly Cys |

FIG. 3BQ

| | |
|---|---|
| (SEQ ID NO: 7731) | Cys Glu Phe Cys Asp Asn Gly Ala Cys Val Ala Cys |
| (SEQ ID NO: 7732) | Cys Glu Phe Cys Asp Asn Gly Ala Cys Gly Gly Cys |
| (SEQ ID NO: 7733) | Cys Glu Phe Cys Asp Asn Gly Ala Cys Gly Ala Cys |
| (SEQ ID NO: 7734) | Cys Glu Phe Cys Asp Asn Gly Thr Cys Thr Gly Cys |
| (SEQ ID NO: 7735) | Cys Glu Phe Cys Asp Asn Gly Thr Cys Thr Ala Cys |
| (SEQ ID NO: 7736) | Cys Glu Phe Cys Asp Asn Gly Thr Cys Val Gly Cys |
| (SEQ ID NO: 7737) | Cys Glu Phe Cys Asp Asn Gly Thr Cys Val Ala Cys |
| (SEQ ID NO: 7738) | Cys Glu Phe Cys Asp Asn Gly Thr Cys Gly Gly Cys |
| (SEQ ID NO: 7739) | Cys Glu Phe Cys Asp Asn Gly Thr Cys Gly Ala Cys |
| (SEQ ID NO: 7740) | Cys Glu Phe Cys Gln Asn Pro Ala Cys Thr Gly Cys |
| (SEQ ID NO: 7741) | Cys Glu Phe Cys Gln Asn Pro Ala Cys Thr Ala Cys |
| (SEQ ID NO: 7742) | Cys Glu Phe Cys Gln Asn Pro Ala Cys Val Gly Cys |
| (SEQ ID NO: 7743) | Cys Glu Phe Cys Gln Asn Pro Ala Cys Val Ala Cys |
| (SEQ ID NO: 7744) | Cys Glu Phe Cys Gln Asn Pro Ala Cys Gly Gly Cys |
| (SEQ ID NO: 7745) | Cys Glu Phe Cys Gln Asn Pro Ala Cys Gly Ala Cys |
| (SEQ ID NO: 7746) | Cys Glu Phe Cys Gln Asn Pro Thr Cys Thr Gly Cys |
| (SEQ ID NO: 7747) | Cys Glu Phe Cys Gln Asn Pro Thr Cys Thr Ala Cys |
| (SEQ ID NO: 7748) | Cys Glu Phe Cys Gln Asn Pro Thr Cys Val Gly Cys |
| (SEQ ID NO: 7749) | Cys Glu Phe Cys Gln Asn Pro Thr Cys Val Ala Cys |
| (SEQ ID NO: 7750) | Cys Glu Phe Cys Gln Asn Pro Thr Cys Gly Gly Cys |
| (SEQ ID NO: 7751) | Cys Glu Phe Cys Gln Asn Pro Thr Cys Gly Ala Cys |
| (SEQ ID NO: 7752) | Cys Glu Phe Cys Gln Asn Gly Ala Cys Thr Gly Cys |
| (SEQ ID NO: 7753) | Cys Glu Phe Cys Gln Asn Gly Ala Cys Thr Ala Cys |
| (SEQ ID NO: 7754) | Cys Glu Phe Cys Gln Asn Gly Ala Cys Val Gly Cys |
| (SEQ ID NO: 7755) | Cys Glu Phe Cys Gln Asn Gly Ala Cys Val Ala Cys |
| (SEQ ID NO: 7756) | Cys Glu Phe Cys Gln Asn Gly Ala Cys Gly Gly Cys |
| (SEQ ID NO: 7757) | Cys Glu Phe Cys Gln Asn Gly Ala Cys Gly Ala Cys |
| (SEQ ID NO: 7758) | Cys Glu Phe Cys Gln Asn Gly Thr Cys Thr Gly Cys |
| (SEQ ID NO: 7759) | Cys Glu Phe Cys Gln Asn Gly Thr Cys Thr Ala Cys |
| (SEQ ID NO: 7760) | Cys Glu Phe Cys Gln Asn Gly Thr Cys Val Gly Cys |
| (SEQ ID NO: 7761) | Cys Glu Phe Cys Gln Asn Gly Thr Cys Val Ala Cys |
| (SEQ ID NO: 7762) | Cys Glu Phe Cys Gln Asn Gly Thr Cys Gly Gly Cys |
| (SEQ ID NO: 7763) | Cys Glu Phe Cys Gln Asn Gly Thr Cys Gly Ala Cys |
| (SEQ ID NO: 7764) | Cys Glu Phe Cys Glu Asn Pro Ala Cys Thr Gly Cys |
| (SEQ ID NO: 7765) | Cys Glu Phe Cys Glu Asn Pro Ala Cys Thr Ala Cys |
| (SEQ ID NO: 7766) | Cys Glu Phe Cys Glu Asn Pro Ala Cys Val Gly Cys |
| (SEQ ID NO: 7767) | Cys Glu Phe Cys Glu Asn Pro Ala Cys Val Ala Cys |
| (SEQ ID NO: 7768) | Cys Glu Phe Cys Glu Asn Pro Ala Cys Gly Gly Cys |
| (SEQ ID NO: 7769) | Cys Glu Phe Cys Glu Asn Pro Ala Cys Gly Ala Cys |
| (SEQ ID NO: 7770) | Cys Glu Phe Cys Glu Asn Pro Thr Cys Thr Gly Cys |
| (SEQ ID NO: 7771) | Cys Glu Phe Cys Glu Asn Pro Thr Cys Thr Ala Cys |
| (SEQ ID NO: 7772) | Cys Glu Phe Cys Glu Asn Pro Thr Cys Val Gly Cys |
| (SEQ ID NO: 7773) | Cys Glu Phe Cys Glu Asn Pro Thr Cys Val Ala Cys |

FIG. 3BR

| | |
|---|---|
| (SEQ ID NO: 7774) | Cys Glu Phe Cys Glu Asn Pro Thr Cys Gly Gly Cys |
| (SEQ ID NO: 7775) | Cys Glu Phe Cys Glu Asn Pro Thr Cys Gly Ala Cys |
| (SEQ ID NO: 7776) | Cys Glu Phe Cys Glu Asn Gly Ala Cys Thr Gly Cys |
| (SEQ ID NO: 7777) | Cys Glu Phe Cys Glu Asn Gly Ala Cys Thr Ala Cys |
| (SEQ ID NO: 7778) | Cys Glu Phe Cys Glu Asn Gly Ala Cys Val Gly Cys |
| (SEQ ID NO: 7779) | Cys Glu Phe Cys Glu Asn Gly Ala Cys Val Ala Cys |
| (SEQ ID NO: 7780) | Cys Glu Phe Cys Glu Asn Gly Ala Cys Gly Gly Cys |
| (SEQ ID NO: 7781) | Cys Glu Phe Cys Glu Asn Gly Ala Cys Gly Ala Cys |
| (SEQ ID NO: 7782) | Cys Glu Phe Cys Glu Asn Gly Thr Cys Thr Gly Cys |
| (SEQ ID NO: 7783) | Cys Glu Phe Cys Glu Asn Gly Thr Cys Thr Ala Cys |
| (SEQ ID NO: 7784) | Cys Glu Phe Cys Glu Asn Gly Thr Cys Val Gly Cys |
| (SEQ ID NO: 7785) | Cys Glu Phe Cys Glu Asn Gly Thr Cys Val Ala Cys |
| (SEQ ID NO: 7786) | Cys Glu Phe Cys Glu Asn Gly Thr Cys Gly Gly Cys |
| (SEQ ID NO: 7787) | Cys Glu Phe Cys Glu Asn Gly Thr Cys Gly Ala Cys |
| (SEQ ID NO: 7788) | Cys Glu Phe Cys Gly Asn Pro Ala Cys Thr Gly Cys |
| (SEQ ID NO: 7789) | Cys Glu Phe Cys Gly Asn Pro Ala Cys Thr Ala Cys |
| (SEQ ID NO: 7790) | Cys Glu Phe Cys Gly Asn Pro Ala Cys Val Gly Cys |
| (SEQ ID NO: 7791) | Cys Glu Phe Cys Gly Asn Pro Ala Cys Val Ala Cys |
| (SEQ ID NO: 7792) | Cys Glu Phe Cys Gly Asn Pro Ala Cys Gly Gly Cys |
| (SEQ ID NO: 7793) | Cys Glu Phe Cys Gly Asn Pro Ala Cys Gly Ala Cys |
| (SEQ ID NO: 7794) | Cys Glu Phe Cys Gly Asn Pro Thr Cys Thr Gly Cys |
| (SEQ ID NO: 7795) | Cys Glu Phe Cys Gly Asn Pro Thr Cys Thr Ala Cys |
| (SEQ ID NO: 7796) | Cys Glu Phe Cys Gly Asn Pro Thr Cys Val Gly Cys |
| (SEQ ID NO: 7797) | Cys Glu Phe Cys Gly Asn Pro Thr Cys Val Ala Cys |
| (SEQ ID NO: 7798) | Cys Glu Phe Cys Gly Asn Pro Thr Cys Gly Gly Cys |
| (SEQ ID NO: 7799) | Cys Glu Phe Cys Gly Asn Pro Thr Cys Gly Ala Cys |
| (SEQ ID NO: 7800) | Cys Glu Phe Cys Gly Asn Gly Ala Cys Thr Gly Cys |
| (SEQ ID NO: 7801) | Cys Glu Phe Cys Gly Asn Gly Ala Cys Thr Ala Cys |
| (SEQ ID NO: 7802) | Cys Glu Phe Cys Gly Asn Gly Ala Cys Val Gly Cys |
| (SEQ ID NO: 7803) | Cys Glu Phe Cys Gly Asn Gly Ala Cys Val Ala Cys |
| (SEQ ID NO: 7804) | Cys Glu Phe Cys Gly Asn Gly Ala Cys Gly Gly Cys |
| (SEQ ID NO: 7805) | Cys Glu Phe Cys Gly Asn Gly Ala Cys Gly Ala Cys |
| (SEQ ID NO: 7806) | Cys Glu Phe Cys Gly Asn Gly Thr Cys Thr Gly Cys |
| (SEQ ID NO: 7807) | Cys Glu Phe Cys Gly Asn Gly Thr Cys Thr Ala Cys |
| (SEQ ID NO: 7808) | Cys Glu Phe Cys Gly Asn Gly Thr Cys Val Gly Cys |
| (SEQ ID NO: 7809) | Cys Glu Phe Cys Gly Asn Gly Thr Cys Val Ala Cys |
| (SEQ ID NO: 7810) | Cys Glu Phe Cys Gly Asn Gly Thr Cys Gly Gly Cys |
| (SEQ ID NO: 7811) | Cys Glu Phe Cys Gly Asn Gly Thr Cys Gly Ala Cys |
| (SEQ ID NO: 7812) | Cys Glu Phe Cys His Asn Pro Ala Cys Thr Gly Cys |
| (SEQ ID NO: 7813) | Cys Glu Phe Cys His Asn Pro Ala Cys Thr Ala Cys |
| (SEQ ID NO: 7814) | Cys Glu Phe Cys His Asn Pro Ala Cys Val Gly Cys |
| (SEQ ID NO: 7815) | Cys Glu Phe Cys His Asn Pro Ala Cys Val Ala Cys |
| (SEQ ID NO: 7816) | Cys Glu Phe Cys His Asn Pro Ala Cys Gly Gly Cys |

FIG. 3BS

| | |
|---|---|
| (SEQ ID NO: 7817) | Cys Glu Phe Cys His Asn Pro Ala Cys Gly Ala Cys |
| (SEQ ID NO: 7818) | Cys Glu Phe Cys His Asn Pro Thr Cys Thr Gly Cys |
| (SEQ ID NO: 7819) | Cys Glu Phe Cys His Asn Pro Thr Cys Thr Ala Cys |
| (SEQ ID NO: 7820) | Cys Glu Phe Cys His Asn Pro Thr Cys Val Gly Cys |
| (SEQ ID NO: 7821) | Cys Glu Phe Cys His Asn Pro Thr Cys Val Ala Cys |
| (SEQ ID NO: 7822) | Cys Glu Phe Cys His Asn Pro Thr Cys Gly Gly Cys |
| (SEQ ID NO: 7823) | Cys Glu Phe Cys His Asn Pro Thr Cys Gly Ala Cys |
| (SEQ ID NO: 7824) | Cys Glu Phe Cys His Asn Gly Ala Cys Thr Gly Cys |
| (SEQ ID NO: 7825) | Cys Glu Phe Cys His Asn Gly Ala Cys Thr Ala Cys |
| (SEQ ID NO: 7826) | Cys Glu Phe Cys His Asn Gly Ala Cys Val Gly Cys |
| (SEQ ID NO: 7827) | Cys Glu Phe Cys His Asn Gly Ala Cys Val Ala Cys |
| (SEQ ID NO: 7828) | Cys Glu Phe Cys His Asn Gly Ala Cys Gly Gly Cys |
| (SEQ ID NO: 7829) | Cys Glu Phe Cys His Asn Gly Ala Cys Gly Ala Cys |
| (SEQ ID NO: 7830) | Cys Glu Phe Cys His Asn Gly Thr Cys Thr Gly Cys |
| (SEQ ID NO: 7831) | Cys Glu Phe Cys His Asn Gly Thr Cys Thr Ala Cys |
| (SEQ ID NO: 7832) | Cys Glu Phe Cys His Asn Gly Thr Cys Val Gly Cys |
| (SEQ ID NO: 7833) | Cys Glu Phe Cys His Asn Gly Thr Cys Val Ala Cys |
| (SEQ ID NO: 7834) | Cys Glu Phe Cys His Asn Gly Thr Cys Gly Gly Cys |
| (SEQ ID NO: 7835) | Cys Glu Phe Cys His Asn Gly Thr Cys Gly Ala Cys |
| (SEQ ID NO: 7836) | Cys Glu Phe Cys Ile Asn Pro Ala Cys Thr Gly Cys |
| (SEQ ID NO: 7837) | Cys Glu Phe Cys Ile Asn Pro Ala Cys Thr Ala Cys |
| (SEQ ID NO: 7838) | Cys Glu Phe Cys Ile Asn Pro Ala Cys Val Gly Cys |
| (SEQ ID NO: 7839) | Cys Glu Phe Cys Ile Asn Pro Ala Cys Val Ala Cys |
| (SEQ ID NO: 7840) | Cys Glu Phe Cys Ile Asn Pro Ala Cys Gly Gly Cys |
| (SEQ ID NO: 7841) | Cys Glu Phe Cys Ile Asn Pro Ala Cys Gly Ala Cys |
| (SEQ ID NO: 7842) | Cys Glu Phe Cys Ile Asn Pro Thr Cys Thr Gly Cys |
| (SEQ ID NO: 7843) | Cys Glu Phe Cys Ile Asn Pro Thr Cys Thr Ala Cys |
| (SEQ ID NO: 7844) | Cys Glu Phe Cys Ile Asn Pro Thr Cys Val Gly Cys |
| (SEQ ID NO: 7845) | Cys Glu Phe Cys Ile Asn Pro Thr Cys Val Ala Cys |
| (SEQ ID NO: 7846) | Cys Glu Phe Cys Ile Asn Pro Thr Cys Gly Gly Cys |
| (SEQ ID NO: 7847) | Cys Glu Phe Cys Ile Asn Pro Thr Cys Gly Ala Cys |
| (SEQ ID NO: 7848) | Cys Glu Phe Cys Ile Asn Gly Ala Cys Thr Gly Cys |
| (SEQ ID NO: 7849) | Cys Glu Phe Cys Ile Asn Gly Ala Cys Thr Ala Cys |
| (SEQ ID NO: 7850) | Cys Glu Phe Cys Ile Asn Gly Ala Cys Val Gly Cys |
| (SEQ ID NO: 7851) | Cys Glu Phe Cys Ile Asn Gly Ala Cys Val Ala Cys |
| (SEQ ID NO: 7852) | Cys Glu Phe Cys Ile Asn Gly Ala Cys Gly Gly Cys |
| (SEQ ID NO: 7853) | Cys Glu Phe Cys Ile Asn Gly Ala Cys Gly Ala Cys |
| (SEQ ID NO: 7854) | Cys Glu Phe Cys Ile Asn Gly Thr Cys Thr Gly Cys |
| (SEQ ID NO: 7855) | Cys Glu Phe Cys Ile Asn Gly Thr Cys Thr Ala Cys |
| (SEQ ID NO: 7856) | Cys Glu Phe Cys Ile Asn Gly Thr Cys Val Gly Cys |
| (SEQ ID NO: 7857) | Cys Glu Phe Cys Ile Asn Gly Thr Cys Val Ala Cys |
| (SEQ ID NO: 7858) | Cys Glu Phe Cys Ile Asn Gly Thr Cys Gly Gly Cys |
| (SEQ ID NO: 7859) | Cys Glu Phe Cys Ile Asn Gly Thr Cys Gly Ala Cys |

FIG. 3BT

| | |
|---|---|
| (SEQ ID NO: 7860) | Cys Glu Phe Cys Leu Asn Pro Ala Cys Thr Gly Cys |
| (SEQ ID NO: 7861) | Cys Glu Phe Cys Leu Asn Pro Ala Cys Thr Ala Cys |
| (SEQ ID NO: 7862) | Cys Glu Phe Cys Leu Asn Pro Ala Cys Val Gly Cys |
| (SEQ ID NO: 7863) | Cys Glu Phe Cys Leu Asn Pro Ala Cys Val Ala Cys |
| (SEQ ID NO: 7864) | Cys Glu Phe Cys Leu Asn Pro Ala Cys Gly Gly Cys |
| (SEQ ID NO: 7865) | Cys Glu Phe Cys Leu Asn Pro Ala Cys Gly Ala Cys |
| (SEQ ID NO: 7866) | Cys Glu Phe Cys Leu Asn Pro Thr Cys Thr Gly Cys |
| (SEQ ID NO: 7867) | Cys Glu Phe Cys Leu Asn Pro Thr Cys Thr Ala Cys |
| (SEQ ID NO: 7868) | Cys Glu Phe Cys Leu Asn Pro Thr Cys Val Gly Cys |
| (SEQ ID NO: 7869) | Cys Glu Phe Cys Leu Asn Pro Thr Cys Val Ala Cys |
| (SEQ ID NO: 7870) | Cys Glu Phe Cys Leu Asn Pro Thr Cys Gly Gly Cys |
| (SEQ ID NO: 7871) | Cys Glu Phe Cys Leu Asn Pro Thr Cys Gly Ala Cys |
| (SEQ ID NO: 7872) | Cys Glu Phe Cys Leu Asn Gly Ala Cys Thr Gly Cys |
| (SEQ ID NO: 7873) | Cys Glu Phe Cys Leu Asn Gly Ala Cys Thr Ala Cys |
| (SEQ ID NO: 7874) | Cys Glu Phe Cys Leu Asn Gly Ala Cys Val Gly Cys |
| (SEQ ID NO: 7875) | Cys Glu Phe Cys Leu Asn Gly Ala Cys Val Ala Cys |
| (SEQ ID NO: 7876) | Cys Glu Phe Cys Leu Asn Gly Ala Cys Gly Gly Cys |
| (SEQ ID NO: 7877) | Cys Glu Phe Cys Leu Asn Gly Ala Cys Gly Ala Cys |
| (SEQ ID NO: 7878) | Cys Glu Phe Cys Leu Asn Gly Thr Cys Thr Gly Cys |
| (SEQ ID NO: 7879) | Cys Glu Phe Cys Leu Asn Gly Thr Cys Thr Ala Cys |
| (SEQ ID NO: 7880) | Cys Glu Phe Cys Leu Asn Gly Thr Cys Val Gly Cys |
| (SEQ ID NO: 7881) | Cys Glu Phe Cys Leu Asn Gly Thr Cys Val Ala Cys |
| (SEQ ID NO: 7882) | Cys Glu Phe Cys Leu Asn Gly Thr Cys Gly Gly Cys |
| (SEQ ID NO: 7883) | Cys Glu Phe Cys Leu Asn Gly Thr Cys Gly Ala Cys |
| (SEQ ID NO: 7884) | Cys Glu Phe Cys Lys Asn Pro Ala Cys Thr Gly Cys |
| (SEQ ID NO: 7885) | Cys Glu Phe Cys Lys Asn Pro Ala Cys Thr Ala Cys |
| (SEQ ID NO: 7886) | Cys Glu Phe Cys Lys Asn Pro Ala Cys Val Gly Cys |
| (SEQ ID NO: 7887) | Cys Glu Phe Cys Lys Asn Pro Ala Cys Val Ala Cys |
| (SEQ ID NO: 7888) | Cys Glu Phe Cys Lys Asn Pro Ala Cys Gly Gly Cys |
| (SEQ ID NO: 7889) | Cys Glu Phe Cys Lys Asn Pro Ala Cys Gly Ala Cys |
| (SEQ ID NO: 7890) | Cys Glu Phe Cys Lys Asn Pro Thr Cys Thr Gly Cys |
| (SEQ ID NO: 7891) | Cys Glu Phe Cys Lys Asn Pro Thr Cys Thr Ala Cys |
| (SEQ ID NO: 7892) | Cys Glu Phe Cys Lys Asn Pro Thr Cys Val Gly Cys |
| (SEQ ID NO: 7893) | Cys Glu Phe Cys Lys Asn Pro Thr Cys Val Ala Cys |
| (SEQ ID NO: 7894) | Cys Glu Phe Cys Lys Asn Pro Thr Cys Gly Gly Cys |
| (SEQ ID NO: 7895) | Cys Glu Phe Cys Lys Asn Pro Thr Cys Gly Ala Cys |
| (SEQ ID NO: 7896) | Cys Glu Phe Cys Lys Asn Gly Ala Cys Thr Gly Cys |
| (SEQ ID NO: 7897) | Cys Glu Phe Cys Lys Asn Gly Ala Cys Thr Ala Cys |
| (SEQ ID NO: 7898) | Cys Glu Phe Cys Lys Asn Gly Ala Cys Val Gly Cys |
| (SEQ ID NO: 7899) | Cys Glu Phe Cys Lys Asn Gly Ala Cys Val Ala Cys |
| (SEQ ID NO: 7900) | Cys Glu Phe Cys Lys Asn Gly Ala Cys Gly Gly Cys |
| (SEQ ID NO: 7901) | Cys Glu Phe Cys Lys Asn Gly Ala Cys Gly Ala Cys |
| (SEQ ID NO: 7902) | Cys Glu Phe Cys Lys Asn Gly Thr Cys Thr Gly Cys |

FIG. 3BU

| | |
|---|---|
| (SEQ ID NO: 7903) | Cys Glu Phe Cys Lys Asn Gly Thr Cys Thr Ala Cys |
| (SEQ ID NO: 7904) | Cys Glu Phe Cys Lys Asn Gly Thr Cys Val Gly Cys |
| (SEQ ID NO: 7905) | Cys Glu Phe Cys Lys Asn Gly Thr Cys Val Ala Cys |
| (SEQ ID NO: 7906) | Cys Glu Phe Cys Lys Asn Gly Thr Cys Gly Gly Cys |
| (SEQ ID NO: 7907) | Cys Glu Phe Cys Lys Asn Gly Thr Cys Gly Ala Cys |
| (SEQ ID NO: 7908) | Cys Glu Phe Cys Met Asn Pro Ala Cys Thr Gly Cys |
| (SEQ ID NO: 7909) | Cys Glu Phe Cys Met Asn Pro Ala Cys Thr Ala Cys |
| (SEQ ID NO: 7910) | Cys Glu Phe Cys Met Asn Pro Ala Cys Val Gly Cys |
| (SEQ ID NO: 7911) | Cys Glu Phe Cys Met Asn Pro Ala Cys Val Ala Cys |
| (SEQ ID NO: 7912) | Cys Glu Phe Cys Met Asn Pro Ala Cys Gly Gly Cys |
| (SEQ ID NO: 7913) | Cys Glu Phe Cys Met Asn Pro Ala Cys Gly Ala Cys |
| (SEQ ID NO: 7914) | Cys Glu Phe Cys Met Asn Pro Thr Cys Thr Gly Cys |
| (SEQ ID NO: 7915) | Cys Glu Phe Cys Met Asn Pro Thr Cys Thr Ala Cys |
| (SEQ ID NO: 7916) | Cys Glu Phe Cys Met Asn Pro Thr Cys Val Gly Cys |
| (SEQ ID NO: 7917) | Cys Glu Phe Cys Met Asn Pro Thr Cys Val Ala Cys |
| (SEQ ID NO: 7918) | Cys Glu Phe Cys Met Asn Pro Thr Cys Gly Gly Cys |
| (SEQ ID NO: 7919) | Cys Glu Phe Cys Met Asn Pro Thr Cys Gly Ala Cys |
| (SEQ ID NO: 7920) | Cys Glu Phe Cys Met Asn Gly Ala Cys Thr Gly Cys |
| (SEQ ID NO: 7921) | Cys Glu Phe Cys Met Asn Gly Ala Cys Thr Ala Cys |
| (SEQ ID NO: 7922) | Cys Glu Phe Cys Met Asn Gly Ala Cys Val Gly Cys |
| (SEQ ID NO: 7923) | Cys Glu Phe Cys Met Asn Gly Ala Cys Val Ala Cys |
| (SEQ ID NO: 7924) | Cys Glu Phe Cys Met Asn Gly Ala Cys Gly Gly Cys |
| (SEQ ID NO: 7925) | Cys Glu Phe Cys Met Asn Gly Ala Cys Gly Ala Cys |
| (SEQ ID NO: 7926) | Cys Glu Phe Cys Met Asn Gly Thr Cys Thr Gly Cys |
| (SEQ ID NO: 7927) | Cys Glu Phe Cys Met Asn Gly Thr Cys Thr Ala Cys |
| (SEQ ID NO: 7928) | Cys Glu Phe Cys Met Asn Gly Thr Cys Val Gly Cys |
| (SEQ ID NO: 7929) | Cys Glu Phe Cys Met Asn Gly Thr Cys Val Ala Cys |
| (SEQ ID NO: 7930) | Cys Glu Phe Cys Met Asn Gly Thr Cys Gly Gly Cys |
| (SEQ ID NO: 7931) | Cys Glu Phe Cys Met Asn Gly Thr Cys Gly Ala Cys |
| (SEQ ID NO: 7932) | Cys Glu Phe Cys Phe Asn Pro Ala Cys Thr Gly Cys |
| (SEQ ID NO: 7933) | Cys Glu Phe Cys Phe Asn Pro Ala Cys Thr Ala Cys |
| (SEQ ID NO: 7934) | Cys Glu Phe Cys Phe Asn Pro Ala Cys Val Gly Cys |
| (SEQ ID NO: 7935) | Cys Glu Phe Cys Phe Asn Pro Ala Cys Val Ala Cys |
| (SEQ ID NO: 7936) | Cys Glu Phe Cys Phe Asn Pro Ala Cys Gly Gly Cys |
| (SEQ ID NO: 7937) | Cys Glu Phe Cys Phe Asn Pro Ala Cys Gly Ala Cys |
| (SEQ ID NO: 7938) | Cys Glu Phe Cys Phe Asn Pro Thr Cys Thr Gly Cys |
| (SEQ ID NO: 7939) | Cys Glu Phe Cys Phe Asn Pro Thr Cys Thr Ala Cys |
| (SEQ ID NO: 7940) | Cys Glu Phe Cys Phe Asn Pro Thr Cys Val Gly Cys |
| (SEQ ID NO: 7941) | Cys Glu Phe Cys Phe Asn Pro Thr Cys Val Ala Cys |
| (SEQ ID NO: 7942) | Cys Glu Phe Cys Phe Asn Pro Thr Cys Gly Gly Cys |
| (SEQ ID NO: 7943) | Cys Glu Phe Cys Phe Asn Pro Thr Cys Gly Ala Cys |
| (SEQ ID NO: 7944) | Cys Glu Phe Cys Phe Asn Gly Ala Cys Thr Gly Cys |
| (SEQ ID NO: 7945) | Cys Glu Phe Cys Phe Asn Gly Ala Cys Thr Ala Cys |

FIG. 3BV

| | |
|---|---|
| (SEQ ID NO: 7946) | Cys Glu Phe Cys Phe Asn Gly Ala Cys Val Gly Cys |
| (SEQ ID NO: 7947) | Cys Glu Phe Cys Phe Asn Gly Ala Cys Val Ala Cys |
| (SEQ ID NO: 7948) | Cys Glu Phe Cys Phe Asn Gly Ala Cys Gly Gly Cys |
| (SEQ ID NO: 7949) | Cys Glu Phe Cys Phe Asn Gly Ala Cys Gly Ala Cys |
| (SEQ ID NO: 7950) | Cys Glu Phe Cys Phe Asn Gly Thr Cys Thr Gly Cys |
| (SEQ ID NO: 7951) | Cys Glu Phe Cys Phe Asn Gly Thr Cys Thr Ala Cys |
| (SEQ ID NO: 7952) | Cys Glu Phe Cys Phe Asn Gly Thr Cys Val Gly Cys |
| (SEQ ID NO: 7953) | Cys Glu Phe Cys Phe Asn Gly Thr Cys Val Ala Cys |
| (SEQ ID NO: 7954) | Cys Glu Phe Cys Phe Asn Gly Thr Cys Gly Gly Cys |
| (SEQ ID NO: 7955) | Cys Glu Phe Cys Phe Asn Gly Thr Cys Gly Ala Cys |
| (SEQ ID NO: 7956) | Cys Glu Phe Cys Pro Asn Pro Ala Cys Thr Gly Cys |
| (SEQ ID NO: 7957) | Cys Glu Phe Cys Pro Asn Pro Ala Cys Thr Ala Cys |
| (SEQ ID NO: 7958) | Cys Glu Phe Cys Pro Asn Pro Ala Cys Val Gly Cys |
| (SEQ ID NO: 7959) | Cys Glu Phe Cys Pro Asn Pro Ala Cys Val Ala Cys |
| (SEQ ID NO: 7960) | Cys Glu Phe Cys Pro Asn Pro Ala Cys Gly Gly Cys |
| (SEQ ID NO: 7961) | Cys Glu Phe Cys Pro Asn Pro Ala Cys Gly Ala Cys |
| (SEQ ID NO: 7962) | Cys Glu Phe Cys Pro Asn Pro Thr Cys Thr Gly Cys |
| (SEQ ID NO: 7963) | Cys Glu Phe Cys Pro Asn Pro Thr Cys Thr Ala Cys |
| (SEQ ID NO: 7964) | Cys Glu Phe Cys Pro Asn Pro Thr Cys Val Gly Cys |
| (SEQ ID NO: 7965) | Cys Glu Phe Cys Pro Asn Pro Thr Cys Val Ala Cys |
| (SEQ ID NO: 7966) | Cys Glu Phe Cys Pro Asn Pro Thr Cys Gly Gly Cys |
| (SEQ ID NO: 7967) | Cys Glu Phe Cys Pro Asn Pro Thr Cys Gly Ala Cys |
| (SEQ ID NO: 7968) | Cys Glu Phe Cys Pro Asn Gly Ala Cys Thr Gly Cys |
| (SEQ ID NO: 7969) | Cys Glu Phe Cys Pro Asn Gly Ala Cys Thr Ala Cys |
| (SEQ ID NO: 7970) | Cys Glu Phe Cys Pro Asn Gly Ala Cys Val Gly Cys |
| (SEQ ID NO: 7971) | Cys Glu Phe Cys Pro Asn Gly Ala Cys Val Ala Cys |
| (SEQ ID NO: 7972) | Cys Glu Phe Cys Pro Asn Gly Ala Cys Gly Gly Cys |
| (SEQ ID NO: 7973) | Cys Glu Phe Cys Pro Asn Gly Ala Cys Gly Ala Cys |
| (SEQ ID NO: 7974) | Cys Glu Phe Cys Pro Asn Gly Thr Cys Thr Gly Cys |
| (SEQ ID NO: 7975) | Cys Glu Phe Cys Pro Asn Gly Thr Cys Thr Ala Cys |
| (SEQ ID NO: 7976) | Cys Glu Phe Cys Pro Asn Gly Thr Cys Val Gly Cys |
| (SEQ ID NO: 7977) | Cys Glu Phe Cys Pro Asn Gly Thr Cys Val Ala Cys |
| (SEQ ID NO: 7978) | Cys Glu Phe Cys Pro Asn Gly Thr Cys Gly Gly Cys |
| (SEQ ID NO: 7979) | Cys Glu Phe Cys Pro Asn Gly Thr Cys Gly Ala Cys |
| (SEQ ID NO: 7980) | Cys Glu Phe Cys Ser Asn Pro Ala Cys Thr Gly Cys |
| (SEQ ID NO: 7981) | Cys Glu Phe Cys Ser Asn Pro Ala Cys Thr Ala Cys |
| (SEQ ID NO: 7982) | Cys Glu Phe Cys Ser Asn Pro Ala Cys Val Gly Cys |
| (SEQ ID NO: 7983) | Cys Glu Phe Cys Ser Asn Pro Ala Cys Val Ala Cys |
| (SEQ ID NO: 7984) | Cys Glu Phe Cys Ser Asn Pro Ala Cys Gly Gly Cys |
| (SEQ ID NO: 7985) | Cys Glu Phe Cys Ser Asn Pro Ala Cys Gly Ala Cys |
| (SEQ ID NO: 7986) | Cys Glu Phe Cys Ser Asn Pro Thr Cys Thr Gly Cys |
| (SEQ ID NO: 7987) | Cys Glu Phe Cys Ser Asn Pro Thr Cys Thr Ala Cys |
| (SEQ ID NO: 7988) | Cys Glu Phe Cys Ser Asn Pro Thr Cys Val Gly Cys |

FIG. 3BW

| SEQ ID NO | | | | | | | | | | |
|---|---|---|---|---|---|---|---|---|---|---|
| (SEQ ID NO: 7989) | Cys | Glu | Phe | Cys | Ser | Asn | Pro | Thr | Cys | Val | Ala | Cys |
| (SEQ ID NO: 7990) | Cys | Glu | Phe | Cys | Ser | Asn | Pro | Thr | Cys | Gly | Gly | Cys |
| (SEQ ID NO: 7991) | Cys | Glu | Phe | Cys | Ser | Asn | Pro | Thr | Cys | Gly | Ala | Cys |
| (SEQ ID NO: 7992) | Cys | Glu | Phe | Cys | Ser | Asn | Gly | Ala | Cys | Thr | Gly | Cys |
| (SEQ ID NO: 7993) | Cys | Glu | Phe | Cys | Ser | Asn | Gly | Ala | Cys | Thr | Ala | Cys |
| (SEQ ID NO: 7994) | Cys | Glu | Phe | Cys | Ser | Asn | Gly | Ala | Cys | Val | Gly | Cys |
| (SEQ ID NO: 7995) | Cys | Glu | Phe | Cys | Ser | Asn | Gly | Ala | Cys | Val | Ala | Cys |
| (SEQ ID NO: 7996) | Cys | Glu | Phe | Cys | Ser | Asn | Gly | Ala | Cys | Gly | Gly | Cys |
| (SEQ ID NO: 7997) | Cys | Glu | Phe | Cys | Ser | Asn | Gly | Ala | Cys | Gly | Ala | Cys |
| (SEQ ID NO: 7998) | Cys | Glu | Phe | Cys | Ser | Asn | Gly | Thr | Cys | Thr | Gly | Cys |
| (SEQ ID NO: 7999) | Cys | Glu | Phe | Cys | Ser | Asn | Gly | Thr | Cys | Thr | Ala | Cys |
| (SEQ ID NO: 8000) | Cys | Glu | Phe | Cys | Ser | Asn | Gly | Thr | Cys | Val | Gly | Cys |
| (SEQ ID NO: 8001) | Cys | Glu | Phe | Cys | Ser | Asn | Gly | Thr | Cys | Val | Ala | Cys |
| (SEQ ID NO: 8002) | Cys | Glu | Phe | Cys | Ser | Asn | Gly | Thr | Cys | Gly | Gly | Cys |
| (SEQ ID NO: 8003) | Cys | Glu | Phe | Cys | Ser | Asn | Gly | Thr | Cys | Gly | Ala | Cys |
| (SEQ ID NO: 8004) | Cys | Glu | Phe | Cys | Thr | Asn | Pro | Ala | Cys | Thr | Gly | Cys |
| (SEQ ID NO: 8005) | Cys | Glu | Phe | Cys | Thr | Asn | Pro | Ala | Cys | Thr | Ala | Cys |
| (SEQ ID NO: 8006) | Cys | Glu | Phe | Cys | Thr | Asn | Pro | Ala | Cys | Val | Gly | Cys |
| (SEQ ID NO: 8007) | Cys | Glu | Phe | Cys | Thr | Asn | Pro | Ala | Cys | Val | Ala | Cys |
| (SEQ ID NO: 8008) | Cys | Glu | Phe | Cys | Thr | Asn | Pro | Ala | Cys | Gly | Gly | Cys |
| (SEQ ID NO: 8009) | Cys | Glu | Phe | Cys | Thr | Asn | Pro | Ala | Cys | Gly | Ala | Cys |
| (SEQ ID NO: 8010) | Cys | Glu | Phe | Cys | Thr | Asn | Pro | Thr | Cys | Thr | Gly | Cys |
| (SEQ ID NO: 8011) | Cys | Glu | Phe | Cys | Thr | Asn | Pro | Thr | Cys | Thr | Ala | Cys |
| (SEQ ID NO: 8012) | Cys | Glu | Phe | Cys | Thr | Asn | Pro | Thr | Cys | Val | Gly | Cys |
| (SEQ ID NO: 8013) | Cys | Glu | Phe | Cys | Thr | Asn | Pro | Thr | Cys | Val | Ala | Cys |
| (SEQ ID NO: 8014) | Cys | Glu | Phe | Cys | Thr | Asn | Pro | Thr | Cys | Gly | Gly | Cys |
| (SEQ ID NO: 8015) | Cys | Glu | Phe | Cys | Thr | Asn | Pro | Thr | Cys | Gly | Ala | Cys |
| (SEQ ID NO: 8016) | Cys | Glu | Phe | Cys | Thr | Asn | Gly | Ala | Cys | Thr | Gly | Cys |
| (SEQ ID NO: 8017) | Cys | Glu | Phe | Cys | Thr | Asn | Gly | Ala | Cys | Thr | Ala | Cys |
| (SEQ ID NO: 8018) | Cys | Glu | Phe | Cys | Thr | Asn | Gly | Ala | Cys | Val | Gly | Cys |
| (SEQ ID NO: 8019) | Cys | Glu | Phe | Cys | Thr | Asn | Gly | Ala | Cys | Val | Ala | Cys |
| (SEQ ID NO: 8020) | Cys | Glu | Phe | Cys | Thr | Asn | Gly | Ala | Cys | Gly | Gly | Cys |
| (SEQ ID NO: 8021) | Cys | Glu | Phe | Cys | Thr | Asn | Gly | Ala | Cys | Gly | Ala | Cys |
| (SEQ ID NO: 8022) | Cys | Glu | Phe | Cys | Thr | Asn | Gly | Thr | Cys | Thr | Gly | Cys |
| (SEQ ID NO: 8023) | Cys | Glu | Phe | Cys | Thr | Asn | Gly | Thr | Cys | Thr | Ala | Cys |
| (SEQ ID NO: 8024) | Cys | Glu | Phe | Cys | Thr | Asn | Gly | Thr | Cys | Val | Gly | Cys |
| (SEQ ID NO: 8025) | Cys | Glu | Phe | Cys | Thr | Asn | Gly | Thr | Cys | Val | Ala | Cys |
| (SEQ ID NO: 8026) | Cys | Glu | Phe | Cys | Thr | Asn | Gly | Thr | Cys | Gly | Gly | Cys |
| (SEQ ID NO: 8027) | Cys | Glu | Phe | Cys | Thr | Asn | Gly | Thr | Cys | Gly | Ala | Cys |
| (SEQ ID NO: 8028) | Cys | Glu | Phe | Cys | Trp | Asn | Pro | Ala | Cys | Thr | Gly | Cys |
| (SEQ ID NO: 8029) | Cys | Glu | Phe | Cys | Trp | Asn | Pro | Ala | Cys | Thr | Ala | Cys |
| (SEQ ID NO: 8030) | Cys | Glu | Phe | Cys | Trp | Asn | Pro | Ala | Cys | Val | Gly | Cys |
| (SEQ ID NO: 8031) | Cys | Glu | Phe | Cys | Trp | Asn | Pro | Ala | Cys | Val | Ala | Cys |

FIG. 3BX

| | |
|---|---|
| (SEQ ID NO: 8032) | Cys Glu Phe Cys Trp Asn Pro Ala Cys Gly Gly Cys |
| (SEQ ID NO: 8033) | Cys Glu Phe Cys Trp Asn Pro Ala Cys Gly Ala Cys |
| (SEQ ID NO: 8034) | Cys Glu Phe Cys Trp Asn Pro Thr Cys Thr Gly Cys |
| (SEQ ID NO: 8035) | Cys Glu Phe Cys Trp Asn Pro Thr Cys Thr Ala Cys |
| (SEQ ID NO: 8036) | Cys Glu Phe Cys Trp Asn Pro Thr Cys Val Gly Cys |
| (SEQ ID NO: 8037) | Cys Glu Phe Cys Trp Asn Pro Thr Cys Val Ala Cys |
| (SEQ ID NO: 8038) | Cys Glu Phe Cys Trp Asn Pro Thr Cys Gly Gly Cys |
| (SEQ ID NO: 8039) | Cys Glu Phe Cys Trp Asn Pro Thr Cys Gly Ala Cys |
| (SEQ ID NO: 8040) | Cys Glu Phe Cys Trp Asn Gly Ala Cys Thr Gly Cys |
| (SEQ ID NO: 8041) | Cys Glu Phe Cys Trp Asn Gly Ala Cys Thr Ala Cys |
| (SEQ ID NO: 8042) | Cys Glu Phe Cys Trp Asn Gly Ala Cys Val Gly Cys |
| (SEQ ID NO: 8043) | Cys Glu Phe Cys Trp Asn Gly Ala Cys Val Ala Cys |
| (SEQ ID NO: 8044) | Cys Glu Phe Cys Trp Asn Gly Ala Cys Gly Gly Cys |
| (SEQ ID NO: 8045) | Cys Glu Phe Cys Trp Asn Gly Ala Cys Gly Ala Cys |
| (SEQ ID NO: 8046) | Cys Glu Phe Cys Trp Asn Gly Thr Cys Thr Gly Cys |
| (SEQ ID NO: 8047) | Cys Glu Phe Cys Trp Asn Gly Thr Cys Thr Ala Cys |
| (SEQ ID NO: 8048) | Cys Glu Phe Cys Trp Asn Gly Thr Cys Val Gly Cys |
| (SEQ ID NO: 8049) | Cys Glu Phe Cys Trp Asn Gly Thr Cys Val Ala Cys |
| (SEQ ID NO: 8050) | Cys Glu Phe Cys Trp Asn Gly Thr Cys Gly Gly Cys |
| (SEQ ID NO: 8051) | Cys Glu Phe Cys Trp Asn Gly Thr Cys Gly Ala Cys |
| (SEQ ID NO: 8052) | Cys Glu Phe Cys Tyr Asn Pro Ala Cys Thr Gly Cys |
| (SEQ ID NO: 8053) | Cys Glu Phe Cys Tyr Asn Pro Ala Cys Thr Ala Cys |
| (SEQ ID NO: 8054) | Cys Glu Phe Cys Tyr Asn Pro Ala Cys Val Gly Cys |
| (SEQ ID NO: 8055) | Cys Glu Phe Cys Tyr Asn Pro Ala Cys Val Ala Cys |
| (SEQ ID NO: 8056) | Cys Glu Phe Cys Tyr Asn Pro Ala Cys Gly Gly Cys |
| (SEQ ID NO: 8057) | Cys Glu Phe Cys Tyr Asn Pro Ala Cys Gly Ala Cys |
| (SEQ ID NO: 8058) | Cys Glu Phe Cys Tyr Asn Pro Thr Cys Thr Gly Cys |
| (SEQ ID NO: 8059) | Cys Glu Phe Cys Tyr Asn Pro Thr Cys Thr Ala Cys |
| (SEQ ID NO: 8060) | Cys Glu Phe Cys Tyr Asn Pro Thr Cys Val Gly Cys |
| (SEQ ID NO: 8061) | Cys Glu Phe Cys Tyr Asn Pro Thr Cys Val Ala Cys |
| (SEQ ID NO: 8062) | Cys Glu Phe Cys Tyr Asn Pro Thr Cys Gly Gly Cys |
| (SEQ ID NO: 8063) | Cys Glu Phe Cys Tyr Asn Pro Thr Cys Gly Ala Cys |
| (SEQ ID NO: 8064) | Cys Glu Phe Cys Tyr Asn Gly Ala Cys Thr Gly Cys |
| (SEQ ID NO: 8065) | Cys Glu Phe Cys Tyr Asn Gly Ala Cys Thr Ala Cys |
| (SEQ ID NO: 8066) | Cys Glu Phe Cys Tyr Asn Gly Ala Cys Val Gly Cys |
| (SEQ ID NO: 8067) | Cys Glu Phe Cys Tyr Asn Gly Ala Cys Val Ala Cys |
| (SEQ ID NO: 8068) | Cys Glu Phe Cys Tyr Asn Gly Ala Cys Gly Gly Cys |
| (SEQ ID NO: 8069) | Cys Glu Phe Cys Tyr Asn Gly Ala Cys Gly Ala Cys |
| (SEQ ID NO: 8070) | Cys Glu Phe Cys Tyr Asn Gly Thr Cys Thr Gly Cys |
| (SEQ ID NO: 8071) | Cys Glu Phe Cys Tyr Asn Gly Thr Cys Thr Ala Cys |
| (SEQ ID NO: 8072) | Cys Glu Phe Cys Tyr Asn Gly Thr Cys Val Gly Cys |
| (SEQ ID NO: 8073) | Cys Glu Phe Cys Tyr Asn Gly Thr Cys Val Ala Cys |
| (SEQ ID NO: 8074) | Cys Glu Phe Cys Tyr Asn Gly Thr Cys Gly Gly Cys |

FIG. 3BY (SEQ ID NO: 8075)  Cys Glu Phe Cys Tyr Asn Gly Thr Cys Gly Ala Cys
(SEQ ID NO: 8076)  Cys Glu Phe Cys Val Asn Pro Ala Cys Thr Gly Cys
(SEQ ID NO: 8077)  Cys Glu Phe Cys Val Asn Pro Ala Cys Thr Ala Cys
(SEQ ID NO: 8078)  Cys Glu Phe Cys Val Asn Pro Ala Cys Val Gly Cys
(SEQ ID NO: 8079)  Cys Glu Phe Cys Val Asn Pro Ala Cys Val Ala Cys
(SEQ ID NO: 8080)  Cys Glu Phe Cys Val Asn Pro Ala Cys Gly Gly Cys
(SEQ ID NO: 8081)  Cys Glu Phe Cys Val Asn Pro Ala Cys Gly Ala Cys
(SEQ ID NO: 8082)  Cys Glu Phe Cys Val Asn Pro Thr Cys Thr Gly Cys
(SEQ ID NO: 8083)  Cys Glu Phe Cys Val Asn Pro Thr Cys Thr Ala Cys
(SEQ ID NO: 8084)  Cys Glu Phe Cys Val Asn Pro Thr Cys Val Gly Cys
(SEQ ID NO: 8085)  Cys Glu Phe Cys Val Asn Pro Thr Cys Val Ala Cys
(SEQ ID NO: 8086)  Cys Glu Phe Cys Val Asn Pro Thr Cys Gly Gly Cys
(SEQ ID NO: 8087)  Cys Glu Phe Cys Val Asn Pro Thr Cys Gly Ala Cys
(SEQ ID NO: 8088)  Cys Glu Phe Cys Val Asn Gly Ala Cys Thr Gly Cys
(SEQ ID NO: 8089)  Cys Glu Phe Cys Val Asn Gly Ala Cys Thr Ala Cys
(SEQ ID NO: 8090)  Cys Glu Phe Cys Val Asn Gly Ala Cys Val Gly Cys
(SEQ ID NO: 8091)  Cys Glu Phe Cys Val Asn Gly Ala Cys Val Ala Cys
(SEQ ID NO: 8092)  Cys Glu Phe Cys Val Asn Gly Ala Cys Gly Gly Cys
(SEQ ID NO: 8093)  Cys Glu Phe Cys Val Asn Gly Ala Cys Gly Ala Cys
(SEQ ID NO: 8094)  Cys Glu Phe Cys Val Asn Gly Thr Cys Thr Gly Cys
(SEQ ID NO: 8095)  Cys Glu Phe Cys Val Asn Gly Thr Cys Thr Ala Cys
(SEQ ID NO: 8096)  Cys Glu Phe Cys Val Asn Gly Thr Cys Val Gly Cys
(SEQ ID NO: 8097)  Cys Glu Phe Cys Val Asn Gly Thr Cys Val Ala Cys
(SEQ ID NO: 8098)  Cys Glu Phe Cys Val Asn Gly Thr Cys Gly Gly Cys
(SEQ ID NO: 8099)  Cys Glu Phe Cys Val Asn Gly Thr Cys Gly Ala Cys
(SEQ ID NO: 8100)  Cys Glu Phe Cys --- Asn Pro Ala Cys Thr Gly Cys
(SEQ ID NO: 8101)  Cys Glu Phe Cys --- Asn Pro Ala Cys Thr Ala Cys
(SEQ ID NO: 8102)  Cys Glu Phe Cys --- Asn Pro Ala Cys Val Gly Cys
(SEQ ID NO: 8103)  Cys Glu Phe Cys --- Asn Pro Ala Cys Val Ala Cys
(SEQ ID NO: 8104)  Cys Glu Phe Cys --- Asn Pro Ala Cys Gly Gly Cys
(SEQ ID NO: 8105)  Cys Glu Phe Cys --- Asn Pro Ala Cys Gly Ala Cys
(SEQ ID NO: 8106)  Cys Glu Phe Cys --- Asn Pro Thr Cys Thr Gly Cys
(SEQ ID NO: 8107)  Cys Glu Phe Cys --- Asn Pro Thr Cys Thr Ala Cys
(SEQ ID NO: 8108)  Cys Glu Phe Cys --- Asn Pro Thr Cys Val Gly Cys
(SEQ ID NO: 8109)  Cys Glu Phe Cys --- Asn Pro Thr Cys Val Ala Cys
(SEQ ID NO: 8110)  Cys Glu Phe Cys --- Asn Pro Thr Cys Gly Gly Cys
(SEQ ID NO: 8111)  Cys Glu Phe Cys --- Asn Pro Thr Cys Gly Ala Cys
(SEQ ID NO: 8112)  Cys Glu Phe Cys --- Asn Gly Ala Cys Thr Gly Cys
(SEQ ID NO: 8113)  Cys Glu Phe Cys --- Asn Gly Ala Cys Thr Ala Cys
(SEQ ID NO: 8114)  Cys Glu Phe Cys --- Asn Gly Ala Cys Val Gly Cys
(SEQ ID NO: 8115)  Cys Glu Phe Cys --- Asn Gly Ala Cys Val Ala Cys
(SEQ ID NO: 8116)  Cys Glu Phe Cys --- Asn Gly Ala Cys Gly Gly Cys
(SEQ ID NO: 8117)  Cys Glu Phe Cys --- Asn Gly Ala Cys Gly Ala Cys

FIG. 3BZ

| SEQ ID NO | Sequence |
|---|---|
| (SEQ ID NO: 8118) | Cys Glu Phe Cys --- Asn Gly Thr Cys Thr Gly Cys |
| (SEQ ID NO: 8119) | Cys Glu Phe Cys --- Asn Gly Thr Cys Thr Ala Cys |
| (SEQ ID NO: 8120) | Cys Glu Phe Cys --- Asn Gly Thr Cys Val Gly Cys |
| (SEQ ID NO: 8121) | Cys Glu Phe Cys --- Asn Gly Thr Cys Val Ala Cys |
| (SEQ ID NO: 8122) | Cys Glu Phe Cys --- Asn Gly Thr Cys Gly Gly Cys |
| (SEQ ID NO: 8123) | Cys Glu Phe Cys --- Asn Gly Thr Cys Gly Ala Cys |
| (SEQ ID NO: 8124) | Cys Glu Leu Cys Ala Asn Pro Ala Cys Thr Gly Cys |
| (SEQ ID NO: 8125) | Cys Glu Leu Cys Ala Asn Pro Ala Cys Thr Ala Cys |
| (SEQ ID NO: 8126) | Cys Glu Leu Cys Ala Asn Pro Ala Cys Val Gly Cys |
| (SEQ ID NO: 8127) | Cys Glu Leu Cys Ala Asn Pro Ala Cys Val Ala Cys |
| (SEQ ID NO: 8128) | Cys Glu Leu Cys Ala Asn Pro Ala Cys Gly Gly Cys |
| (SEQ ID NO: 8129) | Cys Glu Leu Cys Ala Asn Pro Ala Cys Gly Ala Cys |
| (SEQ ID NO: 8130) | Cys Glu Leu Cys Ala Asn Pro Thr Cys Thr Gly Cys |
| (SEQ ID NO: 8131) | Cys Glu Leu Cys Ala Asn Pro Thr Cys Thr Ala Cys |
| (SEQ ID NO: 8132) | Cys Glu Leu Cys Ala Asn Pro Thr Cys Val Gly Cys |
| (SEQ ID NO: 8133) | Cys Glu Leu Cys Ala Asn Pro Thr Cys Val Ala Cys |
| (SEQ ID NO: 8134) | Cys Glu Leu Cys Ala Asn Pro Thr Cys Gly Gly Cys |
| (SEQ ID NO: 8135) | Cys Glu Leu Cys Ala Asn Pro Thr Cys Gly Ala Cys |
| (SEQ ID NO: 8136) | Cys Glu Leu Cys Ala Asn Gly Ala Cys Thr Gly Cys |
| (SEQ ID NO: 8137) | Cys Glu Leu Cys Ala Asn Gly Ala Cys Thr Ala Cys |
| (SEQ ID NO: 8138) | Cys Glu Leu Cys Ala Asn Gly Ala Cys Val Gly Cys |
| (SEQ ID NO: 8139) | Cys Glu Leu Cys Ala Asn Gly Ala Cys Val Ala Cys |
| (SEQ ID NO: 8140) | Cys Glu Leu Cys Ala Asn Gly Ala Cys Gly Gly Cys |
| (SEQ ID NO: 8141) | Cys Glu Leu Cys Ala Asn Gly Ala Cys Gly Ala Cys |
| (SEQ ID NO: 8142) | Cys Glu Leu Cys Ala Asn Gly Thr Cys Thr Gly Cys |
| (SEQ ID NO: 8143) | Cys Glu Leu Cys Ala Asn Gly Thr Cys Thr Ala Cys |
| (SEQ ID NO: 8144) | Cys Glu Leu Cys Ala Asn Gly Thr Cys Val Gly Cys |
| (SEQ ID NO: 8145) | Cys Glu Leu Cys Ala Asn Gly Thr Cys Val Ala Cys |
| (SEQ ID NO: 8146) | Cys Glu Leu Cys Ala Asn Gly Thr Cys Gly Gly Cys |
| (SEQ ID NO: 8147) | Cys Glu Leu Cys Ala Asn Gly Thr Cys Gly Ala Cys |
| (SEQ ID NO: 8148) | Cys Glu Leu Cys Arg Asn Pro Ala Cys Thr Gly Cys |
| (SEQ ID NO: 8149) | Cys Glu Leu Cys Arg Asn Pro Ala Cys Thr Ala Cys |
| (SEQ ID NO: 8150) | Cys Glu Leu Cys Arg Asn Pro Ala Cys Val Gly Cys |
| (SEQ ID NO: 8151) | Cys Glu Leu Cys Arg Asn Pro Ala Cys Val Ala Cys |
| (SEQ ID NO: 8152) | Cys Glu Leu Cys Arg Asn Pro Ala Cys Gly Gly Cys |
| (SEQ ID NO: 8153) | Cys Glu Leu Cys Arg Asn Pro Ala Cys Gly Ala Cys |
| (SEQ ID NO: 8154) | Cys Glu Leu Cys Arg Asn Pro Thr Cys Thr Gly Cys |
| (SEQ ID NO: 8155) | Cys Glu Leu Cys Arg Asn Pro Thr Cys Thr Ala Cys |
| (SEQ ID NO: 8156) | Cys Glu Leu Cys Arg Asn Pro Thr Cys Val Gly Cys |
| (SEQ ID NO: 8157) | Cys Glu Leu Cys Arg Asn Pro Thr Cys Val Ala Cys |
| (SEQ ID NO: 8158) | Cys Glu Leu Cys Arg Asn Pro Thr Cys Gly Gly Cys |
| (SEQ ID NO: 8159) | Cys Glu Leu Cys Arg Asn Pro Thr Cys Gly Ala Cys |
| (SEQ ID NO: 8160) | Cys Glu Leu Cys Arg Asn Gly Ala Cys Thr Gly Cys |

FIG. 3CA

| SEQ ID NO | Sequence |
|---|---|
| (SEQ ID NO: 8161) | Cys Glu Leu Cys Arg Asn Gly Ala Cys Thr Ala Cys |
| (SEQ ID NO: 8162) | Cys Glu Leu Cys Arg Asn Gly Ala Cys Val Gly Cys |
| (SEQ ID NO: 8163) | Cys Glu Leu Cys Arg Asn Gly Ala Cys Val Ala Cys |
| (SEQ ID NO: 8164) | Cys Glu Leu Cys Arg Asn Gly Ala Cys Gly Gly Cys |
| (SEQ ID NO: 8165) | Cys Glu Leu Cys Arg Asn Gly Ala Cys Gly Ala Cys |
| (SEQ ID NO: 8166) | Cys Glu Leu Cys Arg Asn Gly Thr Cys Thr Gly Cys |
| (SEQ ID NO: 8167) | Cys Glu Leu Cys Arg Asn Gly Thr Cys Thr Ala Cys |
| (SEQ ID NO: 8168) | Cys Glu Leu Cys Arg Asn Gly Thr Cys Val Gly Cys |
| (SEQ ID NO: 8169) | Cys Glu Leu Cys Arg Asn Gly Thr Cys Val Ala Cys |
| (SEQ ID NO: 8170) | Cys Glu Leu Cys Arg Asn Gly Thr Cys Gly Gly Cys |
| (SEQ ID NO: 8171) | Cys Glu Leu Cys Arg Asn Gly Thr Cys Gly Ala Cys |
| (SEQ ID NO: 8172) | Cys Glu Leu Cys Asn Asn Pro Ala Cys Thr Gly Cys |
| (SEQ ID NO: 8173) | Cys Glu Leu Cys Asn Asn Pro Ala Cys Thr Ala Cys |
| (SEQ ID NO: 8174) | Cys Glu Leu Cys Asn Asn Pro Ala Cys Val Gly Cys |
| (SEQ ID NO: 8175) | Cys Glu Leu Cys Asn Asn Pro Ala Cys Val Ala Cys |
| (SEQ ID NO: 8176) | Cys Glu Leu Cys Asn Asn Pro Ala Cys Gly Gly Cys |
| (SEQ ID NO: 8177) | Cys Glu Leu Cys Asn Asn Pro Ala Cys Gly Ala Cys |
| (SEQ ID NO: 8178) | Cys Glu Leu Cys Asn Asn Pro Thr Cys Thr Gly Cys |
| (SEQ ID NO: 8179) | Cys Glu Leu Cys Asn Asn Pro Thr Cys Thr Ala Cys |
| (SEQ ID NO: 8180) | Cys Glu Leu Cys Asn Asn Pro Thr Cys Val Gly Cys |
| (SEQ ID NO: 8181) | Cys Glu Leu Cys Asn Asn Pro Thr Cys Val Ala Cys |
| (SEQ ID NO: 8182) | Cys Glu Leu Cys Asn Asn Pro Thr Cys Gly Gly Cys |
| (SEQ ID NO: 8183) | Cys Glu Leu Cys Asn Asn Pro Thr Cys Gly Ala Cys |
| (SEQ ID NO: 8184) | Cys Glu Leu Cys Asn Asn Gly Ala Cys Thr Gly Cys |
| (SEQ ID NO: 8185) | Cys Glu Leu Cys Asn Asn Gly Ala Cys Thr Ala Cys |
| (SEQ ID NO: 8186) | Cys Glu Leu Cys Asn Asn Gly Ala Cys Val Gly Cys |
| (SEQ ID NO: 8187) | Cys Glu Leu Cys Asn Asn Gly Ala Cys Val Ala Cys |
| (SEQ ID NO: 8188) | Cys Glu Leu Cys Asn Asn Gly Ala Cys Gly Gly Cys |
| (SEQ ID NO: 8189) | Cys Glu Leu Cys Asn Asn Gly Ala Cys Gly Ala Cys |
| (SEQ ID NO: 8190) | Cys Glu Leu Cys Asn Asn Gly Thr Cys Thr Gly Cys |
| (SEQ ID NO: 8191) | Cys Glu Leu Cys Asn Asn Gly Thr Cys Thr Ala Cys |
| (SEQ ID NO: 8192) | Cys Glu Leu Cys Asn Asn Gly Thr Cys Val Gly Cys |
| (SEQ ID NO: 8193) | Cys Glu Leu Cys Asn Asn Gly Thr Cys Val Ala Cys |
| (SEQ ID NO: 8194) | Cys Glu Leu Cys Asn Asn Gly Thr Cys Gly Gly Cys |
| (SEQ ID NO: 8195) | Cys Glu Leu Cys Asn Asn Gly Thr Cys Gly Ala Cys |
| (SEQ ID NO: 8196) | Cys Glu Leu Cys Asp Asn Pro Ala Cys Thr Gly Cys |
| (SEQ ID NO: 8197) | Cys Glu Leu Cys Asp Asn Pro Ala Cys Thr Ala Cys |
| (SEQ ID NO: 8198) | Cys Glu Leu Cys Asp Asn Pro Ala Cys Val Gly Cys |
| (SEQ ID NO: 8199) | Cys Glu Leu Cys Asp Asn Pro Ala Cys Val Ala Cys |
| (SEQ ID NO: 8200) | Cys Glu Leu Cys Asp Asn Pro Ala Cys Gly Gly Cys |
| (SEQ ID NO: 8201) | Cys Glu Leu Cys Asp Asn Pro Ala Cys Gly Ala Cys |
| (SEQ ID NO: 8202) | Cys Glu Leu Cys Asp Asn Pro Thr Cys Thr Gly Cys |
| (SEQ ID NO: 8203) | Cys Glu Leu Cys Asp Asn Pro Thr Cys Thr Ala Cys |

FIG. 3CB

| | |
|---|---|
| (SEQ ID NO: 8204 ) | Cys Glu Leu Cys Asp Asn Pro Thr Cys Val Gly Cys |
| (SEQ ID NO: 8205 ) | Cys Glu Leu Cys Asp Asn Pro Thr Cys Val Ala Cys |
| (SEQ ID NO: 8206 ) | Cys Glu Leu Cys Asp Asn Pro Thr Cys Gly Gly Cys |
| (SEQ ID NO: 8207 ) | Cys Glu Leu Cys Asp Asn Pro Thr Cys Gly Ala Cys |
| (SEQ ID NO: 8208 ) | Cys Glu Leu Cys Asp Asn Gly Ala Cys Thr Gly Cys |
| (SEQ ID NO: 8209 ) | Cys Glu Leu Cys Asp Asn Gly Ala Cys Thr Ala Cys |
| (SEQ ID NO: 8210 ) | Cys Glu Leu Cys Asp Asn Gly Ala Cys Val Gly Cys |
| (SEQ ID NO: 8211 ) | Cys Glu Leu Cys Asp Asn Gly Ala Cys Val Ala Cys |
| (SEQ ID NO: 8212 ) | Cys Glu Leu Cys Asp Asn Gly Ala Cys Gly Gly Cys |
| (SEQ ID NO: 8213 ) | Cys Glu Leu Cys Asp Asn Gly Ala Cys Gly Ala Cys |
| (SEQ ID NO: 8214 ) | Cys Glu Leu Cys Asp Asn Gly Thr Cys Thr Gly Cys |
| (SEQ ID NO: 8215 ) | Cys Glu Leu Cys Asp Asn Gly Thr Cys Thr Ala Cys |
| (SEQ ID NO: 8216 ) | Cys Glu Leu Cys Asp Asn Gly Thr Cys Val Gly Cys |
| (SEQ ID NO: 8217 ) | Cys Glu Leu Cys Asp Asn Gly Thr Cys Val Ala Cys |
| (SEQ ID NO: 8218 ) | Cys Glu Leu Cys Asp Asn Gly Thr Cys Gly Gly Cys |
| (SEQ ID NO: 8219 ) | Cys Glu Leu Cys Asp Asn Gly Thr Cys Gly Ala Cys |
| (SEQ ID NO: 8220 ) | Cys Glu Leu Cys Gln Asn Pro Ala Cys Thr Gly Cys |
| (SEQ ID NO: 8221 ) | Cys Glu Leu Cys Gln Asn Pro Ala Cys Thr Ala Cys |
| (SEQ ID NO: 8222 ) | Cys Glu Leu Cys Gln Asn Pro Ala Cys Val Gly Cys |
| (SEQ ID NO: 8223 ) | Cys Glu Leu Cys Gln Asn Pro Ala Cys Val Ala Cys |
| (SEQ ID NO: 8224 ) | Cys Glu Leu Cys Gln Asn Pro Ala Cys Gly Gly Cys |
| (SEQ ID NO: 8225 ) | Cys Glu Leu Cys Gln Asn Pro Ala Cys Gly Ala Cys |
| (SEQ ID NO: 8226 ) | Cys Glu Leu Cys Gln Asn Pro Thr Cys Thr Gly Cys |
| (SEQ ID NO: 8227 ) | Cys Glu Leu Cys Gln Asn Pro Thr Cys Thr Ala Cys |
| (SEQ ID NO: 8228 ) | Cys Glu Leu Cys Gln Asn Pro Thr Cys Val Gly Cys |
| (SEQ ID NO: 8229 ) | Cys Glu Leu Cys Gln Asn Pro Thr Cys Val Ala Cys |
| (SEQ ID NO: 8230 ) | Cys Glu Leu Cys Gln Asn Pro Thr Cys Gly Gly Cys |
| (SEQ ID NO: 8231 ) | Cys Glu Leu Cys Gln Asn Pro Thr Cys Gly Ala Cys |
| (SEQ ID NO: 8232 ) | Cys Glu Leu Cys Gln Asn Gly Ala Cys Thr Gly Cys |
| (SEQ ID NO: 8233 ) | Cys Glu Leu Cys Gln Asn Gly Ala Cys Thr Ala Cys |
| (SEQ ID NO: 8234 ) | Cys Glu Leu Cys Gln Asn Gly Ala Cys Val Gly Cys |
| (SEQ ID NO: 8235 ) | Cys Glu Leu Cys Gln Asn Gly Ala Cys Val Ala Cys |
| (SEQ ID NO: 8236 ) | Cys Glu Leu Cys Gln Asn Gly Ala Cys Gly Gly Cys |
| (SEQ ID NO: 8237 ) | Cys Glu Leu Cys Gln Asn Gly Ala Cys Gly Ala Cys |
| (SEQ ID NO: 8238 ) | Cys Glu Leu Cys Gln Asn Gly Thr Cys Thr Gly Cys |
| (SEQ ID NO: 8239 ) | Cys Glu Leu Cys Gln Asn Gly Thr Cys Thr Ala Cys |
| (SEQ ID NO: 8240 ) | Cys Glu Leu Cys Gln Asn Gly Thr Cys Val Gly Cys |
| (SEQ ID NO: 8241 ) | Cys Glu Leu Cys Gln Asn Gly Thr Cys Val Ala Cys |
| (SEQ ID NO: 8242 ) | Cys Glu Leu Cys Gln Asn Gly Thr Cys Gly Gly Cys |
| (SEQ ID NO: 8243 ) | Cys Glu Leu Cys Gln Asn Gly Thr Cys Gly Ala Cys |
| (SEQ ID NO: 8244 ) | Cys Glu Leu Cys Glu Asn Pro Ala Cys Thr Gly Cys |
| (SEQ ID NO: 8245 ) | Cys Glu Leu Cys Glu Asn Pro Ala Cys Thr Ala Cys |
| (SEQ ID NO: 8246 ) | Cys Glu Leu Cys Glu Asn Pro Ala Cys Val Gly Cys |

FIG. 3CC

| | |
|---|---|
| (SEQ ID NO: 8247) | Cys Glu Leu Cys Glu Asn Pro Ala Cys Val Ala Cys |
| (SEQ ID NO: 8248) | Cys Glu Leu Cys Glu Asn Pro Ala Cys Gly Gly Cys |
| (SEQ ID NO: 8249) | Cys Glu Leu Cys Glu Asn Pro Ala Cys Gly Ala Cys |
| (SEQ ID NO: 8250) | Cys Glu Leu Cys Glu Asn Pro Thr Cys Thr Gly Cys |
| (SEQ ID NO: 8251) | Cys Glu Leu Cys Glu Asn Pro Thr Cys Thr Ala Cys |
| (SEQ ID NO: 8252) | Cys Glu Leu Cys Glu Asn Pro Thr Cys Val Gly Cys |
| (SEQ ID NO: 8253) | Cys Glu Leu Cys Glu Asn Pro Thr Cys Val Ala Cys |
| (SEQ ID NO: 8254) | Cys Glu Leu Cys Glu Asn Pro Thr Cys Gly Gly Cys |
| (SEQ ID NO: 8255) | Cys Glu Leu Cys Glu Asn Pro Thr Cys Gly Ala Cys |
| (SEQ ID NO: 8256) | Cys Glu Leu Cys Glu Asn Gly Ala Cys Thr Gly Cys |
| (SEQ ID NO: 8257) | Cys Glu Leu Cys Glu Asn Gly Ala Cys Thr Ala Cys |
| (SEQ ID NO: 8258) | Cys Glu Leu Cys Glu Asn Gly Ala Cys Val Gly Cys |
| (SEQ ID NO: 8259) | Cys Glu Leu Cys Glu Asn Gly Ala Cys Val Ala Cys |
| (SEQ ID NO: 8260) | Cys Glu Leu Cys Glu Asn Gly Ala Cys Gly Gly Cys |
| (SEQ ID NO: 8261) | Cys Glu Leu Cys Glu Asn Gly Ala Cys Gly Ala Cys |
| (SEQ ID NO: 8262) | Cys Glu Leu Cys Glu Asn Gly Thr Cys Thr Gly Cys |
| (SEQ ID NO: 8263) | Cys Glu Leu Cys Glu Asn Gly Thr Cys Thr Ala Cys |
| (SEQ ID NO: 8264) | Cys Glu Leu Cys Glu Asn Gly Thr Cys Val Gly Cys |
| (SEQ ID NO: 8265) | Cys Glu Leu Cys Glu Asn Gly Thr Cys Val Ala Cys |
| (SEQ ID NO: 8266) | Cys Glu Leu Cys Glu Asn Gly Thr Cys Gly Gly Cys |
| (SEQ ID NO: 8267) | Cys Glu Leu Cys Glu Asn Gly Thr Cys Gly Ala Cys |
| (SEQ ID NO: 8268) | Cys Glu Leu Cys Gly Asn Pro Ala Cys Thr Gly Cys |
| (SEQ ID NO: 8269) | Cys Glu Leu Cys Gly Asn Pro Ala Cys Thr Ala Cys |
| (SEQ ID NO: 8270) | Cys Glu Leu Cys Gly Asn Pro Ala Cys Val Gly Cys |
| (SEQ ID NO: 8271) | Cys Glu Leu Cys Gly Asn Pro Ala Cys Val Ala Cys |
| (SEQ ID NO: 8272) | Cys Glu Leu Cys Gly Asn Pro Ala Cys Gly Gly Cys |
| (SEQ ID NO: 8273) | Cys Glu Leu Cys Gly Asn Pro Ala Cys Gly Ala Cys |
| (SEQ ID NO: 8274) | Cys Glu Leu Cys Gly Asn Pro Thr Cys Thr Gly Cys |
| (SEQ ID NO: 8275) | Cys Glu Leu Cys Gly Asn Pro Thr Cys Thr Ala Cys |
| (SEQ ID NO: 8276) | Cys Glu Leu Cys Gly Asn Pro Thr Cys Val Gly Cys |
| (SEQ ID NO: 8277) | Cys Glu Leu Cys Gly Asn Pro Thr Cys Val Ala Cys |
| (SEQ ID NO: 8278) | Cys Glu Leu Cys Gly Asn Pro Thr Cys Gly Gly Cys |
| (SEQ ID NO: 8279) | Cys Glu Leu Cys Gly Asn Pro Thr Cys Gly Ala Cys |
| (SEQ ID NO: 8280) | Cys Glu Leu Cys Gly Asn Gly Ala Cys Thr Gly Cys |
| (SEQ ID NO: 8281) | Cys Glu Leu Cys Gly Asn Gly Ala Cys Thr Ala Cys |
| (SEQ ID NO: 8282) | Cys Glu Leu Cys Gly Asn Gly Ala Cys Val Gly Cys |
| (SEQ ID NO: 8283) | Cys Glu Leu Cys Gly Asn Gly Ala Cys Val Ala Cys |
| (SEQ ID NO: 8284) | Cys Glu Leu Cys Gly Asn Gly Ala Cys Gly Gly Cys |
| (SEQ ID NO: 8285) | Cys Glu Leu Cys Gly Asn Gly Ala Cys Gly Ala Cys |
| (SEQ ID NO: 8286) | Cys Glu Leu Cys Gly Asn Gly Thr Cys Thr Gly Cys |
| (SEQ ID NO: 8287) | Cys Glu Leu Cys Gly Asn Gly Thr Cys Thr Ala Cys |
| (SEQ ID NO: 8288) | Cys Glu Leu Cys Gly Asn Gly Thr Cys Val Gly Cys |
| (SEQ ID NO: 8289) | Cys Glu Leu Cys Gly Asn Gly Thr Cys Val Ala Cys |

FIG. 3CD

| | |
|---|---|
| (SEQ ID NO: 8290 ) | Cys Glu Leu Cys Gly Asn Gly Thr Cys Gly Gly Cys |
| (SEQ ID NO: 8291 ) | Cys Glu Leu Cys Gly Asn Gly Thr Cys Gly Ala Cys |
| (SEQ ID NO: 8292 ) | Cys Glu Leu Cys His Asn Pro Ala Cys Thr Gly Cys |
| (SEQ ID NO: 8293 ) | Cys Glu Leu Cys His Asn Pro Ala Cys Thr Ala Cys |
| (SEQ ID NO: 8294 ) | Cys Glu Leu Cys His Asn Pro Ala Cys Val Gly Cys |
| (SEQ ID NO: 8295 ) | Cys Glu Leu Cys His Asn Pro Ala Cys Val Ala Cys |
| (SEQ ID NO: 8296 ) | Cys Glu Leu Cys His Asn Pro Ala Cys Gly Gly Cys |
| (SEQ ID NO: 8297 ) | Cys Glu Leu Cys His Asn Pro Ala Cys Gly Ala Cys |
| (SEQ ID NO: 8298 ) | Cys Glu Leu Cys His Asn Pro Thr Cys Thr Gly Cys |
| (SEQ ID NO: 8299 ) | Cys Glu Leu Cys His Asn Pro Thr Cys Thr Ala Cys |
| (SEQ ID NO: 8300 ) | Cys Glu Leu Cys His Asn Pro Thr Cys Val Gly Cys |
| (SEQ ID NO: 8301 ) | Cys Glu Leu Cys His Asn Pro Thr Cys Val Ala Cys |
| (SEQ ID NO: 8302 ) | Cys Glu Leu Cys His Asn Pro Thr Cys Gly Gly Cys |
| (SEQ ID NO: 8303 ) | Cys Glu Leu Cys His Asn Pro Thr Cys Gly Ala Cys |
| (SEQ ID NO: 8304 ) | Cys Glu Leu Cys His Asn Gly Ala Cys Thr Gly Cys |
| (SEQ ID NO: 8305 ) | Cys Glu Leu Cys His Asn Gly Ala Cys Thr Ala Cys |
| (SEQ ID NO: 8306 ) | Cys Glu Leu Cys His Asn Gly Ala Cys Val Gly Cys |
| (SEQ ID NO: 8307 ) | Cys Glu Leu Cys His Asn Gly Ala Cys Val Ala Cys |
| (SEQ ID NO: 8308 ) | Cys Glu Leu Cys His Asn Gly Ala Cys Gly Gly Cys |
| (SEQ ID NO: 8309 ) | Cys Glu Leu Cys His Asn Gly Ala Cys Gly Ala Cys |
| (SEQ ID NO: 8310 ) | Cys Glu Leu Cys His Asn Gly Thr Cys Thr Gly Cys |
| (SEQ ID NO: 8311 ) | Cys Glu Leu Cys His Asn Gly Thr Cys Thr Ala Cys |
| (SEQ ID NO: 8312 ) | Cys Glu Leu Cys His Asn Gly Thr Cys Val Gly Cys |
| (SEQ ID NO: 8313 ) | Cys Glu Leu Cys His Asn Gly Thr Cys Val Ala Cys |
| (SEQ ID NO: 8314 ) | Cys Glu Leu Cys His Asn Gly Thr Cys Gly Gly Cys |
| (SEQ ID NO: 8315 ) | Cys Glu Leu Cys His Asn Gly Thr Cys Gly Ala Cys |
| (SEQ ID NO: 8316 ) | Cys Glu Leu Cys Ile Asn Pro Ala Cys Thr Gly Cys |
| (SEQ ID NO: 8317 ) | Cys Glu Leu Cys Ile Asn Pro Ala Cys Thr Ala Cys |
| (SEQ ID NO: 8318 ) | Cys Glu Leu Cys Ile Asn Pro Ala Cys Val Gly Cys |
| (SEQ ID NO: 8319 ) | Cys Glu Leu Cys Ile Asn Pro Ala Cys Val Ala Cys |
| (SEQ ID NO: 8320 ) | Cys Glu Leu Cys Ile Asn Pro Ala Cys Gly Gly Cys |
| (SEQ ID NO: 8321 ) | Cys Glu Leu Cys Ile Asn Pro Ala Cys Gly Ala Cys |
| (SEQ ID NO: 8322 ) | Cys Glu Leu Cys Ile Asn Pro Thr Cys Thr Gly Cys |
| (SEQ ID NO: 8323 ) | Cys Glu Leu Cys Ile Asn Pro Thr Cys Thr Ala Cys |
| (SEQ ID NO: 8324 ) | Cys Glu Leu Cys Ile Asn Pro Thr Cys Val Gly Cys |
| (SEQ ID NO: 8325 ) | Cys Glu Leu Cys Ile Asn Pro Thr Cys Val Ala Cys |
| (SEQ ID NO: 8326 ) | Cys Glu Leu Cys Ile Asn Pro Thr Cys Gly Gly Cys |
| (SEQ ID NO: 8327 ) | Cys Glu Leu Cys Ile Asn Pro Thr Cys Gly Ala Cys |
| (SEQ ID NO: 8328 ) | Cys Glu Leu Cys Ile Asn Gly Ala Cys Thr Gly Cys |
| (SEQ ID NO: 8329 ) | Cys Glu Leu Cys Ile Asn Gly Ala Cys Thr Ala Cys |
| (SEQ ID NO: 8330 ) | Cys Glu Leu Cys Ile Asn Gly Ala Cys Val Gly Cys |
| (SEQ ID NO: 8331 ) | Cys Glu Leu Cys Ile Asn Gly Ala Cys Val Ala Cys |
| (SEQ ID NO: 8332 ) | Cys Glu Leu Cys Ile Asn Gly Ala Cys Gly Gly Cys |

FIG. 3CE

| | |
|---|---|
| (SEQ ID NO: 8333) | Cys Glu Leu Cys Ile Asn Gly Ala Cys Gly Ala Cys |
| (SEQ ID NO: 8334) | Cys Glu Leu Cys Ile Asn Gly Thr Cys Thr Gly Cys |
| (SEQ ID NO: 8335) | Cys Glu Leu Cys Ile Asn Gly Thr Cys Thr Ala Cys |
| (SEQ ID NO: 8336) | Cys Glu Leu Cys Ile Asn Gly Thr Cys Val Gly Cys |
| (SEQ ID NO: 8337) | Cys Glu Leu Cys Ile Asn Gly Thr Cys Val Ala Cys |
| (SEQ ID NO: 8338) | Cys Glu Leu Cys Ile Asn Gly Thr Cys Gly Gly Cys |
| (SEQ ID NO: 8339) | Cys Glu Leu Cys Ile Asn Gly Thr Cys Gly Ala Cys |
| (SEQ ID NO: 8340) | Cys Glu Leu Cys Leu Asn Pro Ala Cys Thr Gly Cys |
| (SEQ ID NO: 8341) | Cys Glu Leu Cys Leu Asn Pro Ala Cys Thr Ala Cys |
| (SEQ ID NO: 8342) | Cys Glu Leu Cys Leu Asn Pro Ala Cys Val Gly Cys |
| (SEQ ID NO: 8343) | Cys Glu Leu Cys Leu Asn Pro Ala Cys Val Ala Cys |
| (SEQ ID NO: 8344) | Cys Glu Leu Cys Leu Asn Pro Ala Cys Gly Gly Cys |
| (SEQ ID NO: 8345) | Cys Glu Leu Cys Leu Asn Pro Ala Cys Gly Ala Cys |
| (SEQ ID NO: 8346) | Cys Glu Leu Cys Leu Asn Pro Thr Cys Thr Gly Cys |
| (SEQ ID NO: 8347) | Cys Glu Leu Cys Leu Asn Pro Thr Cys Thr Ala Cys |
| (SEQ ID NO: 8348) | Cys Glu Leu Cys Leu Asn Pro Thr Cys Val Gly Cys |
| (SEQ ID NO: 8349) | Cys Glu Leu Cys Leu Asn Pro Thr Cys Val Ala Cys |
| (SEQ ID NO: 8350) | Cys Glu Leu Cys Leu Asn Pro Thr Cys Gly Gly Cys |
| (SEQ ID NO: 8351) | Cys Glu Leu Cys Leu Asn Pro Thr Cys Gly Ala Cys |
| (SEQ ID NO: 8352) | Cys Glu Leu Cys Leu Asn Gly Ala Cys Thr Gly Cys |
| (SEQ ID NO: 8353) | Cys Glu Leu Cys Leu Asn Gly Ala Cys Thr Ala Cys |
| (SEQ ID NO: 8354) | Cys Glu Leu Cys Leu Asn Gly Ala Cys Val Gly Cys |
| (SEQ ID NO: 8355) | Cys Glu Leu Cys Leu Asn Gly Ala Cys Val Ala Cys |
| (SEQ ID NO: 8356) | Cys Glu Leu Cys Leu Asn Gly Ala Cys Gly Gly Cys |
| (SEQ ID NO: 8357) | Cys Glu Leu Cys Leu Asn Gly Ala Cys Gly Ala Cys |
| (SEQ ID NO: 8358) | Cys Glu Leu Cys Leu Asn Gly Thr Cys Thr Gly Cys |
| (SEQ ID NO: 8359) | Cys Glu Leu Cys Leu Asn Gly Thr Cys Thr Ala Cys |
| (SEQ ID NO: 8360) | Cys Glu Leu Cys Leu Asn Gly Thr Cys Val Gly Cys |
| (SEQ ID NO: 8361) | Cys Glu Leu Cys Leu Asn Gly Thr Cys Val Ala Cys |
| (SEQ ID NO: 8362) | Cys Glu Leu Cys Leu Asn Gly Thr Cys Gly Gly Cys |
| (SEQ ID NO: 8363) | Cys Glu Leu Cys Leu Asn Gly Thr Cys Gly Ala Cys |
| (SEQ ID NO: 8364) | Cys Glu Leu Cys Lys Asn Pro Ala Cys Thr Gly Cys |
| (SEQ ID NO: 8365) | Cys Glu Leu Cys Lys Asn Pro Ala Cys Thr Ala Cys |
| (SEQ ID NO: 8366) | Cys Glu Leu Cys Lys Asn Pro Ala Cys Val Gly Cys |
| (SEQ ID NO: 8367) | Cys Glu Leu Cys Lys Asn Pro Ala Cys Val Ala Cys |
| (SEQ ID NO: 8368) | Cys Glu Leu Cys Lys Asn Pro Ala Cys Gly Gly Cys |
| (SEQ ID NO: 8369) | Cys Glu Leu Cys Lys Asn Pro Ala Cys Gly Ala Cys |
| (SEQ ID NO: 8370) | Cys Glu Leu Cys Lys Asn Pro Thr Cys Thr Gly Cys |
| (SEQ ID NO: 8371) | Cys Glu Leu Cys Lys Asn Pro Thr Cys Thr Ala Cys |
| (SEQ ID NO: 8372) | Cys Glu Leu Cys Lys Asn Pro Thr Cys Val Gly Cys |
| (SEQ ID NO: 8373) | Cys Glu Leu Cys Lys Asn Pro Thr Cys Val Ala Cys |
| (SEQ ID NO: 8374) | Cys Glu Leu Cys Lys Asn Pro Thr Cys Gly Gly Cys |
| (SEQ ID NO: 8375) | Cys Glu Leu Cys Lys Asn Pro Thr Cys Gly Ala Cys |

FIG. 3CF (SEQ ID NO: 8376) Cys Glu Leu Cys Lys Asn Gly Ala Cys Thr Gly Cys
(SEQ ID NO: 8377) Cys Glu Leu Cys Lys Asn Gly Ala Cys Thr Ala Cys
(SEQ ID NO: 8378) Cys Glu Leu Cys Lys Asn Gly Ala Cys Val Gly Cys
(SEQ ID NO: 8379) Cys Glu Leu Cys Lys Asn Gly Ala Cys Val Ala Cys
(SEQ ID NO: 8380) Cys Glu Leu Cys Lys Asn Gly Ala Cys Gly Gly Cys
(SEQ ID NO: 8381) Cys Glu Leu Cys Lys Asn Gly Ala Cys Gly Ala Cys
(SEQ ID NO: 8382) Cys Glu Leu Cys Lys Asn Gly Thr Cys Thr Gly Cys
(SEQ ID NO: 8383) Cys Glu Leu Cys Lys Asn Gly Thr Cys Thr Ala Cys
(SEQ ID NO: 8384) Cys Glu Leu Cys Lys Asn Gly Thr Cys Val Gly Cys
(SEQ ID NO: 8385) Cys Glu Leu Cys Lys Asn Gly Thr Cys Val Ala Cys
(SEQ ID NO: 8386) Cys Glu Leu Cys Lys Asn Gly Thr Cys Gly Gly Cys
(SEQ ID NO: 8387) Cys Glu Leu Cys Lys Asn Gly Thr Cys Gly Ala Cys
(SEQ ID NO: 8388) Cys Glu Leu Cys Met Asn Pro Ala Cys Thr Gly Cys
(SEQ ID NO: 8389) Cys Glu Leu Cys Met Asn Pro Ala Cys Thr Ala Cys
(SEQ ID NO: 8390) Cys Glu Leu Cys Met Asn Pro Ala Cys Val Gly Cys
(SEQ ID NO: 8391) Cys Glu Leu Cys Met Asn Pro Ala Cys Val Ala Cys
(SEQ ID NO: 8392) Cys Glu Leu Cys Met Asn Pro Ala Cys Gly Gly Cys
(SEQ ID NO: 8393) Cys Glu Leu Cys Met Asn Pro Ala Cys Gly Ala Cys
(SEQ ID NO: 8394) Cys Glu Leu Cys Met Asn Pro Thr Cys Thr Gly Cys
(SEQ ID NO: 8395) Cys Glu Leu Cys Met Asn Pro Thr Cys Thr Ala Cys
(SEQ ID NO: 8396) Cys Glu Leu Cys Met Asn Pro Thr Cys Val Gly Cys
(SEQ ID NO: 8397) Cys Glu Leu Cys Met Asn Pro Thr Cys Val Ala Cys
(SEQ ID NO: 8398) Cys Glu Leu Cys Met Asn Pro Thr Cys Gly Gly Cys
(SEQ ID NO: 8399) Cys Glu Leu Cys Met Asn Pro Thr Cys Gly Ala Cys
(SEQ ID NO: 8400) Cys Glu Leu Cys Met Asn Gly Ala Cys Thr Gly Cys
(SEQ ID NO: 8401) Cys Glu Leu Cys Met Asn Gly Ala Cys Thr Ala Cys
(SEQ ID NO: 8402) Cys Glu Leu Cys Met Asn Gly Ala Cys Val Gly Cys
(SEQ ID NO: 8403) Cys Glu Leu Cys Met Asn Gly Ala Cys Val Ala Cys
(SEQ ID NO: 8404) Cys Glu Leu Cys Met Asn Gly Ala Cys Gly Gly Cys
(SEQ ID NO: 8405) Cys Glu Leu Cys Met Asn Gly Ala Cys Gly Ala Cys
(SEQ ID NO: 8406) Cys Glu Leu Cys Met Asn Gly Thr Cys Thr Gly Cys
(SEQ ID NO: 8407) Cys Glu Leu Cys Met Asn Gly Thr Cys Thr Ala Cys
(SEQ ID NO: 8408) Cys Glu Leu Cys Met Asn Gly Thr Cys Val Gly Cys
(SEQ ID NO: 8409) Cys Glu Leu Cys Met Asn Gly Thr Cys Val Ala Cys
(SEQ ID NO: 8410) Cys Glu Leu Cys Met Asn Gly Thr Cys Gly Gly Cys
(SEQ ID NO: 8411) Cys Glu Leu Cys Met Asn Gly Thr Cys Gly Ala Cys
(SEQ ID NO: 8412) Cys Glu Leu Cys Phe Asn Pro Ala Cys Thr Gly Cys
(SEQ ID NO: 8413) Cys Glu Leu Cys Phe Asn Pro Ala Cys Thr Ala Cys
(SEQ ID NO: 8414) Cys Glu Leu Cys Phe Asn Pro Ala Cys Val Gly Cys
(SEQ ID NO: 8415) Cys Glu Leu Cys Phe Asn Pro Ala Cys Val Ala Cys
(SEQ ID NO: 8416) Cys Glu Leu Cys Phe Asn Pro Ala Cys Gly Gly Cys
(SEQ ID NO: 8417) Cys Glu Leu Cys Phe Asn Pro Ala Cys Gly Ala Cys
(SEQ ID NO: 8418) Cys Glu Leu Cys Phe Asn Pro Thr Cys Thr Gly Cys

FIG. 3CG

| | |
|---|---|
| (SEQ ID NO: 8419) | Cys Glu Leu Cys Phe Asn Pro Thr Cys Thr Ala Cys |
| (SEQ ID NO: 8420) | Cys Glu Leu Cys Phe Asn Pro Thr Cys Val Gly Cys |
| (SEQ ID NO: 8421) | Cys Glu Leu Cys Phe Asn Pro Thr Cys Val Ala Cys |
| (SEQ ID NO: 8422) | Cys Glu Leu Cys Phe Asn Pro Thr Cys Gly Gly Cys |
| (SEQ ID NO: 8423) | Cys Glu Leu Cys Phe Asn Pro Thr Cys Gly Ala Cys |
| (SEQ ID NO: 8424) | Cys Glu Leu Cys Phe Asn Gly Ala Cys Thr Gly Cys |
| (SEQ ID NO: 8425) | Cys Glu Leu Cys Phe Asn Gly Ala Cys Thr Ala Cys |
| (SEQ ID NO: 8426) | Cys Glu Leu Cys Phe Asn Gly Ala Cys Val Gly Cys |
| (SEQ ID NO: 8427) | Cys Glu Leu Cys Phe Asn Gly Ala Cys Val Ala Cys |
| (SEQ ID NO: 8428) | Cys Glu Leu Cys Phe Asn Gly Ala Cys Gly Gly Cys |
| (SEQ ID NO: 8429) | Cys Glu Leu Cys Phe Asn Gly Ala Cys Gly Ala Cys |
| (SEQ ID NO: 8430) | Cys Glu Leu Cys Phe Asn Gly Thr Cys Thr Gly Cys |
| (SEQ ID NO: 8431) | Cys Glu Leu Cys Phe Asn Gly Thr Cys Thr Ala Cys |
| (SEQ ID NO: 8432) | Cys Glu Leu Cys Phe Asn Gly Thr Cys Val Gly Cys |
| (SEQ ID NO: 8433) | Cys Glu Leu Cys Phe Asn Gly Thr Cys Val Ala Cys |
| (SEQ ID NO: 8434) | Cys Glu Leu Cys Phe Asn Gly Thr Cys Gly Gly Cys |
| (SEQ ID NO: 8435) | Cys Glu Leu Cys Phe Asn Gly Thr Cys Gly Ala Cys |
| (SEQ ID NO: 8436) | Cys Glu Leu Cys Pro Asn Pro Ala Cys Thr Gly Cys |
| (SEQ ID NO: 8437) | Cys Glu Leu Cys Pro Asn Pro Ala Cys Thr Ala Cys |
| (SEQ ID NO: 8438) | Cys Glu Leu Cys Pro Asn Pro Ala Cys Val Gly Cys |
| (SEQ ID NO: 8439) | Cys Glu Leu Cys Pro Asn Pro Ala Cys Val Ala Cys |
| (SEQ ID NO: 8440) | Cys Glu Leu Cys Pro Asn Pro Ala Cys Gly Gly Cys |
| (SEQ ID NO: 8441) | Cys Glu Leu Cys Pro Asn Pro Ala Cys Gly Ala Cys |
| (SEQ ID NO: 8442) | Cys Glu Leu Cys Pro Asn Pro Thr Cys Thr Gly Cys |
| (SEQ ID NO: 8443) | Cys Glu Leu Cys Pro Asn Pro Thr Cys Thr Ala Cys |
| (SEQ ID NO: 8444) | Cys Glu Leu Cys Pro Asn Pro Thr Cys Val Gly Cys |
| (SEQ ID NO: 8445) | Cys Glu Leu Cys Pro Asn Pro Thr Cys Val Ala Cys |
| (SEQ ID NO: 8446) | Cys Glu Leu Cys Pro Asn Pro Thr Cys Gly Gly Cys |
| (SEQ ID NO: 8447) | Cys Glu Leu Cys Pro Asn Pro Thr Cys Gly Ala Cys |
| (SEQ ID NO: 8448) | Cys Glu Leu Cys Pro Asn Gly Ala Cys Thr Gly Cys |
| (SEQ ID NO: 8449) | Cys Glu Leu Cys Pro Asn Gly Ala Cys Thr Ala Cys |
| (SEQ ID NO: 8450) | Cys Glu Leu Cys Pro Asn Gly Ala Cys Val Gly Cys |
| (SEQ ID NO: 8451) | Cys Glu Leu Cys Pro Asn Gly Ala Cys Val Ala Cys |
| (SEQ ID NO: 8452) | Cys Glu Leu Cys Pro Asn Gly Ala Cys Gly Gly Cys |
| (SEQ ID NO: 8453) | Cys Glu Leu Cys Pro Asn Gly Ala Cys Gly Ala Cys |
| (SEQ ID NO: 8454) | Cys Glu Leu Cys Pro Asn Gly Thr Cys Thr Gly Cys |
| (SEQ ID NO: 8455) | Cys Glu Leu Cys Pro Asn Gly Thr Cys Thr Ala Cys |
| (SEQ ID NO: 8456) | Cys Glu Leu Cys Pro Asn Gly Thr Cys Val Gly Cys |
| (SEQ ID NO: 8457) | Cys Glu Leu Cys Pro Asn Gly Thr Cys Val Ala Cys |
| (SEQ ID NO: 8458) | Cys Glu Leu Cys Pro Asn Gly Thr Cys Gly Gly Cys |
| (SEQ ID NO: 8459) | Cys Glu Leu Cys Pro Asn Gly Thr Cys Gly Ala Cys |
| (SEQ ID NO: 8460) | Cys Glu Leu Cys Ser Asn Pro Ala Cys Thr Gly Cys |
| (SEQ ID NO: 8461) | Cys Glu Leu Cys Ser Asn Pro Ala Cys Thr Ala Cys |

FIG. 3CH

| | |
|---|---|
| (SEQ ID NO: 8462) | Cys Glu Leu Cys Ser Asn Pro Ala Cys Val Gly Cys |
| (SEQ ID NO: 8463) | Cys Glu Leu Cys Ser Asn Pro Ala Cys Val Ala Cys |
| (SEQ ID NO: 8464) | Cys Glu Leu Cys Ser Asn Pro Ala Cys Gly Gly Cys |
| (SEQ ID NO: 8465) | Cys Glu Leu Cys Ser Asn Pro Ala Cys Gly Ala Cys |
| (SEQ ID NO: 8466) | Cys Glu Leu Cys Ser Asn Pro Thr Cys Thr Gly Cys |
| (SEQ ID NO: 8467) | Cys Glu Leu Cys Ser Asn Pro Thr Cys Thr Ala Cys |
| (SEQ ID NO: 8468) | Cys Glu Leu Cys Ser Asn Pro Thr Cys Val Gly Cys |
| (SEQ ID NO: 8469) | Cys Glu Leu Cys Ser Asn Pro Thr Cys Val Ala Cys |
| (SEQ ID NO: 8470) | Cys Glu Leu Cys Ser Asn Pro Thr Cys Gly Gly Cys |
| (SEQ ID NO: 8471) | Cys Glu Leu Cys Ser Asn Pro Thr Cys Gly Ala Cys |
| (SEQ ID NO: 8472) | Cys Glu Leu Cys Ser Asn Gly Ala Cys Thr Gly Cys |
| (SEQ ID NO: 8473) | Cys Glu Leu Cys Ser Asn Gly Ala Cys Thr Ala Cys |
| (SEQ ID NO: 8474) | Cys Glu Leu Cys Ser Asn Gly Ala Cys Val Gly Cys |
| (SEQ ID NO: 8475) | Cys Glu Leu Cys Ser Asn Gly Ala Cys Val Ala Cys |
| (SEQ ID NO: 8476) | Cys Glu Leu Cys Ser Asn Gly Ala Cys Gly Gly Cys |
| (SEQ ID NO: 8477) | Cys Glu Leu Cys Ser Asn Gly Ala Cys Gly Ala Cys |
| (SEQ ID NO: 8478) | Cys Glu Leu Cys Ser Asn Gly Thr Cys Thr Gly Cys |
| (SEQ ID NO: 8479) | Cys Glu Leu Cys Ser Asn Gly Thr Cys Thr Ala Cys |
| (SEQ ID NO: 8480) | Cys Glu Leu Cys Ser Asn Gly Thr Cys Val Gly Cys |
| (SEQ ID NO: 8481) | Cys Glu Leu Cys Ser Asn Gly Thr Cys Val Ala Cys |
| (SEQ ID NO: 8482) | Cys Glu Leu Cys Ser Asn Gly Thr Cys Gly Gly Cys |
| (SEQ ID NO: 8483) | Cys Glu Leu Cys Ser Asn Gly Thr Cys Gly Ala Cys |
| (SEQ ID NO: 8484) | Cys Glu Leu Cys Thr Asn Pro Ala Cys Thr Gly Cys |
| (SEQ ID NO: 8485) | Cys Glu Leu Cys Thr Asn Pro Ala Cys Thr Ala Cys |
| (SEQ ID NO: 8486) | Cys Glu Leu Cys Thr Asn Pro Ala Cys Val Gly Cys |
| (SEQ ID NO: 8487) | Cys Glu Leu Cys Thr Asn Pro Ala Cys Val Ala Cys |
| (SEQ ID NO: 8488) | Cys Glu Leu Cys Thr Asn Pro Ala Cys Gly Gly Cys |
| (SEQ ID NO: 8489) | Cys Glu Leu Cys Thr Asn Pro Ala Cys Gly Ala Cys |
| (SEQ ID NO: 8490) | Cys Glu Leu Cys Thr Asn Pro Thr Cys Thr Gly Cys |
| (SEQ ID NO: 8491) | Cys Glu Leu Cys Thr Asn Pro Thr Cys Thr Ala Cys |
| (SEQ ID NO: 8492) | Cys Glu Leu Cys Thr Asn Pro Thr Cys Val Gly Cys |
| (SEQ ID NO: 8493) | Cys Glu Leu Cys Thr Asn Pro Thr Cys Val Ala Cys |
| (SEQ ID NO: 8494) | Cys Glu Leu Cys Thr Asn Pro Thr Cys Gly Gly Cys |
| (SEQ ID NO: 8495) | Cys Glu Leu Cys Thr Asn Pro Thr Cys Gly Ala Cys |
| (SEQ ID NO: 8496) | Cys Glu Leu Cys Thr Asn Gly Ala Cys Thr Gly Cys |
| (SEQ ID NO: 8497) | Cys Glu Leu Cys Thr Asn Gly Ala Cys Thr Ala Cys |
| (SEQ ID NO: 8498) | Cys Glu Leu Cys Thr Asn Gly Ala Cys Val Gly Cys |
| (SEQ ID NO: 8499) | Cys Glu Leu Cys Thr Asn Gly Ala Cys Val Ala Cys |
| (SEQ ID NO: 8500) | Cys Glu Leu Cys Thr Asn Gly Ala Cys Gly Gly Cys |
| (SEQ ID NO: 8501) | Cys Glu Leu Cys Thr Asn Gly Ala Cys Gly Ala Cys |
| (SEQ ID NO: 8502) | Cys Glu Leu Cys Thr Asn Gly Thr Cys Thr Gly Cys |
| (SEQ ID NO: 8503) | Cys Glu Leu Cys Thr Asn Gly Thr Cys Thr Ala Cys |
| (SEQ ID NO: 8504) | Cys Glu Leu Cys Thr Asn Gly Thr Cys Val Gly Cys |

FIG. 3CI

| | |
|---|---|
| (SEQ ID NO: 8505) | Cys Glu Leu Cys Thr Asn Gly Thr Cys Val Ala Cys |
| (SEQ ID NO: 8506) | Cys Glu Leu Cys Thr Asn Gly Thr Cys Gly Gly Cys |
| (SEQ ID NO: 8507) | Cys Glu Leu Cys Thr Asn Gly Thr Cys Gly Ala Cys |
| (SEQ ID NO: 8508) | Cys Glu Leu Cys Trp Asn Pro Ala Cys Thr Gly Cys |
| (SEQ ID NO: 8509) | Cys Glu Leu Cys Trp Asn Pro Ala Cys Thr Ala Cys |
| (SEQ ID NO: 8510) | Cys Glu Leu Cys Trp Asn Pro Ala Cys Val Gly Cys |
| (SEQ ID NO: 8511) | Cys Glu Leu Cys Trp Asn Pro Ala Cys Val Ala Cys |
| (SEQ ID NO: 8512) | Cys Glu Leu Cys Trp Asn Pro Ala Cys Gly Gly Cys |
| (SEQ ID NO: 8513) | Cys Glu Leu Cys Trp Asn Pro Ala Cys Gly Ala Cys |
| (SEQ ID NO: 8514) | Cys Glu Leu Cys Trp Asn Pro Thr Cys Thr Gly Cys |
| (SEQ ID NO: 8515) | Cys Glu Leu Cys Trp Asn Pro Thr Cys Thr Ala Cys |
| (SEQ ID NO: 8516) | Cys Glu Leu Cys Trp Asn Pro Thr Cys Val Gly Cys |
| (SEQ ID NO: 8517) | Cys Glu Leu Cys Trp Asn Pro Thr Cys Val Ala Cys |
| (SEQ ID NO: 8518) | Cys Glu Leu Cys Trp Asn Pro Thr Cys Gly Gly Cys |
| (SEQ ID NO: 8519) | Cys Glu Leu Cys Trp Asn Pro Thr Cys Gly Ala Cys |
| (SEQ ID NO: 8520) | Cys Glu Leu Cys Trp Asn Gly Ala Cys Thr Gly Cys |
| (SEQ ID NO: 8521) | Cys Glu Leu Cys Trp Asn Gly Ala Cys Thr Ala Cys |
| (SEQ ID NO: 8522) | Cys Glu Leu Cys Trp Asn Gly Ala Cys Val Gly Cys |
| (SEQ ID NO: 8523) | Cys Glu Leu Cys Trp Asn Gly Ala Cys Val Ala Cys |
| (SEQ ID NO: 8524) | Cys Glu Leu Cys Trp Asn Gly Ala Cys Gly Gly Cys |
| (SEQ ID NO: 8525) | Cys Glu Leu Cys Trp Asn Gly Ala Cys Gly Ala Cys |
| (SEQ ID NO: 8526) | Cys Glu Leu Cys Trp Asn Gly Thr Cys Thr Gly Cys |
| (SEQ ID NO: 8527) | Cys Glu Leu Cys Trp Asn Gly Thr Cys Thr Ala Cys |
| (SEQ ID NO: 8528) | Cys Glu Leu Cys Trp Asn Gly Thr Cys Val Gly Cys |
| (SEQ ID NO: 8529) | Cys Glu Leu Cys Trp Asn Gly Thr Cys Val Ala Cys |
| (SEQ ID NO: 8530) | Cys Glu Leu Cys Trp Asn Gly Thr Cys Gly Gly Cys |
| (SEQ ID NO: 8531) | Cys Glu Leu Cys Trp Asn Gly Thr Cys Gly Ala Cys |
| (SEQ ID NO: 8532) | Cys Glu Leu Cys Tyr Asn Pro Ala Cys Thr Gly Cys |
| (SEQ ID NO: 8533) | Cys Glu Leu Cys Tyr Asn Pro Ala Cys Thr Ala Cys |
| (SEQ ID NO: 8534) | Cys Glu Leu Cys Tyr Asn Pro Ala Cys Val Gly Cys |
| (SEQ ID NO: 8535) | Cys Glu Leu Cys Tyr Asn Pro Ala Cys Val Ala Cys |
| (SEQ ID NO: 8536) | Cys Glu Leu Cys Tyr Asn Pro Ala Cys Gly Gly Cys |
| (SEQ ID NO: 8537) | Cys Glu Leu Cys Tyr Asn Pro Ala Cys Gly Ala Cys |
| (SEQ ID NO: 8538) | Cys Glu Leu Cys Tyr Asn Pro Thr Cys Thr Gly Cys |
| (SEQ ID NO: 8539) | Cys Glu Leu Cys Tyr Asn Pro Thr Cys Thr Ala Cys |
| (SEQ ID NO: 8540) | Cys Glu Leu Cys Tyr Asn Pro Thr Cys Val Gly Cys |
| (SEQ ID NO: 8541) | Cys Glu Leu Cys Tyr Asn Pro Thr Cys Val Ala Cys |
| (SEQ ID NO: 8542) | Cys Glu Leu Cys Tyr Asn Pro Thr Cys Gly Gly Cys |
| (SEQ ID NO: 8543) | Cys Glu Leu Cys Tyr Asn Pro Thr Cys Gly Ala Cys |
| (SEQ ID NO: 8544) | Cys Glu Leu Cys Tyr Asn Gly Ala Cys Thr Gly Cys |
| (SEQ ID NO: 8545) | Cys Glu Leu Cys Tyr Asn Gly Ala Cys Thr Ala Cys |
| (SEQ ID NO: 8546) | Cys Glu Leu Cys Tyr Asn Gly Ala Cys Val Gly Cys |
| (SEQ ID NO: 8547) | Cys Glu Leu Cys Tyr Asn Gly Ala Cys Val Ala Cys |

FIG. 3CJ

| | |
|---|---|
| (SEQ ID NO: 8548) | Cys Glu Leu Cys Tyr Asn Gly Ala Cys Gly Gly Cys |
| (SEQ ID NO: 8549) | Cys Glu Leu Cys Tyr Asn Gly Ala Cys Gly Ala Cys |
| (SEQ ID NO: 8550) | Cys Glu Leu Cys Tyr Asn Gly Thr Cys Thr Gly Cys |
| (SEQ ID NO: 8551) | Cys Glu Leu Cys Tyr Asn Gly Thr Cys Thr Ala Cys |
| (SEQ ID NO: 8552) | Cys Glu Leu Cys Tyr Asn Gly Thr Cys Val Gly Cys |
| (SEQ ID NO: 8553) | Cys Glu Leu Cys Tyr Asn Gly Thr Cys Val Ala Cys |
| (SEQ ID NO: 8554) | Cys Glu Leu Cys Tyr Asn Gly Thr Cys Gly Gly Cys |
| (SEQ ID NO: 8555) | Cys Glu Leu Cys Tyr Asn Gly Thr Cys Gly Ala Cys |
| (SEQ ID NO: 8556) | Cys Glu Leu Cys Val Asn Pro Ala Cys Thr Gly Cys |
| (SEQ ID NO: 8557) | Cys Glu Leu Cys Val Asn Pro Ala Cys Thr Ala Cys |
| (SEQ ID NO: 8558) | Cys Glu Leu Cys Val Asn Pro Ala Cys Val Gly Cys |
| (SEQ ID NO: 8559) | Cys Glu Leu Cys Val Asn Pro Ala Cys Val Ala Cys |
| (SEQ ID NO: 8560) | Cys Glu Leu Cys Val Asn Pro Ala Cys Gly Gly Cys |
| (SEQ ID NO: 8561) | Cys Glu Leu Cys Val Asn Pro Ala Cys Gly Ala Cys |
| (SEQ ID NO: 8562) | Cys Glu Leu Cys Val Asn Pro Thr Cys Thr Gly Cys |
| (SEQ ID NO: 8563) | Cys Glu Leu Cys Val Asn Pro Thr Cys Thr Ala Cys |
| (SEQ ID NO: 8564) | Cys Glu Leu Cys Val Asn Pro Thr Cys Val Gly Cys |
| (SEQ ID NO: 8565) | Cys Glu Leu Cys Val Asn Pro Thr Cys Val Ala Cys |
| (SEQ ID NO: 8566) | Cys Glu Leu Cys Val Asn Pro Thr Cys Gly Gly Cys |
| (SEQ ID NO: 8567) | Cys Glu Leu Cys Val Asn Pro Thr Cys Gly Ala Cys |
| (SEQ ID NO: 8568) | Cys Glu Leu Cys Val Asn Gly Ala Cys Thr Gly Cys |
| (SEQ ID NO: 8569) | Cys Glu Leu Cys Val Asn Gly Ala Cys Thr Ala Cys |
| (SEQ ID NO: 8570) | Cys Glu Leu Cys Val Asn Gly Ala Cys Val Gly Cys |
| (SEQ ID NO: 8571) | Cys Glu Leu Cys Val Asn Gly Ala Cys Val Ala Cys |
| (SEQ ID NO: 8572) | Cys Glu Leu Cys Val Asn Gly Ala Cys Gly Gly Cys |
| (SEQ ID NO: 8573) | Cys Glu Leu Cys Val Asn Gly Ala Cys Gly Ala Cys |
| (SEQ ID NO: 8574) | Cys Glu Leu Cys Val Asn Gly Thr Cys Thr Gly Cys |
| (SEQ ID NO: 8575) | Cys Glu Leu Cys Val Asn Gly Thr Cys Thr Ala Cys |
| (SEQ ID NO: 8576) | Cys Glu Leu Cys Val Asn Gly Thr Cys Val Gly Cys |
| (SEQ ID NO: 8577) | Cys Glu Leu Cys Val Asn Gly Thr Cys Val Ala Cys |
| (SEQ ID NO: 8578) | Cys Glu Leu Cys Val Asn Gly Thr Cys Gly Gly Cys |
| (SEQ ID NO: 8579) | Cys Glu Leu Cys Val Asn Gly Thr Cys Gly Ala Cys |
| (SEQ ID NO: 8580) | Cys Glu Leu Cys --- Asn Pro Ala Cys Thr Gly Cys |
| (SEQ ID NO: 8581) | Cys Glu Leu Cys --- Asn Pro Ala Cys Thr Ala Cys |
| (SEQ ID NO: 8582) | Cys Glu Leu Cys --- Asn Pro Ala Cys Val Gly Cys |
| (SEQ ID NO: 8583) | Cys Glu Leu Cys --- Asn Pro Ala Cys Val Ala Cys |
| (SEQ ID NO: 8584) | Cys Glu Leu Cys --- Asn Pro Ala Cys Gly Gly Cys |
| (SEQ ID NO: 8585) | Cys Glu Leu Cys --- Asn Pro Ala Cys Gly Ala Cys |
| (SEQ ID NO: 8586) | Cys Glu Leu Cys --- Asn Pro Thr Cys Thr Gly Cys |
| (SEQ ID NO: 8587) | Cys Glu Leu Cys --- Asn Pro Thr Cys Thr Ala Cys |
| (SEQ ID NO: 8588) | Cys Glu Leu Cys --- Asn Pro Thr Cys Val Gly Cys |
| (SEQ ID NO: 8589) | Cys Glu Leu Cys --- Asn Pro Thr Cys Val Ala Cys |
| (SEQ ID NO: 8590) | Cys Glu Leu Cys --- Asn Pro Thr Cys Gly Gly Cys |

FIG. 3CK

| | |
|---|---|
| (SEQ ID NO: 8591) | Cys Glu Leu Cys --- Asn Pro Thr Cys Gly Ala Cys |
| (SEQ ID NO: 8592) | Cys Glu Leu Cys --- Asn Gly Ala Cys Thr Gly Cys |
| (SEQ ID NO: 8593) | Cys Glu Leu Cys --- Asn Gly Ala Cys Thr Ala Cys |
| (SEQ ID NO: 8594) | Cys Glu Leu Cys --- Asn Gly Ala Cys Val Gly Cys |
| (SEQ ID NO: 8595) | Cys Glu Leu Cys --- Asn Gly Ala Cys Val Ala Cys |
| (SEQ ID NO: 8596) | Cys Glu Leu Cys --- Asn Gly Ala Cys Gly Gly Cys |
| (SEQ ID NO: 8597) | Cys Glu Leu Cys --- Asn Gly Ala Cys Gly Ala Cys |
| (SEQ ID NO: 8598) | Cys Glu Leu Cys --- Asn Gly Thr Cys Thr Gly Cys |
| (SEQ ID NO: 8599) | Cys Glu Leu Cys --- Asn Gly Thr Cys Thr Ala Cys |
| (SEQ ID NO: 8600) | Cys Glu Leu Cys --- Asn Gly Thr Cys Val Gly Cys |
| (SEQ ID NO: 8601) | Cys Glu Leu Cys --- Asn Gly Thr Cys Val Ala Cys |
| (SEQ ID NO: 8602) | Cys Glu Leu Cys --- Asn Gly Thr Cys Gly Gly Cys |
| (SEQ ID NO: 8603) | Cys Glu Leu Cys --- Asn Gly Thr Cys Gly Ala Cys |

FIG. 3CL

METHODS AND COMPOSITIONS FOR THE TREATMENT OF GASTROINTESTINAL DISORDERS

PRIORITY CLAIM

This application is a continuation (and claims the benefit of priority under 35 U.S.C. §120) of U.S. patent application Ser. No. 14/024,552 filed Sep. 11, 2013, which is a continuation of U.S. patent application Ser. No. 13/291,526 filed Nov. 8, 2011, which is a continuation of U.S. patent application Ser. No. 12/568,107 filed Sep. 28, 2009, which is a continuation of U.S. patent application Ser. No. 10/868,744 filed Jun. 14, 2004 and also claims the benefit of priority under 35 U.S.C. §119 (e) to U.S. Provisional Application Nos. 60/478,492, filed Jun. 13, 2003; 60/532,361 filed Dec. 23, 2003; and 60/571,386 filed May 14, 2004. The disclosure of the prior applications is considered part of (and is incorporated by reference in) the disclosure of this application.

TECHNICAL FIELD

This invention relates to methods and compositions for treating gastrointestinal disorders, obesity, congestive heart failure, benign prostatic hyperplasia and other disorders.

SEQUENCE LISTING

This application incorporates by reference in its entirety the Sequence Listing entitled "IW012US1CON6_ST25", containing 2.36 MB of data and last modified on Feb. 22, 2016, in computer readable-format (CRF) and electronic .txt format, filed electronically herewith.

BACKGROUND

Irritable bowel syndrome (IBS) is a common chronic disorder of the intestine that affects 20 to 60 million individuals in the US alone (Lehman Brothers, Global Healthcare-Irritable Bowel Syndrome Industry Update, September 1999). IBS is the most common disorder diagnosed by gastroenterologists (28% of patients examined) and accounts for 12% of visits to primary care physicians (Camilleri 2001 *Gastroenterology* 120:652-668). In the US, the economic impact of IBS is estimated at $25 billion annually, through direct costs of health care use and indirect costs of absenteeism from work (Talley 1995 Gastroenterology 109:1736-1741). Patients with IBS have three times more absenteeism from work and report a reduced quality of life. Sufferers may be unable or unwilling to attend social events, maintain employment, or travel even short distances (Drossman 1993 *Dig Dis Sci* 38:1569-1580). There is a tremendous unmet medical need in this population since few prescription options exist to treat IBS.

Patients with IBS suffer from abdominal pain and a disturbed bowel pattern. Three subgroups of IBS patients have been defined based on the predominant bowel habit: constipation-predominant (c-IBS), diarrhea-predominant (d-IBS) or alternating between the two (a-IBS). Estimates of individuals who suffer from c-IBS range from 20-50% of the IBS patients with 30% frequently cited. In contrast to the other two subgroups that have a similar gender ratio, c-IBS is more common in women (ratio of 3:1) (Talley et al. 1995 *Am J Epidemiol* 142:76-83).

The definition and diagnostic criteria for IBS have been formalized in the "Rome Criteria" (Drossman et al. 1999 *Gut* 45:Suppl II:1-81), which are well accepted in clinical practice. However, the complexity of symptoms has not been explained by anatomical abnormalities or metabolic changes. This has led to the classification of IBS as a functional GI disorder, which is diagnosed on the basis of the Rome criteria and limited evaluation to exclude organic disease (Ringel et al. 2001 *Annu Rev Med* 52: 319-338). IBS is considered to be a "biopsychosocial" disorder resulting from a combination of three interacting mechanisms: altered bowel motility, an increased sensitivity of the intestine or colon to pain stimuli (visceral sensitivity) and psychosocial factors (Camilleri 2001 *Gastroenterology* 120:652-668). Recently, there has been increasing evidence for a role of inflammation in the etiology of IBS. Reports indicate that subsets of IBS patients have small but significant increases in colonic inflammatory and mast cells, increased inducible nitric oxide (NO) and synthase (iNOS) and altered expression of inflammatory cytokines (reviewed by Talley 2000, Medscape Coverage of DDW Week).

SUMMARY OF THE INVENTION

The present invention features compositions and related methods for treating IBS and other gastrointestinal disorders and conditions (e.g., gastrointestinal motility disorders, functional gastrointestinal disorders, gastroesophageal reflux disease (GERD), duodenogastric reflux, Crohn's disease, ulcerative colitis, inflammatory bowel disease, functional heartburn, dyspepsia (including functional dyspepsia or nonulcer dyspepsia), gastroparesis, chronic intestinal pseudo-obstruction (or colonic pseudoobstruction), and disorders and conditions associated with constipation, e.g., constipation associated with use of opiate pain killers, post-surgical constipation, and constipation associated with neuropathic disorders as well as other conditions and disorders. The compositions feature peptides that activate the guanylate cyclase C (GC-C) receptor.

The present invention also features compositions and related methods for treating obesity, congestive heart failure and benign prostatic hyperplasia (BPH).

Without being bound by any particular theory, in the case of IBS and other gastrointestinal disorders the peptides are useful because they can increase gastrointestinal motility.

Without being bound by any particular theory, in the case of IBS and other gastrointestinal disorders the peptides are useful, in part, because they can decrease inflammation.

Without being bound by any particular theory, in the case of IBS and other gastrointestinal disorders the peptides are also useful because they can decrease gastrointestinal pain or visceral pain.

The invention features pharmaceutical compositions comprising certain peptides that are capable of activating the guanylate-cyclase C (GC-C) receptor. Also within the invention are pharmaceutical compositions comprising a peptide of the invention as well as combination compositions comprising a peptide of the invention and one or more additional therapeutic agents, e.g., an agent for treating constipation (e.g., a chloride channel activator such as SPI-0211; Sucampo Pharmaceuticals, Inc.; Bethesda, Md., a laxative such as MiraLax; Braintree Laboratories, Braintree Mass.) or some other gastrointestinal disorder. Examples of additional therapeutic agents include: acid reducing agents such as proton pump inhibitors (e.g. omeprazole, esomeprazole, lansoprazole, pantorazole and rabeprazole), H2 receptor blockers (e.g., cimetidine, ranitidine, famotidine and nizatidine), pro-motility agents such as motilin agonists (e.g., GM-611 or mitemcinal fumarate), 5HT receptor agonists (e.g. 5HT4 receptor agonists such as Zelnorm®; 5HT3 receptor agonists such as MKC-733), 5HT receptor antagonists (e.g., 5HT1, 5HT2, 5HT3 (e.g., alosetron), 5HT4 receptor antagonists, muscarinic receptor agonists, anti-inflammatory agents, antispasmodics, antidepressants, centrally-acting analgesic agents such as opioid receptor agonists, opioid receptor antagonists (e.g., naltrexone), agents for the treatment of Inflammatory bowel disease, Crohn's disease and ulcerative colitis (e.g., Traficet-EN™ (Chemo-Centryx, Inc.; San Carlos, Calif.)), agents that treat gastrointestinal or visceral pain, and cGMP phosphodiesterase inhibitors (e.g., motapizone, zaprinast, and suldinac sulfone). The peptides of the invention can also be used in combination with agents such as tianeptine (Stablon®) and other agents described in U.S. Pat. No. 6,683,072, (E)-4 (1,3bis(cyclohexylmethyl)-1,2,34-tetrahydro-2,6-diono-9H-purin-8-yl)cinnamic acid nonaethylene glycol methyl ether ester and related compounds described in WO 02/067942. The peptides can also be used in combination with treatments entailing the administration of microorganisms useful in the treatment of gastrointestinal disorders such as IBS. Probactrix® (The BioBalance Corporation; New York, N.Y.) is one example of a formulation that contains microorganisms useful in the treatment of gastrointestinal disorders. The peptides can also be used in combination with purgatives that draw fluids to the intestine (e.g., Visicol®, a combination of sodium phosphate monobasic monohydrate and sodium phosphate dibasic anhydrate.

In addition, the pharmaceutical compositions can include one or more agents selected from the group consisting of: Ca channel blockers (e.g., ziconotide), complete or partial 5HT receptor antagonists (for example 5HT3 (e.g., alosetron, ATI-7000; Aryx Therapeutics, Santa Clara Calif.), 5HT4, 5HT2, and 5HT1 receptor antagonists), complete or partial 5HT receptor agonists including 5HT3, 5HT2, 5HT4 (e.g., tegaserod, mosapride and renzapride), 5HT1 receptor agonists, CRF receptor agonists (NBI-34041), β-3 adrenoreceptor agonists, opioid receptor agonists (e.g., loperamide, fedotozine, and fentanyl, naloxone, naltrexone, methyl nalozone, nalmefene, cypridime, beta funaltrexamine, naloxonazine, naltrindole, and nor-binaltorphimine, morphine, diphenyloxylate, enkephalin pentapeptide, asimadoline, and trimebutine), NK1 receptor antagonists (e.g., ezlopitant and SR-14033), CCK receptor agonists (e.g., loxiglumide), NK1 receptor antagonists, NK3 receptor antagonists (e.g., talnetant, osanetant (SR-142801), SSR-241586), norepinephrine-serotonin reuptake inhibitors (NSRI; e.g., milnacipran), vanilloid and cannabanoid receptor agonists (e.g., arvanil), sialorphin, sialorphin-related peptides comprising the amino acid sequence QHNPR (SEQ ID NO:85) for example, VQHNPR (SEQ ID NO:86); VRQHNPR (SEQ ID NO:87); VRGQHNPR (SEQ ID NO:88); VRGPQHNPR (SEQ ID NO:89); VRGPRQHNPR (SEQ ID NO:90); VRGPRRQH-NPR (SEQ ID NO:91); and RQHNPR (SEQ ID NO:92), compounds or peptides that are inhibitors of neprilysin, frakefamide (H-Tyr-D-Ala-Phe(F)-Phe-NH$_2$; WO 01/019849 A1), loperamide, Tyr-Arg (kyotorphin), CCK receptor agonists (caerulein), conotoxin peptides, peptide analogs of thymulin, loxiglumide, dexloxiglumide (the R-isomer of loxiglumide) (WO 88/05774). These peptides and compounds can be administered with the peptides of the invention (simultaneously or sequentially). They can also be covalently linked to a peptide of the invention to create therapeutic conjugates.

The invention includes methods for treating various gastrointestinal disorders by administering a peptide that acts as a partial or complete agonist of the GC-C receptor. The peptide contains up to four cysteines that form one or two disulfide bonds. In certain embodiments the disulfide bonds are replaced by other covalent cross-links and in some cases the cysteines are substituted by other residues to provide for alternative covalent cross-links. The peptides may also include at least one trypsin or chymotrypsin cleavage site and/or a carboxy-terminal analgesic peptide or small molecule, e.g., AspPhe or some other analgesic peptide. When present within the peptide, the analgesic peptide or small molecule may be preceded by a chymotrypsin or trypsin cleavage site that allows release of the analgesic peptide or small molecule. The peptides and methods of the invention are also useful for treating pain and inflammation associated with various disorders, including gastrointestinal disorders. Certain peptides include a functional chymotrypsin or trypsin cleavage site located so as to allow inactivation of the peptide upon cleavage. Certain peptides having a functional cleavage site undergo cleavage and gradual inactivation in the digestive tract, and this is desirable in some circumstances. In certain peptides, a functional chymotrypsin site is altered, increasing the stability of the peptide in vivo (e.g., guanylin).

The invention includes methods for treating other disorders such as congestive heart failure and benign prostatic hyperplasia by administering a peptide or small molecule (parenterally or orally) that acts as an agonist of the GC-C receptor. Such agents can be used in combination with natriuretic peptides (e.g., atrial natriuretic peptide, brain natriuretic peptide or C-type natriuretic peptide), a diuretic, or an inhibitor of angiotensin converting enzyme.

The invention features methods and compositions for increasing intestinal motility. Intestinal motility involves spontaneous coordinated distentions and contractions of the stomach, intestines, colon and rectum to move food through the gastrointestinal tract during the digestive process.

The peptide can contain additional carboxy terminal or amino terminal amino acids or both. For example, the peptide can include an amino terminal sequence that facilitates recombinant production of the peptide and is cleaved prior to administration of the peptide to a patient. The peptide can also include other amino terminal or carboxy terminal amino acids. In some cases the additional amino acids protect the peptide, stabilize the peptide or alter the activity of the peptide. In some cases some or all of these additional amino acids are removed prior to administration of the peptide to a patient. The peptide can include 1, 2, 3, 4, 5, 10, 15, 20, 25, 30, 40, 50, 60, 70 80, 90, 100 or more amino acids at its amino terminus or carboxy terminus or both. The number of flanking amino acids need not be the same. For example, there can be 10 additional amino acids at the amino terminus of the peptide and none at the carboxy terminus.

In certain embodiments the peptides include either one or two or more contiguous negatively charged amino acids (e.g., Asp or Glu) or one or two or more contiguous positively charged residues (e.g., Lys or Arg) or one or two or more contiguous positively or negatively charged amino acids at the carboxy terminus. In these embodiments all of the flanking amino acids at the carboxy terminus are either positively or negatively charged. In other embodiments the carboxy terminal charged amino acids are preceded by a Leu. For example, the following amino acid sequences can be added to the carboxy terminus of the peptide: Asp; Asp Lys; Lys Lys Lys Lys Lys Lys (SEQ ID NO:93); Asp Lys Lys Lys Lys Lys Lys (SEQ ID NO:94); Leu Lys Lys; and Leu Asp. It is also possible to simply add Leu at the carboxy terminus.

In a first aspect, the invention features a polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1) wherein:

$Xaa_1$ is Ser, Asn, Tyr, Ala, Gln, Pro, Lys, Gly, or Thr, or is missing;
$Xaa_2$ is His, Asp, Glu, Ala, Ser, Asn, Gly, or is missing;
$Xaa_3$ is Thr, Asp, Ser, Glu, Pro, Val or Leu;
$Xaa_5$ is Asp, Ile or Glu;
$Xaa_6$ is Ile, Trp or Leu;
$Xaa_7$ is Cys, Ser, or Tyr;
$Xaa_8$ is Ala, Val, Thr, Ile, Met or is missing;
$Xaa_9$ is a) any amino acid, b) Phe, Tyr, Asn, Trp, c) an amino acid other than Phe, Trp, or Tyr, d) non-aromatic amino acid or e) is missing;
$Xaa_{10}$ is Ala, Val, Met, Thr or Ile;
$Xaa_{11}$ is Ala or Val;
$Xaa_{13}$ is Ala or Thr;
$Xaa_{14}$ is Gly, Ala or Ser;
$Xaa_{15}$ is Cys, Tyr or is missing; and
$Xaa_{16}$ is: a) Trp, Tyr or Phe to create a chymotrypsin cleavage site; b) Lys or Arg to create a trypsin cleavage site; c) is missing or d) His or Leu or Ser.

In some embodiments, $Xaa_1$ is preceded by Lys or Tyr.

In certain embodiments, a Cys is replaces by any amino acid other than Cys. Certain such polypeptides will have fewer disulfide bonds.

In a related aspect the invention features a composition comprising a polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1) wherein: $Xaa_1$ is Ser, Asn, Tyr, Ala, Gln, Pro, Lys, Gly, or Thr, or is missing; $Xaa_2$ is His, Asp, Glu, Ala, Ser, Asn, Gly, Pro or is missing; $Xaa_3$ is Thr, Asp, Ser, Glu, Pro, Val or Leu; $Xaa_5$ is Asp, Ile or Glu; $Xaa_6$ is Ile, Tip or Leu; $Xaa_7$ is Cys, Ser, or Tyr; $Xaa_8$ is Ala, Val, Thr, Ile, Met or is missing; $Xaa_9$ is Phe, Tyr, Asn, Trp, an amino acid other than Phe, Trp, or Tyr, is a non-aromatic amino acid or is missing; $Xaa_{10}$ is Ala, Val, Met, Thr or Ile; $Xaa_{11}$ is Ala or Val; $Xaa_{13}$ is Ala or Thr; $Xaa_{14}$ is Gly, Ala or Ser; $Xaa_{15}$ is Cys, Tyr or is missing; and $Xaa_{16}$ is: a) Trp, Tyr or Phe to create a chymotrypsin cleavage site; b) Lys or Arg to create a trypsin cleavage site; c) is missing or d) His or Leu or Ser and a pharmaceutically acceptable carrier. In related aspects, the invention features a pharmaceutically acceptable tablet, pill, capsule comprising the peptide.

In a related aspect, the invention features a polypeptide comprising, consisting of or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1) wherein:

$Xaa_1$ is Asn, any amino acid or is missing;
$Xaa_2$ is Asp, Glu, any amino acid or is missing;
$Xaa_3$ is Asp or Glu;
$Xaa_5$ is any amino acid or Glu;
$Xaa_6$ is any amino acid or Leu;
$Xaa_7$ is Cys;
$Xaa_8$ is any amino acid or Val;
$Xaa_9$ is Asn, Gln, Tyr;
$Xaa_{10}$ is any amino acid or Val;
$Xaa_{11}$ is any amino acid or Ala;
$Xaa_{13}$ is any amino acid or Thr;
$Xaa_{14}$ is any amino acid or Gly;
$Xaa_{15}$ is Cys;
$Xaa_{16}$ is any amino acid, Leu or missing In a related aspect, the invention features a polypeptide comprising, consisting of, or consisting essentially of the amino acid sequence: $Asn_1$ $Xaa_2$ $Xaa_3$ $Xaa_4$ $Glu_5$ $Leu_6$ $Xaa_7$ $Val_8$ $Asn_9$ $Xaa_{10}$ $Xaa_{11}$ $Xaa_{12}$ $Thr_{13}$ $Xaa_{14}$ $Xaa_{15}$ $Leu_{16}$ (SEQ ID NO: 2) wherein:

$Xaa_2$ is Asp or Glu;
$Xaa_3$ is Asp or Glu;
$Xaa_4$ is Cys or Mpt (mercaptoproline) or Pen (penicillamine) or Dpr (diaminopropionic acid) or Asp or Glu;
$Xaa_7$ is Cys or Mpt (mercaptoproline) or Pen (penicillamine) or Dpr (diaminopropionic acid) or Asp or Glu;
$Xaa_{10}$ is Val or Pro;
$Xaa_{11}$ is Ala or Aib (alpha-aminoisobutyric acid);
$Xaa_{12}$ is Cys or Mpt (mercaptoproline) or Pen (penicillamine) or Dpr (diaminopropionic acid) or Asp or Glu;
$Xaa_{14}$ is Gly or Ala;
$Xaa_{15}$ is Cys or Mpt (mercaptoproline) or Pen (penicillamine) or Dpr (diaminopropionic acid) or Asp or Glu; and In certain embodiments, where $Xaa_{15}$ is other than Cys or is missing, $Xaa_7$ is Ser or an amino acid other than Cys.

In certain embodiments 1, 2, 3, 4, 5, 6, 7, 8, 9, 10, 11 or 12 of $Xaa_1$, $Xaa_2$, $Xaa_3$, $Xaa_5$, $Xaa_6$, $Xaa_7$, $Xaa_8$, $Xaa_9$, $Xaa_{10}$, $Xaa_{11}$, $Xaa_{13}$, $Xaa_{14}$, and $Xaa_{16}$ are any amino acid other than Cys.

In certain embodiments, $Xaa_9$ is any amino acid other than Gln. In other embodiments where $Xaa_2$ and $Xaa_3$ are Glu, $Xaa_9$ is any amino acid other than Gln.

In certain embodiments $Xaa_1$ and $Xaa_2$ are missing; $Xaa_3$ is Thr; $Xaa_5$ is Glu; $Xaa_6$ is Ile or Leu; $Xaa_8$ is Ala, Val, or Ile; $Xaa_9$ is Phe or Tyr; $Xaa_{10}$ is Ala or Val; $Xaa_{11}$ is Ala; $Xaa_{13}$ is Ala or Thr; $Xaa_{14}$ is Gly; and $Xaa_{16}$ is Trp, Tyr, Phe, Lys, Arg or is missing.

In certain embodiments the polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1) is not cleaved after $Xaa_9$ by chymotrypsin. In these embodiments wherein:

$Xaa_1$ is Ser, Asn, Tyr, Ala, Gln, Pro, Lys, Gly, or Thr, or is missing;
$Xaa_2$ is His, Asp, Glu, Ala, Ser, Asn, or Gly, or is missing;
$Xaa_3$ is Thr, Asp, Ser, Glu, Pro, Val or Leu or is missing;
$Xaa_5$ is Asp, Ile or Glu;
$Xaa_6$ is Ile, Trp or Leu;
$Xaa_7$ is Cys, Ser, or Tyr;
$Xaa_8$ is Ala, Val, Thr, Ile, Met or is missing;
$Xaa_9$ is either: a) any amino acid other than Phe and Tyr, b) any amino acid other than Phe, Tyr, and Trp, c) any amino acid other than Phe, Tyr, Trp, Ile, Leu and Val; d) any amino acid other than Phe, Tyr, Trp, Ile, Leu, Val, and His; d) any non-aromatic amino acid or e) is missing;
$Xaa_{10}$ is Ala, Val, Met, Thr or Ile;
$Xaa_{11}$ is Ala or Val;
$Xaa_{13}$ is Ala or Thr;
$Xaa_{14}$ is Gly, Ala or Ser;
$Xaa_{15}$ is Cys, Tyr or is missing; and
$Xaa_{16}$ is: a) Trp, Tyr or Phe to create a chymotrypsin cleavage site; b) Lys or Arg to create a trypsin cleavage site; c) is missing or d) His or Leu or Ser.

In addition, the invention features variants of $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1) that is not cleaved after $Xaa_9$ by chymotrypsin due to the addition of an amino terminal lysine. An example of such a molecule is a human guanylin variant having an amino terminal lysine: KPGT-CEICAYAACTGC (SEQ ID NO: 3).

In certain embodiments of the peptide comprising, consisting of, or consisting essentially of the amino acid sequence: $Xaa_1\ Xaa_2\ Xaa_3\ Cys_4\ Xaa_5\ Xaa_6\ Xaa_7\ Xaa_8\ Xaa_9\ Xaa_{10}\ Xaa_{11}\ Cys_{12}\ Xaa_{13}\ Xaa_{14}\ Xaa_{15}\ Xaa_{16}$ (SEQ ID NO:1) that is not cleaved after $Xaa_9$ by chymotrypsin, $Xaa_7$ and $Xaa_{15}$ are both Cys.

Also within the invention are variants of PGTCEI-CAYAACTGC (human guanylin) (SEQ ID NO: 4) wherein Y is substituted by any amino acid other than a) Phe; b) any amino acid other than Phe and Trp; c) any amino acid other than Phe, Trp, Ile, Leu and Val; d) any amino acid other than Phe, Trp, Ile, Leu, Val and His; e) any non-aromatic amino acid or f) is missing.

In certain embodiments the polypeptide comprising, consisting of, or consisting essentially of the amino acid sequence: $Xaa_1\ Xaa_2\ Xaa_3\ Cys_4\ Xaa_5\ Xaa_6\ Xaa_7\ Xaa_8\ Xaa_9\ Xaa_{10}\ Xaa_{11}\ Cys_{12}\ Xaa_{13}\ Xaa_{14}\ Xaa_{15}\ Xaa_{16}$ (SEQ ID NO:1) is not cleaved after $Xaa_9$ by either chymotrypsin or trypsin. In these embodiments wherein:

$Xaa_1$ is Ser, Asn, Tyr, Ala, Gln, Pro, Lys, Gly, or Thr, or is missing;
$Xaa_2$ is His, Asp, Glu, Ala, Ser, Asn, or Gly, or is missing;
$Xaa_3$ is Thr, Asp, Ser, Glu, Pro, Val or Leu or is missing;
$Xaa_5$ is Asp, Ile or Glu;
$Xaa_6$ is Ile, Trp or Leu;
$Xaa_7$ is Cys, Ser, or Tyr;
$Xaa_8$ is Ala, Val, Thr, Ile, Met or is missing;
$Xaa_9$ is either: a) any amino acid other than Lys, Arg, Phe and Tyr, b) any amino acid other than Lys, Arg, Phe, Tyr, and Trp, c) any amino acid other than Lys, Arg, Phe, Tyr, Trp, Ile, Leu and Val; d) any amino acid other than Lys, Arg, Phe, Tyr, Trp, Ile, Leu, Val, and His; or e) is missing;
$Xaa_{10}$ is Ala, Val, Met, Thr or Ile;
$Xaa_{11}$ is Ala or Val;
$Xaa_{13}$ is Ala or Thr;
$Xaa_{14}$ is Gly, Ala or Ser;
$Xaa_{15}$ is Cys, Tyr or is missing; and
$Xaa_{16}$ is: a) Trp, Tyr or Phe to create a chymotrypsin cleavage site; b) Lys or Arg to create a trypsin cleavage site; c) is missing or d) His or Leu or Ser.

In certain embodiments of the peptide comprising, consisting of, or consisting essentially of the amino acid sequence: $Xaa_1\ Xaa_2\ Xaa_3\ Cys_4\ Xaa_5\ Xaa_6\ Xaa_7\ Xaa_8\ Xaa_9\ Xaa_{10}\ Xaa_{11}\ Cys_{12}\ Xaa_{13}\ Xaa_{14}\ Xaa_{15}\ Xaa_{16}$ (SEQ ID NO:1) that is not cleaved after $Xaa_9$ by chymotrypsin or trypsin, $Xaa_7$ and $Xaa_{15}$ are both Cys.

Useful variants of PGTCEICAYAACTGC (human guanylin) (SEQ ID NO: 4) that should not be cleaved by chymotrypsin include:

PGTCEICASAACTGC (SEQ ID NO: 5)

PGTCEICATAACTGC (SEQ ID NO: 6)

PGTCEICANAACTGC (SEQ ID NO: 7)

PGTCEICAQAACTGC (SEQ ID NO: 8)

PGTCEICARAACTGC (SEQ ID NO: 9)

PGTCEICAEAACTGC (SEQ ID NO: 10)

PGTCEICADAACTGC (SEQ ID NO: 11)

PGTCEICAGAACTGC (SEQ ID NO: 12)

PGTCEICAAAACTGC (SEQ ID NO: 13)

PGTCEICAMAACTGC. (SEQ ID NO: 14)

Additional variants which are not likely to be cleaved by chymotrypsin under certain conditions include:

PGTCEICAIAACTGC (SEQ ID NO: 15)

PGTCEICALAACTGC (SEQ ID NO: 16)

PGTCEICAVAACTGC (SEQ ID NO: 17)

PGTCEICAHAACTGC (SEQ ID NO: 18)

The invention also features deletion variants of any of the peptides described herein in which one, two, three or four amino acids, other than a Cys, are deleted. Where two (or more) amino acids are deleted and the peptide comprises the sequence: $Cys_a$ Xaa Xaa $Cys_b$ Xaa Xaa Xaa Xaa $Cys_c$ Xaa Xaa $Cys_d$, in some embodiments two or more deletions can be located between $Cys_a$ and $Cys_b$ or between $Cys_b$ and $Cys_c$ or between $Cys_c$ and $Cys_d$. Thus, there can be two or more deletions between two Cys. However, in other embodiments there is at most one deletion between each Cys, i.e., there is no more than one deletion between each of $Cys_a$ and $Cys_b$, $Cys_b$ and $Cys_c$, and $Cys_c$ and $Cys_d$. Thus, the invention includes any of the peptides described herein comprising the sequence $Cys_a$ Xaa Xaa $Cys_b$ Xaa Xaa Xaa Xaa $Cys_c$ Xaa Xaa $Cys_d$ wherein: a) one amino acid between $Cys_a$ and $Cys_b$ is deleted; b) one amino acid between $Cys_b$ and $Cys_c$ is deleted; c) one amino acid between $Cys_c$ and $Cys_d$ is deleted; d) one amino acid between $Cys_a$ and $Cys_b$ is deleted and one amino acid between $Cys_b$ and $Cys_c$ is deleted; e) one amino acid between $Cys_a$ and $Cys_b$ is deleted and one amino acid between $Cys_c$ and $Cys_d$ is deleted; f) one amino acid between $Cys_b$ and $Cys_c$ is deleted and one amino acid between $Cys_c$ and $Cys_d$ is deleted; or g) one amino acid between $Cys_a$ and $Cys_b$ is deleted, one amino acid between $Cys_b$ and $Cys_c$ is deleted, and one amino acid between $Cys_c$ and $Cys_d$ is deleted. In addition, one or more amino acids preceding $Cys_a$ and/or one or more amino acids following $Cys_d$ can be deleted. The various deletion variants are peptides that bind to and/or activate the GC-C receptor.

The invention also features deletion variants of any of the peptides described herein in which one, two, three or four amino acids (or non-natural amino acids or natural or non-natural amino acid analogs), other than a Cys (or an amino acid substituted for Cys, e.g., an amino acid capable of forming a covalent bond to another amino acid) is deleted. Thus, additional variants include those in which a Cys is substituted by an amino acid capable of forming a covalent linkage with another amino acid (e.g., a Cys or a substitute therefore). Such amino acids include: Mpt (mercaptoproline) or Pen (penicillamine) or Dpr (diaminopropionic acid).

FIG. 1A-FIG. 1Q includes deletion variants of human guanylin in which one, two, three or four amino acids are deleted. The deleted amino acids are between $Cys_a$ and $Cys_d$ as well as amino terminal to $Cys_a$.

The invention also features insertion variants of any of the peptides described herein in which one, two, three or four amino acids are inserted.

Where two (or more) amino acids are inserted and the peptide comprises the sequence: $Cys_a$ Xaa Xaa $Cys_b$ Xaa Xaa Xaa Xaa $Cys_c$ Xaa Xaa $Cys_d$, in some embodiments two or more insertions can be located between $Cys_a$ and $Cys_b$ or between $Cys_b$ and $Cys_c$ or between $Cys_c$ and $Cys_d$. However, in other embodiments there is at most one insertion between each of $Cys_a$ and $Cys_b$ or between $Cys_b$ and $Cys_c$ or between $Cys_c$ and $Cys_d$. Thus, the invention includes any of the peptides described herein comprising the sequence $Cys_a$ Xaa Xaa $Cys_b$ Xaa Xaa Xaa Xaa $Cys_c$ Xaa Xaa $Cys_d$ wherein: a) one amino acid is inserted between $Cys_a$ and $Cys_b$; b) one amino acid is inserted between $Cys_b$ and $Cys_c$; c) one amino acid is inserted between $Cys_c$ and $Cys_d$; d) one amino acid is inserted between $Cys_a$ and $Cys_b$ and one amino acid is inserted between $Cys_b$ and $Cys_c$; e) one amino acid is inserted between $Cys_a$ and $Cys_b$ and one amino acid is inserted between $Cys_c$ and $Cys_d$; f) one amino acid is inserted between $Cys_b$ and $Cys_c$ and one amino acid is inserted between $Cys_c$ and $Cys_d$ or g) one amino acid is inserted between $Cys_a$ and $Cys_b$, one amino acid is inserted between $Cys_b$ and $Cys_c$, and one amino acid is inserted between $Cys_c$ and $Cys_d$. In addition, one or more amino acids can be inserted preceding $Cys_a$ and/or one or more amino acids can be inserted following $Cys_d$. The insertions can be any natural or non-natural occurring amino acid (e.g., Gly or Ala) or amino acid analog and where there are more than one insertions present, they can be the same or different. The various deletion variants are peptides that bind to and/or activate the GC-C receptor.

For example, the invention includes the following insertion variants of PGTCGEICAYAACTGC (human guanylin) (SEQ ID NO:19) include:

PGTCEGICAYAACTGC (SEQ ID NO: 20)

PGTCEIGCAYAACTGC (SEQ ID NO: 21)

PGTCEICGAYAACTGC (SEQ ID NO: 22)

PGTCEICAGYAACTGC (SEQ ID NO: 23)

PGTCEICAYGAACTGC (SEQ ID NO: 24)

PGTCEICAYAGACTGC (SEQ ID NO: 25)

PGTCEICAYAAGCTGC (SEQ ID NO: 26)

PGTCEICAYAACGTGC (SEQ ID NO: 27)

PGTCEICAYAACTGGC (SEQ ID NO: 28)

PGTCAEICAYAACTGC (SEQ ID NO: 29)

PGTCEAICAYAACTGC (SEQ ID NO: 30)

PGTCEIACAYAACTGC (SEQ ID NO: 31)

PGTCEICAAYAACTGC (SEQ ID NO: 32)

PGTCEICAYAAACTGC (SEQ ID NO: 33)

PGTCEICAYAACATGC (SEQ ID NO: 34)

PGTCEICAYAACTAGC (SEQ ID NO: 35)

PGTCEICAYAACTGAC (SEQ ID NO: 36)

PGTCAEICAAYAACTGC (SEQ ID NO: 37)

PGTCEAICAAYAACTGC (SEQ ID NO: 38)

PGTCEIACAAYAACTGC (SEQ ID NO: 39)

Other insertion variants of human guanylin can have up to four amino acids (i.e., 0, 1, 2, 3 or 4 natural or non-natural amino acids) inserted after each of the 15 amino acids in human guanylin. Thus, the invention includes peptides having the sequence: Pro $Xaa_{(0-4)}$ Gly $Xaa_{(0-4)}$ Thr $Xaa_{(0-4)}$ Cys $Xaa_{(0-4)}$ Glu $Xaa_{(0-4)}$ Ile $Xaa_{(0-4)}$ Cys $Xaa_{(0-4)}$ Ala $Xaa_{(0-4)}$ Tyr $Xaa_{(0-4)}$ Ala $Xaa_{(0-4)}$ Ala $Xaa_{(0-4)}$ Cys $Xaa_{(0-4)}$ Thr $Xaa_{(0-4)}$ Gly $Xaa_{(0-4)}$ Cys $Xaa_{(0-4)}$ (SEQ ID NO: 95). The inserted amino acids can be any amino acid and can be the same or different. In certain embodiments the inserted amino acids are all Gly or all Ala or a combination of Gly and Ala.

Figure 2B:
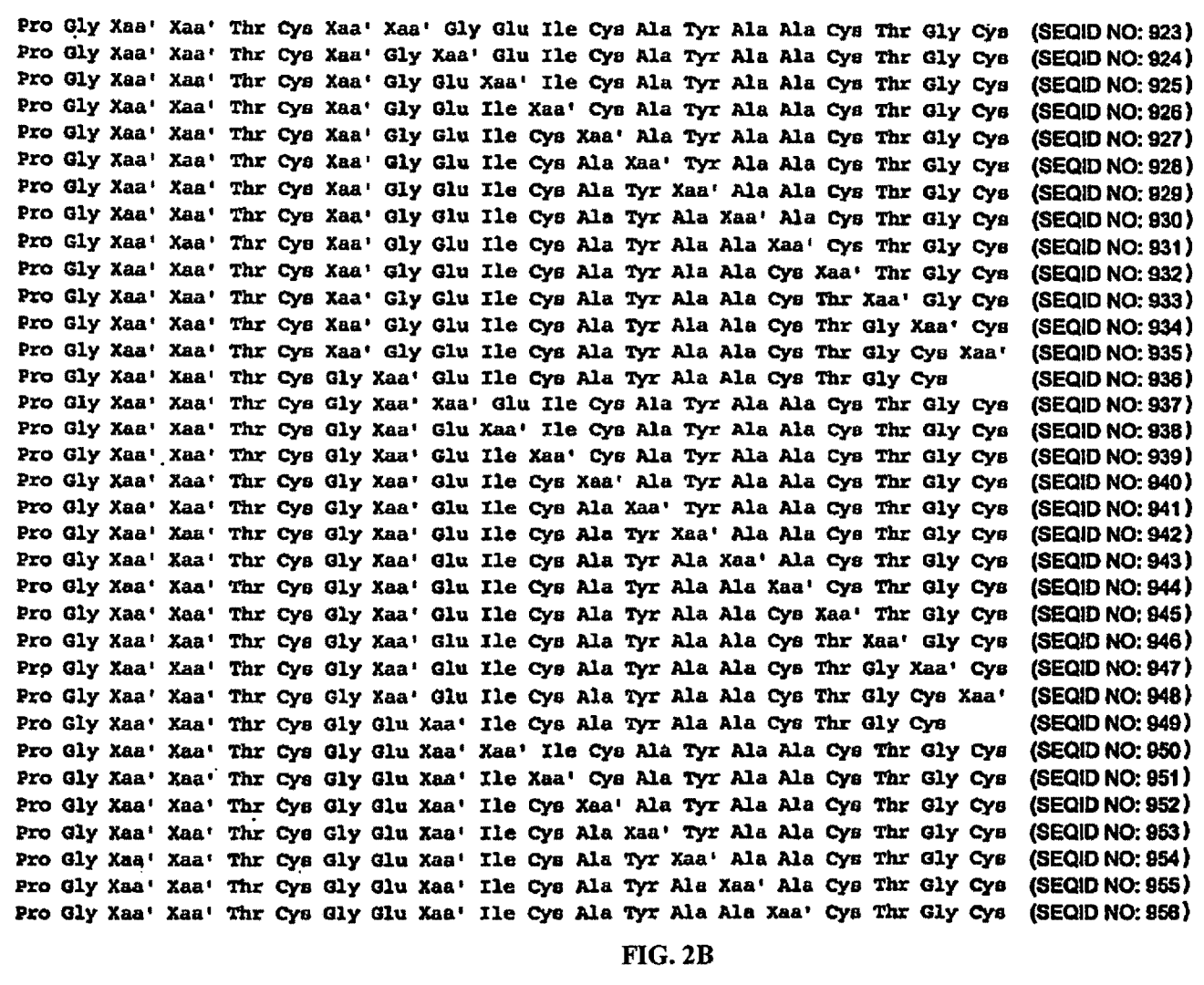
Figure 2K:
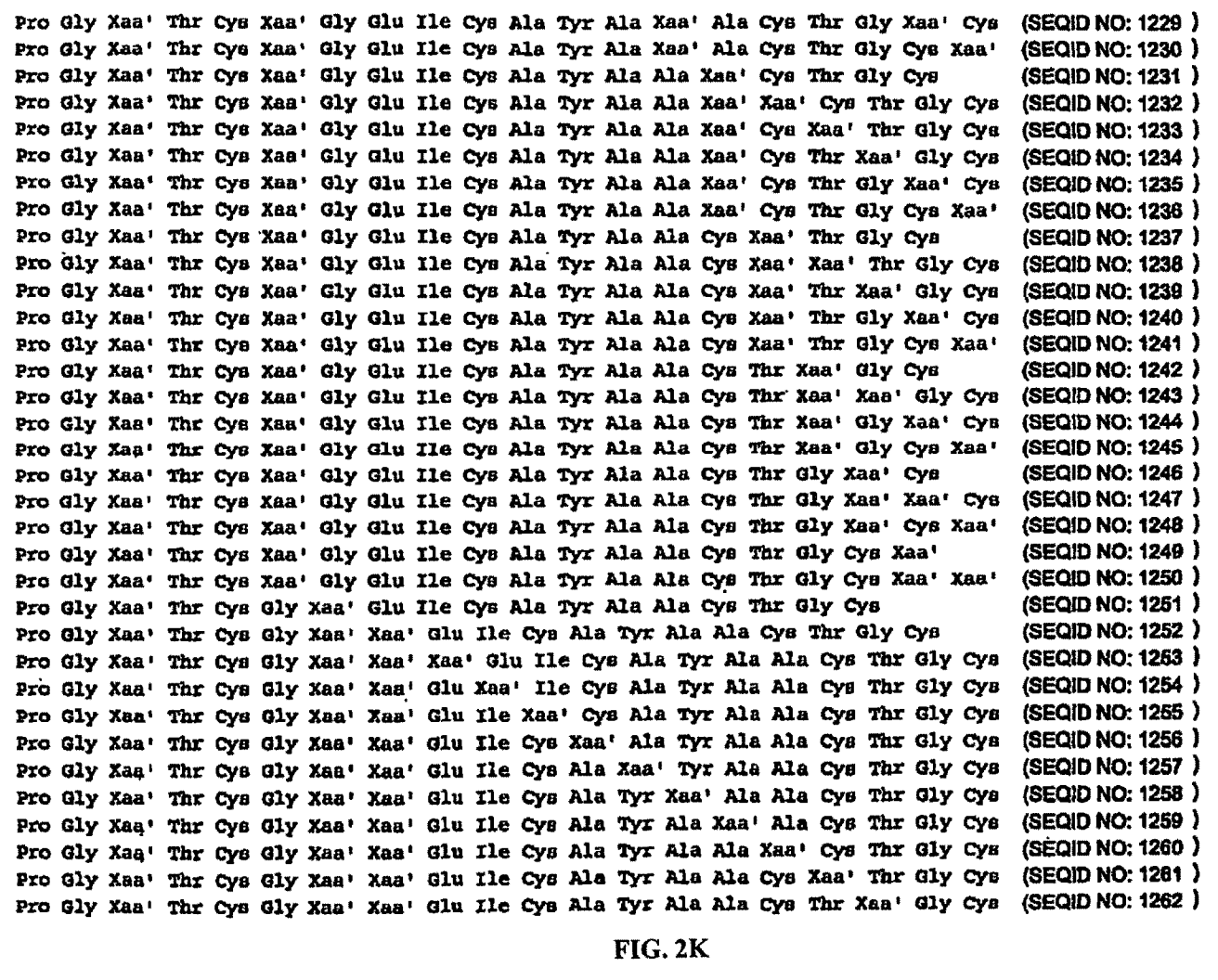
Figure 2U:
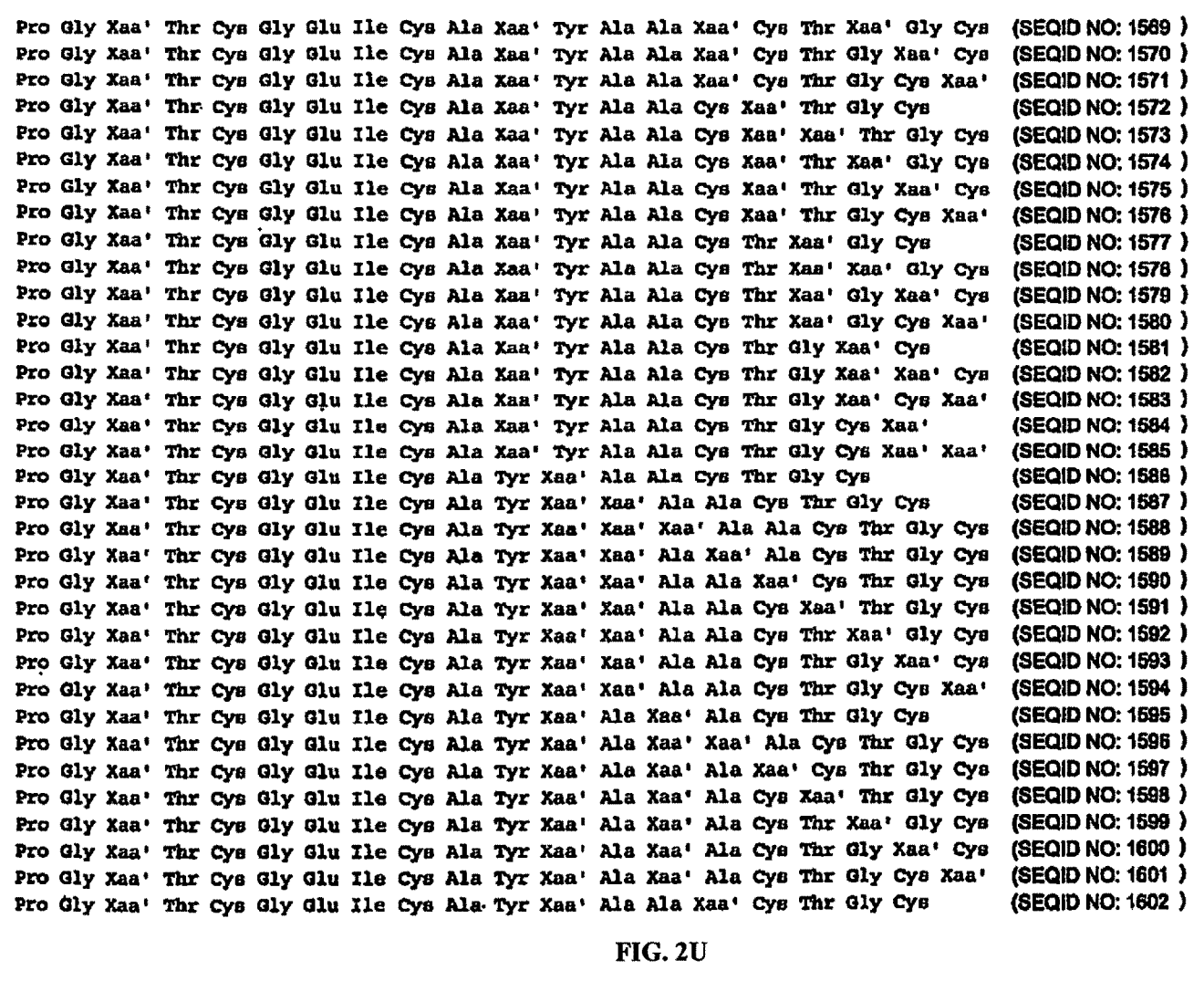

FIG. 2A-FIG. 2DJ depicts insertion variants of human guanylin in which one, two, three or four amino acids are inserted. The inserted amino acids are between $Cys_a$ and $Cys_d$ as well as amino terminal to $Cys_a$ and carboxy terminal to $Cys_d$.

The invention also features variants of peptides having the sequence $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1), e.g., variants of PGTCEICAYAACTGC human guanylin (SEQ ID NO: 4) in which up to four amino acids are deleted and/or up to four amino acids are inserted. The insertions and deletions can be between Cys4 and Cys12 in SEQ ID NO:1 or they can be amino terminal to Cys4 and/or carboxy terminal to Cys12 in SEQ ID NO:1

When $Xaa_{16}$ is Trp, Tyr or Phe, the peptide has a chymotrypsin cleavage site that is located at a position where cleavage will liberate the portion of the peptide carboxy-terminal to $Xaa_{16}$. When $Xaa_{16}$ is Lys or Arg, the peptide has a trypsin cleavage site that is located at a position where cleavage will liberate portion of the peptide carboxy-terminal to $Xaa_{16}$. Thus, if the peptide includes an analgesic peptide carboxy-terminal to $Xaa_{16}$, the peptide will be liberated in the digestive tract upon exposure to the appropriate protease. Among the analgesic peptides which can be included in the peptide are: AspPhe, endomorphin-1, endomorphin-2, nocistatin, dalargin, lupron, and substance P and other analgesic peptides described herein.

When $Xaa_1$ or the amino-terminal amino acid of the peptide of the invention (e.g., $Xaa_2$ or $Xaa_3$) is Trp, Tyr or Phe, the peptide has a chymotrypsin cleavage site that is located at a position where cleavage will liberate the portion of the peptide amino-terminal to $Xaa_1$ (or $Xaa_2$ or $Xaa_3$) along with $Xaa_1$, $Xaa_2$ or $Xaa_3$. When $Xaa_1$ or the amino-terminal amino acid of the peptide of the invention (e.g., $Xaa_2$ or $Xaa_3$) is Lys or Arg, the peptide has a trypsin cleavage site that is located at a position where cleavage will liberate portion of the peptide amino-terminal to $Xaa_1$ along with $Xaa_1$, $Xaa_2$ or $Xaa_3$). Thus, for example, if the peptide includes an analgesic peptide amino-terminal to $Xaa_1$, the peptide will be liberated in the digestive tract upon exposure to the appropriate protease. Among the analgesic peptides which can be included in the peptide are: AspPhe, endomorphin-1, endomorphin-2, nocistatin, dalargin, lupron, and substance p and other analgesic peptides described herein.

The peptides can linked, e.g., covalently linked to any of a variety of other analgesic peptides or analgesic compounds. Thus, a peptide described herein can be linked to a second therapeutic agent, e.g., an agent for treating constipation (e.g., a chloride channel activator such as SPI-0211; Sucampo Pharmaceuticals, Inc.; Bethesda, Md., a laxative such as MiraLax; Braintree Laboratories, Braintree Mass.) or some other gastrointestinal disorder. Examples of a second therapeutic agent include: acid reducing agents such as proton pump inhibitors (e.g., omeprazole, esomeprazole, lansoprazole, pantorazole and rabeprazole), H2 receptor blockers (e.g., cimetidine, ranitidine, famotidine and nizatidine), pro-motility agents such as motilin agonists (e.g., GM-611 or mitemcinal fumarate), 5HT receptor agonists (e.g., 5HT4 receptor agonists such as Zelnorm®; 5HT3 receptor agonists such as MKC-733), 5HT receptor antagonists (e.g., 5HT1, 5HT2, 5HT3 (e.g., alosetron), 5HT4 receptor antagonists, muscarinic receptor agonists, anti-inflammatory agents, antispasmodics, antidepressants, centrally-acting analgesic agents such as opioid receptor agonists, opioid receptor antagonists (e.g., naltrexone), agents for the treatment of Inflammatory bowel disease, Crohn's disease and ulcerative colitis (e.g., Traficet-EN™ (ChemoCentryx, Inc.; San Carlos, Calif.), agents that treat gastrointestinal or visceral pain, and cGMP phosphodiesterase inhibitors (motapizone, zaprinast, and suldinac sulfone). The peptides of the invention can also be linked to agents such a tianeptine (Stablon®) and other agents described in U.S. Pat. No. 6,683,072; (E)-4 (1,3bis(cyclohexylmethyl)-1,2,34-tetrahydro-2,6-diono-9H-purin-8-yl)cinnamic acid nonaethylene glycol methyl ether ester and related compounds described in WO 02/067942. The peptides can be linked to an agent selected from the group consisting of: Ca channel blockers (e.g., ziconotide), complete or partial 5HT receptor antagonists (for example 5HT3 (e.g., alosetron, ATI-7000; Aryx Therapeutics, Santa Clara Calif.), 5HT4, 5HT2, and 5HT1 receptor antagonists), complete or partial 5HT receptor agonists including 5HT3, 5HT2, 5HT4 (e.g., tegaserod, mosapride and renzapride) and 5HT1 receptor agonists, CRF receptor agonists (NBI-34041), β-3 adrenoreceptor agonists, opioid receptor agonists (e.g., loperamide, fedotozine, and fentanyl, naloxone, naltrexone, methyl nalozone, nalmefene, cypridime, beta funaltrexamine, naloxonazine, naltrindole, and nor-binaltorphimine, morphine, diphenyloxylate, enkephalin pentapeptide, asimadoline, and trimebutine), NK1 receptor antagonists (e.g., ezlopitant and SR-14033), CCK receptor agonists (e.g., loxiglumide), NK1 receptor antagonists, NK3 receptor antagonists (e.g., talnetant, osanetant (SR-142801), SSR-241586), norepinephrine-serotonin reuptake inhibitors (NSRI; e.g., milnacipran), vanilloid and cannabanoid receptor agonists (e.g., arvanil), sialorphin, sialorphin-related peptides comprising the amino acid sequence QHNPR (SEQ ID NO: 85) for example, VQHNPR (SEQ ID NO: 86); VRQHNPR (SEQ ID NO: 87); VRGQHNPR (SEQ ID NO: 88); VRGPQHNPR (SEQ ID NO: 89); VRGPRQHNPR (SEQ ID NO: 90); VRGPRRQH-NPR (SEQ ID NO: 91); and RQHNPR (SEQ ID NO: 92), compounds or peptides that are inhibitors of neprilysin, frakefamide (H-Tyr-D-Ala-Phe(F)-Phe-$NH_2$; WO 01/019849 A1), loperamide, Tyr-Arg (kyotorphin), CCK receptor agonists (caerulein), conotoxin peptides, peptide analogs of thymulin, loxiglumide, dexloxiglumide (the R-isomer of loxiglumide) (WO 88/05774) and other analgesic peptides or compounds.

Amino acid, non-amino acid, peptide and non-peptide spacers can be interposed between a peptides of the invention and a peptide that has some other biological function, e.g., an analgesic peptide or a peptide used to treat obesity. The linker can be one that is cleaved from the flanking peptides in vivo or one that remains linked to the flanking peptides in vivo. For example, glycine, beta-alanine, glycyl-glycine, glycyl-beta-alanine, gamma-aminobutyric acid, 6-aminocaproic acid, L-phenylalanine, L-tryptophan and glycil-L-valil-L-phenylalanine can be used as a spacer (Chaltin et al. 2003 Helvetica Chimica Acta 86:533-547; Caliceti et al. 1993 FARMCO 48:919-32) as can polyethylene glycols (Butterworth et al. 1987 J. Med. Chem 30:1295-302) and maleimide derivatives (King et al. 2002 Tetrahedron Lett. 43:1987-1990). Various other linkers are described in the literature (Nestler 1996 Molecular Diversity 2:35-42; Finn et al. 1984 Biochemistry 23:2554-8; Cook et al. 1994 Tetrahedron Lett. 35:6777-80; Brokx et al. 2002 Journal of Controlled Release 78:115-123; Griffin et al. 2003 J. Am. Chem. Soc. 125:6517-6531; Robinson et al. 1998 Proc. Natl. Acad. Sci. USA 95:5929-5934.

The peptides can include the amino acid sequence of a peptide that occurs naturally in a vertebrate (e.g., mammalian) species or in a bacterial species. In addition, the peptides can be partially or completely non-naturally occurring peptides. Also within the invention are peptidomimetics corresponding to the peptides of the invention.

When fully folded, disulfide bonds are present between the first and third cysteines and between the second and fourth cysteines, e.g., there is a disulfide bond between $Cys_4$ and $Cys_{12}$ and a disulfide bond between $Xaa_7$ and $Xaa_{15}$ (when $Xaa_7$ is a Cys and $Xaa_{15}$ is a Cys). In some embodiments, the peptide has only one disulfide bond, e.g., between the first and third cysteines (i.e., $Cys_4$ and $Cys_{12}$; corresponds to the first and second cysteines when $Xaa_7$ is other than Cys). In certain embodiments one or more Cys can be replaced by Mpt (mercaptoproline) or Pen (penicillamine) or Dpr (diaminopropionic acid) or some other amino acid that can covalently link to another amino acid (e.g., Cys, Mpt, Pen or Dpr). In some embodiments, one or both members of a pair of Cys residues which normally form a disulfide bond can be replaced by homocysteine, 3-mercaptoproline (Kolodziej et al. 1996 *Int J Pept Protein Res* 48:274); 8, a dimethylcysteine (Hunt et al. 1993 *Int J Pept Protein Res* 42:249) or diaminopropionic acid (Smith et al. 1978 *J Med Chem* 21:117) to form alternative internal cross-links at the positions of the normal disulfide bonds.

In addition, one or more disulfide bonds can be replaced by alternative covalent cross-links, e.g., an amide bond, an ester linkage, an alkyl linkage, a thio ester linkage, a lactam bridge, a carbamoyl linkage, a urea linkage, a thiourea linkage, a phosphonate ester linkage, an alkyl linkage, and alkenyl linkage, an ether, a thioether linkage, or an amino linkage. For example, Ledu et al. (Proceedings Nat'l Acad. Sci. 100:11263-78, 2003) described methods for preparing lactam and amide cross-links. Schafmeister et al. (J. Am.

Chem. Soc. 122:5891, 2000) describes stable, all carbon cross-links. In some cases, the generation of such alternative cross-links requires replacing the Cys residues with other residues such as Lys or Glu or non-naturally occurring amino acids.

In certain embodiments one or more amino acids can be replaced by a non-naturally occurring amino acid or a naturally or non-naturally occurring amino acid analog. For example, an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr). Phg and norTyr and other amino acids including Phe and Tyr can be substituted by, e.g., a halogen, —CH3, —OH, —CH$_2$NH$_3$, —C(O)H, —CH$_2$CH$_3$, —CN, —CH$_2$CH$_2$CH$_3$, —SH, or another group.

Further examples of unnatural amino acids include: an unnatural analogue of tyrosine; an unnatural analogue of glutamine; an unnatural analogue of phenylalanine; an unnatural analogue of serine; an unnatural analogue of threonine; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, $^{13}$C, $^{15}$N, or $^{18}$O); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α.-hydroxy containing acid; an amino thio acid containing amino acid; an α, α disubstituted amino acid; a β-amino acid; a cyclic amino acid other than proline; an O-methyl-L-tyrosine; an L-3-(2-naphthyl)alanine; a 3-methyl-phenylalanine; a p-acetyl-L-phenylalanine; an 0-4-allyl-L-tyrosine; a 4-propyl-L-tyrosine; a tri-O-acetyl-GlcNAcβ-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; a isopropyl-L-phenylalanine; L-3-(2-naphthyl)alanine; an amino-, isopropyl-, or O-allyl-containing phenylalanine analogue; a dopa, O-methyl-L-tyrosine; a glycosylated amino acid; a p-(propargyloxy) phenylalanine, dimethyl-Lysine, hydroxy-proline, mercaptopropionic acid, methyl-lysine, 3-nitro-tyrosine, norleucine, pyro-glutamic acid, Z (Carbobenzoxyl), ε-Acetyl-Lysine, β-alanine, aminobenzoyl derivative, aminobutyric acid (Abu), citrulline, aminohexanoic acid, aminoisobutyric acid, cyclohexylalanine, d-cyclohexylalanine, hydroxyproline, nitro-arginine, nitro-phenylalanine, nitro-tyrosine, norvaline, octahydroindole carboxylate, ornithine, penicillamine, tetrahydroisoquinoline, acetamidomethyl protected amino acids and a pegylated amino acid. Further examples of unnatural amino acids can be found in U.S. 20030108885, U.S. 20030082575, and the references cited therein.

In some embodiments, an amino acid can be replaced by a naturally-occurring, non-essential amino acid, e.g., taurine.

Methods to manufacture peptides containing unnatural amino acids can be found in, for example, U.S. 20030108885, U.S. 20030082575, Deiters et al., J Am Chem Soc. (2003) 125:11782-3, Chin et al., Science (2003) 301: 964-7, and the references cited therein.

Peptides that include non-natural amino acids can also be prepared using the methods described in WO02086075.

The peptides of the invention can be modified using standard modifications. Modifications may occur at the amino (N-), carboxy (C-) terminus, internally or a combination of any of the preceeding. In one aspect of the invention, there may be more than one type of modification on the peptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cy3 or Cy5. The peptides of the invention may also be modified by 2, 4-dinitrophenyl (DNP), DNP-lysin, modification by 7-Amino-4-methyl-coumarin (AMC), flourescein, NBD (7-Nitrobenz-2-Oxa-1,3-Diazole), p-nitro-anilide, rhodamine B, EDANS (5-((2-aminoethyl)amino)naphthalene-1-sulfonic acid), dabcyl, dabsyl, dansyl, texas red, FMOC, and Tamra (Tetramethylrhodamine). The peptides of the invention may also be conjugated to, for example, BSA or KLH (Keyhole Limpet Hemocyanin).

The invention also features a purified polypeptide comprising, consisting of or consisting essentially of the amino acid sequence: Xaa$_1$ Xaa$_2$ Xaa$_3$ Cys$_4$ Xaa$_5$ Xaa$_6$ Xaa$_7$ Xaa$_8$ Xaa$_9$ Xaa$_{10}$ Xaa$_{11}$ Cys$_{12}$ Xaa$_{13}$ Xaa$_{14}$ Xaa$_{15}$ Xaa$_{16}$ (SEQ ID NO:1) wherein:

Xaa$_1$ is any amino acid or is missing;
Xaa$_2$ is any amino acid or is missing;
Xaa$_3$ is any amino acid or is missing;
Xaa$_5$ is Glu;
Xaa$_6$ is Tyr, Trp, Phe or Leu;
Xaa$_7$ is Cys;
Xaa$_8$ is any of the 20 naturally-occurring amino acids other than Cys or is missing;
Xaa$_9$ is any of the 20 naturally-occurring amino acids;
Xaa$_{10}$ is Pro or Gly;
Xaa$_{11}$ is any of the 20 naturally-occurring amino acids;
Xaa$_{13}$ is Thr, Val or Gly;
Xaa$_{14}$ is Gly or Ala;
Xaa$_{15}$ is Cys; and
Xaa$_{16}$ is any of the 20 naturally-occurring amino acids or is missing.

In various embodiments: Xaa$_9$ is Asn; Xaa$_{11}$ is Ala or Thr; Xaa$_8$ is missing; and Xaa$_{16}$ is Tyr.

In other embodiments Xaa4 is immediately preceded by an amino acid sequence selected from: Ser His Thr; Pro Ser Thr; Thr; Pro Asp Pro; Ile Ala Glu Asp Ser His Thr (SEQ ID NO:8604); Ile Ala Gln Asp Pro Ser Thr (SEQ ID NO:8605); Ala Asn Thr; Asn Thr; Asp Pro Asn Thr (SEQ ID NO:8606); Lys Asn Thr; Pro Asn Thr; Ile Ala Gln Asp Pro Asn Thr (SEQ ID NO:8607); Lys Pro Asn Thr (SEQ ID NO:8608); Asp Pro Gly Thr; Pro Gly Thr; Glu Asp Pro Gly Thr (SEQ ID NO:8609); Glu Asp Pro Gly Thr (SEQ ID NO:8610); Pro Gly Thr; Pro Ala Thr; Val Ala Ala Arg Ala Asp Leu (SEQ ID NO:8611); Gly Asp Asp; Asn Asp Glu; Gln Glu Asp; Asn Asp Asp; Arg Thr Ile Ala Asn Asp Asp (SEQ ID NO:8612); Thr Ile Ala Asn Asp Asp (SEQ ID NO:8613); Asp Asp; Arg Thr Met Asp Asn Asp Glu (SEQ ID NO:8614); Arg Thr Ile Ala Gly Asp Asp (SEQ ID NO:8615); Arg Thr Ile Ala Asn Asp (SEQ ID NO:8616); Asp; Glu Asp; Arg Ser Ile Ser Gln Glu Asp (SEQ ID NO:8617); Thr Asp Glu; Arg Thr Ile Ala Thr Asp Glu (SEQ ID NO:8618); Glu; Ile Ile Thr Pro Pro Asp Pro (SEQ ID NO:8619); Gln Glu Leu; Lys Asp Asp; Gln Glu Glu; Arg Tyr Ile Asn Gln Glu Glu (SEQ ID NO:8620); Ala Ser Ser Tyr Ala Ser (SEQ ID NO:8621); and Thr Ser Ser Tyr Ala Ser (SEQ ID NO:8622).

The invention further features a purified polypeptide comprising, consisting of or consisting essentially the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1) wherein:

$Xaa_1$ is: a) Ser, Asn, Tyr, Ala, Gln, Pro, Lys, Gly, or Thr, or is missing; b) preceded by Lys or Tyr; c) any amino acid; d) missing; e) any amino acid other than Cys; or f) Lys or Arg;

$Xaa_2$ is: a) His, Asp, Glu, Ala, Ser, Asn, Gly, or is missing; b) His, Asp, Glu, Ala, Ser, Asn, Gly, Pro or is missing; c) Asp, Glu, any amino acid or is missing; d) Asp or Glu; e) any amino acid other than Cys; e) Glu; f) missing; g) Trp, Tyr or Phe; or h) Lys or Arg;

$Xaa_3$ is: a) Thr, Asp, Ser, Glu, Pro, Val or Leu; Asp or Glu; b) any amino acid other than Cys; c) Glu; d) Thr; e) Thr, Asp, Ser, Glu, Pro, Val or Leu or is missing; f) Trp, Tyr or Phe; or g) Lys or Arg;

$Xaa_4$ is: a) Cys, Mpt (mercaptoproline), Pen (penicillamine), Dpr (diaminopropionic acid), Asp, or Glu;

$Xaa_5$ is: a) any amino acid; b) Glu, Asp, Gln, Gly or Pro; c) Glu; d) Glu or Asp; e) Asp, Ile or Glu; f) any amino acid; or g) any amino acid other than Cys;

$Xaa_6$ is: a) Leu, Ile, Val, Ala, Lys, Arg, Trp, Tyr or Phe; b) Leu, Ile, Val, Lys, Arg, Tyr or Phe; Leu, Ile, Lys, Arg, Trp, Tyr or Phe; c) Leu, Ile, Val, Trp, Tyr or Phe; d) Trp, Tyr, Phe or Leu; e) Leu, Ile or Val; f) Ile, Trp or Leu; g) Trp, Tyr or Phe; h) Ile or Leu; i) Tyr; j) any amino acid; k) any amino acid except Leu; l) any natural or non-natural aromatic amino acid; or m) any amino acid other than Cys;

$Xaa_7$ is: a) Cys, Ser, or Tyr; Cys; b) Cys, Mpt (mercaptoproline), Pen (penicillamine), Dpr (diaminopropionic acid), Asp or Glu; c) Ser; or d) an amino acid other than Cys;

$Xaa_8$ is: a) Ala, Val, or Ile; b) Ala, Val, Thr, Ile, Met or is missing; c) any amino acid; d) Val; e) any amino acid other than Cys; or f) missing;

$Xaa_9$ is: a) any amino acid; b) any amino acid other than Phe and Tyr; c) any amino acid other than Phe, Tyr, and Trp; d) any amino acid other than Phe, Tyr, Trp, Ile, Leu and Val; e) any amino acid other than Phe, Tyr, Trp, Ile, Leu, Val, and His; f) any amino acid other than Gln; g) any amino acid other than Lys, Arg, Phe, Tyr, and Trp; h) any amino acid other than Lys, Arg, Phe, Tyr, Trp, Ile, Leu and Val; i) any amino acid other than Lys, Arg, Phe, Tyr, Trp, Ile, Leu, Val, and His; j) any non-aromatic amino acid; k) missing; l) Phe, Tyr, Asn, or Trp; m) Asn, Tyr, Asp or Ala; n) Asn, Gln, or Tyr; o) Phe or Tyr; p) Asn; or q) any amino acid other than Cys;

$Xaa_{10}$ is: a) Ala, Pro or Gly; b) Pro or Gly; c) Pro; d) Ala, Val, Met, Thr or Ile; e) any amino acid; f) Val; g) Val or Pro; h) Ala or Val; i) any amino acid other than Cys; j) Pro; or k) Gly;

$Xaa_{11}$ is: a) any amino acid; b) Ala, Leu, Ser, Gly, Val, Glu, Gln, Ile, Leu, Lys, Arg, or Asp; c) Ala or Gly; d) Ala; e) Ala or Val; f) any amino acid; g) Ala or Aib (alpha-aminoisobutyric acid); h) any amino acid other than Cys; i) Ala or Thr; or j) Thr.

$Xaa_{12}$ is: a) Cys, Mpt (mercaptoproline), Pen (penicillamine), Dpr (diaminopropionic acid), Asp, or Glu; or b) any amino acid other than Cys;

$Xaa_{13}$ is: a) Thr, Ala, Asn, Lys, Arg, or Trp; b) Thr, Ala, Lys, Arg, or Trp; c) any amino acid; d) any non-aromatic amino acid; e) Thr, Ala, or Trp; f) Trp, Tyr or Phe; g) Thr or Ala; h) any amino acid; i) Thr; j) any amino acid other than Cys; k) Thr, Val, or Gly; l) Thr or Val, m) Thr or Gly, n) Val or Thr; o) Val; p) Thr; or q) Gly;

$Xaa_{14}$ is: a) Gly, Pro or Ala; b) Gly; c) any amino acid; d) Gly, Ala or Ser; e) Gly or Ala; f) any amino acid other than Cys; or g) Ala;

$Xaa_{15}$ is: a) Cys, Tyr or is missing; b) Cys; c) Cys, Mpt (mercaptoproline), Pen (penicillamine), Dpr (diaminopropionic acid), Asp, Glu; or d) any amino acid other than Cys or is missing; and $Xaa_{16}$ is: a) Trp, Tyr, Phe, Asn, Ile, Val, His or Leu; b) Trp, Tyr, Phe, Asn or Leu; c) Trp, Tyr, Phe or Leu; d) Trp, Tyr, or Phe; e) Leu, Ile or Val; f) His, Leu or Ser; g) Tyr or Leu; Lys or Arg; h) His; i) any amino acid, j) Leu, or missing; k) Trp, Tyr, Phe, Lys, Arg or is missing; l) missing; m) any amino acid other than Cys; or n) Tyr.

Also featured is purified polypeptide comprising, consisting of or consisting essentially of the amino acid sequence: $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ (SEQ ID NO:1) wherein:

$Xaa_1$ is any amino acid or is missing;
$Xaa_2$ is any amino acid or is missing;
$Xaa_3$ is any amino acid or is missing;
$Xaa_4$ is Cys, Mpt (mercaptoproline), Pen (penicillamine), Dpr (diaminopropionic acid), Asp or Glu;
$Xaa_5$ is Glu;
$Xaa_6$ is Tyr, Trp, Phe or Leu;
$Xaa_7$ is Cys, Mpt (mercaptoproline), Pen (penicillamine), Dpr (diaminopropionic acid), Asp or Glu;
$Xaa_8$ is any amino acid other than Cys or is missing;
$Xaa_9$ is any amino acid;
$Xaa_{10}$ is Pro or Gly;
$Xaa_{11}$ is any amino acid;
$Xaa_{12}$ is Cys, Mpt (mercaptoproline), Pen (penicillamine), Dpr (diaminopropionic acid), Asp or Glu;
$Xaa_{13}$ is Thr, Val or Gly;
$Xaa_{14}$ is Gly or Ala;
$Xaa_{15}$ is Cys, Mpt (mercaptoproline), Pen (penicillamine), Dpr (diaminopropionic acid), Asp or Glu; and
$Xaa_{16}$ is any amino acid or is missing.

The various peptides can be present with a counterion. Useful counterions include salts of: acetate, benzenesulfonate, benzoate, calcium edetate, camsylate, carbonate, citrate, edetate (EDTA), edisylate, embonate, esylate, fumarate, gluceptate, gluconate, glutamate, glycollylarsanilate, hexylresorcinate, iodide, bromide, chloride, hydroxynaphthoate, isethionate, lactate, lactobionate, estolate, maleate, malate, mandelate, mesylate, mucate, napsylate, nitrate, pantothenate, phosphate, salicylate, stearate, succinate, sulfate, tartarate, theoclate, acetamidobenzoate, adipate, alginate, aminosalicylate, anhydromethylenecitrate, ascorbate, aspartate, camphorate, caprate, caproate, caprylate, cinnamate, cyclamate, dichloroacetate, formate, gentisate, glucuronate, glycerophosphate, glycolate, hippurate, fluoride, malonate, napadisylate, nicotinate, oleate, orotate, oxalate, oxoglutarate, palmitate, pectinate, pectinate polymer, phenylethylbarbiturate, picrate, propionate, pidolate, sebacate, rhodanide, tosylate, tannate In a second aspect, the invention also features a therapeutic or prophylactic method comprising administering a composition comprising a purified peptide comprising, consisting essentially or consisting of the amino acid sequence of SEQ ID NO:1. For the treatment of gastrointestinal disorders, the peptide can be administered orally, by rectal suppository or parenterally.

In various embodiments, the patient is suffering from a gastrointestinal disorder; the patient is suffering from a disorder selected from the group consisting of: a gastrointestinal motility disorder, irritable bowel syndrome, a functional gastrointestinal disorder, gastroesophageal reflux disease, duodenogastric reflux, functional heartburn, dyspepsia, functional dyspepsia, nonulcer dyspepsia, gastroparesis, chronic intestinal pseudo-obstruction, colonic pseudo-obstruction, obesity, congestive heart failure, or benign prostatic hyperplasia; the composition is administered orally; the peptide comprises 150, 140, 130, 120, 110, 100, 90, 80, 70, 60, 50, 40, or 30 or fewer amino acids. In other embodiments, the peptide comprises 20 or fewer amino acids, and the peptide comprises no more than 5 amino acids prior to $Cys_4$. In other embodiments the peptide comprises no more than 20, 15, 10, or 5 peptides subsequent to $Cys_{15}$. In certain embodiments $Xaa_{16}$ is a chymotrypsin or trypsin cleavage site and an analgesic peptide is present immediately following $Xaa_{16}$.

Among the useful peptides are those comprising, consisting of or consisting essentially of any of the following amino acid sequences:

(opossum guanylin) (SEQ ID NO: 40)
SHTCEICAFAACAGC;

(human guanylin) (SEQ ID NO: 4)
PGTCEICAYAACTGC;

(pig guanylin) (SEQ ID NO: 41)
PSTCEICAYAACAGC;

(rat guanylin) (SEQ ID NO: 42)
PNTCEICAYAACTGC;

(European eel guanylin, inferred) (SEQ ID NO: 43)
PDPCEICANAACTGCL;

(human uroguanylin) (SEQ ID NO: 44)
NDDCELCVNVACTGCL;

(opossum lymphoguanylin) (SEQ ID NO: 45)
QEECELCINMACTGY;

(pig uroguanylin) (SEQ ID NO: 46)
GDDCELCVNVACTGCS;

(guinea pig uroguanylin) (SEQ ID NO: 47)
NDECELCVNIACTGC;

(rat uroguanylin) (SEQ ID NO: 48)
TDECELCINVACTGC;

(opossum uroguanylin) (SEQ ID NO: 49)
QEDCELCINVACTGC;

(EAST 1) (SEQ ID NO: 50)
MPSTQYIRRPASSYASCIWCTTACASCHGRTTKPSLAT;

(SEQ ID NO: 51)
MPSTQYIRRPASSYASCIWCATACASCHGRTTKPSLAT;

(SEQ ID NO: 52)
MPSTQYIRRPTSSYASCIWCATACASCHGRTTKPSLAT;

(SEQ ID NO: 53)
MPSTQYIRRPTSSYASCIWCATVCASCHGRTTKPSLAT;

(SEQ ID NO: 54)
MPSTQYIRRPASSYASCIWYATACASCHGRTTEPSLAT;

(opossum lymphoguanylin analog) (SEQ ID NO: 55)
QEECELSINMACTGY;

(Japanese eel guanylin) (SEQ ID NO: 56)
YDECEICMFAACTGC;

(Zebrafish guanylin, inferred) (SEQ ID NO: 57)
VCEICAFAACTGC;

(Japenese eel renoguanylin, inferred) (SEQ ID NO: 58)
ADLCEICAFAACTGCL;

(SEQ ID NO: 59)
PGTCEICAYAACTGCL;

(SEQ ID NO: 60)
PGTCEICAYAACTGCLKK;

(SEQ ID NO: 61)
PNTCEICAYAACTGCKKKKKK;

(SEQ ID NO: 62)
PNTCEICAYAACTGCD;

(SEQ ID NO: 63)
PNTCEICAYAACTGCDK;

(SEQ ID NO: 64)
YPNTCEICAYAACTGC;

(SEQ ID NO: 65)
KNTCEICAYAACTGC (SEQ ID NO: 66)
KPNTCEICAYAACTGC;

(SEQ ID NO: 67)
EDPGTCEICAYAACTGC;

(SEQ ID NO: 68)
VTVQDG NFSFSLESVK KLKDLQEPQE PRVGKLRNFA PIPGEPVVPI LCSNPNFPEE LKPLCKEPNA QEILQRLEEIAEDPGTCEICAYAACTGC;

(SEQ ID NO: 69)
DPGTCEICAYAACTGC;

(SEQ ID NO: 70)
MNAFLLSALC LLGAWAALAG GVTVQDGNFS FSLESVKKLK DLQEPQEPRV GKLRNFAPIP GEPVVPILCS NPNFPEELKP LCKEPNAQEI LQRLEEIAED PGTCEICAYAACTGC;

-continued

```
                                               (SEQ ID NO: 71)
MNAFLLFALC LLGAWAALAG GVTVQDGNFS FSLEPRVGKL

RNFAPIPGEP VVPILCSNPN FPEELKPLCK EPNAQEILQR

LEEIAEDPGTCEICAYAACTGC;

(SEQ ID NO: 72)
TGSMNAFLLF ALCLLGAWAA LAGGVTVQDG NFSFSLEPRV

GKLRNFAPIP GEPVVPILCS NPNFPEELKP LCKEPNAQEI

LQRLEEIAEDPGTCEICAYAACTGCLEG;

(SEQ ID NO: 73)
NDECELCVNVACTGCL;

(SEQ ID NO: 74)
ECELCVNVACTGCL;

(SEQ ID NO: 75)
EDCELCINVACTGC;

(SEQ ID NO: 76)
NDDCELCVACTGCL;

(SEQ ID NO: 77)
FKTLRTIANDDCELCVNVACTGCL;

(SEQ ID NO: 78)
FKTLRTIANDDCLCVNVACTGCL;

(SEQ ID NO: 79)
DDCELCVNVACTGCL;

(SEQ ID NO: 80)
DCELCVNVACTGCL;

(SEQ ID NO: 81)
CELCVNVACTGCL;

(SEQ ID NO: 82)
KDDCELCVNVACTGCL;

(SEQ ID NO. 83)
PNTCEICANPACTGC.
```

The peptides can include the amino acid sequence of a peptide that occurs naturally in a vertebrate (e.g., mammalian) species or in a bacterial species. In addition, the peptides can be partially or completely non-naturally occurring peptides.

In a third aspect, the invention features a method for treating a patient suffering from constipation, the method comprising administering a composition comprising a peptide comprising, consisting essentially or consisting of the amino acid sequence of SEQ ID NO:1. Clinically accepted criteria that define constipation range from the frequency of bowel movements, the consistency of feces and the ease of bowel movement. One common definition of constipation is less than three bowel movements per week. Other definitions include abnormally hard stools or defecation that requires excessive straining (Schiller 2001 *Aliment Pharmacol Ther* 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple sclerosis, Parkinson's disease, spinal cord lesions, Neurofibromatosis, autonomic neuropathy, Chagas disease, Hirschsprung disease and cystic fibrosis. Constipation may also be the result of surgery or due to the use of drugs such as analgesics (like opioids), antihypertensives, anticonvulsants, antidepressants, antispasmodics and antipsychotics.

In various embodiments, the constipation is associated with use of a therapeutic agent; the constipation is associated with a neuropathic disorder; the constipation is post-surgical constipation; the constipation is associated with a gastrointestinal disorder; the constipation is idiopathic (functional constipation or slow transit constipation); the constipation is associated with neuropathic, metabolic or endocrine disorder (e.g., diabetes mellitus, hypothyroidism, hyperthyroidism, hypocalcaemia, Multiple Sclerosis, Parkinson's disease, spinal cord lesions, neurofibromatosis, autonomic neuropathy, Chagas disease, Hirschsprung disease or cystic fibrosis). Constipation may also be the result of surgery or due to the use of drugs such as analgesics (e.g., opioids), antihypertensives, anticonvulsants, antidepressants, antispasmodics and antipsychotics.

In a fourth aspect, the invention features a method for treating a patient suffering a gastrointestinal disorder, the method comprising administering to the patient a composition comprising a purified peptide comprising, consisting essentially of or consisting of the amino acid sequence of SEQ ID NO:1.

In various embodiments, the patient is suffering from a gastrointestinal disorder; the patient is suffering from a disorder selected from the group consisting of: a gastrointestinal motility disorder, irritable bowel syndrome, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction; Crohn's disease, ulcerative colitis, Inflammatory bowel disease, colonic pseudo-obstruction, obesity, congestive heart failure, and benign prostatic hyperplasia.

In a fifth aspect, the invention features a method for increasing gastrointestinal motility in a patient, the method comprising administering to the patient a composition comprising a purified peptide comprising, consisting essentially of or consisting of the amino acid sequence of SEQ ID NO:1.

In a sixth aspect, the invention features a method for decreasing gastrointestinal pain or visceral pain in a patient, the method comprising administering to the patient a composition comprising a purified peptide comprising, consisting essentially of or consisting of the amino acid sequence of SEQ ID NO:1.

In a seventh aspect, the invention features a method for increasing the activity of an intestinal guanylate cyclase (GC-C) receptor in a patient, the method comprising administering to the patient a composition comprising a purified peptide comprising, consisting essentially of or consisting of the amino acid sequence of SEQ ID NO:1.

In an eighth aspect, the invention features an isolated nucleic acid molecule comprising a nucleotide sequence encoding a peptide comprising, consisting essentially of or consisting of the amino acid sequence of SEQ ID NO:1.

In a ninth aspect, the invention features a composition comprising a purified polypeptide comprising, consisting essentially of or consisting of the amino acid sequence of SEQ ID NO:1. In an embodiment, the composition is a pharmaceutical composition.

In a tenth aspect, the invention features a method for treating obesity, the method comprising administering a composition comprising a purified peptide comprising, consisting essentially of or consisting of the amino acid sequence of SEQ ID NO:1. The peptide can be administered in combination with one or more agents for treatment of obesity, for example, gut hormone fragment peptide $YY_{3-36}$ ($PYY_{3-36}$) (*N. Engl. J. Med.* 349:941, 2003; ikpeapge daspeelnry yaslrhylnl vtrqry) or a variant thereof, glp-1 (glucagon-like peptide-1), exendin-4 (an inhibitor of glp-1), sibutramine, phentermine, phendimetrazine, benzphetamine hydrochloride (Didrex), orlistat (Xenical), diethylpropion hydrochloride (Tenuate), fluoxetine (Prozac), bupropion, ephedra, chromium, garcinia cambogia, benzocaine, bladderwrack (focus vesiculosus), chitosan, nomame herba, galega (Goat's Rue, French Lilac), conjugated linoleic acid, L-carnitine, fiber (psyllium, plantago, guar fiber), caffeine, dehydroepiandrosterone, germander (teucrium chamaedrys), B-hydroxy-β-methylbutyrate, ATL-962 (Alizyme PLC), and pyruvate. A peptide useful for treating obesity can be administered as a co-therapy with a peptide of the invention either as a distinct molecule or as part of a fusion protein with a peptide of the invention. Thus, for example, $PYY_{3-36}$ can be fused to the carboxy or amino terminus of a peptide of the invention. Such a fusion protein can include a chymostrypsin or trypsin cleavage site that can permit cleavage to separate the two peptides. A peptide useful for treating obesity can be administered as a co-therapy with electrostimulation (U.S. 20040015201).

In an eleventh aspect, the invention features a method for treating congestive heart failure, the method comprising: administering to the patient a composition comprising a purified peptide comprising, consisting essentially of or consisting of the amino acid sequence of SEQ ID NO:1. The peptide can be administered in combination with one or more agents for treatment of congestive heart failure, for example, a natriuretic peptide such as atrial natriuretic peptide, brain natriuretic peptide or C-type natriuretic peptide), a diuretic, or an inhibitor of angiotensin converting enzyme.

In a twelfth aspect, the invention features a method for treating benign prostatic hyperplasia, the method comprising: administering to the patient a composition comprising a purified peptide comprising, consisting essentially of or consisting of the amino acid sequence of SEQ ID NO:1.

The peptide can be administered in combination with one or more agents for treatment of BPH, for example, a 5-alpha reductase inhibitor (e.g., finasteride) or an alpha adrenergic inhibitor (e.g., doxazosine).

In a thirteenth aspect, the invention features a method for treating a patient suffering a gastrointestinal disorder, the method comprising administering to the patient a composition comprising a complete or partial agonist of the GC-C receptor. In various embodiments, the patient is suffering from a gastrointestinal disorder; the patient is suffering from a disorder selected from the group consisting of: a gastrointestinal motility disorder, irritable bowel syndrome, a functional gastrointestinal disorder, gastroesophageal reflux disease, functional heartburn, dyspepsia, functional dyspepsia, nonulcer dyspepsia, gastroparesis, chronic intestinal pseudo-obstruction, and colonic pseudo-obstruction.

In a fourteenth aspect, the invention features a method for treating a patient suffering from constipation, the method comprising administering a composition comprising a complete or partial agonist of the GC-C receptor.

In a fifteenth aspect, the invention features a method for increasing gastrointestinal motility in a patient, the method comprising administering to the patient a composition comprising a complete or partial agonist of the GC-C receptor.

In a sixteenth aspect, the invention features a method for decreasing gastrointestinal pain or visceral pain in a patient, the method comprising administering to the patient a composition comprising a complete or partial agonist of the GC-C receptor.

In a seventeenth aspect, the invention features a method for treating congestive heart failure, the method comprising administering a complete or partial agonist of the GC-C receptor. GC-C agonists can act in the kidney and adrenal gland to control natriuresis, kaliuresis, and diuresis thereby reducing the build-up of fluid associated with congestive heart failure (Lorenz et al. *J Clin Invest* 112:1138, 2003; Carrithers et al. *Kidney Int* 65:40, 2004). The agonist can be administered in combination with one or more agents for treatment of congestive heart failure, for example, a natriuretic peptide such as atrial natriuretic peptide, brain natriuretic peptide or C-type natriuretic peptide), a diuretic, or an inhibitor of angiotensin converting enzyme.

In an eighteenth aspect, the invention features a method for treating BPH, the method comprising administering a complete or partial agonist of the GC-C receptor. GC-C agonists acting in the prostate can reduce cellular hypertrophy and complications associated with cellular hypertrophy. The agonist can be administered in combination with one or more agents for treatment of BPH, for example, a 5-alpha reductase inhibitor (e.g., finasteride) or an alpha adrenergic inhibitor (e.g., doxazosine).

In a nineteenth aspect, the invention features a method for treating obesity, the method comprising administering a complete or partial agonist of the GC-C receptor. The agonist can be administered in combination with one or more agents for treatment of obesity, for example, sibutramine.

The peptides and agonists of the GC-C receptor can be used to treat constipation or decreased intestinal motility, slow digestion or slow stomach emptying. The peptides can be used to relieve one or more symptoms of IBS (bloating, pain, constipation), GERD (acid reflux into the esophagus), duodenogastric reflux, functional dyspepsia, or gastroparesis (nausea, vomiting, bloating, delayed gastric emptying) and other disorders described herein.

Clinically accepted criteria that define constipation range from the frequency of bowel movements, the consistency of feces and the ease of bowel movement. One common definition of constipation is less than three bowel movements per week. Other definitions include abnormally hard stools or defecation that requires excessive straining (Schiller 2001, Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple Sclerosis, Parkinson's disease, spinal cord lesions, Neurofibromatosis, autonomic neuropathy, Chagas disease, Hirschsprung's disease and cystic fibrosis. Constipation may also be the result of surgery or due to the use of drugs such as analgesics (like opioids), antihypertensives, anticonvulsants, antidepressants, antispasmodics and antipsychotics.

In a twentieth aspect, the invention features isolated nucleic acid molecules comprising or consisting of a sequence encoding a peptide of the invention. The invention also features vectors, e.g., expression vectors that include such nucleic acid molecules and can be used to express a peptide of the invention in a cultured cell (e.g., a eukaryotic cell or a prokaryotic cell). The vector can further include one or more regulatory elements, e.g., a heterologous promoter or elements required for translation operably linked to the sequence encoding the peptide. In some cases the nucleic acid molecule will encode an amino acid sequence that includes the amino acid sequence of a peptide of the invention. For example, the nucleic acid molecule can encode a preprotein or a preproprotein that can be processed to produce a peptide of the invention.

A vector that includes a nucleotide sequence encoding a peptide of the invention or a peptide or polypeptide comprising a peptide of the invention may be either RNA or DNA, single- or double-stranded, prokaryotic, eukaryotic, or viral. Vectors can include transposons, viral vectors, episomes, (e.g., plasmids), chromosomes inserts, and artificial chromosomes (e.g. BACs or YACs). Suitable bacterial hosts for expression of the encode peptide or polypeptide include, but are not limited to, E. coli. Suitable eukaryotic hosts include yeast such as S. cerevisiae, other fungi, vertebrate cells, invertebrate cells (e.g., insect cells), plant cells, human cells, human tissue cells, and whole eukaryotic organisms. (e.g., a transgenic plant or a transgenic animal). Further, the vector nucleic acid can be used to generate a virus such as vaccinia or baculovirus.

As noted above the invention includes vectors and genetic constructs suitable for production of a peptide of the invention or a peptide or polypeptide comprising such a peptide. Generally, the genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art and may be functional in, but are not limited to, a bacterium, yeast, plant, or animal cell. The expression vector can also include a translation regulatory sequence (e.g., an untranslated 5' sequence, an untranslated 3' sequence, a poly A addition site, or an internal ribosome entry site), a splicing sequence or splicing regulatory sequence, and a transcription termination sequence. The vector can be capable of autonomous replication or it can integrate into host DNA.

The invention also includes isolated host cells harboring one of the forgoing nucleic acid molecules and methods for producing a peptide by culturing such a cell and recovering the peptide or a precursor of the peptide. Recovery of the peptide or precursor may refer to collecting the growth solution and need not involve additional steps of purification. Proteins of the present invention, however, can be purified using standard purification techniques, such as, but not limited to, affinity chromatography, thermaprecipitation, immunoaffinity chromatography, ammonium sulfate precipitation, ion exchange chromatography, filtration, electrophoresis and hydrophobic interaction chromatography.

In a twenty first aspect, the invention features a method of increasing the level of cyclic guanosine 3'-monophosphate (cGMP) in an organ, tissue (e.g, the intestinal mucosa), or cell (e.g., a cell bearing GC-A receptor) by administering a composition that includes a peptide of the invention.

The details of one or more embodiments of the invention are set forth in the accompanying description and claims. The publications and patents referenced herein are incorporated by reference.

DRAWINGS

FIG. 1A-FIG. 1Q depicts deletion variants of human guanylin in which one, two, three or four amino acids are deleted. The deleted amino acids are between $Cys_a$ and $Cys_d$ as well as amino terminal to $Cys_a$.

FIG. 2A-FIG. 2DJ depicts insertion variants of human guanylin in which one, two, three or four amino acids are inserted. The inserted amino acids are between $Cys_a$ and $Cys_d$ as well as amino terminal to $Cys_a$ and carboxy terminal to $Cys_d$.

FIG. 3A-FIG. 3CL depicts various polypeptides which include the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:1) wherein: $Xaa_1$ is any amino acid or is missing; $Xaa_2$ is any amino acid or is missing; $Xaa_3$ is any amino acid or is missing; $Xaa_5$ is Glu; $Xaa_6$ is Tyr, Trp, Phe or Leu; $Xaa_7$ is Cys;
$Xaa_8$ is any of the 20 naturally-occurring amino acids other than Cys or is missing; $Xaa_9$ is any of the 20 naturally-occurring amino acids; $Xaa_{10}$ is Pro or Gly; $Xaa_{11}$ is any of the 20 naturally-occurring amino acids; $Xaa_{13}$ is Thr, Val or Gly; $Xaa_{14}$ is Gly or Ala; $Xaa_{15}$ is Cys; and $Xaa_{16}$ is any of the 20 naturally-occurring amino acids or is missing.

DETAILED DESCRIPTION

The peptides of the invention bind to the guanylate cyclase (GC-C) receptor, a key regulator of fluid and electrolyte balance in the intestine and kidney. When stimulated, this receptor, which is located on the apical membrane of the intestinal epithelial surface, causes an increase in intestinal epithelial cyclic GMP (cGMP). This increase in cGMP is believed to cause a decrease in water and sodium absorption and an increase in chloride and potassium ion secretion, leading to changes in intestinal fluid and electrolyte transport and increased intestinal motility. The intestinal GC-C receptor possesses an extracellular ligand binding region, a transmembrane region, an intracellular protein kinase-like region and a cyclase catalytic domain. Proposed functions for the GC-C receptor are the fluid and electrolyte homeostasis, the regulation of epithelial cell proliferation and the induction of apoptosis (Shaibhubhai 2002 Curr Opin Drug Dis Devel 5:261-268).

In addition to being expressed in gastrointestinal epithelial cells, GC-C is expressed in extra-intestinal tissues including kidney, lung, pancreas, pituitary, adrenal, developing liver, heart and male and female reproductive tissues (reviewed in Vaandrager 2002 Mol Cell Biochem 230:73-83). This suggests that the GC-C receptor agonists can be used in the treatment of disorders outside the GI tract, for example, congestive heart failure and benign prostatic hyperplasia.

Ghrelin, a peptide hormone secreted by the stomach, is a key regulator of appetite in humans. Ghrelin expression levels are regulated by fasting and by gastric emptying. (Kim et al., 2003, Neuroreprt 14:1317-20; Gualillo et al., 2003, FEBS Letts 552: 105-9). Thus, by increasing gastrointestinal motility, GC-C receptor agonists may also be used to regulate obesity.

In humans, the GC-C receptor is activated by guanylin (Gn) (U.S. Pat. No. 596,097), uroguanylin (Ugn) (U.S. Pat. No. 5,140,102) and lymphoguanylin (Forte et al. 1999 Endocrinology 140:1800-1806).

Many gastrointestinal disorders, including IBS, are associated with abdominal or visceral pain. Certain of the peptides of the invention include the analgesic or anti-nociceptive tags such as the carboxy-terminal sequence AspPhe immediately following a Trp, Tyr or Phe (i.e., a chymotrypsin cleavage site) or following Lys or Arg (a trypsin cleavage site). Chymotrypsin in the intestinal tract will cleave such peptides immediately carboxy terminal to the Trp, Phe or Tyr residue, releasing the dipeptide, AspPhe. This dipeptide has been shown to have analgesic activity is animal models (Abdikkahi et al. 2001 Fundam Clin Phar-

*macol* 15:117-23; Nikfar et al 1997, 29:583-6; Edmundson et al 1998 *Clin Pharmacol Ther* 63:580-93). In this manner such peptides can treat both pain and inflammation. Other analgesic peptides can be present at the carboxy terminus of the peptide (following a cleavage site) including: endomorphin-1, endomorphin-2, nocistatin, dalargin, lupron, and substance P. As described in greater detail below, various analgesic peptides and compounds can be covalently linked to or used in combination therapy with the therapeutic peptides described herein.

In the human body an inactive form of chymotrypsin, chymotrypsinogen is produced in the pancreas. When this inactive enzyme reaches the small intestine it is converted to active chymotrypsin by the excision of two di-peptides. Active chymotrypsin will cleave peptides at the peptide bond on the carboxy-terminal side of Trp, Tyr or Phe. The presence of active chymotrypsin in the intestinal tract will lead to cleavage of certain of the peptides of the invention having an appropriately positioned chymotrypsin cleavage site. Certain of the peptides of the invention include a Trp, Tyr or Phe immediately followed by a carboxy-terminal analgesic peptide. It is expected that chymotrypsin cleavage will release the analgesic peptide from peptide of the invention having an appropriately positioned chymotrypsin cleavage site as the peptide passes through the intestinal tract.

Trypsinogen, like chymotrypsin, is a serine protease that is produced in the pancreas and is present in the digestive tract. The active form, trypsin, will cleave peptides having a Lys or Arg. The presence of active trypsin in the intestinal tract will lead to cleavage of certain of the peptides of the invention having an appropriately positioned trypsin cleavage site. It is expected that chymotrypsin cleavage will release the analgesic peptide from peptide of the invention having an appropriately positioned trypsin cleavage site as the peptide passes through the intestinal tract.

In some cases, the peptides of the invention are produced as a prepro protein. The prepro protein can include any suitable prepro sequence, including, for example, mnafllsalc llgawaalag gvtvqdgnfs fslesvkklk dlqepqepry gklrnfapip gepvvpilcs npnfpeelkp lckepnaqei lqrleeiaed (SEQ ID NO:) and mgcraasgll pgvavvllll lqstqsvyiq yqgfrvqles nfiddsdleaq wapspriqaq sllpavchhp alpqdlqpvc asqeassific firth (SEQ ID NO:) or a bacterial leader sequence such as: mkksilfiflsv-lsfspfaqdakpvesskekitleskkenialdcsnksgpesmn. Where the peptide is produced by a bacterial cell, e.g., *E. coli*, the forgoing leader sequence will be cleaved and the mature peptide will be efficiently secreted from the bacterial cell. U.S. Pat. No. 5,395,490 describes vectors, expression systems and methods for the efficient production of certain mature peptides having disulfide bonds in bacterial cells and methods for achieving efficient secretion of such mature peptides. The vectors, expression systems and methods described in U.S. Pat. No. 5,395,490 can be used to produce the polypeptides of the present invention.

Variant Peptides

The invention includes variant peptides that can include one, two, three, four, or five or more (e.g., 6, 7, 8, 9, 10, 11, 12, 13, 14, or 15) amino acid substitutions compared to any of the peptides described above. The substitution(s) can be conservative or non-conservative. The naturally-occurring amino acids can be substituted by D-isomers of any amino acid, non-natural amino acids, natural and non-natural amino acid analogs, and other groups. A conservative amino acid substitution results in the alteration of an amino acid for a similar acting amino acid, or amino acid of like charge, polarity, or hydrophobicity. At some positions, even conservative amino acid substitutions can reduce the activity of the peptide. A conservative substitution can substitute a naturally-occurring amino acid for a non-naturally-occurring amino acid. Among the naturally occurring amino acid substitutions generally considered conservative are:

| For Amino Acid | Code | Replace with any of |
|---|---|---|
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro | |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

In some circumstances it can be desirable to treat patients with a variant peptide that binds to and activates intestinal GC-C receptor, but is less active or more active than the non-variant form of the peptide. Reduced activity can arise from reduced affinity for the receptor or a reduced ability to activate the receptor once bound or reduced stability of the peptide. Increased activity can arise from increased affinity for the receptor or an increased ability to activate the receptor once bound or increased stability of the peptide.

In some peptides one or both members of one or both pairs of Cys residues which normally form a disulfide bond can be replaced by homocysteine, 3-mercaptoproline (Kolodziej et al. 1996 *Int J Pept Protein Res* 48:274); 4, 4 dimethylcysteine (Hunt et al. 1993 *Int J Pept Protein Res* 42:249) or diaminopropionic acid (Smith et al. 1978 *J Med Chem* 21:117) to form alternative internal cross-links at the positions of the normal disulfide bonds.

Production of Peptides

Useful peptides can be produced either in bacteria including, without limitation, *E. coli*, or in other existing systems for peptide or protein production (e.g., *Bacillus subtilis*, baculovirus expression systems using *Drosophila* Sf9 cells, yeast or filamentous fungal expression systems, mammalian cell expression systems), or they can be chemically synthesized.

If the peptide or variant peptide is to be produced in bacteria, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally-occurring bacterial ST peptide. The secreted, mature peptide can be purified from the culture medium.

The sequence encoding a peptide of the invention is can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B subtilis, Pseudomonas, Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide of the invention can also be fused to a nucleic acid encoding a polypeptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single polypeptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants of the invention in protein expression systems other than bacteria, and well known to those skilled in the art, can also be used to produce peptides in a biological system.

Mature peptides and variants thereof can be synthesized by the solid-phase method using an automated peptide synthesizer. For example, the peptide can be synthesized on Cyc(4-CH$_2$ Bxl)-OCH$_2$-4-(oxymethyl)-phenylacetamidomethyl resin using a double coupling program. Protecting groups must be used appropriately to create the correct disulfide bond pattern. For example, the following protecting groups can be used: t-butyloxycarbonyl (alpha-amino groups); acetamidomethyl (thiol groups of Cys residues B and E); 4-methylbenyl (thiol groups of Cys residues C and F); benzyl (y-carboxyl of glutamic acid and the hydroxyl group of threonine, if present); and bromobenzyl (phenolic group of tyrosine, if present). Coupling is effected with symmetrical anhydride of t-butoxylcarbonylamino acids or hydroxybenzotriazole ester (for asparagine or glutamine residues), and the peptide is deprotected and cleaved from the solid support in hydrogen fluoride, dimethyl sulfide, anisole, and p-thiocresol using 8/1/1/0.5 ratio (v/v/v/w) at 0° C. for 60 min. After removal of hydrogen fluoride and dimethyl sulfide by reduced pressure and anisole and p-thiocresol by extraction with ethyl ether and ethyl acetate sequentially, crude peptides are extracted with a mixture of 0.5M sodium phosphate buffer, pH 8.0 and N,N-dimethylformamide using 1/1 ratio, v/v. The disulfide bond for Cys residues B and E is the formed using dimethyl sulfoxide (Tam et al. (1991) *J. Am. Chem. Soc.* 113:6657-62). The resulting peptide is the purified by reverse-phase chromatography. The disulfide bond between Cys residues C and F is formed by first dissolving the peptide in 50% acetic acid in water. Saturated iodine solution in glacial acetic acid is added (1 ml iodine solution per 100 ml solution). After incubation at room temperature for 2 days in an enclosed glass container, the solution is diluted five-fold with deionized water and extracted with ethyl ether four times for removal of unreacted iodine. After removal of the residual amount of ethyl ether by rotary evaporation the solution of crude product is lyophilized and purified by successive reverse-phase chromatography.

Intestinal GC-C Receptor Binding and Activity Assays

The ability of peptides, variant peptides and other compounds to bind to and activate the intestinal GC-C receptor can be tested using the T84 human colon carcinoma cell line (American Type Culture Collection (Bethesda, Md.).

Briefly, cells are grown to confluency in 24-well culture plates with a 1:1 mixture of Ham's F12 medium and Dulbecco's modified Eagle's medium (DMEM), supplemented with 5% fetal calf serum and are used at between passages 54 and 60.

Monolayers of T84 cells in 24-well plates are washed twice with 1 ml/well DMEM, then incubated at 37° C. for 10 min with 0.45 ml DMEM containing 1 mM isobutylmethylxanthine (IBMX), a cyclic nucleotide phosphodiesterase inhibitor. Test peptides (50 Tl) are then added and incubated for 30 minutes at 37° C. The media is aspirated and the reaction is terminated by the addition of ice cold 0.5 ml of 0.1N HCl. The samples are held on ice for 20 minutes and then evaporated to dryness using a heat gun or vacuum centrifugation. The dried samples are resuspended in 0.5 ml of phosphate buffer provided in the Cayman Chemical Cyclic GMP EIA kit (Cayman Chemical, Ann Arbor, Mich.). Cyclic GMP is measured by EIA according to procedures outlined in the Cayman Chemical Cyclic GMP EIA kit.

For the binding assay, T84 cell monolayers in 24-well plates are washed twice with 1 ml of binding buffer (DMEM containing 0.05% bovine serum albumin and 25 mM HEPES, pH 7.2), then incubated for 30 min at 37° C. in the presence of mature radioactively labeled *E. coli* ST peptide and the test material at various concentrations. The cells are then washed 4 times with 1 ml of DMEM and solubilized with 0.5 ml/well 1N NaOH. The level of radioactivity in the solubilized material is then determined using standard methods.

Murine Gastrointestinal Transit (GIT) Assay

In order to determine whether a test compound or a peptide, increases the rate of gastrointestinal transit, the test compound can be tested in the murine gastrointestinal transit (GIT) assay (Moon et al. *Infection and Immunity* 25:127, 1979). In this assay, charcoal, which can be readily visualized in the gastrointestinal tract is administered to mice after the administration of a test compound. The distance traveled by the charcoal is measured and expressed as a percentage of the total length of the colon.

Mice are fasted with free access to water for 12 to 16 hours before the treatment with peptide or control buffer. The peptides are orally administered at 1 Tg/kg-1 mg/kg of peptide in buffer (20 mM Tris pH 7.5) seven minutes before being given an oral dose of 5% Activated Carbon (Aldrich 242276-250G). Control mice are administered buffer only before being given a dose of Activated Carbon. After 15 minutes, the mice are sacrificed and their intestines from the stomach to the cecum are dissected. The total length of the intestine as well as the distance traveled from the stomach to the charcoal front is measured for each animal and the results are expressed as the percent of the total length of the intestine traveled by the charcoal front. Results are reported as the average of 10 mice±standard deviation. A comparison of the distance traveled by the charcoal between the mice treated with peptide versus the mice treated with vehicle alone is performed using a Student's t test and a statistically significant difference is considered for P<0.05. Positive controls for this assay may include commercially available wild-type ST peptide (Sigma-Aldrich, St Louis, Mo.) and Zelnorm®, a drug approved for IBS that is an agonist for the serotonin receptor 5HT4.

Suckling Mouse Model of Intestinal Secretion (SuMi Assay)

The peptides of the invention can be tested for their ability to increase intestinal secretion using a suckling mouse model of intestinal secretion. In this model a test compound is administered to suckling mice that are between seven and nine days old. After the mice are sacrificed, the gastrointestinal tract from the stomach to the cecum is dissected ("guts"). The remains ("carcass") as well as the guts are weighed and the ratio of guts to carcass weight is calculated. If the ratio is above 0.09, one can conclude that the test compound increases intestinal secretion. Controls for this assay may include wild-type ST peptide and Zelnorm®

Phenylbenzoquinone-Induced Writhing Model

The PBQ-induced writhing model can be used to assess pain control activity of the peptides and GC-C receptor agonists of the invention. This model is described by Siegmund et al. (1957 Proc. Soc. Exp. Bio. Med. 95:729-731). Briefly, one hour after oral dosing with a test compound, e.g., a peptide, morphine or vehicle, 0.02% phenylbenzoquinone (PBQ) solution (12.5 mL/kg) is injected by intraperitoneal route into the mouse. The number of stretches and writhings are recorded from the $5^{th}$ to the $10^{th}$ minute after PBQ injection, and can also be counted between the $35^{th}$ and $40^{th}$ minute and between the $60^{th}$ and $65^{th}$ minute to provide a kinetic assessment. The results are expressed as the number of stretches and writhings (mean±SEM) and the percentage of variation of the nociceptive threshold calculated from the mean value of the vehicle-treated group. The statistical significance of any differences between the treated groups and the control group is determined by a Dunnett's test using the residual variance after a one-way analysis of variance (P<0.05) using SigmaStat Software.

Colonic Hyperalgesia Animal Models

Hypersensitivity to colorectal distension is a common feature in patients with IBS and may be responsible for the major symptom of pain. Both inflammatory and non-inflammatory animal models of visceral hyperalgesia to distension have been developed to investigate the effect of compounds on visceral pain in IBS.

I. Trinitrobenzenesulphonic Acid (TNBS)-Induced Rectal Allodynia Model

Male Wistar rats (220-250 g) are premedicated with 0.5 mg/kg of acepromazine injected intraperitoneally (IP) and anesthetized by intramuscular administration of 100 mg/kg of ketamine. Pairs of nichrome wire electrodes (60 cm in length and 80 µm in diameter) are implanted in the striated muscle of the abdomen, 2 cm laterally from the white line. The free ends of electrodes are exteriorized on the back of the neck and protected by a plastic tube attached to the skin. Electromyographic (EMG) recordings are started 5 days after surgery. Electrical activity of abdominal striated muscle is recorded with an electroencephalograph machine (Mini VIII, Alvar, Paris, France) using a short time constant (0.03 sec.) to remove low-frequency signals (<3 Hz).

Ten days post surgical implantation, trinitrobenzenesulphonic acid (TNBS) is administered to induce rectal inflammation. TNBS (80 mg $kg^{-1}$ in 0.3 ml 50% ethanol) is administered intrarectally through a silicone rubber catheter introduced at 3 cm from the anus under light diethyl-ether anesthesia, as described (Morteau et al. 1994 Dig Dis Sci 39:1239). Following TNBS administration, rats are placed in plastic tunnels where they are severely limited in mobility for several days before colorectal distension (CRD). Experimental compound is administered one hour before CRD which is performed by insertion into the rectum, at 1 cm of the anus, a 4 cm long balloon made from a latex condom (Gue et al, 1997 *Neurogastroenterol. Motil.* 9:271). The balloon is fixed on a rigid catheter taken from an embolectomy probe (Fogarty). The catheter attached balloon is fixed at the base of the tail. The balloon, connected to a barostat is inflated progressively by step of 15 mmHg, from 0 to 60 mmHg, each step of inflation lasting 5 min. Evaluation of rectal sensitivity, as measured by EMG, is performed before (1-2 days) and 3 days following rectal instillation of TNBS.

The number of spike bursts that corresponds to abdominal contractions is determined per 5 min periods. Statistical analysis of the number of abdominal contractions and evaluation of the dose-effects relationships is performed by a one way analysis of variance (ANOVA) followed by a post-hoc (Student or Dunnett tests) and regression analysis for ED50 if appropriate.

II. Stress-Induced Hyperalgesia Model

Male Wistar Rats (200-250 g) are surgically implanted with nichrome wire electrodes as in the TNBS model. Ten days post surgical implantation, partial restraint stress (PRS), is performed as described by Williams et al. for two hours (Williams et al. 1988 Gastroenterology 64:611). Briefly, under light anaesthesia with ethyl-ether, the foreshoulders, upper forelimbs and thoracic trunk are wrapped in a confining harness of paper tape to restrict, but not prevent body movements. Control sham-stress animals are anaesthetized but not wrapped. Thirty minutes before the end of the PRS session, the animals are administered testcompound or vehicle. Thirty minutes to one hour after PRS completion, the CRD distension procedure is performed as described above for the TNBS model with barostat at pressures of 15, 30, 45 and 60 mm Hg. Statistical analysis on the number of bursts is determined and analyzed as in the TNBS model above.

Administration of Peptides and GC-C Receptor Agonists

For treatment of gastrointestinal disorders, the peptides and agonists of the invention are can be administered orally, e.g., as a tablet or cachet containing a predetermined amount of the active ingredient, pellet, gel, paste, syrup, bolus, electuary, slurry, capsule; powder; granules; as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The peptides and agonists can be co-administered with other agents used to treat gastrointestinal disorders including but not limited to acid suppressing agents such as Histamine-2 receptor agonists (H2As) and proton pump inhibitors (PPIs). The peptides and agonists can also be administered by rectal suppository. For the treatment of disorders outside the gastrointestinal tract such as congestive heart failure and benign prostatic hypertrophy, peptides and agonists can be administered parenterally or orally.

The peptides described herein can be used alone or in combination with other agents. For example, the peptides can be administered together with one or more analgesic peptides or compounds. The analgesic peptide and/or compound can be covalently attached to a peptide described herein or it can be a separate agent that is administered together with or sequentially with a peptide described herein in a combination therapy.

Combination therapy can be achieved by administering two or more agents, e.g., a peptide described herein and an analgesic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The agents, alone or in combination, can be combined with any pharmaceutically acceptable carrier or medium. Thus, they can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose, diluents, lubricants, binders, disintegrating agents, and the like), etc. If desired, tablet dosages of the disclosed compositions may be coated by standard aqueous or nonaqueous techniques.

Compositions of the present invention may also optionally include other therapeutic ingredients, anti-caking agents, preservatives, sweetening agents, colorants, flavors, desiccants, plasticizers, dyes, and the like. Any such optional ingredient must be compatible with the compound of the invention to insure the stability of the formulation.

The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myo-inositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents such as:
BINDERS: corn starch, potato starch, other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch (e.g., STARCH 1500® and STARCH 1500 LM®, sold by Colorcon, Ltd.), hydroxypropyl methyl cellulose, microcrystalline cellulose (e.g. AVICEL™, such as, AVICEL-PH-101™, -103™ and -105™, sold by FMC Corporation, Marcus Hook, Pa., USA), or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, or mixtures thereof, DISINTEGRANTS: agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, or mixtures thereof, LUBRICANTS: calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W. R. Grace Co., Baltimore, Md. USA), a coagulated aerosol of synthetic silica (Deaussa Co., Plano, Tex. USA), a pyrogenic silicon dioxide (CAB-O-SIL, Cabot Co., Boston, Mass. USA), or mixtures thereof, ANTI-CAKING AGENTS: calcium silicate, magnesium silicate, silicon dioxide, colloidal silicon dioxide, talc, or mixtures thereof, ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof, and COATING AGENTS: sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, or mixtures thereof.

The agents either in their free form or as a salt can be combined with a polymer such as polylactic-glycolic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly(M-caprolactone) and poly(alkylene oxide) (U.S. 20030068384) to create a sustained release formulation. Such formulations can be used to implants that release a peptide or another agent over a period of a few days, a few weeks or several months depending on the polymer, the particle size of the polymer, and the size of the implant (see, e.g., U.S. Pat. No. 6,620,422). Other sustained release formulations and polymers for use in such formulations are described in EP 0 467 389 A2, WO 93/24150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. No. 5,968,895, U.S. Pat. No. 6,180,608, U.S. 20030171296, U.S. 20020176841, U.S. Pat. No. 5,672, 659, U.S. Pat. No. 5,893,985, U.S. Pat. No. 5,134,122, U.S. Pat. No. 5,192,741, U.S. Pat. No. 5,192,741, U.S. Pat. No. 4,668,506, U.S. Pat. No. 4,713,244, U.S. Pat. No. 5,445,832 U.S. Pat. No. 4,931,279, U.S. Pat. No. 5,980,945, WO 02/058672, WO 9726015, WO 97/04744, and, US20020019446. In such sustained release formulations microparticles of peptide are combined with microparticles of polymer. One or more sustained release implants can be placed in the large intestine, the small intestine or both. U.S. Pat. No. 6,011,011 and WO 94/06452 describe a sustained release formulation providing either polyethylene glycols (i.e. PEG 300 and PEG 400) or triacetin. WO 03/053401 describes a formulation which may both enhance bioavailability and provide controlled release of the agent within the GI tract. Additional controlled release formulations are described in WO 02/38129, EP 326 151, U.S. Pat. No. 5,236,704, WO 02/30398, WO 98/13029; U.S. 20030064105, U.S. 20030138488A1, U.S. 20030216307A1,U.S. Pat. No. 6,667,060, WO 01/49249, WO 01/49311, WO 01/49249, WO 01/49311, and U.S. Pat. No. 5,877,224.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115-124)). The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranassaly using the formulation described in U.S. Pat. No. 5,179,079. Formulations suitable for parenteral injection are described in WO 00/62759. The agents can be administered using the casein formulation described in U. S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-powder inhalers (DPIs)) can also be used in intranasal applications. Aerosol formulations are stable dispersions or suspensions of solid material and liquid droplets in a gaseous medium and can be placed into pressurized acceptable propellants, such as hydrofluroalkanes (HFAs, i.e. HFA-134a and HFA-227, or a mixture thereof), dichlorodifluoromethane (or other chlorofluocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a C8-C16 fatty acid salt, a bile salt, a phospholipid, or alkyl saccharide are advantageous in that some of them also reportedly enhance absorption of the peptide in the formulation. Also suitable in the invention are dry powder formulations comprising a therapeutically effective amount of active compound blended with an appropriate carrier and adapted for use in connection with a dry-powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. No. 5,230,884, U.S. Pat. No. 5,292,499, WO 017/8694, WO 01/78696, U.S. 2003019437, U. S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. No. 5,348,730, U.S. Pat. No. 6,436,367, WO 91/04011, and U.S. Pat. No. 6,294,153 and U.S. Pat. No. 6,290,987 describes a liposomal based formulation that can be administered via aerosol or other means. Powder formulations for inhalation are described in U.S. 20030053960 and WO 01/60341. The agents can be administered intranasally as described in U.S. 20010038824. Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agents can be a free acid or base, or a pharmacologically acceptable salt thereof. Solids can be dissolved or dispersed immediately prior to administration or earlier. In some circumstances the preparations include a preservative to prevent the growth of microorganisms. The pharmaceutical forms suitable for injection can include sterile aqueous or organic solutions or dispersions which include, e.g., water, an alcohol, an organic solvent, an oil or other solvent or dispersant (e.g., glycerol, propylene glycol, polyethylene glycol, and vegetable oils). The formulations may contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Pharmaceutical agents can be sterilized by filter sterilization or by other suitable means.

The agent can be fused to immunoglobulins or albumin, or incorporated into a liposome to improve half-life. The agent can also be conjugated to polyethylene, glycol (PEG) chains. Methods for pegylation and additional formulations containing PEG-conjugates (i.e. PEG-based hydrogels, PEG modified liposomes) can be found in Harris and Chess, Nature Reviews Drug Discovery 2: 214-221 and the references therein. The peptides of the invention may also be conjugated to, for example, alkyl groups (e.g., C1-C20 straight or branched alkyl groups); fatty acid radicals; and combinations of PEG; alkyl groups and fatty acid radicals (see U.S. Pat. No. 6,309,633; Soltero et al., 2001 Innovations in Pharmaceutical Technology 106-110). The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

The agents described herein and combination therapy agents can be packaged as a kit that includes single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation.

Methods to increase chemical and/or physical stability of the agents the described herein are found in U.S. Pat. No. 6,541,606, U.S. Pat. No. 6,068,850, U.S. Pat. No. 6,124,261, U.S. Pat. No. 5,904,935, and WO 00/15224, U.S. 20030069182 (via the addition of nicotinamide), U.S. 20030175230A1, U.S. 20030175230A1, U.S. 20030175239A1, U.S. 20020045582, U.S. 20010031726, WO 02/26248, WO 03/014304, WO 98/00152A1, WO 98/00157A1, WO 90/12029, WO 00/04880, and WO 91/04743, WO 97/04796 and the references cited therein.

Methods to increase bioavailability of the agents described herein are found in U.S. Pat. No. 6,008,187, U.S. Pat. No. 5,424,289, U.S. 20030198619, WO 90/01329, WO 01/49268, WO 00/32172, and WO 02/064166. Glycyrrhizinate can also be used as an absorption enhancer (see, e.g., EP397447). WO 03/004062 discusses *Ulex europaeus* I (UEAl) and UEAI mimetics which may be used to target the agents of the invention to the GI tract.

Analgesic Agents

The peptides described herein can be used in combination therapy with an analgesic agent, e.g., an analgesic compound or an analgesic peptide. The analgesic agent can optionally be covalently attached to a peptide described herein. Among the useful analgesic agents are: Ca channel blockers, 5HT receptor antagonists (for example 5HT3, 5HT4 and 5HT1 receptor antagonists), opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSRI), vanilloid and cannabanoid receptor agonists, and sialorphin. Analgesics agents in the various classes are described in the literature.

Among the useful analgesic peptides are sialorphin-related peptides, including those comprising the amino acid sequence QHNPR (SEQ ID NO:85), including: VQHNPR (SEQ ID NO:86); VRQHNPR (SEQ ID NO:87); VRGQHNPR (SEQ ID NO:88); VRGPQHNPR (SEQ ID NO:89); VRGPRQHNPR (SEQ ID NO:90); VRGPRRQHNPR (SEQ ID NO:91); and RQHNPR (SEQ ID NO:92). Sialorphin-related peptides bind to neprilysin and inhibit neprilysin-mediated breakdown of substance P and Met-enkephalin. Thus, compounds or peptides that are inhibitors of neprilysin are useful analgesic agents which can be administered with the peptides of the invention in a co-therapy or linked to the peptides of the invention, e.g., by a covalent bond. Sialophin and related peptides are described in U.S. Pat. No. 6,589,750; U.S. 20030078200 A1; and WO 02/051435 A2.

Opioid receptor antagonists and agonists can be administered with the peptides of the invention in co-therapy or linked to the peptide of the invention, e.g., by a covalent bond. For example, opioid receptor antagonists such as naloxone, naltrexone, methyl nalozone, nalmefene, cypridime, beta funaltrexamine, naloxonazine, naltrindole, and nor-binaltorphimine are thought to be useful in the treatment of IBS. It can be useful to formulate opioid antagonists of this type is a delayed and sustained release formulation such that initial release of the antagonist is in the mid to distal small intestine and/or ascending colon. Such antagonists are described in WO 01/32180 A2. Enkephalin pentapeptide (HOE825; Tyr-D-Lys-Gly-Phe-L-homoserine) is an agonist of the mu and delta opioid receptors and is thought to be useful for increasing intestinal motility (Eur. J. Pharm.

219:445, 1992), and this peptide can be used in conjunction with the peptides of the invention. Also useful is trimebutine which is thought to bind to mu/delta/kappa opioid receptors and activate release of motilin and modulate the release of gastrin, vasoactive intestinal peptide, gastrin and glucagons. Kappa opioid receptor agonists such as fedotozine, ketocyclazocine, and compounds described in WO 03/097051 A2 can be used with or linked to the peptides of the invention. In addition, mu opioid receptor agonists such as morphine, diphenyloxylate, frakefamide (H-Tyr-D-Ala-Phe(F)-Phe-NH$_2$; WO 01/019849 A1) and loperamide can be used.

Tyr-Arg (kyotorphin) is a dipeptide that acts by stimulating the release of met-enkephalins to elicit an analgesic effect (J. Biol. Chem. 262:8165, 1987). Kyotorphin can be used with or linked to the peptides of the invention.

CCK receptor agonists such as caerulein from amphibians and other species are useful analgesic agents that can be used with or linked to the peptides of the invention.

Conotoxin peptides represent a large class of analgesic peptides that act at voltage gated Ca channels, NMDA receptors or nicotinic receptors. These peptides can be used with or linked to the peptides of the invention.

Peptide analogs of thymulin (FR 2830451) can have analgesic activity and can be used with or linked to the peptides of the invention.

CCK (CCKa or CCKb) receptor antagonists, including loxiglumide and dexloxiglumide (the R-isomer of loxiglumide) (WO 88/05774) can have analgesic activity and can be used with or linked to the peptides of the invention.

Other useful analgesic agents include 5-HT4 agonists such as tegaserod/zelnorm and lirexapride. Such agonists are described in: EP1321142 A1, WO 03/053432A1, EP 505322 A1, EP 505322 B1, U.S. Pat. No. 5,510,353, EP 507672 A1, EP 507672 B1, and U.S. Pat. No. 5,273,983.

Calcium channel blockers such as ziconotide and related compounds described in, for example, EP 625162B1, U.S. Pat. No. 5,364,842, U.S. Pat. No. 5,587,454, U.S. Pat. No. 5,824,645, U.S. Pat. No. 5,859,186, U.S. Pat. No. 5,994,305, U.S. Pat. No. 6,087,091, U.S. Pat. No. 6,136,786, WO 93/13128 A1, EP 1336409 A1, EP 835126 A1, EP 835126 B1, U.S. Pat. No. 5,795,864, U.S. Pat. No. 5,891,849, U.S. Pat. No. 6,054,429, WO 97/01351 A1, can be used with or linked to the peptides of the invention.

Various antagonists of the NK-1, NK-2, and NK-3 receptors (for a review see Giardina et al. 2003 Drugs 6:758) can be can be used with or linked to the peptides of the invention. NK1 receptor antagonists such as: aprepitant (Merck & Co Inc), vofopitant, ezlopitant (Pfizer, Inc.), R-673 (Hoffmann-La Roche Ltd), SR-14033 and related compounds described in, for example, EP 873753 A1, U.S. 20010006972 A1, U.S. 20030109417 A1, WO 01/52844 A1, can be used with or linked to the peptides of the invention.

NK-2 receptor antagonists such as nepadutant (Menarini Ricerche SpA), saredutant (Sanofi-Synthelabo), SR-144190 (Sanofi-Synthelabo) and UK-290795 (Pfizer Inc) can be used with or linked to the peptides of the invention.

NK3 receptor antagonists such as osanetant (Sanofi-Synthelabo), talnetant and related compounds described in, for example, WO 02/094187 A2, EP 876347 A1, WO 97/21680 A1, U.S. Pat. No. 6,277,862, WO 98/11090, WO 95/28418, WO 97/19927, and Boden et al. (*J Med Chem.* 39:1664-75, 1996) can be used with or linked to the peptides of the invention.

Norepinephrine-serotonin reuptake inhibitors such as milnacipran and related compounds described in WO 03/077897 A1 can be used with or linked to the peptides of the invention.

Vanilloid receptor antagonists such as arvanil and related compounds described in WO 01/64212 A1 can be used with or linked to the peptides of the invention.

Where the analgesic is a peptide and is covalently linked to a peptide described herein the resulting peptide may also include at least one trypsin or chymotrypsin cleavage site. When present within the peptide, the analgesic peptide may be preceded by (if it is at the carboxy terminus) or followed by (if it is at the amino terminus) a chymotrypsin or trypsin cleavage site that allows release of the analgesic peptide.

In addition to sialorphin-related peptides, analgesic peptides include: AspPhe, endomorphin-1, endomorphin-2, nocistatin, dalargin, lupron, zicnotide, and substance P.

Methods of Treatment

The peptides of the invention can be used alone or in combination therapy for the treatment or prevention of cancer, pre-cancerous growths, or metastatic growths. For example, they can be used for the prevention or treatment of colorectal/local metastasized colorectal cancer, gastrointestinal tract cancer, lung cancer, cancer or pre-cancerous growths or metastatic growths of epithelial cells, polyps, breast, colorectal, lung, ovarian, pancreatic, prostatic, renal, stomach, bladder, liver, esophageal and testicular carcinoma, carcinoma (e.g., basal cell, basosquamous, Brown-Pearce, ductal carcinoma, Ehrlich tumor, Krebs, Merkel cell, small or non-small cell lung, oat cell, papillary, bronchiolar, squamous cell, transitional cell, Walker), leukemia (e.g., B-cell, T-cell, HTLV, acute or chronic lymphocytic, mast cell, myeloid), histiocytonia, histiocytosis, Hodgkin's disease, non-Hodgkin's lymphoma, plasmacytoma, reticuloendotheliosis, adenoma, adeno-carcinoma, adenofibroma, adenolymphoma, ameloblastoma, angiokeratoma, angiolymphoid hyperplasia with eosinophilia, sclerosing angioma, angiomatosis, apudoma, branchionia, malignant carcinoid syndrome, carcinoid heart disease, carcinosarcoma, cementoma, cholangioma, cholesteatoma, chondrosarcoma, chondroblastoma, chondrosarcoma, chordoma, choristoma, craniopharyngioma, chrondrorna, cylindroma, cystadenocarcinoma, cystadenoma, cystosarconia phyllodes, dysgenninoma, ependymoma, Ewing sarcoma, fibroma, fibrosarcoma, giant cell tumor, ganglioneuroma, glioblastoma, glomangioma, granulosa cell tumor, gynandroblastoma, hamartoma, hemangioendothelioma, hemangioma, hemangio-pericytoma, hemangiosarcoma, hepatoma, islet cell tumor, Kaposi sarcoma, leiomyoma, leiomyosarcoma, leukosarcoma, Leydig cell tumor, lipoma, liposarcoma, lymphaugioma, lymphangiomyoma, lymphangiosarcoma, medulloblastoma, meningioma, mesenchymoma, mesonephroma, mesothelioma, myoblastoma, myoma, myosarcoma, myxoma, myxosarcoma, neurilemmoma, neuroma, neuroblastoma, neuroepithelioma, neurofibroma, neurofibromatosis, odontoma, osteoma, osteosarcoma, papilloma, paraganglioma, paraganglionia. nonchroinaffin, pinealoma, rhabdomyoma, rhabdomyosarcoma, Sertoli cell tumor, teratoma, theca cell tumor, and other diseases in which cells have become dysplastic, immortalized, or transformed.

The peptides of the invention can be used alone or in combination therapy for the treatment or prevention of Familial Adenomatous Polyposis (FAP) (autosomal dominant syndrome) that precedes colon cancer, hereditary non-polyposis colorectal cancer (HNPCC), and inherited autosomal dominant syndrome.

For treatment or prevention of cancer, pre-cancerous growths and metastatic growths, the peptides can be used alone or in combination therapy with radiation or chemotherapeutic agents, an inhibitor of a cGMP-dependent phosphodiesterase or a selective cyclooxygenase-2 inhibitor (a number of selective cyclooxygenase-2 inhibitors are described in WO02062369, hereby incorporated by reference).

The peptides can be for treatment or prevention of inflammation. Thus, they can be used alone or in combination with inhibitors of cGMP-dependent phosphodiesterase or a selective cyclooxygenase-2 inhibitor for treatment of: organ inflammation, IBD (e.g, Crohn's disease, ulcerative colitis), asthma, nephritis, hepatitis, pancreatitis, bronchitis, cystic fibrosis, ischemic bowel diseases, intestinal inflammations/allergies, coeliac disease, proctitis, eosnophilic gastroenteritis, mastocytosis, and other inflammatory disorders.

The peptides can also be used alone or in combination therapy to treat or prevent insulin-related disorders, for example: II diabetes mellitus, hyperglycemia, obesity, disorders associated with disturbances in glucose or electrolyte transport and insulin secretion in cells, or endocrine disorders. They can be also used in insulin resistance treatment and post-surgical and non-post surgery decrease in insulin responsiveness.

The peptides can be used alone or in combination therapy to prevent or treat respiratory disorders, including, inhalation, ventilation and mucus secretion disorders, pulmonary hypertension, chronic obstruction of vessels and airways, and irreversible obstructions of vessels and bronchi.

The peptides can be used in combination therapy with a phosphodiesterase inhibitor (examples of such inhibitors can be found in U.S. Pat. No. 6,333,354, hereby incorporated by reference).

The peptides can also be used alone or in combination therapy to prevent or treat: retinopathy, nephropathy, diabetic angiopathy, and edema formation The peptides can also be used alone or in combination therapy to prevent or treat neurological disorders, for example, headache, anxiety, movement disorders, aggression, psychosis, seizures, panic attacks, hysteria, sleep disorders, depression, schizoaffective disorders, sleep apnea, attention deficit syndromes, memory loss, and narcolepsy. They may also be used as a sedative.

The peptides and detectably labeled peptides can be used as markers to identify, detect, stage, or diagnosis diseases and conditions of the small intestine, including:

Crohn's disease, colitis, inflammatory bowel disease, tumors, benign tumors, such as benign stromal tumors, adenoma, angioma, adenomatous (pedunculated and sessile) polyps, malignant, carcinoid tumors, endocrine cell tumors, lymphoma, adenocarcinoma, foregut, midgut, and hindgut carcinoma, gastroinstestinal stromal tumor (GIST), such as leiomyoma, cellular leiomyoma, leiomyoblastoma, and leiomyosarcoma, gastrointestinal autonomic nerve tumor, malabsorption syndromes, celiac diseases, diverticulosis, Meckel's diverticulum, colonic diverticula, megacolon, Hirschsprung's disease, irritable bowel syndrome, mesenteric ischemia, ischemic colitis, colorectal cancer, colonic polyposis, polyp syndrome, intestinal adenocarcinoma, Liddle syndrome, Brody myopathy, infantile convulsions, and choreoathetosis The peptides can be conjugated to another molecule (e.g, a diagnostic or therapeutic molecule) to target cells bearing the GCC receptor, e.g., cystic fibrosis lesions and specific cells lining the intestinal tract. Thus, they can be used to target radioactive moieties or therapeutic moieties to the intestine to aid in imaging and diagnosing or treating colorectal/metastasized or local colorectal cancer and to deliver normal copies of the p53 tumor suppressor gene to the intestinal tract.

The peptides can be used alone or in combination therapy to treat erectile dysfunction.

The peptides can be used alone or in combination therapy to treat inner ear disorders, e.g., to treat Meniere's disease, including symptoms of the disease such as vertigo, hearing loss, tinnitus, sensation of fullness in the ear, and to maintain fluid homeostasis in the inner ear.

The peptides can be used alone or in combination therapy to treat disorders associated with fluid and sodium retention, e.g., diseases of the electrolyte-water/electrolyte transport system within the kidney, gut and urogenital system, congestive heart failure, hypertension, hypotension, liver cirrhosis, and nephrotic syndrome. In addition they can be used to facilitate diuresis or control intestinal fluid.

The peptides can be used alone or in combination therapy to treat disorders associated with chloride or bicarbonate secretion, e.g., Cystic Fibrosis.

The peptides can be used alone or in combination therapy to treat disorders associated with bile secretion. In addition, they can be used to facilitate or control chloride and bile fluid secretion in the gall bladder.

The peptides can be used alone or in combination therapy to treat disorders associated with liver cell regeneration.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09840536B2). An electronic copy of the "Sequence Listing" will also be available from the USPTO upon request and payment of the fee set forth in 37 CFR 1.19(b)(3).

The invention claimed is:

1. A method for treating a patient suffering from constipation-predominant irritable bowel syndrome, the method comprising orally administering to the patient a composition comprising a polypeptide consisting of the amino acid sequence Asn Asp Glu Cys Glu Leu Cys Val Asn Val Ala Cys Thr Gly Cys Leu (SEQ ID NO: 73), wherein one or two amino acids are substituted by the D-isomer of the amino acid.

2. The method of claim 1, wherein two amino acids are substituted by the D-isomer of the amino acid.

3. A method for treating a patient suffering from constipation, the method comprising orally administering to the patient a composition comprising a polypeptide consisting of the amino acid sequence Asn Asp Glu Cys Glu Leu Cys Val Asn Val Ala Cys Thr Gly Cys Leu (SEQ ID NO: 73), wherein one or two amino acids are substituted by the D-isomer of the amino acid.

4. The method of claim 3, wherein two amino acids are substituted by the D-isomer of the amino acid.

* * * * *